(12) United States Patent
Terry et al.

(10) Patent No.: US 12,246,129 B2
(45) Date of Patent: Mar. 11, 2025

(54) VAPORIZING UNIT WITH USE AUTHORIZATION

(71) Applicant: RAI STRATEGIC HOLDINGS, INC., Winston-Salem, NC (US)

(72) Inventors: Nathan Andrew Terry, Lowman, ID (US); Noah Mark Minskoff, Palo Alto, CA (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 90 days.

(21) Appl. No.: 18/163,623

(22) Filed: Feb. 2, 2023

(65) Prior Publication Data

US 2023/0173202 A1    Jun. 8, 2023

Related U.S. Application Data

(63) Continuation of application No. 17/658,210, filed on Apr. 6, 2022, now Pat. No. 12,133,952, which is a
(Continued)

(51) Int. Cl.
*A61M 15/00* (2006.01)
*A24F 40/44* (2020.01)
(Continued)

(52) U.S. Cl.
CPC ......... *A61M 15/0001* (2014.02); *A24F 40/44* (2020.01); *A24F 40/46* (2020.01);
(Continued)

(58) Field of Classification Search
None
See application file for complete search history.

(56) References Cited

U.S. PATENT DOCUMENTS 438,310 A   10/1890  Edison
705,919 A    7/1902  Gill
(Continued)

FOREIGN PATENT DOCUMENTS

AU        276250 A     7/1965
CN       2293957 Y    10/1998
(Continued)

OTHER PUBLICATIONS

Andrus et al., "Nicotine Microaerosol Inhaler", Can Respir Journal, vol. 6, No. 6, 1999, pp. 509-512.
(Continued)

*Primary Examiner* — Dennis R Cordray
(74) *Attorney, Agent, or Firm* — Womble Bond Dickinson (US) LLP; Chris Humphrey; John V. Forcier

(57) ABSTRACT

A personal vapor inhaling unit is disclosed. An electronic flameless vapor inhaler unit that may simulate a cigarette has a cavity that receives a cartridge in the distal end of the inhaler unit. The cartridge brings a substance to be vaporized in contact with a wick. When the unit is activated, and the user provides suction, the substance to be vaporized is drawn out of the cartridge, through the wick, and is atomized by the wick into a cavity containing a heating element. The heating element vaporizes the atomized substance. The vapors then continue to be pulled by the user through a mouthpiece and mouthpiece cover where they may be inhaled.

19 Claims, 173 Drawing Sheets

Related U.S. Application Data continuation of application No. 16/010,932, filed on Jun. 18, 2018, now Pat. No. 11,344,683, which is a continuation-in-part of application No. 14/701,046, filed on Apr. 30, 2015, now Pat. No. 9,999,250, which is a continuation-in-part of application No. 14/279,174, filed on May 15, 2014, now Pat. No. 10,136,672, which is a continuation-in-part of application No. 13/698,020, filed on Nov. 14, 2012, now Pat. No. 9,259,035, which is a continuation-in-part of application No. 12/780,871, filed on May 15, 2010, now abandoned, and a continuation-in-part of application No. 12/780,872, filed on May 15, 2010, now Pat. No. 8,746,240, and a continuation-in-part of application No. 12/780,873, filed on May 15, 2010, now Pat. No. 9,861,772, and a continuation-in-part of application No. 12/780,874, filed on May 15, 2010, now Pat. No. 8,550,068, and a continuation-in-part of application No. 12/780,875, filed on May 15, 2010, now Pat. No. 8,757,147, and a continuation-in-part of application No. 12/780,876, filed on May 15, 2010, now Pat. No. 9,095,175, and a continuation-in-part of application No. 12/780,877, filed on May 15, 2010, now Pat. No. 8,314,591, said application No. 16/010,932 is a continuation-in-part of application No. 14/285,605, filed on May 22, 2014, now Pat. No. 10,159,278, which is a continuation-in-part of application No. 12/780,873, filed on May 15, 2010, now Pat. No. 9,861,772, said application No. 16/010,932 is a continuation-in-part of application No. 14/716,204, filed on May 19, 2015, now abandoned, and a continuation-in-part of application No. 14/275,494, filed on May 12, 2014, now Pat. No. 10,092,713, which is a continuation-in-part of application No. 12/780,875, filed on May 15, 2010, now Pat. No. 8,757,147.

(60) Provisional application No. 61/987,005, filed on May 1, 2014, provisional application No. 62/000,101, filed on May 19, 2014.

(51) Int. Cl.
*A24F 40/46* (2020.01)
*A24F 40/485* (2020.01)
*A61M 11/04* (2006.01)
*A61M 15/06* (2006.01)
*A24F 40/10* (2020.01)
*A61M 16/00* (2006.01)

(52) U.S. Cl.
CPC ......... *A24F 40/485* (2020.01); *A61M 11/041* (2013.01); *A61M 11/042* (2014.02); *A61M 15/0025* (2014.02); *A61M 15/0035* (2014.02); *A61M 15/06* (2013.01); *A24F 40/10* (2020.01); *A61M 2016/0018* (2013.01); *A61M 2205/0205* (2013.01); *A61M 2205/0233* (2013.01); *A61M 2205/13* (2013.01); *A61M 2205/3592* (2013.01); *A61M 2205/3653* (2013.01); *A61M 2205/3693* (2013.01); *A61M 2205/505* (2013.01); *A61M 2205/52* (2013.01); *A61M 2205/59* (2013.01); *A61M 2205/80* (2013.01); *A61M 2205/8206* (2013.01); *A61M 2230/005* (2013.01); *A61M 2230/65* (2013.01)

(56) References Cited

U.S. PATENT DOCUMENTS

| | | |
|---|---|---|
| 780,087 A | 1/1905 | Burt |
| 1,016,844 A | 2/1912 | Moonelis |
| 1,084,304 A | 1/1914 | Vaughn |
| 1,147,416 A | 7/1915 | MacDonald |
| 1,347,631 A | 7/1920 | Jean |
| 1,446,087 A | 2/1923 | Griffin |
| 1,514,682 A | 11/1924 | Wilson |
| 1,517,584 A | 12/1924 | Reece |
| 1,771,366 A | 7/1930 | Wyss et al. |
| 1,879,128 A | 9/1932 | Despe |
| 2,032,695 A | 3/1936 | Gimera |
| 2,057,353 A | 10/1936 | Whittemore, Jr. |
| 2,086,192 A | 7/1937 | Schumaker |
| 2,104,266 A | 1/1938 | McCormick |
| 2,140,516 A | 12/1938 | Cowan |
| 2,461,664 A | 2/1949 | Smith |
| 2,472,282 A | 6/1949 | Burchett |
| 2,545,851 A | 3/1951 | Kardos |
| 2,959,664 A | 11/1960 | Fenn |
| 3,060,429 A | 10/1962 | Winston |
| 3,200,819 A | 8/1965 | Gilbert |
| 3,203,025 A | 8/1965 | Schreur |
| 3,234,357 A | 2/1966 | Seuthe |
| 3,258,015 A | 6/1966 | Ellis et al. |
| 3,281,637 A | 10/1966 | Hultquist |
| 3,292,635 A | 12/1966 | Kolodny |
| 3,356,094 A | 12/1967 | Ellis et al. |
| 3,385,303 A | 5/1968 | Hind |
| 3,428,053 A | 2/1969 | Schoenbaum |
| 3,431,393 A | 3/1969 | Katsuda |
| 3,479,561 A | 11/1969 | Janning |
| 3,486,508 A | 12/1969 | Sipos |
| 3,502,588 A | 3/1970 | Winberg |
| 3,516,417 A | 6/1970 | Moses |
| 3,614,056 A | 10/1971 | Alvarez |
| 3,651,240 A | 3/1972 | Kirkpatrick |
| 3,685,521 A | 8/1972 | Dock |
| 3,685,522 A | 8/1972 | Kleinhans |
| 3,738,374 A | 6/1973 | Bennett |
| 3,747,120 A | 7/1973 | Stemme |
| 3,751,969 A | 8/1973 | Schrock |
| 3,766,000 A | 10/1973 | Gibson et al. |
| 3,844,294 A | 10/1974 | Webster |
| 3,860,012 A | 1/1975 | Selke |
| 3,878,850 A | 4/1975 | Gibson et al. |
| 3,931,824 A | 1/1976 | Miano et al. |
| 3,933,643 A | 1/1976 | Colvin et al. |
| 3,934,117 A | 1/1976 | Schladitz |
| 3,943,941 A | 3/1976 | Boyd et al. |
| 4,016,878 A | 4/1977 | Castel et al. |
| 4,044,777 A | 8/1977 | Boyd et al. |
| 4,079,742 A | 3/1978 | Rainer et al. |
| 4,190,046 A | 2/1980 | Virag |
| 4,207,457 A | 6/1980 | Haglund et al. |
| 4,219,031 A | 8/1980 | Rainer et al. |
| 4,219,032 A | 8/1980 | Tabatznik et al. |
| 4,233,993 A | 11/1980 | Miano et al. |
| 4,259,970 A | 4/1981 | Green, Jr. |
| 4,270,552 A | 6/1981 | Jenkins et al. |
| 4,284,089 A | 8/1981 | Ray |
| 4,286,604 A | 9/1981 | Ehretsmann et al. |
| 4,303,083 A | 12/1981 | Burruss, Jr. |
| 4,326,544 A | 4/1982 | Hardwick et al. |
| 4,340,072 A | 7/1982 | Bolt et al. |
| 4,347,855 A | 9/1982 | Lanzillotti et al. |
| 4,391,285 A | 7/1983 | Burnett et al. |
| 4,429,703 A | 2/1984 | Haber |
| 4,506,682 A | 3/1985 | Muller |
| 4,531,178 A | 7/1985 | Uke |
| 4,589,428 A | 5/1986 | Keritsis |
| 4,629,665 A | 12/1986 | Matsuo |
| 4,635,651 A | 1/1987 | Jacobs |
| 4,637,407 A | 1/1987 | Bonanno et al. |
| 4,676,237 A | 6/1987 | Wood et al. |
| 4,700,727 A | 10/1987 | Torigian |

(56) References Cited

U.S. PATENT DOCUMENTS

| | | |
|---|---|---|
| 4,708,151 A | 11/1987 | Shelar |
| 4,714,082 A | 12/1987 | Banerjee et al. |
| 4,735,217 A | 4/1988 | Gerth et al. |
| 4,756,318 A | 7/1988 | Clearman et al. |
| 4,768,676 A | 9/1988 | Kaneko |
| 4,771,295 A | 9/1988 | Baker et al. |
| 4,771,795 A | 9/1988 | White et al. |
| 4,771,796 A | 9/1988 | Myer |
| 4,776,353 A | 10/1988 | Lilja et al. |
| 4,793,365 A | 12/1988 | Sensabaugh, Jr. et al. |
| 4,797,692 A | 1/1989 | Ims |
| 4,800,903 A | 1/1989 | Ray et al. |
| 4,807,809 A | 2/1989 | Pryor et al. |
| 4,819,665 A | 4/1989 | Roberts et al. |
| 4,823,817 A | 4/1989 | Luke |
| 4,836,225 A | 6/1989 | Sudoh |
| 4,848,374 A | 7/1989 | Chard et al. |
| 4,848,376 A | 7/1989 | Lilja et al. |
| 4,874,000 A | 10/1989 | Tamol et al. |
| 4,878,506 A | 11/1989 | Pinck et al. |
| 4,892,109 A | 1/1990 | Strubel |
| 4,893,639 A | 1/1990 | White |
| 4,907,606 A | 3/1990 | Lilja et al. |
| 4,913,168 A | 4/1990 | Potter et al. |
| 4,917,119 A | 4/1990 | Potter et al. |
| 4,917,121 A | 4/1990 | Riehl |
| 4,917,128 A | 4/1990 | Clearman et al. |
| 4,920,990 A | 5/1990 | Lawrence et al. |
| 4,922,901 A | 5/1990 | Brooks et al. |
| 4,924,886 A | 5/1990 | Litzinger |
| 4,938,236 A | 7/1990 | Banerjee et al. |
| 4,941,483 A | 7/1990 | Ridings et al. |
| 4,941,486 A | 7/1990 | Dube et al. |
| 4,945,448 A | 7/1990 | Bremenour |
| 4,945,929 A | 8/1990 | Egilmex |
| 4,945,931 A | 8/1990 | Gori |
| 4,947,874 A | 8/1990 | Brooks et al. |
| 4,947,875 A | 8/1990 | Brooks et al. |
| 4,961,438 A | 10/1990 | Korte |
| 4,966,171 A | 10/1990 | Serrano et al. |
| 4,968,263 A | 11/1990 | Silbernagel |
| 4,969,476 A | 11/1990 | Bale et al. |
| 4,972,855 A | 11/1990 | Kuriyama et al. |
| 4,977,908 A | 12/1990 | Luke |
| 4,981,522 A | 1/1991 | Nichols et al. |
| 4,986,286 A | 1/1991 | Roberts et al. |
| 4,990,939 A | 2/1991 | Sekiya et al. |
| 4,991,606 A | 2/1991 | Serrano et al. |
| 5,005,593 A | 4/1991 | Fagg |
| 5,019,122 A | 5/1991 | Clearman et al. |
| 5,020,548 A | 6/1991 | Farrier et al. |
| 5,025,814 A | 6/1991 | Raker |
| 5,033,483 A | 7/1991 | Clearman et al. |
| 5,040,551 A | 8/1991 | Schlatter et al. |
| 5,042,510 A | 8/1991 | Curtiss et al. |
| 5,046,514 A | 9/1991 | Bolt |
| 5,050,621 A | 9/1991 | Creighton et al. |
| 5,060,667 A | 10/1991 | Strubel |
| 5,060,671 A | 10/1991 | Counts et al. |
| 5,060,676 A | 10/1991 | Hearn et al. |
| 5,065,776 A | 11/1991 | Lawson et al. |
| 5,072,744 A | 12/1991 | Luke et al. |
| 5,074,321 A | 12/1991 | Gentry et al. |
| 5,076,296 A | 12/1991 | Nystrom et al. |
| 5,076,297 A | 12/1991 | Farrier et al. |
| 5,092,353 A | 3/1992 | Montoya |
| 5,093,894 A | 3/1992 | Deevi et al. |
| 5,095,921 A | 3/1992 | Losee et al. |
| 5,097,850 A | 3/1992 | Braunshteyn et al. |
| 5,099,861 A | 3/1992 | Clearman et al. |
| 5,101,839 A | 4/1992 | Jakob et al. |
| 5,105,835 A | 4/1992 | Drewett et al. |
| 5,105,836 A | 4/1992 | Gentry et al. |
| 5,105,837 A | 4/1992 | Barnes et al. |
| 5,105,838 A | 4/1992 | White et al. |
| 5,115,820 A | 5/1992 | Hauser |
| 5,124,200 A | 6/1992 | Mallonee |
| 5,129,409 A | 7/1992 | White et al. |
| 5,144,962 A | 9/1992 | Counts et al. |
| 5,146,934 A | 9/1992 | Deevi et al. |
| 5,148,821 A | 9/1992 | Best et al. |
| 5,159,940 A | 11/1992 | Hayward et al. |
| 5,159,942 A | 11/1992 | Brinkley et al. |
| 5,177,424 A | 1/1993 | Connors |
| 5,178,167 A | 1/1993 | Riggs et al. |
| 5,179,966 A | 1/1993 | Losee et al. |
| 5,183,062 A | 2/1993 | Clearman et al. |
| 5,203,335 A | 4/1993 | Noujaim et al. |
| 5,211,684 A | 5/1993 | Shannon et al. |
| 5,224,265 A | 7/1993 | Dux et al. |
| 5,224,498 A | 7/1993 | Deevi et al. |
| 5,228,460 A | 7/1993 | Sprinkel et al. |
| 5,240,014 A | 8/1993 | Deevi et al. |
| 5,240,016 A | 8/1993 | Nichols et al. |
| 5,246,018 A | 9/1993 | Deevi et al. |
| 5,249,586 A | 10/1993 | Morgan et al. |
| 5,255,674 A | 10/1993 | Oftedal et al. |
| 5,261,424 A | 11/1993 | Sprinkel, Jr. |
| 5,266,746 A | 11/1993 | Nishihara |
| 5,269,327 A | 12/1993 | Counts et al. |
| 5,271,419 A | 12/1993 | Arzonico et al. |
| 5,282,798 A | 2/1994 | Bruse et al. |
| 5,285,798 A | 2/1994 | Banerjee et al. |
| 5,293,883 A | 3/1994 | Edwards |
| 5,322,075 A | 6/1994 | Deevi et al. |
| 5,327,915 A | 7/1994 | Porenski et al. |
| 5,327,917 A | 7/1994 | Lekwauwa et al. |
| 5,345,951 A | 9/1994 | Serrano et al. |
| 5,345,955 A | 9/1994 | Clearman et al. |
| 5,353,813 A | 10/1994 | Deevi et al. |
| 5,357,984 A | 10/1994 | Farrier et al. |
| 5,360,023 A | 11/1994 | Blakley et al. |
| 5,366,122 A | 11/1994 | Guentert et al. |
| 5,369,723 A | 11/1994 | Counts et al. |
| 5,372,148 A | 12/1994 | McCafferty et al. |
| 5,388,574 A | 2/1995 | Ingebrethsen |
| 5,388,594 A | 2/1995 | Counts et al. |
| 5,396,911 A | 3/1995 | Casey, III et al. |
| 5,408,574 A | 4/1995 | Deevi et al. |
| 5,468,936 A | 11/1995 | Deevi et al. |
| 5,479,948 A | 1/1996 | Counts et al. |
| 5,497,791 A | 3/1996 | Bowen et al. |
| 5,498,850 A | 3/1996 | Das |
| 5,498,855 A | 3/1996 | Deevi et al. |
| 5,499,636 A | 3/1996 | Baggett, Jr. et al. |
| 5,505,214 A | 4/1996 | Collins et al. |
| 5,515,842 A | 5/1996 | Ramseyer et al. |
| 5,521,576 A | 5/1996 | Collins |
| 5,530,225 A | 6/1996 | Hajaligol |
| 5,533,530 A | 7/1996 | Young et al. |
| 5,551,451 A | 9/1996 | Riggs et al. |
| 5,564,442 A | 10/1996 | MacDonald et al. |
| 5,573,692 A | 11/1996 | Das et al. |
| 5,588,446 A | 12/1996 | Clearman |
| 5,591,368 A | 1/1997 | Fleischhauer et al. |
| 5,593,792 A | 1/1997 | Farrier et al. |
| 5,595,577 A | 1/1997 | Bensalem et al. |
| 5,595,706 A | 1/1997 | Sikka et al. |
| 5,598,868 A | 2/1997 | Jakob et al. |
| 5,611,360 A | 3/1997 | Tang |
| 5,613,504 A | 3/1997 | Collins et al. |
| 5,613,505 A | 3/1997 | Campbell et al. |
| 5,637,430 A | 6/1997 | Shimizu et al. |
| 5,646,666 A | 7/1997 | Cowger et al. |
| 5,649,554 A | 7/1997 | Sprinkel et al. |
| 5,659,656 A | 8/1997 | Das |
| 5,665,262 A | 9/1997 | Hajaligol et al. |
| 5,666,976 A | 9/1997 | Adams et al. |
| 5,666,977 A | 9/1997 | Higgins et al. |
| 5,666,978 A | 9/1997 | Counts et al. |
| 5,687,746 A | 11/1997 | Rose et al. |
| 5,692,525 A | 12/1997 | Counts et al. |
| 5,692,526 A | 12/1997 | Adams et al. |
| 5,703,633 A | 12/1997 | Gehrer et al. |

(56) References Cited

U.S. PATENT DOCUMENTS

| | | |
|---|---|---|
| 5,708,258 A | 1/1998 | Counts et al. |
| 5,709,202 A | 1/1998 | Lloyd et al. |
| 5,715,844 A | 2/1998 | Young et al. |
| 5,726,421 A | 3/1998 | Fleischhauer et al. |
| 5,727,571 A | 3/1998 | Meiring et al. |
| 5,730,158 A | 3/1998 | Collins et al. |
| 5,732,685 A | 3/1998 | Nakamura |
| 5,743,251 A | 4/1998 | Howell et al. |
| 5,745,985 A | 5/1998 | Ghosh et al. |
| 5,750,964 A | 5/1998 | Counts et al. |
| 5,778,899 A | 7/1998 | Saito et al. |
| 5,799,663 A | 9/1998 | Gross et al. |
| 5,816,263 A | 10/1998 | Counts et al. |
| 5,819,751 A | 10/1998 | Barnes et al. |
| 5,819,756 A | 10/1998 | Mielordt |
| 5,829,453 A | 11/1998 | White et al. |
| 5,865,185 A | 2/1999 | Collins et al. |
| 5,865,186 A | 2/1999 | Volsey, II |
| 5,878,752 A | 3/1999 | Adams et al. |
| 5,880,439 A | 3/1999 | Deevi et al. |
| 5,893,371 A | 4/1999 | Rose et al. |
| 5,894,841 A | 4/1999 | Voges |
| 5,915,387 A | 6/1999 | Baggett, Jr. et al. |
| 5,934,289 A | 8/1999 | Watkins et al. |
| 5,944,025 A | 8/1999 | Cook et al. |
| 5,954,979 A | 9/1999 | Counts et al. |
| 5,967,148 A | 10/1999 | Harris et al. |
| 5,996,589 A | 12/1999 | St. Charles |
| 6,026,820 A | 2/2000 | Baggett, Jr. et al. |
| 6,033,623 A | 3/2000 | Deevi et al. |
| 6,040,560 A | 3/2000 | Fleischhauer et al. |
| 6,053,176 A | 4/2000 | Adams et al. |
| 6,062,213 A | 5/2000 | Fuisz et al. |
| 6,089,857 A | 7/2000 | Matsuura et al. |
| 6,095,152 A | 8/2000 | Beven et al. |
| 6,095,153 A | 8/2000 | Kessler et al. |
| 6,102,036 A | 8/2000 | Slutsky et al. |
| 6,102,688 A | 8/2000 | Mifune et al. |
| 6,116,247 A | 9/2000 | Banyasz et al. |
| 6,119,700 A | 9/2000 | Fleischhauer et al. |
| 6,125,853 A | 10/2000 | Susa et al. |
| 6,125,866 A | 10/2000 | Nichols et al. |
| 6,146,934 A | 11/2000 | Gardner et al. |
| 6,155,268 A | 12/2000 | Takeuchi |
| 6,164,287 A | 12/2000 | White |
| 6,182,670 B1 | 2/2001 | White et al. |
| 6,196,218 B1 | 3/2001 | Voges |
| 6,196,219 B1 | 3/2001 | Hess et al. |
| 6,217,315 B1 | 4/2001 | Mifune et al. |
| 6,232,784 B1 | 5/2001 | Dulasky |
| 6,234,167 B1 | 5/2001 | Cox et al. |
| 6,285,017 B1 | 9/2001 | Brickell |
| 6,289,898 B1 | 9/2001 | Fournier et al. |
| 6,311,561 B1 | 11/2001 | Bang et al. |
| 6,322,268 B1 | 11/2001 | Kaufmann et al. |
| 6,349,728 B1 | 2/2002 | Pham |
| 6,397,852 B1 | 6/2002 | McAdam |
| 6,408,856 B1 | 6/2002 | McAdam |
| 6,418,938 B1 | 7/2002 | Fleischhauer et al. |
| 6,443,146 B1 | 9/2002 | Voges |
| 6,446,426 B1 | 9/2002 | Sweeney et al. |
| 6,476,151 B1 | 11/2002 | Araki et al. |
| 6,501,052 B2 | 12/2002 | Cox et al. |
| 6,516,796 B1 | 2/2003 | Cox et al. |
| 6,532,965 B1 | 3/2003 | Abhulimen et al. |
| 6,537,186 B1 | 3/2003 | Veluz |
| 6,557,552 B1 | 5/2003 | Cox et al. |
| 6,578,584 B1 | 6/2003 | Beven et al. |
| 6,591,841 B1 | 7/2003 | White et al. |
| 6,598,607 B2 | 7/2003 | Adiga et al. |
| 6,601,776 B1 | 8/2003 | Oljaca et al. |
| 6,615,840 B1 | 9/2003 | Fournier et al. |
| 6,620,659 B2 | 9/2003 | Emmma et al. |
| 6,637,430 B1 | 10/2003 | Voges et al. |
| 6,681,769 B2 | 1/2004 | Sprinkel, Jr. et al. |
| 6,688,313 B2 | 2/2004 | Wrenn et al. |
| 6,690,121 B1 | 2/2004 | Weindorf |
| 6,715,494 B1 | 4/2004 | McCoy |
| 6,719,443 B2 | 4/2004 | Gutstein et al. |
| 6,722,763 B1 | 4/2004 | Hsu et al. |
| 6,730,832 B1 | 5/2004 | Dominguez et al. |
| 6,766,220 B1 | 7/2004 | McRae et al. |
| 6,772,756 B2 | 8/2004 | Shayan |
| 6,772,757 B2 | 8/2004 | Sprinkel, Jr. |
| 6,803,545 B2 | 10/2004 | Blake et al. |
| 6,803,550 B2 | 10/2004 | Sharpe et al. |
| 6,804,458 B2 | 10/2004 | Sherwood et al. |
| 6,810,883 B2 | 11/2004 | Felter et al. |
| 6,823,873 B2 | 11/2004 | Nichols et al. |
| 6,854,461 B2 | 2/2005 | Nichols et al. |
| 6,854,470 B1 | 2/2005 | Pu |
| 6,885,814 B2 | 4/2005 | Saito et al. |
| 6,923,179 B2 | 8/2005 | Gupta et al. |
| 6,938,986 B2 | 9/2005 | Macler et al. |
| 6,994,096 B2 | 2/2006 | Rostami et al. |
| 7,040,314 B2 | 5/2006 | Nguyen et al. |
| 7,117,867 B2 | 10/2006 | Cox et al. |
| 7,147,170 B2 | 12/2006 | Nguyen et al. |
| 7,163,015 B2 | 1/2007 | Moffitt |
| 7,167,776 B2 | 1/2007 | Maharajh et al. |
| 7,173,222 B2 | 2/2007 | Cox et al. |
| 7,185,659 B2 | 3/2007 | Sharpe |
| 7,234,470 B2 | 6/2007 | Yang |
| 7,284,424 B2 | 10/2007 | Kanke et al. |
| 7,290,549 B2 | 11/2007 | Banerjee et al. |
| 7,293,565 B2 | 11/2007 | Griffin et al. |
| 7,337,782 B2 | 3/2008 | Thompson |
| 7,392,809 B2 | 7/2008 | Larson et al. |
| 7,400,940 B2 | 7/2008 | McRae et al. |
| 7,445,007 B2 | 11/2008 | Balch et al. |
| 7,500,479 B2 | 3/2009 | Nichols et al. |
| D590,988 S | 4/2009 | Hon |
| D590,989 S | 4/2009 | Hon |
| D590,990 S | 4/2009 | Hon |
| D590,991 S | 4/2009 | Hon |
| 7,513,253 B2 | 4/2009 | Kobayashi et al. |
| 7,645,442 B2 | 1/2010 | Hale et al. |
| D614,346 S | 4/2010 | Lik |
| 7,690,385 B2 | 4/2010 | Moffitt |
| 7,692,123 B2 | 4/2010 | Baba et al. |
| 7,726,320 B2 | 6/2010 | Robinson et al. |
| 7,775,459 B2 | 8/2010 | Martens, III et al. |
| 7,810,505 B2 | 10/2010 | Yang |
| 7,832,410 B2 | 11/2010 | Hon |
| 7,845,359 B2 | 12/2010 | Montaser |
| 7,896,006 B2 | 3/2011 | Hamano et al. |
| 7,983,113 B2 | 7/2011 | Krueger et al. |
| D644,375 S | 8/2011 | Zhou |
| 7,997,280 B2 | 8/2011 | Rosenthal |
| 8,003,080 B2 | 8/2011 | Rabinowitz et al. |
| 8,042,550 B2 | 10/2011 | Urtsev et al. |
| D649,708 S | 11/2011 | Oneil |
| 8,079,371 B2 | 12/2011 | Robinson et al. |
| 8,091,558 B2 | 1/2012 | Martzel |
| D653,803 S | 2/2012 | Timmermans |
| D655,036 S | 2/2012 | Zhou |
| 8,127,772 B2 | 3/2012 | Montaser |
| D657,047 S | 4/2012 | Minskoff et al. |
| 8,156,944 B2 | 4/2012 | Han |
| D662,257 S | 6/2012 | Alelov |
| 8,191,555 B2 | 6/2012 | Herbrich et al. |
| 8,205,622 B2 | 6/2012 | Pan |
| D666,355 S | 8/2012 | Alelov |
| 8,291,918 B2 | 10/2012 | Magnon |
| 8,314,591 B2 | 11/2012 | Terry et al. |
| 8,322,350 B2 | 12/2012 | Lipowicz |
| 8,342,184 B2 | 1/2013 | Inagaki et al. |
| D675,777 S | 2/2013 | Wu |
| D677,000 S | 2/2013 | Liu |
| D677,001 S | 2/2013 | Liu |
| 8,365,742 B2 | 2/2013 | Hon |
| 8,371,310 B2 | 2/2013 | Brenneise |
| 8,375,957 B2 | 2/2013 | Hon |
| 8,393,331 B2 | 3/2013 | Hon |

(56) References Cited

U.S. PATENT DOCUMENTS

| | | |
|---|---|---|
| 8,402,976 B2 | 3/2013 | Fernando et al. |
| D681,268 S | 4/2013 | Wu |
| D681,269 S | 4/2013 | Wu |
| 8,430,106 B2 | 4/2013 | Potter et al. |
| D682,090 S | 5/2013 | Scatterday |
| D682,565 S | 5/2013 | McDonald |
| 8,434,478 B2 | 5/2013 | Yamada et al. |
| D683,897 S | 6/2013 | Liu |
| D683,898 S | 6/2013 | Liu |
| D683,899 S | 6/2013 | Liu |
| D684,311 S | 6/2013 | Liu |
| 8,459,271 B2 | 6/2013 | Inagaki |
| D685,522 S | 7/2013 | Potter et al. |
| 8,479,747 B2 | 7/2013 | O'Connell |
| 8,490,628 B2 | 7/2013 | Hon |
| 8,495,998 B2 | 7/2013 | Schennum |
| D687,999 S | 8/2013 | Liu |
| D688,415 S | 8/2013 | Kim |
| D688,416 S | 8/2013 | Liu |
| D688,418 S | 8/2013 | Liu |
| 8,499,766 B1 | 8/2013 | Newton |
| 8,505,548 B2 | 8/2013 | Hearn |
| 8,511,318 B2 | 8/2013 | Hon |
| 8,517,032 B2 | 8/2013 | Urtsev et al. |
| 8,528,569 B1 | 9/2013 | Newton |
| 8,539,959 B1 | 9/2013 | Scatterday |
| D691,324 S | 10/2013 | Saliman |
| D692,612 S | 10/2013 | Lowenthal et al. |
| D692,614 S | 10/2013 | Robinson |
| 8,550,068 B2 | 10/2013 | Terry et al. |
| 8,550,069 B2 | 10/2013 | Alelov |
| 8,558,147 B2 | 10/2013 | Greim et al. |
| D692,915 S | 11/2013 | Brinda et al. |
| D693,054 S | 11/2013 | Verleur |
| D693,055 S | 11/2013 | Manca et al. |
| 8,578,942 B2 | 11/2013 | Schennum |
| D696,051 S | 12/2013 | Scatterday |
| D696,455 S | 12/2013 | Abroff |
| D696,815 S | 12/2013 | Abroff |
| 8,596,460 B2 | 12/2013 | Scatterday |
| 8,602,037 B2 | 12/2013 | Inagaki |
| D697,482 S | 1/2014 | Cheng |
| 8,634,709 B2 | 1/2014 | Maharajh et al. |
| D699,391 S | 2/2014 | Abroff et al. |
| D700,397 S | 2/2014 | Manca et al. |
| D700,738 S | 3/2014 | Rennick et al. |
| D700,739 S | 3/2014 | Manca et al. |
| D700,994 S | 3/2014 | Alarcon et al. |
| 8,678,012 B2 | 3/2014 | Li et al. |
| D702,876 S | 4/2014 | Liu |
| 8,689,786 B2 | 4/2014 | Schennum |
| 8,689,804 B2 | 4/2014 | Fernando et al. |
| 8,689,805 B2 | 4/2014 | Hon |
| 8,695,794 B2 | 4/2014 | Scatterday |
| 8,707,965 B2 | 4/2014 | Newton |
| D704,549 S | 5/2014 | Liu |
| D704,629 S | 5/2014 | Liu |
| D704,630 S | 5/2014 | Liu |
| D705,814 S | 5/2014 | Liberti et al. |
| 8,714,161 B2 | 5/2014 | Liu |
| 8,733,345 B2 | 5/2014 | Siller |
| 8,733,346 B2 | 5/2014 | Rinker |
| D706,976 S | 6/2014 | Wu |
| D707,389 S | 6/2014 | Liu |
| 8,746,240 B2 | 6/2014 | Terry et al. |
| 8,752,557 B2 | 6/2014 | Lipowicz |
| 8,757,169 B2 | 6/2014 | Gysland |
| 8,893,726 B2 | 11/2014 | Hon |
| 8,899,228 B2 | 12/2014 | Linton et al. |
| 10,036,548 B2 | 7/2018 | Liu |
| 2001/0026788 A1 | 10/2001 | Piskorz |
| 2002/0136886 A1 | 9/2002 | He et al. |
| 2002/0146242 A1 | 10/2002 | Vieira |
| 2003/0011579 A1 | 1/2003 | Gong et al. |
| 2003/0033055 A1 | 2/2003 | McRae et al. |
| 2003/0108342 A1 | 6/2003 | Sherwood et al. |
| 2003/0131859 A1 | 7/2003 | Li et al. |
| 2003/0189826 A1 | 10/2003 | Yoon |
| 2003/0226837 A1 | 12/2003 | Blake et al. |
| 2004/0020500 A1 | 2/2004 | Wrenn et al. |
| 2004/0020508 A1 | 2/2004 | Earl |
| 2004/0035409 A1 | 2/2004 | Harwig et al. |
| 2004/0055613 A1 | 3/2004 | Horian |
| 2004/0084044 A1 | 5/2004 | Childers et al. |
| 2004/0089314 A1 | 5/2004 | Felter et al. |
| 2004/0118401 A1 | 6/2004 | Smith et al. |
| 2004/0129280 A1 | 7/2004 | Woodson et al. |
| 2004/0149282 A1 | 8/2004 | Hickle |
| 2004/0149296 A1 | 8/2004 | Rostami et al. |
| 2004/0173229 A1 | 9/2004 | Crooks et al. |
| 2004/0198127 A1 | 10/2004 | Yamamoto et al. |
| 2004/0200488 A1 | 10/2004 | Felter et al. |
| 2004/0226568 A1 | 11/2004 | Takeuchi et al. |
| 2004/0234916 A1 | 11/2004 | Hale et al. |
| 2004/0261802 A1 | 12/2004 | Griffin et al. |
| 2005/0016549 A1 | 1/2005 | Banerjee et al. |
| 2005/0016550 A1 | 1/2005 | Katase |
| 2005/0066986 A1 | 3/2005 | Nestor et al. |
| 2005/0115243 A1 | 6/2005 | Adle |
| 2005/0172976 A1 | 8/2005 | Newman et al. |
| 2006/0016453 A1 | 1/2006 | Kim |
| 2006/0021614 A1 | 2/2006 | Wermeling et al. |
| 2006/0070633 A1 | 4/2006 | Rostami et al. |
| 2006/0093977 A1 | 5/2006 | Pellizzari et al. |
| 2006/0185687 A1 | 8/2006 | Hearn et al. |
| 2006/0196518 A1 | 9/2006 | Hon |
| 2006/0221594 A1 | 10/2006 | Thuot Rann et al. |
| 2006/0283468 A1 | 12/2006 | Lipowicz |
| 2007/0030306 A1 | 2/2007 | Okamura et al. |
| 2007/0062549 A1 | 3/2007 | Holton et al. |
| 2007/0074734 A1 | 4/2007 | Braunshteyn et al. |
| 2007/0102013 A1 | 5/2007 | Adams et al. |
| 2007/0215167 A1 | 9/2007 | Llewellyn Crooks et al. |
| 2007/0240711 A1 | 10/2007 | Hamano |
| 2007/0267031 A1 | 11/2007 | Hon |
| 2007/0283972 A1 | 12/2007 | Monsees et al. |
| 2008/0056691 A1 | 3/2008 | Wingo et al. |
| 2008/0085103 A1 | 4/2008 | Beland et al. |
| 2008/0092912 A1 | 4/2008 | Robinson et al. |
| 2008/0099011 A1 | 5/2008 | Gonda et al. |
| 2008/0138423 A1 | 6/2008 | Gonda |
| 2008/0149118 A1 | 6/2008 | Oglesby et al. |
| 2008/0257367 A1 | 10/2008 | Paterno et al. |
| 2008/0276947 A1 | 11/2008 | Martzel |
| 2008/0302374 A1 | 12/2008 | Wengert et al. |
| 2009/0065010 A1 | 3/2009 | Shands |
| 2009/0095311 A1 | 4/2009 | Han |
| 2009/0095312 A1 | 4/2009 | Herbrich et al. |
| 2009/0114737 A1 | 5/2009 | Yu et al. |
| 2009/0126745 A1 | 5/2009 | Hon |
| 2009/0151717 A1 | 6/2009 | Bowen et al. |
| 2009/0178672 A1 | 7/2009 | Mullinger et al. |
| 2009/0188490 A1 | 7/2009 | Han |
| 2009/0230117 A1 | 9/2009 | Fernando et al. |
| 2009/0255534 A1 | 10/2009 | Paterno |
| 2009/0260641 A1 | 10/2009 | Monsees et al. |
| 2009/0260642 A1 | 10/2009 | Monsees et al. |
| 2009/0272379 A1 | 11/2009 | Thorens et al. |
| 2009/0283103 A1 | 11/2009 | Nielsen et al. |
| 2009/0293892 A1 | 12/2009 | Williams et al. |
| 2009/0320864 A1 | 12/2009 | Rowley |
| 2010/0024834 A1 | 2/2010 | Oglesby et al. |
| 2010/0031968 A1 | 2/2010 | Sheikh et al. |
| 2010/0043809 A1 | 2/2010 | Magnon |
| 2010/0059073 A1 | 3/2010 | Hoffmann et al. |
| 2010/0083959 A1 | 4/2010 | Siller |
| 2010/0126505 A1 | 5/2010 | Rinker |
| 2010/0163063 A1 | 7/2010 | Fernando et al. |
| 2010/0200006 A1 | 8/2010 | Robinson et al. |
| 2010/0229881 A1 | 9/2010 | Hearn |
| 2010/0242974 A1 | 9/2010 | Pan |
| 2010/0242975 A1 | 9/2010 | Hearn |
| 2010/0242976 A1 | 9/2010 | Katayama et al. |
| 2010/0300467 A1 | 12/2010 | Kuistila et al. |

(56) References Cited

U.S. PATENT DOCUMENTS

| | | |
|---|---|---|
| 2010/0307518 A1 | 12/2010 | Wang |
| 2010/0313901 A1 | 12/2010 | Fernando et al. |
| 2011/0005535 A1 | 1/2011 | Xiu |
| 2011/0011286 A1 | 1/2011 | Strasser |
| 2011/0011396 A1 | 1/2011 | Fang |
| 2011/0036363 A1 | 2/2011 | Urtsev et al. |
| 2011/0036365 A1 | 2/2011 | Chong et al. |
| 2011/0094523 A1 | 4/2011 | Thorens et al. |
| 2011/0120482 A1 | 5/2011 | Brenneise |
| 2011/0126848 A1 | 6/2011 | Zuber et al. |
| 2011/0147486 A1 | 6/2011 | Greim et al. |
| 2011/0155153 A1 | 6/2011 | Thorens et al. |
| 2011/0155718 A1 | 6/2011 | Greim et al. |
| 2011/0162663 A1 | 7/2011 | Bryman |
| 2011/0168194 A1 | 7/2011 | Hon |
| 2011/0226236 A1 | 9/2011 | Buchberger |
| 2011/0232654 A1 | 9/2011 | Mass |
| 2011/0265806 A1 | 11/2011 | Alarcon et al. |
| 2011/0266236 A1 | 11/2011 | Clark et al. |
| 2011/0277760 A1 | 11/2011 | Terry et al. |
| 2011/0277761 A1 | 11/2011 | Terry et al. |
| 2011/0277764 A1 | 11/2011 | Terry et al. |
| 2011/0277780 A1 | 11/2011 | Terry et al. |
| 2011/0290244 A1 | 12/2011 | Schennum |
| 2011/0290248 A1 | 12/2011 | Schennum |
| 2011/0290266 A1 | 12/2011 | Koller |
| 2011/0290267 A1 | 12/2011 | Yamada et al. |
| 2011/0290269 A1 | 12/2011 | Shimizu |
| 2011/0297166 A1 | 12/2011 | Takeuchi et al. |
| 2011/0304282 A1 | 12/2011 | Li et al. |
| 2011/0309157 A1 | 12/2011 | Yang et al. |
| 2012/0006342 A1 | 1/2012 | Rose et al. |
| 2012/0006343 A1 | 1/2012 | Renaud et al. |
| 2012/0042885 A1 | 2/2012 | Stone et al. |
| 2012/0060853 A1 | 3/2012 | Robinson et al. |
| 2012/0111346 A1 | 5/2012 | Rinker et al. |
| 2012/0111347 A1 | 5/2012 | Hon |
| 2012/0118301 A1 | 5/2012 | Montaser |
| 2012/0118307 A1 | 5/2012 | Tu |
| 2012/0132643 A1 | 5/2012 | Choi et al. |
| 2012/0138052 A1 | 6/2012 | Hearn et al. |
| 2012/0138054 A1 | 6/2012 | Hearn et al. |
| 2012/0145169 A1 | 6/2012 | Wu |
| 2012/0152244 A1 | 6/2012 | Yomtov |
| 2012/0152246 A1 | 6/2012 | Yomtov |
| 2012/0160251 A1 | 6/2012 | Hammel et al. |
| 2012/0167906 A1 | 7/2012 | Gysland |
| 2012/0186594 A1 | 7/2012 | Liu |
| 2012/0199146 A1 | 8/2012 | Marangos |
| 2012/0199663 A1 | 8/2012 | Qiu |
| 2012/0204889 A1 | 8/2012 | Xiu |
| 2012/0211015 A1 | 8/2012 | Li et al. |
| 2012/0227752 A1 | 9/2012 | Alelov |
| 2012/0231464 A1 | 9/2012 | Yu et al. |
| 2012/0234315 A1 | 9/2012 | Li et al. |
| 2012/0247494 A1 | 10/2012 | Oglesby et al. |
| 2012/0255567 A1 | 10/2012 | Rose et al. |
| 2012/0260926 A1 | 10/2012 | Tu et al. |
| 2012/0260927 A1 | 10/2012 | Liu |
| 2012/0273589 A1 | 11/2012 | Hon |
| 2012/0279512 A1 | 11/2012 | Hon |
| 2012/0285475 A1 | 11/2012 | Liu |
| 2012/0298123 A1 | 11/2012 | Woodcock et al. |
| 2012/0312313 A1 | 12/2012 | Frija |
| 2012/0318882 A1 | 12/2012 | Abehasera |
| 2012/0325227 A1 | 12/2012 | Robinson et al. |
| 2012/0325228 A1 | 12/2012 | Williams |
| 2013/0008457 A1 | 1/2013 | Zheng et al. |
| 2013/0019862 A1 | 1/2013 | Yamada et al. |
| 2013/0019887 A1 | 1/2013 | Liu |
| 2013/0025609 A1 | 1/2013 | Liu |
| 2013/0037031 A1 | 2/2013 | Gredat |
| 2013/0037041 A1 | 2/2013 | Worm et al. |
| 2013/0037042 A1 | 2/2013 | Hearn et al. |
| 2013/0042865 A1 | 2/2013 | Monsees et al. |
| 2013/0056012 A1 | 3/2013 | Hearn et al. |
| 2013/0056013 A1 | 3/2013 | Terry et al. |
| 2013/0061861 A1 | 3/2013 | Hearn |
| 2013/0068239 A1 | 3/2013 | Youn |
| 2013/0074854 A1 | 3/2013 | Lipowicz |
| 2013/0074857 A1 | 3/2013 | Buchberger |
| 2013/0081623 A1 | 4/2013 | Buchberger |
| 2013/0081625 A1 | 4/2013 | Rustad et al. |
| 2013/0081642 A1 | 4/2013 | Safari |
| 2013/0087160 A1 | 4/2013 | Gherghe |
| 2013/0104916 A1 | 5/2013 | Bellinger et al. |
| 2013/0125906 A1 | 5/2013 | Hon |
| 2013/0139833 A1 | 6/2013 | Hon |
| 2013/0140200 A1 | 6/2013 | Scatterday |
| 2013/0146489 A1 | 6/2013 | Scatterday |
| 2013/0152954 A1 | 6/2013 | Youn |
| 2013/0160764 A1 | 6/2013 | Liu |
| 2013/0160765 A1 | 6/2013 | Liu |
| 2013/0167853 A1 | 7/2013 | Liu |
| 2013/0167854 A1 | 7/2013 | Shin |
| 2013/0169230 A1 | 7/2013 | Li et al. |
| 2013/0180533 A1 | 7/2013 | Kim et al. |
| 2013/0192615 A1 | 8/2013 | Tucker et al. |
| 2013/0192616 A1 | 8/2013 | Tucker et al. |
| 2013/0192617 A1 | 8/2013 | Thompson |
| 2013/0192618 A1 | 8/2013 | Li et al. |
| 2013/0192619 A1 | 8/2013 | Tucker et al. |
| 2013/0192620 A1 | 8/2013 | Tucker et al. |
| 2013/0192621 A1 | 8/2013 | Li et al. |
| 2013/0192622 A1 | 8/2013 | Tucker et al. |
| 2013/0192623 A1 | 8/2013 | Tucker et al. |
| 2013/0199528 A1 | 8/2013 | Goodman et al. |
| 2013/0206154 A1 | 8/2013 | Fernando et al. |
| 2013/0213417 A1 | 8/2013 | Chong et al. |
| 2013/0213418 A1 | 8/2013 | Tucker et al. |
| 2013/0213419 A1 | 8/2013 | Tucker et al. |
| 2013/0213420 A1 | 8/2013 | Hon |
| 2013/0220315 A1 | 8/2013 | Conley et al. |
| 2013/0220316 A1 | 8/2013 | Oglesby et al. |
| 2013/0228190 A1 | 9/2013 | Weiss et al. |
| 2013/0243410 A1 | 9/2013 | Nichols et al. |
| 2013/0247924 A1 | 9/2013 | Scatterday et al. |
| 2013/0248385 A1 | 9/2013 | Scatterday et al. |
| 2013/0255675 A1 | 10/2013 | Liu |
| 2013/0255702 A1 | 10/2013 | Griffith, Jr. et al. |
| 2013/0263869 A1 | 10/2013 | Zhu |
| 2013/0276798 A1 | 10/2013 | Hon |
| 2013/0276799 A1 | 10/2013 | Davidson et al. |
| 2013/0276802 A1 | 10/2013 | Scatterday |
| 2013/0276804 A1 | 10/2013 | Hon |
| 2013/0284190 A1 | 10/2013 | Scatterday et al. |
| 2013/0284191 A1 | 10/2013 | Scatterday et al. |
| 2013/0284192 A1 | 10/2013 | Peleg et al. |
| 2013/0284194 A1 | 10/2013 | Newton |
| 2013/0298905 A1 | 11/2013 | Levin et al. |
| 2013/0298922 A1 | 11/2013 | Xiang et al. |
| 2013/0300350 A1 | 11/2013 | Xiang |
| 2013/0306064 A1 | 11/2013 | Thorens et al. |
| 2013/0306065 A1 | 11/2013 | Thorens et al. |
| 2013/0306074 A1 | 11/2013 | Bowditch et al. |
| 2013/0306084 A1 | 11/2013 | Flick |
| 2013/0306692 A1 | 11/2013 | Mangum et al. |
| 2013/0312739 A1 | 11/2013 | Rome et al. |
| 2013/0312742 A1 | 11/2013 | Monsees et al. |
| 2013/0313139 A1 | 11/2013 | Scatterday et al. |
| 2013/0319404 A1 | 12/2013 | Feriani et al. |
| 2013/0319407 A1 | 12/2013 | Liu |
| 2013/0319431 A1 | 12/2013 | Cyphert et al. |
| 2013/0319435 A1 | 12/2013 | Flick |
| 2013/0319436 A1 | 12/2013 | Liu |
| 2013/0319438 A1 | 12/2013 | Liu |
| 2013/0319439 A1 | 12/2013 | Gorelick et al. |
| 2013/0319440 A1 | 12/2013 | Capuano |
| 2013/0319989 A1 | 12/2013 | Liu |
| 2013/0319999 A1 | 12/2013 | Plojoux et al. |
| 2013/0333700 A1 | 12/2013 | Buchberger |
| 2013/0333711 A1 | 12/2013 | Liu |
| 2013/0333712 A1 | 12/2013 | Scatterday |
| 2013/0336358 A1 | 12/2013 | Liu |

(56) References Cited

U.S. PATENT DOCUMENTS

| | | |
|---|---|---|
| 2013/0340750 A1 | 12/2013 | Thorens et al. |
| 2013/0340775 A1* | 12/2013 | Juster .......... H04L 12/1827 |
| | | 131/273 |
| 2013/0340778 A1 | 12/2013 | Liu |
| 2013/0340779 A1 | 12/2013 | Liu |
| 2013/0341218 A1 | 12/2013 | Liu |
| 2013/0342157 A1 | 12/2013 | Liu |
| 2014/0000636 A1 | 1/2014 | O'Connell |
| 2014/0000637 A1 | 1/2014 | O'Connell |
| 2014/0000638 A1 | 1/2014 | Sebastian et al. |
| 2014/0004844 A1 | 1/2014 | Ge |
| 2014/0007891 A1 | 1/2014 | Liu |
| 2014/0007892 A1 | 1/2014 | Liu |
| 2014/0014124 A1 | 1/2014 | Glasberg et al. |
| 2014/0014125 A1 | 1/2014 | Fernando et al. |
| 2014/0014126 A1 | 1/2014 | Peleg et al. |
| 2014/0020693 A1 | 1/2014 | Cochand et al. |
| 2014/0020696 A1 | 1/2014 | Liu |
| 2014/0020697 A1 | 1/2014 | Liu |
| 2014/0034070 A1 | 2/2014 | Schennum |
| 2014/0034071 A1 | 2/2014 | Levitz et al. |
| 2014/0041655 A1 | 2/2014 | Barron et al. |
| 2014/0044857 A1 | 2/2014 | Hua et al. |
| 2014/0048086 A1 | 2/2014 | Zhanghua |
| 2014/0053856 A1 | 2/2014 | Liu |
| 2014/0053857 A1 | 2/2014 | Liu |
| 2014/0053858 A1 | 2/2014 | Liu |
| 2014/0060524 A1 | 3/2014 | Liu |
| 2014/0060527 A1 | 3/2014 | Liu |
| 2014/0060528 A1 | 3/2014 | Liu |
| 2014/0060529 A1 | 3/2014 | Zhang |
| 2014/0060554 A1 | 3/2014 | Collett et al. |
| 2014/0060555 A1 | 3/2014 | Chang et al. |
| 2014/0060556 A1 | 3/2014 | Liu |
| 2014/0062417 A1 | 3/2014 | Li et al. |
| 2014/0069424 A1 | 3/2014 | Poston et al. |
| 2014/0069425 A1 | 3/2014 | Zhang |
| 2014/0069444 A1 | 3/2014 | Cyphert et al. |
| 2014/0076310 A1 | 3/2014 | Newton |
| 2014/0083442 A1 | 3/2014 | Scatterday |
| 2014/0083443 A1 | 3/2014 | Liu |
| 2014/0096781 A1 | 4/2014 | Sears et al. |
| 2014/0096782 A1 | 4/2014 | Ampolini et al. |
| 2014/0102463 A1 | 4/2014 | Jones |
| 2014/0103020 A1 | 4/2014 | Al-Qaffas |
| 2014/0107815 A1 | 4/2014 | LaMothe |
| 2014/0109898 A1 | 4/2014 | Li et al. |
| 2014/0109905 A1 | 4/2014 | Yamada et al. |
| 2014/0109921 A1 | 4/2014 | Chen |
| 2014/0116455 A1 | 5/2014 | Youn |
| 2014/0123989 A1 | 5/2014 | LaMothe |
| 2014/0123990 A1 | 5/2014 | Timmermans |
| 2014/0130796 A1 | 5/2014 | Liu |
| 2014/0130797 A1 | 5/2014 | Liu |
| 2014/0130816 A1 | 5/2014 | Liu |
| 2014/0130817 A1 | 5/2014 | Li et al. |
| 2014/0144453 A1 | 5/2014 | Capuano et al. |
| 2014/0150783 A1 | 6/2014 | Liu |
| 2014/0150784 A1 | 6/2014 | Liu |
| 2014/0150785 A1 | 6/2014 | Malik et al. |
| 2014/0150810 A1 | 6/2014 | Hon |
| 2014/0157583 A1 | 6/2014 | Ward et al. |
| 2014/0166027 A1 | 6/2014 | Fuisz et al. |
| 2014/0166028 A1 | 6/2014 | Fuisz et al. |
| 2014/0166029 A1 | 6/2014 | Weigensberg et al. |
| 2014/0166030 A1 | 6/2014 | Li et al. |
| 2014/0174459 A1 | 6/2014 | Burstyn |
| 2014/0174968 A1 | 6/2014 | Scatterday |
| 2014/0182608 A1 | 7/2014 | Egoyants et al. |
| 2014/0182610 A1 | 7/2014 | Liu |
| 2014/0182611 A1 | 7/2014 | Liu |
| 2014/0182612 A1 | 7/2014 | Chen |
| 2014/0186015 A1 | 7/2014 | Breiwa, III et al. |
| 2014/0196736 A1 | 7/2014 | Fernando et al. |
| 2014/0209105 A1 | 7/2014 | Sears et al. |
| 2014/0253144 A1 | 9/2014 | Novak, III et al. |
| 2014/0261408 A1 | 9/2014 | DePiano et al. |
| 2014/0261486 A1 | 9/2014 | Potter et al. |
| 2014/0261487 A1 | 9/2014 | Chapman et al. |
| 2014/0261495 A1 | 9/2014 | Novak, III et al. |
| 2014/0270727 A1 | 9/2014 | Ampolini et al. |
| 2014/0270729 A1 | 9/2014 | DePiano et al. |
| 2014/0270730 A1 | 9/2014 | DePiano et al. |
| 2014/0299125 A1 | 10/2014 | Buchberger |
| 2014/0305453 A1 | 10/2014 | Hon |
| 2014/0318560 A1 | 10/2014 | Hon |
| 2014/0345631 A1 | 11/2014 | Bowen et al. |

FOREIGN PATENT DOCUMENTS

| | | |
|---|---|---|
| CN | 1233436 A | 11/1999 |
| CN | 1541577 A | 11/2004 |
| CN | 2719043 Y | 8/2005 |
| CN | 201018927 Y | 2/2008 |
| CN | 201067079 Y | 6/2008 |
| CN | 201085044 Y | 7/2008 |
| DE | 2704218 A1 | 8/1978 |
| DE | 102006004484 A1 | 8/2007 |
| EP | 0295122 A2 | 12/1988 |
| EP | 0358114 A2 | 3/1990 |
| EP | 0430559 A2 | 6/1991 |
| EP | 0430566 A2 | 6/1991 |
| EP | 0501419 A1 | 9/1992 |
| EP | 0503767 A1 | 9/1992 |
| EP | 0845220 A1 | 6/1998 |
| EP | 1584910 A1 | 10/2005 |
| EP | 1618803 A1 | 1/2006 |
| GB | 191125575 A | 3/1912 |
| GB | 588117 A | 5/1947 |
| GB | 755475 A | 8/1956 |
| GB | 1431045 A | 4/1976 |
| GB | 2070409 A | 9/1981 |
| JP | H9-326299 A | 12/1997 |
| JP | 2000041654 A | 2/2000 |
| JP | P2001-291598 | 10/2001 |
| KR | 2002-0067473 A | 8/2002 |
| WO | WO-1986002528 A1 | 5/1986 |
| WO | WO-1997048293 A1 | 12/1997 |
| WO | WO-1998016125 A1 | 4/1998 |
| WO | WO-2000028843 A1 | 5/2000 |
| WO | WO-2002037990 A2 | 5/2002 |
| WO | WO-2004080216 A1 | 9/2004 |
| WO | WO-2004095955 A1 | 11/2004 |
| WO | WO-2005099494 A1 | 10/2005 |
| WO | WO-2007078273 A1 | 7/2007 |
| WO | WO-2007131449 A1 | 11/2007 |
| WO | WO-2007131450 A1 | 11/2007 |
| WO | WO-2008139411 A2 | 11/2008 |

OTHER PUBLICATIONS

Avallone et al., "Mark's Standard Handbook for Mechanical Engineers," published 1978, p. 15-6 (3 pg.).

Cengel et al., "Thermodynamics: An Engineering Approach," (5th ed. 2006) (excerpts) ("Thermodynamics"), 9 pgs.

Dally, James W., "Packaging of Electronic Systems: A Mechanical Engineering Approach" (excerpts) (1990), 18 pgs.

Fuchs, N.A. "The Mechanics of Aerosols" (1989), 22 pgs.

Messler, Jr., Robert W., "Joining of Materials and Structures," Elsevier Butterworth-Heinemann 2004—Excerpt, 4 pgs.

Mosdesign Semiconductor Corp. Datasheet for M1600 LED Drivers ("Mosdesign M1600 Datasheet"), 1 pg.

MPL 502 Series Specifications, Micro Pneumatic Logic, Inc., (Mar. 11, 2006), http://www.pressureswitch.com/PDFs/0502STANDARDA.pdf [https ://web.archive .org/web/20060311132848/http://vvww.pressureswitch.com/PDFs/0502STANDARDA.pdf], 17 pqs.

MPL Pressure Switch Solutions, Micro Pneumatic Logic, Inc., (Product Brochure) (Mar. 11, 2006), http://www.pressureswitch.com/PDFs/2000_MPLBrochure.pdf [https://web.archive.org/web/20060311132419/htto://www.pressuresvvitd1.com/PDFs/2000 MPLBrochure.pdf]. 2 pgs.

(56) References Cited

OTHER PUBLICATIONS

Rohsenow, Warren M., "Heat, Mass, And Momentum Transfer", copyright 1961 Prentice-Hall, 3 pgs.
Speck, James A., "Mechanical Fastening, Joining, and Assembly," Marcel Dekker, Inc. 1997, 4 pgs.
Thermal Ink-Jet Print Cartridge Designer's Guide (2nd Edition Hewlett Packard) ("Jet Print Cartridge Designers Guide"), 12 pgs.
USPTO, Final Written Decision, U.S. Pat. No. 8,314,591, Nov. 15, 2021, pp. 1-42, Paper 21.

\* cited by examiner

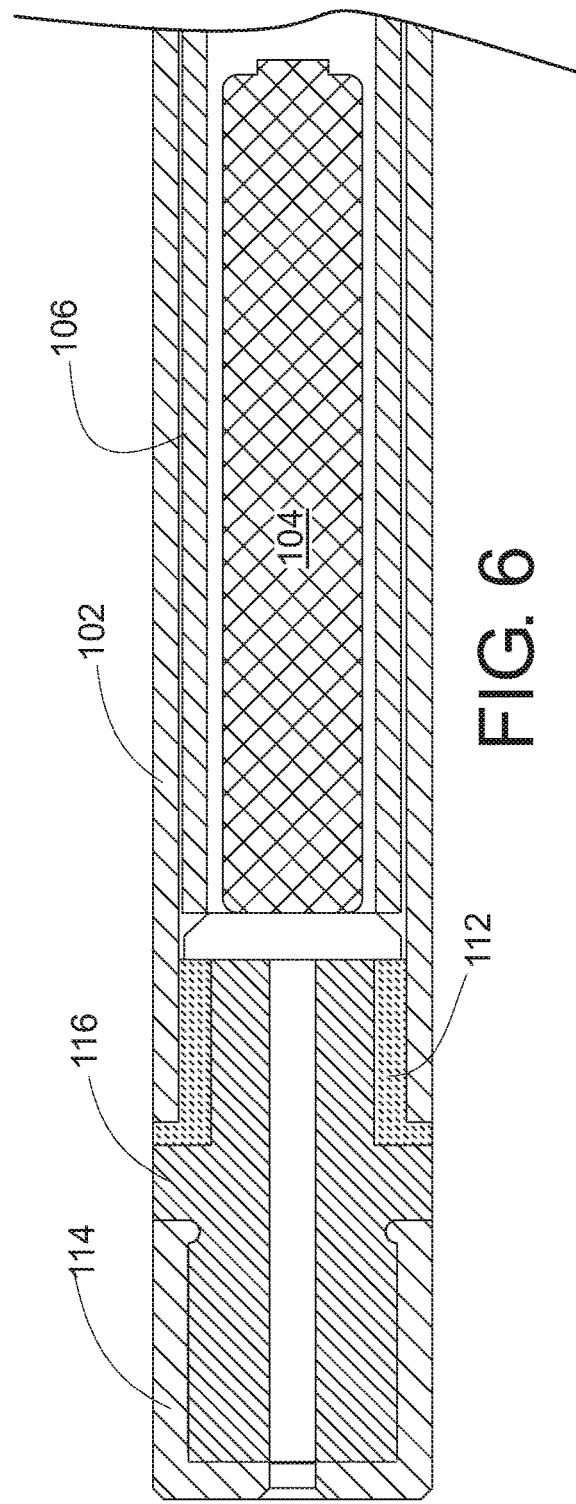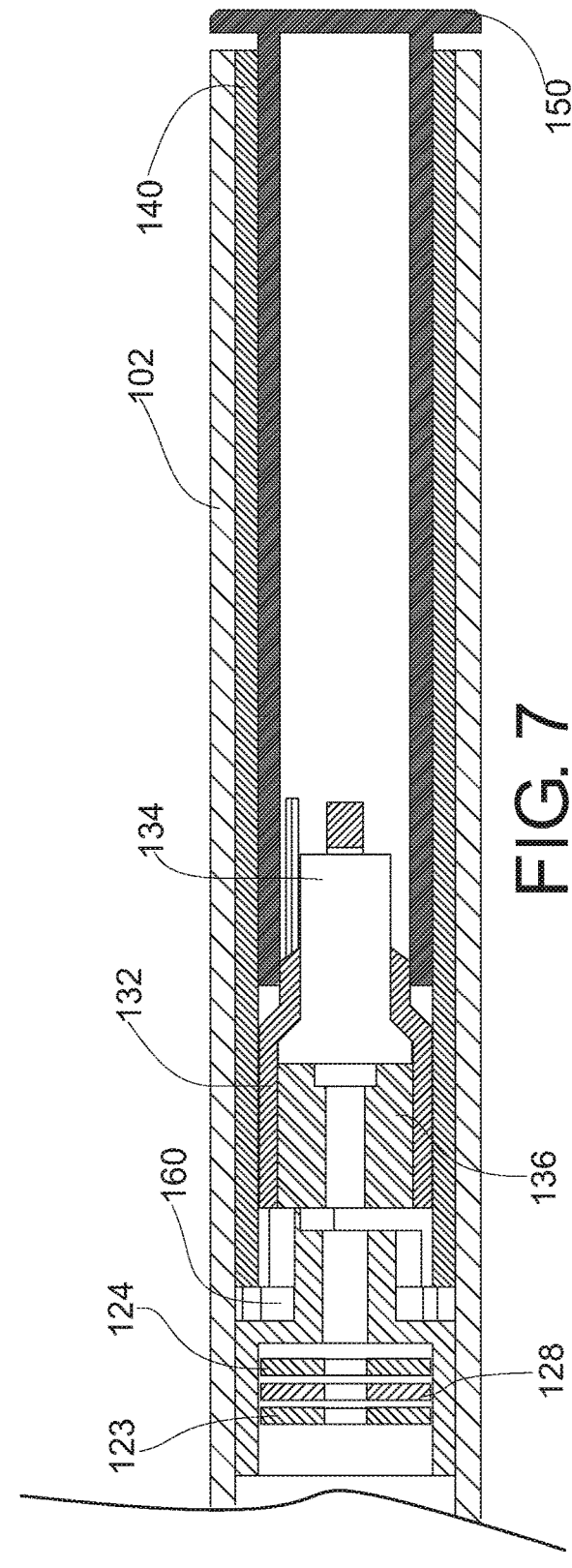

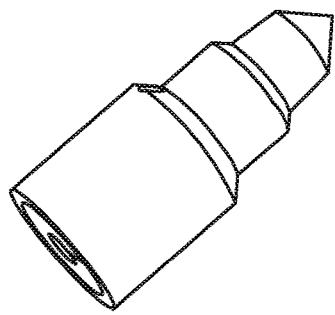
FIG. 54
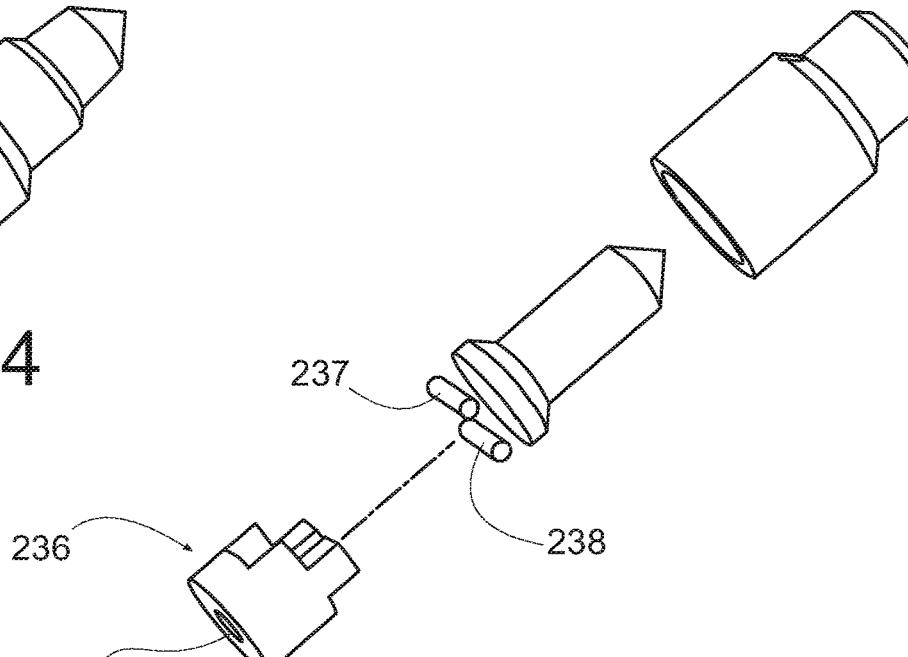
FIG. 55
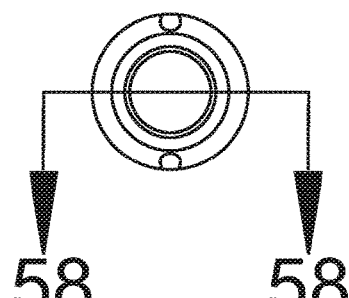
FIG. 57
FIG. 56
FIG. 58

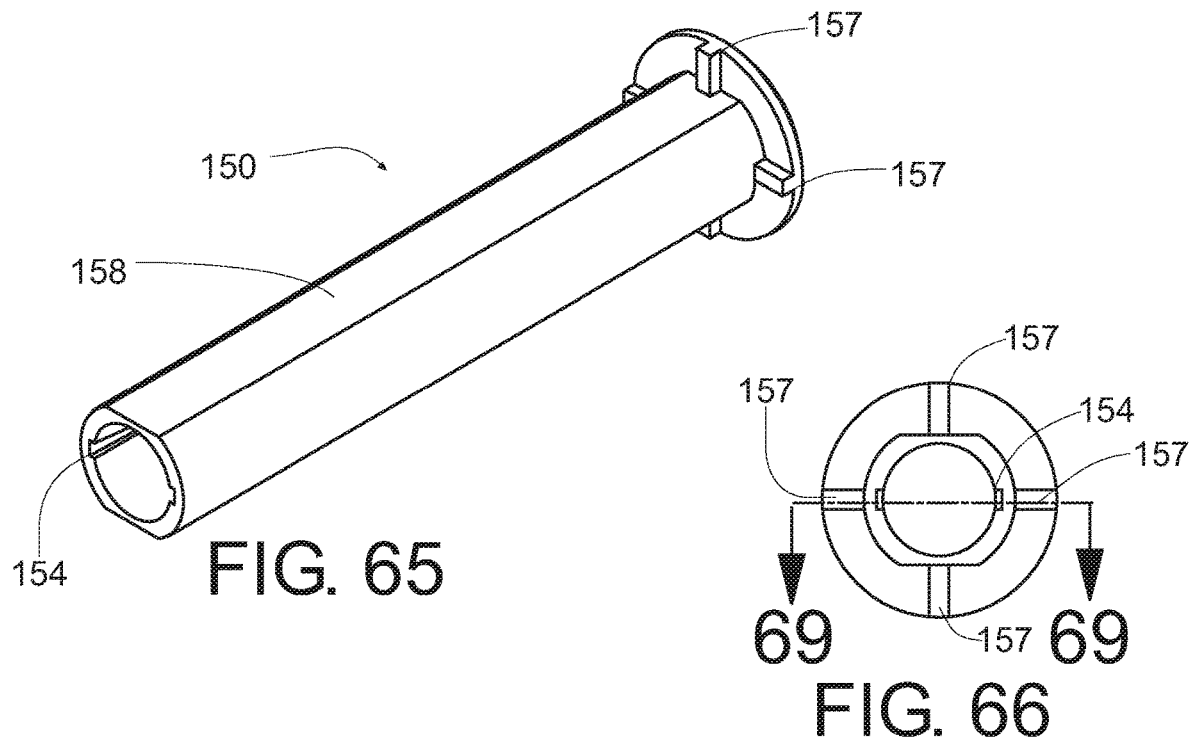
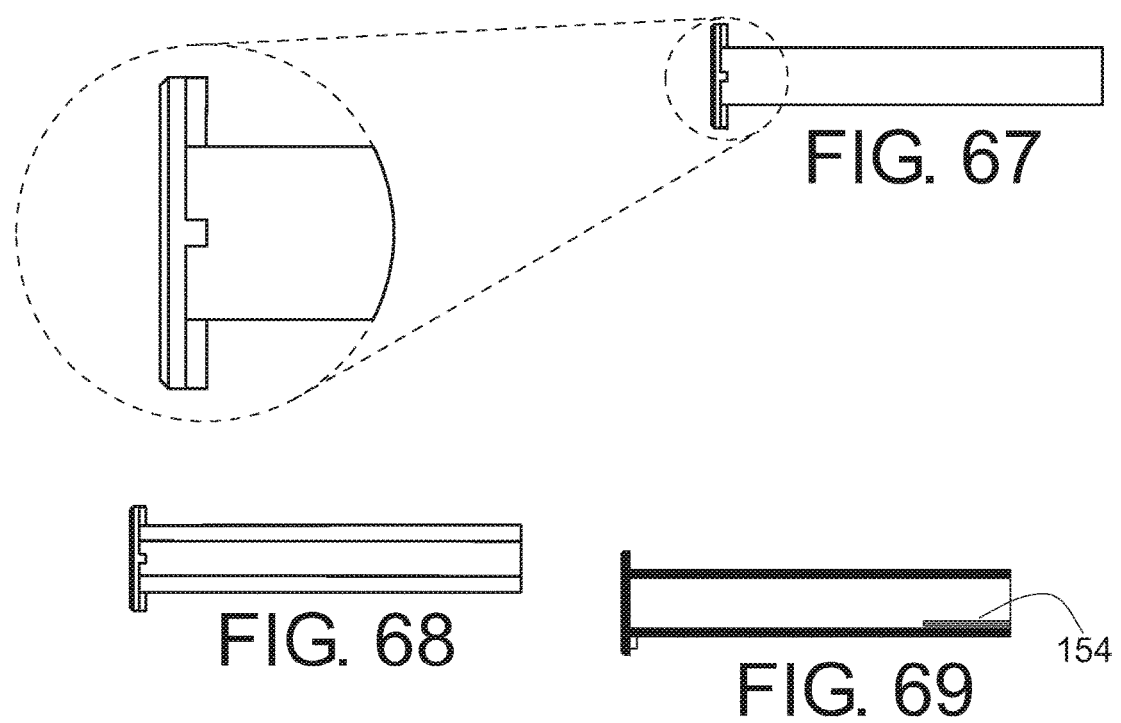

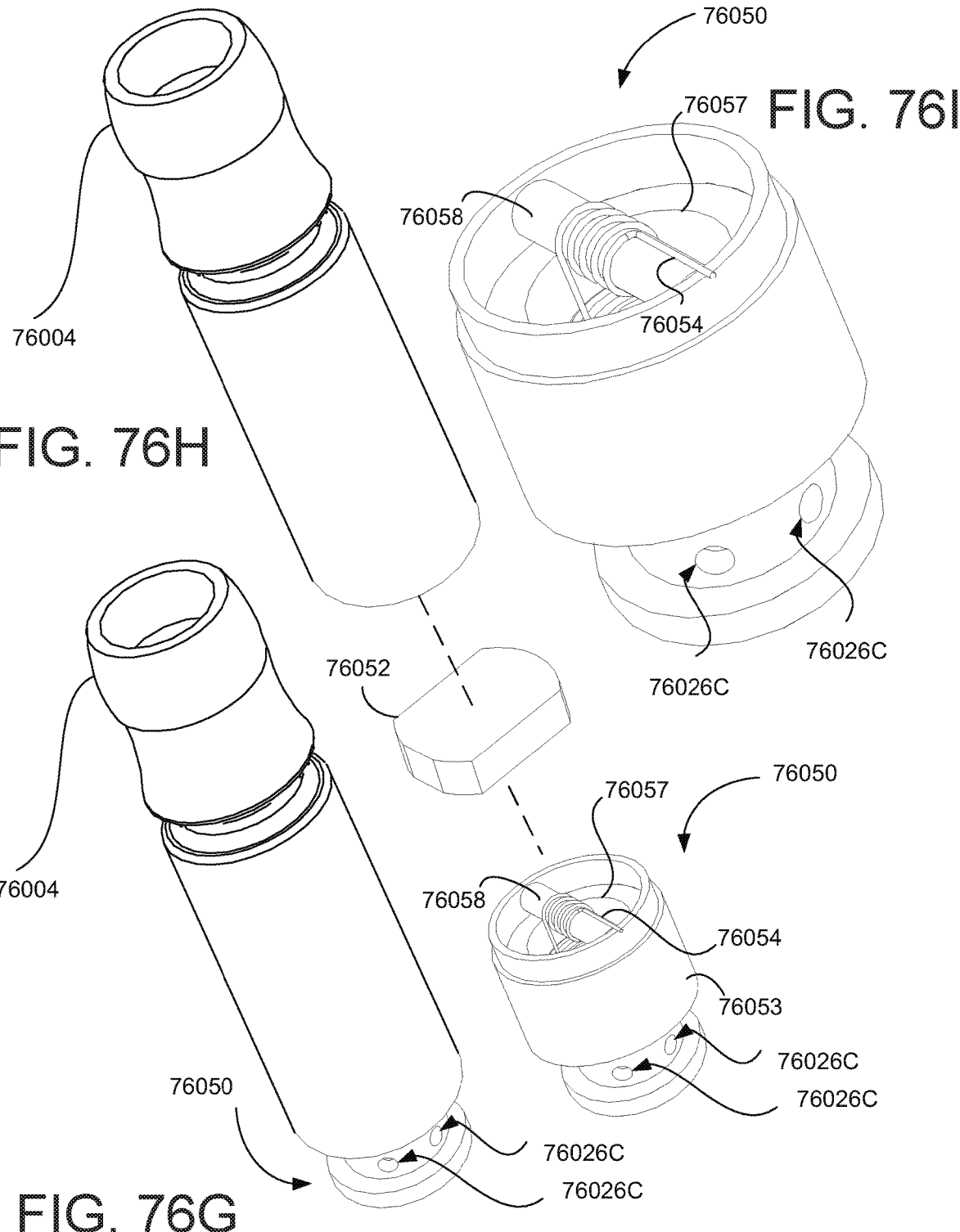

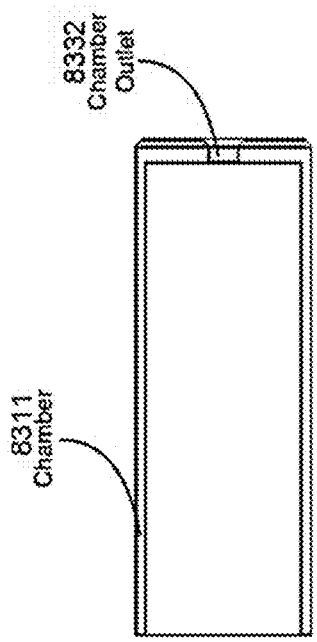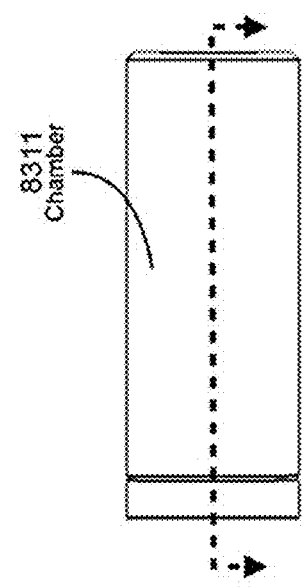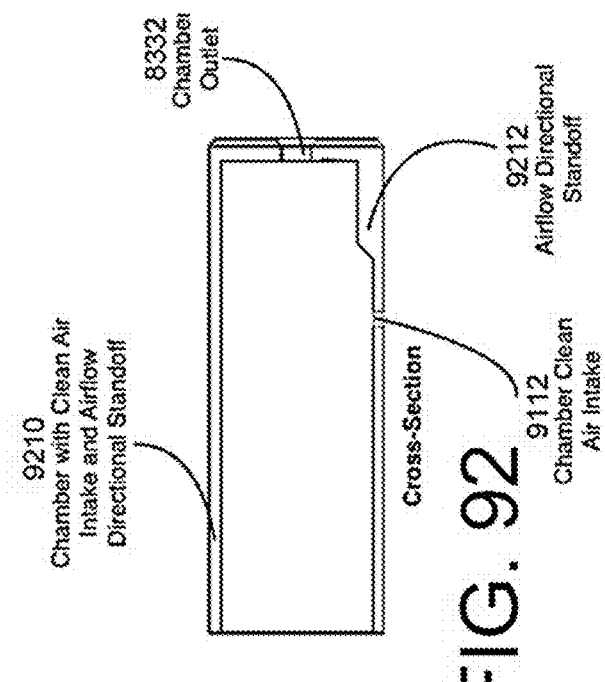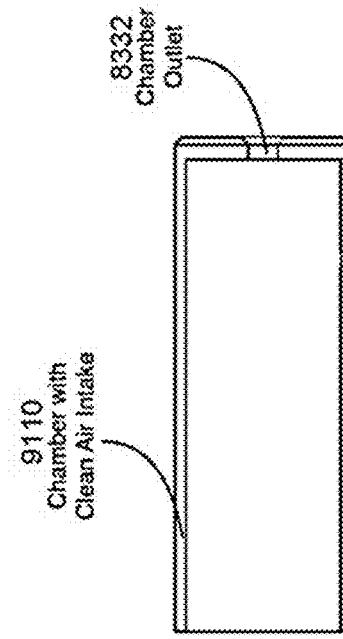

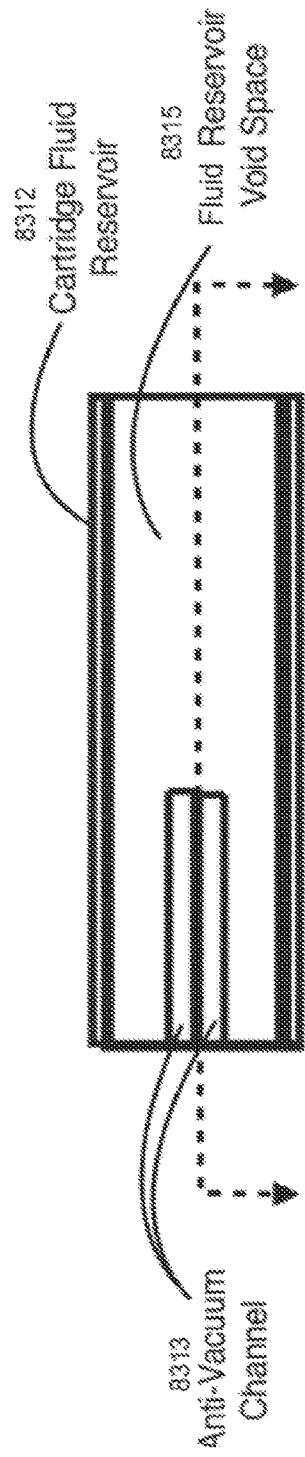
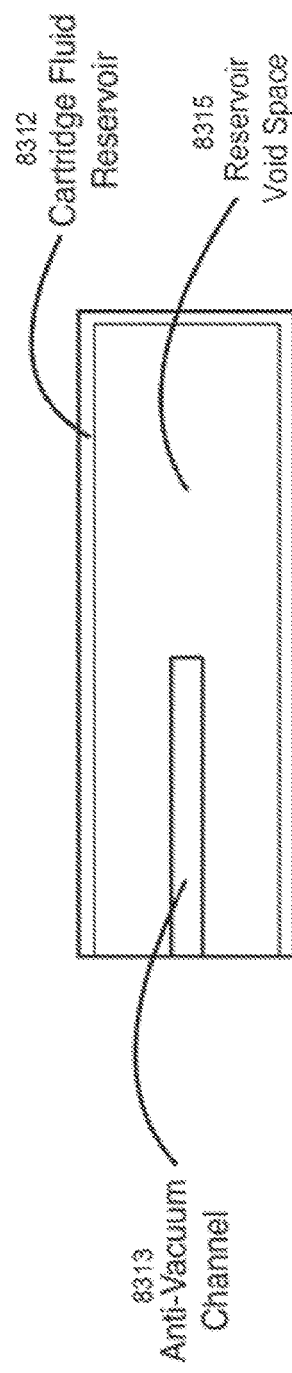
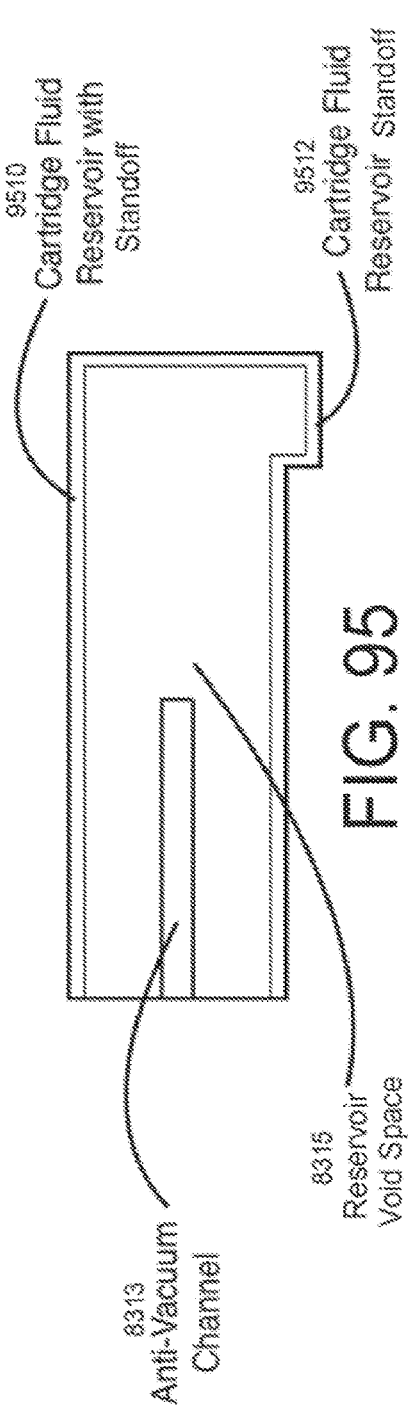
FIG. 93
FIG. 94
FIG. 95

Vaporization Chamber
Shown in Cross Section

Reference Key:  ⬚ Vaporization Chamber

| Inner Surface of Vaporization Chamber Boundary

IR reflective Tube to house the proximal wick.

Proximal wick

FIG. 130
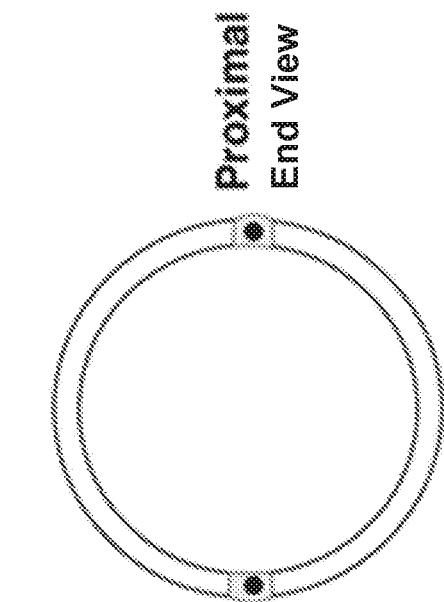
Proximal End View
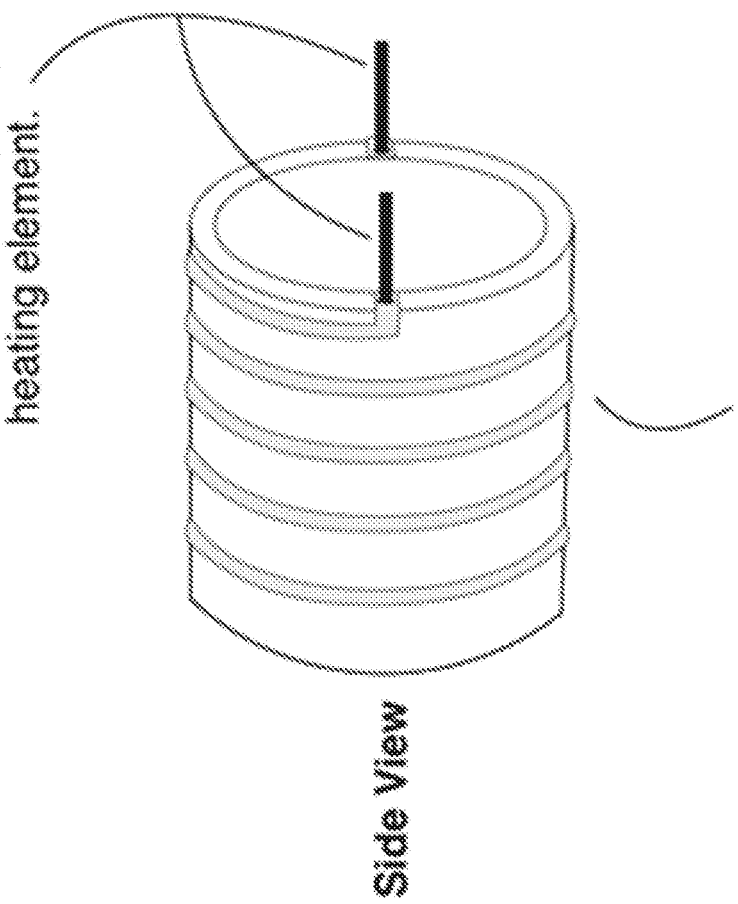
Embodiment shown with embedded metal contacts to facilitate energizing heating element.
Proximal wick housing shown with directly written heating element on exterior surface. Component comprised of an IR emissive material.
Side View IR Reflective Housing Proximal wick housing shown with directly written heating element on exterior surface.

| Glycerine percent weight | Temperature (°C) | | | | | | | | | | |
|---|---|---|---|---|---|---|---|---|---|---|---|
| | 0 | 10 | 20 | 30 | 40 | 50 | 60 | 70 | 80 | 90 | 100 |
| 0 | 1.792 | 1.308 | 1.005 | 0.8007 | 0.6560 | 0.5494 | 0.4688 | 0.4061 | 0.3565 | 0.3165 | 0.2838 |
| 10 | 2.44 | 1.74 | 1.31 | 1.03 | 0.826 | 0.680 | 0.575 | 0.500 | – | – | – |
| 20 | 3.44 | 2.41 | 1.76 | 1.35 | 1.07 | 0.879 | 0.731 | 0.635 | – | – | – |
| 30 | 5.14 | 3.49 | 2.50 | 1.87 | 1.46 | 1.16 | 0.956 | 0.816 | 0.690 | – | – |
| 40 | 8.25 | 5.37 | 3.72 | 2.72 | 2.07 | 1.62 | 1.30 | 1.09 | 0.918 | 0.763 | 0.668 |
| 50 | 14.6 | 9.01 | 6.00 | 4.21 | 3.10 | 2.37 | 1.86 | 1.53 | 1.25 | 1.05 | 0.910 |
| 60 | 29.9 | 17.4 | 10.8 | 7.19 | 5.08 | 3.76 | 2.85 | 2.29 | 1.84 | 1.52 | 1.28 |
| 65 | 45.7 | 25.3 | 15.2 | 9.85 | 6.80 | 4.89 | 3.66 | 2.91 | 2.28 | 1.86 | 1.55 |
| 67 | 55.5 | 29.9 | 17.7 | 11.3 | 7.73 | 5.50 | 4.09 | 3.23 | 2.50 | 2.03 | 1.68 |
| 70 | 76 | 38.8 | 22.5 | 14.1 | 9.40 | 6.61 | 4.86 | 3.78 | 2.90 | 2.34 | 1.93 |
| 75 | 132 | 65.2 | 35.5 | 21.2 | 13.6 | 9.25 | 6.61 | 5.01 | 3.80 | 3.00 | 2.43 |
| 80 | 255 | 116 | 60.1 | 33.9 | 20.8 | 13.6 | 9.42 | 6.94 | 5.13 | 4.03 | 3.18 |
| 85 | 540 | 223 | 109 | 58 | 33.5 | 21.2 | 14.2 | 10.0 | 7.28 | 5.52 | 4.24 |
| 90 | 1310 | 498 | 219 | 109 | 60.0 | 35.5 | 22.5 | 15.5 | 11.0 | 7.93 | 6.00 |
| 91 | 1590 | 592 | 259 | 127 | 68.1 | 39.8 | 25.1 | 17.1 | 11.9 | 8.62 | 6.40 |
| 92 | 1950 | 729 | 310 | 147 | 78.3 | 44.8 | 28.0 | 19.0 | 13.1 | 9.46 | 6.82 |
| 93 | 2400 | 860 | 367 | 172 | 89 | 51.5 | 31.6 | 21.2 | 14.4 | 10.3 | 7.54 |
| 94 | 2930 | 1040 | 437 | 202 | 105 | 58.4 | 35.4 | 23.6 | 15.8 | 11.2 | 8.19 |
| 95 | 3690 | 1270 | 523 | 237 | 121 | 67.0 | 39.9 | 26.4 | 17.5 | 12.4 | 9.08 |
| 96 | 4600 | 1580 | 624 | 281 | 142 | 77.8 | 45.4 | 29.7 | 19.6 | 13.6 | 10.1 |
| 97 | 5770 | 1950 | 765 | 340 | 166 | 88.9 | 51.9 | 33.6 | 21.9 | 15.1 | 10.9 |
| 98 | 7370 | 2460 | 939 | 409 | 196 | 104 | 59.8 | 38.5 | 24.8 | 17.0 | 12.2 |
| 99 | 9420 | 3090 | 1150 | 500 | 235 | 122 | 69.1 | 43.6 | 27.8 | 19.0 | 13.3 |
| 100 | 12070 | 3900 | 1410 | 612 | 284 | 142 | 81.3 | 50.6 | 31.9 | 21.3 | 14.8 |

FIG. 158

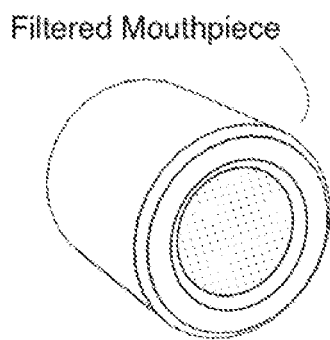 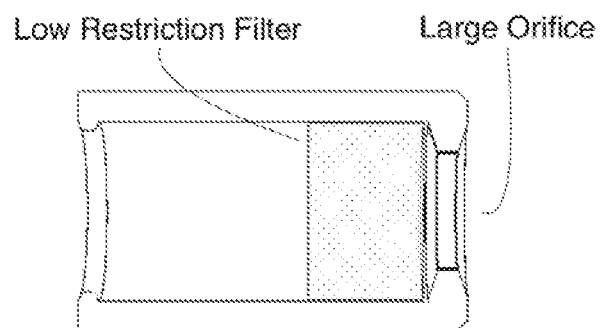 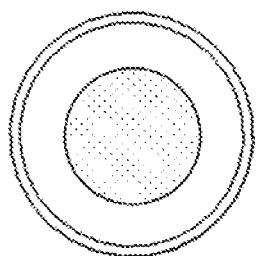 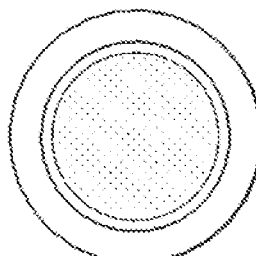
FIG. 167

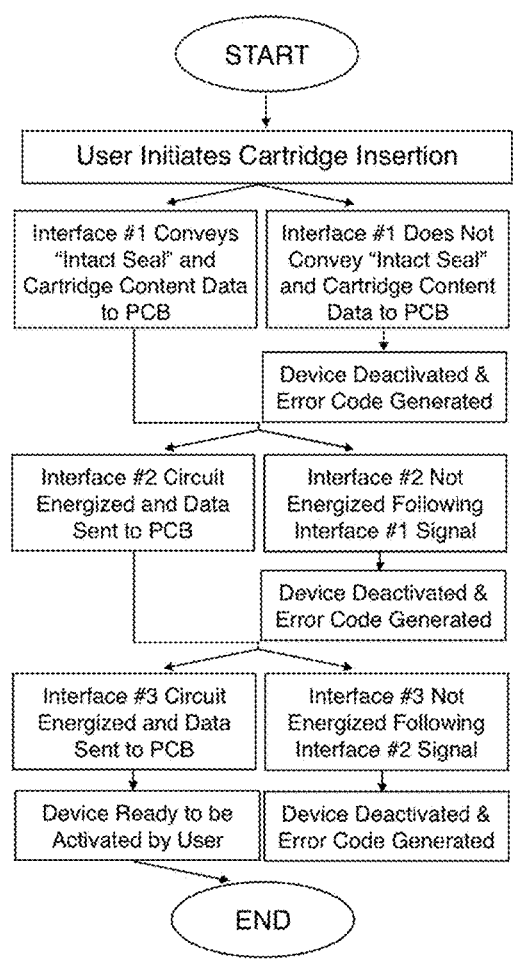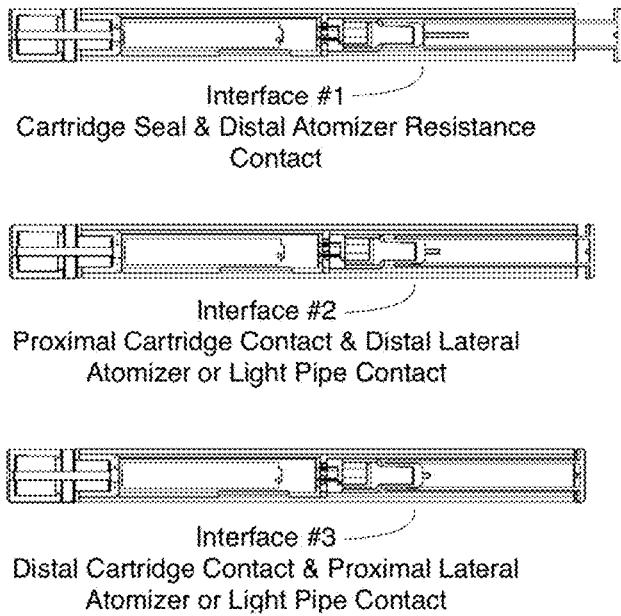
FIG. 172

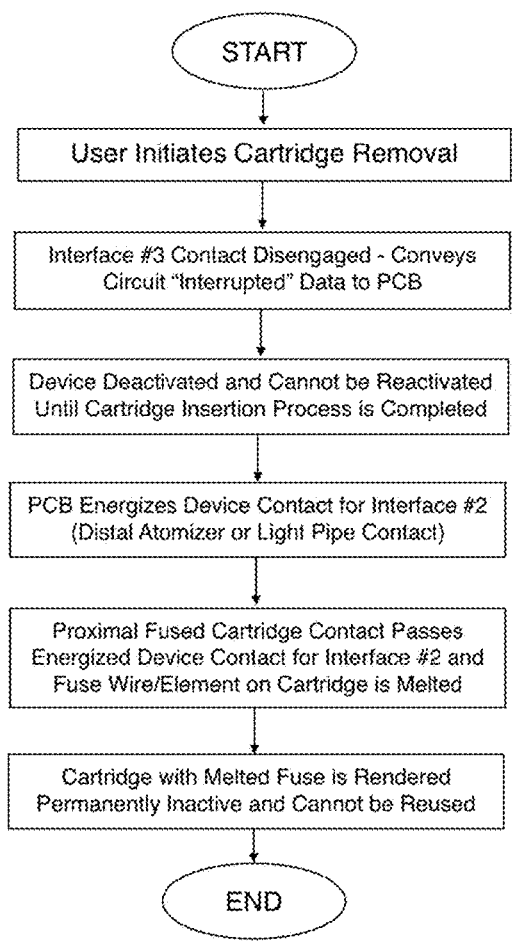
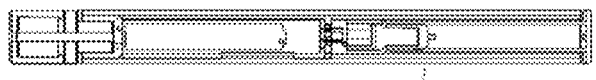
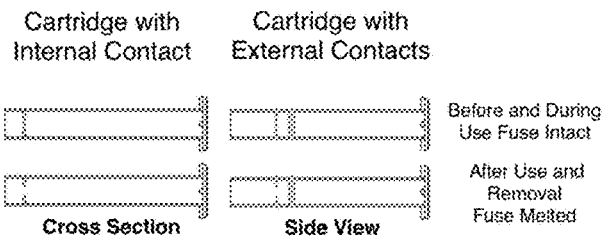
FIG. 173

FIG. 174
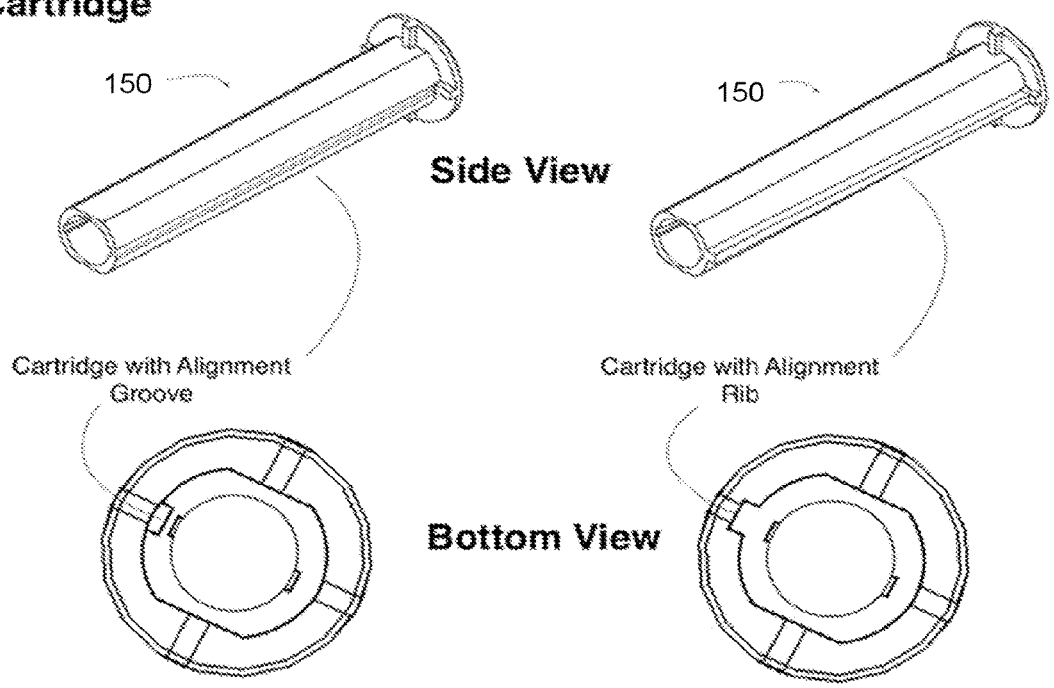
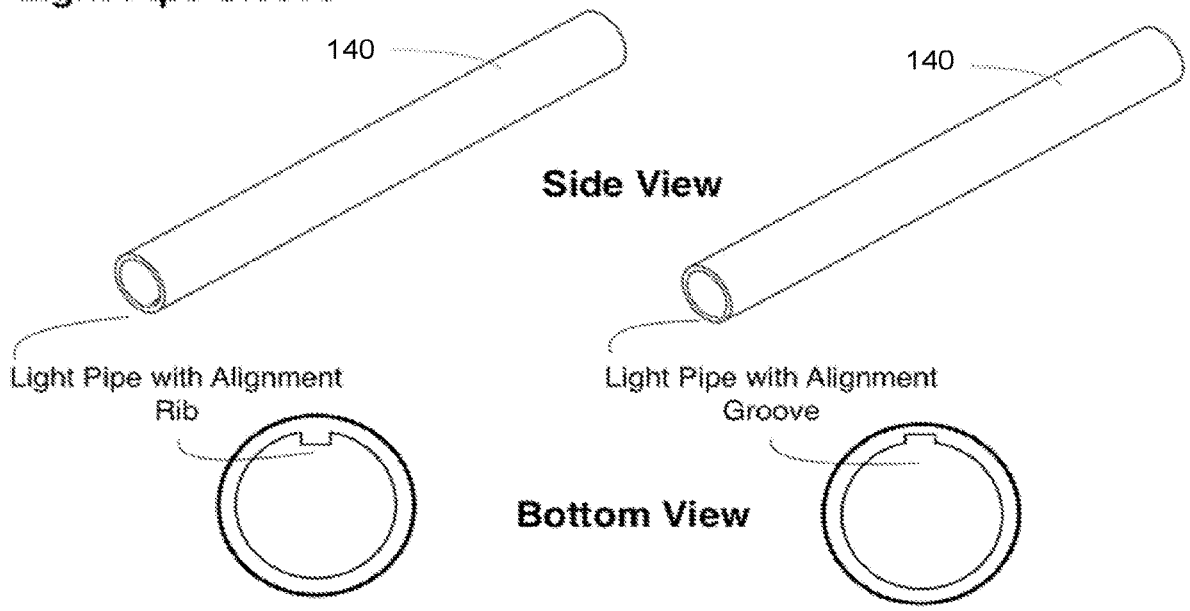

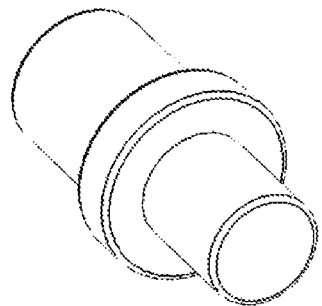
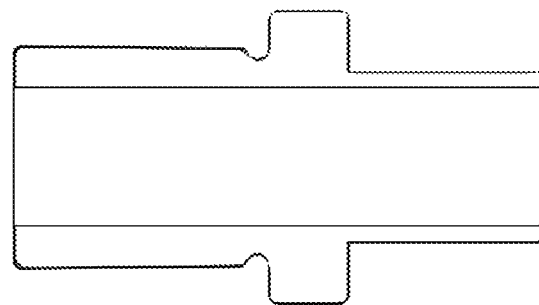
Perspective View
Cross Section
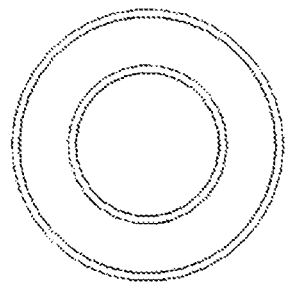
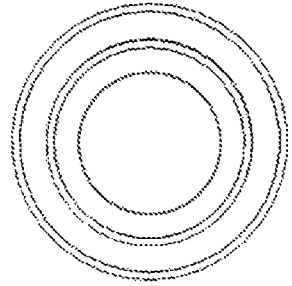
Top View
Bottom View
FIG. 184

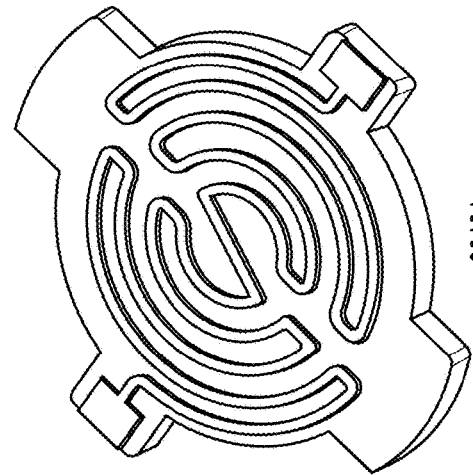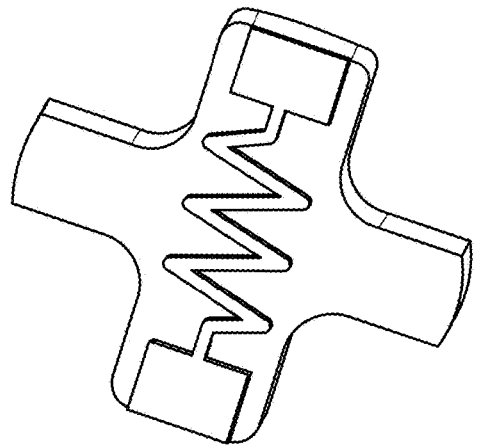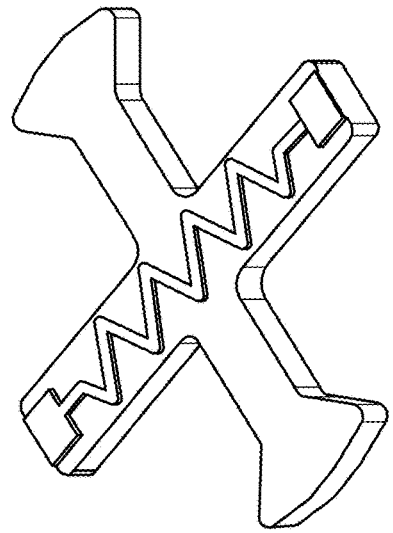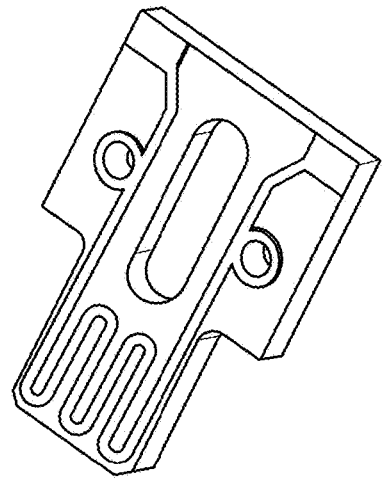
FIG. 204

VAPORIZING UNIT WITH USE AUTHORIZATION

CROSS-REFERENCE TO RELATED APPLICATIONS

This application is a continuation of U.S. patent application Ser. No. 17/658,210, entitled "VAPORIZER RELATED SYSTEMS, METHODS, AND APPARATUS", filed on Apr. 6, 2022, which claims priority as a continuation of U.S. patent application Ser. No. 16/010,932, entitled, "VAPORIZER RELATED SYSTEMS, METHODS, AND APPARATUS", filed on Jun. 18, 2018, which claims priority as a continuation-in-part to U.S. patent application Ser. No. 14/701,046, entitled "VAPORIZER RELATED SYSTEMS, METHODS, AND APPARATUS," filed on Apr. 3, 2015, which claims priority to U.S. Provisional Application No. 61/987,005, entitled "VAPORIZER RELATED SYSTEMS, METHODS, AND APPARATUS," filed on May 1, 2014, and which claims priority as a continuation-in-part to U.S. patent application Ser. No. 14/279,174, entitled "SOLDERLESS DIRECTLY WRITTEN HEATING ELEMENTS," filed on May 15, 2014, which is a continuation-in-part to U.S. patent application Ser. No. 13/698,020, entitled "SOLDERLESS PERSONAL VAPORIZING INHALER," filed Nov. 14, 2012, now U.S. Pat. No. 9,259,035, which is a continuation-in-part of the following U.S. applications filed on May 15, 2010: U.S. application Ser. No. 12/780,871, entitled "PERSONAL VAPORIZING INHALER WITH MOUTHPIECE COVER", U.S. application Ser. No. 12/780,872, entitled "ACTIVATION TRIGGER FOR A PERSONAL VAPORIZING INHALER", now U.S. Pat. No. 8,746,240; U.S. application Ser. No. 12/780,873, entitled "PERSONAL VAPORIZING INHALER CARTRIDGE," now U.S. Pat. No. 9,861,772; U.S. application Ser. No. 12/780,874, entitled "ATOMIZER-VAPORIZER FOR A PERSONAL VAPORIZING INHALER", now U.S. Pat. No. 8,550,068; U.S. application Ser. No. 12/780,875, entitled "PERSONAL VAPORIZING INHALER WITH INTERNAL LIGHT SOURCE," filed May 15, 2010, now U.S. Pat. No. 8,757,147; U.S. application Ser. No. 12/780,876, entitled "DATA LOGGING PERSONAL VAPORIZING INHALER", now U.S. Pat. No. 9,095,175; and U.S. application Ser. No. 12/780,877, entitled "CHARGING CASE FOR A PERSONAL VAPORIZING INHALER," now U.S. Pat. No. 8,314,591; wherein the entirety of each of the aforementioned applications is hereby incorporated by reference.

This application claims priority as a continuation-in-part to U.S. application Ser. No. 14/285,605, entitled "ASSEMBLY DIRECTED AIRFLOW", filed on May 22, 2014, which is a continuation-in-part application of U.S. application Ser. No. 12/780,873, entitled "PERSONAL VAPORIZING INHALER CARTRIDGE," filed May 15, 2010, now U.S. Pat. No. 9,861,772; wherein the entirety of each of the aforementioned applications is hereby incorporated by reference.

This application claims priority as a continuation-in-part to U.S. patent application Ser. No. 14/716,204, entitled "CARTRIDGE VAPORIZER IN A PERSONAL VAPORIZER UNIT," filed on May 19, 2015, which claims priority to U.S. Provisional Application No. 62/000,101, entitled "CARTRIDGE VAPORIZER SYSTEMS, METHODS, AND APPARATUS," filed on May 19, 2014; wherein the entirety of each of the aforementioned applications is hereby incorporated by reference.

This application claims priority as a continuation-in-part to U.S. application Ser. No. 14/275,494, entitled "PERSONAL VAPORIZING INHALER WITH TRANSLUCENT WINDOW", filed on May 12, 2014, which is a continuation application of U.S. application Ser. No. 12/780,875, entitled "PERSONAL VAPORIZING INHALER WITH INTERNAL LIGHT SOURCE," filed May 15, 2010, now U.S. Pat. No. 8,757,147; wherein the entirety of each of the aforementioned applications is hereby incorporated by reference.

The application is related to U.S. patent application Ser. No. 14/276,894, entitled "VAPORIZER CONFIGURATION, CONTROL, AND REPORTING" filed on May 13, 2014, which is a continuation-in-part to U.S. patent application Ser. No. 12/780,876, entitled "DATA LOGGING PERSONAL VAPORIZING INHALER" filed on May 15, 2010, wherein the entire disclosure of each is herein incorporated by reference. This application is also related to the following U.S. applications. U.S. application Ser. No. 14/273,612, entitled "DISTAL END INSERTED PERSONAL VAPORIZING INHALER CARTRIDGE," filed on May 9, 2014, now U.S. Pat. No. 9,427,711; U.S. application Ser. No. 14/275,454, entitled "PERSONAL VAPORIZING INHALER ASSEMBLY," filed on May 12, 2014, now U.S. Pat. No. 9,555,203; U.S. application Ser. No. 14/274,447, entitled "PERSONAL VAPORIZING INHALER WITH DATA TRANSFER," filed on May 9, 2014; U.S. application Ser. No. 14/278,087, entitled "COMMUNICATION BETWEEN PERSONAL VAPORIZING INHALER ASSEMBLIES," filed on May 15, 2014, now U.S. Pat. No. 9,861,773; and U.S. application Ser. No. 14/284,994, entitled "VAPORIZER ASSEMBLY AND CARTRIDGE," filed on May 22, 2014, now U.S. Pat. No. 9,352,288; wherein the entirety of each of the aforementioned applications is hereby incorporated by reference.

TECHNICAL FIELD

This invention relates to personal vapor inhaling units and more particularly to an atomizer/vaporizer of an electronic flameless vapor inhaler unit that may simulate a cigarette or deliver nicotine and other medications to the oral mucosa, pharyngeal mucosa, tracheal, and pulmonary membranes.

BACKGROUND

An alternative to smoked tobacco products, such as cigarettes, cigars, or pipes is a personal vaporizer Inhaled doses of heated and atomized flavor, which provides a physical sensation similar to smoking. However, because a personal vaporizer is typically electrically powered, no tobacco, smoke, or combustion is usually involved in its operation. For portability, and to simulate the physical characteristics of a cigarette, cigar, or pipe, a personal vaporizer may be battery powered. In addition, a personal vaporizer may be loaded with a nicotine bearing substance and/or a medication bearing substance. The personal vaporizer may provide an inhaled dose of nicotine and/or medication by way of the heated and atomized substance. Thus, personal vaporizers may also be known as electronic cigarettes, or e-cigarettes. Personal vaporizers may be used to administer flavors, medicines, drugs, or substances that are vaporized and then inhaled.

BRIEF DESCRIPTION OF THE DRAWINGS

FIG. 54 is a perspective view of an atomizer housing and wicks of a personal vaporizer unit.

FIG. 55 is an exploded view of the atomizer housing, wire guides, and wicks of FIG. 54.

FIG. 56 is a side view of the atomizer housing and wicks of FIG. 54.

FIG. 57 is a distal end view of the atomizer housing and wicks of FIG. 54.

FIG. 58 is a cross-section view of the atomizer housing and wicks along the cut line shown in FIG. 57.

FIG. 65 is a perspective view of a cartridge of a personal vaporizer unit.

FIG. 66 is a proximal end view of the cartridge of FIG. 65.

FIG. 67 is a side view of the cartridge of FIG. 65.

FIG. 68 is a top view of the cartridge of FIG. 65.

FIG. 69 is a cross-section view of the cartridge along the cut line shown in FIG. 66.

FIG. 89 is an illustration showing an axial cut line through a distal assembly.

FIG. 90 is a cross-section view of a distal assembly cartridge chamber main body along the cut line shown in FIG. 89.

FIG. 91 is a cross-section view of a distal assembly cartridge chamber main body with clean air intake along the cut line shown in FIG. 89.

FIG. 92 is a cross-section view of a distal assembly cartridge chamber main body with clean air intake and airflow directional standoff along the cut line shown in FIG. 89.

FIG. 93 is an illustration showing a cut line through a cartridge liquid reservoir main body.

FIG. 94 is a cross-section view of a cartridge liquid reservoir main body along the cut line shown in FIG. 93.

FIG. 95 is a cross-section view of cartridge liquid reservoir main body with cartridge liquid reservoir standoff along the cut line shown in FIG. 93.

FIG. 114 illustrates a perspective view of a directly written heating element disposed through a proximal wick element of a personal vaporizer unit.

FIG. 114A illustrates an end view of contact points for a directly written heating element disposed through a proximal wick element of a personal vaporizer unit.

FIG. 115 is a perspective view showing directly written heating elements disposed on the wire guides of FIG. 59.

FIG. 115A illustrates an end view of contact points on a wick which supports wire guides having directly written heating elements.

FIG. 116 illustrates two opposing side views of a wire guide that has a directly written heating element.

FIG. 117 illustrates two opposing side views of a support element that has a directly written heating element.

FIG. 118 illustrates a coiled wire heating element and cylindrical support member.

FIG. 119 illustrates a vaporization chamber cross section.

FIG. 120 is a diagram of IR emissivity.

FIG. 121 is a diagram of IR reflectivity.

FIG. 122 is a diagram of IR absorption.

FIG. 123 illustrates a cross section of a proximal wick shown in FIG. 35 with a heating element.

Figure 124:
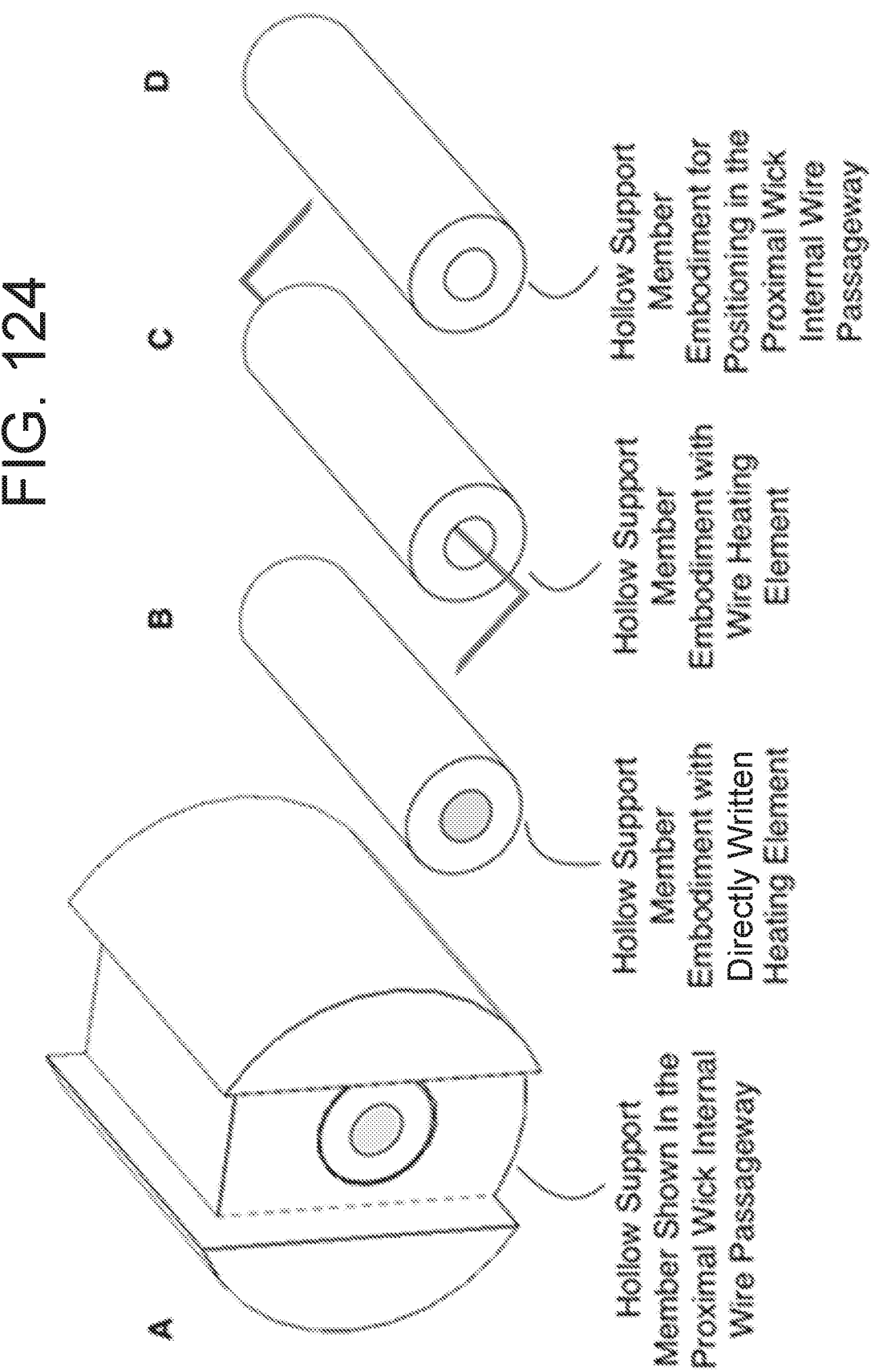

FIG. 124 shows an embodiment of the heating element and support member/wire guide that is a tube and positioned in the internal wire passageway of the proximal wick.

Figure 125:
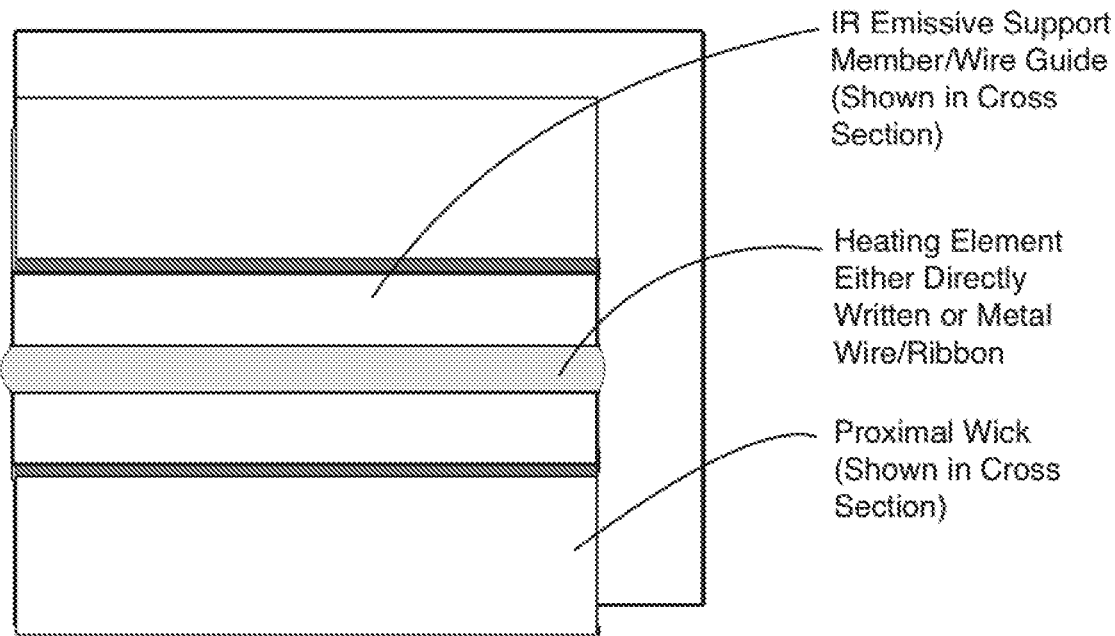

FIG. 125 shows a cross-section view of a proximal wick with a hollow support member positioned in the internal wire passageway.

Figure 126:
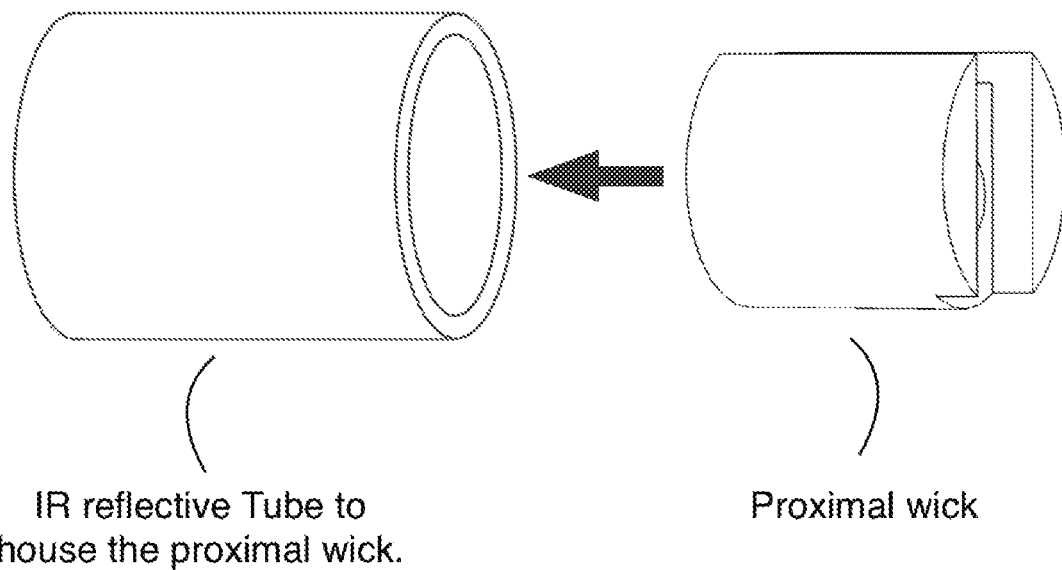

FIG. 126 is a side perspective view of the IR reflective housing for the proximal wick.

Figure 127:
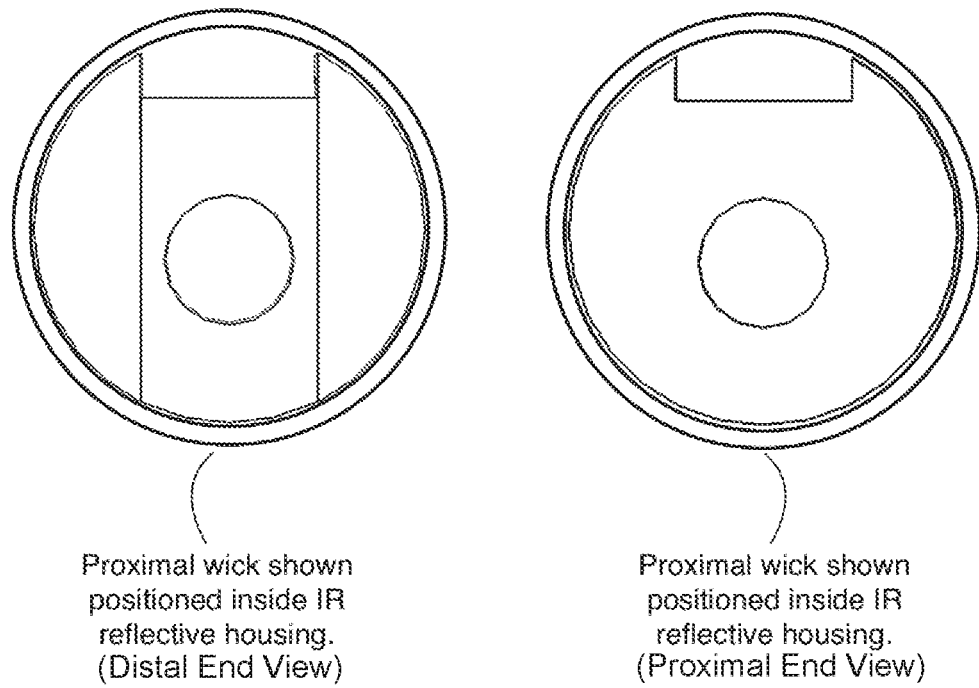

FIG. 127 illustrates a distal end view and a proximal end view of the IR reflective housing and proximal wick assembly.

Figure 128:
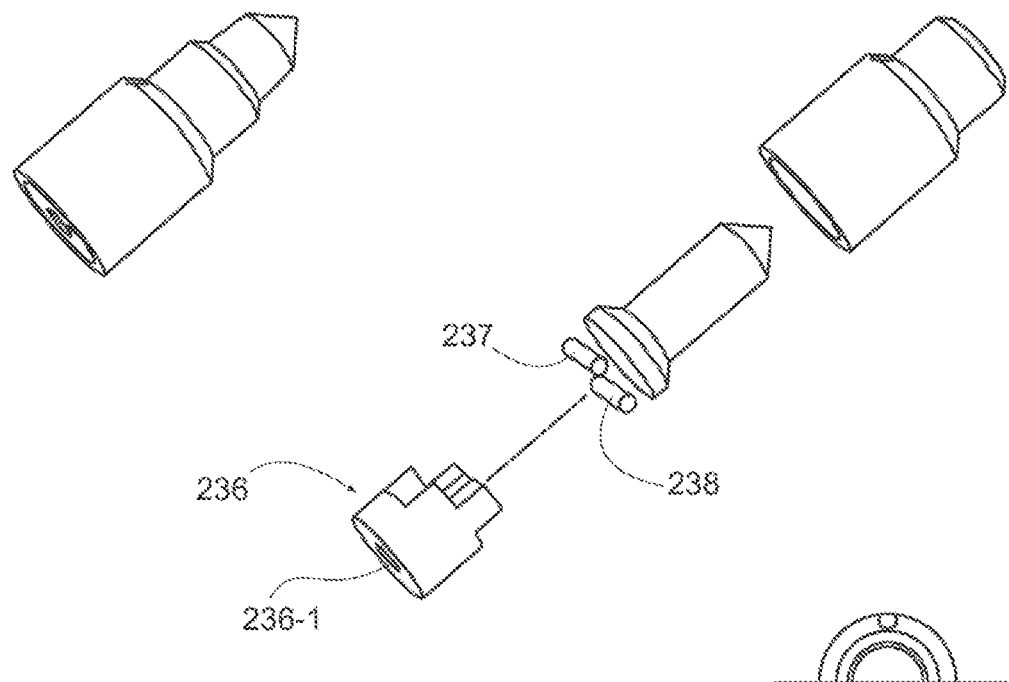

FIG. 128 is a perspective view of an atomizer housing and wicks of a personal vaporizer unit and includes an exploded view of the atomizer housing, wire guides, and wicks.

Figure 129:
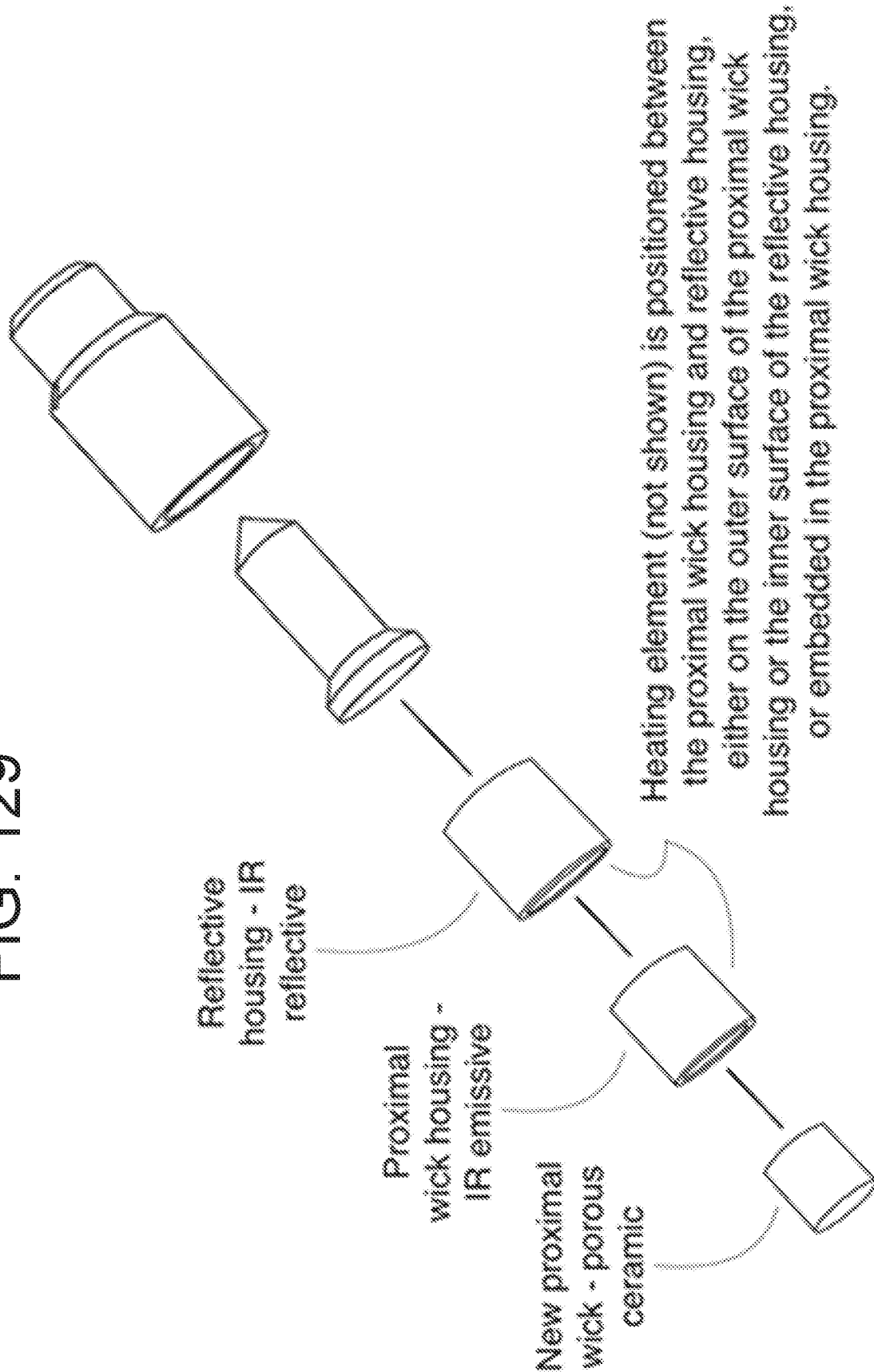

FIG. 129 is an alternative embodiment of FIG. 128.

FIG. 130 is a proximal wick housing with heating element and embedded electrical contacts.

Figure 131:
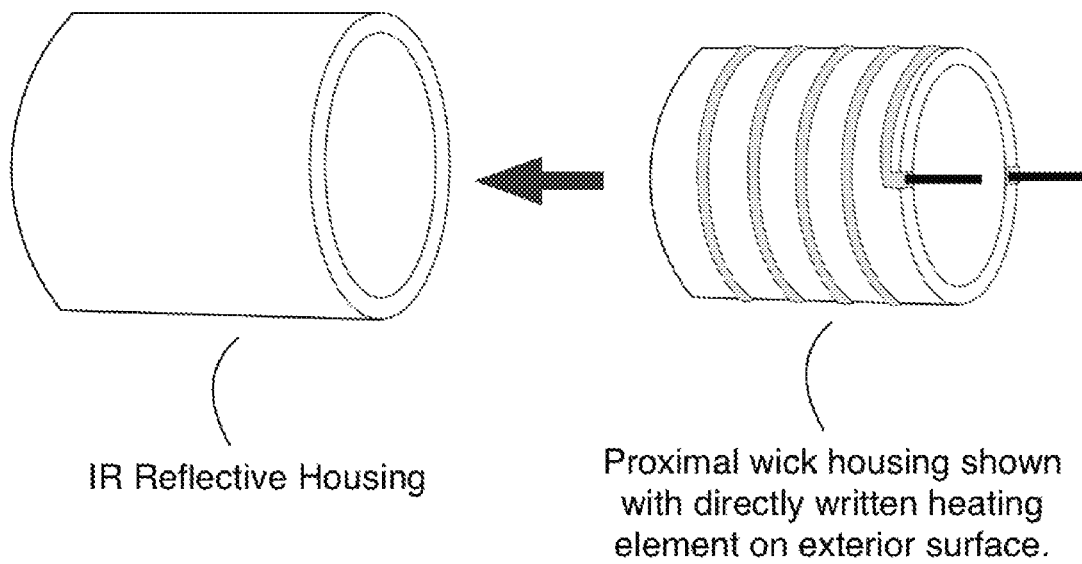

FIG. 131 illustrates one embodiment for the IR reflective housing and proximal wick housing.

Figure 132:
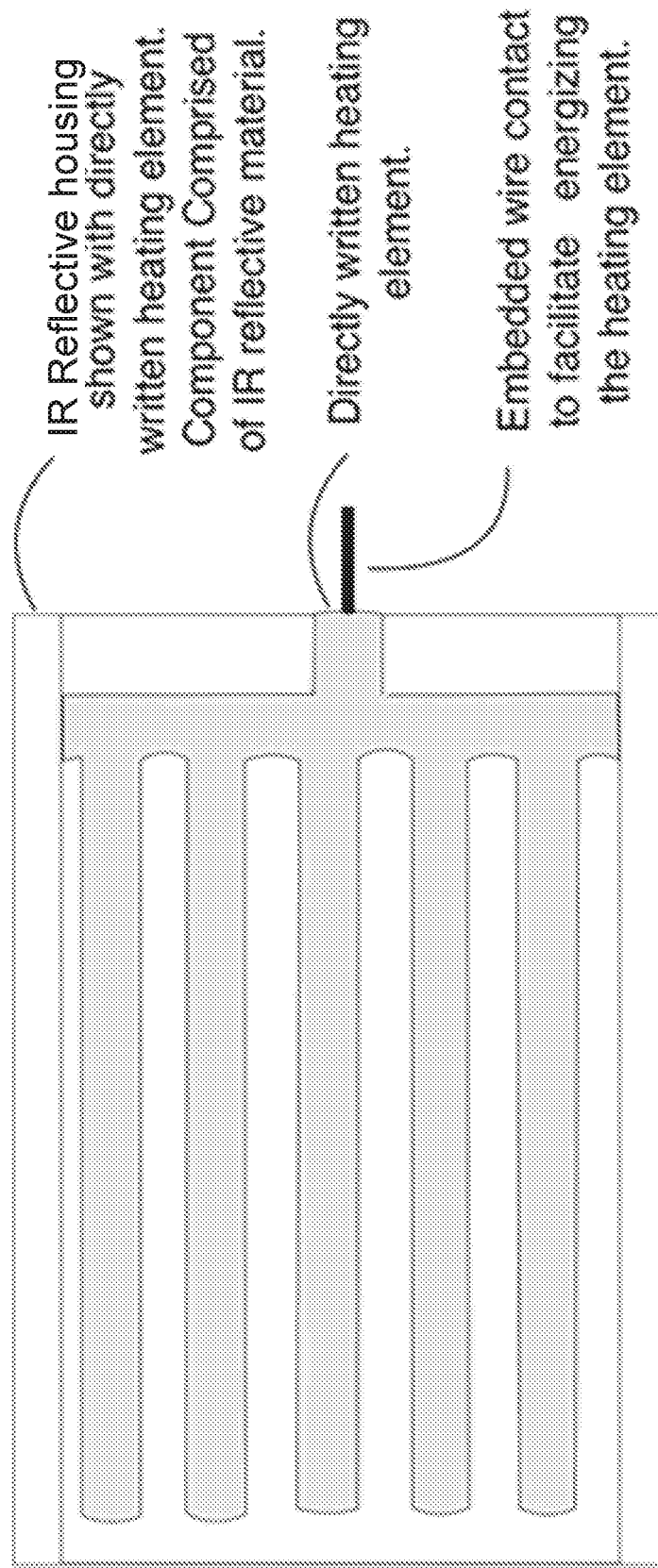

FIG. 132 illustrates an alternative embodiment where the heating element is positioned on the internal surface of the IR reflective housing.

Figure 133:
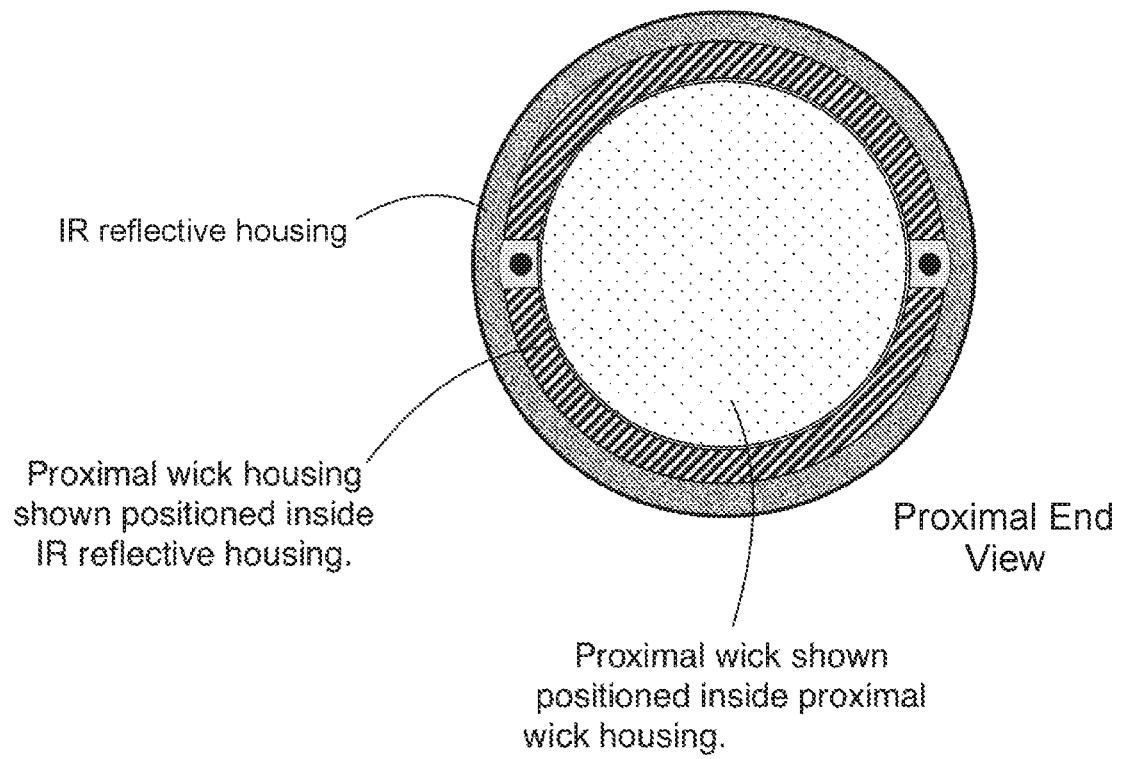

FIG. 133 illustrates a proximal end view of one embodiment of a complete assembly.

Figure 134:
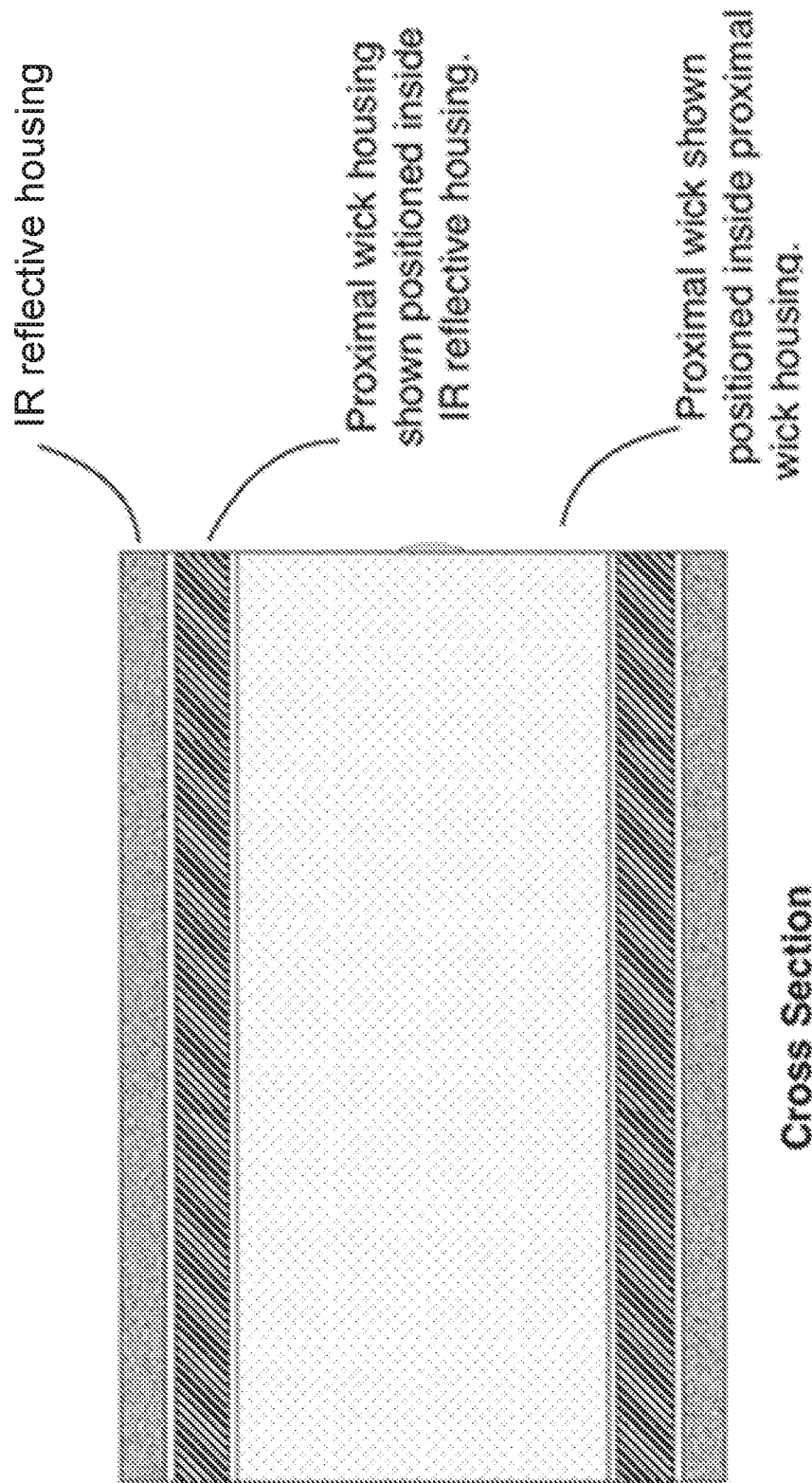

FIG. 134 illustrates a cross-section view of one embodiment of a complete assembly.

Figure 135:
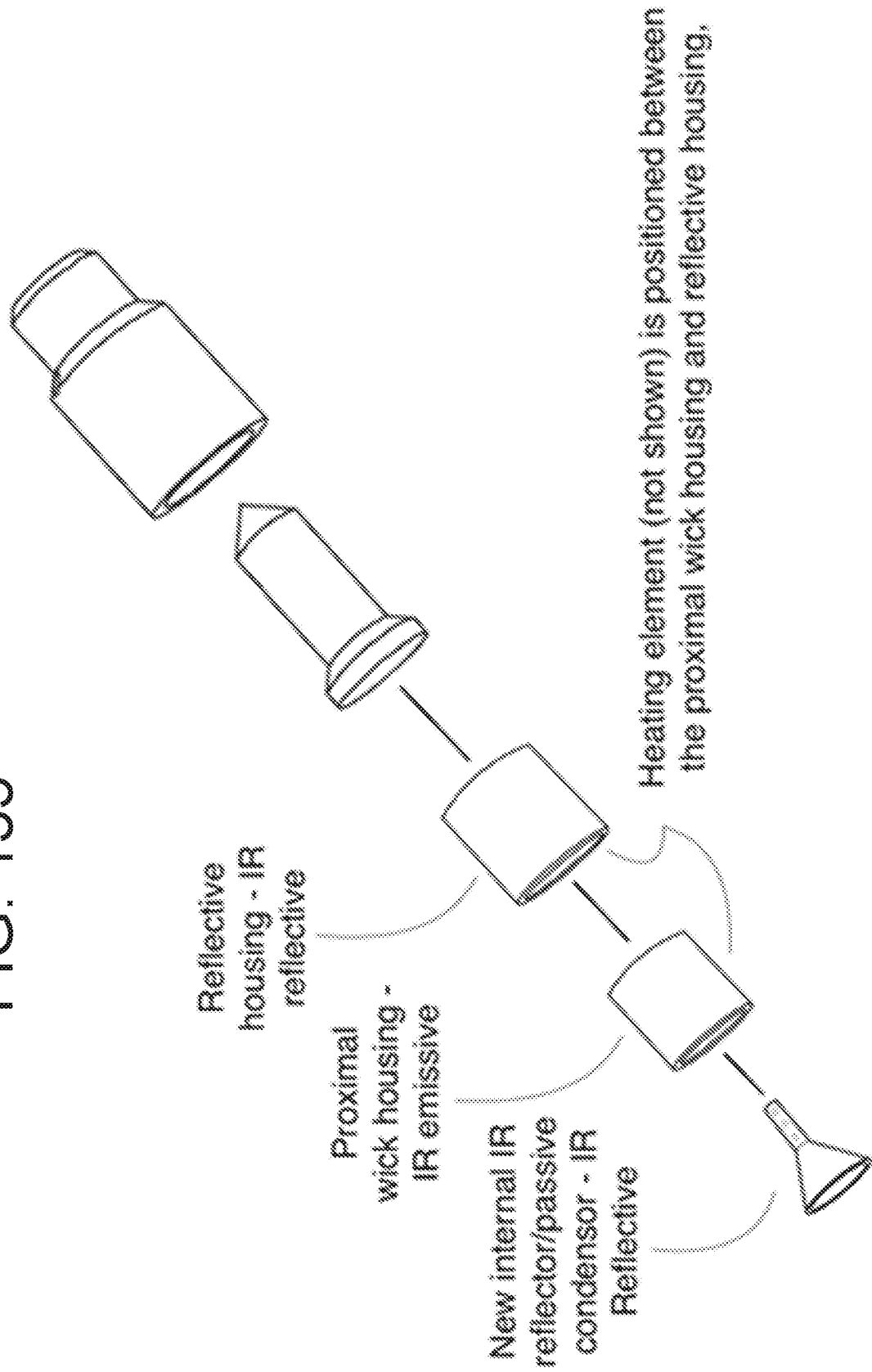

FIG. 135 is an alternative embodiment utilizing an internal IR reflector/passive condenser.

Figure 136:
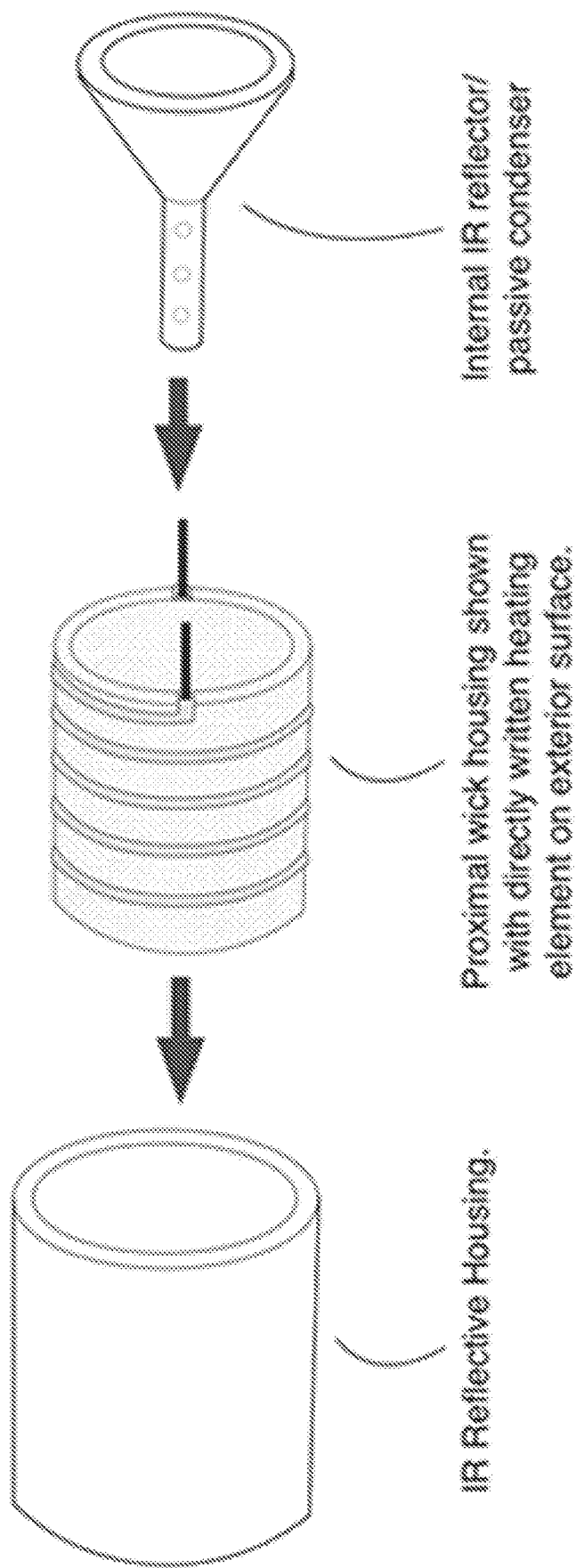

FIG. 136 illustrates the positioning of the components that comprise the new assembly.

Figure 137:
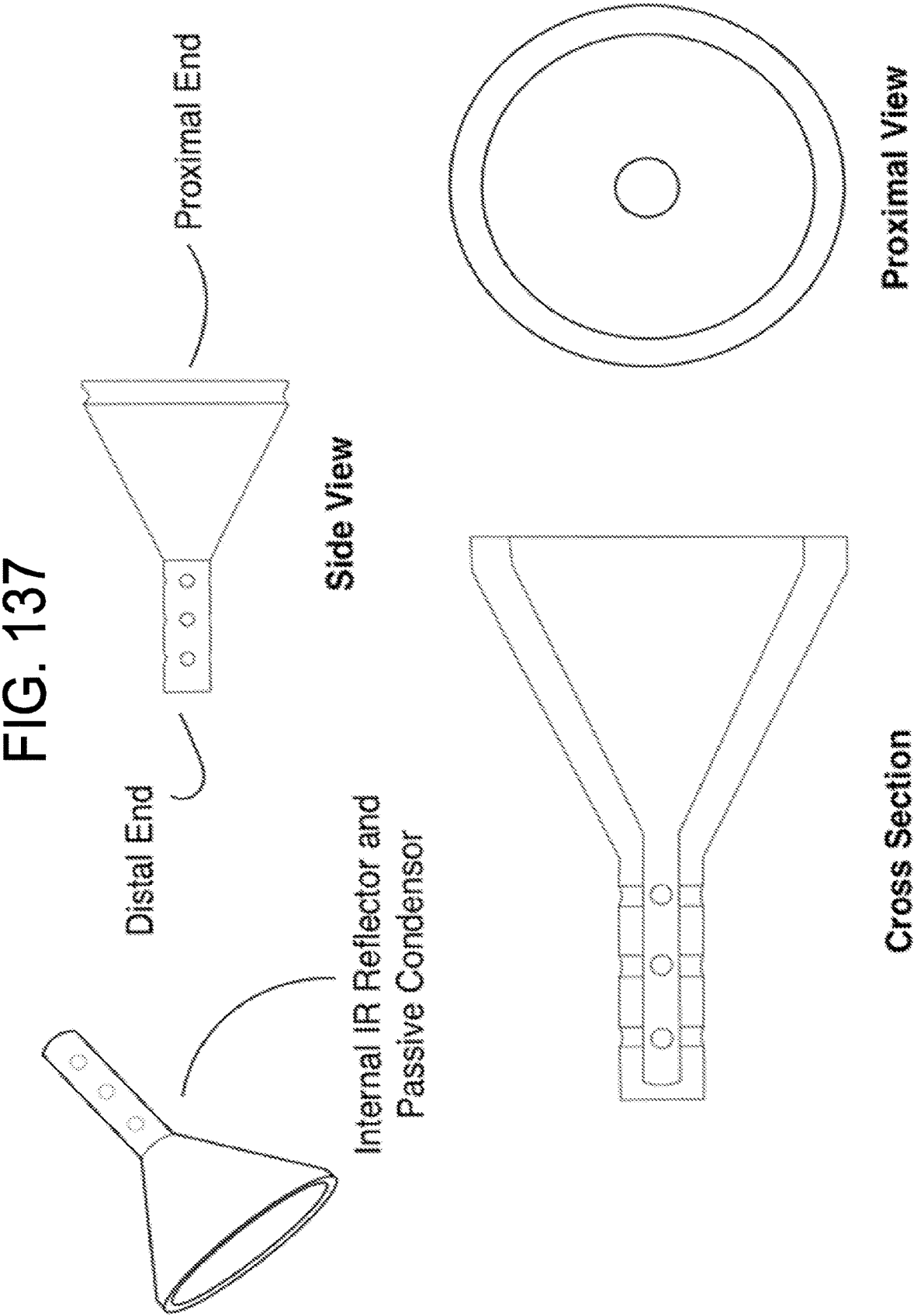

FIG. 137 illustrates the internal IR reflector/passive condenser from multiple perspectives.

Figure 138:
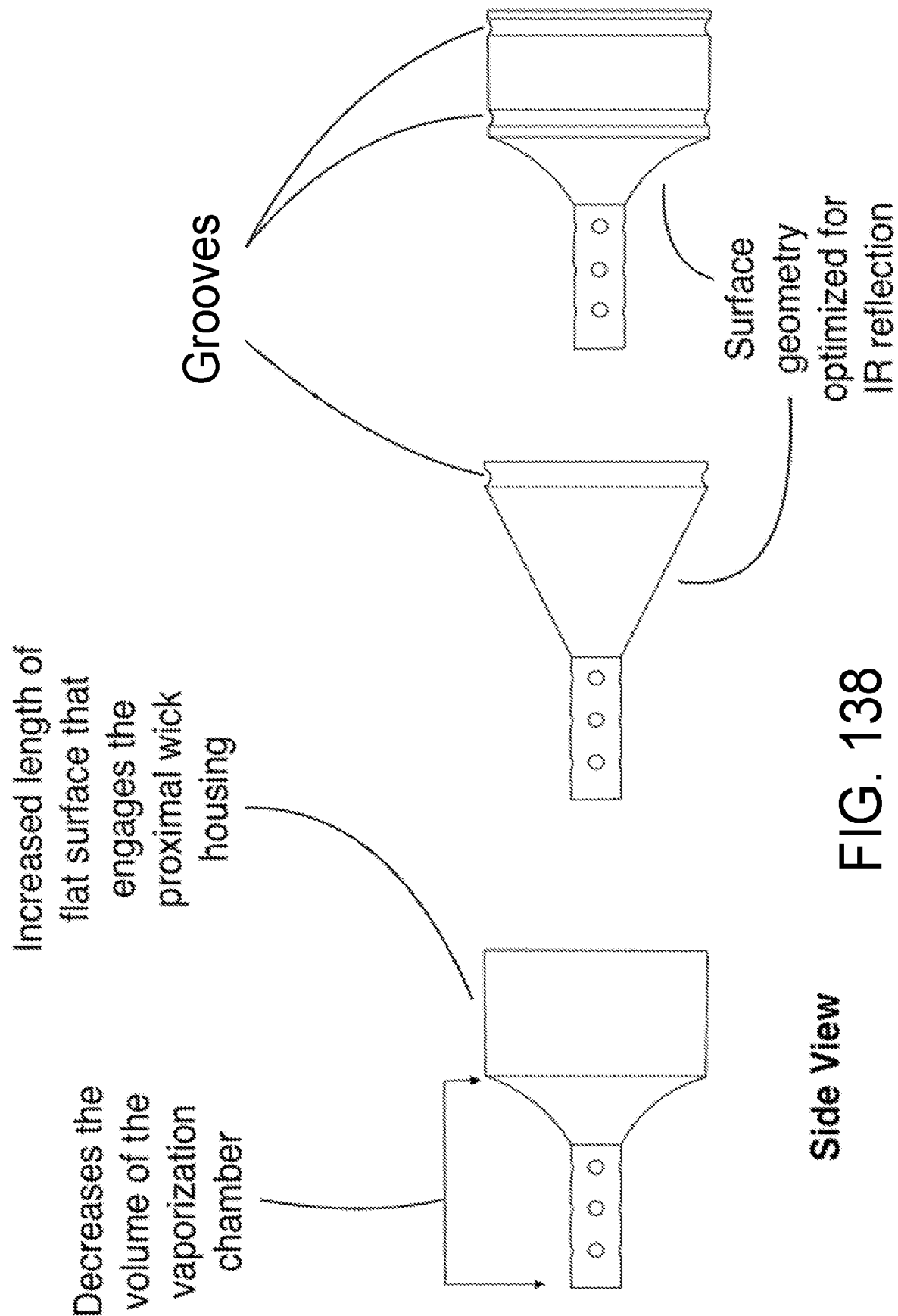

FIG. 138 illustrates some relevant features of the internal IR reflector/passive condenser component.

Figure 139:
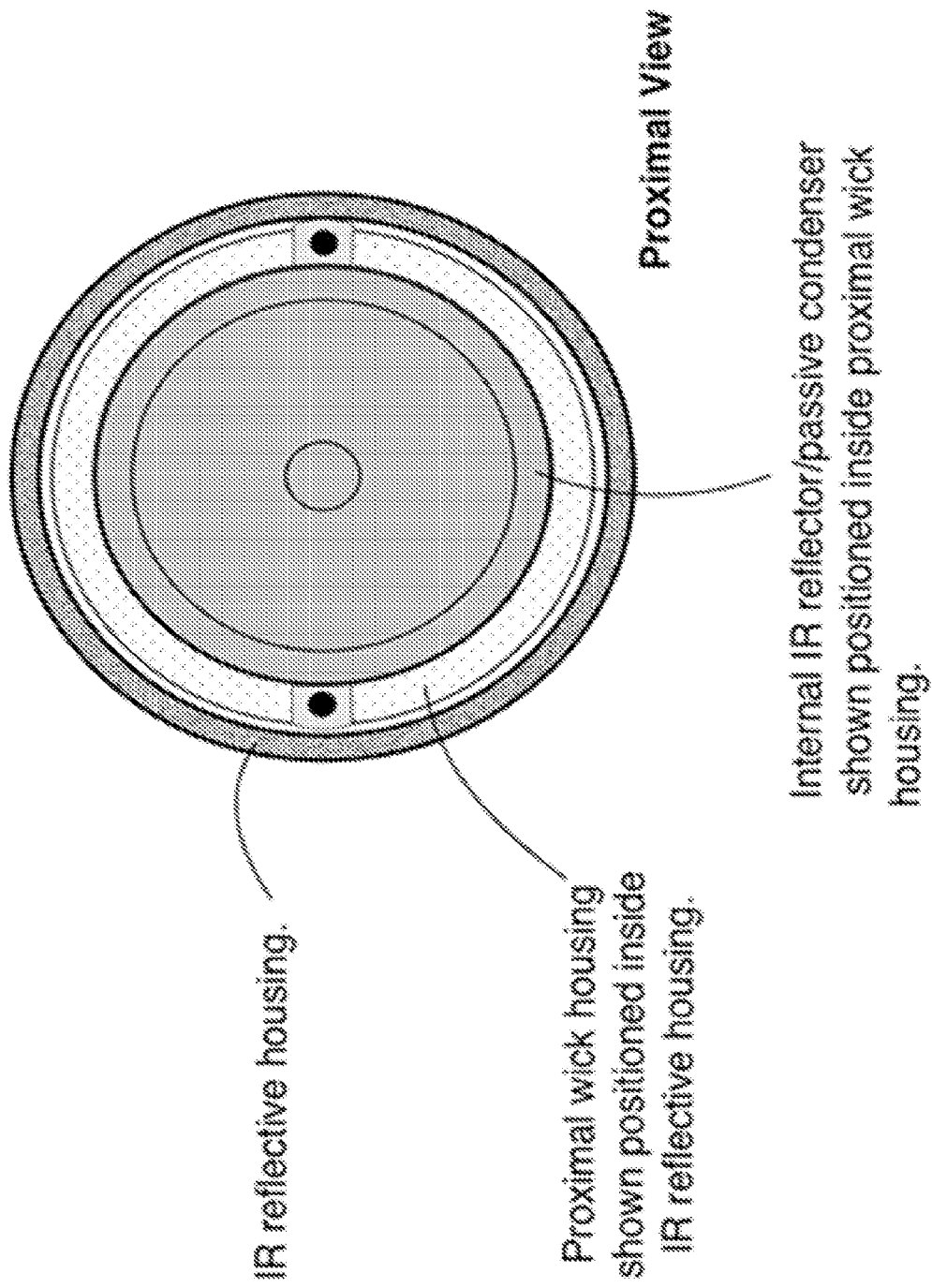

FIG. 139 illustrates the nested arrangement of the components that comprise the new assembly.

Figure 140:
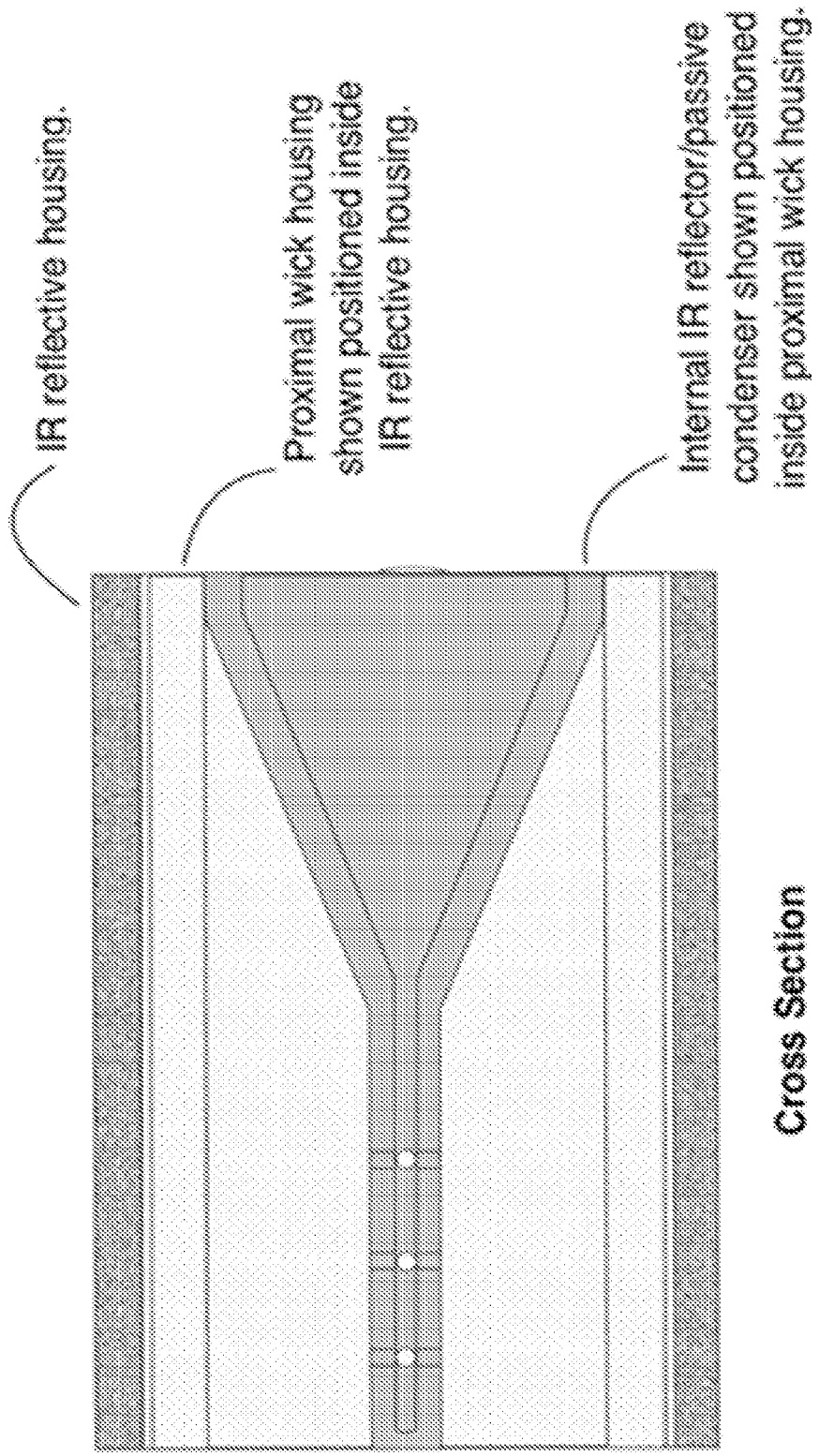

FIG. 140 illustrates a cross-section view of the nested arrangement of the components that comprise the new assembly.

Figure 141:
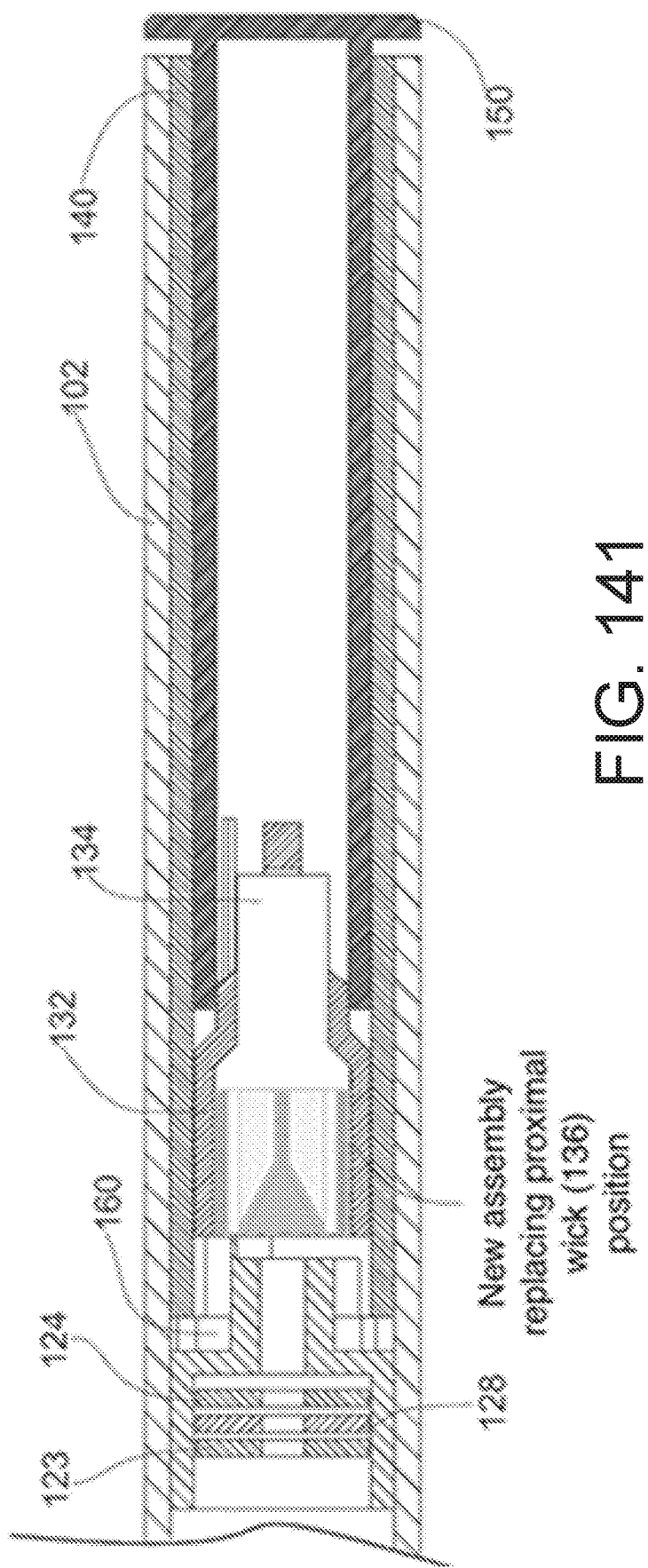

FIG. 141 shows the positioning of an alternative new assembly in the distal portion of the vaporizer.

Figure 142:
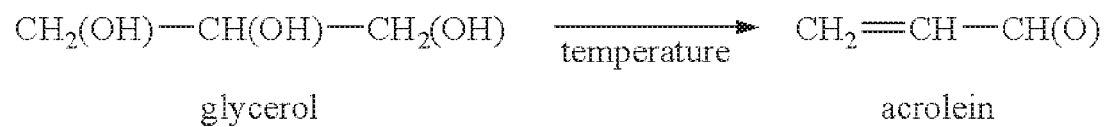

FIG. 142 is a reference formula for the chemical conversion/degradation reaction of glycerol to acrolein.

Figure 143:
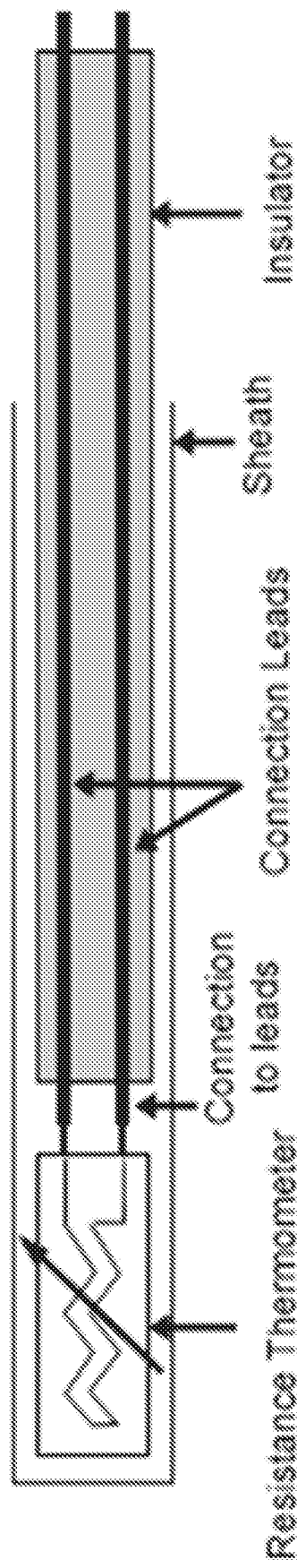

FIG. 143 is one embodiment of a resistance temperature detector ("RTD").

Figure 144:
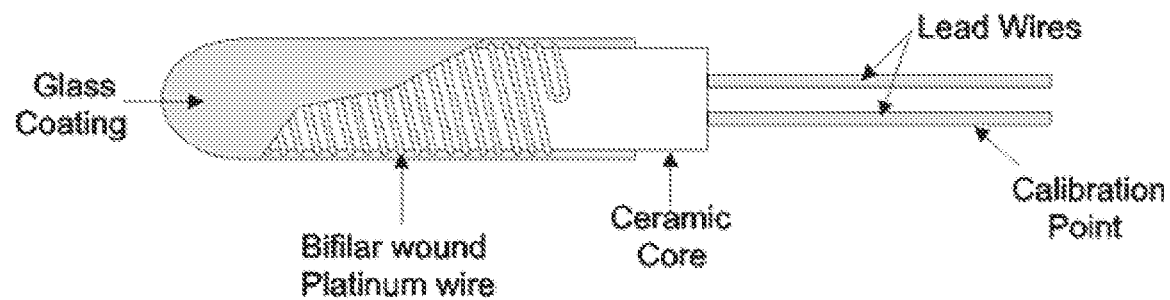

FIG. 144 is one embodiment of a wire wound RTD.

Figure 145:
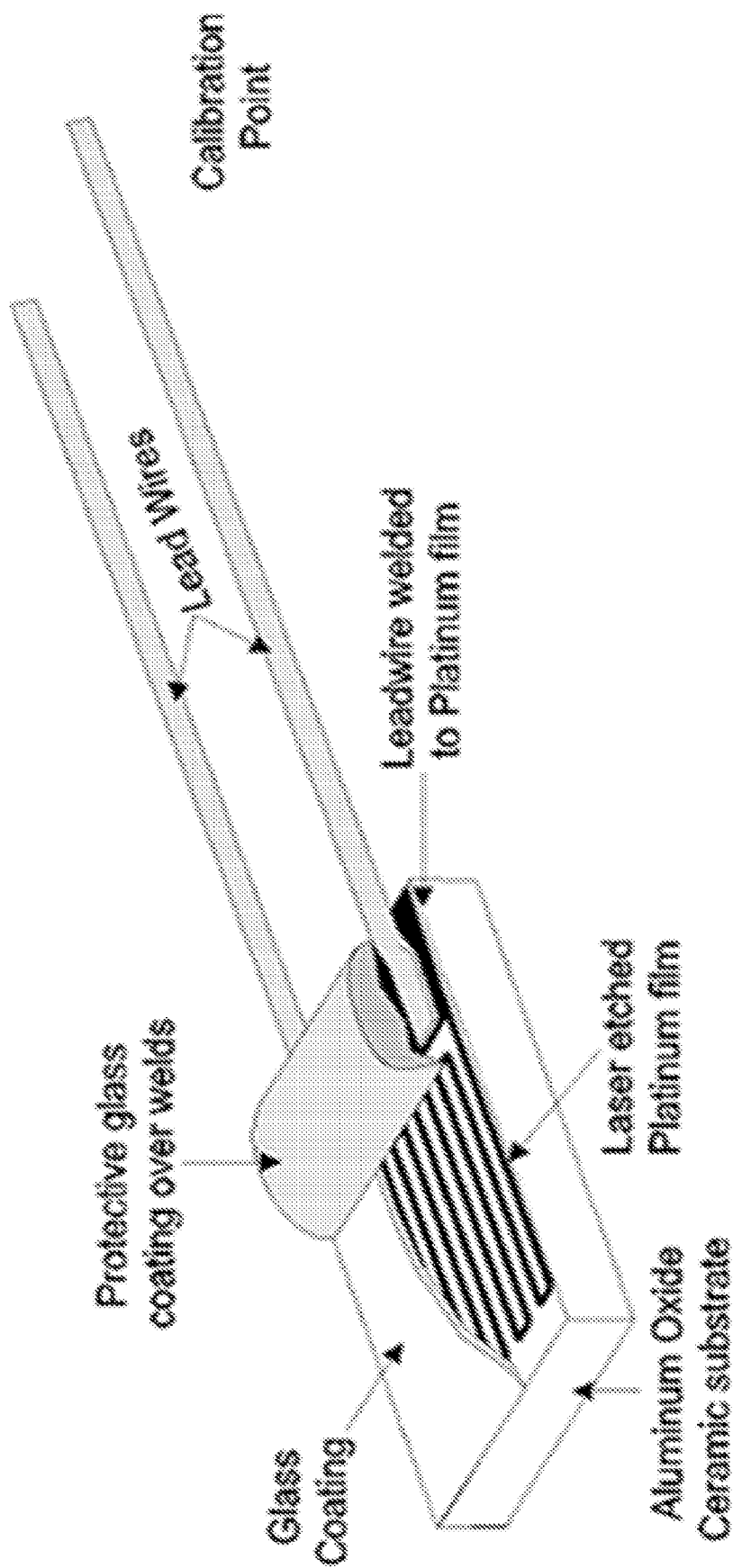

FIG. 145 is one embodiment of a thin film RTD.

Figure 146:
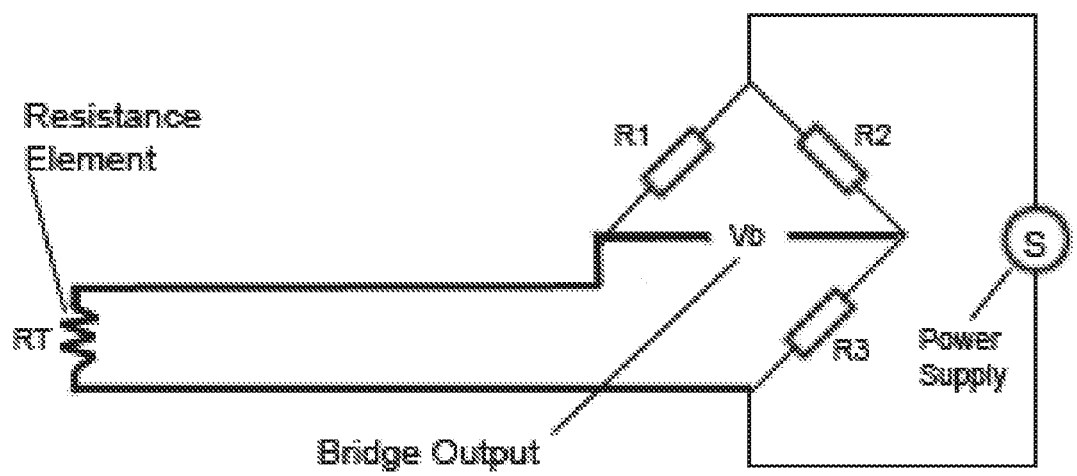

FIG. 146 is an exemplary wiring configuration for a two wire RTD.

Figure 147:
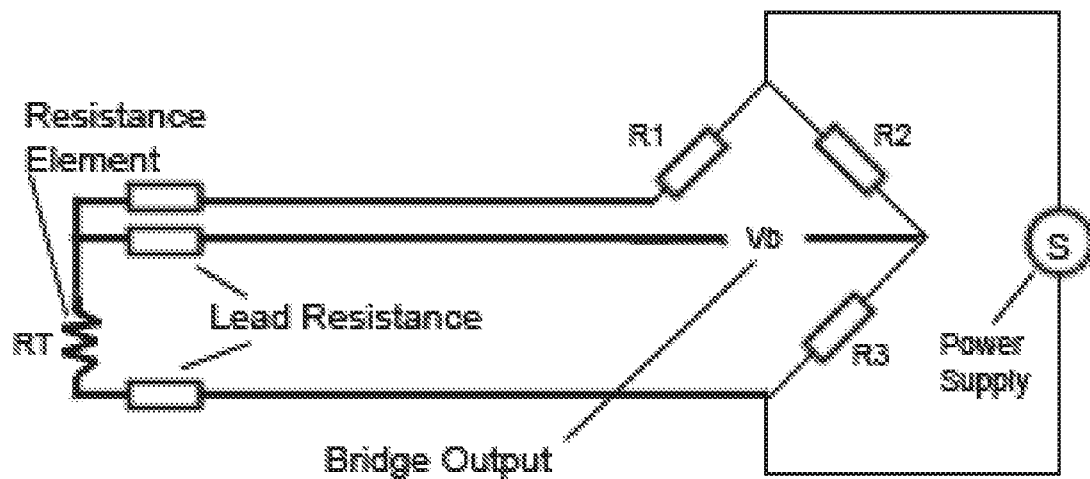

FIG. 147 is an exemplary wiring configuration for a three wire RTD.

Figure 148:
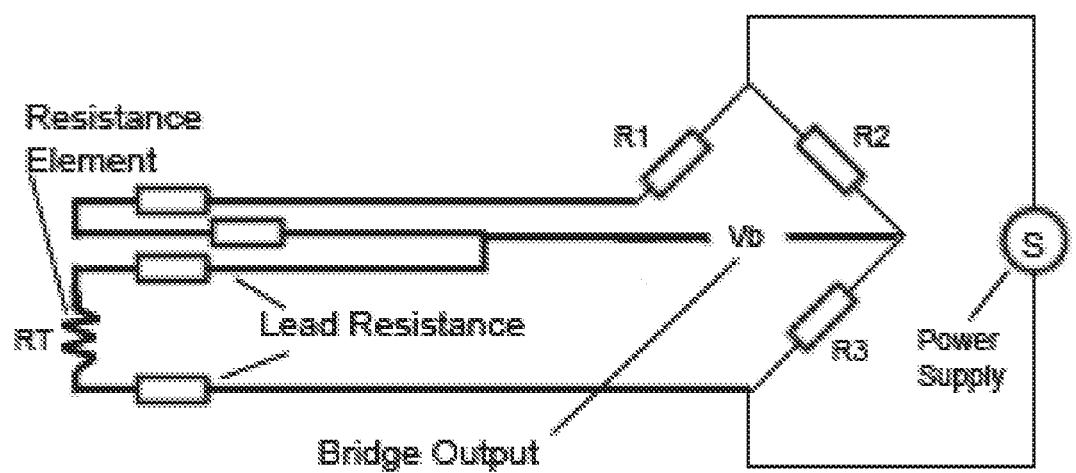

FIG. 148 is an exemplary wiring configuration for a four wire RTD.

Figure 149:
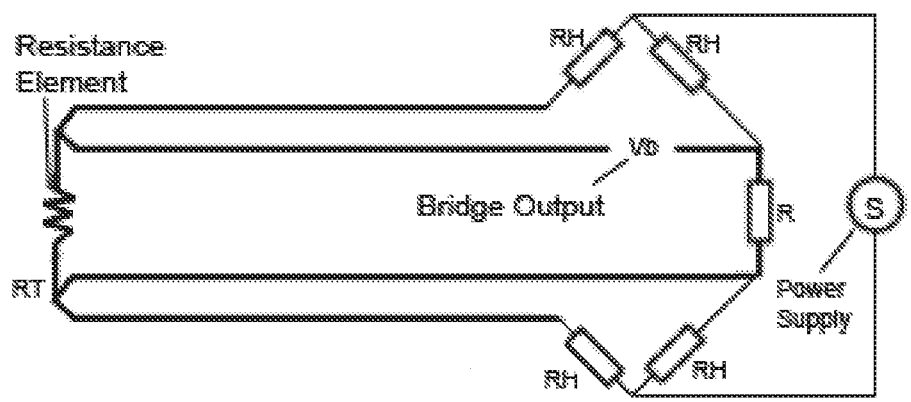

FIG. 149 is an alternative embodiment of a four wire RTD.

Figure 150:
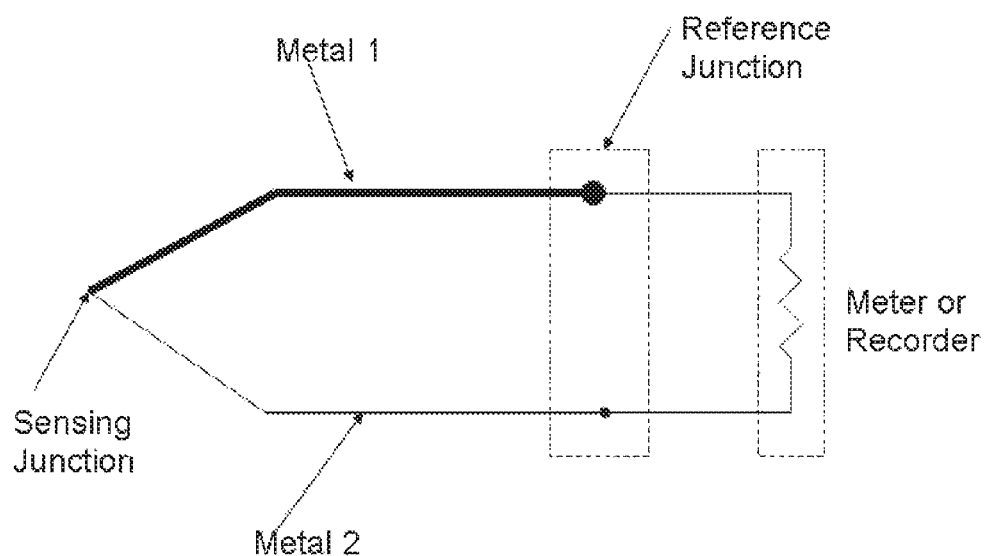

FIG. 150 is an exemplary thermocouple wiring diagram.

Figure 151:
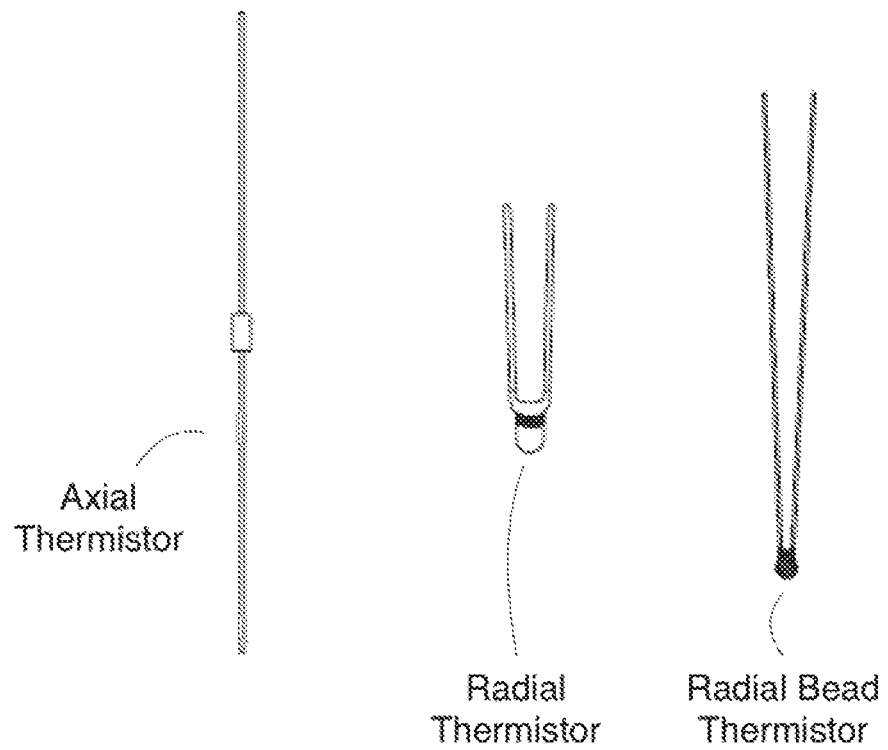

FIG. 151 is an embodiment of types of thermistor configurations.

Figure 152:
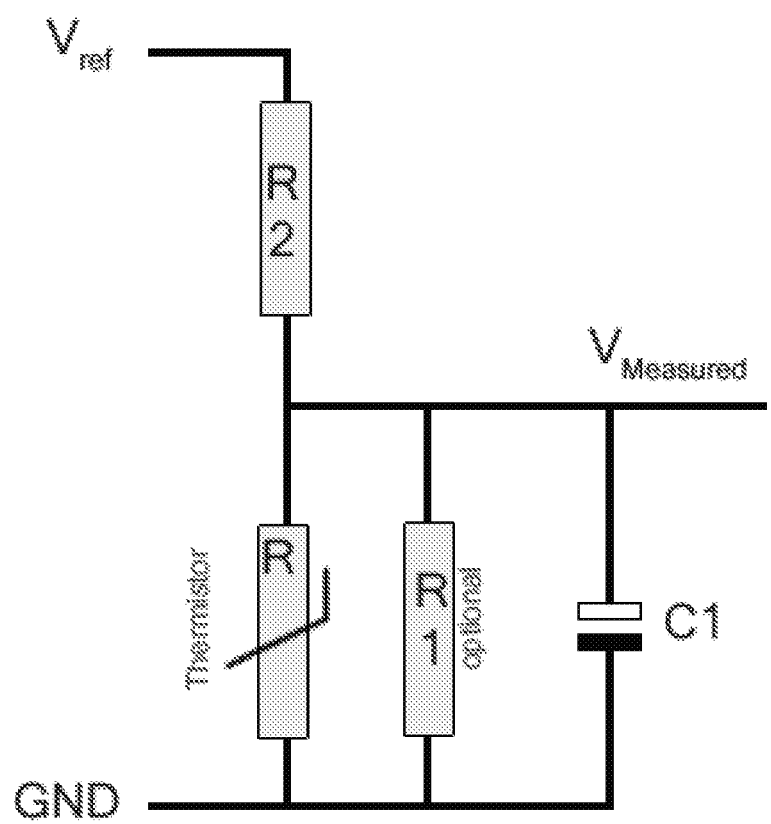

FIG. 152 is an embodiment of thermistor wiring configuration.

Figure 153:
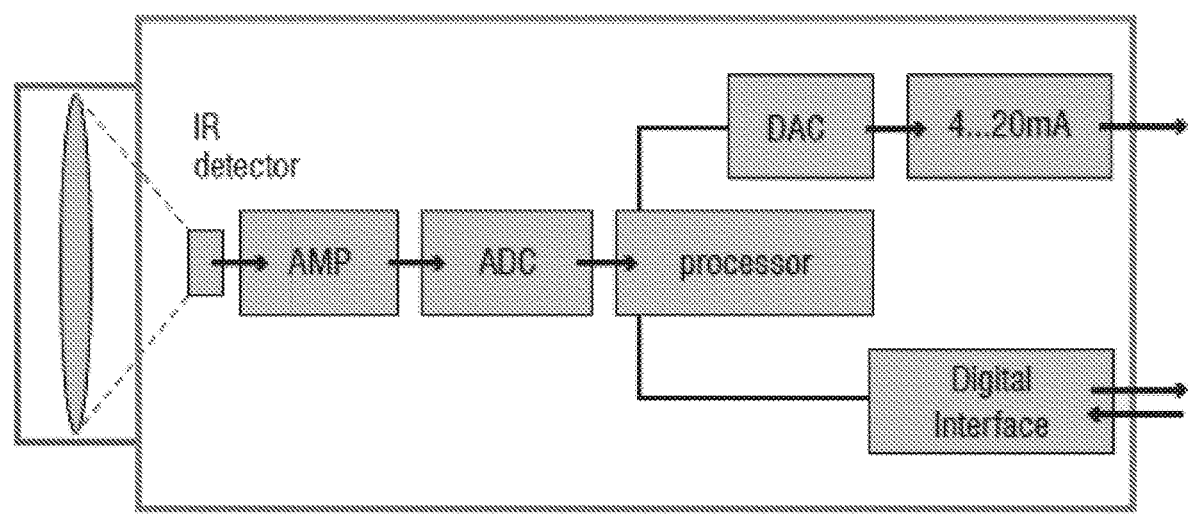

FIG. 153 is a diagram of operation and construction of an IR temperature sensor.

Figure 154:
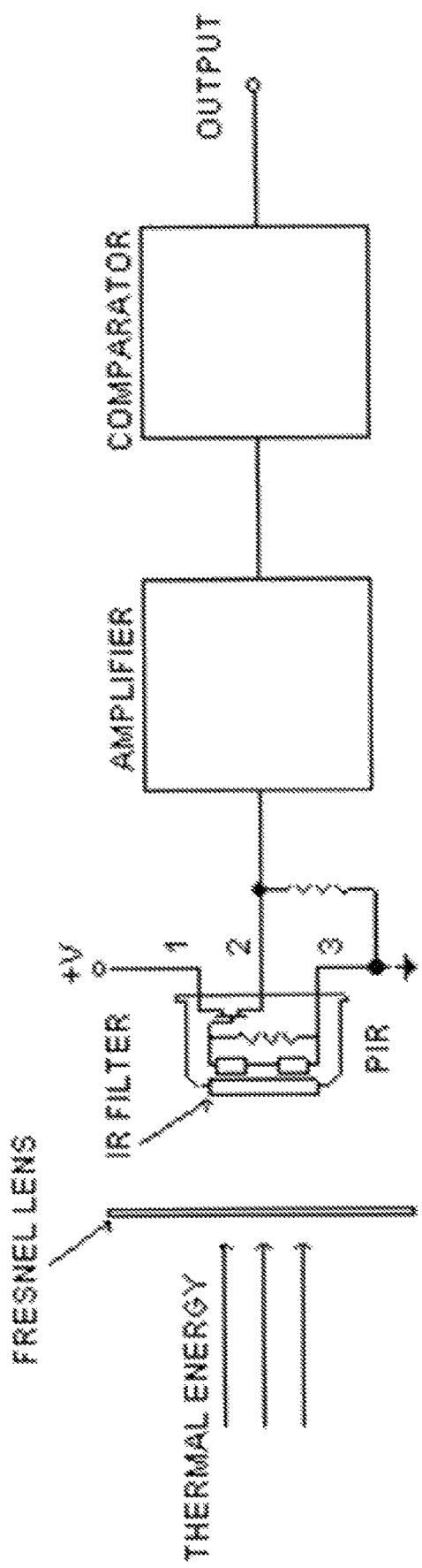

FIG. 154 is an exemplary configuration of an IR temperature sensor.

Figure 155:
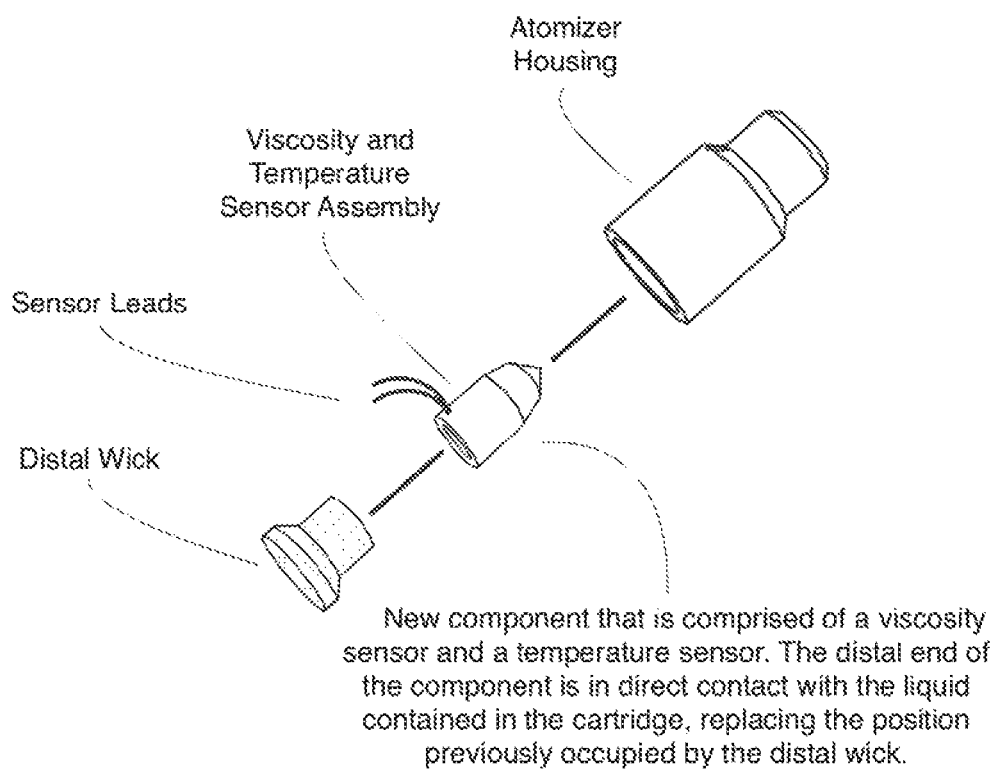

FIG. 155 illustrates the positioning of the viscosity and temperature senor assembly in relation to an atomizer housing and the distal wick.

Figure 156:
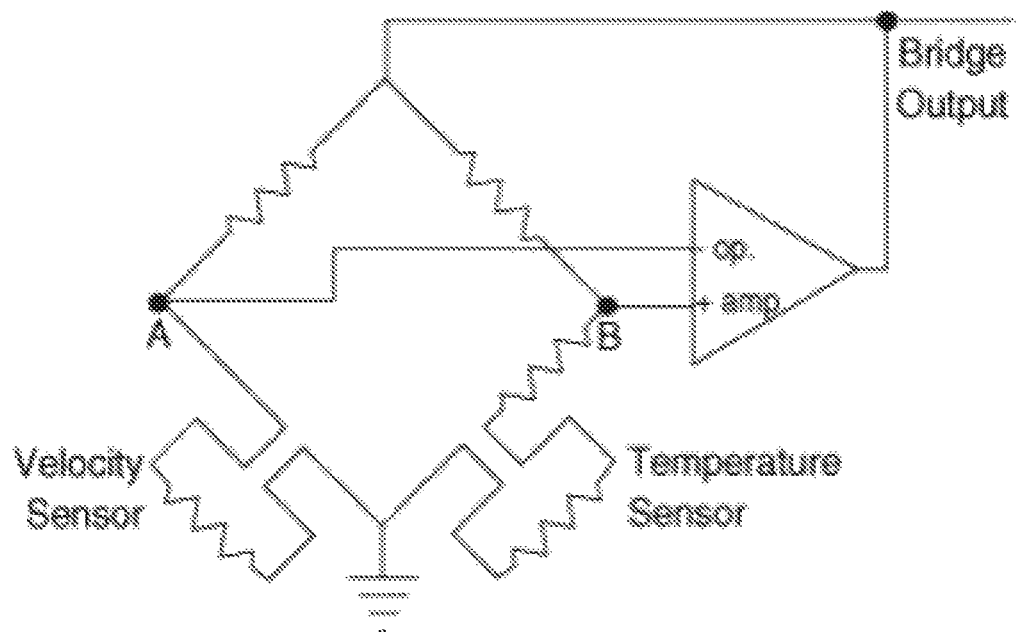

FIG. 156 illustrates a constant temperature anemometer wiring configuration.

Figure 157:
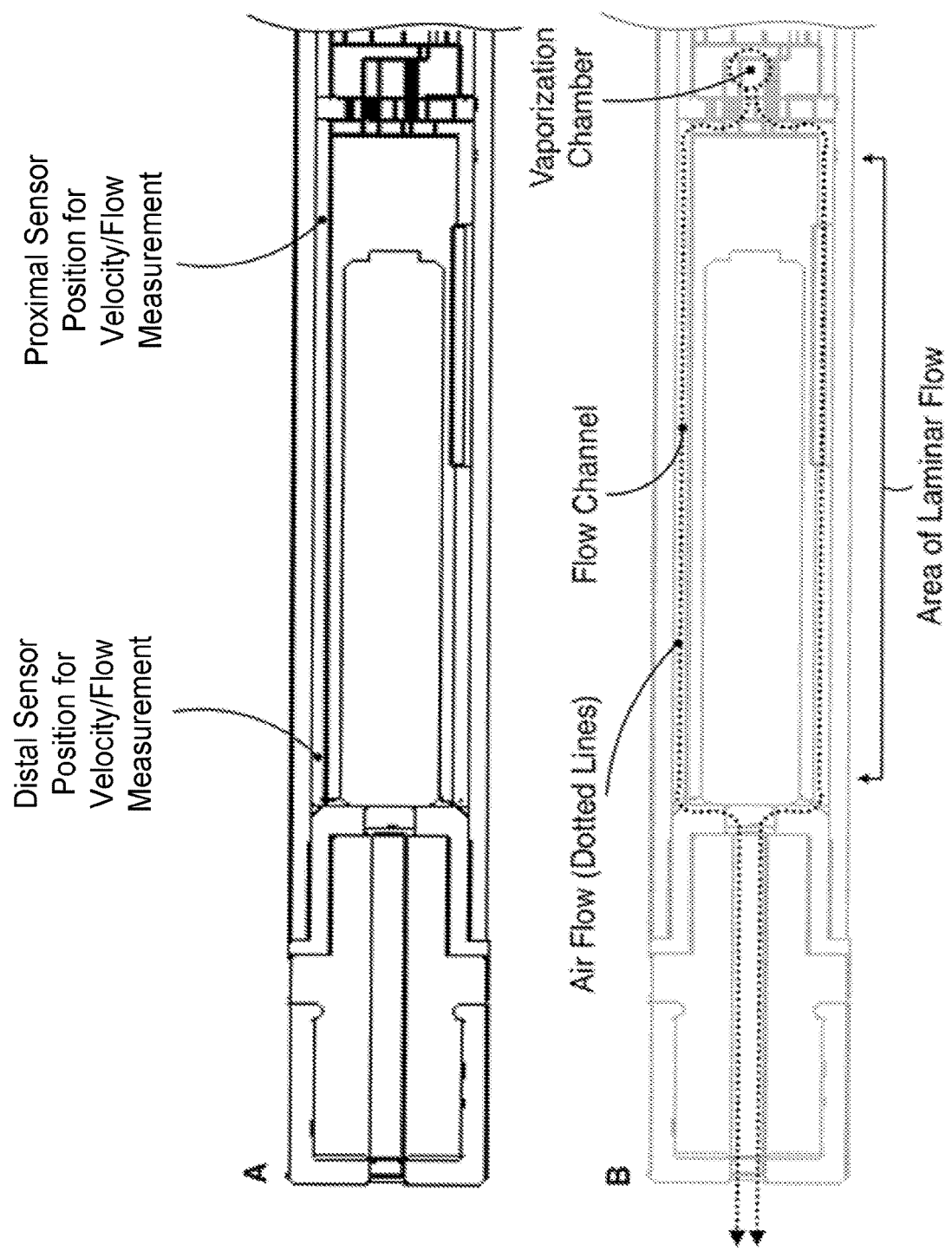

FIG. 157 is a cross section showing a proximal section of a device illustrating flow channels, a path of airflow, and positioning of a calorimeter flow sensor.

FIG. 158 illustrates viscosities of aqueous glycerol (Glycerin) solutions in centipoises/mPa.

Figure 159:
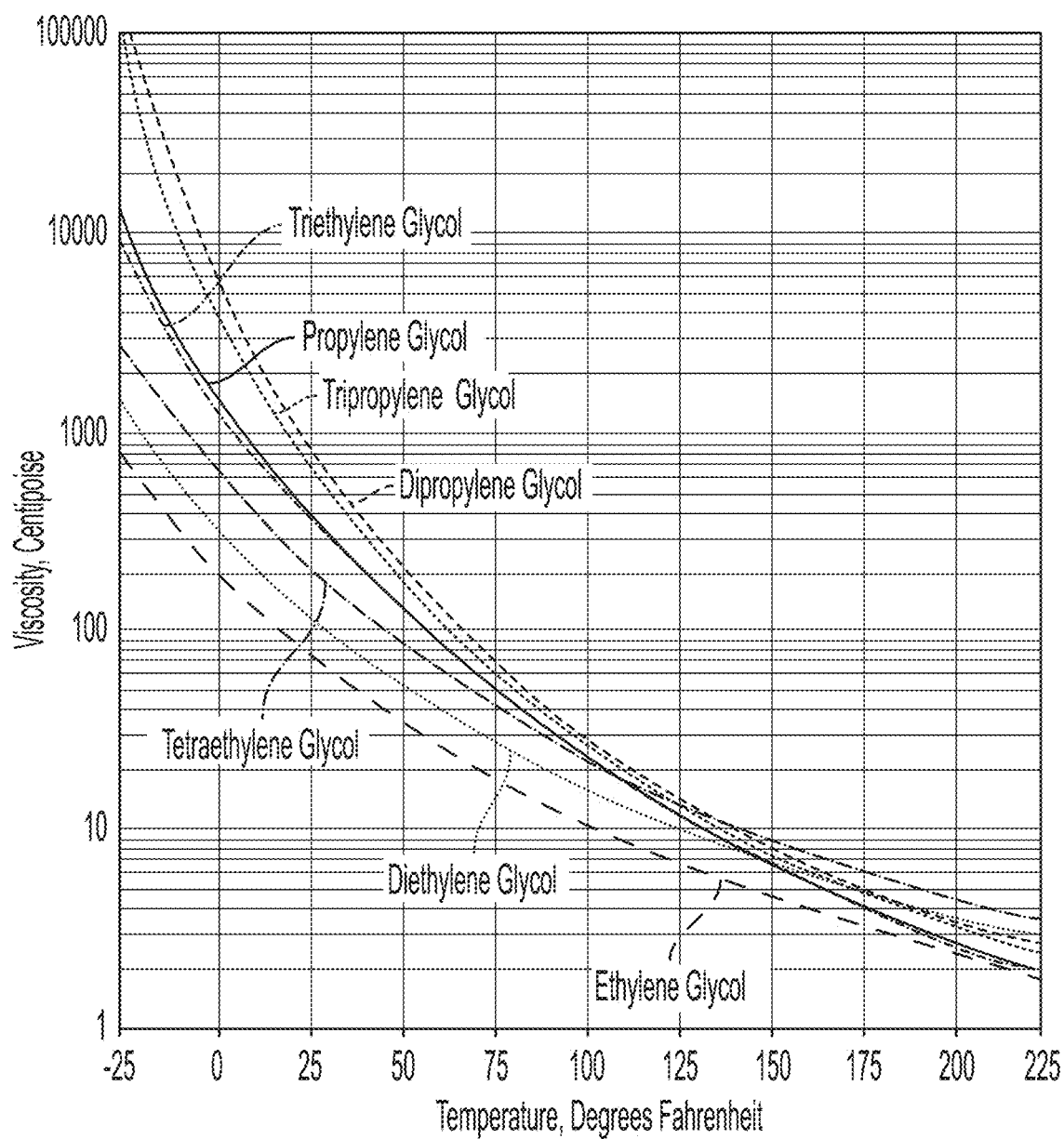

FIG. 159 illustrates temperature viscosity of anhydrous glycols.

Figure 160:
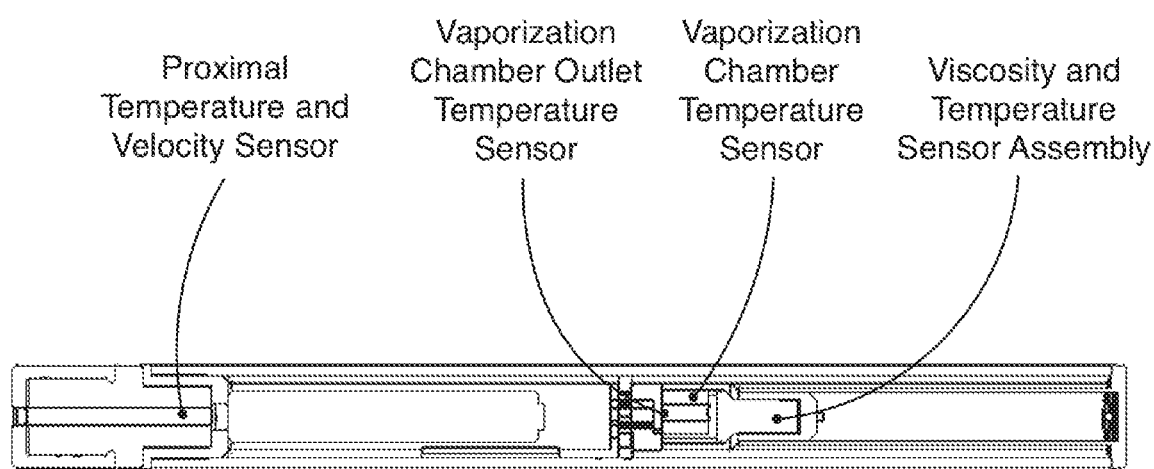

FIG. 160 illustrates exemplary locations for the sensors.

Figure 161:
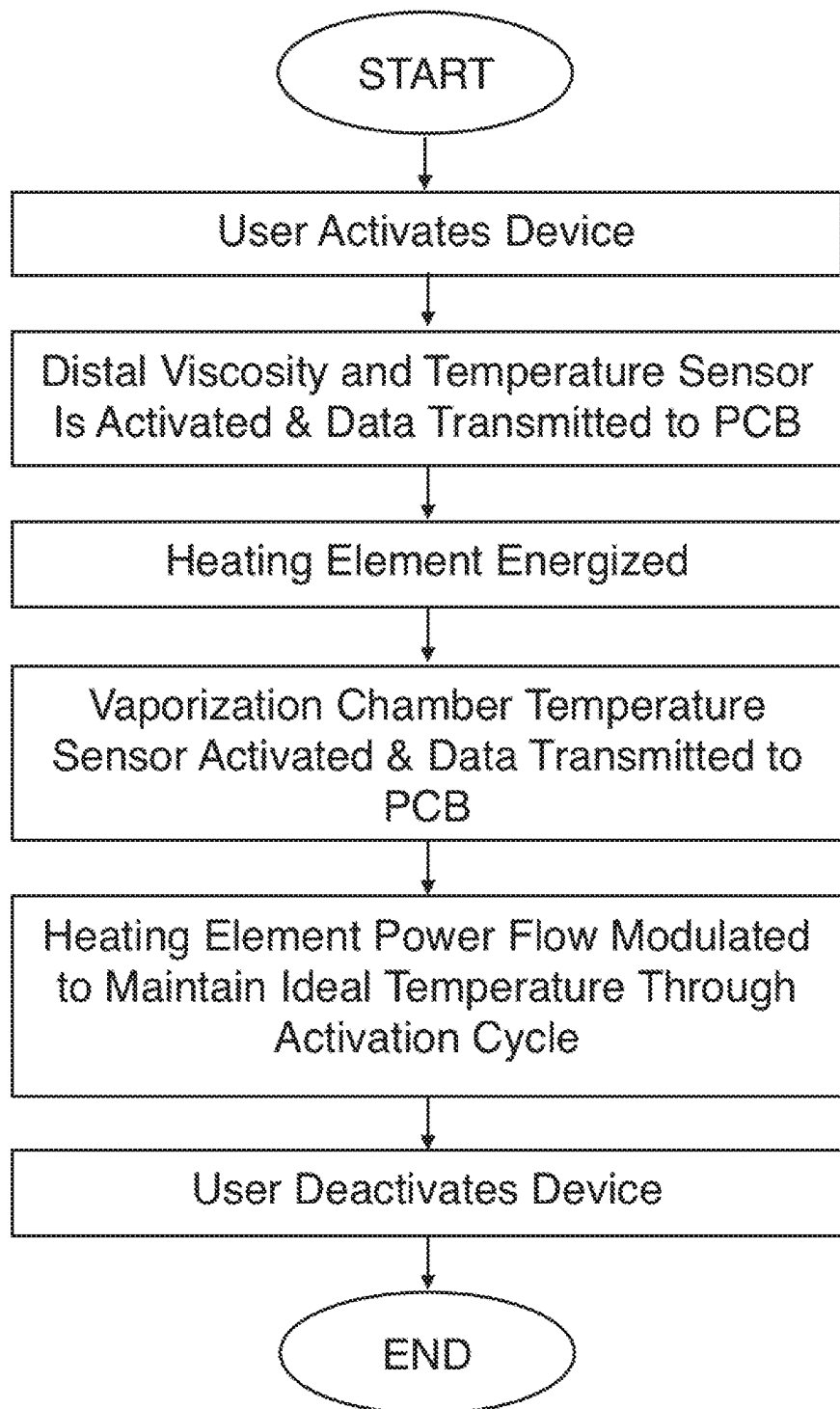

FIG. 161 is a diagram illustrating sensor controlled/dependent activation cycle.

Figure 162:
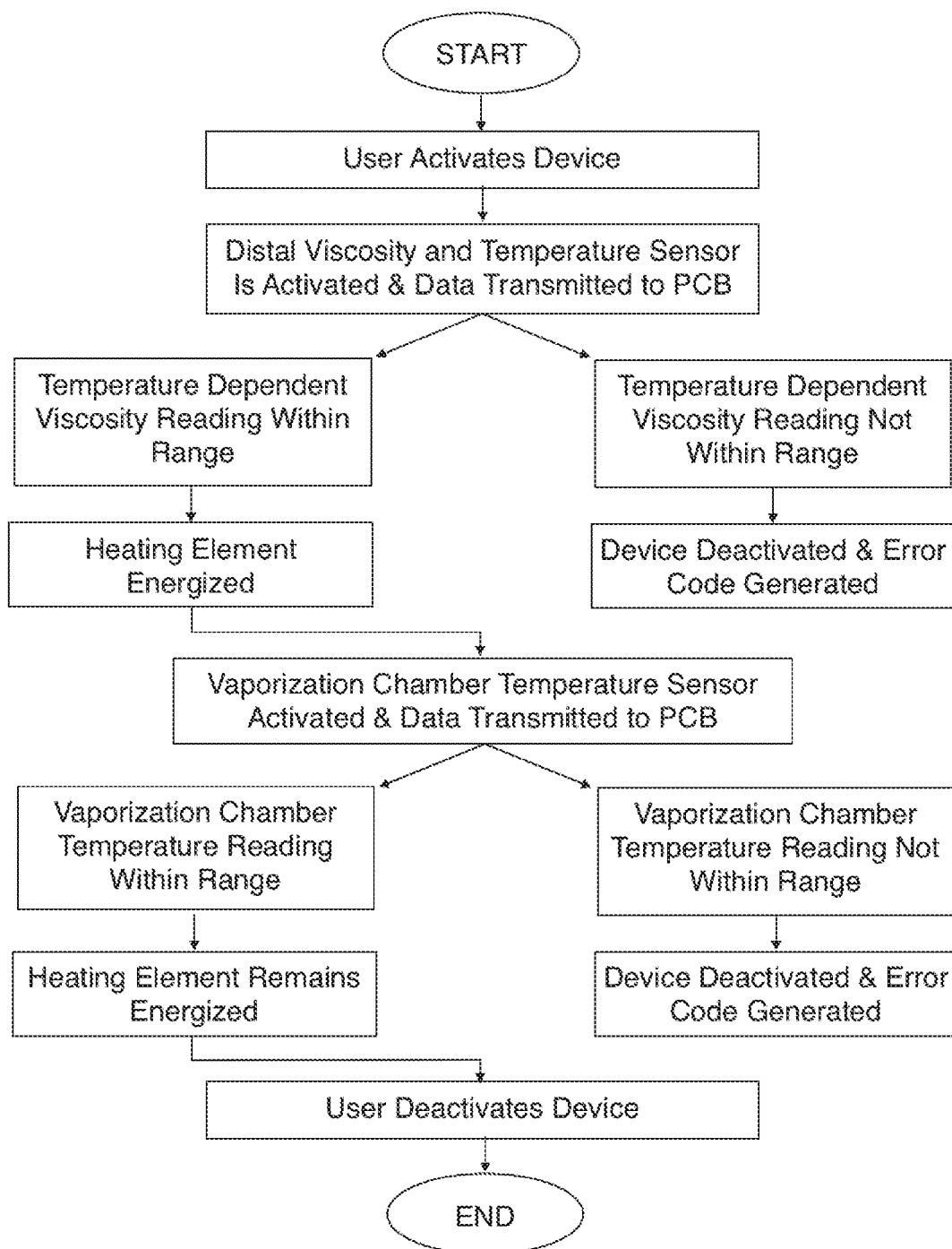

FIG. 162 is a diagram illustrating a sensor controlled/dependent activation cycle with deactivation of device dependent on sensor readings within an acceptable range.

Figure 163:
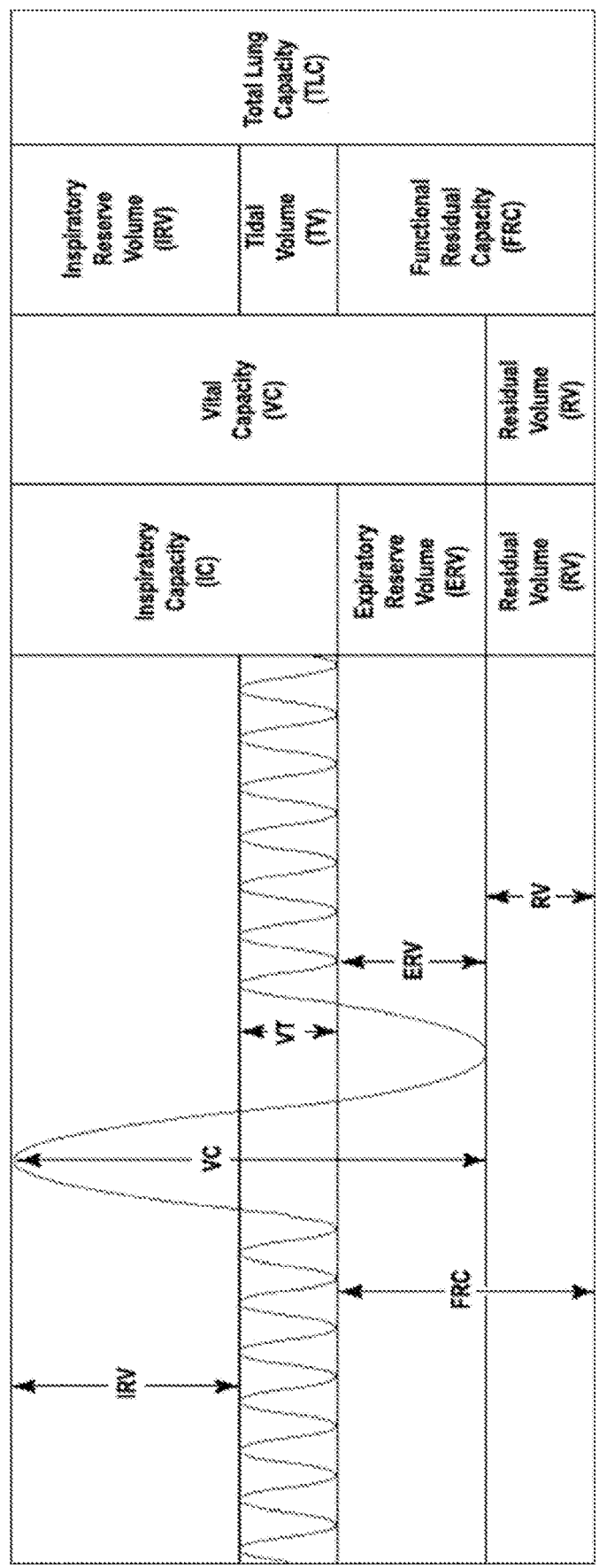

FIG. 163 is a spirograph showing lung capacity and pulmonary metrics relevant to function testing.

Figure 164:
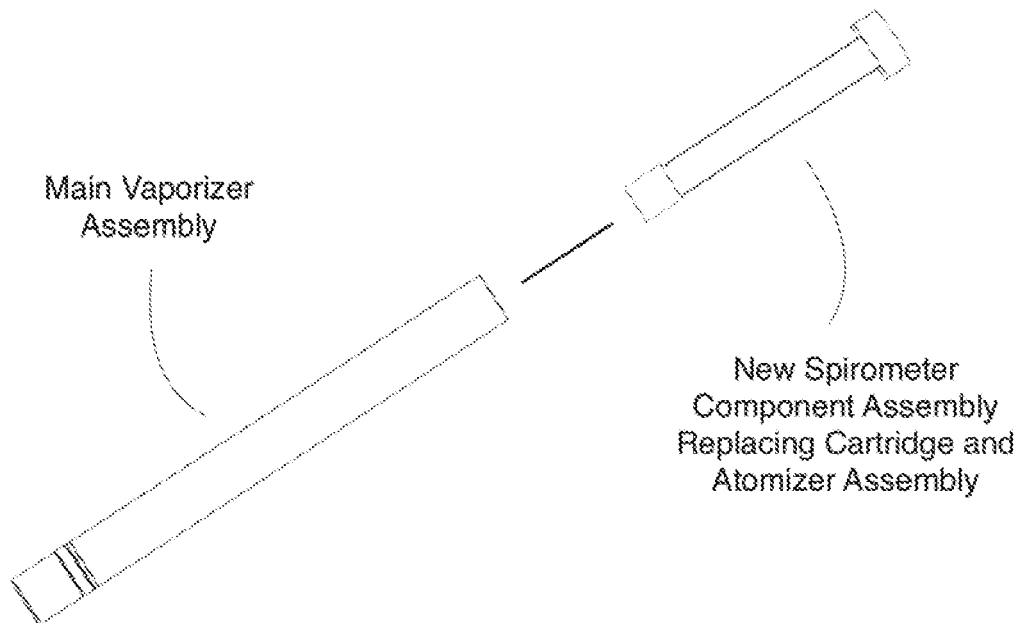

FIG. 164 illustrates a vaporizer with a digital interface cartridge assembly.

Figure 165:
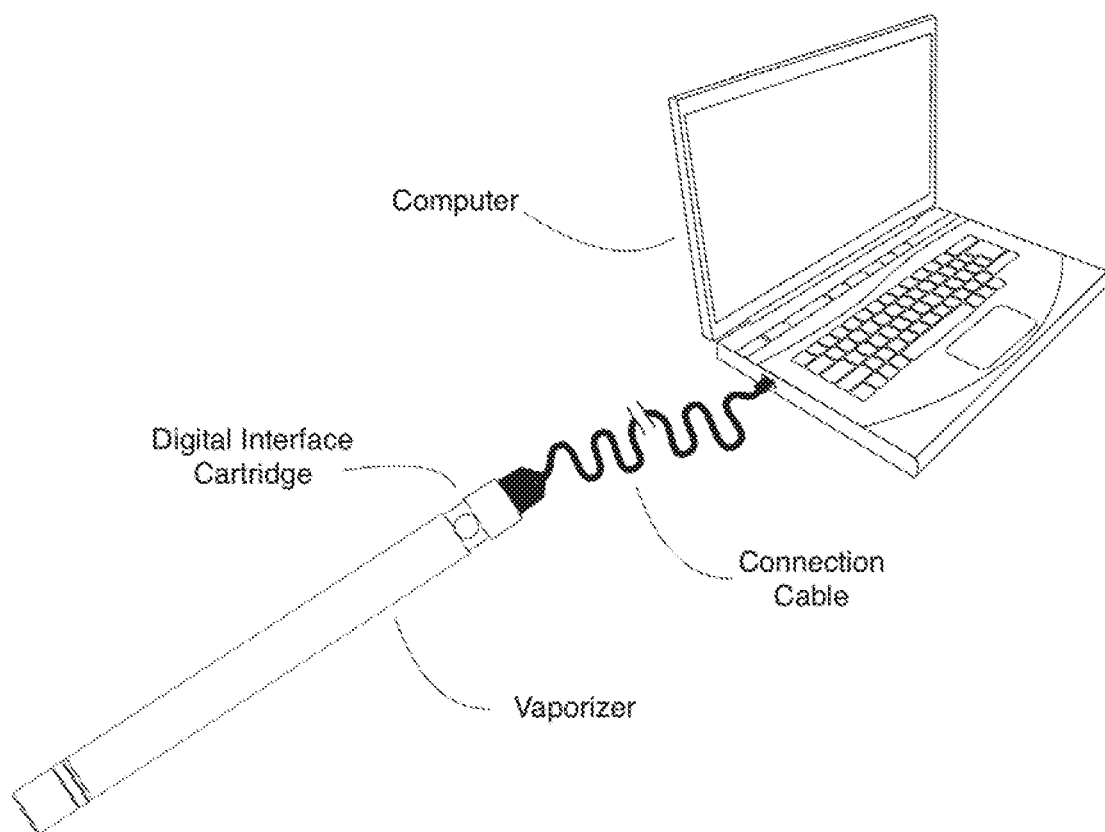

FIG. 165 illustrates an embodiment of a vaporizer functioning as a spirometer that is connected to a digital interface.

Figure 166:
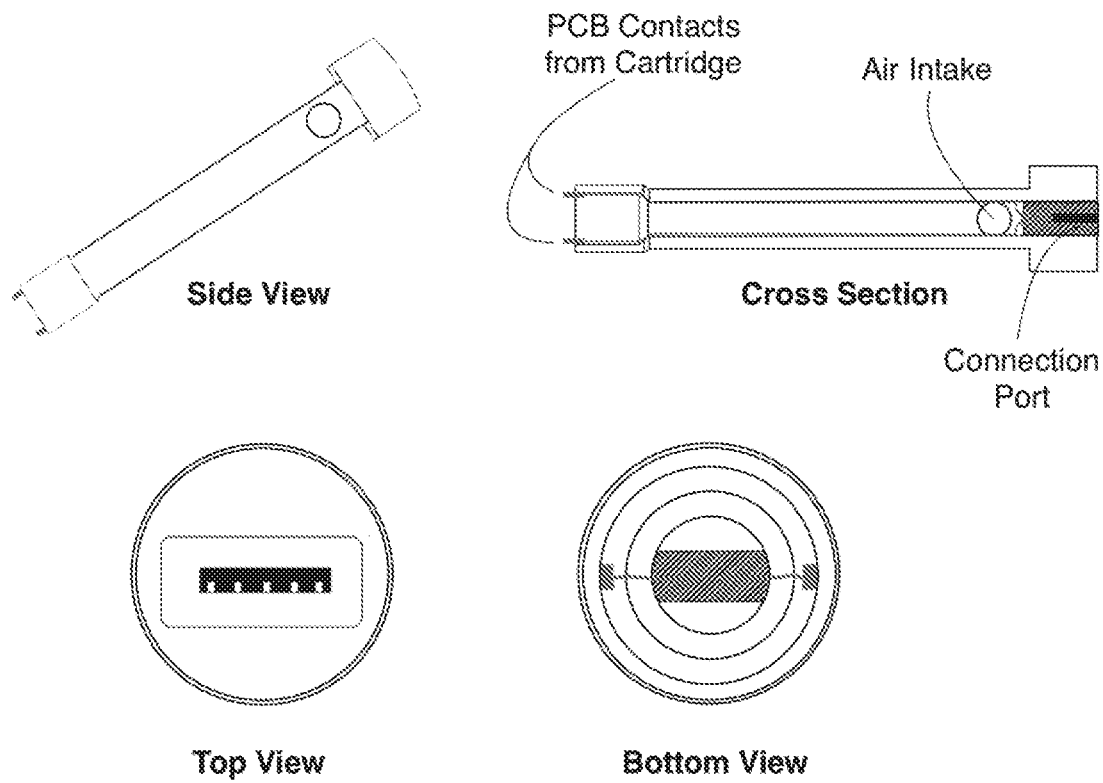

FIG. 166 illustrates a general overview of the digital interface component.

FIG. 167 illustrates the configuration of a mouthpiece intended for use with device in the spirometer application.

Figure 168:
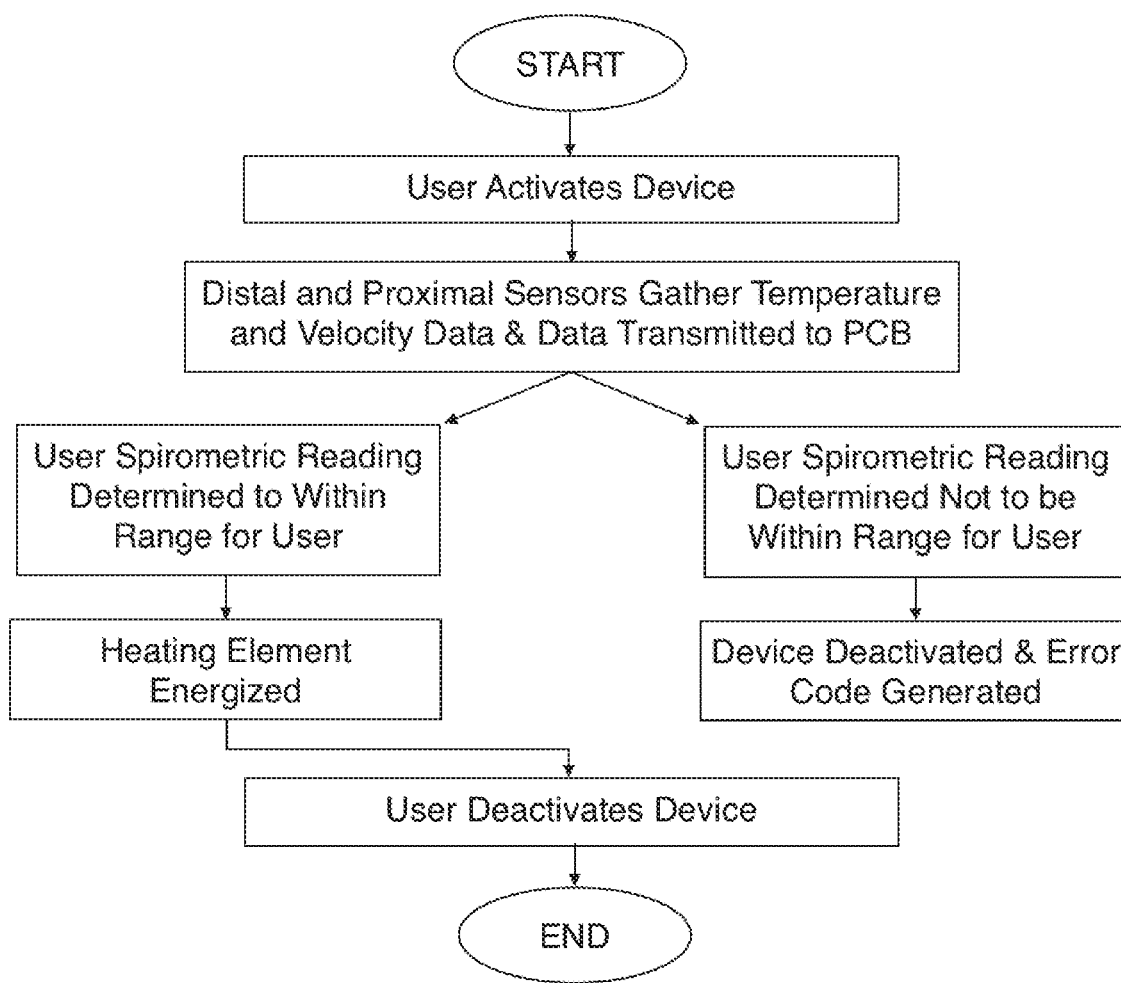

FIG. 168 is a diagram illustrating sensor controlled/dependent activation cycle with deactivation of device dependent on sensor readings for a user specific spirometric profile within an acceptable range.

Figure 169:
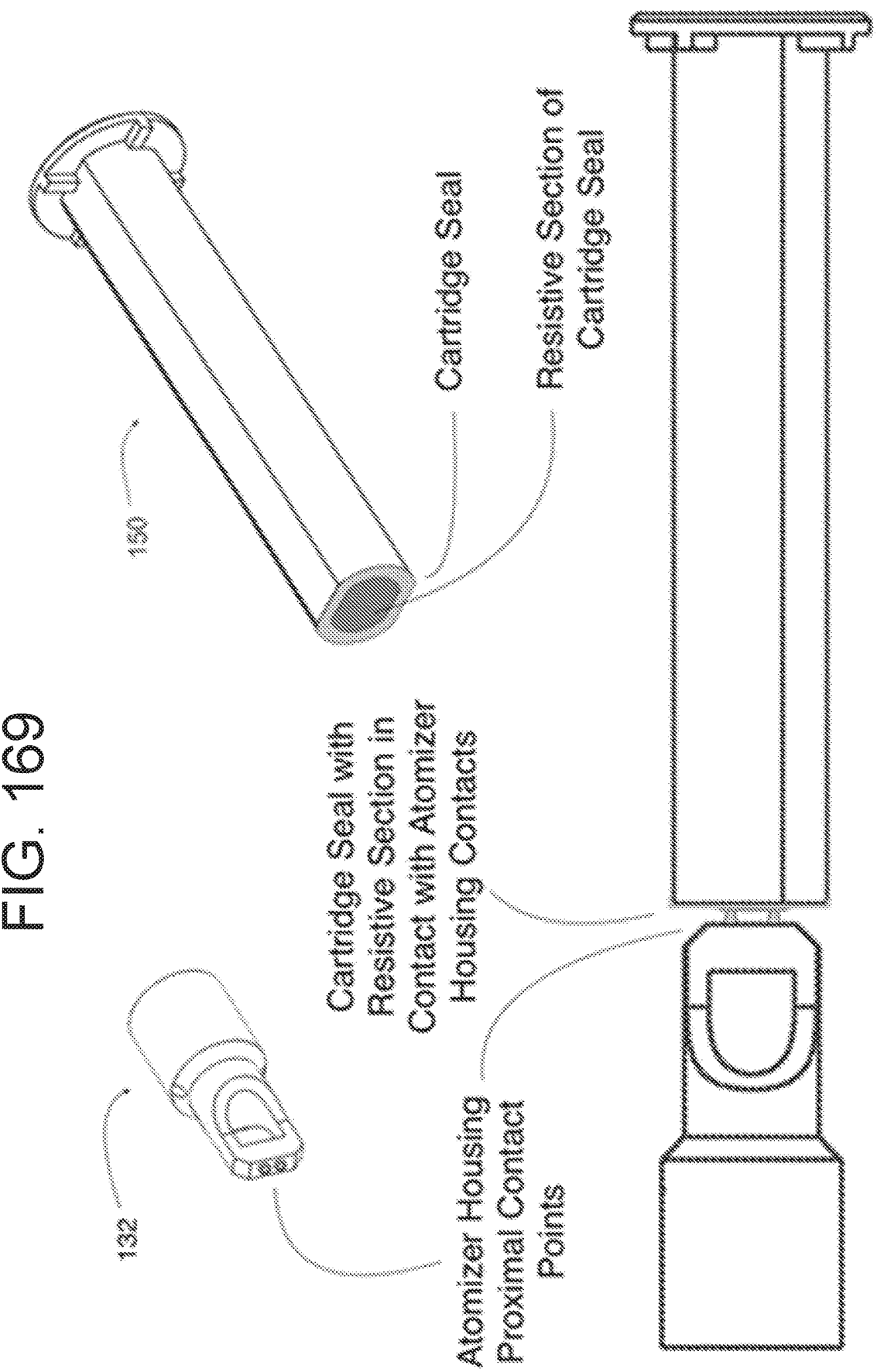

FIG. 169 illustrates a cartridge with seal and resistive section for interfacing with contacts on the atomizer housing.

Figure 170:
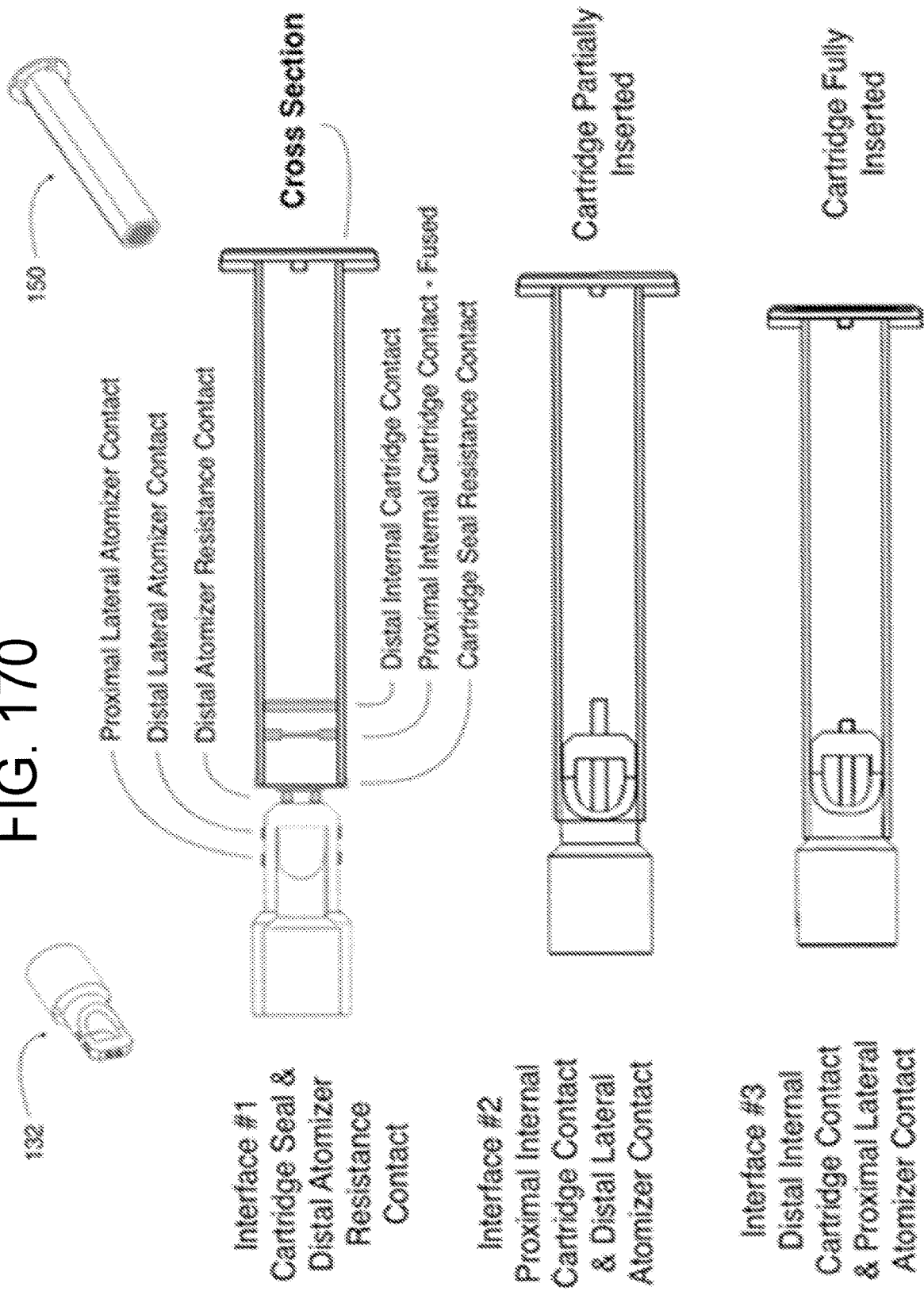

FIG. 170 illustrates an atomizer housing contacts and cartridge weal and internal cartridge contact arrangement.

Figure 171:
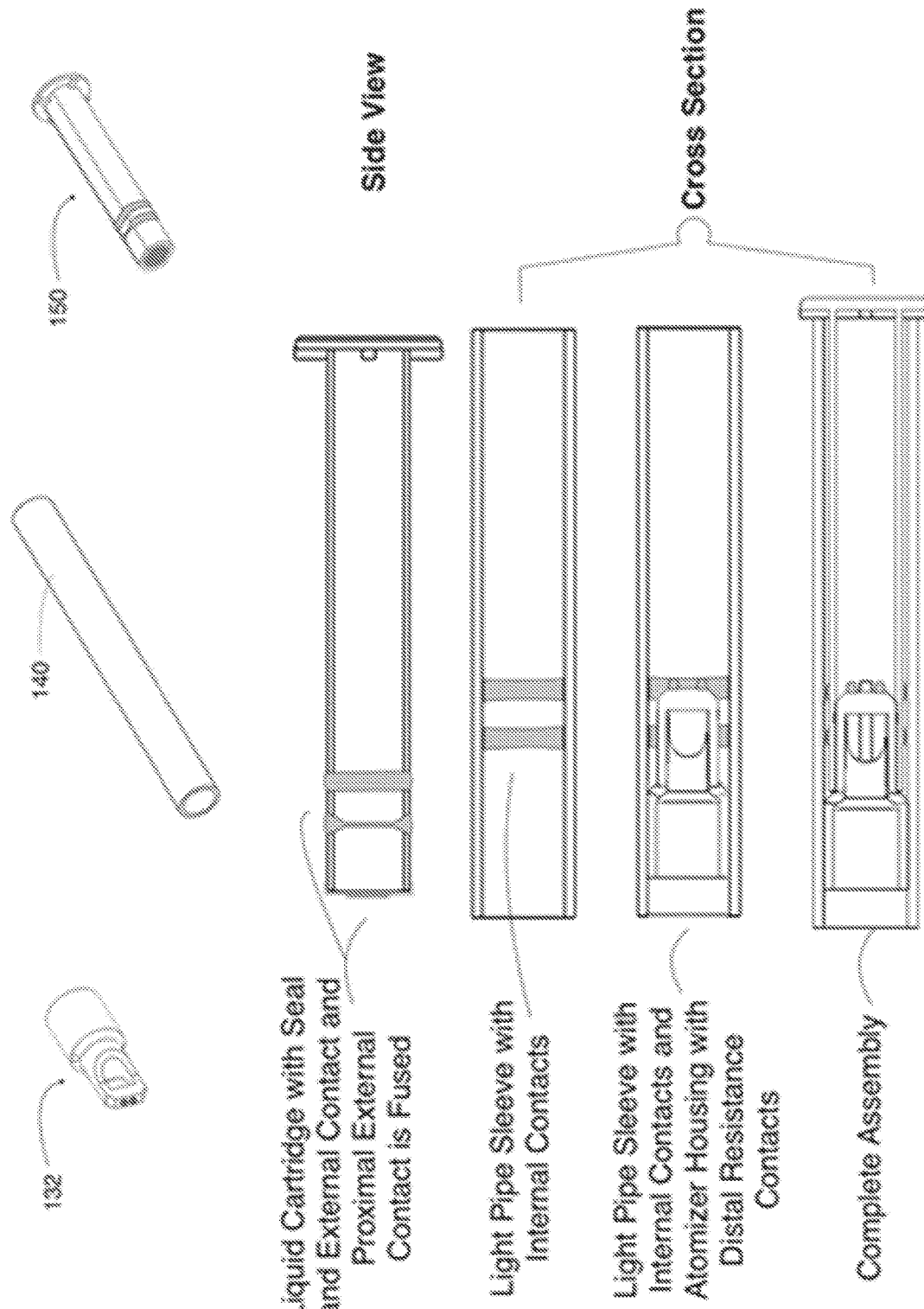

FIG. 171 illustrates an atomizer housing contacts, light pipe sleeve contacts, cartridge seal and external cartridge contact arrangement.

FIG. 172 illustrates a contact mediated sequential cartridge insertion process.

FIG. 173 illustrates contact mediated sequential cartridge removal process.

FIG. 174 illustrates a liquid cartridge and light pipe sleeve features.

Figure 175:
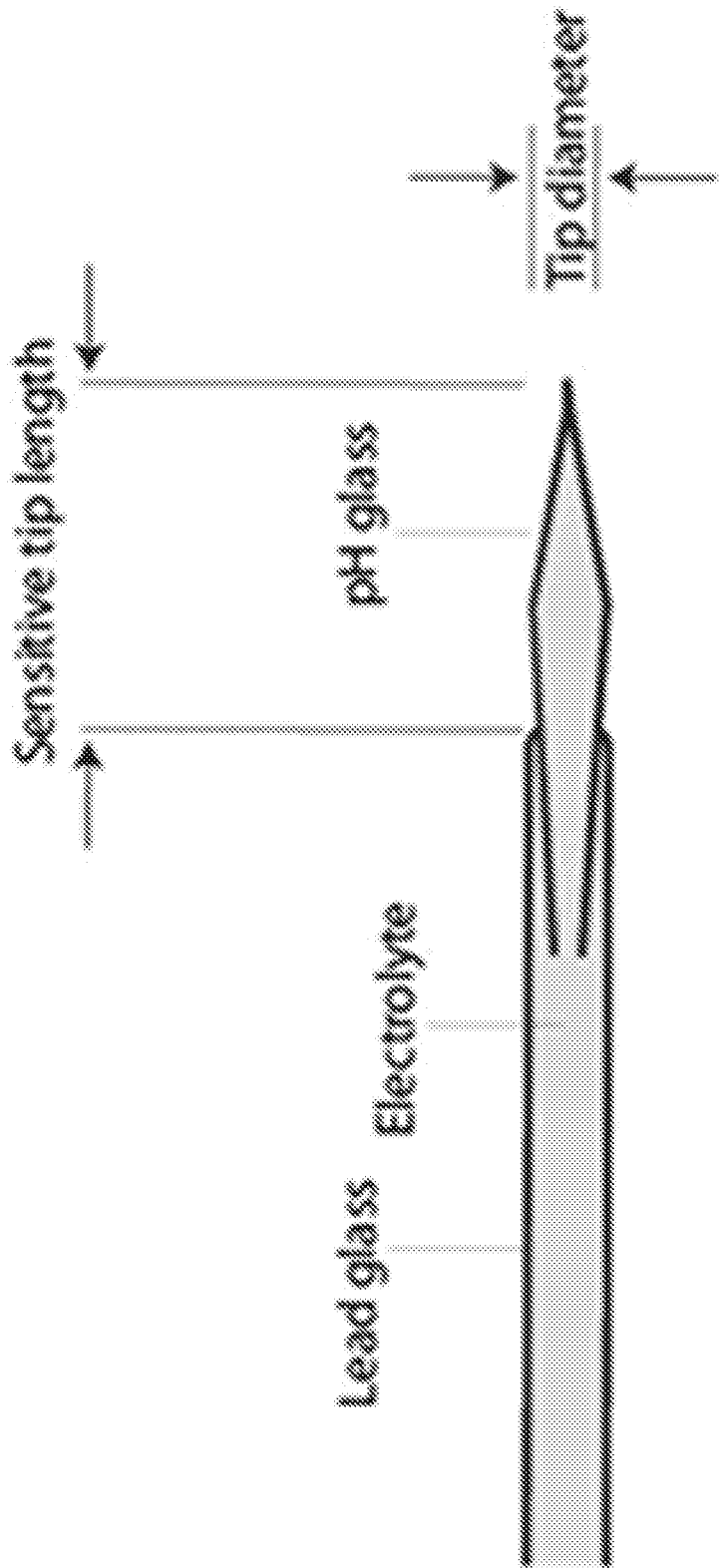

FIG. 175 illustrates a configuration of a microelectrode for the purpose of measuring pH in a liquid medium.

Figure 176:
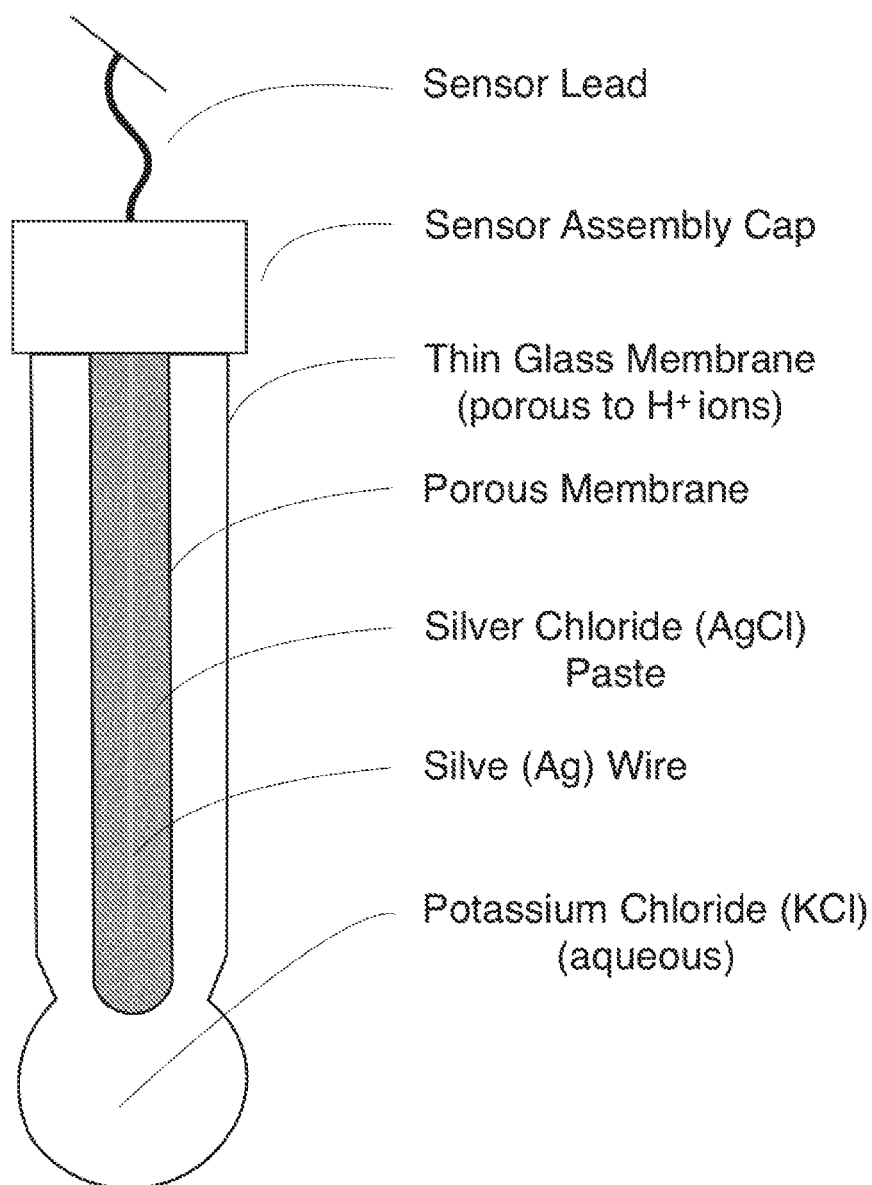

FIG. 176 illustrates a pH sensor assembly where the sensor is effectively impermeable except for Hydrogen ions that allow for pH measurement of the sample fluid.

Figure 177:
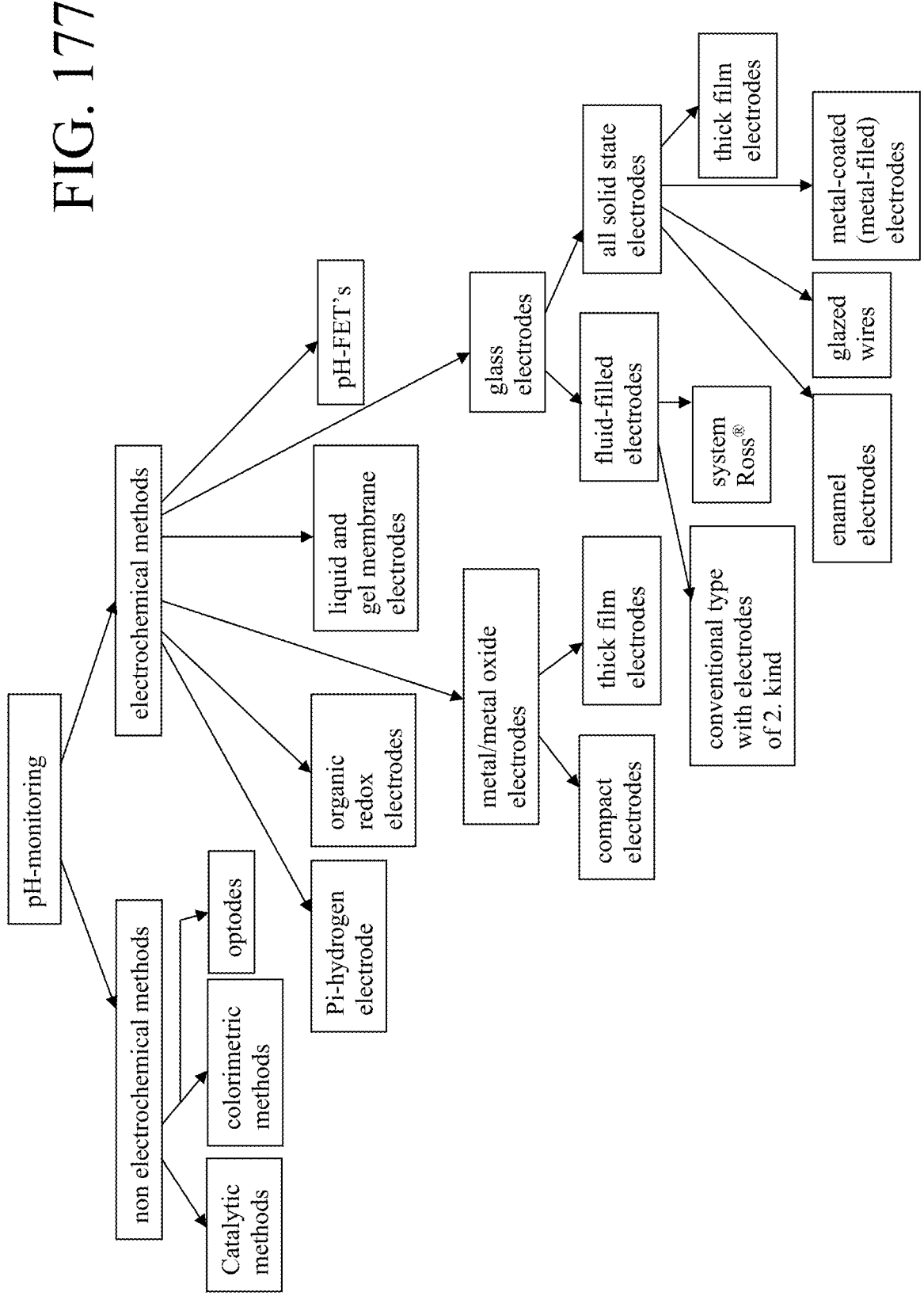

FIG. 177 illustrates various methods and technologies for measuring pH in liquid samples.

Figure 178:
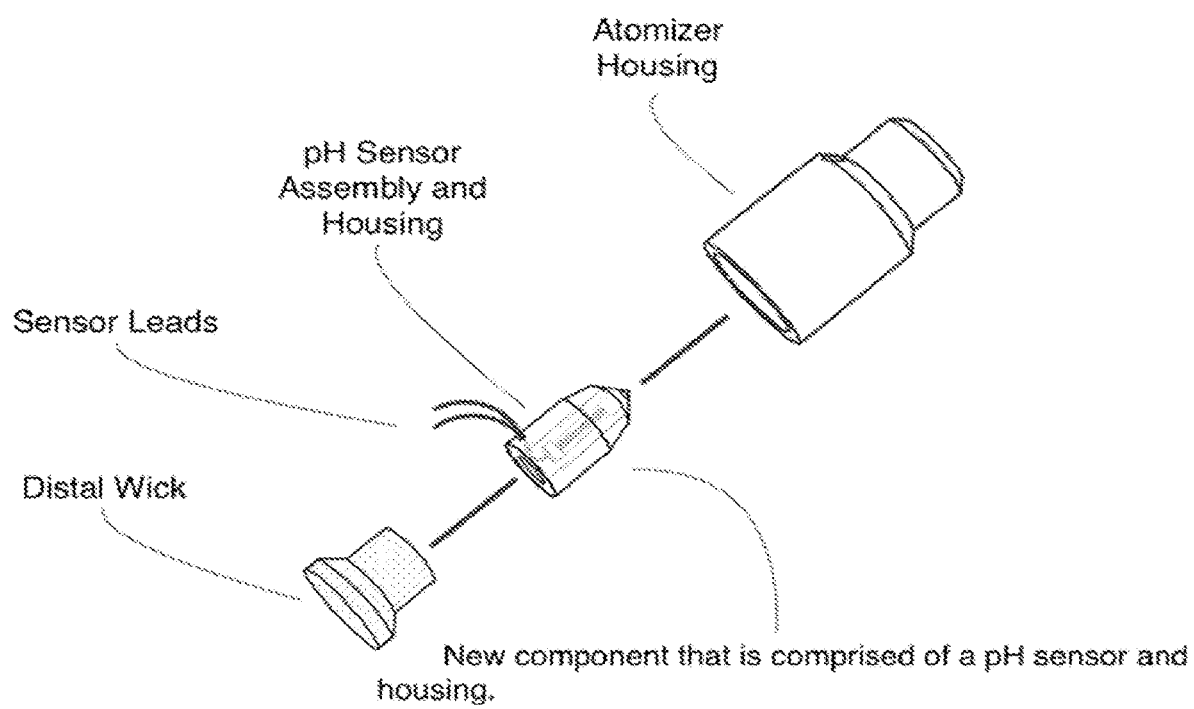

FIG. 178 illustrates a pH sensor assembly and housing in relation to the atomizer housing and distal wick.

Figure 179:
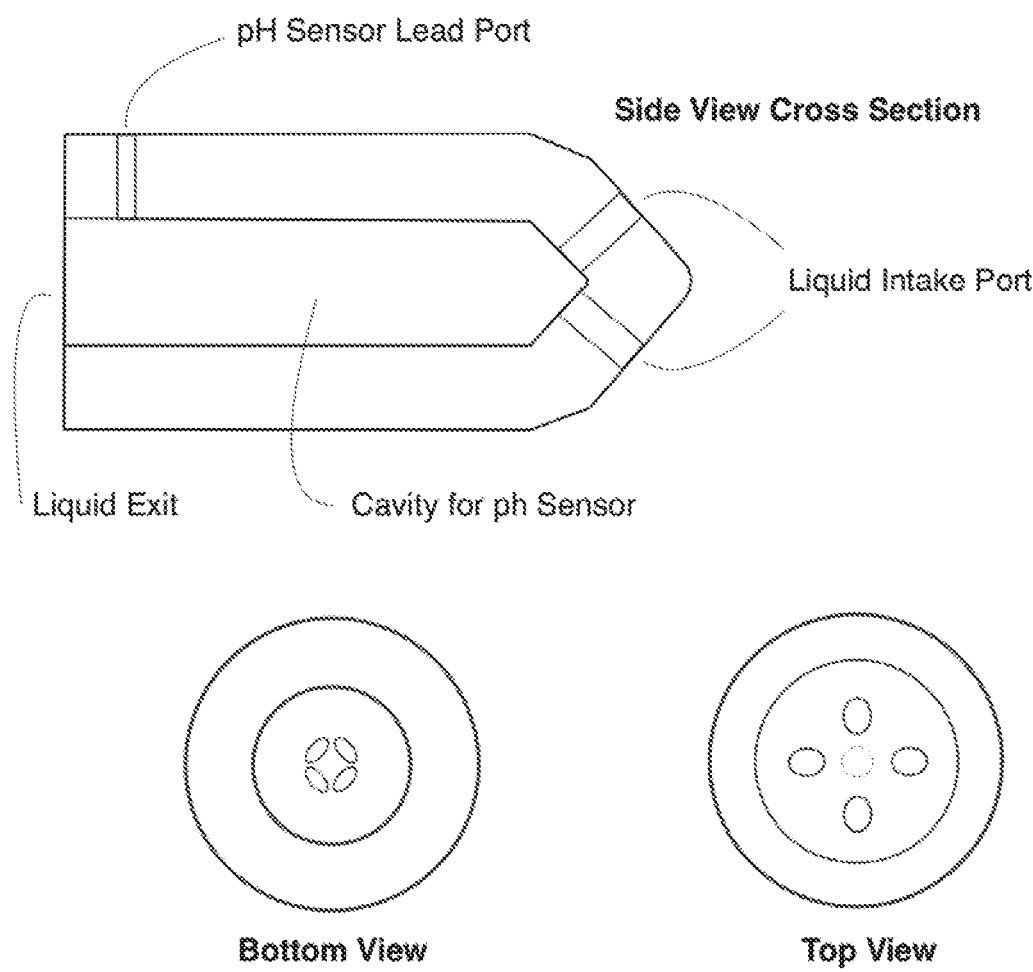

FIG. 179 illustrates a pH sensor housing.

Figure 180:
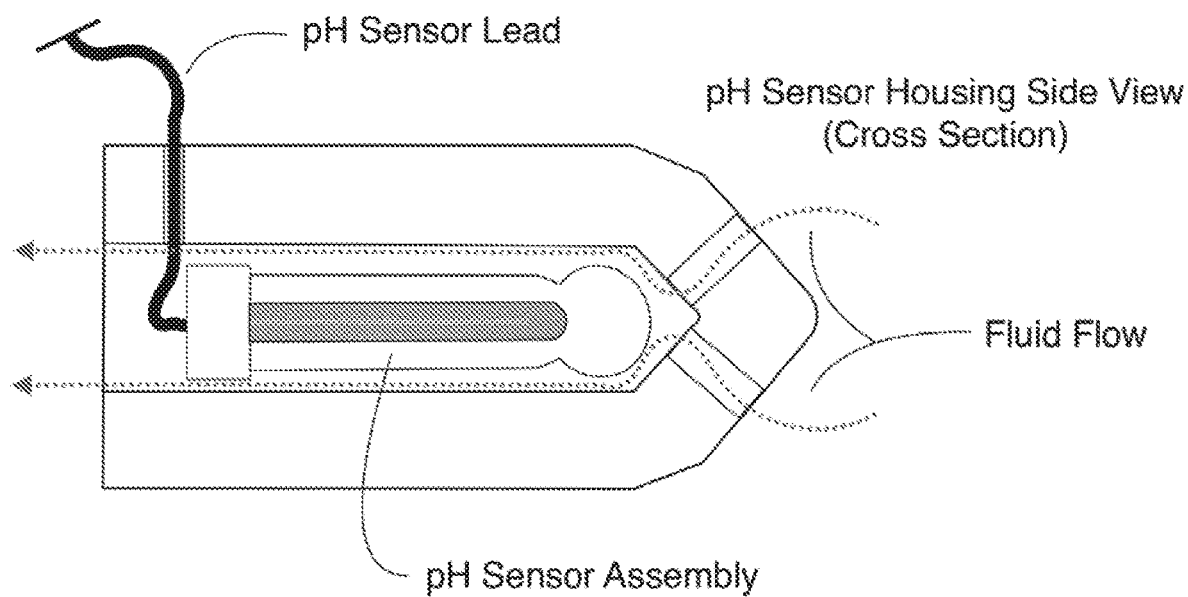

FIG. 180 illustrates a pH sensor housing and pH sensor assembly.

Figure 181:
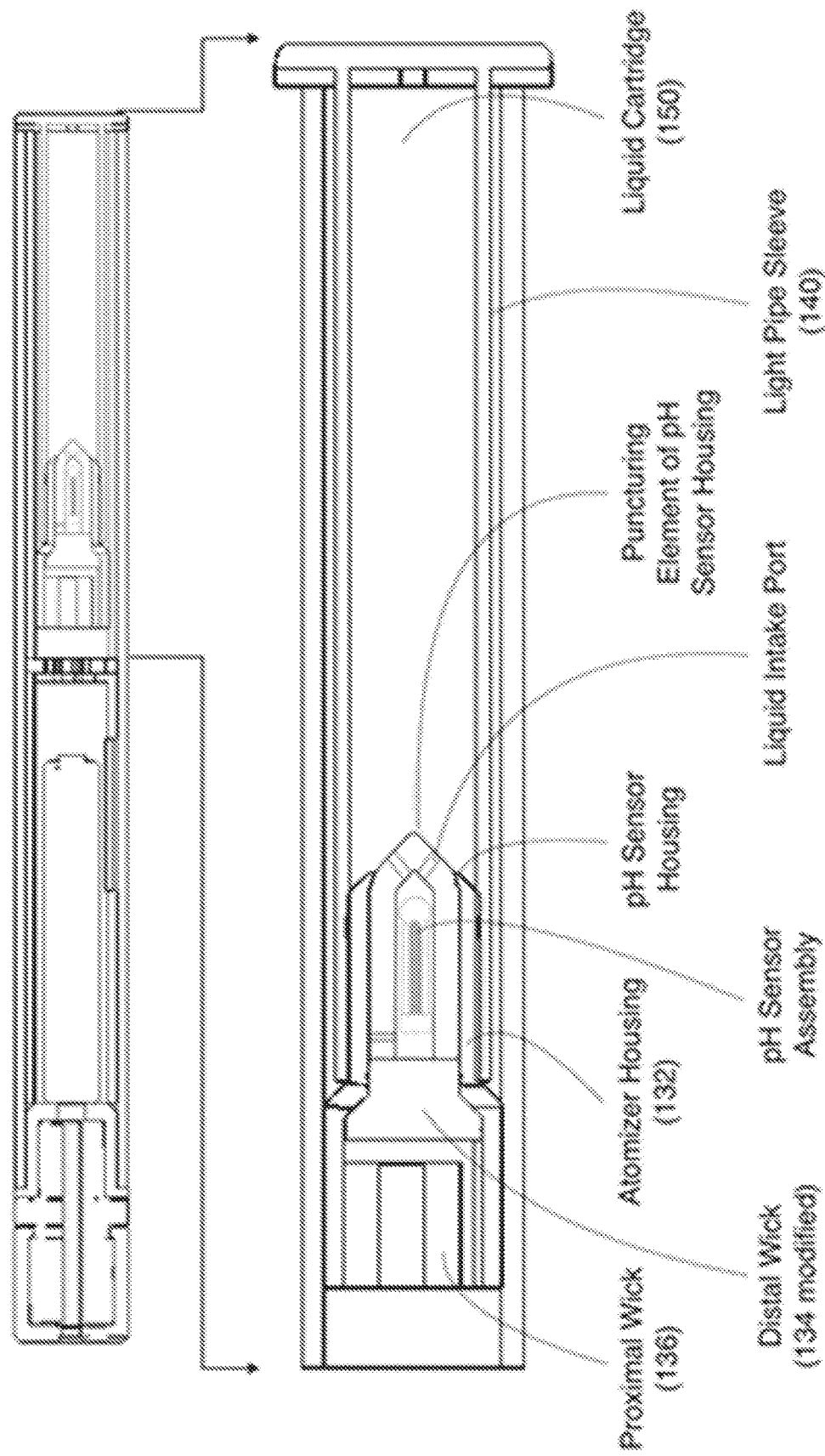

FIG. 181 illustrates a cross-section view of a pH sensor assembly and housing.

Figure 182:
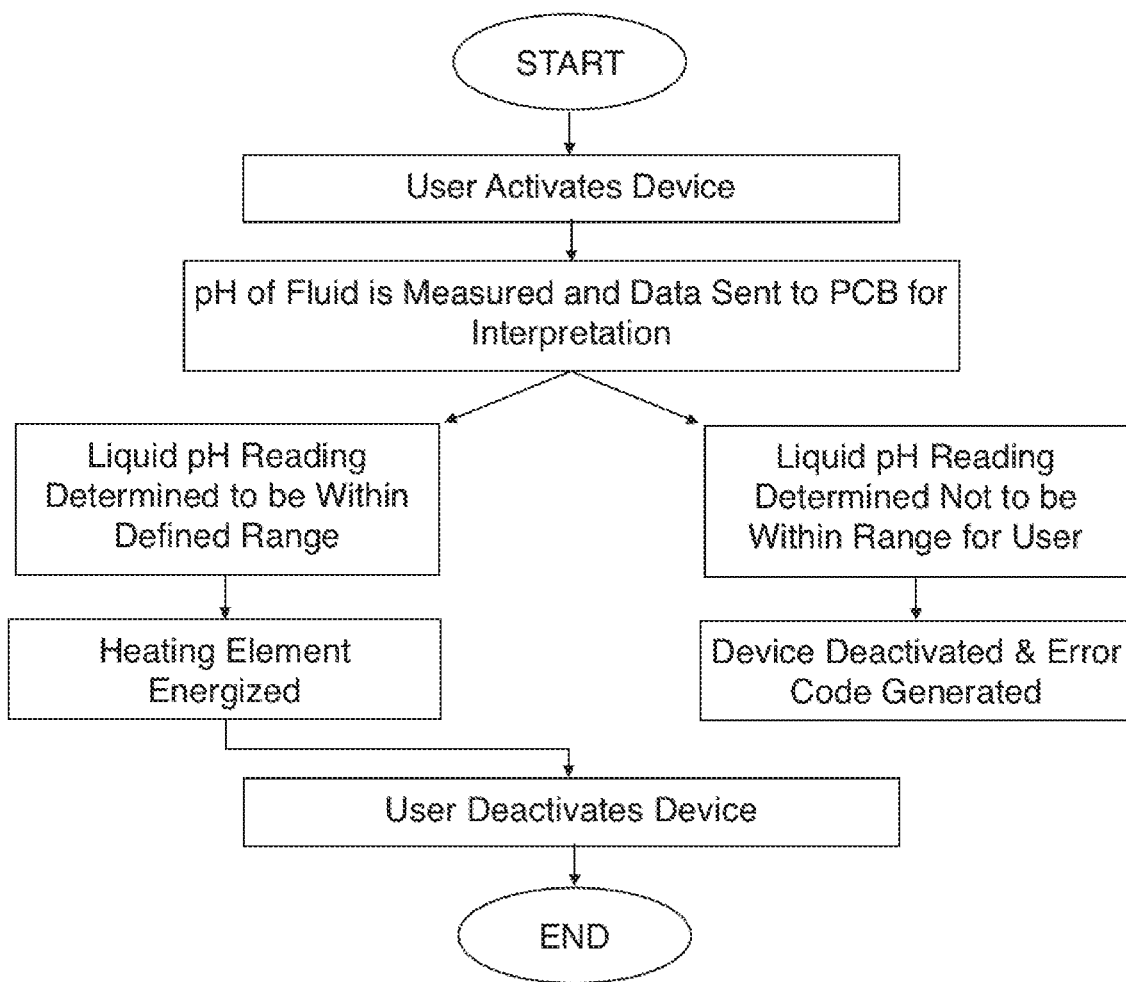

FIG. 182 illustrates a pH sensor controlled/dependent activation cycle.

Figure 183:
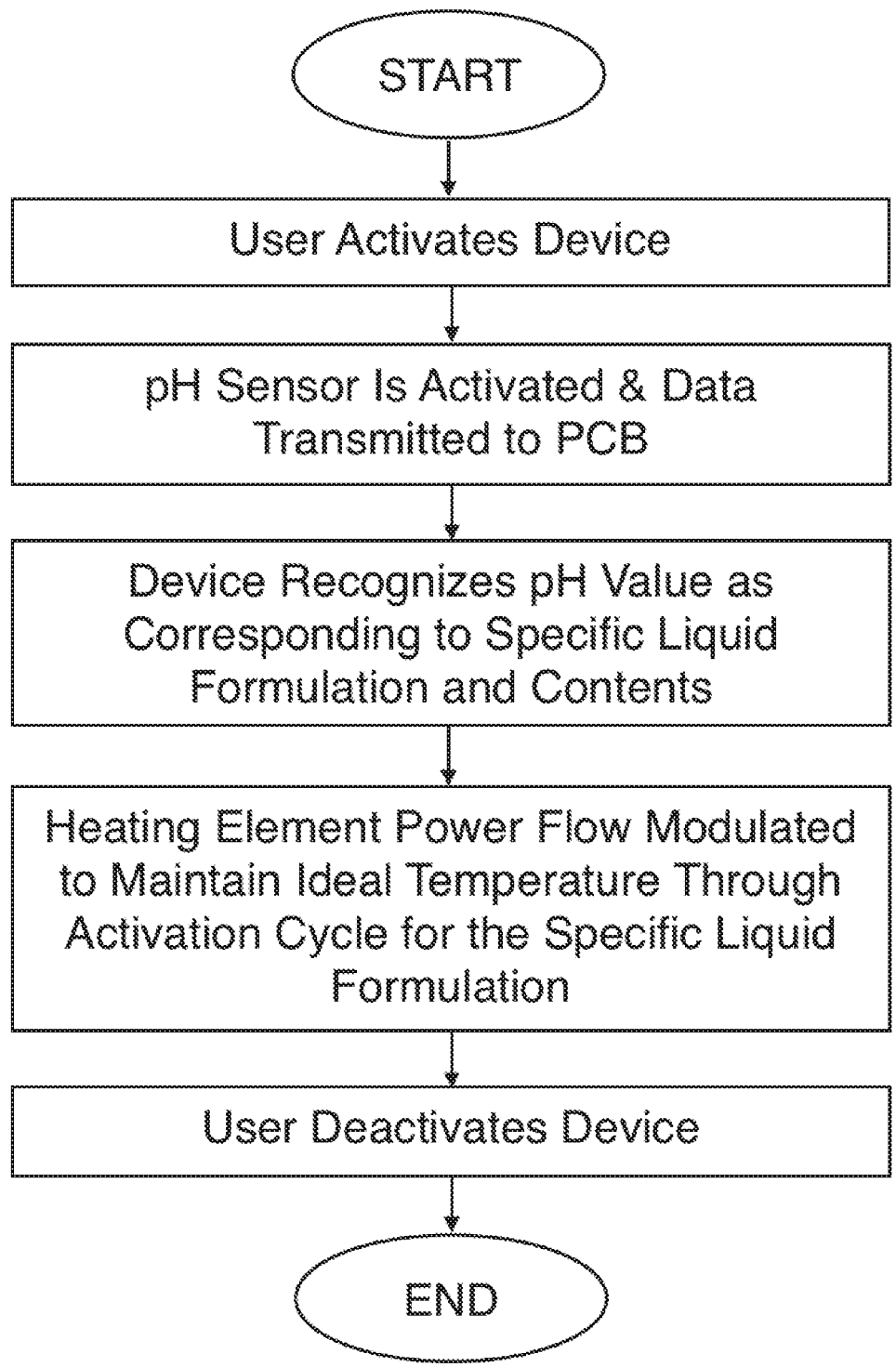

FIG. 183 illustrates a pH sensor controlled/dependent device modulation.

FIG. 184 illustrates a modified embodiment of the vaporizer mouthpiece that has a larger internal diameter to allow for space to position the turbine assembly.

Figure 185:
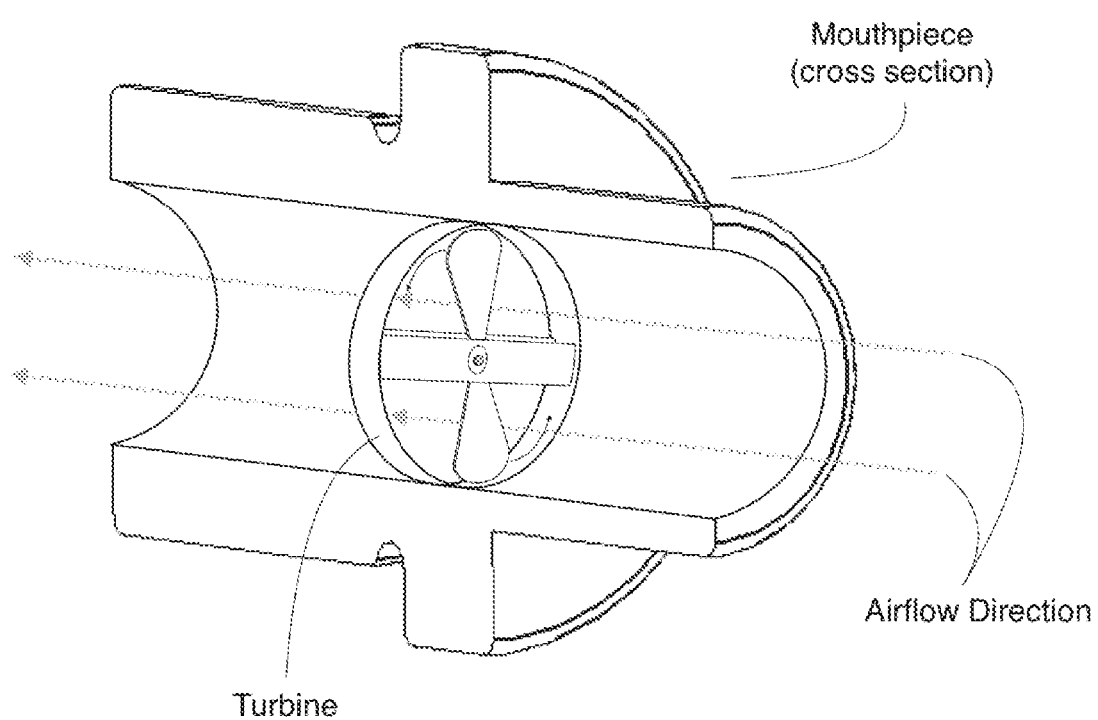

FIG. 185 illustrates a cross-section view of a mouthpiece with a turbine assembly.

Figure 186:
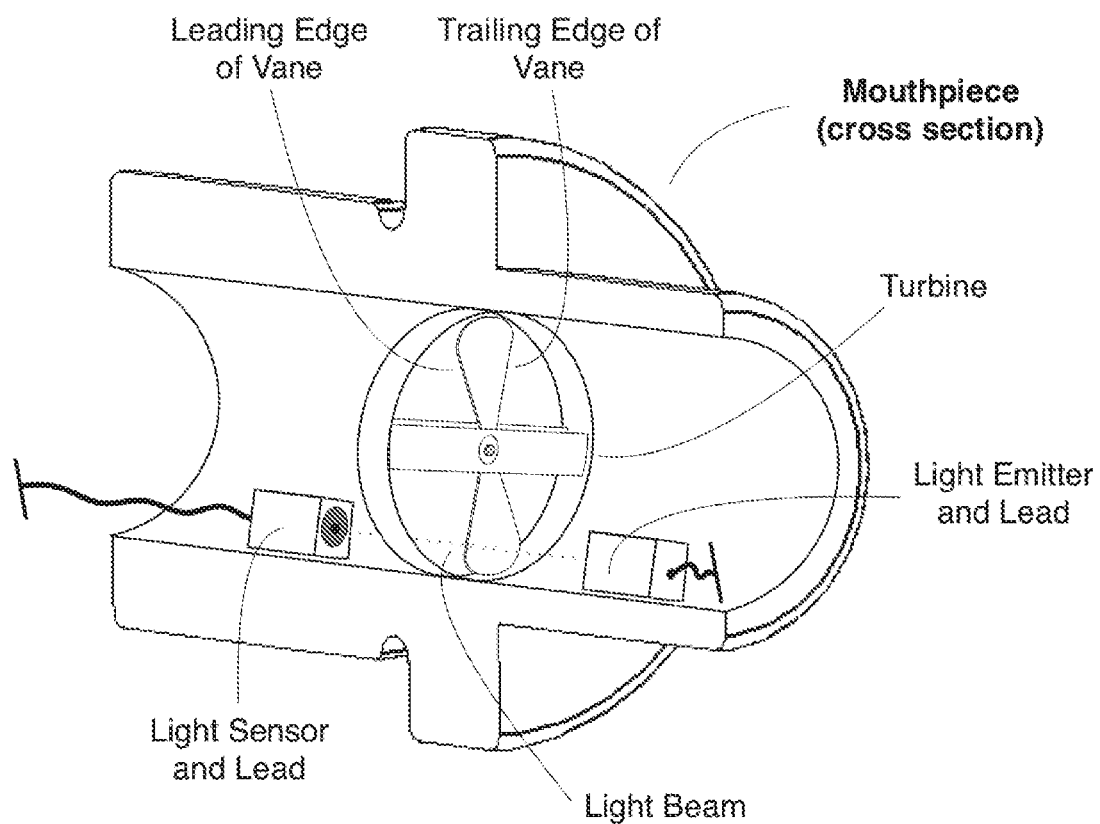

FIG. 186 illustrates a cross section of a mouthpiece with a turbine assembly, emitter, and sensor.

Figure 187:
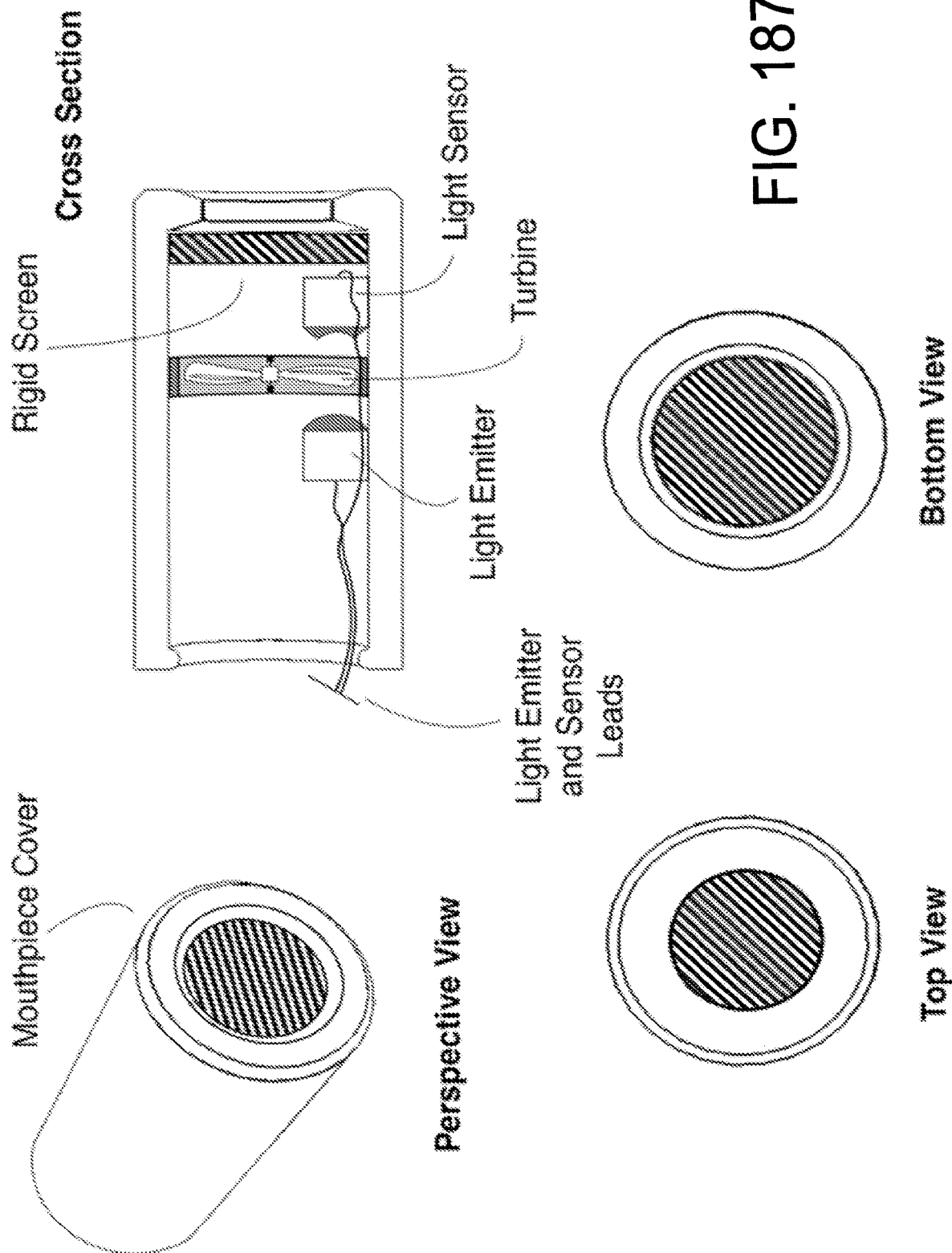

FIG. 187 illustrates a mouthpiece cover with turbine and sensor assembly.

Figure 188:
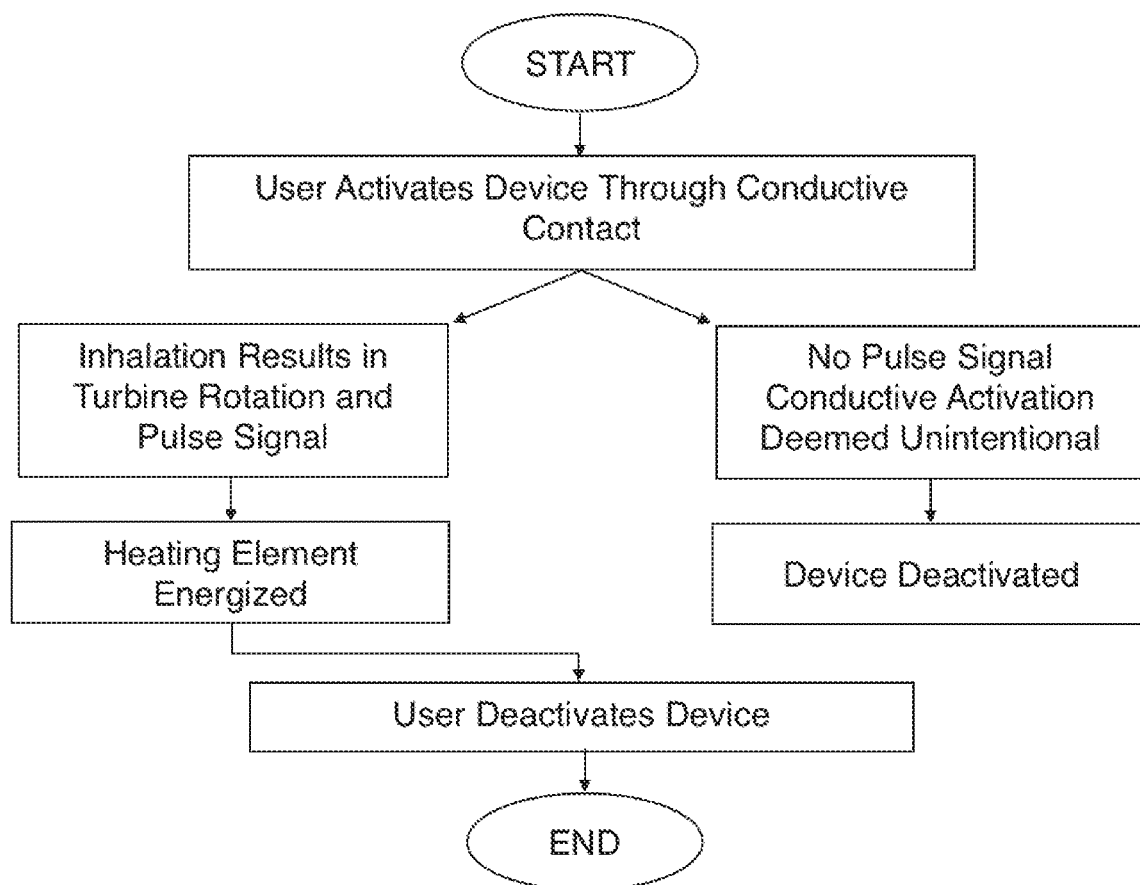

FIG. 188 illustrates a pulse signal mediated activation of the vaporizer.

Figure 189:
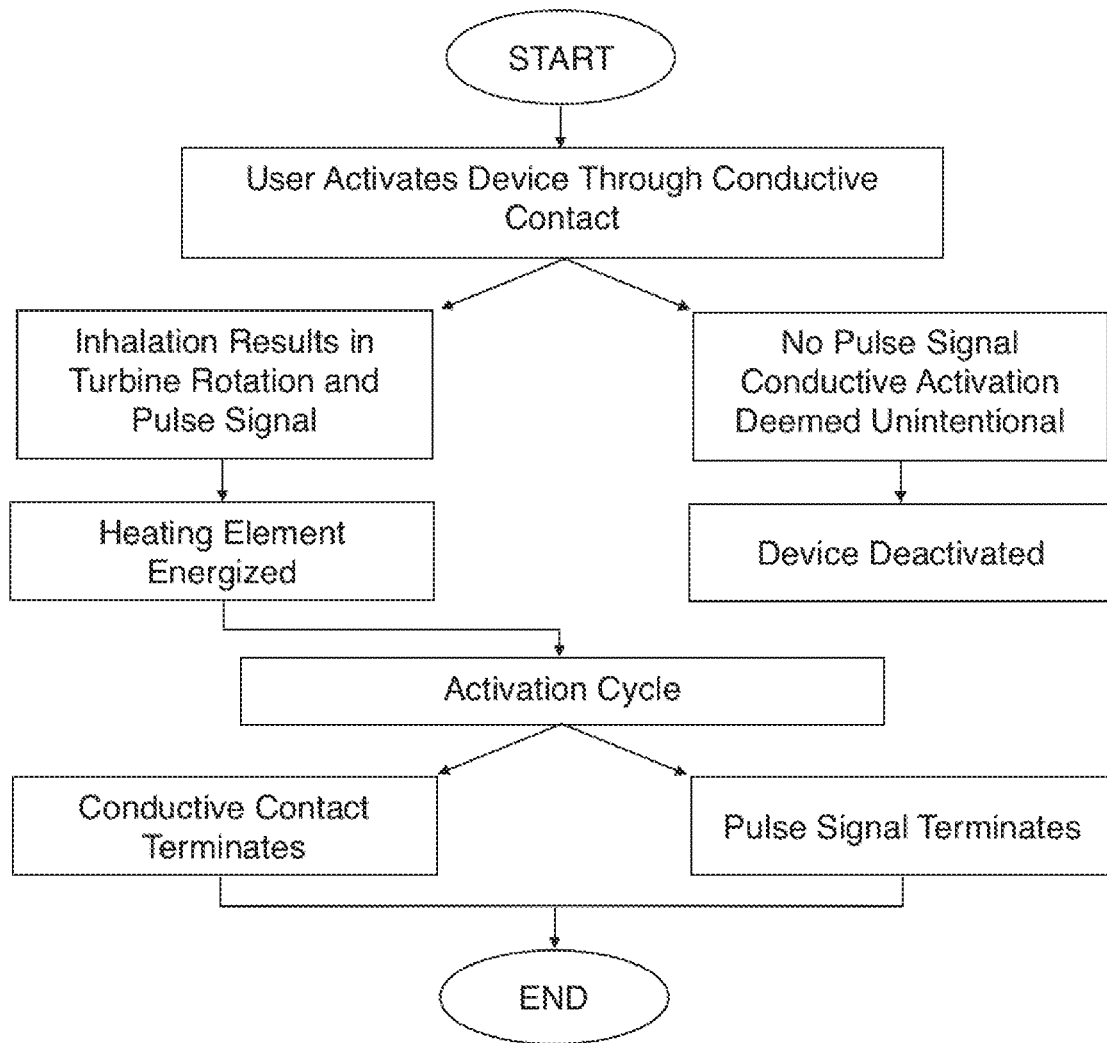

FIG. 189 illustrates a pulse signal mediated deactivation of the vaporizer.

Figure 190:
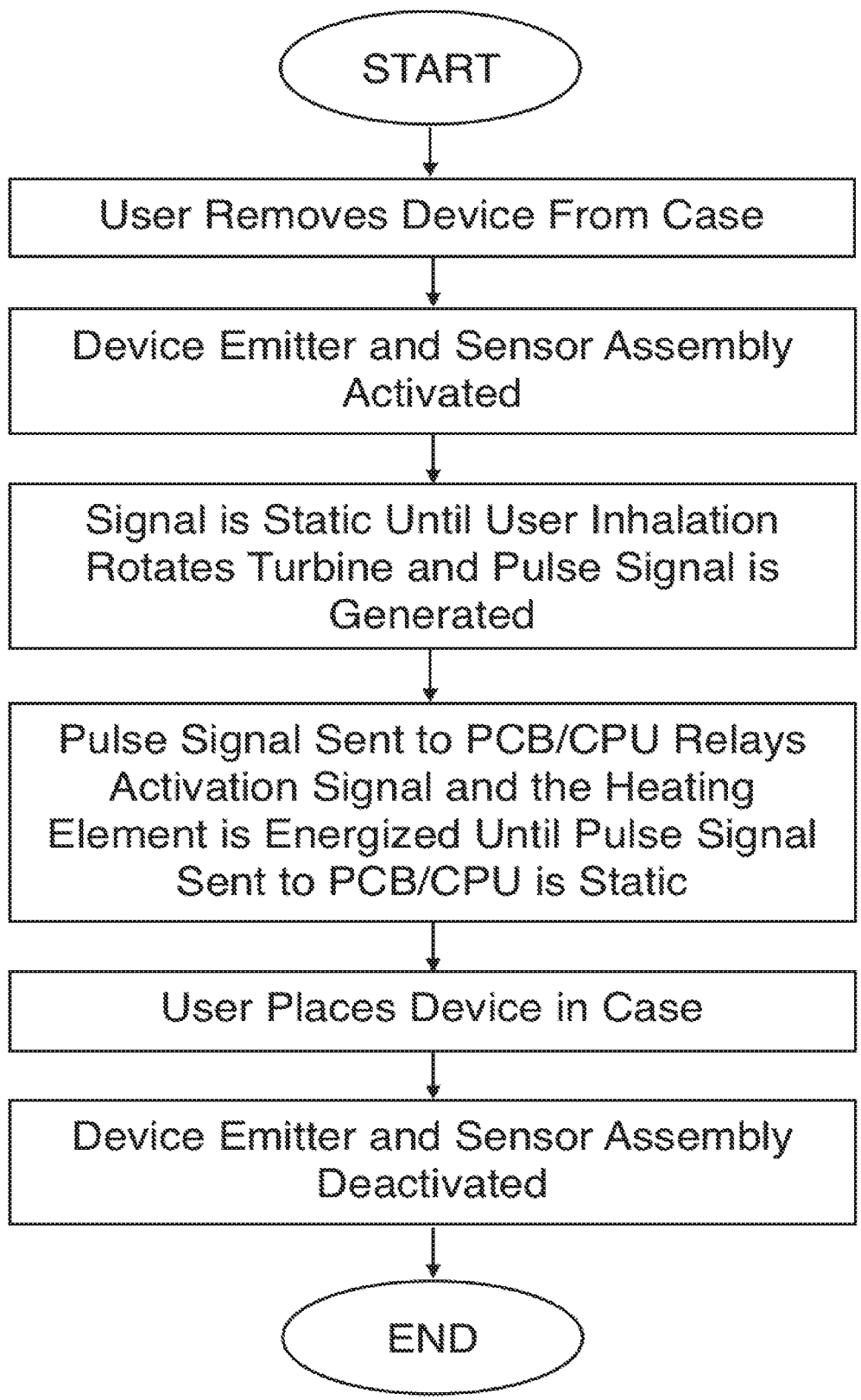

FIG. 190 is a process for turbine and sensor assembly device activation.

Figure 191:
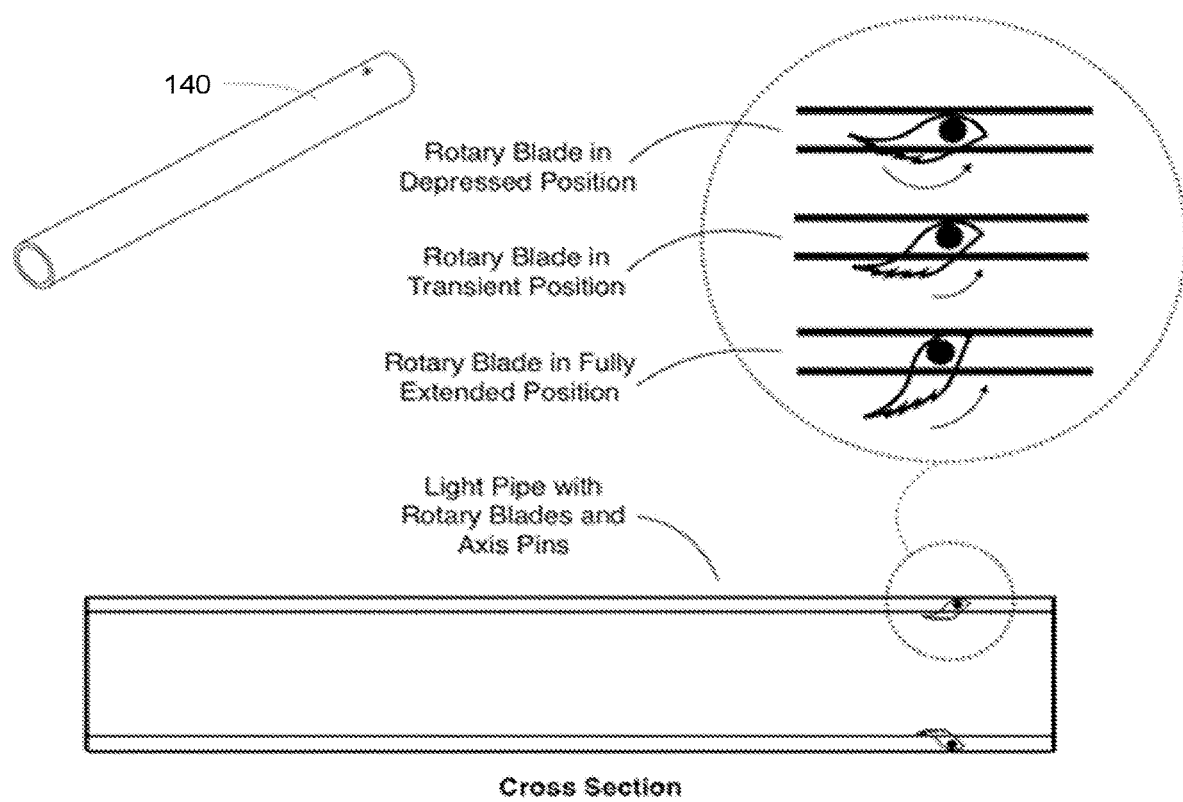

FIG. 191 illustrates the positioning and rotational dynamics of the rotating blade(s).

Figure 192:
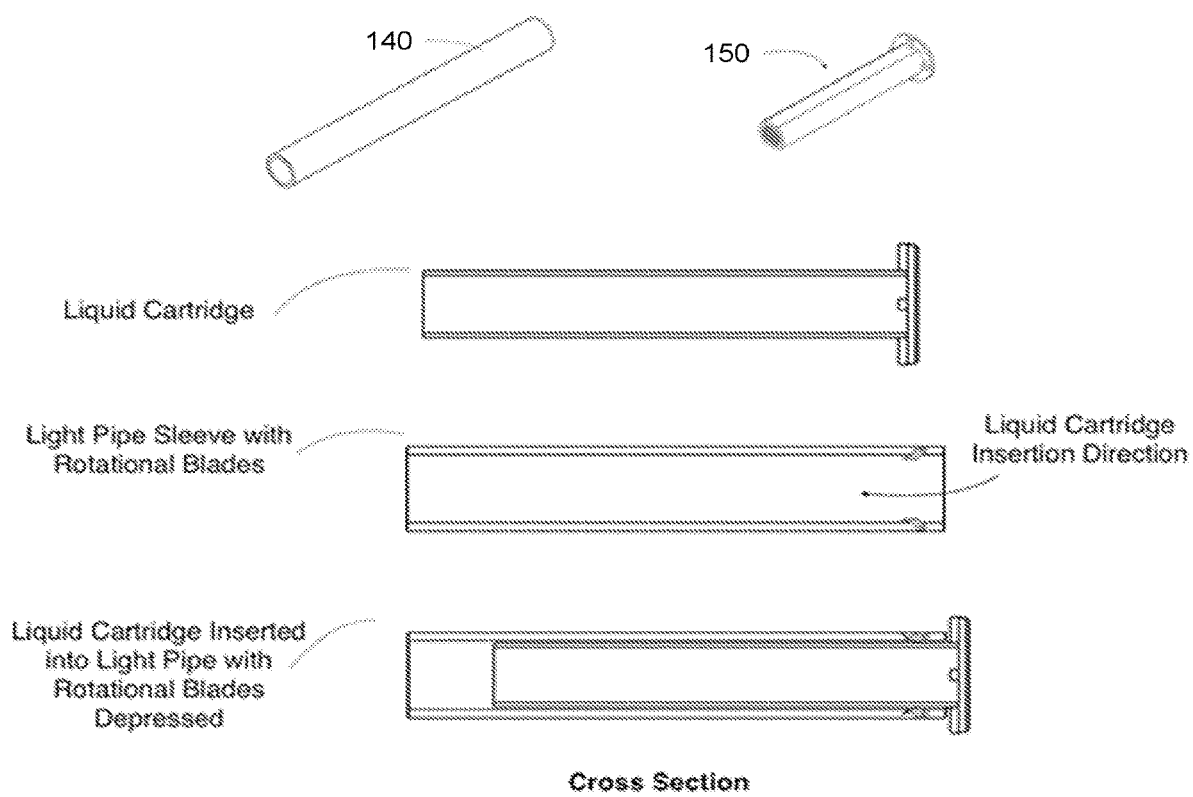

FIG. 192 illustrates the liquid cartridge and light pipe sleeve and rotation blade(s) during liquid cartridge insertion.

Figure 193:
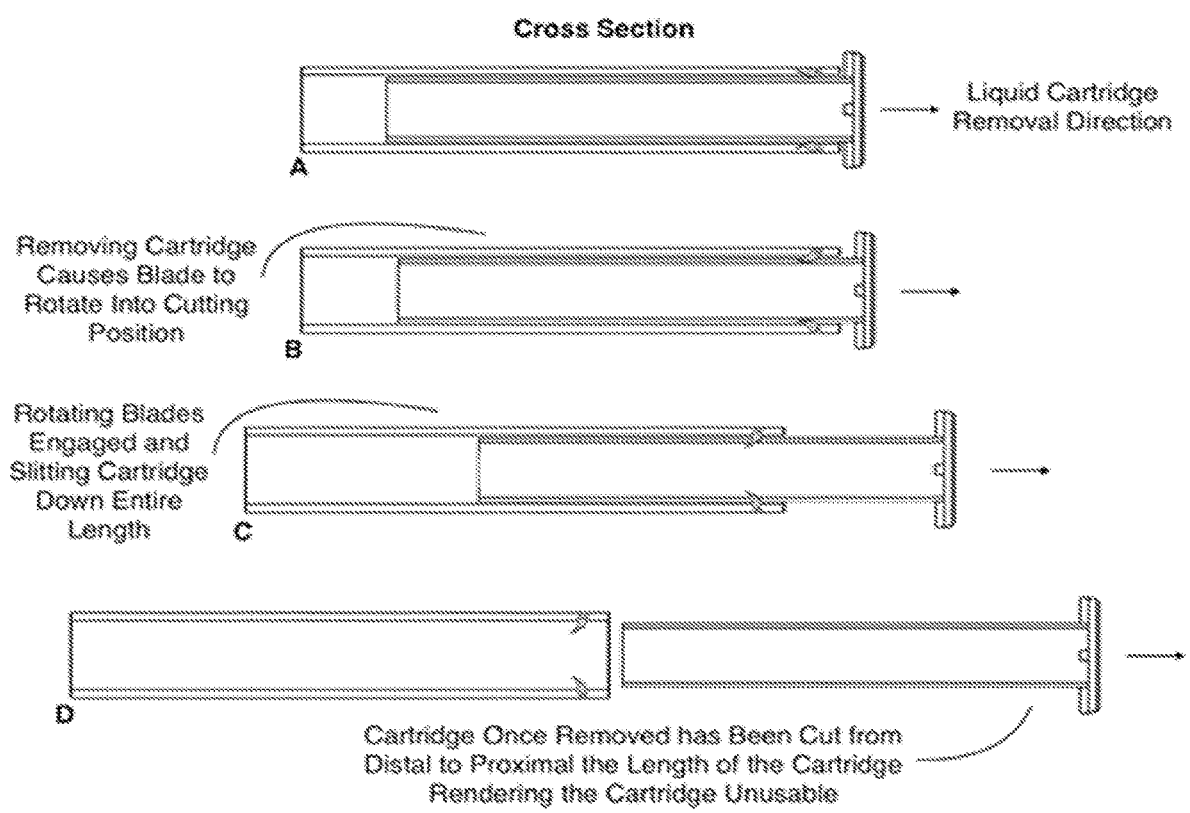

FIG. 193 illustrates the cartridge and light pipe sleeve and rotation blade(s) during a liquid cartridge removal process.

Figure 194:
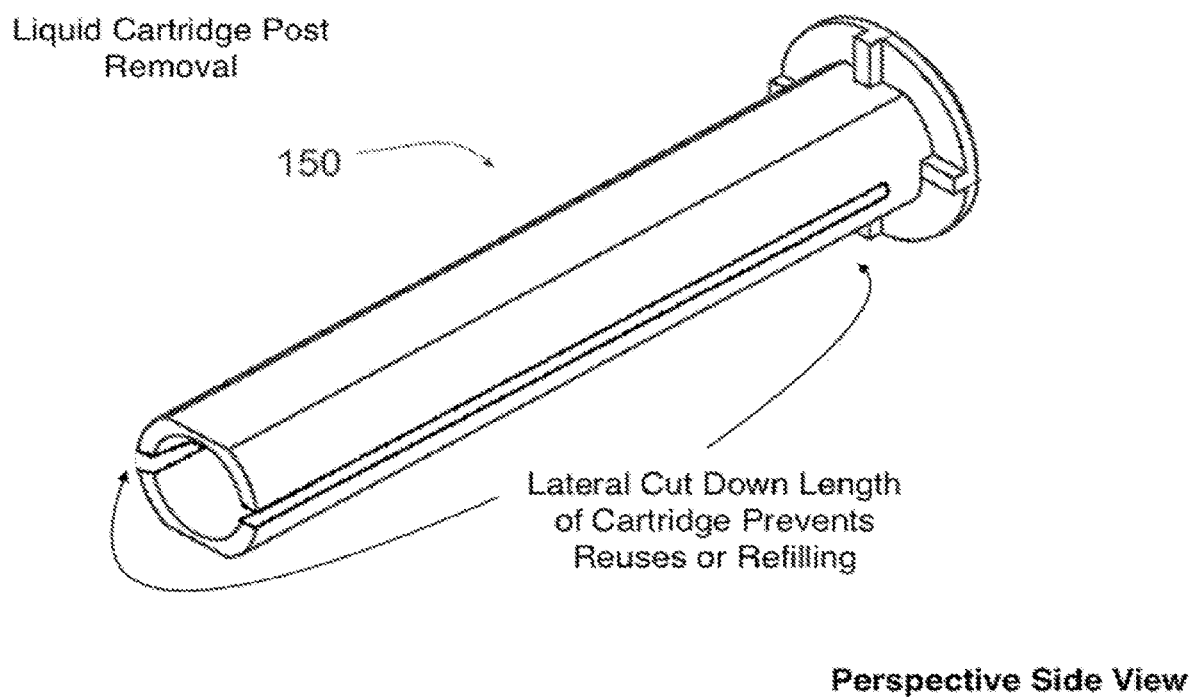

FIG. 194 illustrates the liquid cartridge post removal.

Figure 195:
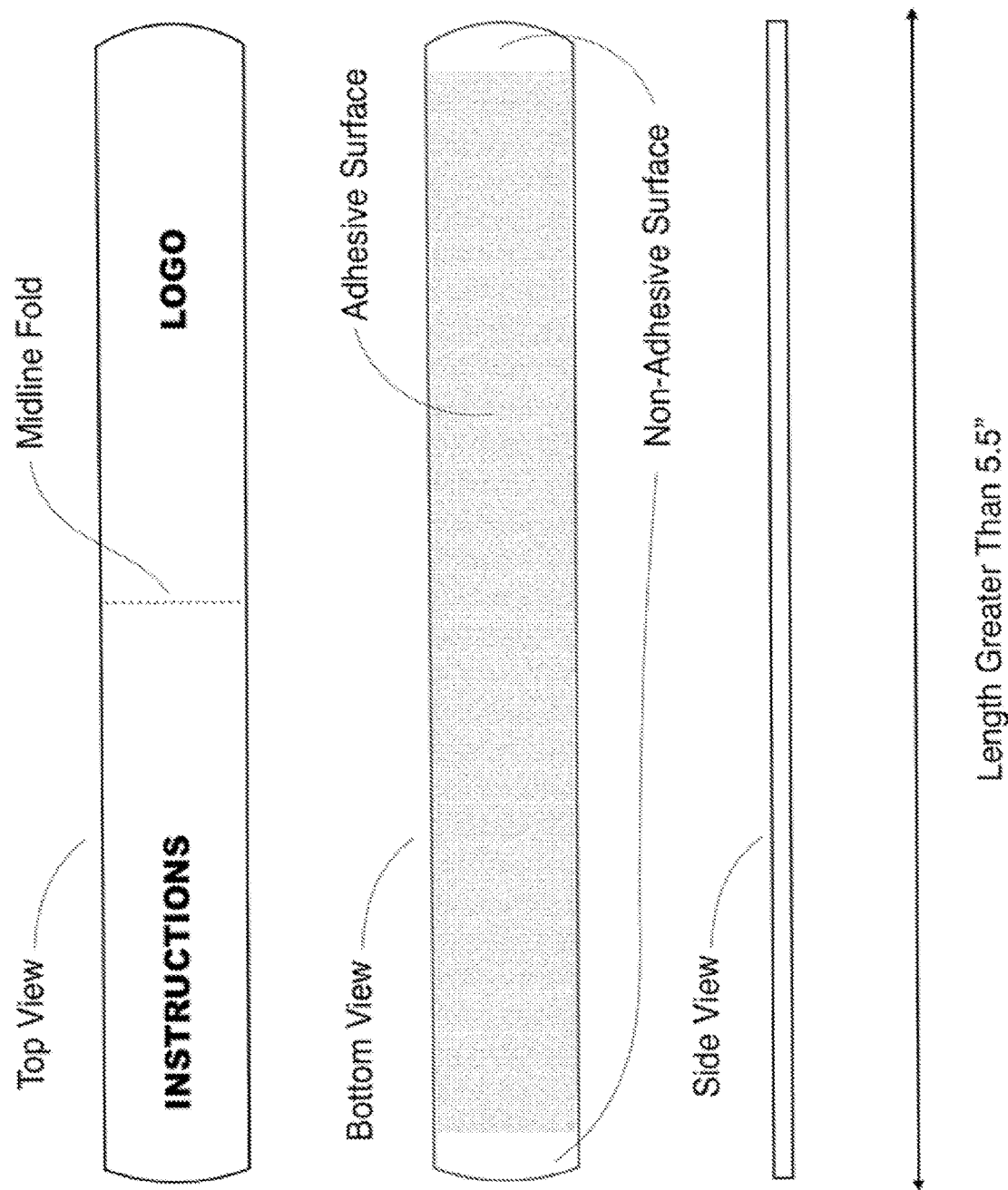

FIG. 195 illustrates an adhesive strip type of packaging embodiment.

Figure 196:
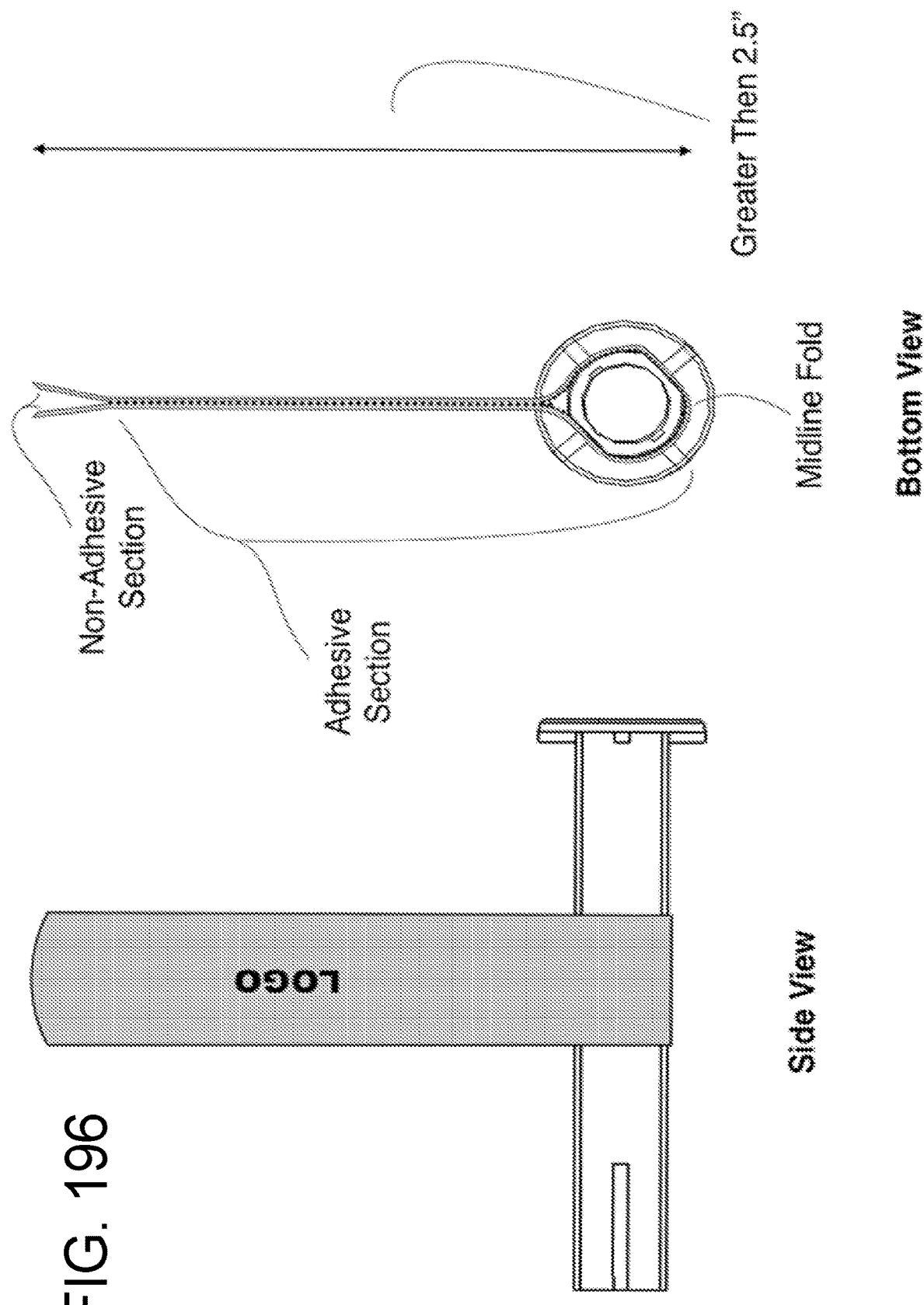

FIG. 196 illustrates the adhesive strip packaging embodiment with a liquid cartridge.

Figure 197:
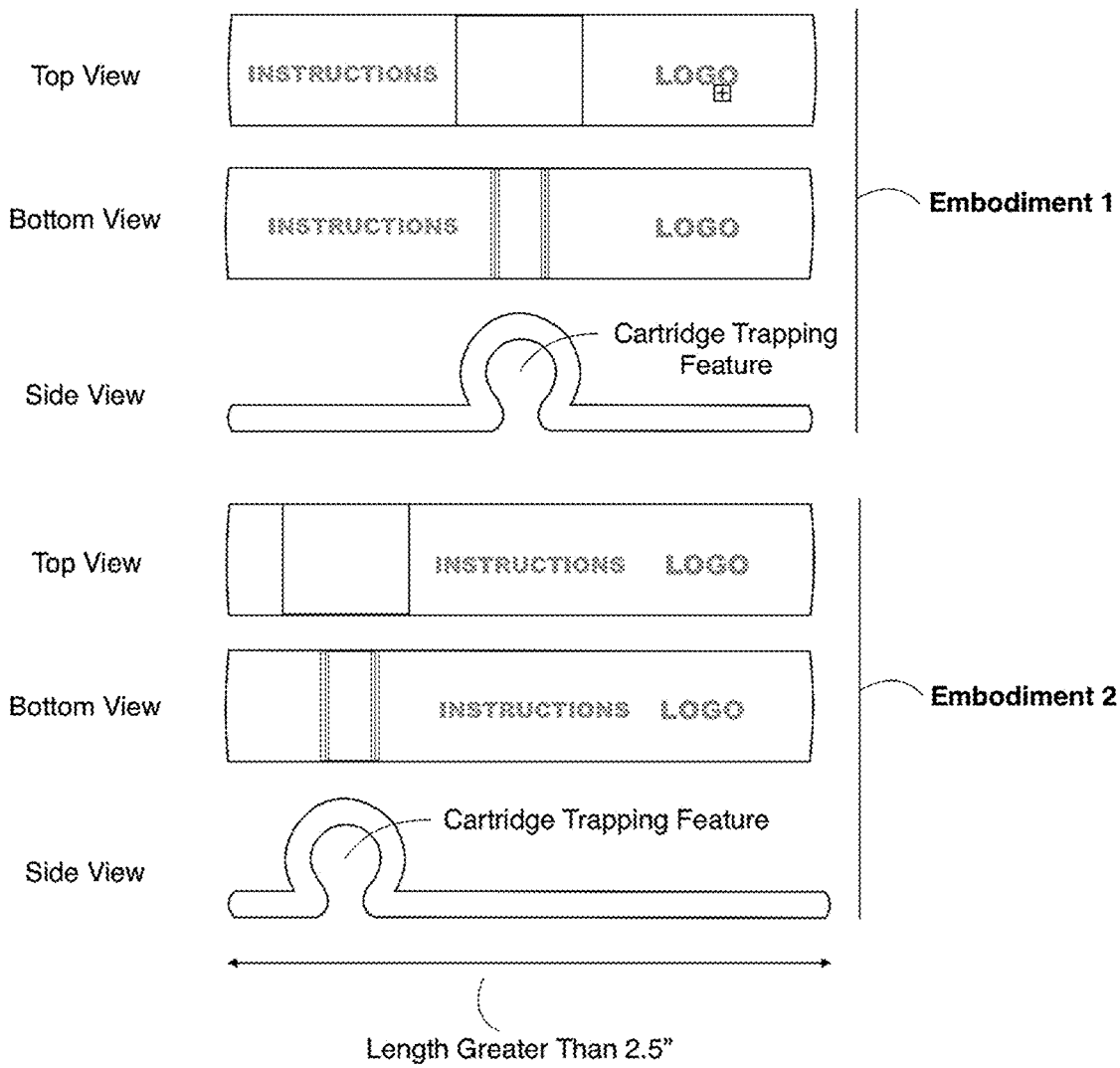

FIG. 197 illustrates cartridge packaging having a C-shaped cartridge capturing element.

Figure 198:
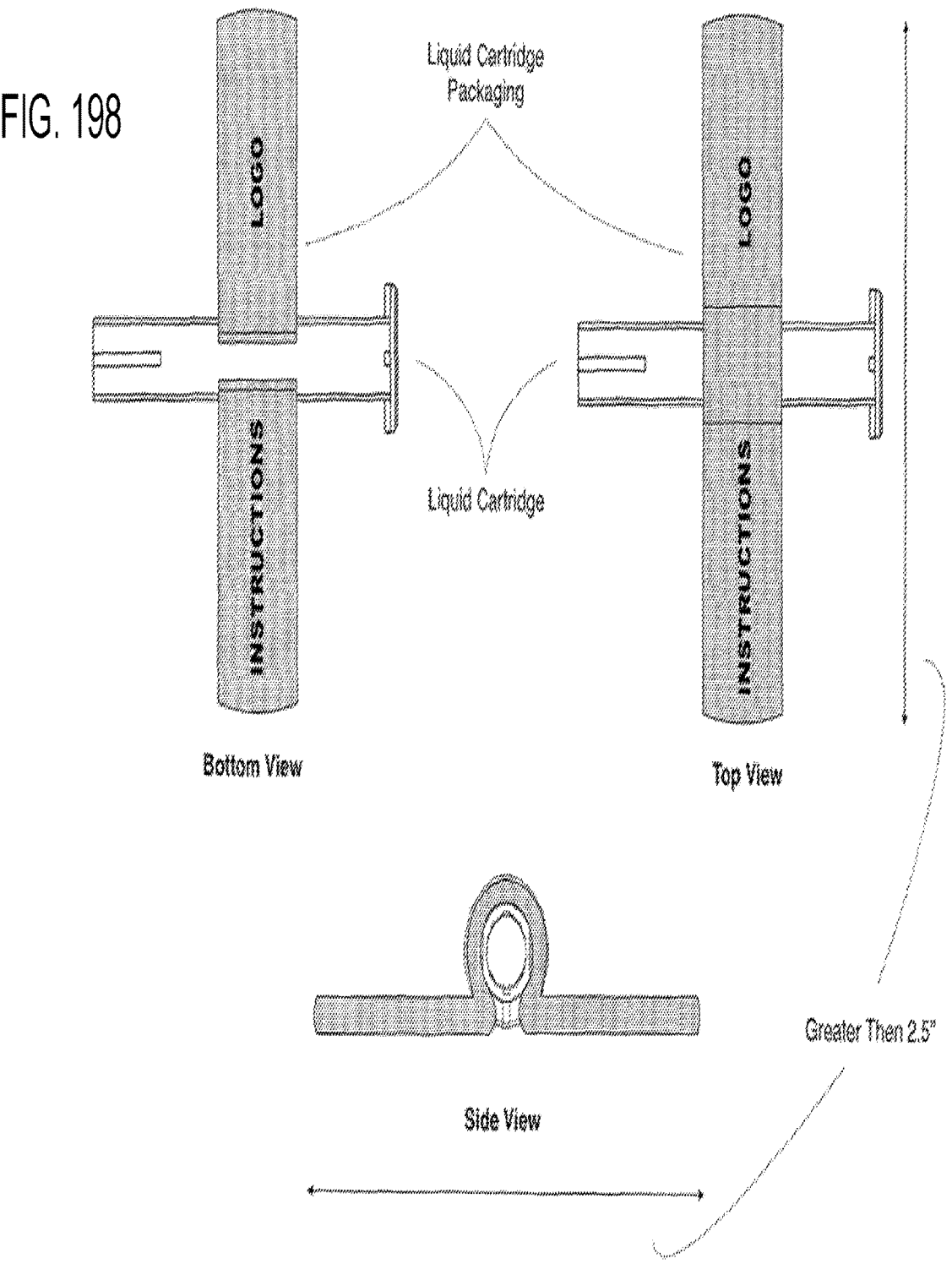

FIG. 198 illustrates cartridge packaging having a C-shaped cartridge capturing element with the cartridge.

Figure 199:
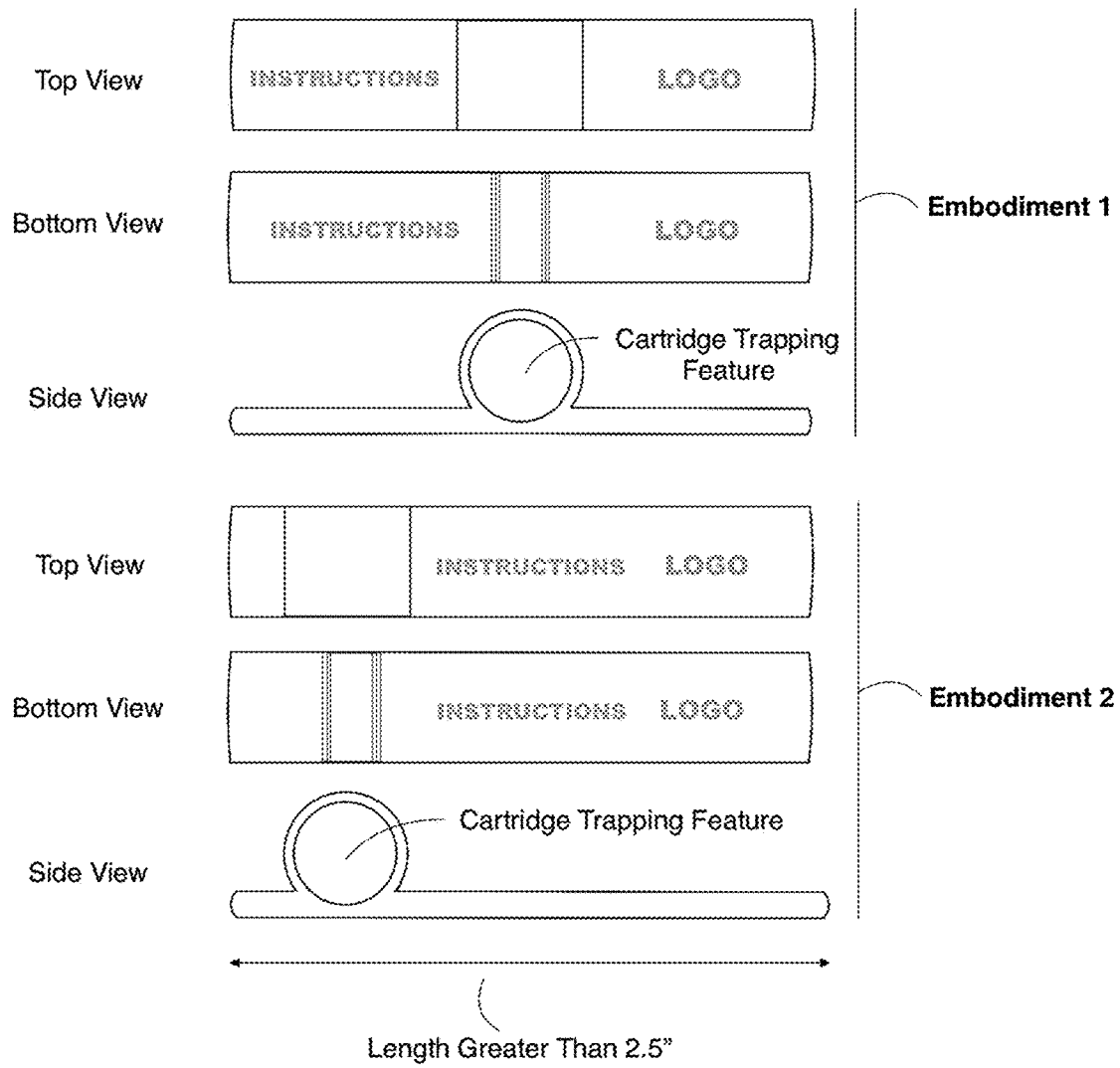

FIG. 199 illustrates a cartridge packaging embodiment having a substantially circular shaped cartridge capturing element.

Figure 200:
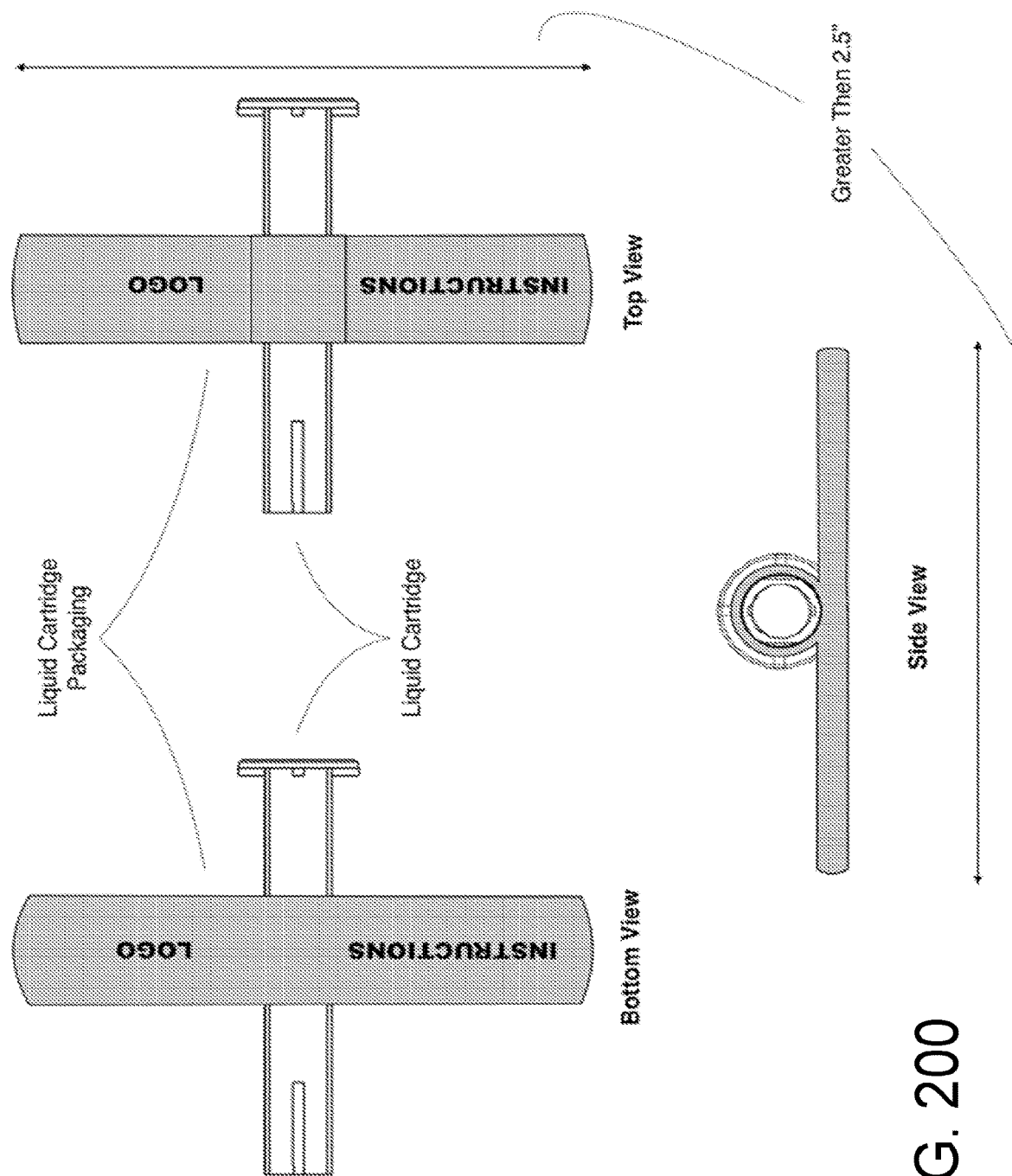

FIG. 200 illustrates a cartridge packaging embodiment having a substantially circular shaped cartridge capturing element with the cartridge.

Figure 201:
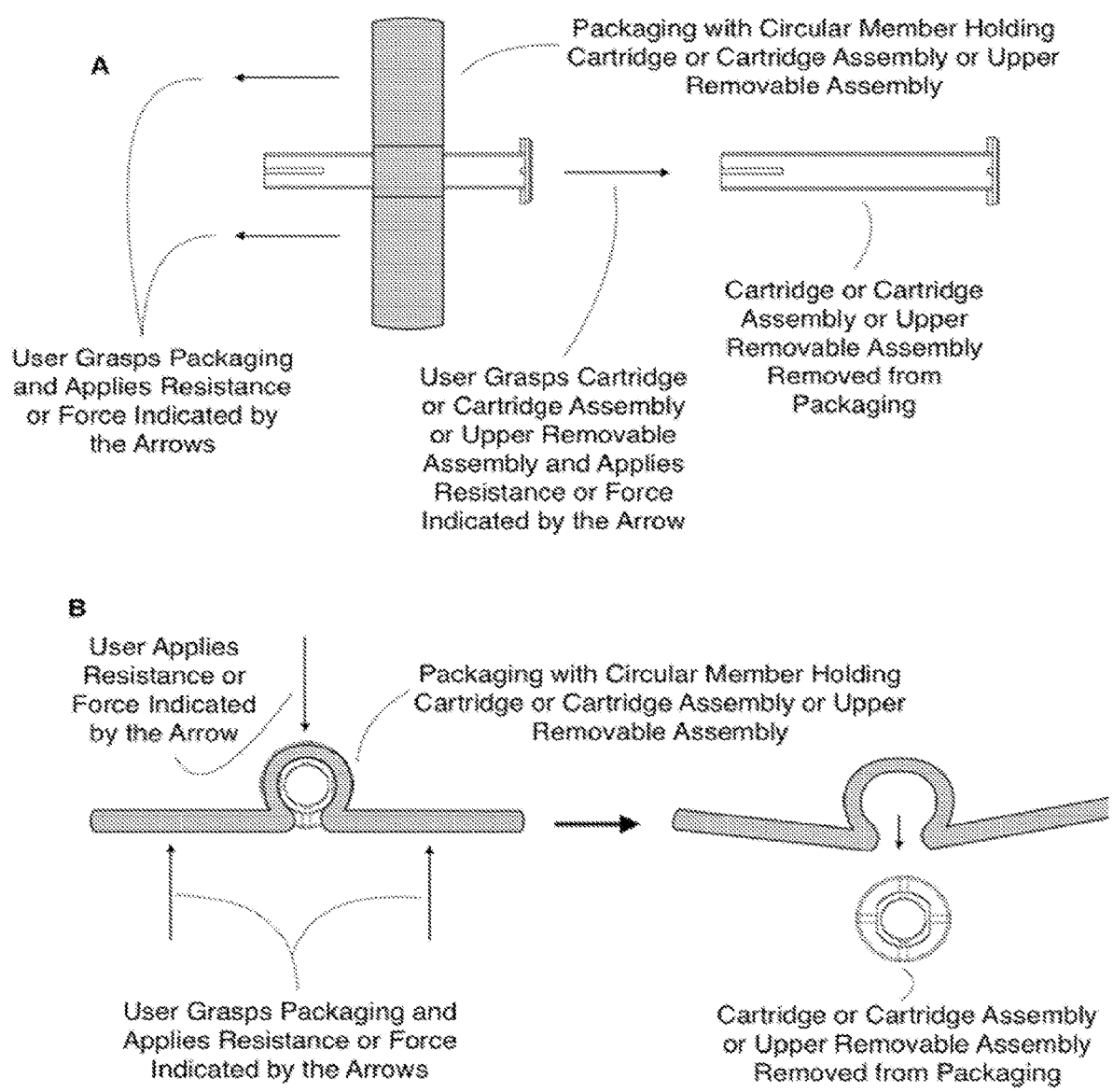

FIG. 201 illustrates removal of the cartridge or cartridge assembly from the packaging.

Figure 202:
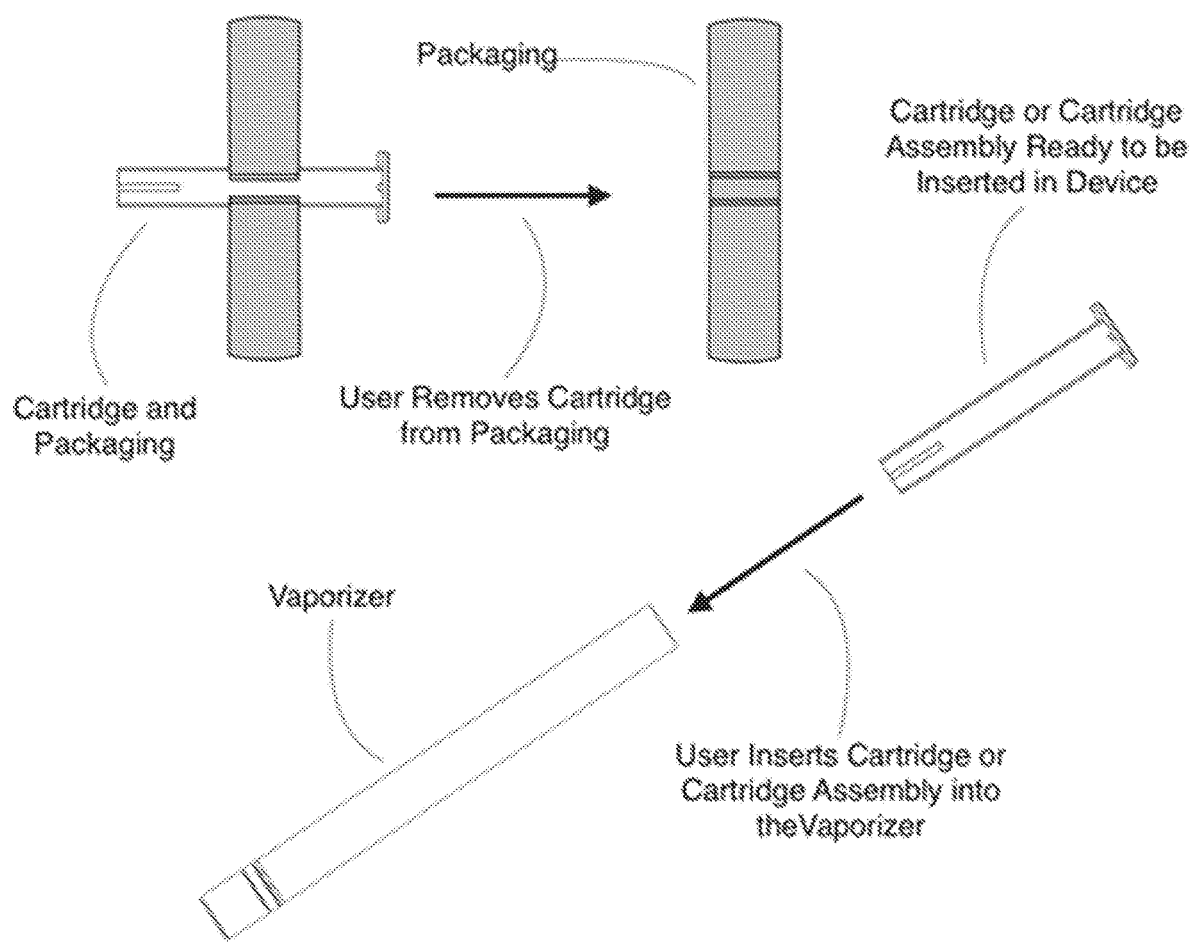

FIG. 202 illustrates a process of removing a cartridge or cartridge assembly from the packaging and inserting into the device for usage.

Figure 203:
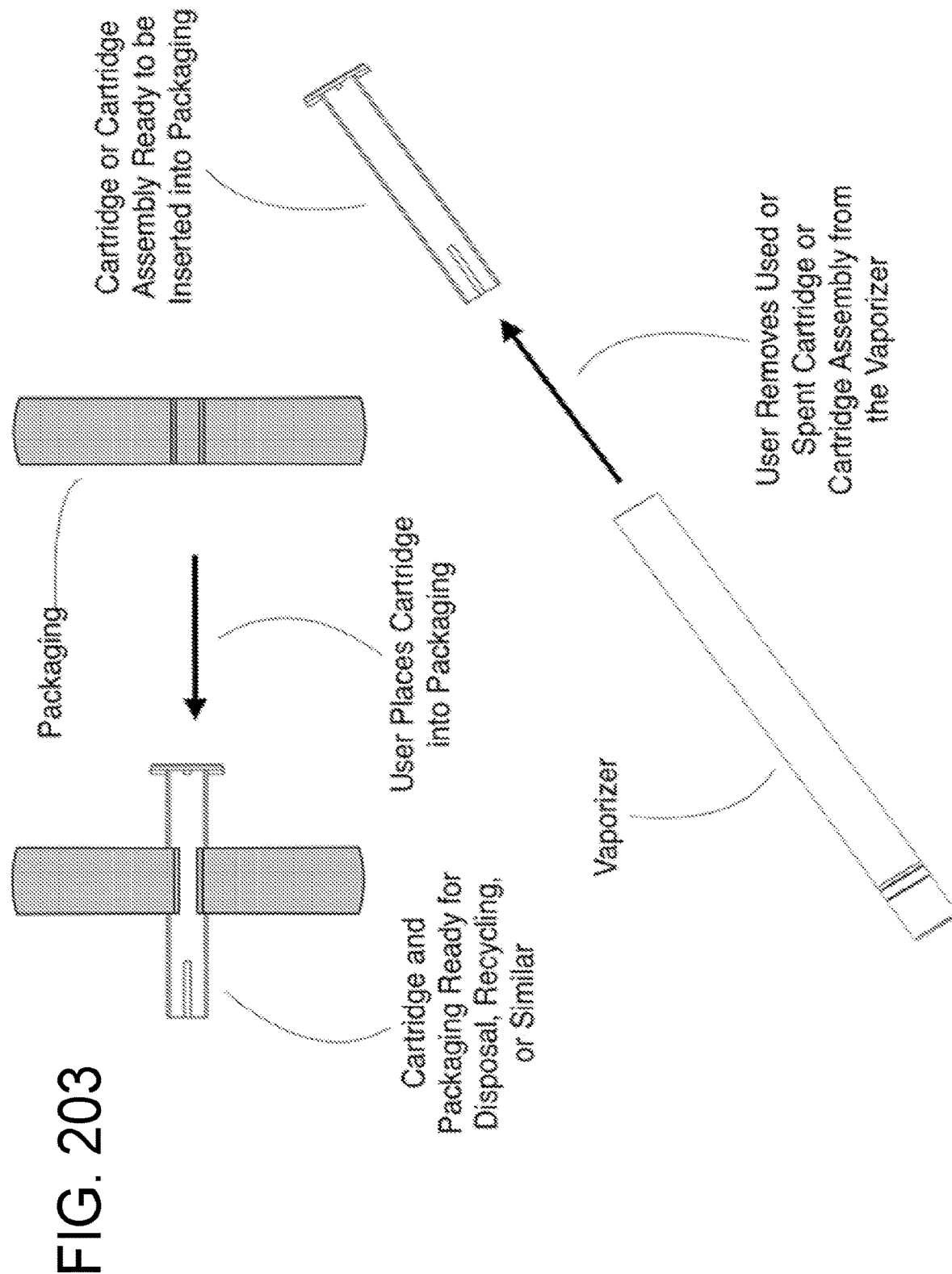

FIG. 203 illustrates a process of removing a cartridge or cartridge assembly from the device and inserting into the packaging for disposal.

FIG. 204 illustrates exemplary printed heater configurations.

Figure 205:
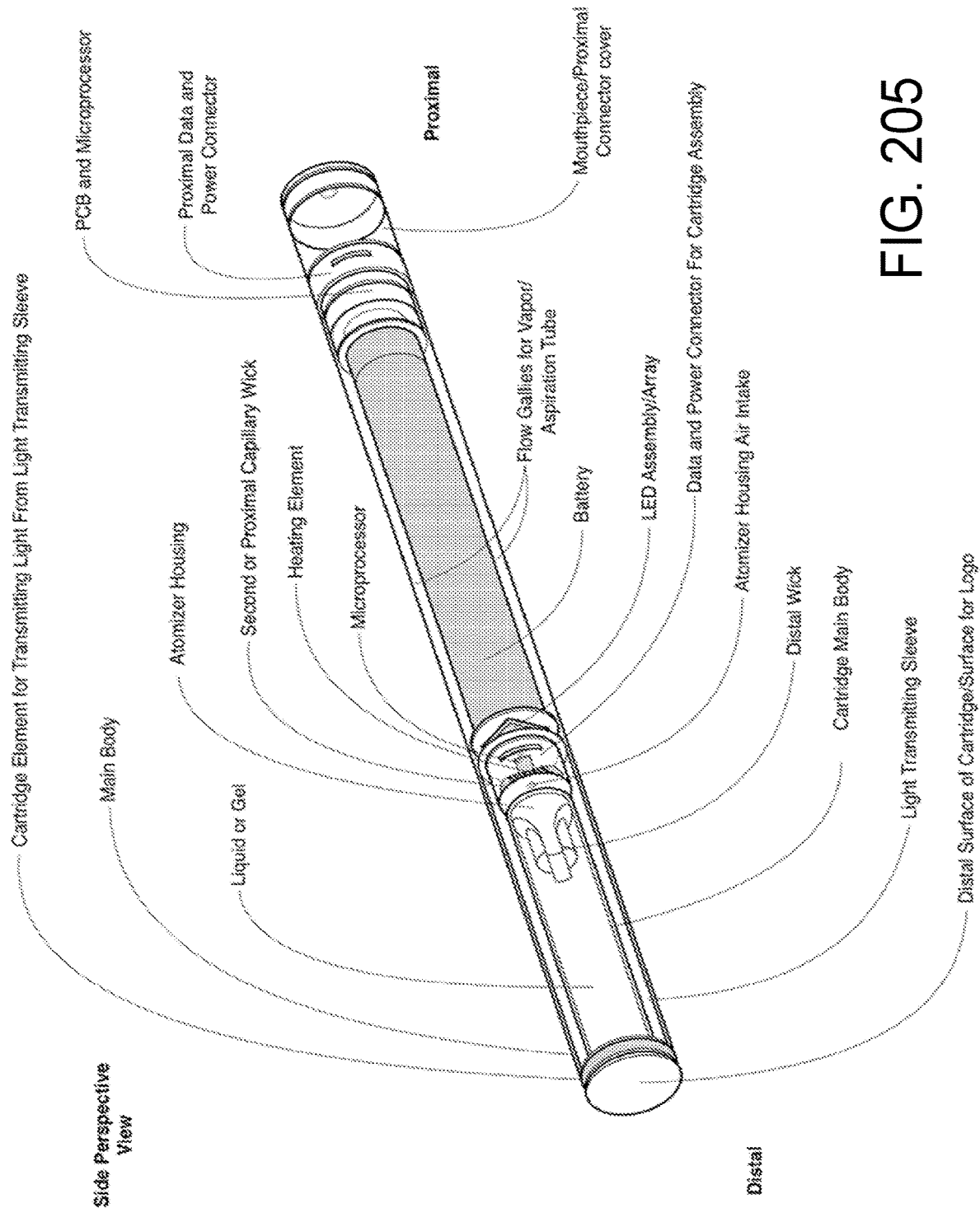

FIG. 205 is a diagram of personal vaporizer unit (PVU).

Figure 206:
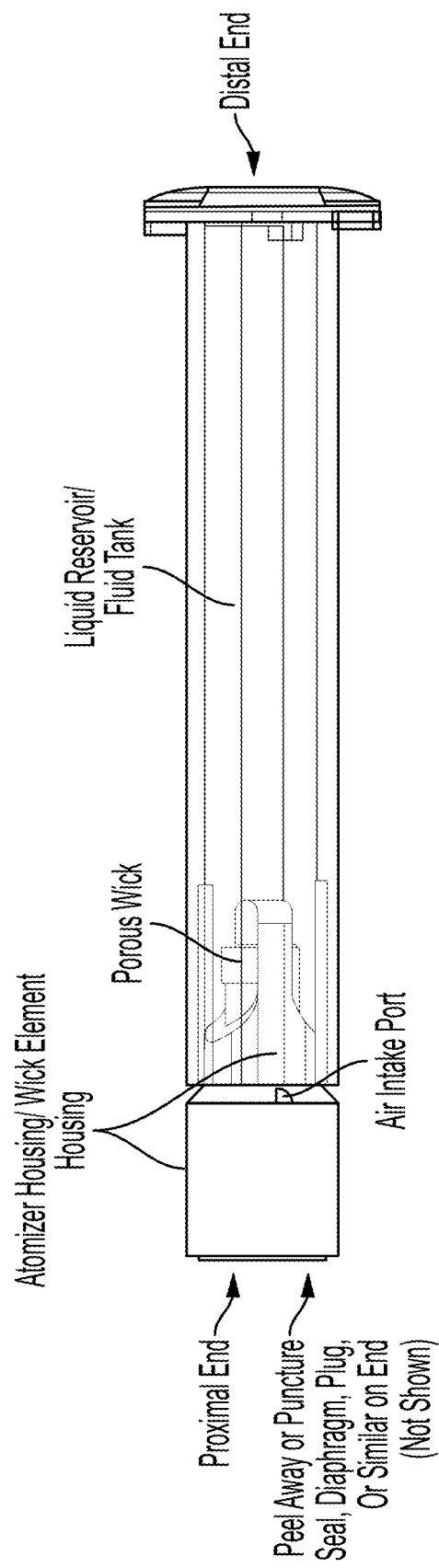

FIG. 206 is a side view of cartridge assembly.

Figure 207:
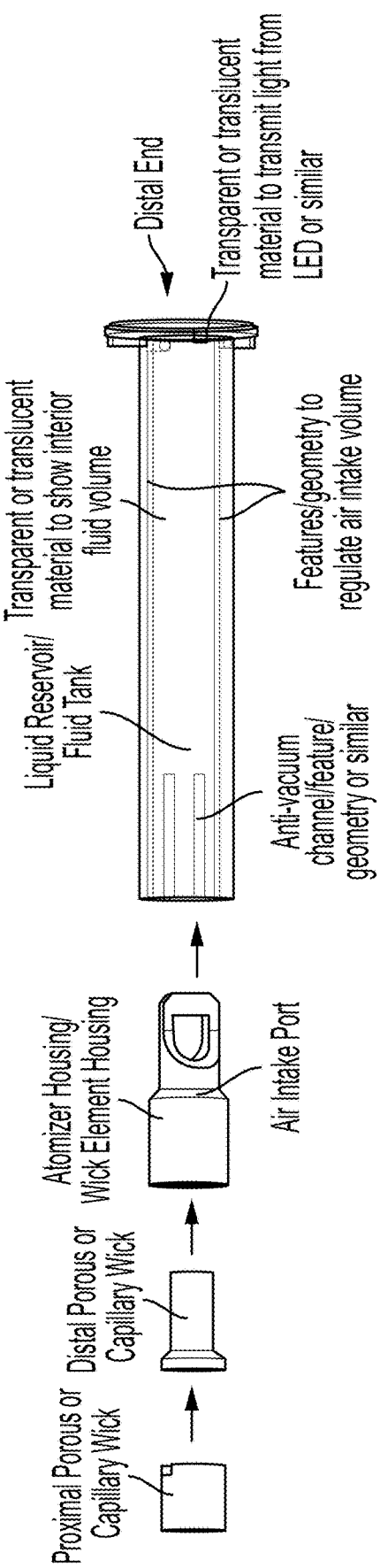

FIG. 207 is an alternative view of the cartridge assembly.

Figure 208:
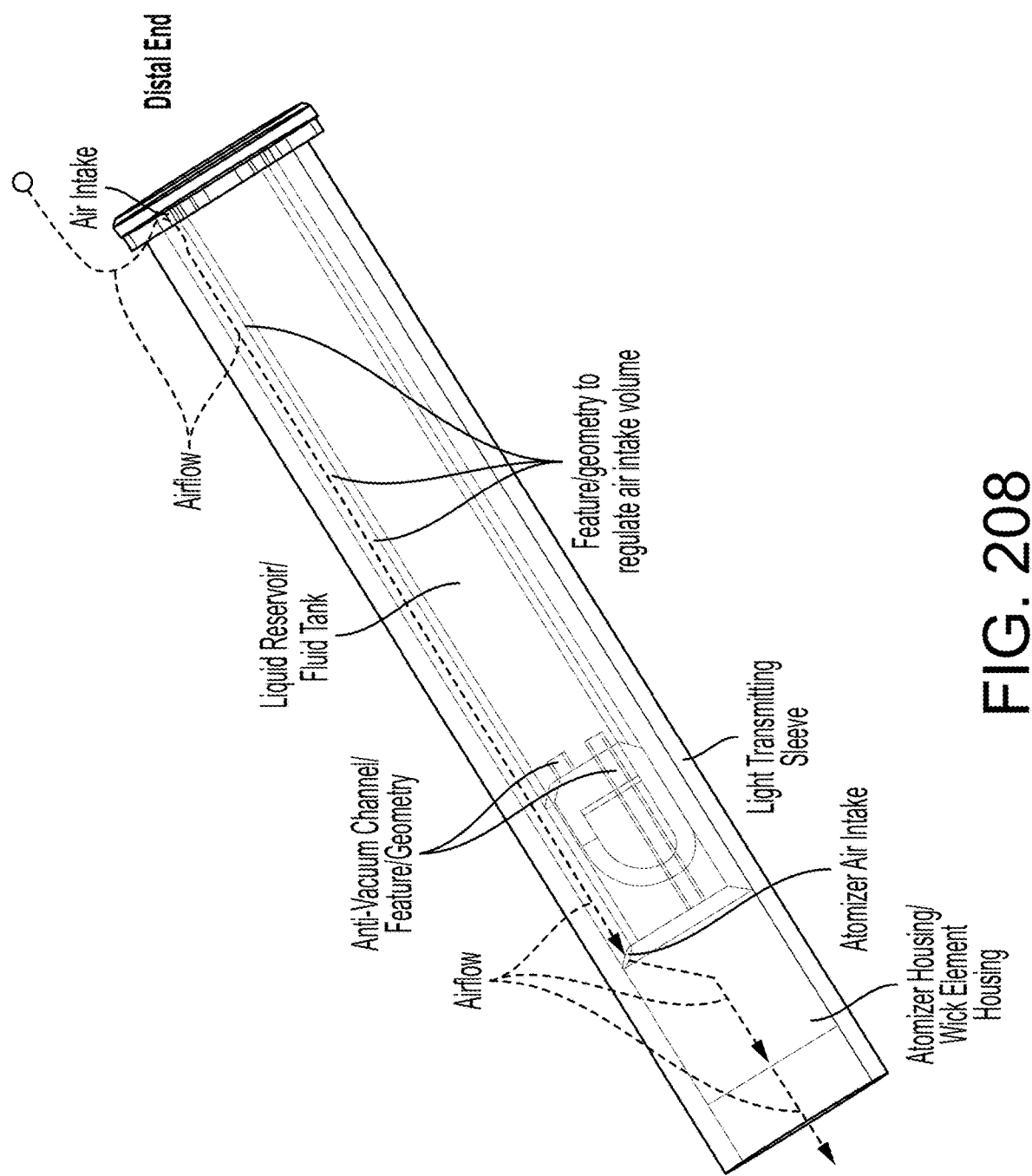

FIG. 208 is an alternative view of the cartridge assembly positioned with a light transmitting sleeve.

Figure 209:
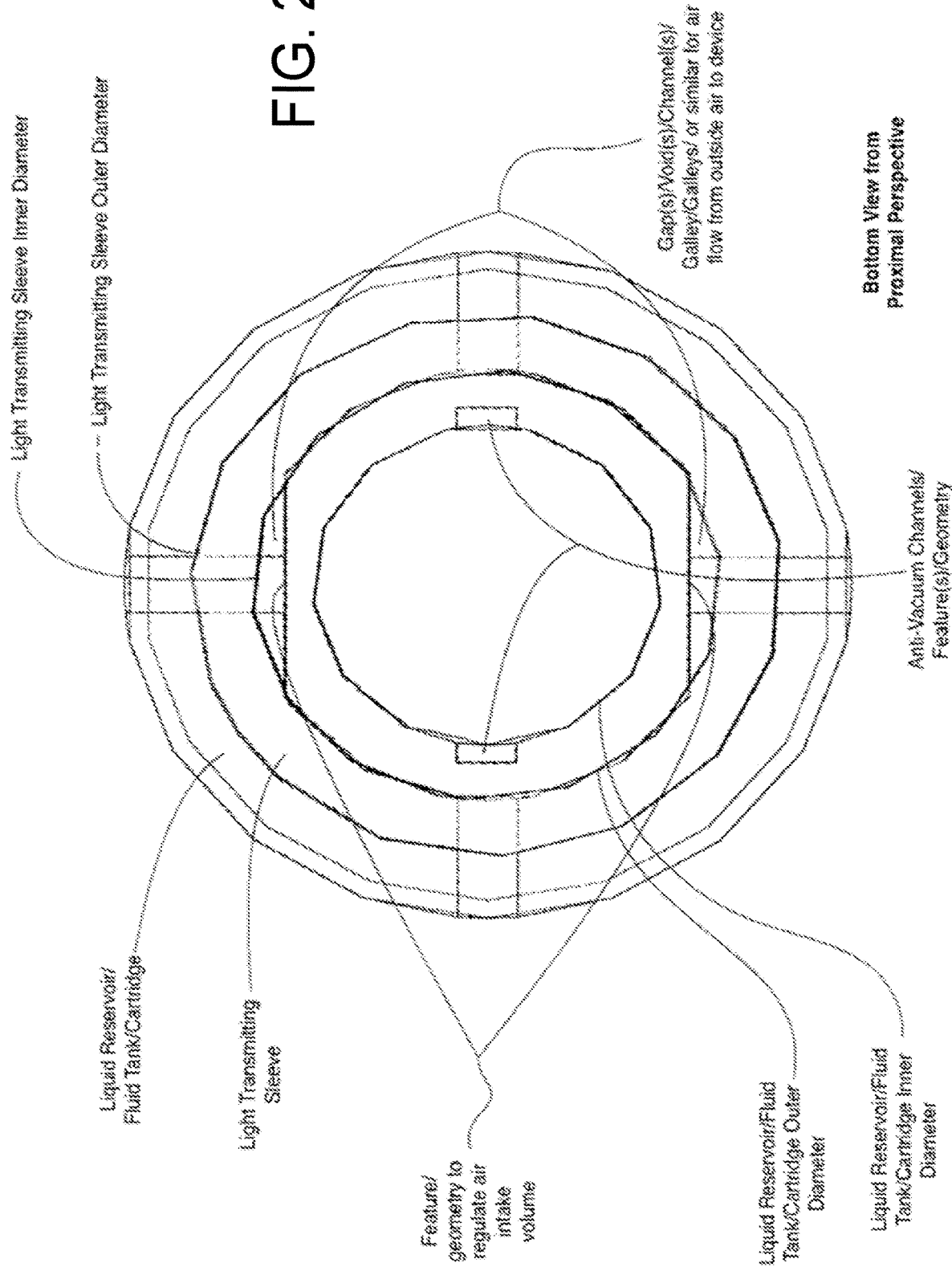

FIG. 209 is a proximal view of the cartridge and light transmitting sleeve.

Figure 210:
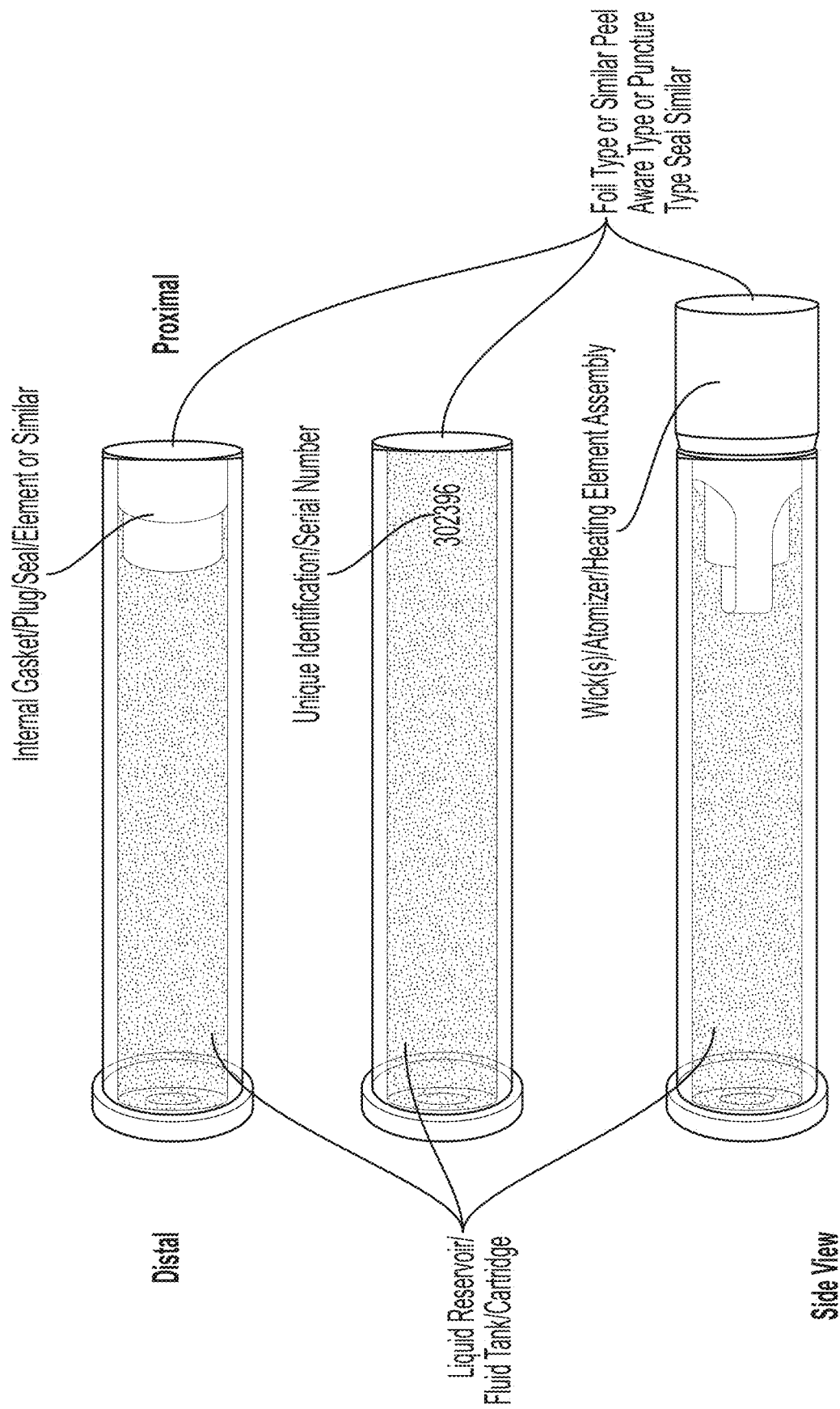

FIG. 210 is another embodiment of the cartridge and cartridge assembly.

Figure 211:
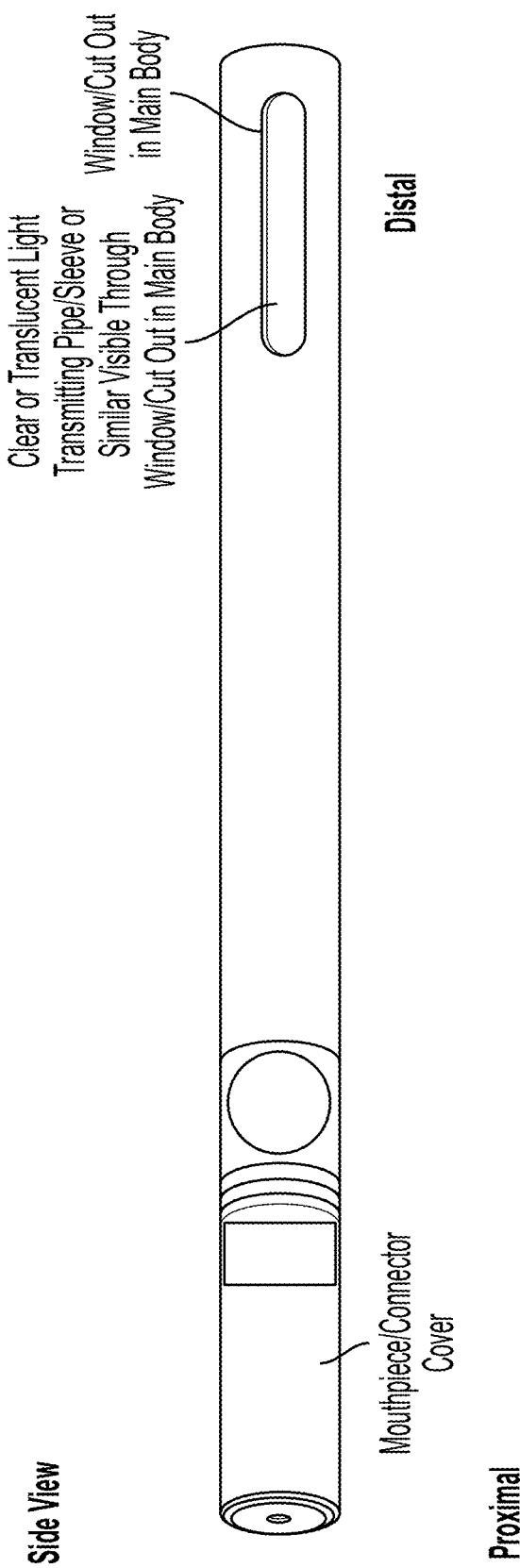

FIG. 211 is side view of the PVU without the cartridge or cartridge assembly.

Figure 212:
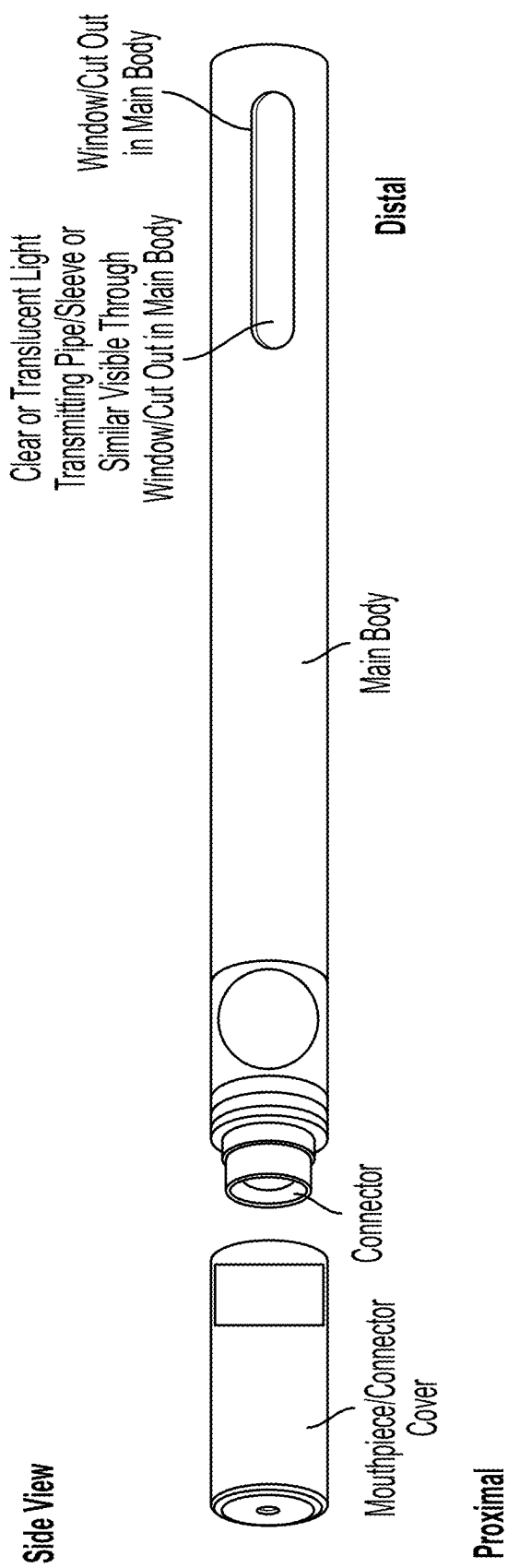

FIG. 212 is a side view of the PVU without the cartridge or cartridge assembly installed and mouthpiece/proximal connector cover removed.

Figure 213:
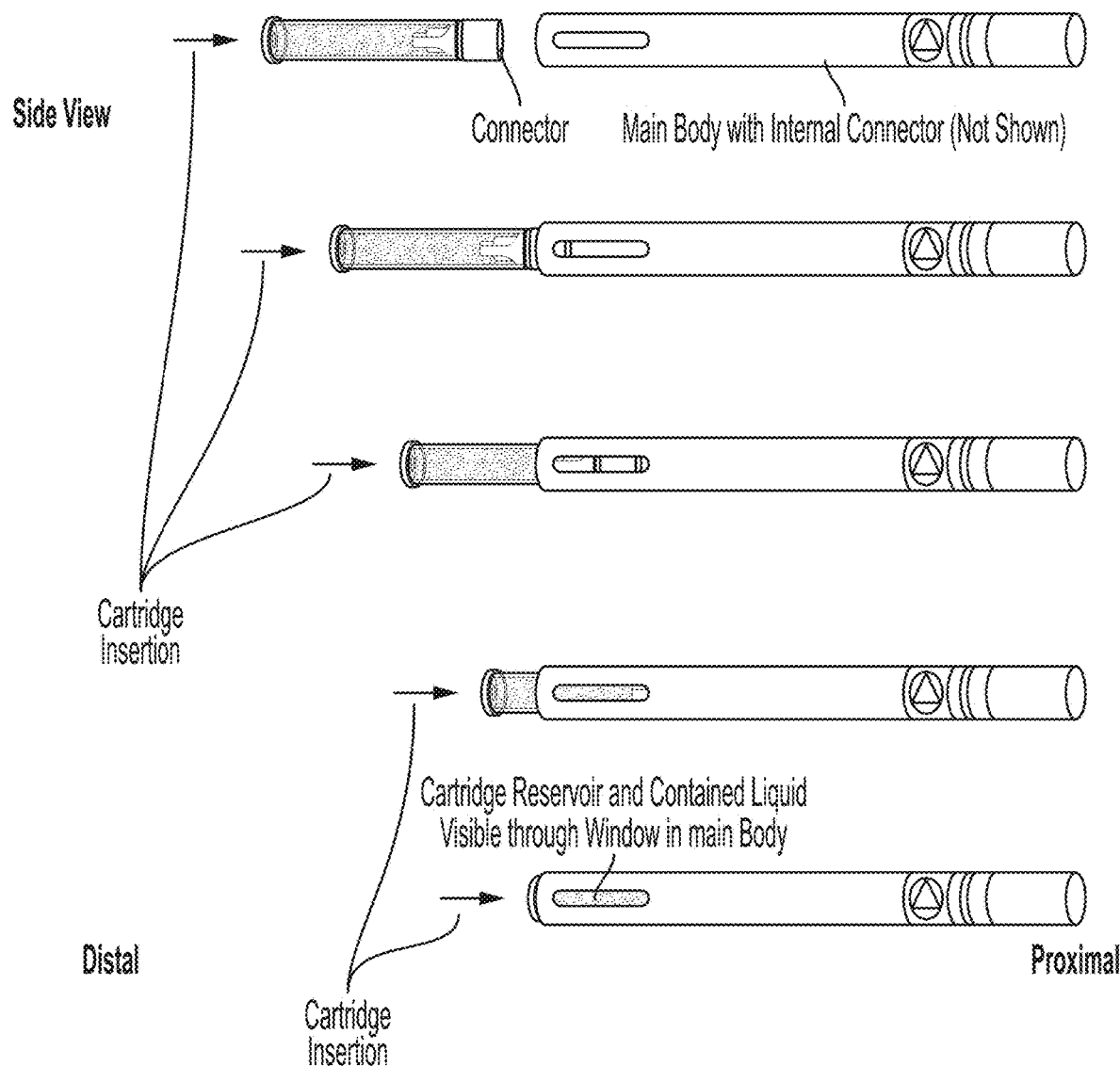

FIG. 213 is a cartridge assembly insertion into the PVU.

Figure 214:
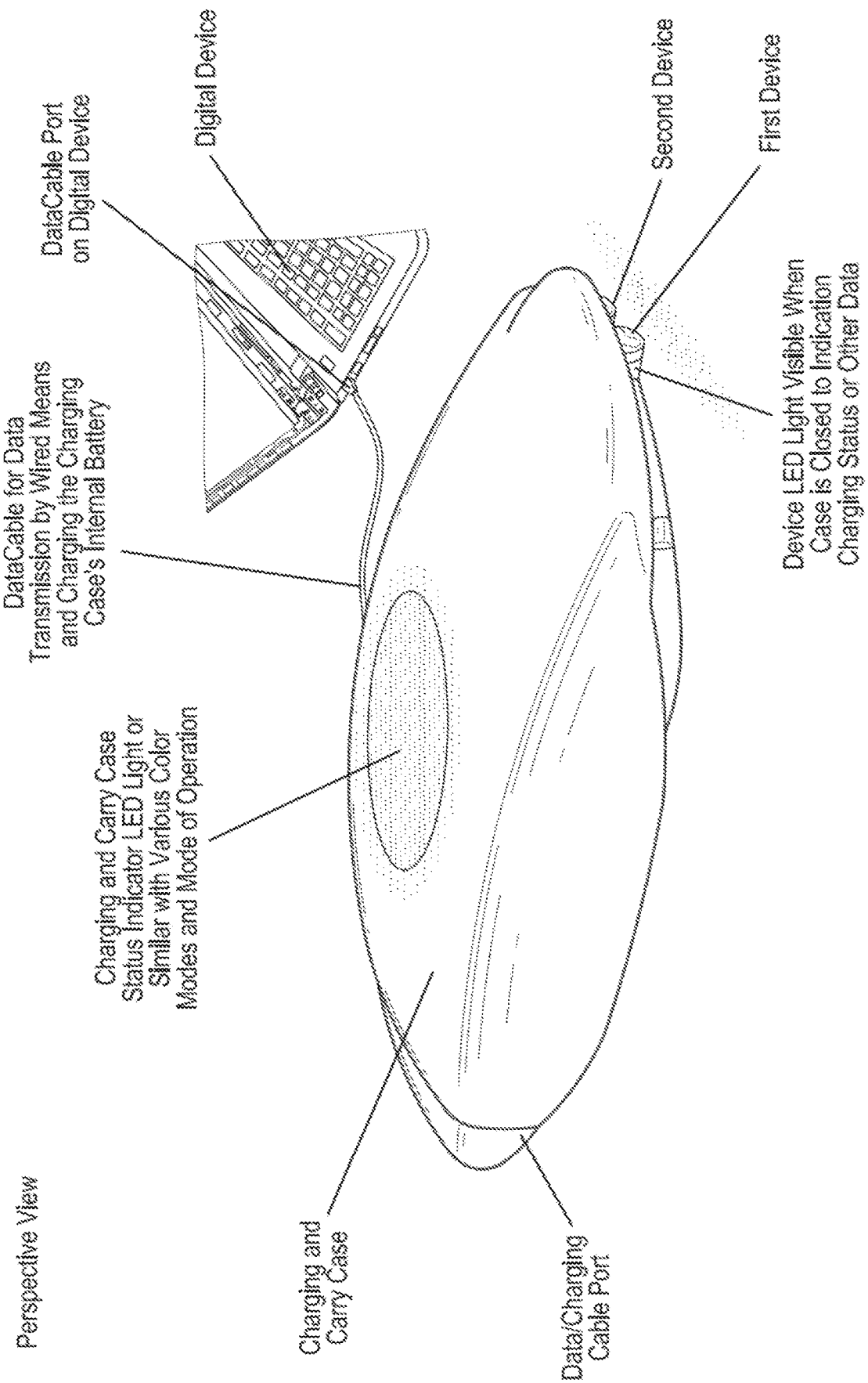

FIG. 214 is an embodiment of a case with a closed PVU storage that includes PVU charging and PVU data logging.

Figure 215:
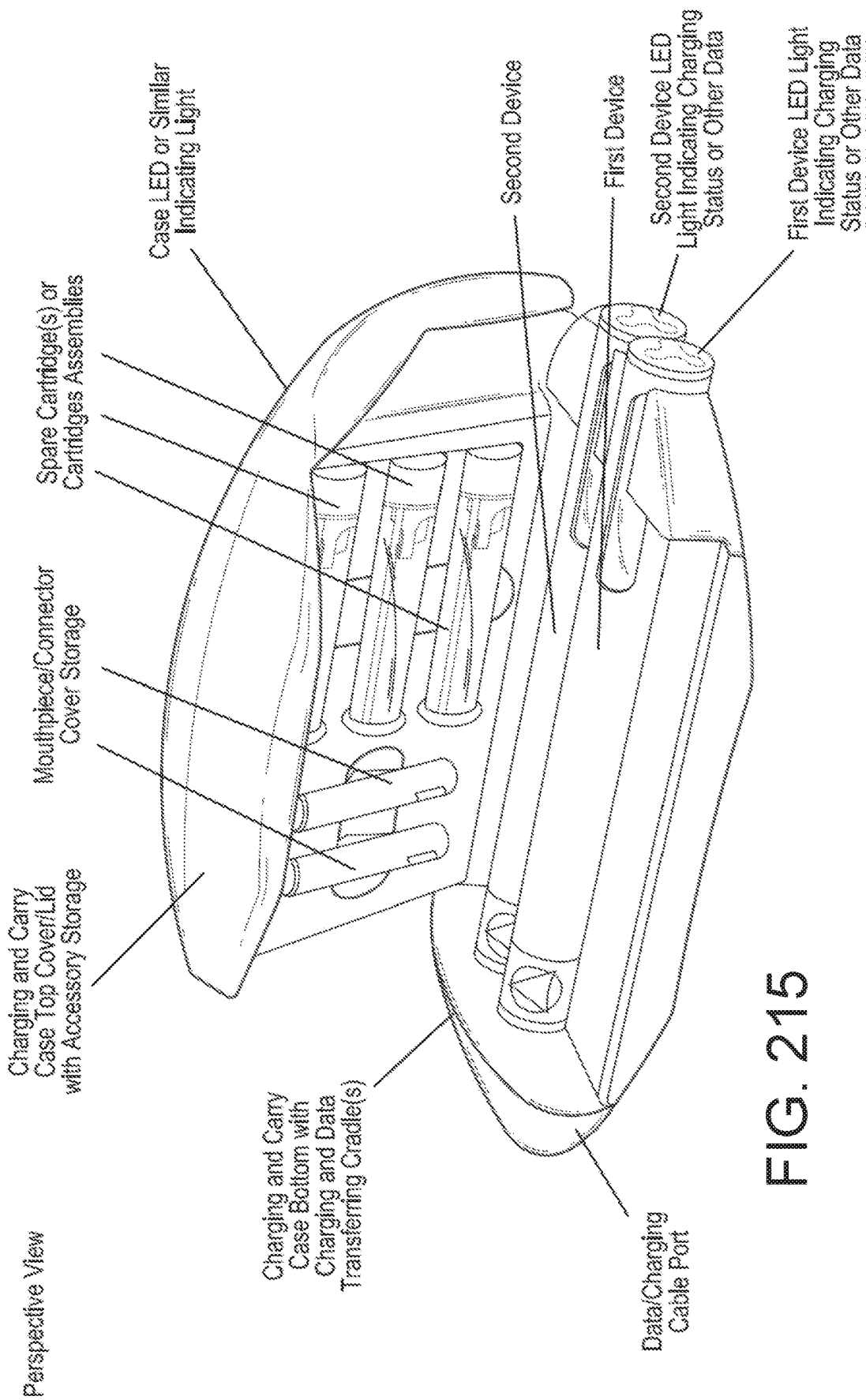

FIG. 215 is an embodiment of an open case.

DETAILED DESCRIPTION

In an embodiment, a personal vaporizer unit comprises a mouthpiece configured for contact with the mouth of a person. At least part of this mouthpiece has an antimicrobial surface. This mouthpiece may also comprise silicone rubber, thermoplastic elastomer, organosilane, silver impregnated polymer, silver impregnated thermoplastic elastomer, and/or polymer. The mouthpiece may be removed from the personal vaporizer for washing or replacement, without using a tool. The mouthpiece may be provided in different colors. Designs or other patterns may be visible on the outside of the mouthpiece.

In an embodiment, a personal vaporizer unit comprises a first conductive surface configured to contact a first body part of a person holding the personal vaporizer unit, and a second conductive surface, conductively isolated from the first conductive surface, configured to contact a second body part of the person. When the personal vaporizer unit detects a change in conductivity between the first conductive surface and the second conductive surface, the vaporizer is activated to vaporize a substance so that the vapors may be inhaled by the person holding the vaporizer unit. The first body part and the second body part may be a lip or parts of a hand(s). The two conductive surfaces may also be used to charge a battery contained in the personal vaporizer unit. The two conductive surfaces may also form, or be part of, a connector that may be used to output data stored in a memory.

In an embodiment, a personal vaporizer unit comprises a chamber configured to receive a cartridge. The cartridge may hold a substance to be vaporized. The chamber may be configured at the distal end of the personal vaporizer unit. A user may inhale the vaporized substance at the proximal end of the personal vaporizer unit. At least one space between the exterior surface of the cartridge and an interior surface of the chamber may define a passage for air to be drawn from outside the personal vaporizer unit, near the distal end, through the personal vaporizer unit to be inhaled by the user along with the vaporized substance. The personal vaporizer unit may also include a puncturing element that breaks a seal on the cartridge to allow a substance in the cartridge to be vaporized. An end surface of the cartridge may be translucent to diffuse light produced internally to the personal vaporizer unit. The translucent end may be etched or embossed with letters, symbols, or other indicia that are illuminated by the light produced internally to the personal vaporizer unit.

In an embodiment, a personal vaporizer unit comprises a first wick element and a second wick element having a porous ceramic. The first wick element is adapted to directly contact a liquid held in a reservoir. The reservoir may be contained by a cartridge that is removable from the personal vaporizer unit. A heating element is disposed through the second wick element. An air gap is defined between the first wick element and the second wick element with the heating element exposed to the air gap. Air enters the first wick element through a hole in a housing holding the first wick element.

In an embodiment, a personal vaporizer unit comprises a light source internal to an opaque cylindrical housing that approximates the appearance of a smoking article. A cylindrical light tube is disposed inside the opaque cylindrical housing to conduct light emitted by the light source to an end of the opaque cylindrical housing. This allows the light to be visible outside of the opaque cylindrical housing of the vaporizer.

In an embodiment, a personal vaporizer unit comprises a microprocessor, a memory, and a connector. The connector outputs data stored in the memory. The microprocessor may gather, and store in the memory, information including, but not limited to, the number of cycles the device has been triggered, the duration of the cycles, the number of cartridges of fluid that are delivered. The microprocessor may also gather and store times and dates associated with other information gathered and stored. The microprocessor may detect an empty cartridge by detecting a specific change in resistance between a wick and a housing that is equivalent to a "dry wick," and thus signifies an empty cartridge.

In an embodiment, a case comprises a cradle adapted to hold a personal vaporizer unit. The personal vaporizer unit has dimensions approximating a smoking article. The case includes a battery and at least two contacts. The two contacts may form an electrical contact with the personal vaporizer unit when the personal vaporizer unit is in the cradle. The two contacts may conduct charge from the battery to the personal vaporizer unit to charge the personal vaporizer unit. The case may also download and store data retrieved from the personal vaporizer unit. The case may download and store this data via the at least two contacts. The case may send this data to a computer via wired or wireless links. The case may have more than one cradle and sets of contacts (e.g., two sets of two contacts in order to hold and charge two personal vaporizer units).

Figure 1:
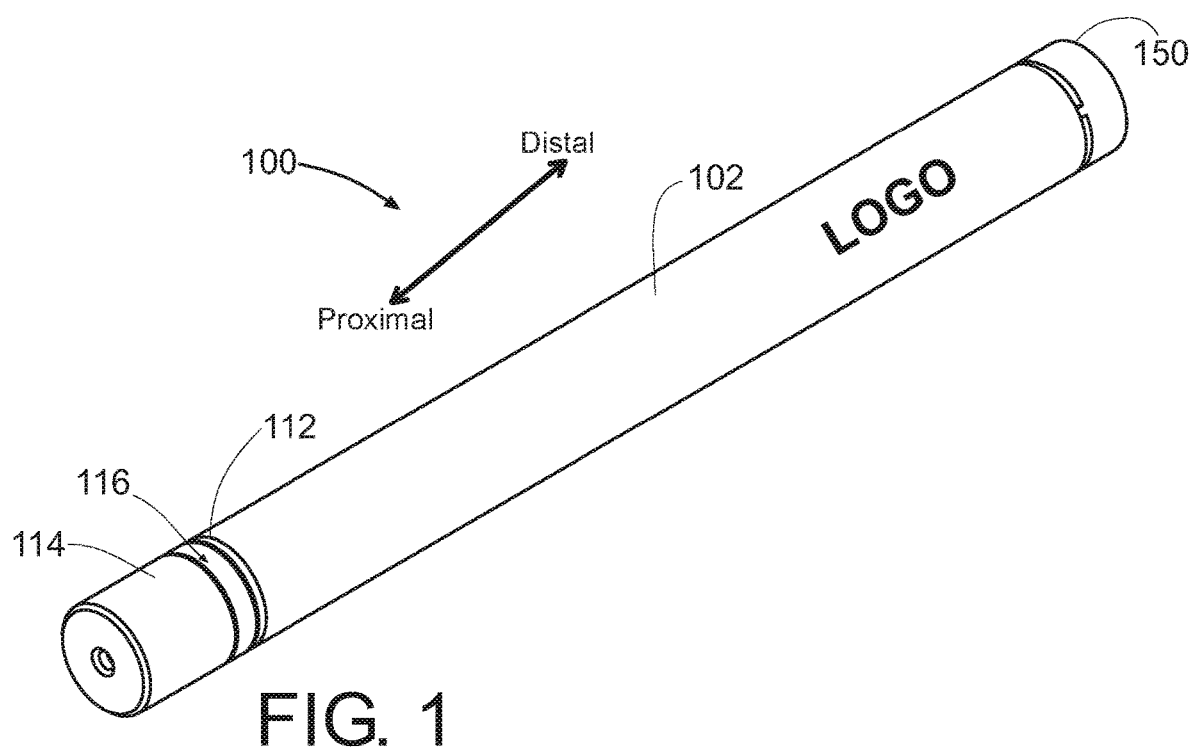
FIG. 1 is a perspective view of a personal vaporizer unit or electronic cigarette ("e-Cig").

FIG. 1 is a perspective view of a personal vaporizer unit or electronic cigarette ("e-Cig"). In FIG. 1, personal vaporizer unit 100 comprises outer main shell 102, mouthpiece cover 114, mouthpiece 116, and mouthpiece insulator 112. Proximal refers to the component that is closest to the user interface (mouth/lips) and Distal is an end opposite from the user interface. The mouthpiece 116 and mouthpiece cover 114 define the proximal end of personal vaporizer unit 100. The opposite end of personal vaporizer unit 100 will be referred to as the distal end. A cartridge 150 may be inserted into the distal end of personal vaporizer unit 100. The mouthpiece cover 114 is the most proximal component and the cartridge 150 is the most distal component. Cartridge 150 may hold the substance to be vaporized by personal vaporizer unit 100. The substance after vaporizing may be inhaled by a user holding the personal vaporizer unit 100. The substance may be in the form of a liquid or gel.

Figure 2:
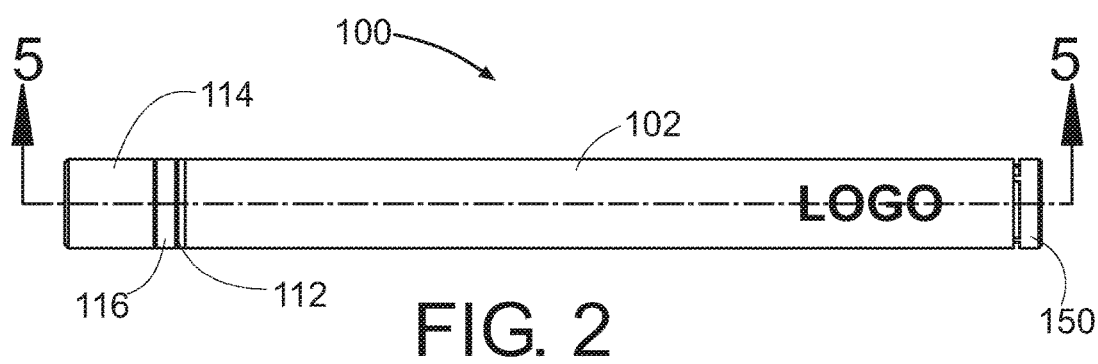
FIG. 2 is a side view of a personal vaporizer unit.

FIG. 2 is a side view of a personal vaporizer unit. FIG. 2 illustrates personal vaporizer unit 100 as viewed from the side. FIG. 2 illustrates personal vaporizer unit 100 comprising outer main shell 102, mouthpiece cover 114, mouthpiece 116, and mouthpiece insulator 112. FIG. 2 also illustrates cartridge 150 inserted into the distal end of personal vaporizer unit 100.

Figure 3:
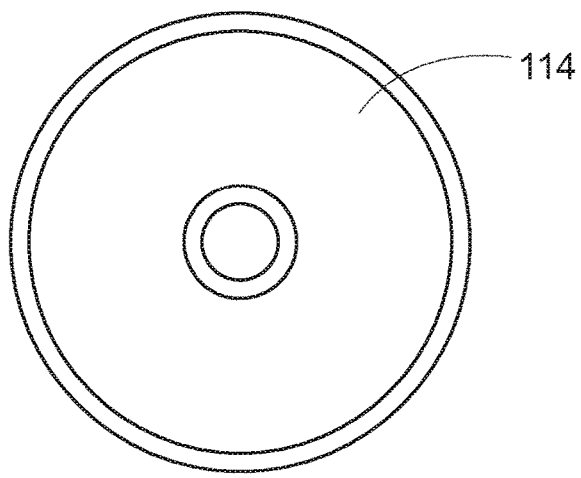
FIG. 3 is an end view of the proximal end of a personal vaporizer unit.
Figure 4A:
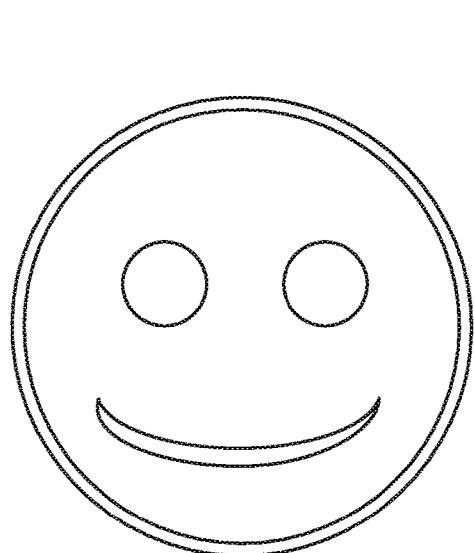
FIG. 4A is an end view of the distal end of a personal vaporizer unit having an embossed cartridge.
Figure 4:
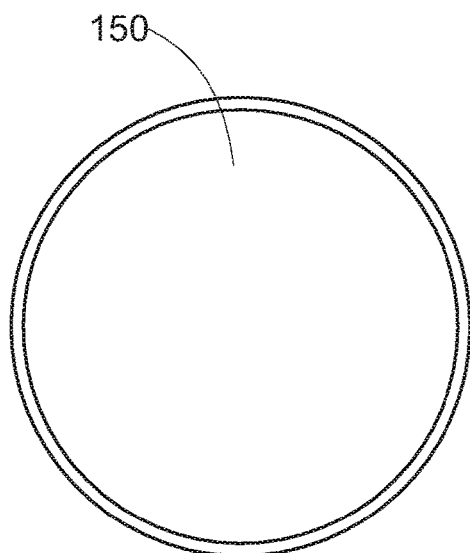
FIG. 4 is an end view of the distal end of a personal vaporizer unit.

FIG. 3 is an end view of the proximal end of a personal vaporizer unit. FIG. 3 shows the proximal end view of personal vaporizer unit 100 comprising mouthpiece cover 114. FIG. 4 is an end view of the distal end of a personal vaporizer unit. FIG. 4 shows the distal end view of personal vaporizer unit 100 comprising the visible portion of cartridge 150. FIG. 4A is an alternative end view of personal vaporizer unit 100 comprising a visible portion of cartridge 150 that has visible logos, letters, or other symbols. These visible logos, letters, or other symbols may be illuminated or backlit by a light source internal to the personal vaporizer unit 100. The light source may be activated intermittently under the control of a microprocessor or other electronics internal to personal vaporizer unit 100. The light source may be activated in such a manner as to simulate the glowing ash of a cigar or cigarette.

Figures 5, 6, 7:
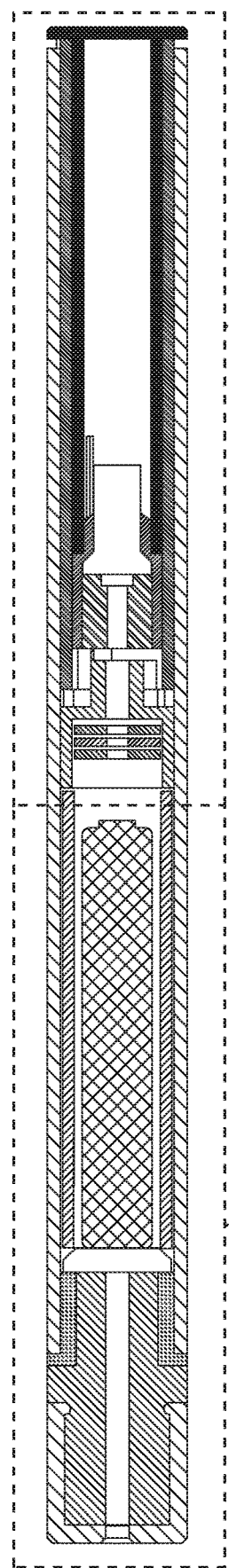
FIG. 5 is a figure map of FIGS. 6 and 7.
FIG. 6 is a cross-section view of the proximal portion of a personal vaporizer unit along the cut line shown in FIG. 2.
FIG. 7 is a cross-section view of the distal portion of a personal vaporizer unit along the cut line shown in FIG. 2.

FIG. 5 is a figure map of FIGS. 6 and 7. FIG. 6 is a cross-section view of the proximal portion of a personal vaporizer unit along the cut line shown in FIG. 2. In FIG. 6, the proximal portion of personal vaporizer unit 100 comprises mouthpiece cover 114, mouthpiece 116, mouthpiece insulator 112, outer main shell 102, battery support 106, and battery 104. The mouthpiece cover 114 surrounds and is engaged with the proximal end of mouthpiece 116. Mouthpiece 116 and outer main shell 102 are preferably made of an electrically conductive material(s). Mouthpiece 116 is separated from outer main shell 102 by mouthpiece insulator 112. Mouthpiece 116 and outer main shell 102 are thus electrically isolated from each other by mouthpiece insulator 112.

In an embodiment, personal vaporizer unit 100 is configured such that outer main shell 102 comprises a first conductive surface configured to contact a first body part of a person holding personal vaporizer unit 100. Mouthpiece 116 comprises a second conductive surface, which is conductively isolated from the first conductive surface. This second conductive surface is configured to contact a second body part of the person. When personal vaporizer unit 100 detects a change in conductivity between the first conductive surface and the second conductive surface, a vaporizer internal to personal vaporizer unit 100 is activated to vaporize a substance in cartridge 150 so that the vapors may be inhaled by the person holding personal vaporizer unit 100. The first body part and the second body part may be a lip or parts of a hand(s). The two conductive surfaces of outer main shell 102 and mouthpiece 116, respectively, may also be used to charge battery 104 contained in the personal vaporizer unit 100. The two conductive surfaces of outer main shell 102 and mouthpiece 116, respectively, may also be used to output (or input) data stored (or to be stored) in a memory (not shown).

Battery support 106 functions to hold battery 104 in a position which is fixed relative to outer main shell 102. Battery support 106 is also configured to allow air and vaporized substance to pass from the distal end of personal vaporizer unit 100 past battery 104 along one or more passageways. After air and the vapors of the vaporized substance pass by battery 104, they may pass through openings in mouthpiece 116, mouthpiece cover 114, and mouthpiece insulator 112, to be inhaled by a user.

FIG. 7 is a cross-section view of the distal portion of a personal vaporizer unit along the cut line shown in FIG. 2. In FIG. 7, the distal end portion of personal vaporizer unit 100 comprises outer main shell 102, light pipe sleeve 140, atomizer housing 132, distal wick 134, proximal wick 136, PC-board 123, PC-board 124, spacer 128, and main housing 160. FIG. 7 also illustrates cartridge 150 inserted into the distal end of personal vaporizer unit 100. As can be seen in FIG. 7, cartridge 150 may hold a substance (e.g., a liquid or gel) in direct contact with distal wick 134. The substance may be drawn through distal wick 134 to be vaporized inside atomizer assembly. The atomizer assembly comprises atomizer housing 132, distal wick 134, proximal wick 136, and a heating element (not shown).

Figure 8:
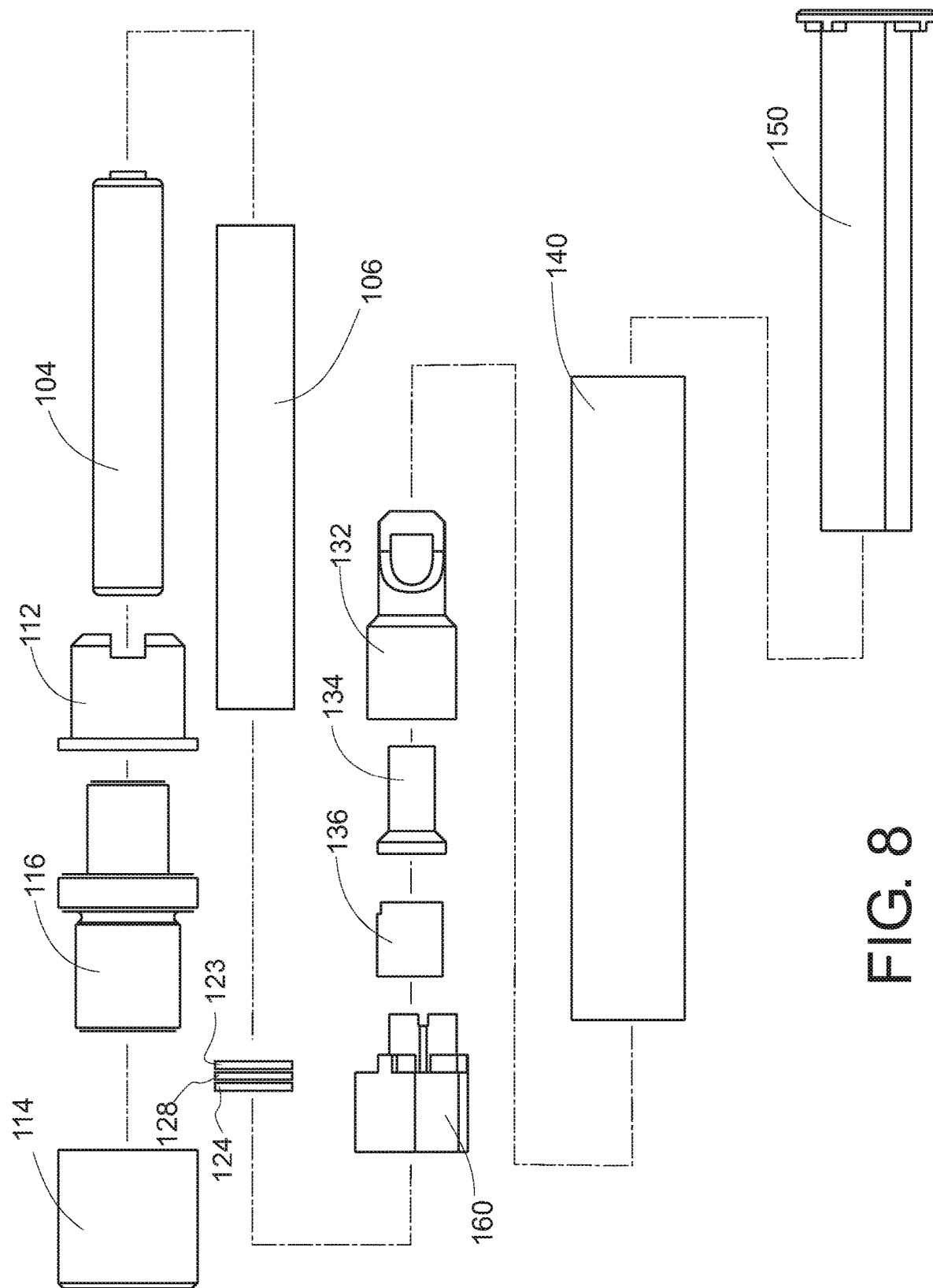
FIG. 8 is an exploded side view of components of a personal vaporizer unit.
Figure 9:
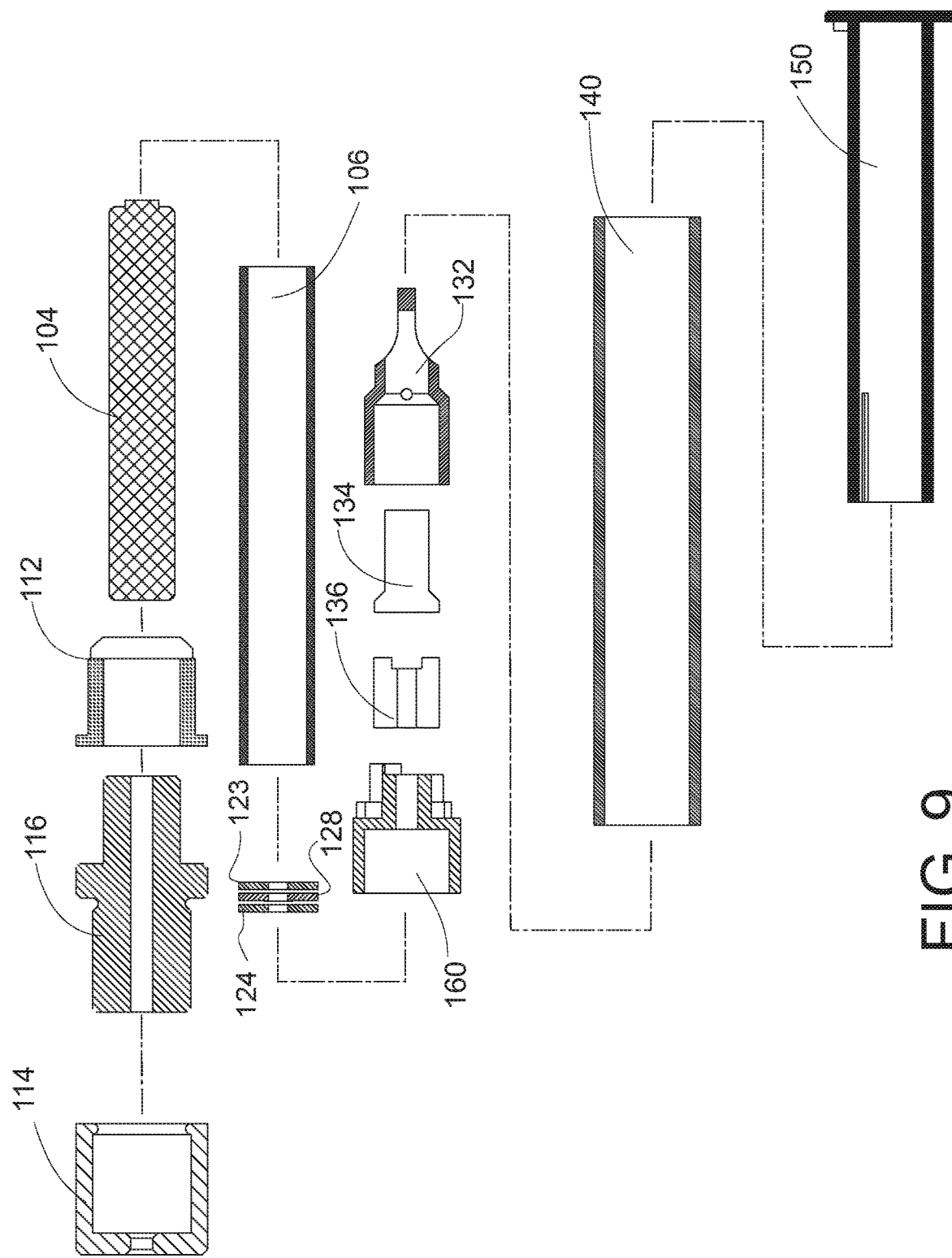
FIG. 9 is an exploded cross-section view of components of a personal vaporizer unit along the cut line shown in FIG. 2.

FIG. 8 is an exploded side view of components of a personal vaporizer unit. FIG. 9 is an exploded cross-section view of components of a personal vaporizer unit along the cut line shown in FIG. 2.

In FIGS. 8 and 9, personal vaporizer unit 100 comprises (from left to right) mouthpiece cover 114, mouthpiece 116, mouthpiece insulator 112, battery 104, battery support 106, PC-board 123, spacer 128, PC-board 124, main housing 160, proximal wick 136, distal wick 134, atomizer housing 132, light pipe sleeve 140, and cartridge 150. Mouthpiece cover 114 surrounds and covers the proximal end of mouthpiece 116. The distal end of mouthpiece 116 is inserted into mouthpiece insulator 112. Battery 104 is held in place by battery support 106. PC-board 123, spacer 128 and PC-board 124 are disposed within main housing 160. Proximal wick 136 and distal wick 134 are disposed within atomizer housing 132.

Atomizer housing 132 (and therefore proximal wick 136, distal wick 134) are disposed inside light pipe sleeve 140 and outer main shell 102. (Note: for clarity, outer main shell 102 is not shown in FIGS. 8 and 9.) Light pipe sleeve 140 is disposed within outer main shell 102. Light pipe sleeve 140 is positioned such that light emitted from a light source mounted on PC-board 124 may be conducted via light pipe sleeve 140 to a location where it is visible on the outside of personal vaporizer unit 100.

Cartridge 150 is disposed within light pipe sleeve 140. When assembled, a substance contained within cartridge 150 is held in direct contact with distal wick 134. When cartridge 150 is inserted into personal vaporizer unit 100 atomizer housing 132 or distal wick 134 may puncture a seal or cap that contains the substance to be vaporized within cartridge 150. Once punctured, the substance held within a reservoir of cartridge 150 may come in direct contact with distal wick 134.

Figure 10:
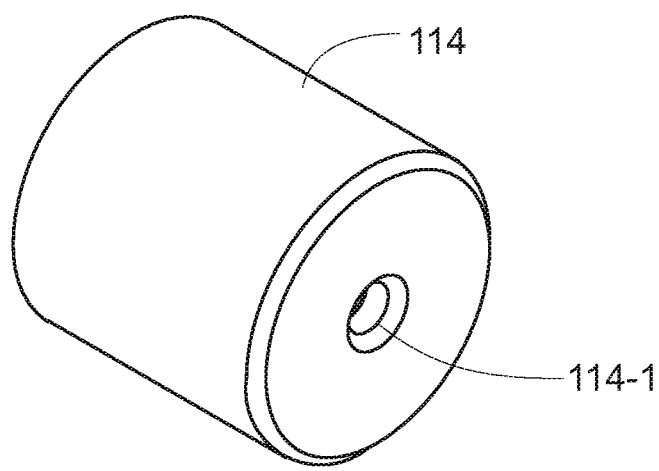
FIG. 10 is a perspective view of a mouthpiece cover of a personal vaporizer unit.
Figure 11:
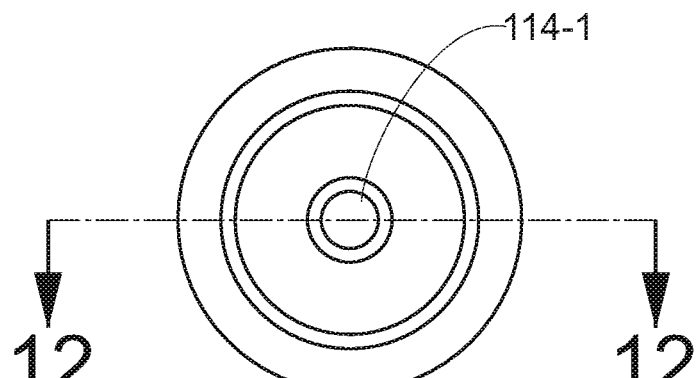
FIG. 11 is a distal end view of the mouthpiece cover of FIG. 10.
Figure 12:
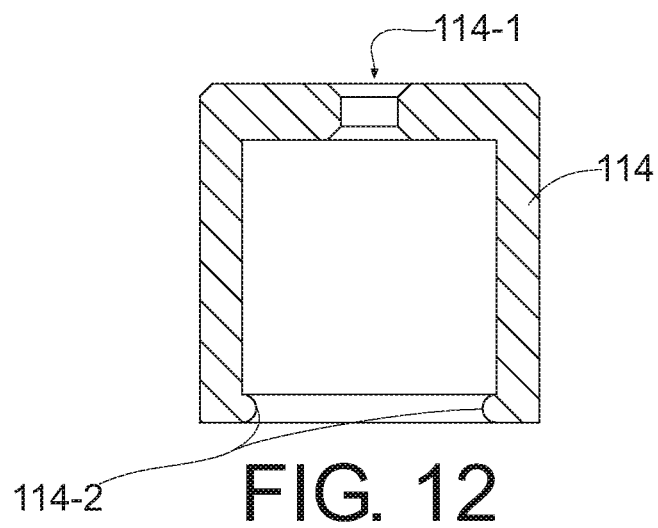
FIG. 12 is a cross-section view of the mouthpiece cover along the cut line shown in FIG. 11.

FIG. 10 is a perspective view of a mouthpiece cover of a personal vaporizer unit. FIG. 11 is a distal end view of the mouthpiece cover of FIG. 10. FIG. 12 is a cross-section view of the mouthpiece cover along the cut line shown in FIG. 11. As can be seen in FIGS. 10-12, mouthpiece cover 114 has an opening 114-1 that allows air and the vaporized substance to be drawn through mouthpiece cover 114. Mouthpiece cover 114 is configured for contact with the mouth of a person. In an embodiment, at least part of the mouthpiece cover has an antimicrobial surface. This antimicrobial surface of mouthpiece cover 114 may comprise, but is not limited to: silicone rubber, thermoplastic elastomer, organosilane, silver impregnated polymer, silver impregnated thermoplastic elastomer, and/or polymer. Mouthpiece cover 114 is also configured to be removable from personal vaporizer unit 100 by a user without the use of tools. This allows mouthpiece cover 114 to be replaced and/or washed. In an embodiment, mouthpiece cover 114 may be held in place on personal vaporizer unit 100 by annular ridge 114-2 which interfaces with a groove on mouthpiece 116 of personal vaporizer unit 100 to secure mouthpiece cover 114 in place. In another embodiment, mouthpiece cover 114 may be held in place on personal vaporizer unit 100 by a friction fit.

Figure 13:
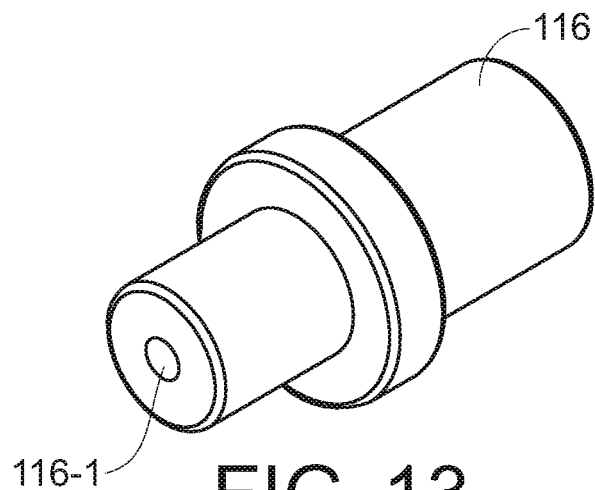
FIG. 13 is a perspective view of a mouthpiece of a personal vaporizer unit.
Figure 14:
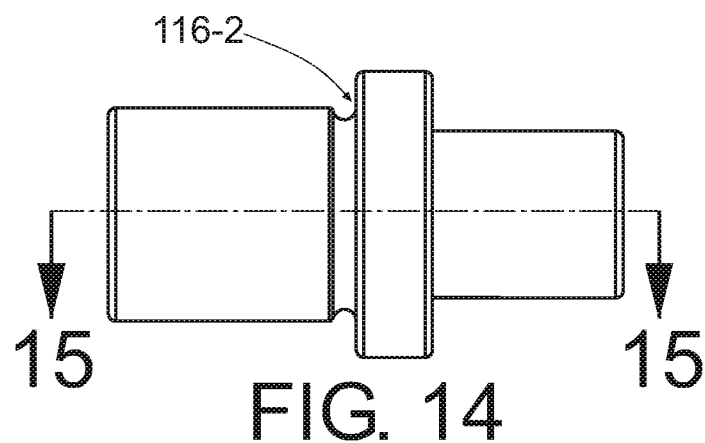
FIG. 14 is a side view of the mouthpiece of FIG. 13.
Figure 15:
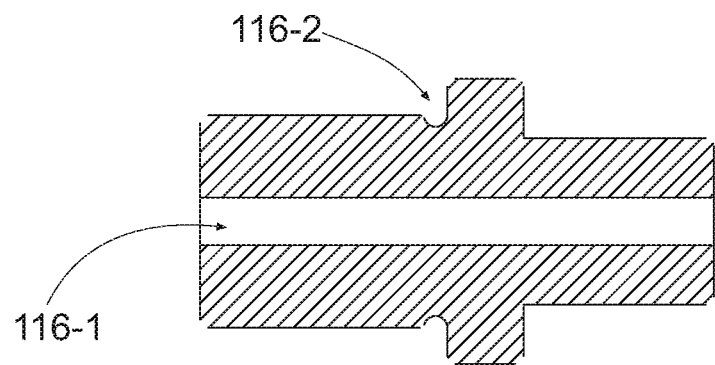
FIG. 15 is a cross-section view of the mouthpiece along the cut line shown in FIG. 14.

FIG. 13 is a perspective view of a mouthpiece of a personal vaporizer unit. FIG. 14 is a side view of the mouthpiece of FIG. 13. FIG. 15 is a cross-section view of the mouthpiece along the cut line shown in FIG. 14. As can be seen in FIGS. 13-15, mouthpiece 116 has a passageway 116-1 that allows air and the vaporized substance to be drawn through mouthpiece 116. Mouthpiece 116 may comprise a conductive surface or material configured to contact a first body part of a person holding personal vaporizer unit 100. This first body part may be part of a hand, or at least one lip of the person holding personal vaporizer unit 100. In an embodiment, mouthpiece 116 has an annular groove 116-2 around an outside surface. This groove is configured to receive annular ridge 114-2. Thus, annular groove 116-2 helps secure mouthpiece cover 114 to personal vaporizer unit 100.

Figure 16:
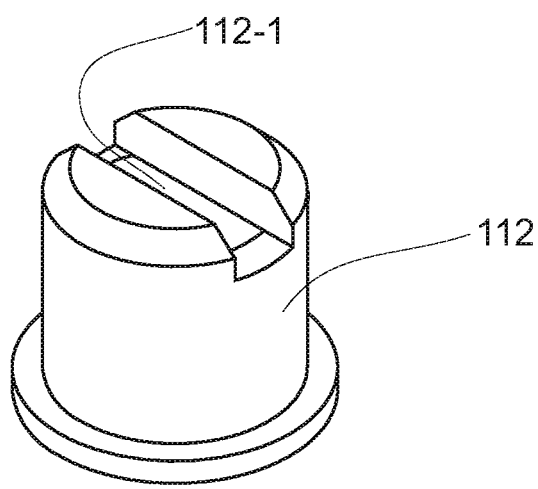
FIG. 16 is a perspective view of a mouthpiece insulator of a personal vaporizer unit.
Figure 17:
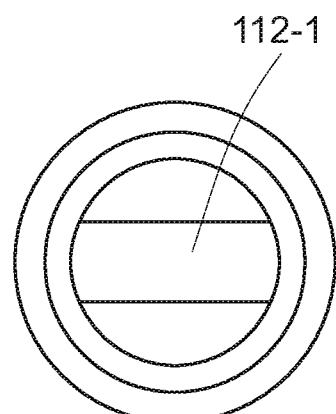
FIG. 17 is a distal end view of the mouthpiece insulator of FIG. 16.
Figure 18:
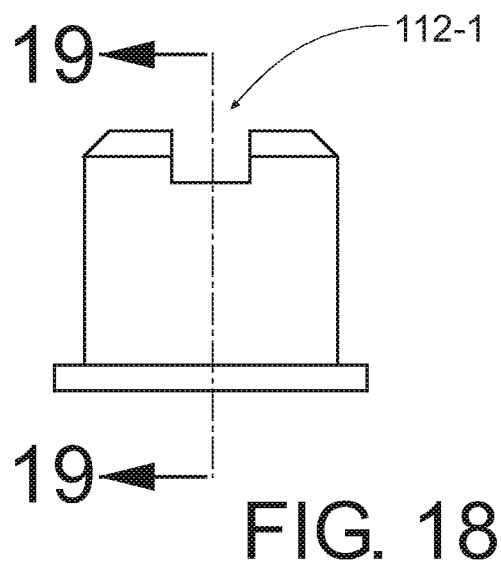
FIG. 18 is a side view of the mouthpiece insulator of FIG. 16.
Figure 19:
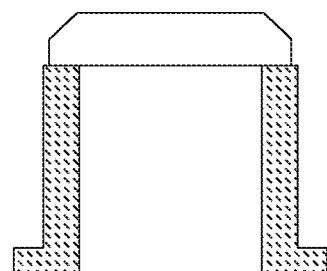
FIG. 19 is a cross-section view of the mouthpiece insulator along the cut line shown in FIG. 18.

FIG. 16 is a perspective view of a mouthpiece insulator of a personal vaporizer unit. FIG. 17 is a distal end view of the mouthpiece insulator of FIG. 16. FIG. 18 is a side view of the mouthpiece insulator of FIG. 16. FIG. 19 is a cross-section view of the mouthpiece insulator along the cut line shown in FIG. 18. As discussed previously, mouthpiece insulator 112 is disposed between outer main shell 102 and mouthpiece 116. As can be seen in FIGS. 16-18, mouthpiece insulator 112 has a passageway 112-1 that allows air and the vaporized substance to be drawn through mouthpiece insulator 112. Because mouthpiece insulator 112 is disposed between outer main shell 102 and mouthpiece 116, mouthpiece insulator 112 can electrically isolate outer main shell 102 and mouthpiece 116. Thus, in an embodiment, mouthpiece insulator 112 comprises, or is made of, a non-electrically conductive material. This electrical isolation between outer main shell 102 and mouthpiece 116 allow electrical impedance changes between outer main shell 102 and mouthpiece 116 to be detected.

For example, a first conductive surface on mouthpiece 116 may be configured to contact a first body part of a person holding personal vaporizer unit 100. A second conductive surface on outer main shell 102 (which is conductively isolated from said first conductive surface by mouthpiece insulator 112) may be configured to contact a second body part of the person. Personal vaporizer unit 100 may then activate in response to detecting a change in conductivity between the first conductive surface and the second conductive surface. In an embodiment, this change in conductivity may comprise a drop in impedance between the first conductive surface and the second conductive surface. In an embodiment, the change in conductivity may comprise a change in capacitance between the first conductive surface and the second conductive surface. The first body part may be a finger. The second body part may be a lip. The second body part may be a second finger. In an embodiment, the first conductive surface and the second conductive surface may be used to pass a charging current to battery 104. The first and second conductive surfaces may also be used to transfer data to or from personal vaporizer unit 100.

Figure 20:
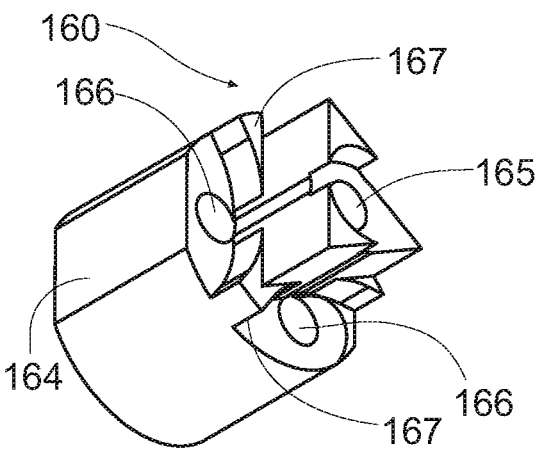
FIG. 20 is a perspective view of a main housing of a personal vaporizer unit.
Figure 21:
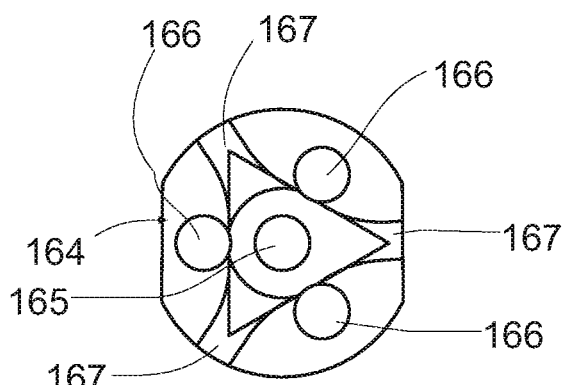
FIG. 21 is a distal end view of the main housing of FIG. 20.
Figure 22:
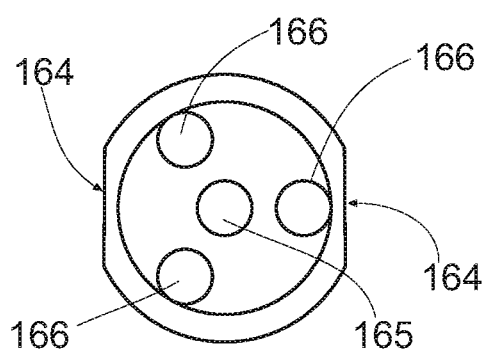
FIG. 22 is a proximal end view of the main housing of FIG. 20.
Figure 23:
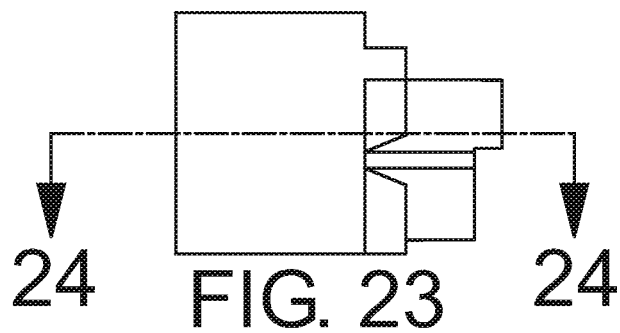
FIG. 23 is a side view of the main housing of FIG. 20.
Figure 24:
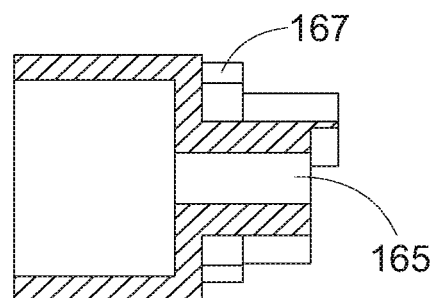
FIG. 24 is a cross-section view of the main housing along the cut line shown in FIG. 23.

FIG. 20 is a perspective view of a main housing of a personal vaporizer unit. FIG. 21 is a distal end view of the main housing of FIG. 20. FIG. 22 is a proximal end view of the main housing of FIG. 20. FIG. 23 is a side view of the main housing of FIG. 20. FIG. 24 is a cross-section view of the main housing along the cut line shown in FIG. 23. Main housing 160 is configured to hold PC-boards 123 and 124, and spacer 128. Main housing 160 is configured to fit within outer main shell 102 via a friction fit. Main housing 160 has several holes 166 that allow light generated by a light source(s) on PC-board 124 to pass. Once this light passes through holes 166, it may be coupled into light pipe sleeve 140 where it is conducted to a visible location on the outside of personal vaporizer unit 100.

Main housing 160 also has a hole 165 that allows an electrical conductor (not shown) to run from PC-board 123 or PC-board 124 through main housing 160. This electrical conductor may be, or connect to, a heating element (not shown). This heating element may help vaporize the substance to be inhaled by the user of personal vaporizer unit 100. This heating element may be controlled by circuitry on PC-board 123 or PC-board 124. This heating element may be activated in response to a change in conductivity between the first conductive surface and the second conductive surface, described previously.

The exterior of main housing 160 may also have a flat surface 164 (or other geometry) forming a galley that is configured to allow the vaporized substance and air to pass between the main housing 160 and the outer main shell 102. Once the vaporized substance and air pass by main housing 160, they may travel through passageway 112-1, passageway 116-1, and opening 114-1 to be inhaled by a user of personal vaporizer unit 100. The exterior of main housing 160 may also have one or more standoffs 167 (or other geometries) that are configured to allow air and the vaporized substance to reach the passageway formed by flat surface 164 and outer main shell 102.

Figure 25:
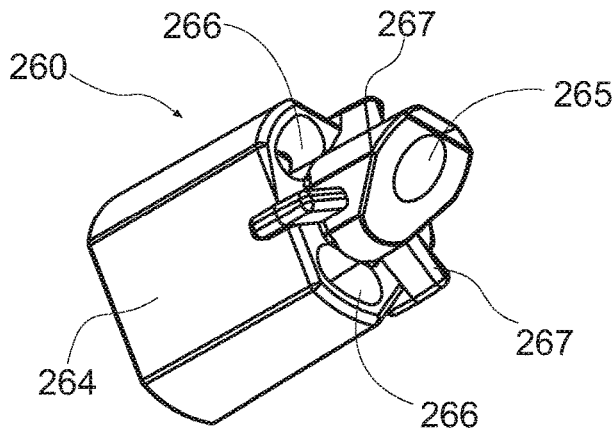
FIG. 25 is a perspective view of a main housing of a personal vaporizer unit according to another embodiment.
Figure 26:
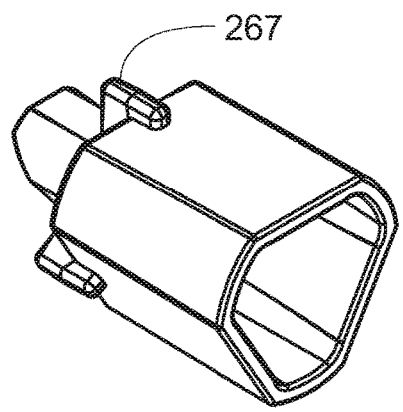
FIG. 26 is a second perspective view of the main housing of FIG. 25.
Figure 27:
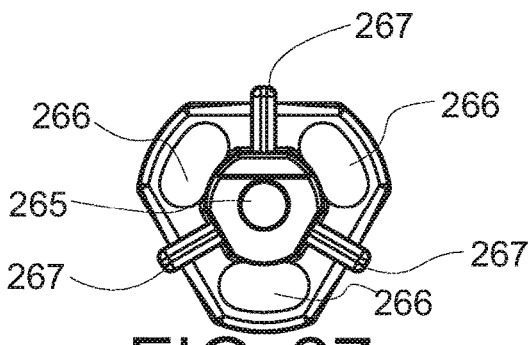
FIG. 27 is a distal end view of the main housing of FIG. 25.
Figure 29:
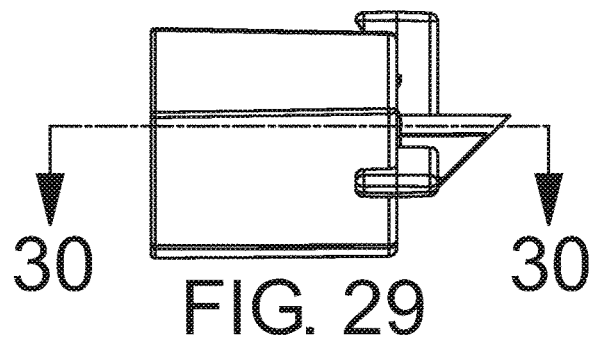
FIG. 29 is a side view of the main housing of FIG. 25.
Figure 28:
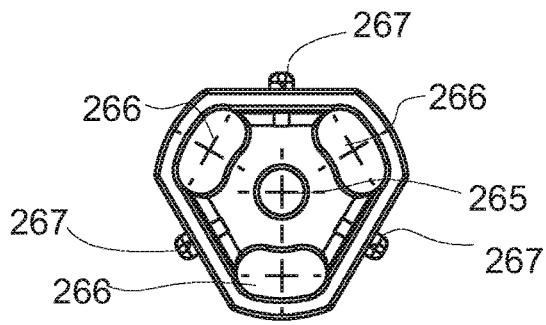
FIG. 28 is a proximal end view of the main housing of FIG. 25.
Figure 30:
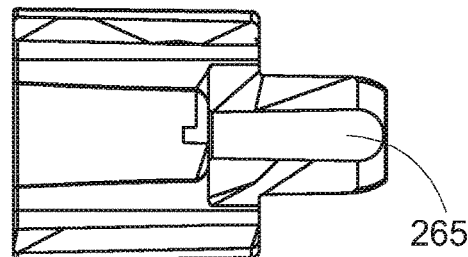
FIG. 30 is a cross-section view of the main housing along the cut line shown in FIG. 29.

FIG. 25 is a perspective view of a main housing of a personal vaporizer unit according to another embodiment. FIG. 26 is a second perspective view of the main housing of FIG. 25. FIG. 27 is a distal end view of the main housing of FIG. 25. FIG. 28 is a proximal end view of the main housing of FIG. 25. FIG. 29 is a side view of the main housing of FIG. 25. FIG. 30 is a cross-section view of the main housing along the cut line shown in FIG. 29. Main housing 260 may be used as an alternative embodiment to main housing 160.

Main housing 260 is configured to hold PC-boards 123 and 124, and spacer 128. Main housing 260 is configured to fit within outer main shell 102 via a friction fit. Main housing 260 has several holes 266 that allow light generated by a light source(s) on PC-board 124 to pass. Once this light passes through holes 266, it may be coupled into light pipe sleeve 140 where it is conducted to a visible location on the outside of personal vaporizer unit 100.

Main housing 260 also has a hole 265 that allows an electrical conductor (not shown) to run from PC-board 123 or PC-board 124 through main housing 260. This electrical conductor may be, or connect to, a heating element (not shown). This heating element may help vaporize the substance to be inhaled by the user of personal vaporizer unit 100. This heating element may be controlled by circuitry on PC-board 123 or PC-board 124. This heating element may be activated in response to a change in conductivity between the first conductive surface and the second conductive surface, described previously.

The exterior of main housing 260 may also have flat surfaces 264 (or other geometry) that form a galley that is configured to allow the vaporized substance and air to pass between the main housing 260 and the outer main shell 102. Once the vaporized substance and air pass by main housing 260, they may travel through passageway 112-1, passageway 116-1, and opening 114-1 to be inhaled by a user of personal vaporizer unit 100. The exterior of main housing 260 may also have one or more standoffs 267 (or other geometries) that are configured to allow air and the vaporized substance to reach the passageway formed by flat surfaces 264 and outer main shell 102.

Figure 31:
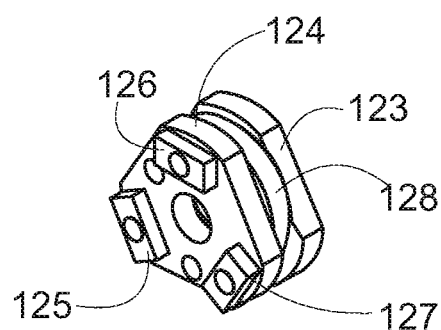
FIG. 31 is a perspective view of a printed circuit board (PCB or PC-board) assembly of a personal vaporizer unit.
Figure 32:
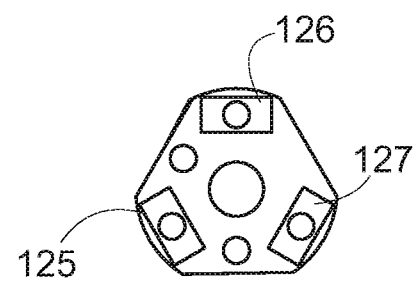
FIG. 32 is a distal end view of the PCB assembly of FIG. 31.
Figure 33:
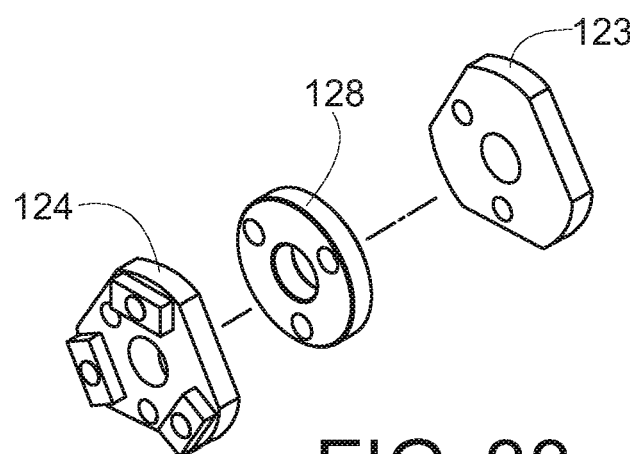
FIG. 33 is a perspective exploded view of the PCB assembly of FIG. 31.
Figure 34:
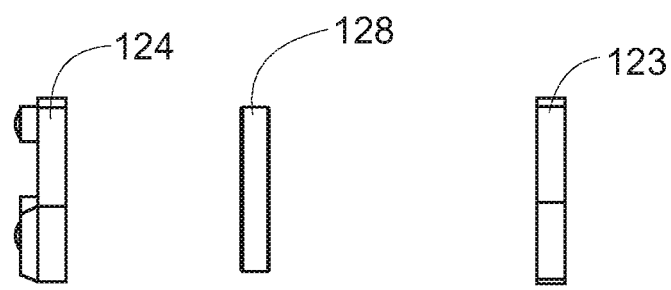
FIG. 34 is a side exploded view of the PCB assembly of FIG. 31.

FIG. 31 is a perspective view of a printed circuit board assembly of a personal vaporizer unit. FIG. 32 is a distal end view of the PCB assembly of FIG. 31. FIG. 33 is a perspective exploded view of the PCB assembly of FIG. 31. FIG. 34 is a side exploded view of the PCB assembly of FIG. 31. As can be seen in FIGS. 31-34, the PCB assembly is comprised of PC-board 123 and PC-board 124 separated by a spacer 128. PC-board 124 may have mounted upon it light emitting diodes (LEDs) 125-127 or other light sources. LEDs 125-127 are configured and positioned such that when they produce light, that light passes through holes 166 or 266 in main housings 160 and 260, respectively. This light may then be conducted by light pipe sleeve 140 to a location where it will be visible exterior to personal vaporizer unit 100.

PC-board 123 may have mounted on it a microprocessor, memory, or other circuitry (not shown) to activate or otherwise control personal vaporizer unit 100. This microprocessor may store data about the operation of personal vaporizer unit 100 in the memory. For example, the microprocessor may determine and store the number of cycles personal vaporizer unit 100 has been triggered. The microprocessor may also store a time and/or date associated with one or more of these cycles. The microprocessor may cause this data to be output via a connector. The connector may be comprised of the first and second conductive surfaces of mouthpiece 116 and/or outer main shell 102.

In an embodiment, the microprocessor may determine a duration associated with various cycles where personal vaporizer unit 100 has been triggered. These durations (or a number based on these durations, such as an average) may be stored in the memory. The microprocessor may cause these numbers to be output via the connector. The microprocessor may determine an empty cartridge condition and store a number associated with a number of times said empty cartridge condition occurs. The microprocessor, or other circuitry, may determine an empty cartridge condition based on a resistance between atomizer housing 132 or 232 and a wick 134, 234, 136, or 236. The microprocessor may also store a time and/or date associated with one or more of these empty cartridge conditions. The number of times an empty cartridge condition is detected, times, and/or dates associated with these empty cartridge conditions may be output via the connector.

Battery 104, PC-board 123, PC-board 124, and all electronics internal to personal vaporizer unit 100 may be sealed in a plastic or plastic and epoxy compartment within the device. This compartment may include main housing 160 or 260. All penetrations in this compartment may be sealed. Thus, only wires will protrude from the compartment. The compartment may be filled with epoxy after the assembly of battery 104, PC-board 123, PC-board 124, and LEDs 125-127. The compartment may be ultrasonically welded closed after assembly of battery 104, PC-board 123, PC-board 124, and LEDs 125-127. This sealed compartment is configured such that all vapor within personal vaporizer unit 100 does not come in contact with the electronics on PC-boards 123, 124.

Figure 35:
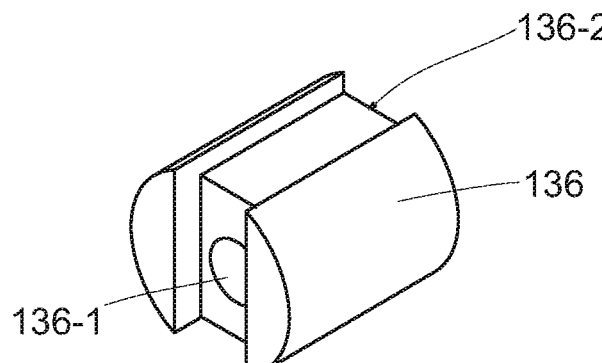
FIG. 35 is a perspective view of a proximal wick element of a personal vaporizer unit.
Figure 35A:
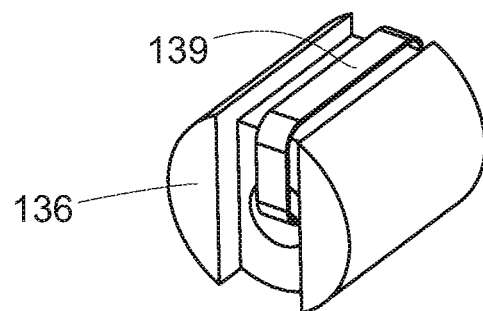
FIG. 35A is a perspective view of a heating element disposed through a proximal wick element of a personal vaporizer unit.
Figure 35B:
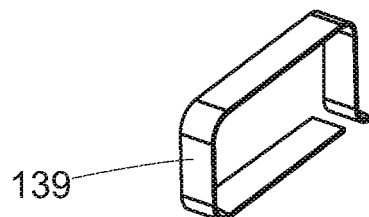
FIG. 35B is a perspective view of a heating element of a personal vaporizer unit.
Figure 36:
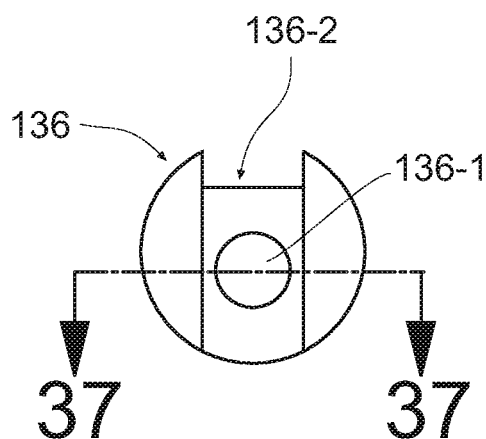
FIG. 36 is a distal end view of the wick element of FIG. 35.
Figure 37:
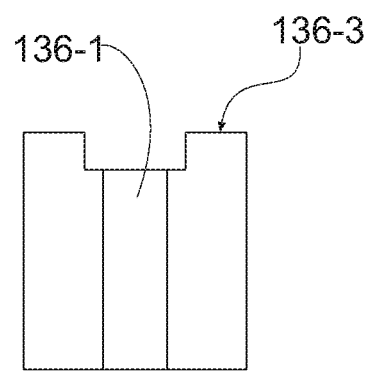
FIG. 37 is a cross-section view of the wick element along the cut line shown in FIG. 36.

FIG. 35 is a perspective view of a proximal wick element of a personal vaporizer unit. FIG. 35 shows a proximal wick 136, internal wire passageway 136-1 and external wire passageway 136-2. FIG. 35A is a perspective view of a heating element disposed through a proximal wick element of a personal vaporizer unit. FIG. 35B is a perspective view of a heating element of a personal vaporizer unit. FIG. 36 is a distal end view of the wick element of FIG. 35. FIG. 37 is a cross-section view of the wick element along the cut line shown in FIG. 35. Proximal wick 136 is configured to fit within atomizer housing 132. As can be seen in FIGS. 35-37, proximal wick 136 includes internal wire passageway 136-1 and external wire passageway 136-2. These wire passageways allow a conductor or a heating element 139 to be positioned through proximal wick 136 (via internal wire passageway 136-1). This conductor or heating element 139 may also be positioned in external wire passageway 136-2. Thus, as shown in FIG. 35A, a conductor or heating element 139 may be wrapped around a portion of proximal wick 136 by running the conductor or heating element 139 through internal wire passageway 136-1, around the distal end of proximal wick 136, and through external wire passageway 136-2 to return to approximately its point of origin. The heating element 139 may, when personal vaporizer unit 100 is activated, heat proximal wick 136 in order to facilitate vaporization of a substance.

Figure 38:
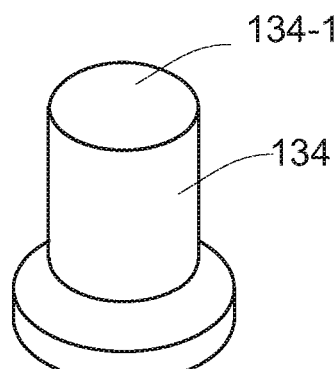
FIG. 38 is a perspective view of a distal wick element of a personal vaporizer unit.
Figure 39:
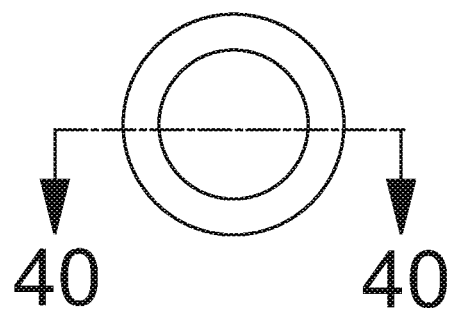
FIG. 39 is a distal end view of the wick element of FIG. 38.
Figure 40:
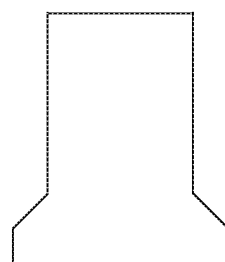
FIG. 40 is a cross-section view of the wick element along the cut line shown in FIG. 39.

FIG. 38 is a perspective view of a distal wick element of a personal vaporizer unit. FIG. 39 is a distal end view of the wick element of FIG. 38. FIG. 40 is a cross-section view of the wick element along the cut line shown in FIG. 39. Distal wick 134 is configured to fit within atomizer housing 132. As can be seen in FIGS. 38-40, distal wick 134 comprises two cylinders of different diameters. A chamfered surface transitions from the smaller diameter of the distal end of distal wick 134 to a larger diameter at the proximal end of distal wick 134. The cylinder at the distal end terminates with a flat surface end 134-1. This flat surface end 134-1 is the end of distal wick 134 and is a surface that is placed in direct contact with a substance to be vaporized when cartridge 150 is inserted into the distal end of personal vaporizer unit 100. The proximal end of distal wick 134 is typically in contact with proximal wick 136. However, at least a part of proximal wick 136 and distal wick 134 are separated by an air gap. When distal wick 134 and proximal wick 136 are used together, this air gap is formed between distal wick 134 and proximal wick 136 by standoffs 136-3 as shown in FIG. 37.

Figure 41:
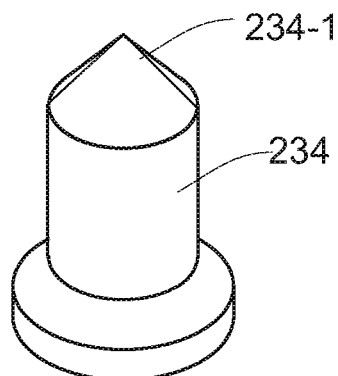
FIG. 41 is a perspective view of a distal wick element of a personal vaporizer unit according to another embodiment.
Figure 42:
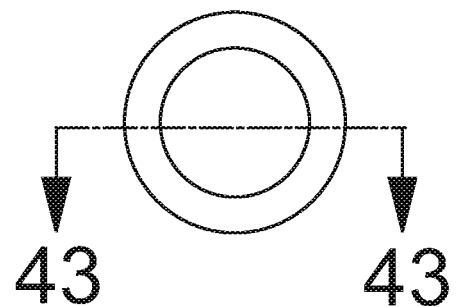
FIG. 42 is a distal end view of the wick element of FIG. 41.
Figure 43:
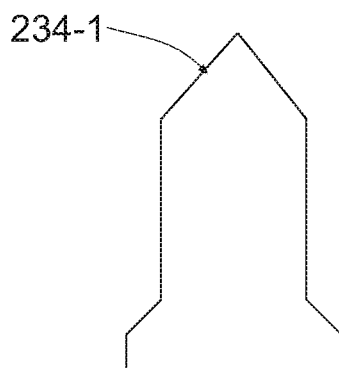
FIG. 43 is a cross-section view of the wick element along the cut line shown in FIG. 42.
Figure 59:
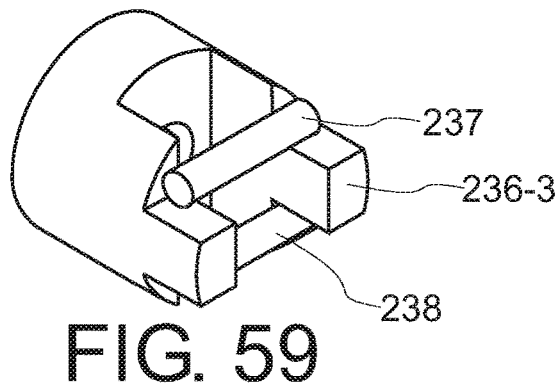
FIG. 59 is a perspective view of the proximal wick and wire guides of FIGS. 54-58.

FIG. 41 is a perspective view of a distal wick element of a personal vaporizer unit. FIG. 42 is a distal end view of the wick element of FIG. 41. FIG. 43 is a cross-section view of the wick element along the cut line shown in FIG. 42. Distal wick 234 may be used as an alternative embodiment to distal wick 134. Distal wick 234 is configured to fit within atomizer housing 232. As can be seen in FIGS. 41-43, distal wick 234 comprises two cylinders of different diameters, and a cone or pointed end 234-1. A chamfered surface transitions from the smaller diameter of the distal end of distal wick 234 to a larger diameter at the proximal end of distal wick 234. The cylinder at the distal end terminates with a pointed end 234-1. This pointed end 234-1 is the end of distal wick 234 and is in direct contact with a substance to be vaporized. This pointed end 234-1 may also break a seal on cartridge 150 to allow the substance to be vaporized to come in direct contact with distal wick 234. The proximal end of distal wick 234 is typically in contact with proximal wick 136, 236. However, at least a part of proximal wick 136, 236 and distal wick 234 are separated by an air gap. When distal wick 234 and proximal wick 136, 236 are used together, this air gap is formed between distal wick 234 and proximal wick 136, 236 by standoffs 136-3, 236-3 as shown in FIGS. 37, 59.

Figure 44:
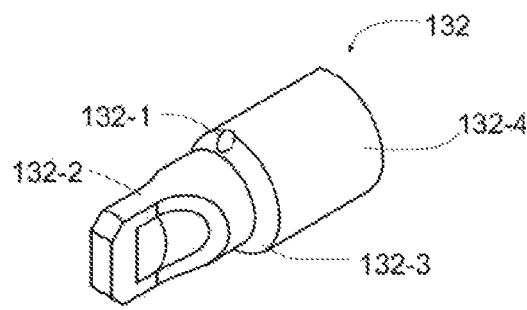
FIG. 44 is a perspective view of an atomizer housing of a personal vaporizer unit.
Figure 45:
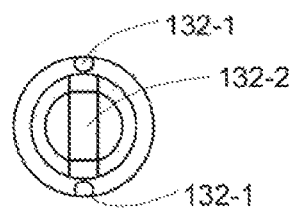
FIG. 45 is a distal end view of the atomizer housing of FIG. 44.
Figure 46:
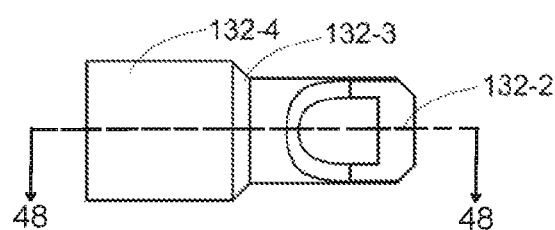
FIG. 46 is a side view of the atomizer housing of FIG. 44.
Figure 47:
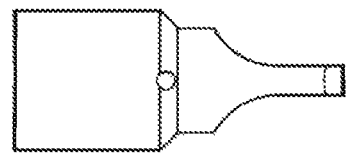
FIG. 47 is a top view of the atomizer housing of FIG. 44.
Figure 48:
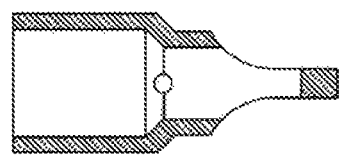
FIG. 48 is a cross-section view of the atomizer housing along the cut line shown in FIG. 46.

FIG. 44 is a perspective view of an atomizer housing of a personal vaporizer unit. FIG. 45 is a distal end view of the atomizer housing of FIG. 44. FIG. 46 is a side view of the atomizer housing of FIG. 44. FIG. 47 is a top view of the atomizer housing of FIG. 44. FIG. 48 is a cross-section view of the atomizer housing along the cut line shown in FIG. 46. Atomizer housing 132 is configured to fit within outer main shell 102. As can be seen in FIGS. 44-48, atomizer housing 132 comprises roughly two cylinders of different diameters. A chamfered surface 132-3 transitions from the smaller diameter of the distal end of atomizer housing 132 to a larger diameter at the proximal end 132-4 of atomizer housing 132. The larger diameter at the proximal end 132-4 of atomizer housing 132 is configured to be press fit into light pipe sleeve 140. The cylinder at the distal end terminates with a spade shaped tip 132-2. This spade shaped tip 132-2 may break a seal on cartridge 150 to allow the substance to be vaporized to come in direct contact with distal wick 134. Other shaped tips are possible (e.g., needle or spear shaped).

Chamfered surface 132-3 has one or more holes 132-1. These holes allow air to pass, via suction, through atomizer housing 132 into distal wick 134. This suction may be supplied by the user of personal vaporizer unit 100 sucking or inhaling on mouthpiece cover 114 and/or mouthpiece 116. The air that is sucked into distal wick 134 enters distal wick 134 on or near the chamfered surface between the two cylinders of distal wick 134. The air that is sucked into distal wick 134 displaces some of the substance being vaporized that has been absorbed by distal wick 134 causing it to be atomized as it exits distal wick 134 into the air gap formed between distal wick 134 and proximal wick 136. The heating element disposed around proximal wick 136 may then vaporize at least some of the atomized substance. In an embodiment, one or more holes 132-1 may range in diameter between 0.02 and 0.0625 inches.

In an embodiment, placing holes 132-1 at the leading edge of the chamfered surface places a set volume of the substance to be vaporized in the path of incoming air. This incoming air has nowhere to go but through the large diameter (or "head") end of the distal wick 134. When the air enters this area in distal wick 134 it displaces the substance to be vaporized that is suspended in distal wick 134 towards an air cavity between distal wick 134 and proximal wick 136. When the displaced substance to be vaporized reaches the surface of distal wick 134, it is forced out of the wick by the incoming air and the negative pressure of the cavity. This produces an atomized cloud of the substance to be vaporized. In an embodiment, the diameter of the head end of the distal wick 134 may be varied and be smaller than the diameter of the proximal wick 136. This allows for a tuned volume of air to bypass proximal wick 136 and directly enter the cavity between distal wick 134 and proximal wick 136 without first passing through proximal wick 136.

Figure 49:
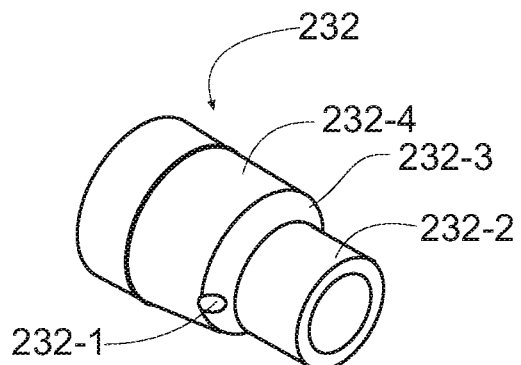
FIG. 49 is a perspective view of an atomizer housing of a personal vaporizer unit according to another embodiment.
Figure 50:
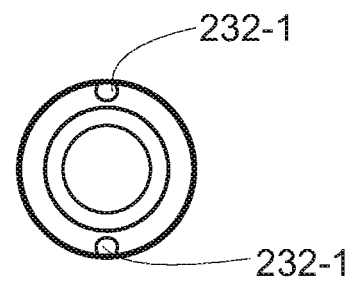
FIG. 50 is a distal end view of the atomizer housing of FIG. 49.
Figure 51:
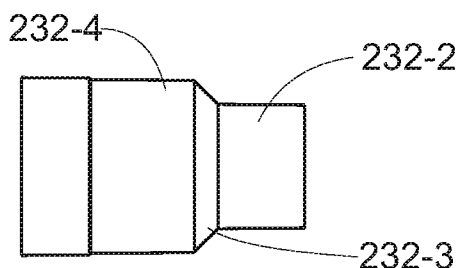
FIG. 51 is a side view of the atomizer housing of FIG. 49.
Figure 52:
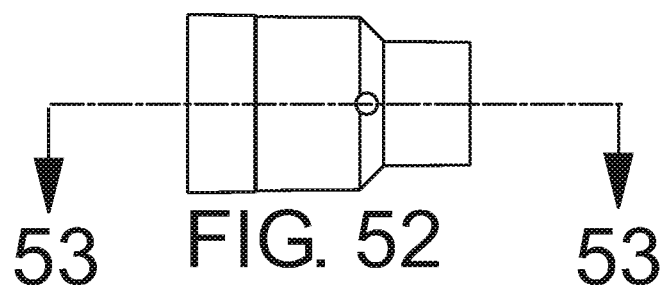
FIG. 52 is a top view of the atomizer housing of FIG. 49.
Figure 53:
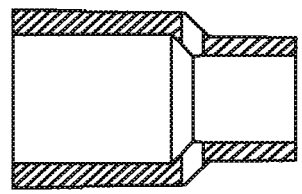
FIG. 53 is a cross-section view of the atomizer housing along the cut line shown in FIG. 52.

FIG. 49 is a perspective view of an atomizer housing of a personal vaporizer unit. FIG. 50 is a distal end view of the atomizer housing of FIG. 49. FIG. 51 is a side view of the atomizer housing of FIG. 49. FIG. 52 is a top view of the atomizer housing of FIG. 49. FIG. 53 is a cross-section view of the atomizer housing along the cut line shown in FIG. 52. Atomizer housing 232 is an alternative embodiment, for use with distal wick 234, to atomizer housing 132. Atomizer housing 232 is configured to fit within outer main shell 102 and light pipe sleeve 140. As can be seen in FIGS. 49-53, atomizer housing 232 comprises roughly two cylinders of different diameters. A chamfered surface 232-3 transitions from the smaller diameter of the distal end of atomizer housing 232 to a larger diameter at the proximal end 232-4 of atomizer housing 232. The larger diameter at the proximal end 232-4 of atomizer housing 232 is configured to be press fit into light pipe sleeve 140. The cylinder at the distal end terminates with an open cylinder tip 232-2. This open cylinder tip 232-2 allows the pointed end 234-1 of distal wick 234 to break a seal on cartridge 150 to allow the substance to be vaporized to come in direct contact with distal wick 234.

Chamfered surface 232-3 has one or more holes 232-1. These holes allow air to pass, via suction, through atomizer housing 232 into distal wick 234. The air that is sucked into distal wick 234 enters distal wick 234 on or near the chamfered surface between the two cylinders of distal wick 234. The air that is sucked into distal wick 234 displaces some of the substance being vaporized that has been absorbed by distal wick 234 causing it to be atomized as it exits distal wick 234 into the air gap formed between distal wick 234 and proximal wick 136. The heating element disposed around proximal wick 136 may then vaporize at least some of the atomized substance being vaporized. In an embodiment, one or more holes 232-1 may range in diameter between 0.02 and 0.0625 inches.

In an embodiment, placing holes 232-1 at the leading edge of the chamfered surface places a set volume of the substance to be vaporized in the path of incoming air. This incoming air has nowhere to go but through the head end of the distal wick 234. When the air enters this area in distal wick 234 it displaces the substance to be vaporized that is suspended in distal wick 234 towards an air cavity between distal wick 234 and proximal wick 236. When the displaced substance to be vaporized reaches the surface of distal wick 234, it is forced out of the wick by the incoming air and the negative pressure of the cavity. This produces an atomized cloud of the substance to be vaporized. In an embodiment, the diameter of the head end of distal wick 234 may be varied and be smaller than the diameter of the proximal wick 236. This allows for a tuned volume of air to bypass proximal wick 236 and directly enter the cavity between distal wick 234 and proximal wick 236 without first passing through proximal wick 236.

FIG. 54 is a perspective view of an atomizer housing and wicks of a personal vaporizer unit. FIG. 55 is an exploded view of the atomizer housing, wire guides, and wicks of FIG. 54. FIG. 56 is a side view of the atomizer housing and wicks of FIG. 54. FIG. 57 is a distal end view of the atomizer housing and wicks of FIG. 54. FIG. 58 is a cross-section view of the atomizer housing and wicks along the cut line shown in FIG. 57. The atomizer housing and wicks shown in FIGS. 54-58 is an alternative embodiment for use with proximal wick 236. The embodiment shown in FIGS. 54-58 use atomizer housing 232, distal wick 234, proximal wick 236, wire guide 237, and wire guide 238. Proximal wick 236 is configured to fit within atomizer housing 232. As can be seen in FIGS. 54-58, proximal wick 236 includes internal wire passageway 236-1. This wire passageway 236-1 allows a conductor or a heating element (not shown) to be positioned through proximal wick 236 (via internal wire passageway 236-1). The conductor or heating element may be positioned around wire guide 237 and wire guide 238. Thus, a conductor or heating element may run through wire passageway 236-1, around wire guides 237 and 238, and then back through wire passageway 236-1 to return to approximately its point of origin. The heating element may, when personal vaporizer unit 100 is activated, heat proximal wick 236 in order to facilitate vaporization of a substance.

Figure 59A:
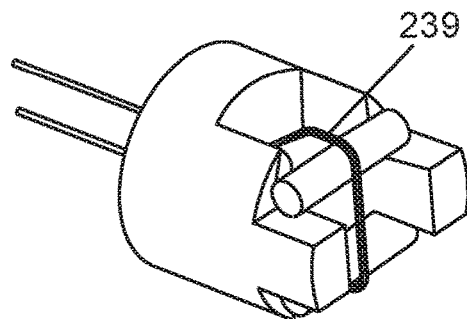
FIG. 59A is a perspective view showing a heating element disposed through the proximal wick and around the wire guides of FIGS. 54-58.
Figure 59B:
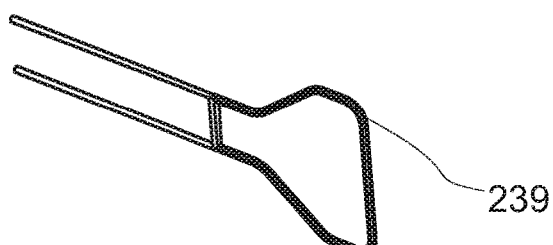
FIG. 59B is a perspective view of the heating element of a personal vaporizer unit.
Figure 60:
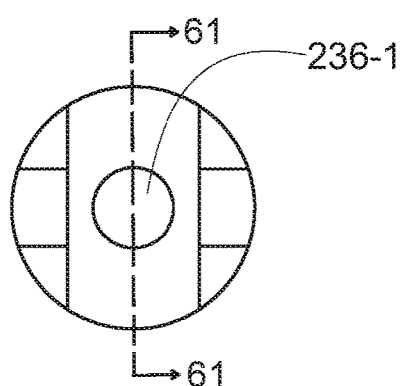
FIG. 60 is a distal end view of the proximal wick element of FIGS. 54-58.
Figure 61:
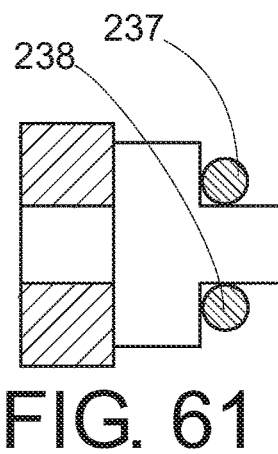
FIG. 61 is a cross-section view of the proximal wick element and wire guides along the cut line shown in FIG. 60.

FIG. 59 is a perspective view of the proximal wick assembly of FIGS. 54-58. FIG. 59A is a perspective view showing a heating element disposed through the proximal wick and around the wire guides of FIGS. 54-58. FIG. 59B is a perspective view of the heating element of a personal vaporizer unit. FIG. 60 is a distal end view of the proximal wick element and wire guides of FIGS. 54-58. FIG. 61 is a cross-section view of the proximal wick element and wire guides along the cut line shown in FIG. 60. As can be seen in FIG. 59A, a conductor or heating element 239 may run through internal wire passageway 236-1, around wire guides 237 and 238, and then back through internal wire passageway 236-1 to return to approximately its point of origin.

In an embodiment, distal wicks 134, 234, and proximal wicks 136, 236, may be made of, or comprise, for example a porous ceramic. Distal wicks 134, 234, and proximal wicks 136, 236, may be made of, or comprise aluminum oxide, silicon carbide, magnesia partial stabilized zirconia, yttria tetragonal zirconia polycrystal, porous metal (e.g., steel, aluminum, platinum, titanium, and the like), ceramic coated porous metal, woven metal, spun metal, metal wool (e.g., steel wool), porous polymer, porous coated polymer, porous silica (i.e., glass), and/or porous Pyrex. Distal wicks 134, 234, and proximal wicks 136, 236, may be made of or comprise other materials that can absorb a substance to be vaporized.

The conductor or heating element that is disposed through proximal wick 136 or 236 may be made of, or comprise, for example: nickel chromium, iron chromium aluminum, stainless steel, gold, platinum, tungsten molybdenum, or a piezoelectric material. The conductor or heating element that is disposed through proximal wick 136 or 236 can be made of, or comprise, other materials that become heated when an electrical current is passed through them.

Figure 62:
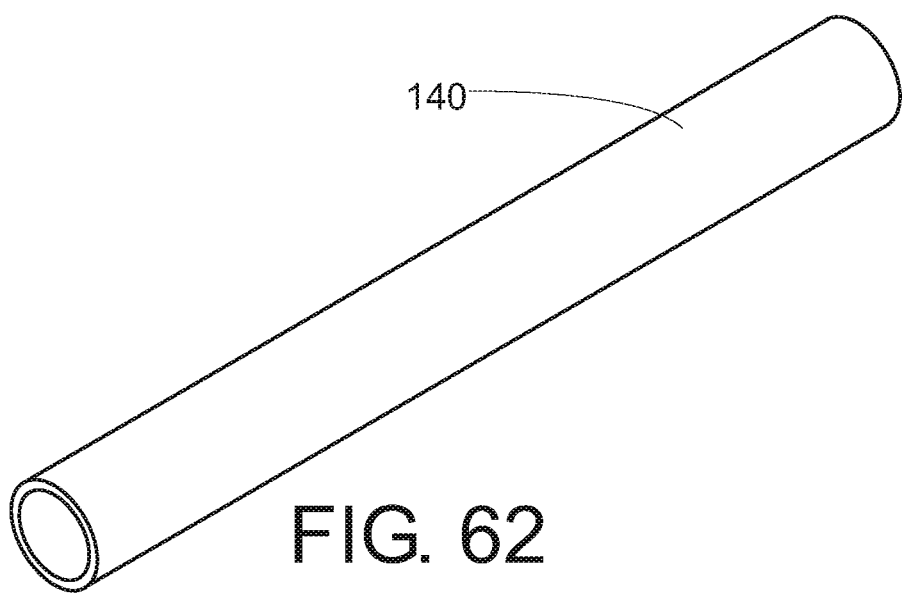
FIG. 62 is a perspective view of a light pipe sleeve of a personal vaporizer unit.
Figure 63:
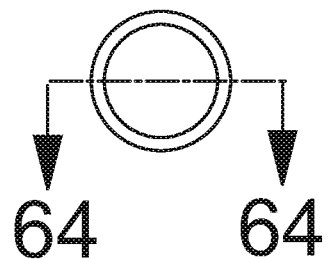
FIG. 63 is an end view of the light pipe sleeve of FIG. 62.
Figure 64:
FIG. 64 is a cross-section view of the light pipe sleeve along the cut line shown in FIG. 63.

FIG. 62 is a perspective view of a light pipe sleeve of a personal vaporizer unit. FIG. 63 is an end view of the light pipe sleeve of FIG. 62. FIG. 64 is a cross-section view of the light pipe sleeve along the cut line shown in FIG. 63. Light pipe sleeve 140 is configured to be disposed within outer main shell 102. Light pipe sleeve 140 is also configured to hold cartridge 150 and atomizer housing 132 or 232. As discussed previously, light pipe sleeve 140 is configured to conduct light entering the proximal end of light pipe sleeve 140 (e.g., from LEDs 125-127) to the distal end of light pipe sleeve 140. Typically, the light exiting the distal end of light pipe sleeve 140 will be visible from the exterior of personal vaporizer unit 100. The light exiting the distal end of light pipe sleeve 140 may be diffused by cartridge 150. The light exiting the distal end of light pipe sleeve 140 may illuminate characters and/or symbols drawn, printed, written, or embossed, etc., in an end of cartridge 150. In an embodiment, light exiting light pipe sleeve 140 may illuminate a logo, characters and/or symbols cut through outer main shell 102. In an embodiment, light pipe sleeve 140 is made of, or comprises, a translucent acrylic plastic.

FIG. 65 is a perspective view of a cartridge of a personal vaporizer unit. FIG. 66 is a proximal end view of the cartridge of FIG. 65. FIG. 67 is a side view of the cartridge of FIG. 65. FIG. 68 is a top view of the cartridge of FIG. 65. FIG. 69 is a cross-section view of the cartridge along the cut line shown in FIG. 66. As shown in FIGS. 65-69, cartridge 150 comprises a hollow cylinder section with at least one exterior flat surface 158. The flat surface 158 forms, when cartridge 150 is inserted into the distal end of personal vaporizer unit 100, an open space between the exterior surface of the cartridge and an interior surface of light pipe sleeve 140. This space defines a passage for air to be drawn from outside personal vaporizer unit 100, through personal vaporizer unit 100 to be inhaled by the user along with the vaporized substance. This space also helps define the volume of air drawn into personal vaporizer unit 100. By defining the volume of air typically drawn into the unit, different mixtures of vaporized substance to air may be produced.

The hollow portion of cartridge 150 is configured as a reservoir to hold the substance to be vaporized by personal vaporizer unit 100. The hollow portion of cartridge 150 holds the substance to be vaporized in direct contact with distal wick 134 or 234. This allows distal wick 134 or 234 to become saturated with the substance to be vaporized. The area of distal wick 134 or 234 that is in direct contact with the substance to be vaporized may be varied in order to deliver different doses of the substance to be vaporized. For example, cartridges 150 with differing diameter hollow portions may be used to deliver different doses of the substance to be vaporized to the user.

Cartridge 150 may be configured to confine the substance to be vaporized by a cap or seal (not shown) on the proximal end. This cap or seal may be punctured by the end of atomizer housing 132, or the pointed end 234-1 of distal wick 234.

When inserted into personal vaporizer unit 100, cartridge standoffs 157 define an air passage between the end of light pipe sleeve 140 and outer main shell 102. This air passage allows air to reach the air passage defined by flat surface 158.

The hollow portion of cartridge 150 also includes one or more channels 154. The end of these channels are exposed to air received via the air passage(s) defined by flat surface 158. These channels allow air to enter the hollow portion of cartridge 150 as the substance contained in cartridge 150 is drawn into a distal wick 134 or 234. Allowing air to enter the hollow portion of cartridge 150 as the substance contained in cartridge 150 is removed prevents a vacuum from forming inside cartridge 150. This vacuum could prevent the substance contained in cartridge 150 from being absorbed into distal wick 134 or 234.

In an embodiment, cartridge 150 may be at least partly translucent. Thus cartridge 150 may act as a light diffuser so that light emitted by one or more of LEDs 125-127 is visible external to personal vaporizer unit 100.

Figure 70:
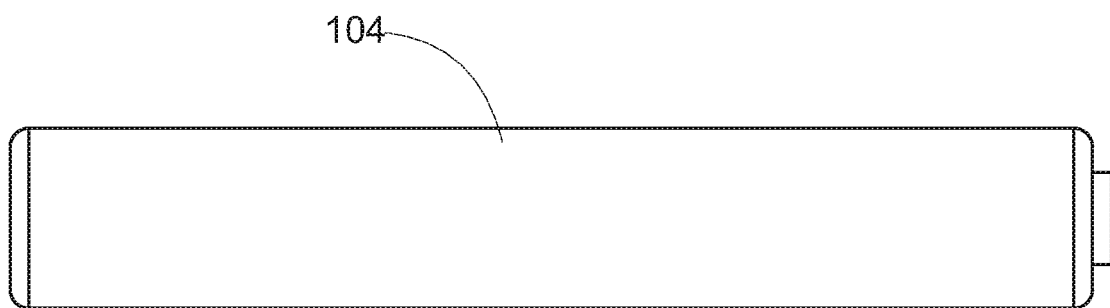
FIG. 70 is a side view of a battery of a personal vaporizer unit.
Figure 71:
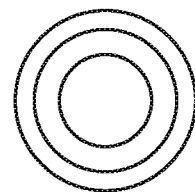
FIG. 71 is an end view of the battery of FIG. 70.
Figure 72:
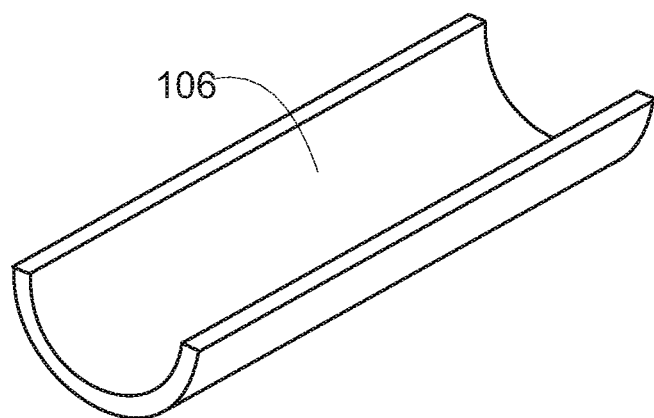
FIG. 72 is a perspective view of a battery support of a personal vaporizer unit.

FIG. 70 is a side view of a battery of a personal vaporizer unit. FIG. 71 is an end view of the battery of FIG. 70. FIG. 72 is a perspective view of a battery support of a personal vaporizer unit. As can be seen in FIG. 72, battery support 106 does not form a complete cylinder that completely surrounds battery 104. This missing portion of a cylinder forms a passageway that allows air and the vaporized substance to pass by the battery from the atomizer assembly to the mouthpiece 116 so that it may be inhaled by the user.

Figure 73:
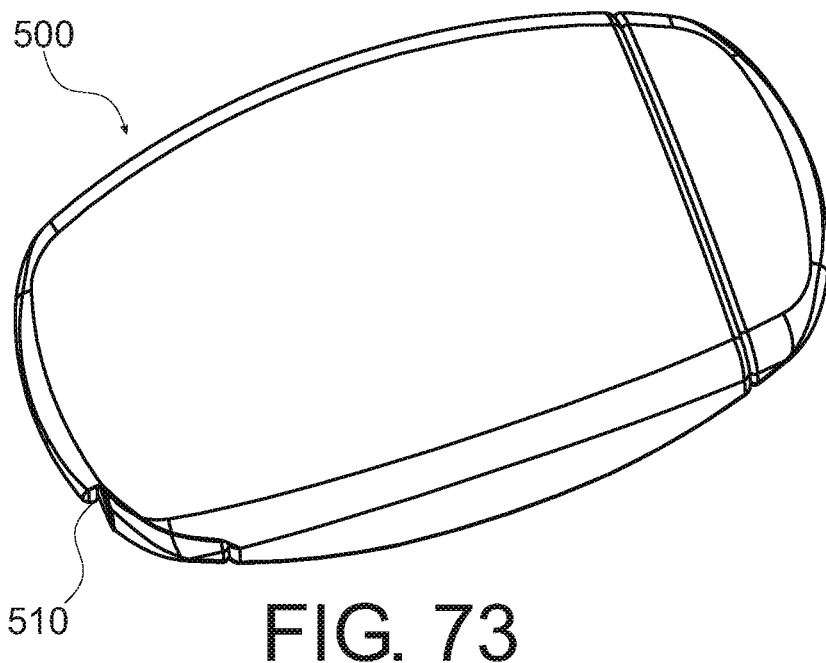
FIG. 73 is a top perspective view of a personal vaporizer unit case.
Figure 74:
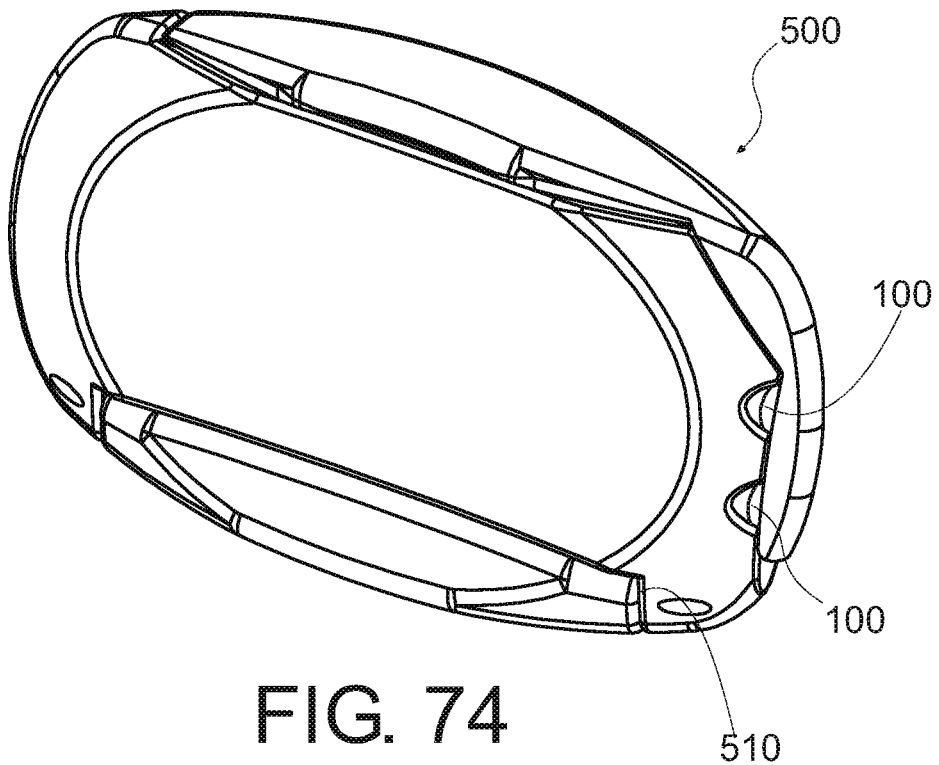
FIG. 74 is a bottom perspective view of a personal vaporizer unit case.

FIG. 73 is a top perspective view of a personal vaporizer unit case. FIG. 74 is a bottom perspective view of a personal vaporizer unit case. Personal vaporizer case 500 is configured to hold one or more personal vaporizer units 100. Personal vaporizer case 500 includes a connector 510 to interface to a computer. This connector allows case 500 to transfer data from personal vaporizer unit 100 to a computer via connector 510. Case 500 may also transfer data from personal vaporizer unit 100 via a wireless interface. This wireless interface may comprise an infrared (IR) transmitter, a Bluetooth interface, an 802.11 specified interface, and/or communicate with a cellular telephone network. Data from a personal vaporizer unit 100 may be associated with an identification number stored by personal vaporizer unit 100. Data from personal vaporizer unit 100 may be transmitted via the wireless interface in association with the identification number.

Personal vaporizer case 500 includes a battery that may hold charge that is used to recharge a personal vaporizer unit 100. Recharging of personal vaporizer unit 100 may be managed by a charge controller that is part of case 500.

When case 500 is holding a personal vaporizer unit 100, at least a portion of the personal vaporizer unit 100 is visible from the outside of case 500 to allow a light emitted by personal vaporizer unit 100 to provide a visual indication of a state of personal vaporizer unit 100. This visual indication is visible outside of case 500.

Personal vaporizer unit 100 is activated by a change in impedance between two conductive surfaces. In an embodiment, these two conductive surfaces are part of outer main shell 102 and mouthpiece 116. These two conductive surfaces may also be used by case 500 to charge battery 104. These two conductive surfaces may also be used by case 500 to read data out of personal vaporizer unit 100.

In an embodiment, when a user puts personal vaporizer unit 100 in his/her mouth and provides "suction," air is drawn into personal vaporizer unit 100 though a gap between the end of outer main shell 102 and cartridge 150. In an embodiment, this gap is established by standoffs 157. Air travels down galley(s) formed by flat surface(s) 158 and the inner surface of light pipe sleeve 140. The air then reaches a "ring" shaped galley between atomizer housing 132, cartridge 150, and light pipe sleeve 140. Air travels to distal wick 134 via one or more holes 132-1, in chamfered surface(s) 132-3. Air travels to distal wick 234 via one or more holes 232-1, in chamfered surface(s) 232-3. Air is also allowed to enter cartridge 150 via one or more channels 154. This air entering cartridge 150 via channels 154 "back fills" for the substance being vaporized which enters distal wick 134. The substance being vaporized is held in direct contact with distal wick 134 or 234 by cartridge 150. The substance being vaporized is absorbed by and may saturate distal wick 134 or 234 and proximal wick 136 or 236.

The incoming air drawn through holes 132-1 displaces from saturated distal wick 134 the substance being vaporized. The displaced substance being vaporized is pulled from distal wick element 134 into a cavity between distal wick 134 and proximal wick 136. This cavity may also contain a heating element that has been heated to between 150-200° C. The displaced substance being vaporized is pulled from distal wick element 134 in small (e.g., atomized) droplets. These atomized droplets are vaporized by the heating element.

In an embodiment, when a user puts personal vaporizer unit 100 in his/her mouth and provides "suction," air is drawn into personal vaporizer unit 100 though a gap between the end of outer main shell 102 and cartridge 150. In an embodiment, this gap is established by standoffs 157. Air travels down galley(s) formed by flat surface(s) 158 and the inner surface of light pipe sleeve 140. The air then reaches a "ring" shaped galley between atomizer housing 232, cartridge 150, and light pipe sleeve 140. Air travels to distal wick 234 via one or more holes 232-1, in chamfered surface(s) 232-3. Air is also allowed to enter cartridge 150 via one or more channels 154. This air entering cartridge 150 via channels 154 "back fills" for the substance being vaporized which enters distal wick 234. The substance being vaporized is held in direct contact with distal wick 234 by cartridge 150. The substance being vaporized is absorbed by and may saturate distal wick 234 and proximal wick 236.

The incoming air drawn through holes 232-1 displaces from saturated distal wick 234 the substance being vaporized. The displaced substance being vaporized is pulled from distal wick 234 into a cavity between distal wick 234 and proximal wick 236. This cavity may also contain a heating element that has been heated to between 150-200° C. The displaced substance being vaporized is pulled from distal wick 234 in small (e.g., atomized) droplets. These atomized droplets are vaporized by the heating element.

In both of the previous two embodiments, the vaporized substance and air are drawn down a galley adjacent to battery 104, through mouthpiece insulator 112, mouthpiece 116, and mouthpiece cover 114. After exiting personal vaporizer unit 100, the vapors may be inhaled by a user.

The systems, controller, and functions described above may be implemented with or executed by one or more computer systems. The methods described above may be stored on a computer readable medium. Personal vaporizer unit 100, case 500, system 10800 (FIG. 108), system 10900 (FIG. 109), system 11000 (FIG. 110), communication system 11100 (FIG. 111), and/or authorization system 11200 (FIG. 112) may be, comprise, or include computer systems.

Figure 75:
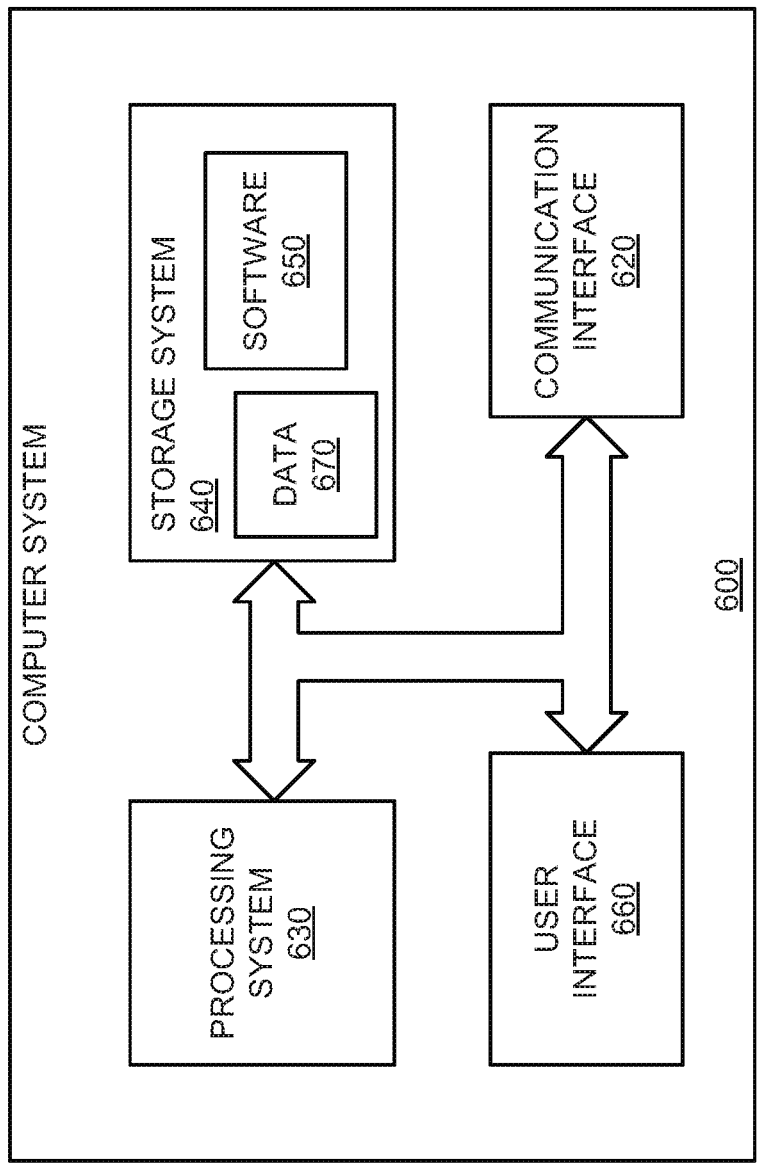
FIG. 75 is a block diagram of a computer system.

FIG. 75 illustrates a block diagram of a computer system. The system may be used for data storage or calculation, such as with the sensors described below. Computer system 600 includes communication interface 620, processing system 630, storage system 640, and user interface 660. Processing system 630 is operatively coupled to storage system 640. Storage system 640 stores software 650 and data 670. Processing system 630 is operatively coupled to communication interface 620 and user interface 660. Computer system 600 may comprise a programmed general-purpose computer. Computer system 600 may include a microprocessor. Computer system 600 may comprise programmable or special purpose circuitry. Computer system 600 may be distributed among multiple devices, processors, storage, and/or interfaces that together comprise elements 620-670.

Communication interface 620 may comprise a network interface, modem, port, bus, link, transceiver, or other communication device. Communication interface 620 may be distributed among multiple communication devices. Processing system 630 may comprise a microprocessor, microcontroller, logic circuit, or other processing device. Processing system 630 may be distributed among multiple processing devices. User interface 660 may comprise a keyboard, mouse, voice recognition interface, microphone and speakers, graphical display, touch screen, or other type of user interface device. User interface 660 may be distributed among multiple interface devices. Storage system 640 may comprise a disk, tape, integrated circuit, RAM, ROM, network storage, server, or other memory function. Storage system 640 may be a computer readable medium. Storage system 640 may be distributed among multiple memory devices.

Processing system 630 retrieves and executes software 650 from storage system 640. Processing system may retrieve and store data 670. Processing system may also retrieve and store data via communication interface 620. Processing system 630 may create or modify software 650 or data 670 to achieve a tangible result. Processing system 630 may control communication interface 620 or user interface 660 to achieve a tangible result. Processing system 630 may retrieve and execute remotely stored software via communication interface 620.

Software 650 and remotely stored software may comprise an operating system, utilities, drivers, networking software, and other software typically executed by a computer system. Software 650 may comprise an application program, applet, firmware, or other form of machine-readable processing instructions typically executed by a computer system. When executed by processing system 630, software 650 or remotely stored software may direct computer system 600 to operate as described herein.

Figure 76A:
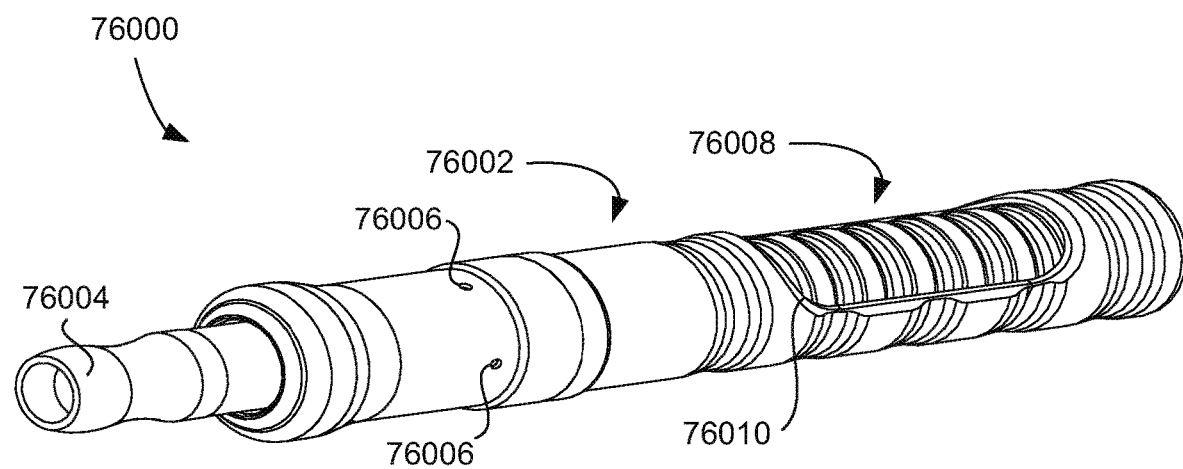
FIGS. 76A-76S show various views of another vaporizer embodiment.
Figure 76B:
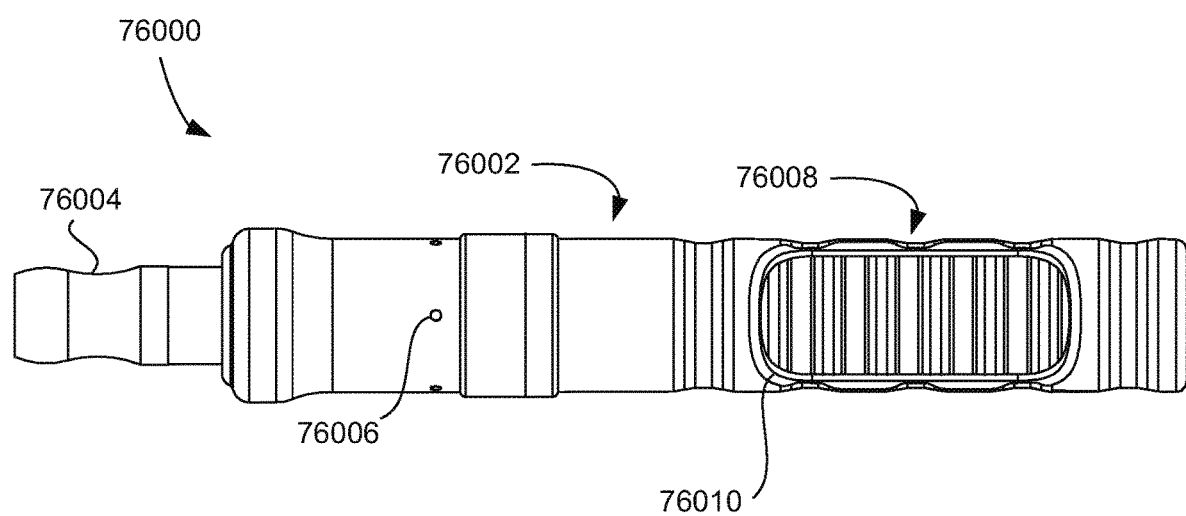
Figure 76C:
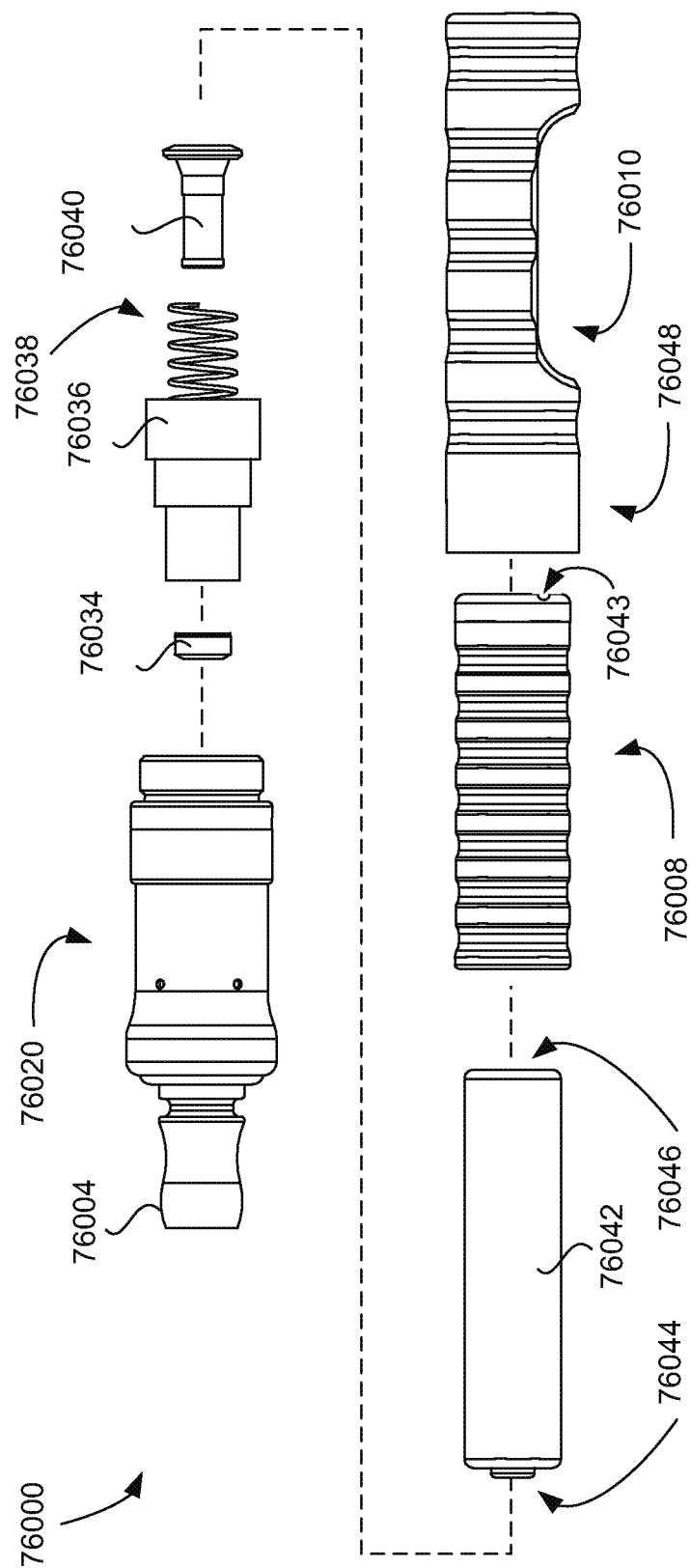
Figure 76D:
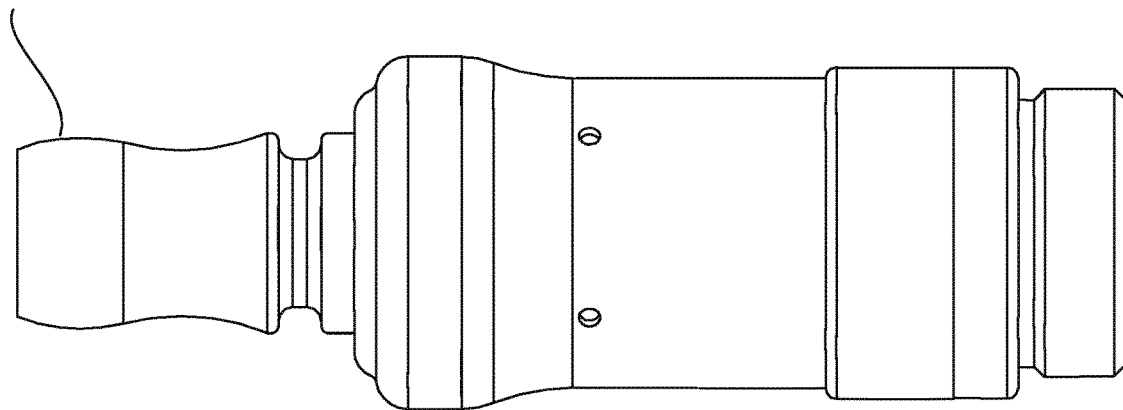
Figure 76E:
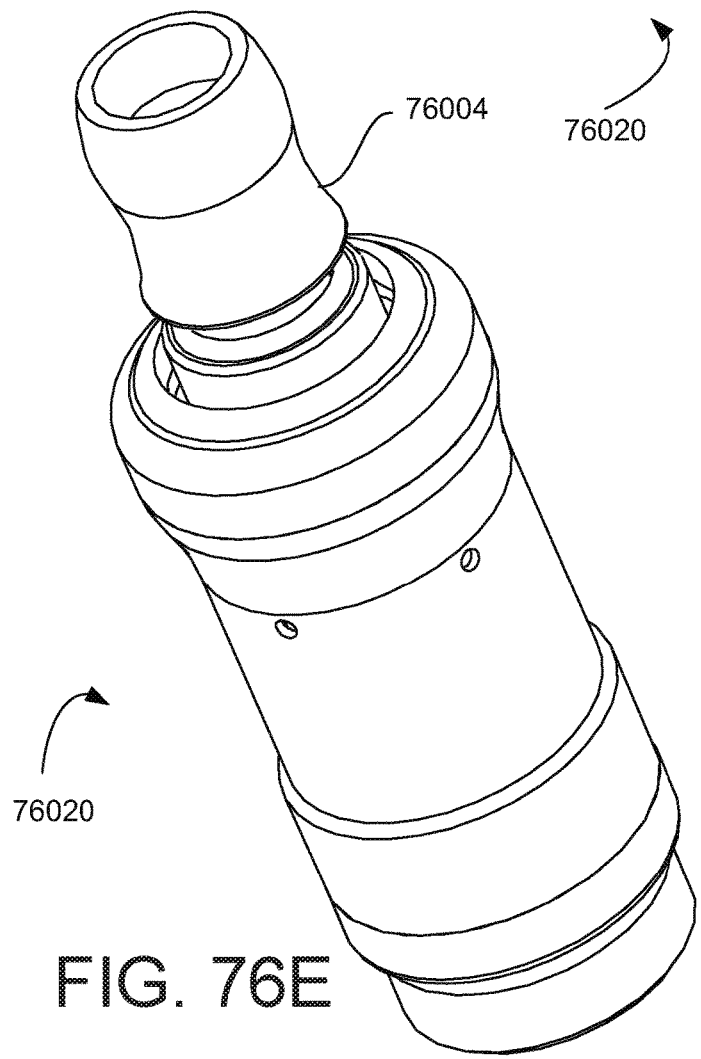
Figure 76F:
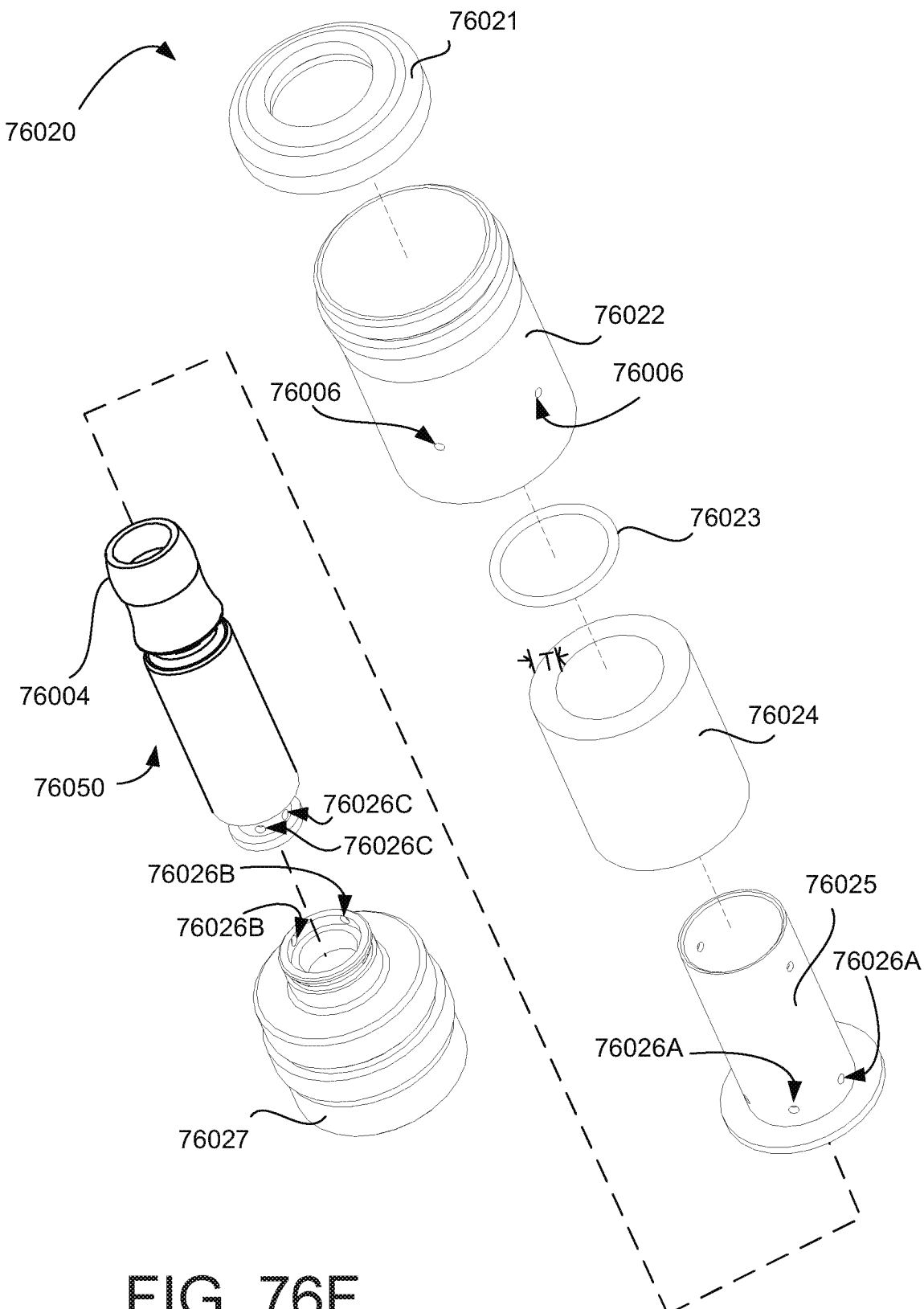
Figure 76J:
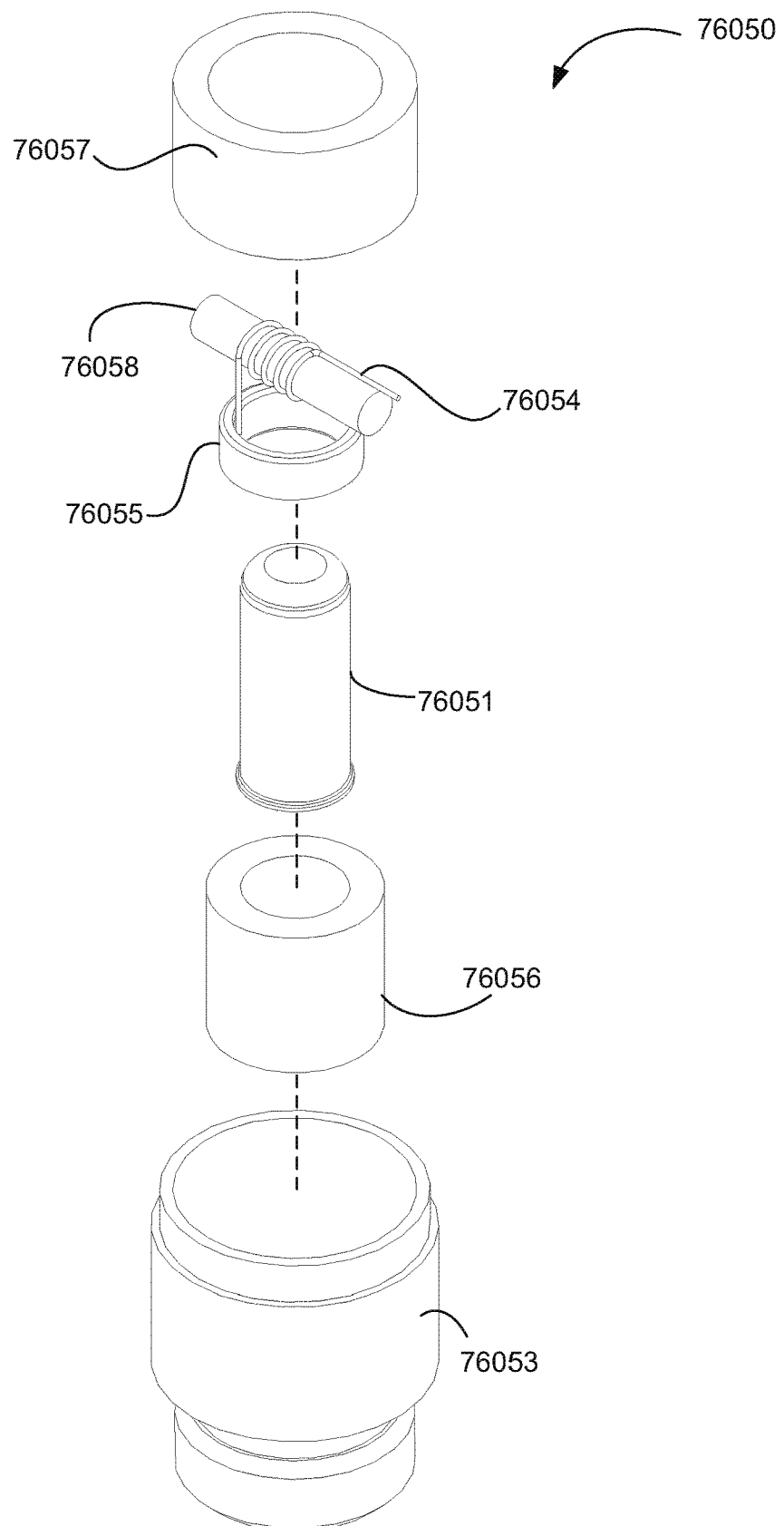
Figure 76K:
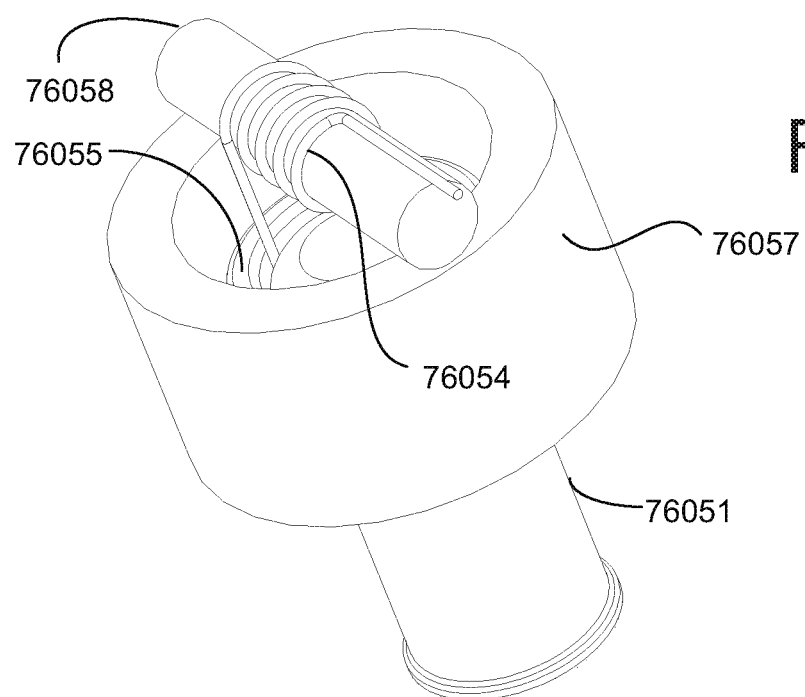
Figure 76L:
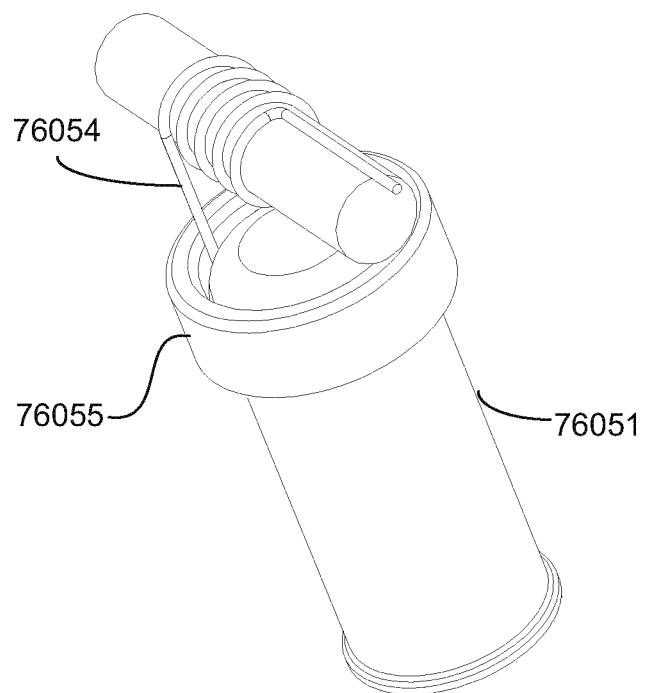
Figure 76M:
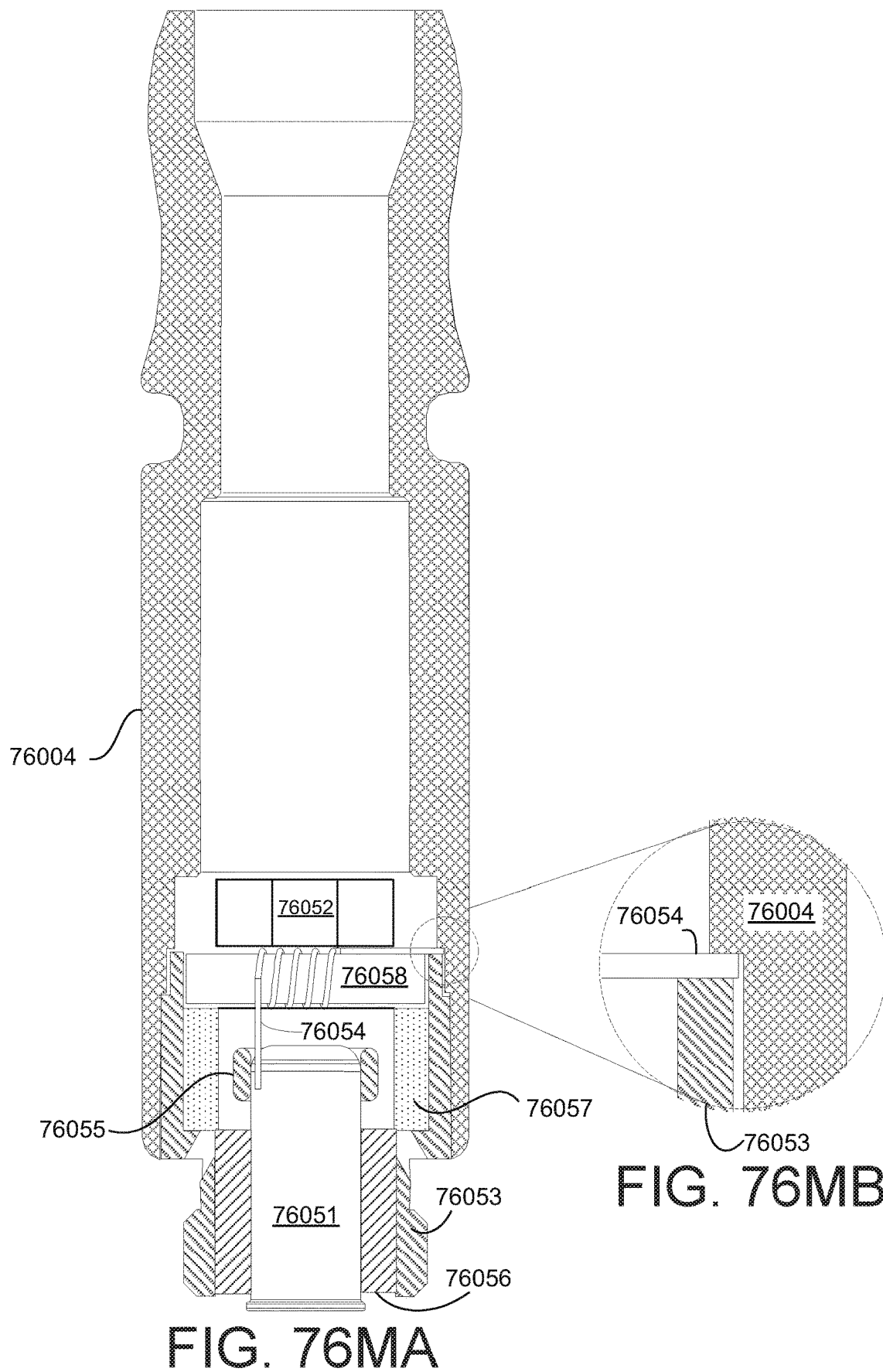
Figure 76N:
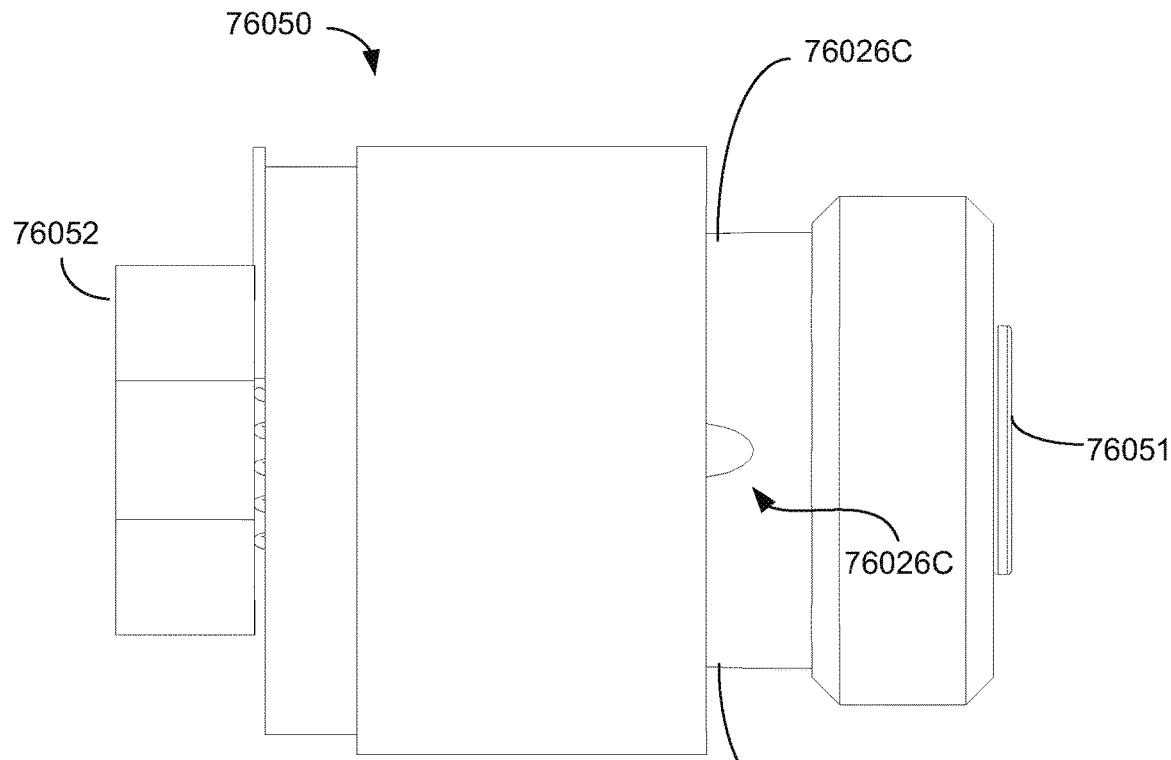
Figure 76O:
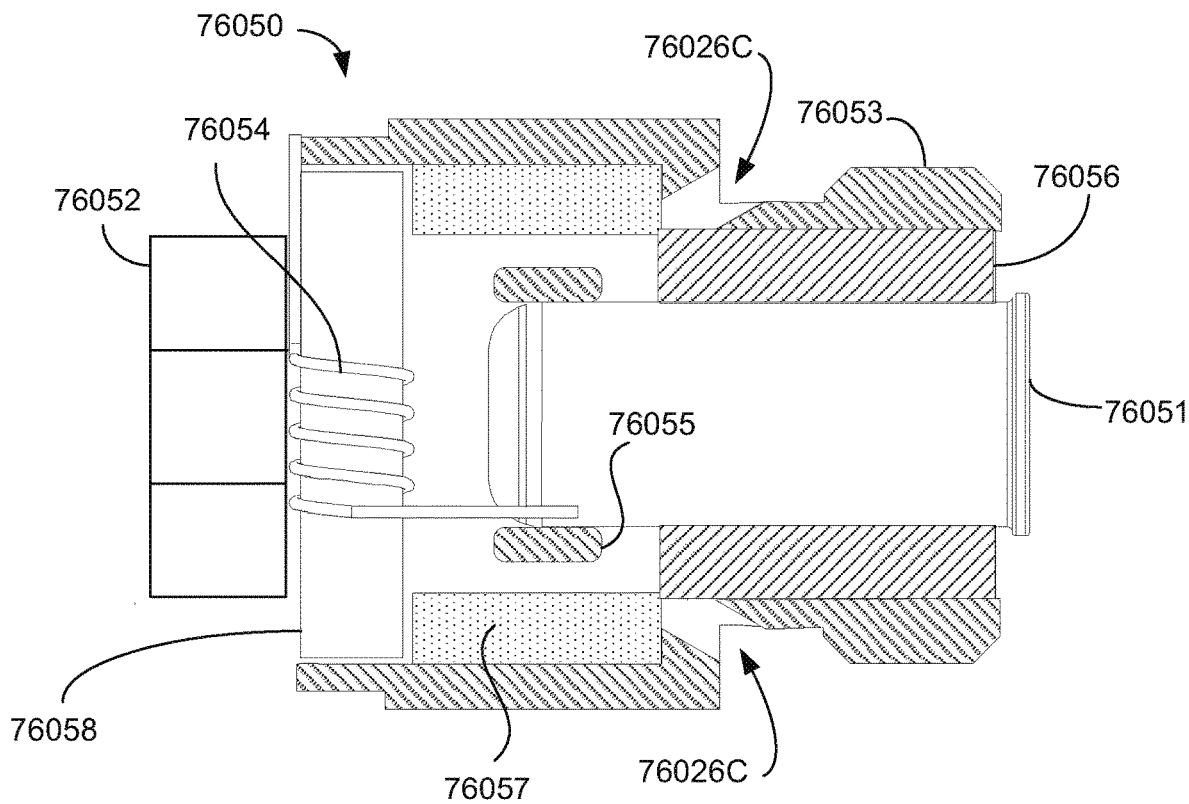
Figure 76P:
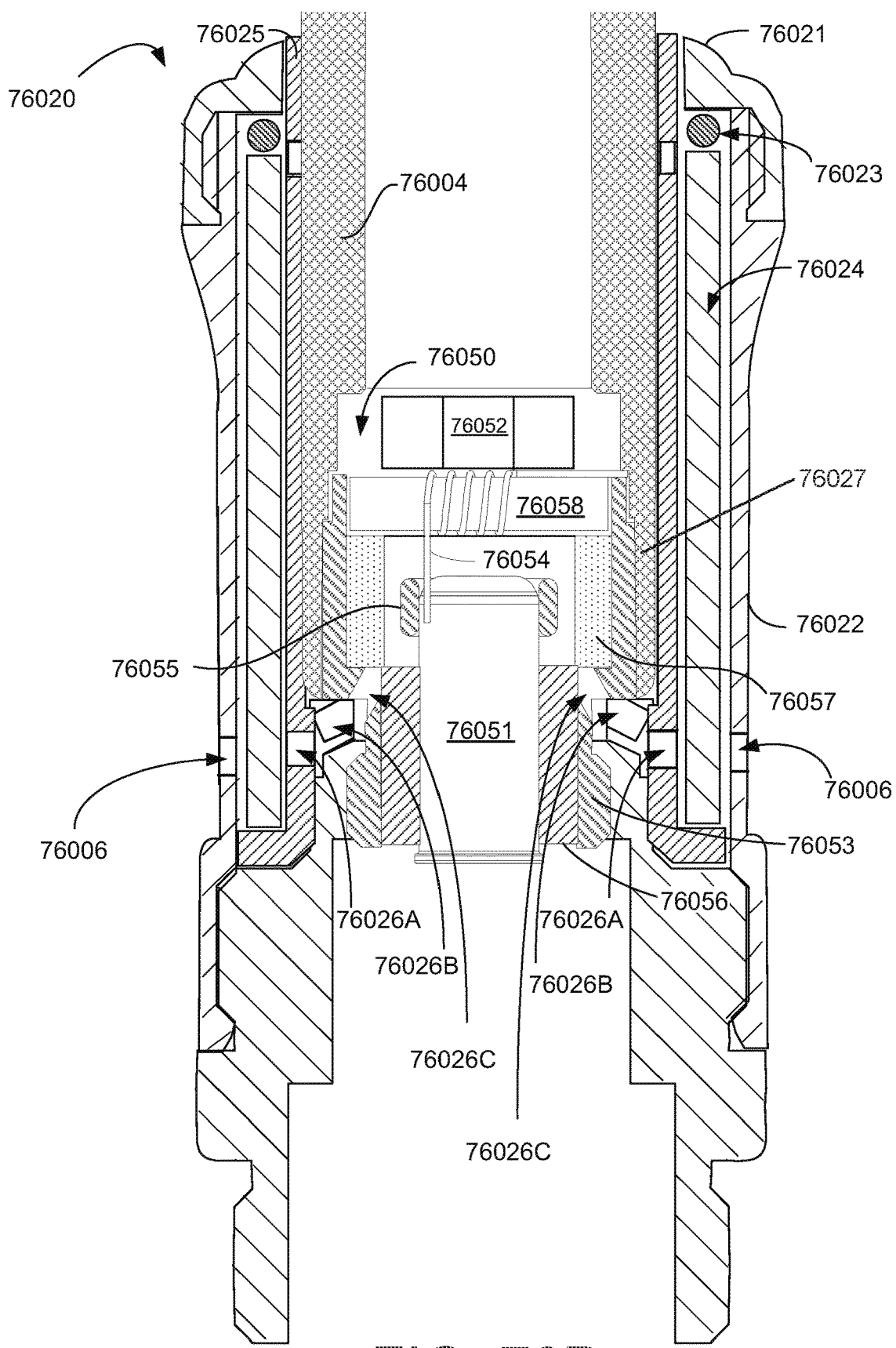
Figure 76Q:
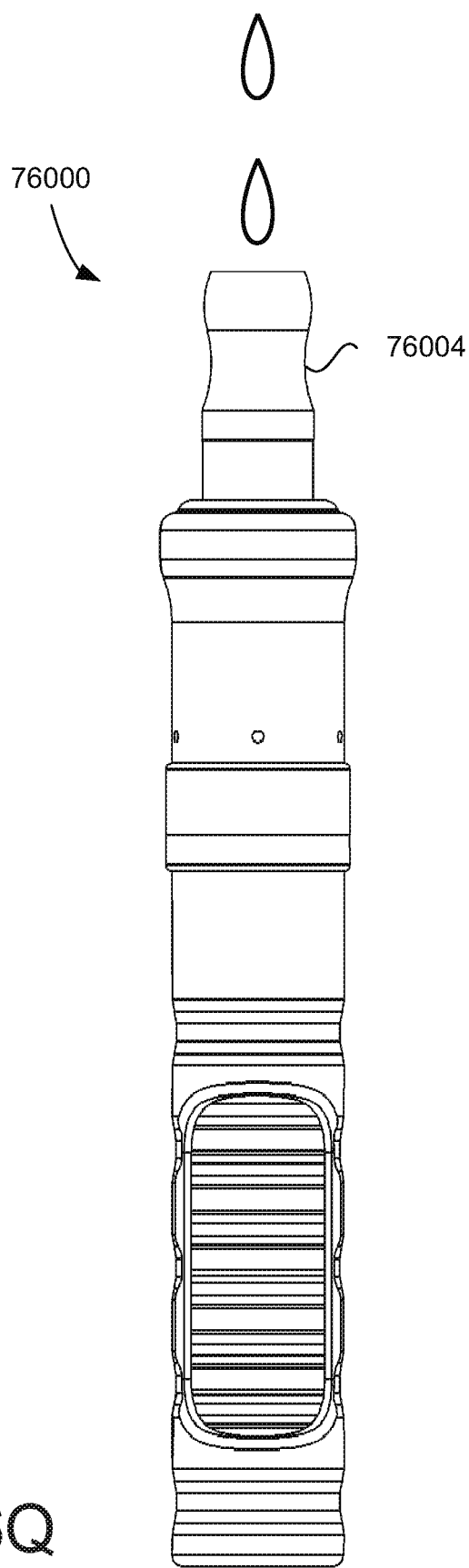
Figure 76R:
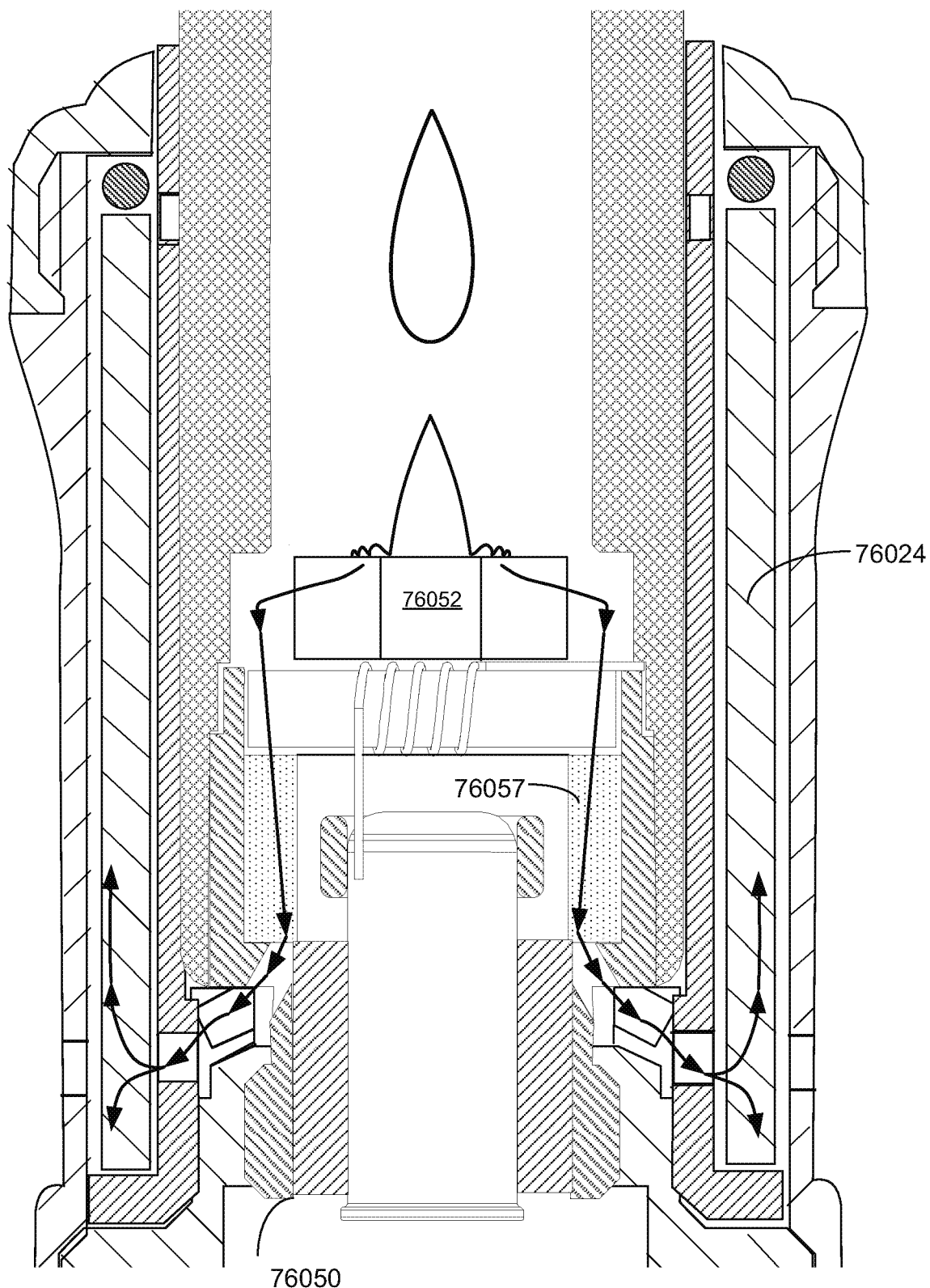
Figure 76S:
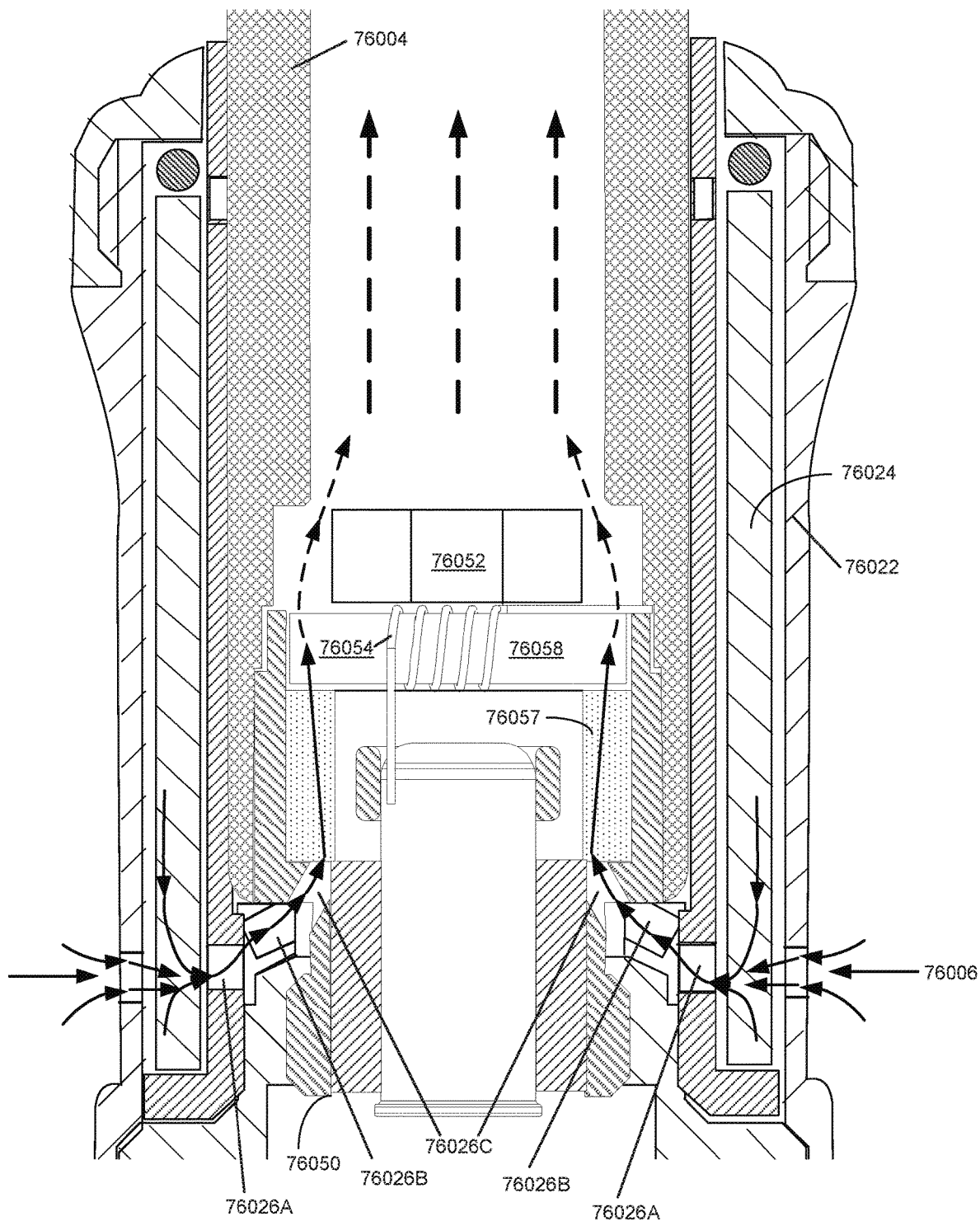

FIGS. 76A-76S show various views of another vaporizer 76000 embodiment. In particular, FIG. 76A shows a perspective view of vaporizer 76000, while FIG. 76B shows a side view of vaporizer 76000. Vaporizer 76000 may have a housing 76002 comprising an oral aspiration tube 76004 for transporting vapor to a user's mouth. As the user's mouth aspirates at the oral aspiration tube 76004, taking in vapor, air may be taken into the vaporizer 76000 through air intake ports 76006.

A battery carrier sleeve 76008 may be slidably coupled with the housing 76002 for guiding alternative movement of the battery carrier sleeve 76008 between an extended position and a retracted position. The vaporizer 76000 may be electrically activated to produce vapor when the battery carrier sleeve 76008 is moved into the extended position. Vapor production may be suspended, and the vaporizer 76000 may be temporarily deactivated, when the battery carrier sleeve 76008 is moved into the retracted position.

The battery carrier sleeve 76008 may be disposed within the housing 76002. The housing 76002 may have an aperture 76010 extending into the housing 76002 and arranged adjacent to a surface of the battery carrier sleeve 76008. The surface of the battery carrier sleeve 76008 may be arranged so as to be manually accessible through the aperture 76010 by a user for controlling the movement of battery carrier sleeve 76008 between the retracted position and the extended position.

FIG. 76C shows an exploded view of vaporizer 76000. Vaporizer 76000 may comprise oral aspiration tube 76004, vaporizer assembly 76020, contact pellet 76034, bushing 76036, resilient member 76038 and battery contact post 76040. Battery carrier sleeve 76008 may be adapted for receiving a battery 76042. The battery carrier sleeve 76008 may comprise an air circulation vent 76043, which may extend through the battery carrier sleeve 76008 for cooling the battery 76042. Material of the battery carrier sleeve 76008 may be selected so that the battery carrier sleeve 76008 may have a high thermal conductivity, substantially greater than approximately ten Watts per Kelvin-Meter, for sinking heat from the battery during operation of the vaporizer. Further, material of the battery carrier sleeve 76008 may be selected so that the battery carrier sleeve 76008 may have a very high thermal conductivity, substantially greater than approximately one-hundred Watts per Kelvin-Meter, for sinking of heat from the battery during operation of the vaporizer. For example, the battery carrier sleeve 76008 may comprise aluminum.

Battery 76042 may have at least one battery terminal. Battery 76042 may have a positive polarity battery terminal 76044 at one extremity of the battery 76042. Battery 76042 may have a negative polarity battery terminal 76046 at opposing extremity of the battery 76042. Battery carrier sleeve 76008 may be slidably coupled with housing sleeve 76048. The surface of the battery carrier sleeve 76008 may be arranged so as to be manually accessible through aperture 76010 by a user for controlling the movement of battery carrier sleeve 76008 between the retracted position and the extended position.

It should be understood that the invention is not limited to the battery polarity arrangement just discussed and shown in exploded view in FIG. 76C, since battery polarity may be reversed with respect to that which is explicitly shown in FIG. 76C, without substantial adverse effect on operation of vaporizer 76000. More specifically, the battery carrier sleeve 76008 may receive battery 76042 having positive and negative polarity battery terminals 76044, 76046, and battery contact post 76040 may be arranged for electrically coupling with either battery terminal 76044, 76046, independent of any polarity of either battery terminal 76044, 76046.

FIG. 76D shows a detailed side view of vaporizer assembly 76020 and oral aspiration tube 76004. FIG. 76E shows a detailed perspective view of vaporizer assembly 76020 and oral aspiration tube 76004. FIG. 76F shows a perspective exploded view of vaporizer assembly 76020 together with oral aspiration tube 76004.

As shown in the exploded view of FIG. 76F, the vaporizer assembly 76020 may comprise a cap 76021, an outer reservoir cover 76022, a resilient o-ring 76023, absorptive ceramic reservoir 76024, a supportive inner reservoir sleeve 76025, an atomizer assembly 76050 and a supportive atomizer fluid interface 76027. Cap 76021 may be removable, and in particular absorptive ceramic reservoir 76024 may be removable by a user of the vaporizer, so as to provide for cleaning or replacement of the absorptive ceramic reservoir 76024

The oral aspiration tube 76004 discussed previously herein may be fluidly coupled with the atomizer assembly 76050 for transporting vapor from the atomizer assembly 76050 to the user's mouth. When electrically activated, atomizer assembly 76050 can change liquid into vapor. Absorptive ceramic reservoir 76024 may provide for volume storage of the liquid. For example, the liquid may comprise a miscible liquid, and the absorptive ceramic reservoir 76024 may be adapted for volume storage of the miscible liquid.

Absorptive ceramic reservoir 76024 may be fluidly coupled with the atomizer assembly 76050 for providing the liquid to the atomizer assembly 76050, in response to aspiration by the user. In particular, air intake ports 76006 may extend through outer reservoir cover 76022, and may be fluidly coupled with the absorptive ceramic reservoir 76024 for bubbling air into the absorptive ceramic reservoir 76024 in response to aspiration by the user.

A first set of liquid transport apertures 76026A may extend through supportive inner reservoir sleeve 76025, for transporting liquid aspirated from the absorptive ceramic reservoir 76024 through the supportive inner reservoir sleeve 76025. Similarly, a second set of liquid transport apertures 76026B may extend through supportive atomizer fluid interface 76027, for transporting liquid aspirated from the absorptive ceramic reservoir 76024 through the supportive atomizer fluid interface 76027. Similarly, a third set of liquid transport apertures 76026C may extend into atomizer assembly 76050, for transporting liquid aspirated from the absorptive ceramic reservoir 76024 into atomizer assembly 76050.

In other words, the first and second sets of liquid transport apertures 76026A, 76026B may form at least one liquid aspiration channel 76026A, 76026B, which may be fluidly coupled between the atomizer assembly 76050 and the absorptive ceramic reservoir 76024 for aspirating the liquid from the absorptive ceramic reservoir 76024 in response to aspiration by the user. As shown in exploded view in FIG. 76F, air intake ports 76006 and the liquid aspiration channel 76026A, 76026B may each be arranged at respective opposing surfaces of the absorptive ceramic reservoir 76024, so as to promote the aspiration of liquid from the absorptive ceramic reservoir 76024.

As shown in FIG. 76F, the absorptive ceramic reservoir 76024 may have a substantially annular cross section. The absorptive ceramic reservoir 76024 may be substantially cylindrically shaped. Atomizer assembly 76050 may be coaxially arranged with such substantially cylindrical shape of the absorptive ceramic reservoir 76024. As shown in FIG. 76F, resilient o-ring 76023 may be arranged adjacent to an extremity of the substantially cylindrical shape of the absorptive ceramic reservoir 76024, for providing at least some shock protection to the absorptive ceramic reservoir 76024.

As shown in FIG. 76F the substantially cylindrical shape of absorptive ceramic reservoir 76024 may comprise a cylinder wall having a thickness dimension “T”. To provide for volume storage of the liquid, and to provide for some strength of the absorptive ceramic reservoir 76024, the thickness dimension “T” may be greater than approximately a couple of millimeters. To provide for some user convenience and some compact thinness of the absorptive ceramic reservoir 76024, the thickness dimension “T” may be less than approximately tens of millimeters. Accordingly, the thickness dimension “T” may be within a range from approximately a couple of millimeters to approximately tens of millimeters.

To provide for some user convenience, and to avoid an excessive need to refill the absorptive ceramic reservoir 76024 continually, the absorptive ceramic reservoir 76024 may have liquid absorption volume of greater than approximately half a milliliter. In particular, the absorptive ceramic reservoir 76024 may have a liquid absorption volume sufficient for more than approximately seventy-five full aspiration cycles through the user’s mouth and substantially filling a user’s lungs. To provide for some user convenience and some compactness of the absorptive ceramic reservoir 76024, the absorptive ceramic reservoir 76024 may have liquid absorption volume less than approximately ten milliliters. Accordingly, the absorptive ceramic reservoir 76024 may have a liquid absorption volume within a range from approximately half a milliliter to approximately ten milliliters.

The absorptive ceramic reservoir 76024 may comprise a macroporous ceramic. The macroporous ceramic may be substantially hydrophilic. Further, the macroporous ceramic may comprise a substantially open pore structured ceramic. Moreover, the macroporous ceramic may comprise a substantially interconnected macroporous ceramic.

The macroporous ceramic may comprise an oxide ceramic. More particularly, the macroporous ceramic may comprise Aluminum Oxide. Since the atomizer assembly 76050 may generate heat, to provide for some user safety the absorptive ceramic reservoir 76024 may be substantially a non-flammable. To provide for some safety of the user inhaling vapors of the vaporizer, the absorptive ceramic reservoir 76024 may be substantially chemically inert.

Parameters of the macroporous ceramic may be chosen so as to provide for some ease of use of the user aspirating the liquid from the absorptive ceramic reservoir 76024. The macroporous ceramic may have an air entry value within a range from approximately one fifth of a pound per square inch to approximately eight pounds per square inch. The macroporous ceramic may have a porosity within a range from approximately forty percent to approximately ninety percent. The macroporous ceramic may have an average pore size within a range from approximately twenty five microns to approximately one hundred and fifty microns.

In addition to providing some ease of aspiration, parameters such as porosity greater than approximately forty percent and/or average pore size greater than approximately twenty five microns may provide some wicking efficiency, in filling the absorptive ceramic reservoir 76024 with liquid. Parameters such as porosity less than approximately ninety percent and/or average pore size less than approximately one hundred and fifty microns may provide for some strength of the absorptive ceramic reservoir 76024. To provide some balance between ease of aspiration, wicking efficiency and strength, the macroporous ceramic may have an average pore size of approximately seventy microns.

Use of the previously described macroporous ceramic need not be strictly limited to the absorptive ceramic reservoir 76024. As will be discussed subsequently herein other vaporizer components may be comprised of the macroporous ceramic as just described.

FIG. 76G shows a detailed perspective view of atomizer assembly 76050 together with oral aspiration tube 76004. FIG. 76H shows a perspective exploded view of atomizer assembly 76050 together with oral aspiration tube 76004. FIG. 76I shows a detailed perspective view of atomizer assembly 76050. FIGS. 76G-76I show the third set of liquid transport apertures 76026C, which may extend into atomizer assembly 76050, for transporting liquid aspirated from the absorptive ceramic reservoir 76024 into atomizer assembly 76050, as mentioned previously herein.

The perspective exploded view of FIG. 76H shows splatter shield 76052 which may be arranged with atomizer assembly 76050 and oral aspiration tube 76004. Splatter shield 76052 may be removable by a user of the vaporizer 76000. Splatter shield 76052 may be disposed within the oral aspiration tube 76004. Splatter shield 76052 may be fluidly coupled with lumen of the oral aspiration tube 76004 for substantially shielding the user’s mouth from liquid splatter when the user’s mouth aspirates the oral aspiration tube 76004.

Splatter shield 76052 may comprise an absorptive ceramic splatter shield. Absorptive ceramic splatter shield 76052 may comprise the macroporous ceramic described and discussed previously herein. As already discussed, the macroporous ceramic may be substantially hydrophilic. Further, the macroporous ceramic may comprise a substantially open pore structured ceramic. Moreover, the macroporous ceramic may comprise a substantially interconnected macroporous ceramic.

As already discussed, the macroporous ceramic may comprise an oxide ceramic. More particularly, the macroporous ceramic may comprise Aluminum Oxide. Since the atomizer assembly 76050 may generate heat, to provide for some user safety the splatter shield 76052 may be substantially a non-flammable. To provide for some safety of the user inhaling vapors of the vaporizer, the splatter shield 76052 may be substantially chemically inert.

Parameters of the macroporous ceramic may be chosen so as to provide for some ease of use of air or vapor entry into the splatter shield 76052. The macroporous ceramic may have an air entry value within a range from approximately one fifth of a pound per square inch to approximately eight pounds per square inch. The macroporous ceramic may have a porosity within a range from approximately forty percent to approximately ninety percent. The macroporous ceramic may have an average pore size within a range from approximately twenty five microns to approximately one hundred and fifty microns.

In addition to providing some ease of air or vapor entry, parameters such as porosity greater than approximately forty percent and/or average pore size greater than approximately twenty five microns may provide some wicking efficiency, in filling as discussed in greater detail subsequently herein. Parameters such as porosity less than approximately ninety percent and/or average pore size less than approximately one hundred and fifty microns may provide for some strength of the splatter shield 76052. To provide some balance between ease of aspiration, wicking efficiency and strength, the macroporous ceramic may have an average pore size of approximately seventy microns.

Similarly, wick element 76057 of atomizer assembly 76050 shown in FIGS. 76H and 76I may likewise comprise the macroporous ceramic described and discussed previously herein. As just discussed, the macroporous ceramic may be substantially hydrophilic. Further, the macroporous ceramic may comprise a substantially open pore structured ceramic. Moreover, the macroporous ceramic may comprise a substantially interconnected macroporous ceramic.

As already discussed, the macroporous ceramic may comprise an oxide ceramic. More particularly, the macroporous ceramic may comprise Aluminum Oxide. Since the atomizer assembly 76050 may generate heat, to provide for some user safety the wick element 76057 may be substantially a non-flammable. To provide for some safety of the user inhaling vapors of the vaporizer, the wick element 76057 may be substantially chemically inert.

Parameters of the macroporous ceramic may be chosen so as to provide for some ease of use of the user aspirating the liquid from the wick element 76057. The macroporous ceramic may have an air entry value within a range from approximately one fifth of a pound per square inch to approximately eight pounds per square inch. The macroporous ceramic may have a porosity within a range from approximately forty percent to approximately ninety percent. The macroporous ceramic may have an average pore size within a range from approximately twenty five microns to approximately one hundred and fifty microns.

In addition to providing some ease of the user aspirating the liquid from the wick element 76057, parameters such as porosity greater than approximately forty percent and/or average pore size greater than approximately twenty five microns may provide some wicking efficiency, in filling as discussed in greater detail subsequently herein. Parameters such as porosity less than approximately ninety percent and/or average pore size less than approximately one hundred and fifty microns may provide for some strength of the wick element 76057. To provide some balance between ease of aspiration, wicking efficiency and strength, the macroporous ceramic may have an average pore size of approximately seventy microns.

As shown in shown in FIGS. 76H and 76I, wick element 76057 may have a lumen. Wick element 76057 may be substantially cylindrical about the lumen. Heating element 76054 may be proximately arranged with the lumen. An air gap may be defined between at least a first portion of the wick element 76057 and a second portion of heating element 76054. Heating element 76054 may be arranged adjacent to the wick element 76057 for receiving liquid aspirated from the ceramic wick element 76057 in response to aspiration by the user's mouth. Heating element 76054 may be substantially "L" shaped, as shown in FIGS. 76H and 76I.

More generally, FIGS. 76H and 76I show absorptive member 76057, which may be rigid, or may be substantially rigid. Absorptive member 76057 may directly contact the liquid to be changed into vapor. Absorptive member 76057 may have a lumen. Absorptive member 76057 may be substantially cylindrical about the lumen. Heating element 76054 may be proximately arranged with the lumen. An air gap may be defined between at least a first portion of the absorptive member 76057 and a second portion of heating element 76054. Heating element 76054 may be arranged adjacent to absorptive member 76057 for receiving liquid aspirated from the absorptive member 76057 in response to aspiration by the user's mouth.

As shown in shown in FIGS. 76H and 76I, an air gap may be defined between at least a first portion of the absorptive member 76057, which was just discussed, and a second portion of a substantially non-absorptive member 76058. Substantially non-absorptive member 76058 may be substantially hydrophobic. Substantially non-absorptive member 76058 may be substantially non-porous. Substantially non-absorptive member 76058 may comprise glass. Substantially non-absorptive member 76058 may comprise a ceramic. Substantially non-absorptive member 76058 may comprise stabilized zirconia.

Substantially non-absorptive member 76058 may be thermally coupled with the heating element 76054 for changing liquid into vapor. Substantially non-absorptive member 76058 may have a surface area that is greater than a surface area of the heating element 76054 for changing the liquid into the vapor. Heating element 76054 may comprise wire coiled about the substantially non-absorptive member 76058. Substantially non-absorptive member 76058 may have a thermal conductivity that is substantially less than a thermal conductivity of the heating element 76054. Substantially non-absorptive member 76058 may be proximally arranged with the heating element 76054 for substantially reflecting heat from the heating element 76054. Substantially non-absorptive member 76058 may maintain a temperature less than approximately two hundred and eighty degrees Celsius during activation of the heating element 76054.

More generally, FIGS. 76H and 76I show heating element support member 76058, which may be mechanically coupled with the heating element 76054 for supporting the heating element 76054. Heating element support member 76058 may have a stiffness that is substantially greater than a stiffness of the heating element 76054. Heating element support member 76058 may be rigid or may be substantially rigid. Heating element 76054 and the heating element support member 76058 may be arranged substantially coaxially. Heating element 76054 may comprise wire coiled about the heating element support member 76058. An air gap may be defined between at least a first portion of the wick element 76057 and a second portion of the heating element support member 76058.

Heating element support member 76058 may be substantially hydrophobic. Heating element support member 76058 may comprise glass. Heating element support member 76058 may comprise a ceramic. Heating element support member 76058 may comprise stabilized zirconia.

FIG. 76J shows an exploded view of atomizer assembly 76050. In addition to showing wick element 76057, heating element 76054 and heating element support member 76058, the atomizer assembly 76050 of FIG. 76J may further comprise first pressure member 76055, inner contact member 76051, insulator 76056 and outer contact member 76053. As shown in exploded view in FIG. 76J, and as more particularly shown in detailed views in FIGS. 76K and 76L, first pressure member 76055 may sandwich a first extremity of the heating element 76054 over inner contact member 76051 to effect first solderless pressure contacts.

More particularly, first pressure member 76055 may comprise a pressure cap which may sandwich the first extremity of the heating element 76054 over the inner contact member 76051 to effect first solderless pressure contacts. Inner contact member 76051 and first pressure member 76055 may comprise metal members. Inner contact member 76051 may comprise an inner contact post. FIG. 76K shows wick element 76057, heating element 76054, heating element support member 76058, first pressure member 76055 and inner contact member 76051. FIG. 76L is similar to FIG. 76K, except that wick element 76057 is not shown in FIG. 76L, for purposes of more particularly illustrating first pressure member 76055 (which may sandwich a first extremity of the heating element 76054 over inner contact member 76051 to effect first solderless pressure contacts.)

FIG. 76MA is a partial cutaway view showing oral aspiration tube 76004, splatter shield 76052, wick element 76057, heating element 76054, heating element support member 76058, first pressure member 76055, inner contact member 76051, insulator 76056 and outer contact member 76053. As shown in FIG. 76MA, and as more particularly shown in detailed view in FIG. 76MB, a second pressure member may comprise at least a portion of the oral aspiration tube 76004. Second pressure member may sandwich the second extremity of the heating element 76054 over outer contact member 76053 to effect second solderless pressure contacts. Outer contact member 76053 may comprise an outer contact sleeve. Accordingly, oral aspiration tube 76004 may have an extremity, which may be arranged for sandwiching the second extremity of the heating element 76054 over the outer contact sleeve to effect second solderless pressure contacts. Outer contact member 76053 and the second pressure member from 76004 may comprise metal members.

As shown in FIG. 76MA heating element 76054 may be electrically coupled between the inner contact member 76051 and the outer contact member 76053 for energizing the heating element 76054 when the heating element 76054 is activated. Heating element 76054 may be electrically coupled between the inner contact member 76051 and the outer contact member 76053 for conducting a flow of battery power when the heating element 76054 is activated.

Electrical insulation material 76056 may be interposed between the inner contact member 76051 and the outer contact member 76053. Substantially annular insulation 76056 may be interposed between the inner contact member 76051 and the outer contact member 76053. The electrical insulation material 76056 may be selected for substantially avoiding outgassing at approximately three hundred degrees Celsius. The electrical insulation material 76056 may be selected for substantially maintaining dimensional stability at approximately three hundred degrees Celsius. The electrical insulation material 76056 may comprise polytetrafluoroethylene.

FIG. 76N shows a detailed side view of atomizer assembly 76050 together with splatter shield 76052. FIG. 76O shows splatter shield 76052 together with a detailed cutaway view of atomizer assembly 76050. The atomizer assembly may comprise a first electrical contact including at least inner contact member 76051 (which may comprise inner contact post), as shown in FIG. 76O. Atomizer assembly 76050 may further comprise a second electrical contact including at least outer contact member 76053 (which may comprise outer contact sleeve). Atomizer assembly 76050 may further comprise heating element 76054 electrically coupled between the inner contact member 76051 and the outer contact member 76053. Heating element 76054 may be made of, or comprise, for example: nickel chromium, iron chromium aluminum, stainless steel, gold, platinum, tungsten molybdenum, or a piezoelectric material. When electrically activated, heating element 76054 may heat liquid into vapor. The atomizer assembly 76050 may further comprise substantially annular electrical insulation 76056 interposed between the inner contact member 76051 and the outer contact member 76053.

FIG. 76O shows the third set of liquid transport apertures 76026C, which may extend into atomizer assembly 76050, for transporting liquid aspirated from the absorptive ceramic reservoir into atomizer assembly 76050, as mentioned previously herein. The atomizer assembly 76050 may comprise wick element 76057 arranged for directly contacting liquid aspirated from the absorptive ceramic reservoir in response to aspiration by the user.

As shown in FIG. 76O, heating element support member 76058 may be separated from the wick element 76057 by an air gap, and may be arranged for receiving liquid aspirated from the wick element in response to aspiration the user. Heating element support member 76058 may be thermally coupled with heating element 76054. For example, as shown in FIG. 76O, heating element may be coiled about heating element support member 76058.

FIG. 76P of vaporizer assembly 76020 is in cutaway view to show cap 76021, outer reservoir cover 76022, a resilient o-ring 76023, absorptive ceramic reservoir 76024, a supportive inner reservoir sleeve 76025, an atomizer assembly 76050 and a supportive atomizer fluid interface 76027, which were discussed previously herein with respect to the exploded view of vaporizer assembly 76020 in FIG. 76F. As shown in cutaway view in FIG. 76P, absorptive ceramic reservoir 76024 may be fluidly coupled with the atomizer assembly 76050 for providing the liquid to the atomizer assembly 76050, in response to aspiration by the user. As shown, air intake ports 76006 may extend through outer reservoir cover 76022, and may be fluidly coupled with the absorptive ceramic reservoir 76024 for bubbling air into the absorptive ceramic reservoir 76024 in response to aspiration by the user.

FIG. 76P shows in cutaway view the first set of liquid transport apertures 76026A, which may extend through supportive inner reservoir sleeve 76025, for transporting liquid aspirated from the absorptive ceramic reservoir 76024 through the supportive inner reservoir sleeve 76025. Similarly, FIG. 76P shows in cutaway view the second set of liquid transport apertures 76026B, which may extend through supportive atomizer fluid interface 76027, for transporting liquid aspirated from the absorptive ceramic reservoir 76024 through the supportive atomizer fluid interface 76027. Similarly, FIG. 76P shows in cutaway view the third set of liquid transport apertures 76026C, which may extend into atomizer assembly 76050, for transporting liquid aspirated from the absorptive ceramic reservoir 76024 into atomizer assembly 76050. The atomizer assembly 76050 may comprise wick element 76057 arranged for directly contacting liquid aspirated from the absorptive ceramic reservoir 76024 in response to aspiration by the user.

In other words, FIG. 76P shows in cutaway view the first and second sets of liquid transport apertures 76026A, 76026B, which may form at least one liquid aspiration channel 76026A, 76026B, and which may be fluidly coupled between the atomizer assembly 76050 and the absorptive ceramic reservoir 76024 for aspirating the liquid from the absorptive ceramic reservoir 76024 in response to aspiration by the user. As shown in cutaway view in FIG. 76P, air intake ports 76006 and the liquid aspiration channel 76026A, 76026B may each be arranged at respective opposing surfaces of the absorptive ceramic reservoir 76024, so as to promote the aspiration of liquid from the absorptive ceramic reservoir 76024.

The absorptive ceramic reservoir of the vaporizer may be arranged for filling, or refilling, by the user dripping liquid. For example, FIG. 76Q shows a side view of vaporizer 76000, for illustrating filling or re-filling of the absorptive ceramic reservoir of the vaporizer 76000 with liquid, by dripping drops of liquid as shown in FIG. 76Q down oral aspiration tube 76004. As shown in further detail in detailed cutaway partial view in FIG. 76R of the vaporizer, drops of liquid may flow through splatter shield 76052, and may flow through wick element 76057 of atomizer assembly 76050 as depicted by notional lines and associated arrowheads. As further depicted by notional lines and associated arrowheads in FIG. 76R, liquid may flow from wick element 76057, out of atomizer assembly 76050 through the third set of liquid transport apertures extending into atomizer assembly 76050, through the second and first sets of liquid transport apertures forming the liquid aspiration channel, and into the absorptive ceramic reservoir 76024, so as to fill or refill the absorptive ceramic reservoir 76024 with liquid. Accordingly, the absorptive ceramic reservoir 76024 may be arranged with the liquid aspiration channel for filling or refilling the absorptive ceramic reservoir 76024 by disposing liquid into the liquid aspiration channel.

FIG. 76S is a detailed cutaway partial view of the vaporizer to illustrate aspiration of liquid into the atomizer assembly 76050, and to illustrate the atomizer assembly 76050 when activated to change the liquid into vapor. Air, as depicted in FIG. 76S by notional arrows, may be bubbled into the absorptive ceramic reservoir 76024 through air intake ports 76006 of outer reservoir cover 76022, in response to aspiration by the user. As depicted in FIG. 76S by notional arrows, liquid may be mixed with air and aspirated from absorptive ceramic reservoir 76024 through first and second sets of liquid transport apertures 76026A, 76026B, which may form the liquid aspiration channel. The liquid aspiration channel 76026A, 76026B may be fluidly coupled between the atomizer assembly 76050 and the absorptive ceramic reservoir 76024 for aspirating the liquid from the absorptive ceramic reservoir 76024 to the wick element 76057 and heating element support member 76058 of the atomizer assembly 76050, in response to aspiration by the user.

The aspiration channel 76026A, 76026B may be coupled with the wick element 76057 for bubbling air into the wick element 76057 in response to aspiration by the user's mouth. The aspiration channel 76026A, 76026B may be coupled with the wick element 76057 for aspirating liquid into the wick element 76057 in response to aspiration by the user's mouth.

More generally, the aspiration channel 76026A, 76026B may be coupled with absorptive member 76057 for bubbling air into the absorptive member 76057 in response to aspiration by the user's mouth. The aspiration channel 76026A, 76026B may be coupled with absorptive member 76057 for aspirating liquid into the absorptive member 76057 in response to aspiration by the user's mouth.

As depicted in FIG. 76S by notional dashed arrows, vapors may flow from heating element support member 76058 when heated by electrical activation of heating element 76054 (and heated by heating element support member 76058), for changing the liquid into the vapors. Splatter shield 76052 may be fluidly coupled with lumen of the oral aspiration tube 76004 for substantially shielding the user's mouth from liquid splatter when the user's mouth aspirates the oral aspiration tube 76004.

Figure 77A:
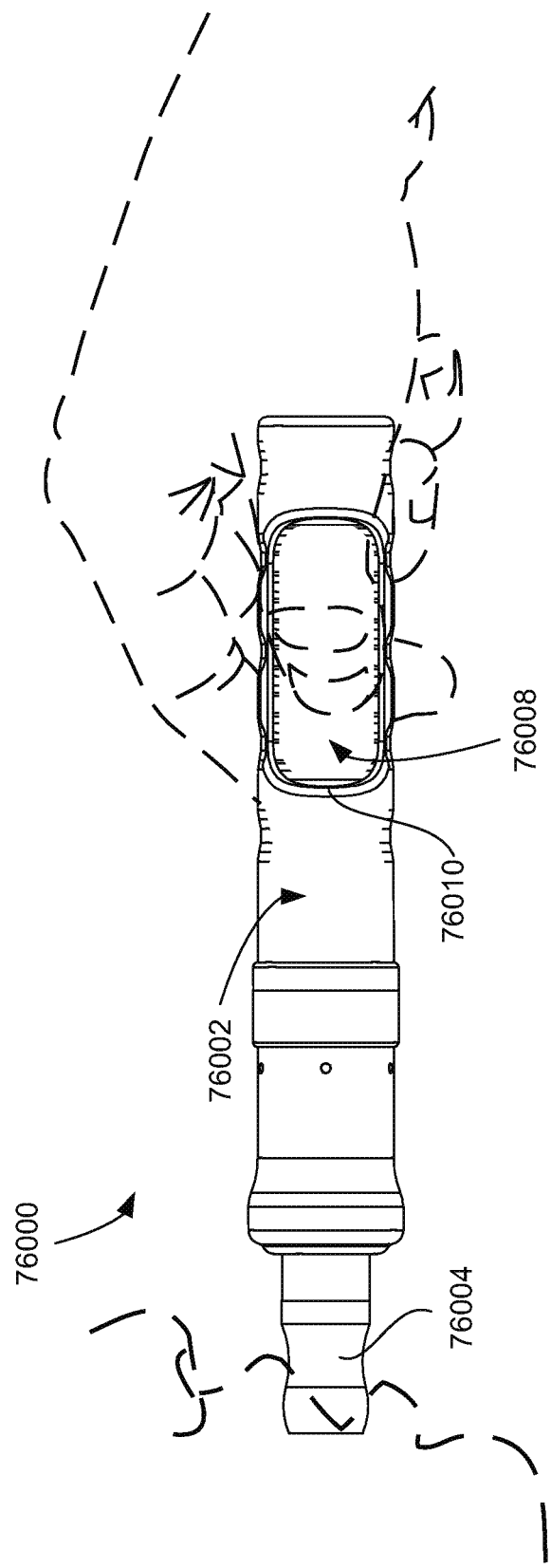
FIGS. 77A-77F are various sequential views illustrating vaporizer operation.

Operation of vaporizer 76000 is depicted in various sequential views in FIGS. 77A-77F. In initial sequential side view, FIG. 77A shows vaporizer 76000, which may have housing 76002 comprising oral aspiration tube 76004 for aspiration by user's mouth. For illustrative purposes, a profile of the user's mouth is depicted using dashed lines. As discussed previously herein, battery carrier sleeve 76008 may be slidably coupled with housing 76002 for guiding alternative movement of the battery carrier sleeve 76008 between an extended position and a retracted position. The vaporizer 76000 may be electrically activated to produce vapor when the battery carrier sleeve 76008 is moved into the extended position. Vapor production may be suspended, and the vaporizer 76000 may be temporarily deactivated, when the battery carrier sleeve 76008 is moved into the retracted position.

Figure 77B:
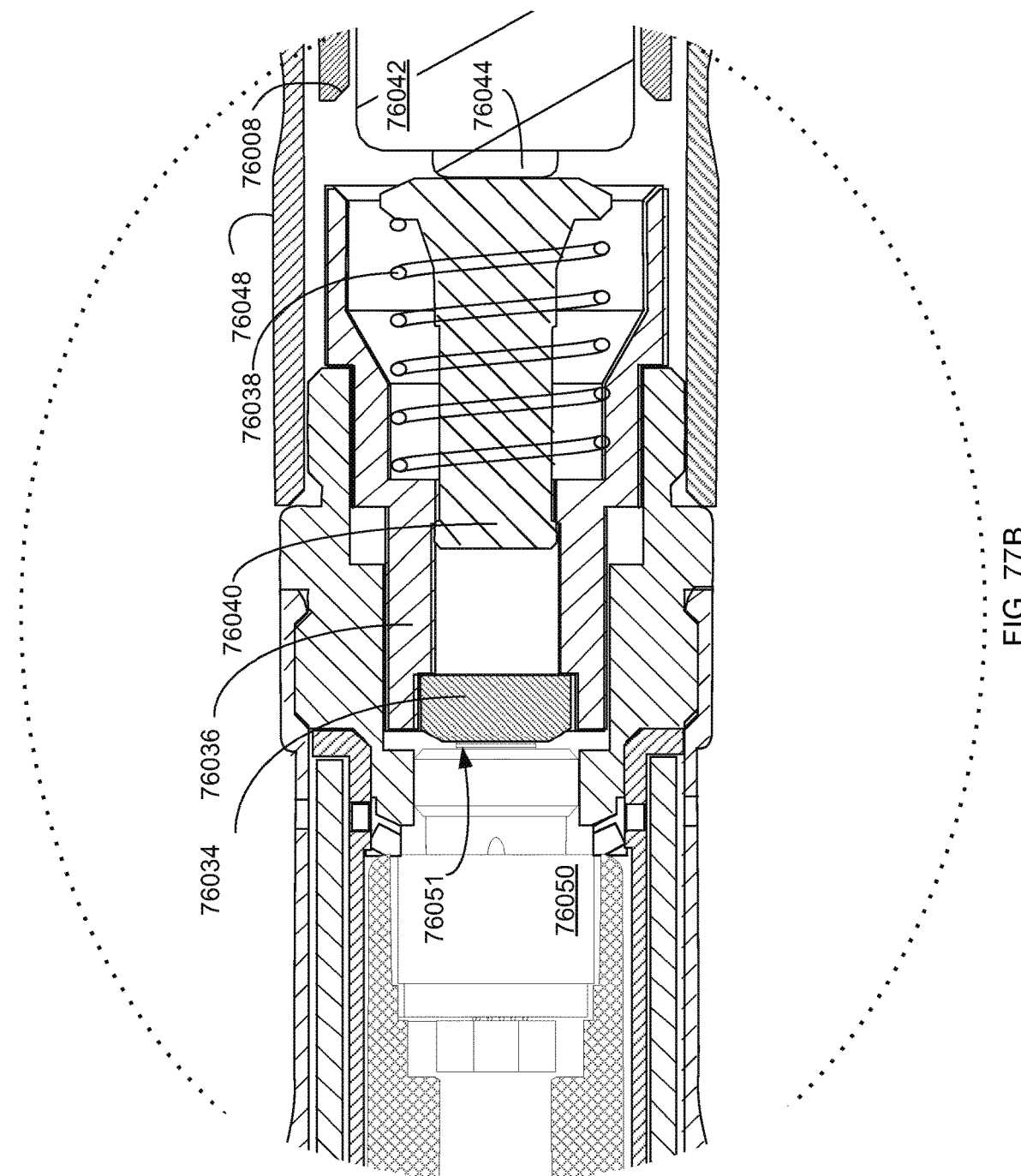

The battery carrier sleeve 76008 may be disposed within the housing 76002. The housing 76002 may have aperture 76010 extending into the housing 76002 and arranged adjacent to the surface of the battery carrier sleeve 76008. The surface of the battery carrier sleeve 76008 may be arranged so as to be manually accessible through the aperture 76010 by the user for controlling the movement of battery carrier sleeve 76008 between the retracted position and the extended position. In FIG. 77A, the battery carrier sleeve 76008 is shown in retracted position. Similarly, the user's thumb, which is depicted in dashed line as engaging the surface of the battery carrier sleeve 76008, is likewise retracted. FIG. 77B is a detailed cutaway partial view showing the battery carrier sleeve 76008 in the retracted position as in FIG. 77A.

Figure 77C:
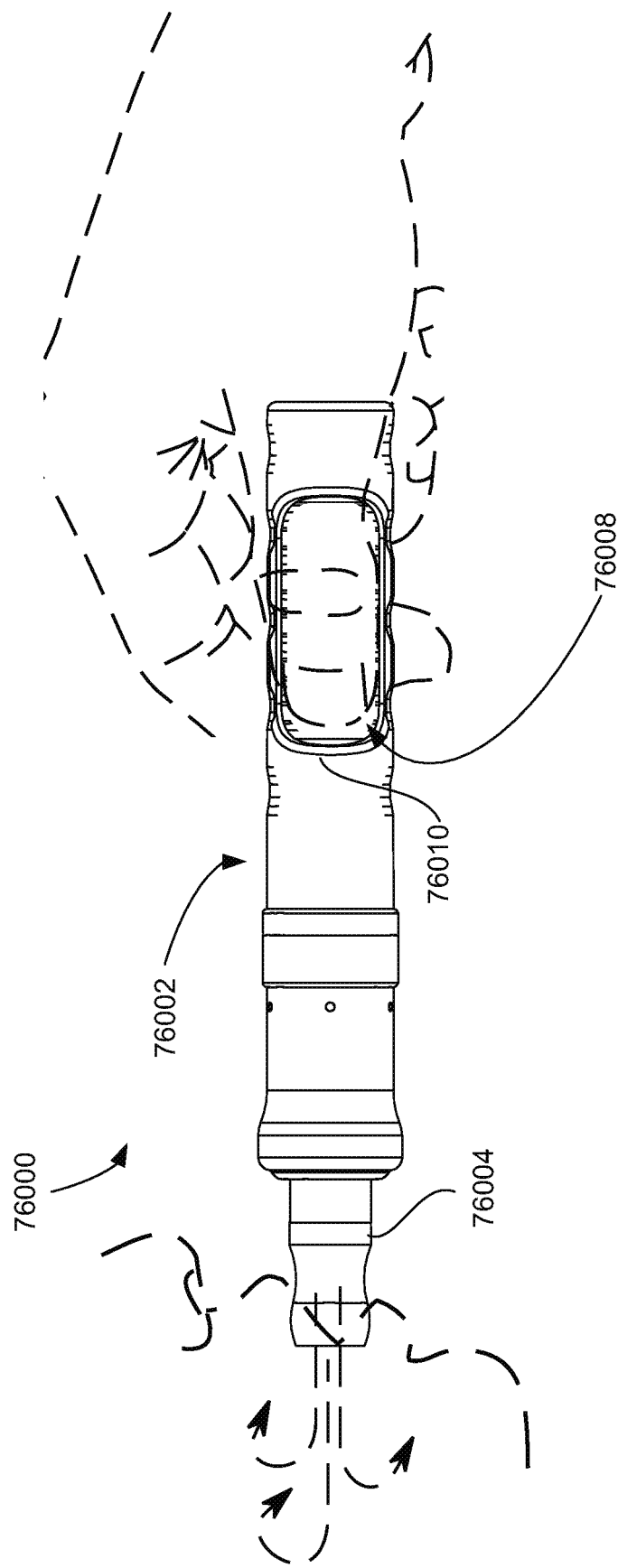
Figure 77D:
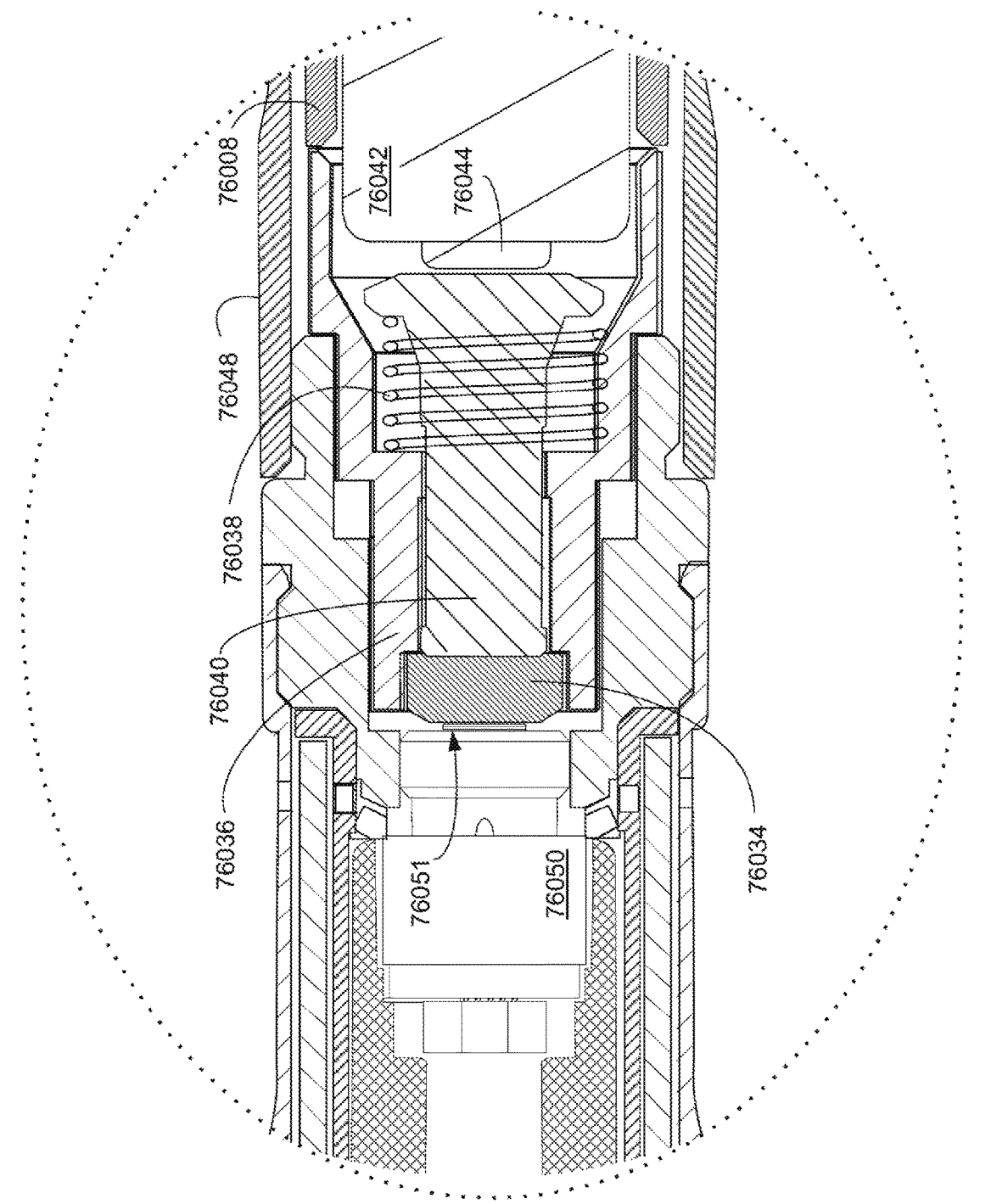

In subsequent sequential side view in FIG. 77C, the battery carrier sleeve 76008 is shown in extended position for electrically activating the atomizer assembly of vaporizer 76000 to change liquid into vapor. Similarly, the user's thumb, which is depicted in dashed line as engaging the surface of the battery carrier sleeve 76008, is likewise extended. FIG. 77D is a detailed cutaway partial view showing the battery carrier sleeve 76008 in the extended position as in FIG. 77C. Vapors produced by the vaporizer in response to such manual activation by the user are representatively illustrated in FIG. 77C by dashed arrows extending from oral aspiration tube 76004. The vapors depicted as dashed arrows are shown extending into the user's mouth in response to aspiration by user's mouth. For illustrative purposes, the profile of the user's mouth is depicted using dashed lines.

Figure 77E:
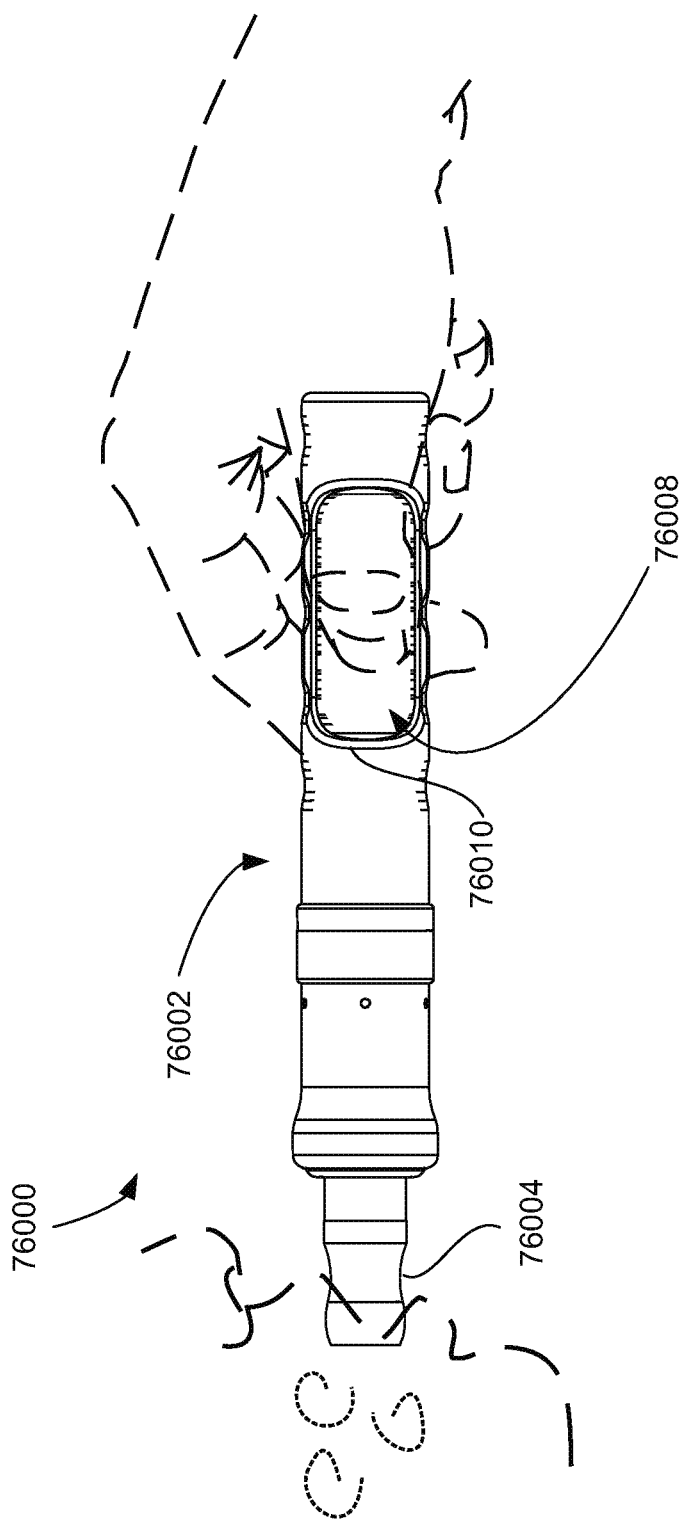
Figure 77F:
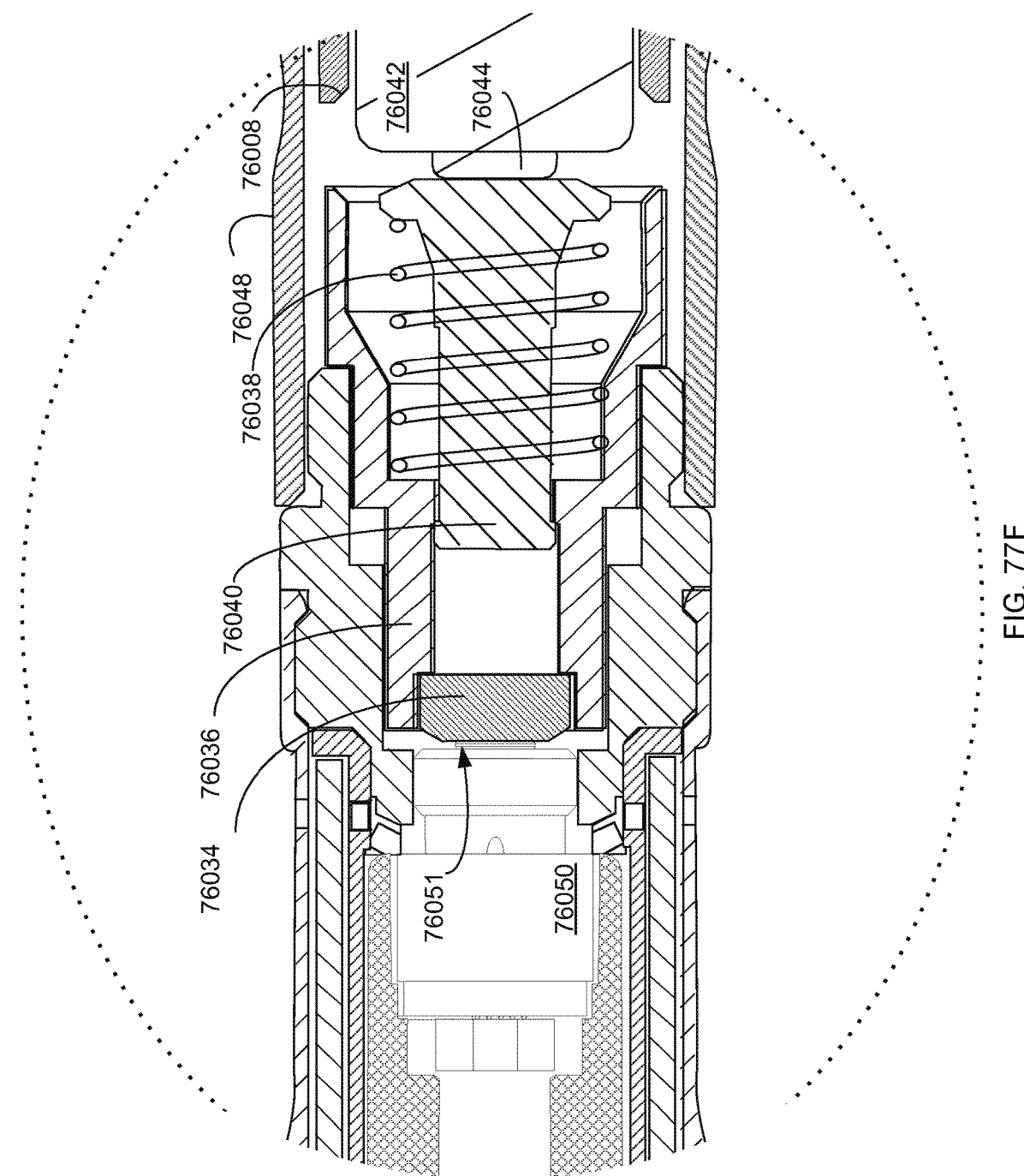

In subsequent sequential side view in FIG. 77E, the battery carrier sleeve 76008 is shown once again in retracted position for electrically deactivating the atomizer assembly of vaporizer 76000. Similarly, the user's thumb, which is depicted in dashed line as engaging the surface of the battery carrier sleeve 76008, is likewise retracted. FIG. 77F is a detailed cutaway partial view showing the battery carrier sleeve 76008 in the retracted position as in FIG. 77E. FIG. 77E shows remainder aspirated vapors depicted as dashed line curls in the mouth of the user. For illustrative purposes, the profile of the user's mouth is depicted using dashed lines.

As particularly shown in FIG. 77D, the atomizer assembly 76050 may comprise first electrical contact (for example, including at least inner contact member 76051) for selectively conducting a flow of battery power from battery 76042 to the atomizer assembly 76050 when the battery carrier sleeve 76008 is in the extended position as shown in FIG. 77D. First electrical contact (for example, including at least inner contact member 76051) may selectively interrupt the flow of battery power from battery 76042 to the atomizer assembly 76050 when the battery carrier sleeve 76008 is in the retracted position, as shown in FIGS. 77B and 77F.

As particularly shown in FIG. 77D, the battery carrier sleeve 76008 and battery contact post 76040 may be arranged for electrically coupling battery terminal 76044 of battery 76042 with contact pellet 76034 and inner contact member 76051 of the atomizer assembly 76050, when the battery carrier sleeve 76008 is in the extended position. Battery carrier sleeve 76008 and battery contact post 76040 may be arranged for electrically isolating the battery terminal 76044 from contact pellet 76034 and inner contact member 76051 of the atomizer assembly 76050, when the battery carrier sleeve 76008 is in the retracted position, as shown in FIGS. 77B and 77F. In particular, when the battery carrier sleeve 76008 is in the retracted position as shown in FIGS. 77B and 77F, there may be an air gap interposed between the battery contact post 76040 and contact pellet/inner contact member 76034,76051 of the atomizer assembly 76050, for electrically isolating battery contact post 76040 from contact pellet/inner contact member 76034, 76051. As shown in FIGS. 77B, 77D and 77F, bushing 76036 may retain contact pellet 76034 in electrical coupling with the inner contact member 76051 of the atomizer assembly 76050 (for example, with the extremity of inner contact member 76051 of the atomizer assembly 76050).

FIGS. 77B and 77F show expanded resilient member 76038, for example as an expanded spring, which may be disposed within the housing sleeve 76048 and bushing 76036. Resilient member 76038 may be coupled with the battery carrier sleeve 76008 for urging the battery carrier sleeve 76008 into the retracted position, as shown in FIGS. 77B and 77F. FIG. 77D shows resilient member 76038 as compressed, for example as a compressed spring, when battery carrier sleeve 76008 is in the extended position shown in FIG. 77D.

In other words, FIGS. 77A-77F show operation of an electrical switch comprising battery carrier sleeve 76008 slidably coupled with the housing for guiding alternative movement of the battery carrier sleeve 76008 between an extended position and a retracted position. The electrical switch may be closed for activating the atomizer assembly 76050 to change the liquid into the vapor when the battery carrier sleeve 76008 is in the extended position. The electrical switch may be open for deactivating the atomizer assembly 76050 when the battery carrier sleeve 76008 is in the retracted position. The electrical switch may be manually controllable by the user of the vaporizer, by manual control of the movement of the battery carrier sleeve 76008.

The electrical switch may be a momentary on-off switch. Momentary on-off switch may be "on", as shown in FIG. 77D, so long as the user may hold the battery carrier sleeve 76008 in the extended position, against restoring force of compressed resilient member 76038 (in other words, against restoring force of a compressed spring). Momentary on-off switch may be "off", as shown in FIGS. 77B and 77F, so long as the user may relax hold on the battery carrier sleeve 76008, so that battery carrier sleeve 76008 is restored to retracted position, by restoring force as resilient member 76038 expands (in other words, as the spring expands). Accordingly, the electrical switch may be normally open, until closed by operation of the electrical switch.

Figure 78:
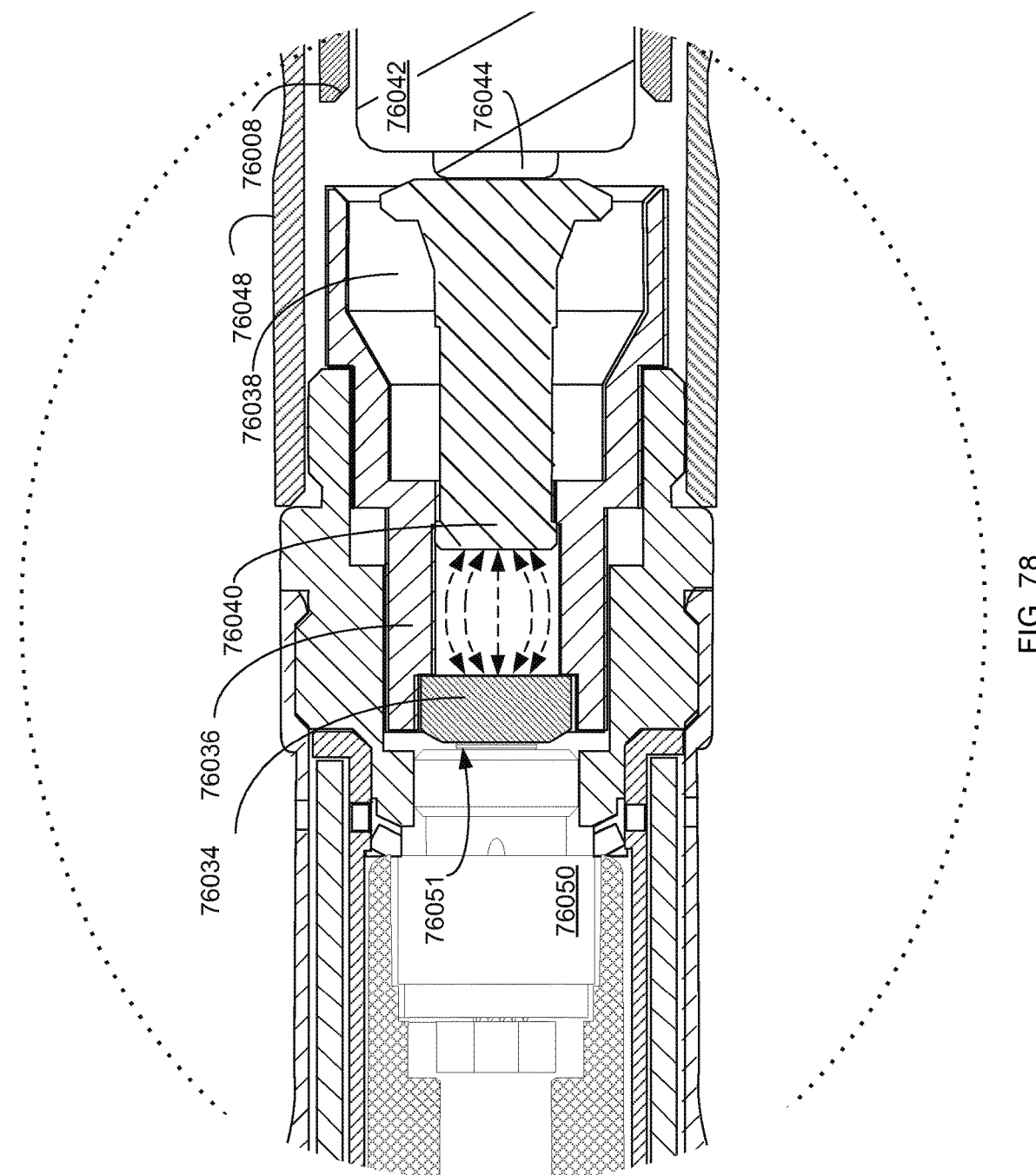
FIG. 78 shows an alternative embodiment.

FIG. 78 shows an alternative embodiment, which is generally similar to the other embodiment just discussed for FIGS. 76A-76S and 77A-77F, except that in the alternative embodiment of FIG. 78, the previously discussed resilient member may be omitted. In the alternative embodiment of FIG. 78, magnetically opposing magnetic members 76034, 76040 may provide the restoring force to urge the battery carrier sleeve 76008 back into the retracted position. In other words, contact pellet 76034 and battery contact post 76040 may be magnetized and arranged with magnetically opposing and magnetically repulsive polarities. Notional arrows are shown in FIG. 78 to depict lines of repulsive magnetic force, for urging the battery carrier sleeve 76008 into the retracted position.

Figure 79:
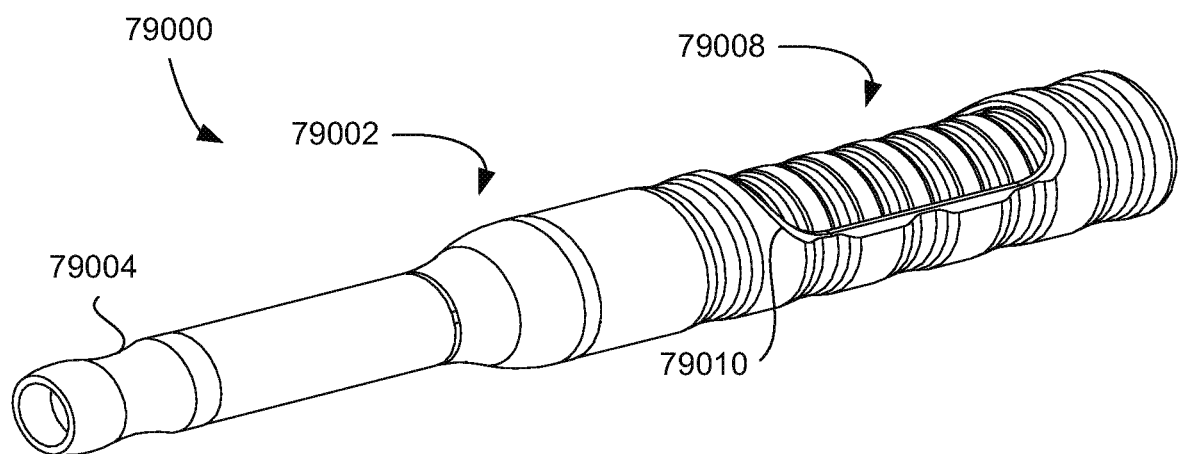
FIG. 79 shows another alternative embodiment.

FIG. 79 shows another alternative embodiment, which is generally similar to the other embodiment just discussed for FIGS. 76A-76S and 77A-77F, except that in the alternative embodiment of FIG. 79, the previously discussed absorptive ceramic reservoir may be omitted (and associated outer reservoir cover 76022, resilient o-ring 76023 and supportive inner reservoir sleeve 76025 may likewise be omitted.) Without the absorptive ceramic reservoir for volume storage of liquid, liquid capacity of the alternative embodiment shown in FIG. 79 may be different. For example, some liquid capacity may be provided by liquid disposed in the wick of the atomizer assembly.

Without absorptive ceramic reservoir, vaporizer 79000 shown in FIG. 79 may have a more slender housing 79002 coupled with oral aspiration tube 79004 for transporting vapor to a user's mouth. Battery carrier sleeve 79008 may be slidably coupled with the housing 79002 for guiding alternative movement of the battery carrier sleeve 79008 between extended position and retracted position. Vaporizer 79000 may be electrically activated to produce vapor when the battery carrier sleeve 79008 is moved into the extended position. Vapor production may be suspended, and the vaporizer 79000 may be temporarily deactivated, when the battery carrier sleeve 79008 is moved into the retracted position.

The battery carrier sleeve 79008 may be disposed within the housing 79002. The housing 79002 may have an aperture 79010 extending into the housing 79002 and arranged adjacent to a surface of the battery carrier sleeve 79008. The surface of the battery carrier sleeve 79008 may be arranged so as to be manually accessible through the aperture 79010 by a user for controlling the movement of battery carrier sleeve 79008 between the retracted position and the extended position.

Figure 80A:
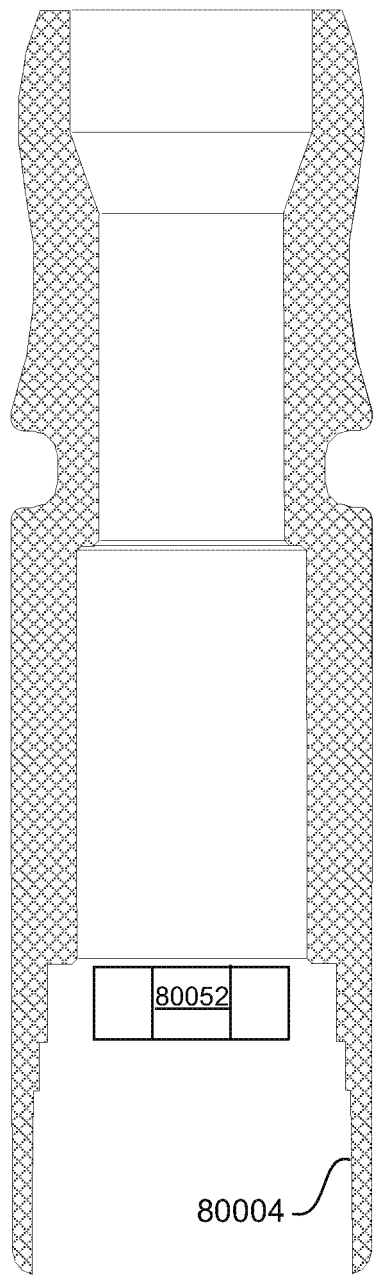
FIGS. 80A and 80B show yet another alternative embodiment.
Figure 80B:
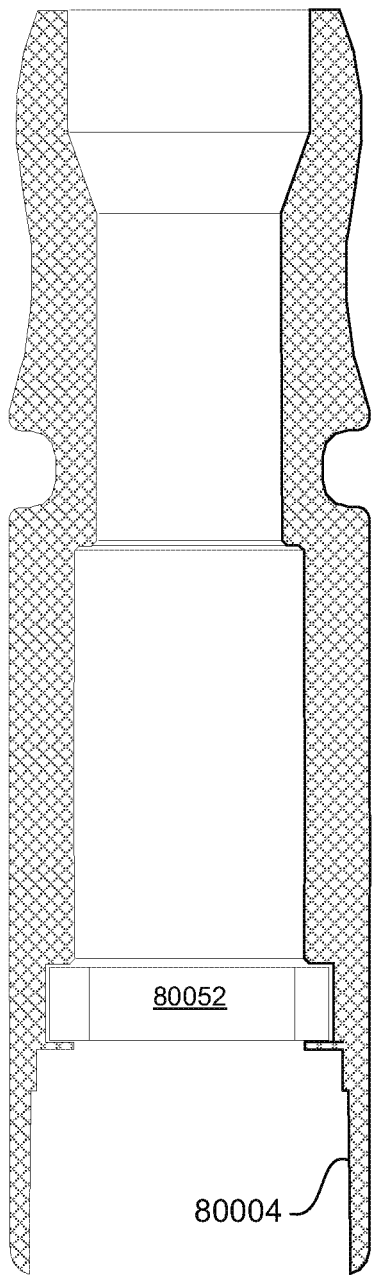

FIGS. 80A and 80B show yet another alternative embodiment. FIGS. 80A and 80B are partial cutaway views showing oral aspiration tube 80004 and splatter shield 80052. FIGS. 80A and 80B particular show alternative rotation orientation side views of oral aspiration tube 80004 and splatter shield 80052. FIG. 80A is oriented to show a narrow width dimension along a minor axis of splatter shield 80052. Air gaps shown in FIG. 80A, which may be defined between the oral aspiration tube 80004 and the narrow width dimension of the splatter shield 80052 may provide for vapor flow around the splatter shield 80052.

FIG. 80B is oriented a quarter turn relative to FIG. 80A, so as to show a broad width dimension along a major axis of splatter shield 80052. The broad width dimension of the splatter shield 80052 shown in FIG. 80B may provide for retention engagement of the broad width dimension of splatter shield 80052 by the oral aspiration tube 80004. The oral aspiration tube 80004 may be formed about the broad width dimension of splatter shield 80052 in retention engagement of the broad width dimension of splatter shield 80052. The oral aspiration tube 80004 may be coupled with the splatter shield 80052 so as to retain the non-flammable spatter shield 80052 with the oral aspiration tube 80004 when the oral aspiration tube 80004 is removed from the vaporizer.

Figure 81:
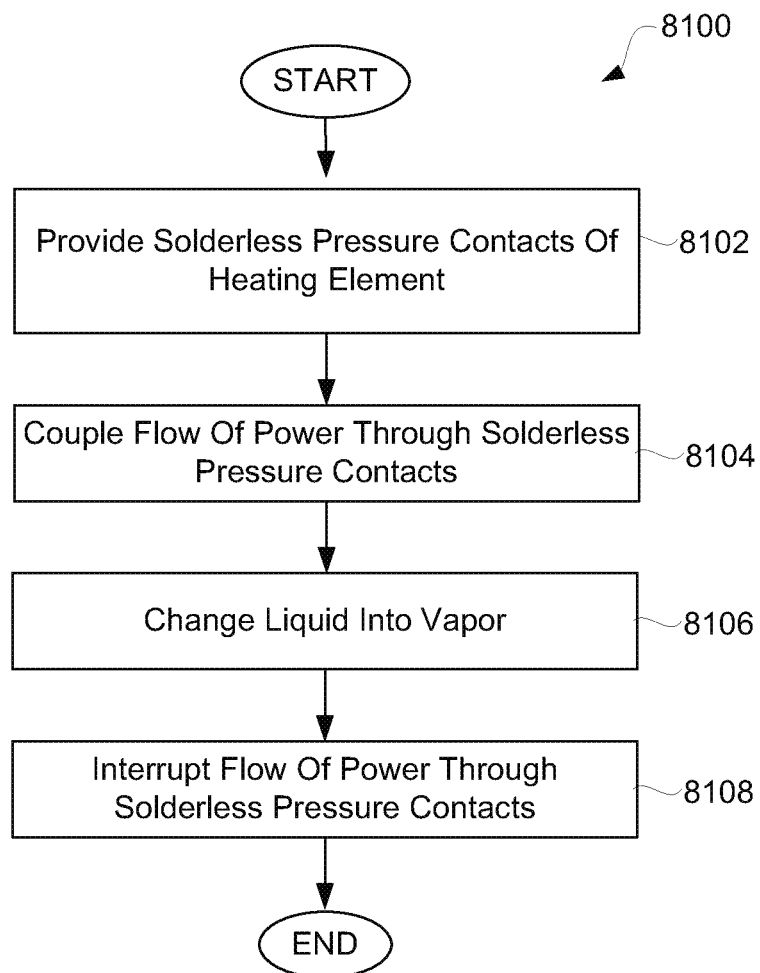
FIG. 81 is a flow diagram of a vaporizer operation process according to one embodiment.

FIG. 81 is a flow diagram of a vaporizer operation process 8100 according to one embodiment. In accordance with process 8100 shown in FIG. 81, the process may begin with providing 8102 solderless pressure contacts of a heating element. The process 8100 may continue with coupling 8104 a flow of power through the solderless pressure contacts to electrically activate the heating element. The process 8100 may continue with changing 8106 a liquid into a vapor in response to electrical activation of the heating element. The process 8100 may continue with interrupting 8108 the flow of power through the solderless pressure contacts to electrically deactivate the heating element. Once the flow of power through the solderless pressure contacts has been interrupted 8108, the process 8100 can end.

Figure 82:
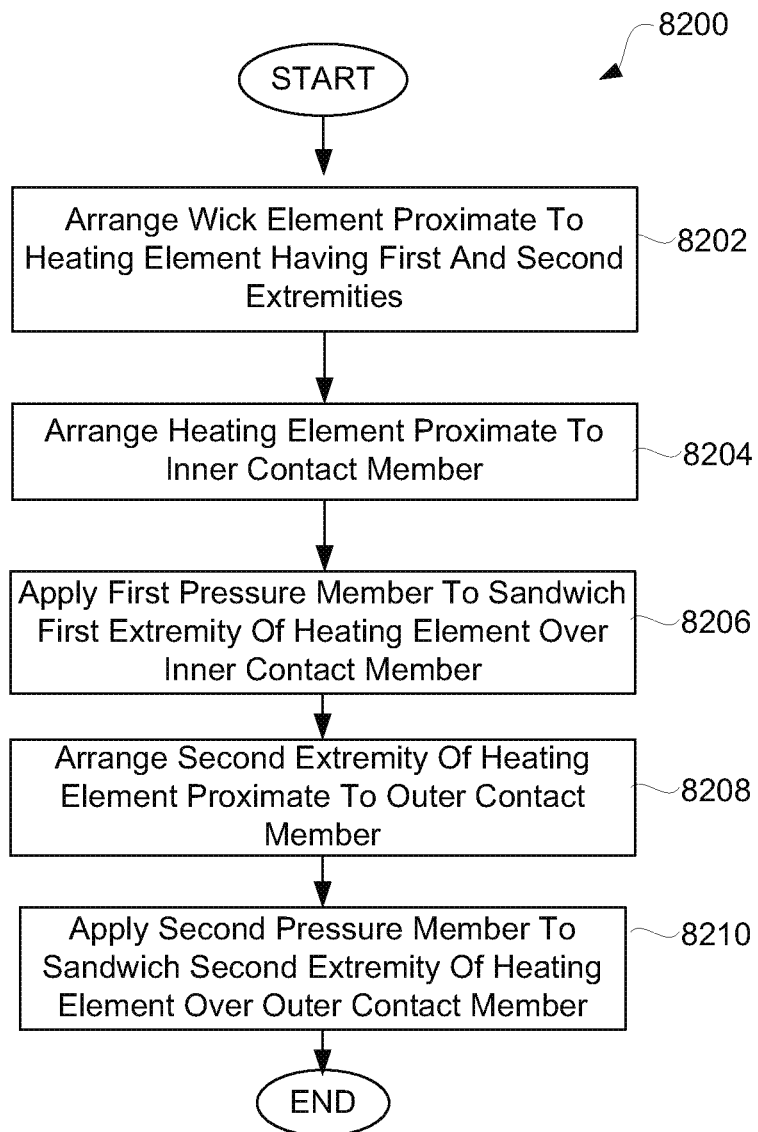
FIG. 82 is a flow diagram of a vaporizer assembly process according to one embodiment.

FIG. 82 is a flow diagram of a vaporizer assembly process 8200 according to one embodiment. In accordance with process 8200 shown in FIG. 82, the process may begin with arranging 8202 a wick element proximate to a heating element having first and second extremities. The process 8200 may continue with arranging 8204 the heating element proximate to an inner contact member. The process 8200 may continue with applying 8206 a first pressure member to sandwich the first extremity of the heating element over said inner contact member to effect first solderless pressure electrical contacts. The process 8200 may continue with arranging 8208 the second extremity of the heating element proximate to an outer contact member. The process 8200 may continue with applying 8210 second pressure member to sandwich the second extremity of the heating element over said outer contact member to effect second solderless pressure electrical contacts. Once the second pressure member has been applied 8210, the process 8200 can end.

The advantages of the invention are numerous. Different aspects, embodiments or implementations may yield one or more of the following advantages. One advantage may be that soldering of the heating element may be substantially avoided. Another advantage may be that toxic lead and/or toxic lead vapors of lead based solder may be substantially avoided. Another advantage is that upon heating of the atomizer assembly, user inhalation of toxins from lead based solders may be substantially avoided. Another advantage is that solderless pressure contacts may provide ease or efficiency in assembly.

Figure 83:
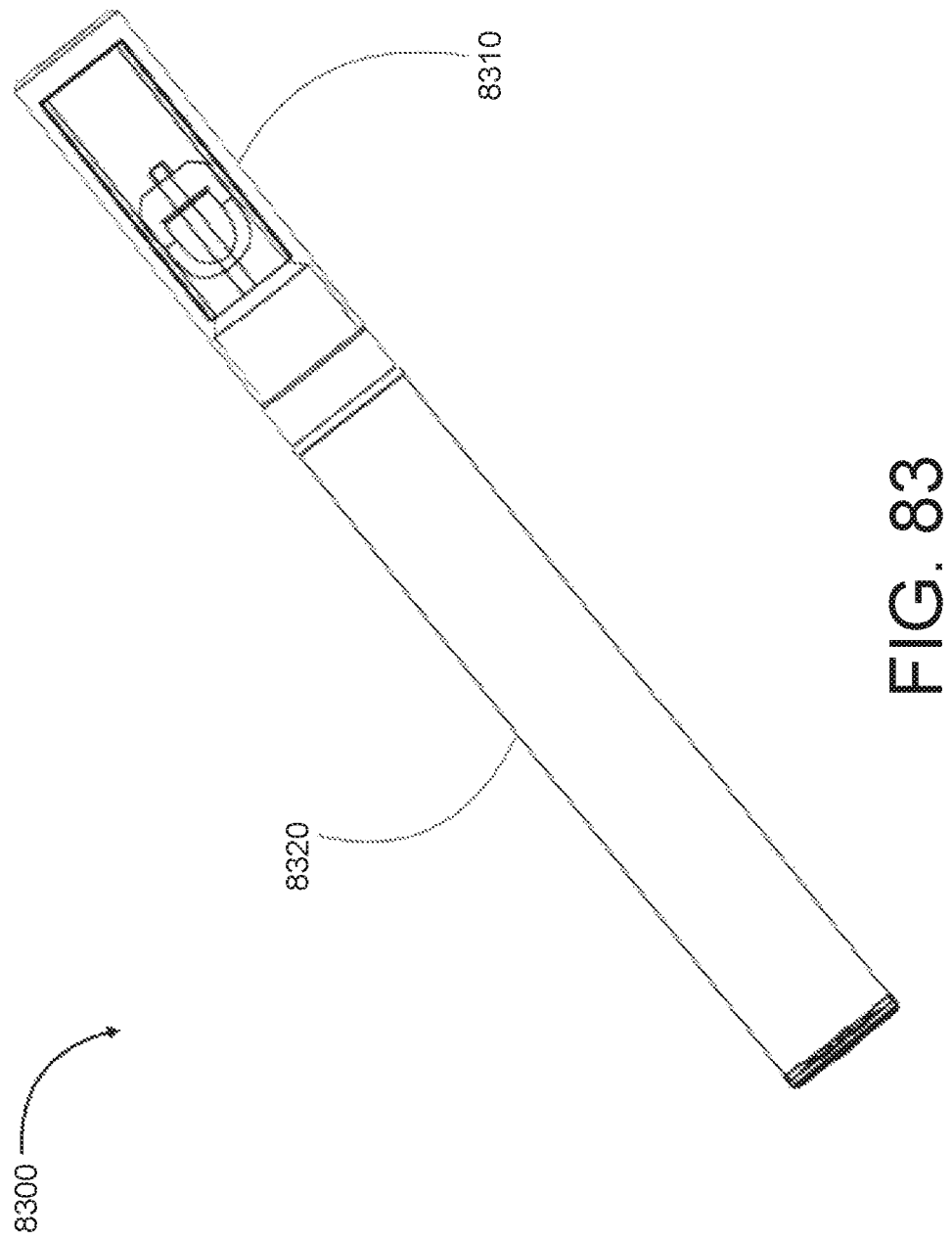
FIG. 83 is a partial cutaway view of a personal vaporizer unit.
Figure 84:
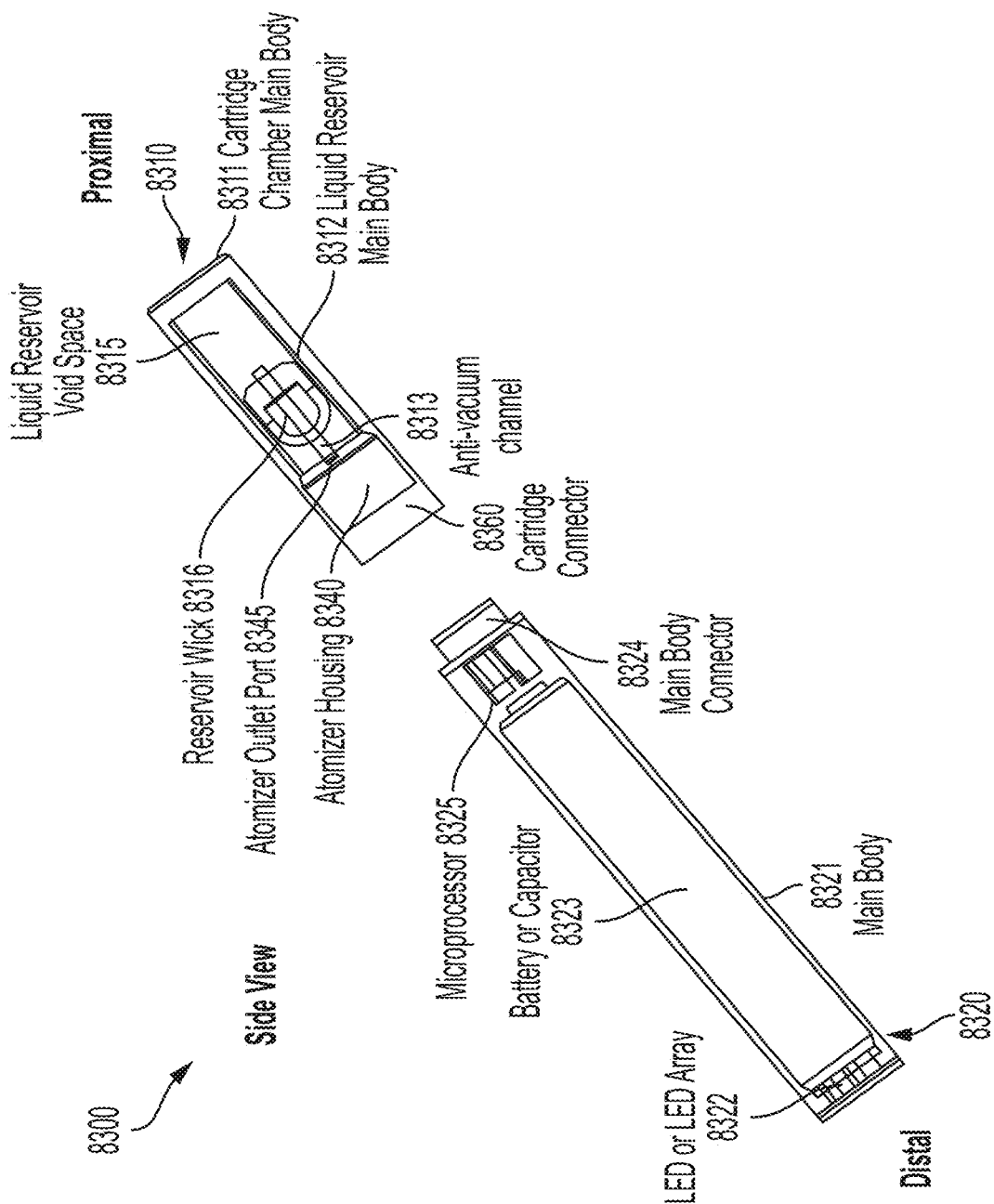
FIG. 84 is a cutaway view of a personal vaporizer unit.

FIG. 83 is a partial cutaway view of a personal vaporizer unit. In FIG. 83, personal vaporizer unit 8300 comprises proximal assembly 8310 and distal assembly 8320. FIG. 84 is a cutaway view of a personal vaporizer unit. In FIG. 84, distal assembly 8320 comprises main body 8321, and LED (or LED array) 8322, battery (or capacitor) 8323, main body connector 8324, and microprocessor 8325. Also in FIG. 84, proximal assembly 8310 includes cartridge chamber main body 8311, cartridge liquid reservoir main body 8312, anti-vacuum channel 8313, a void space in cartridge liquid reservoir 8315, reservoir wick 8316, atomizer housing 8340, and cartridge connector 8360. Atomizer housing 8340 includes atomizer outlet port 8345. LED 8322 is disposed at the distal end of distal assembly 8320. Battery 8323 is disposed within main body 8321. Main body connector 8324 is disposed at the proximal end of main body 8321. Microprocessor 8325 is disposed within main body 8321. Main body connector 8324 is designed to interface with cartridge connector 8360. Main body connector 8324 and cartridge connector 8360 include contacts (not shown in FIG. 84) to allow electrical signals, data, and/or power to be transferred between distal assembly 8320 and proximal assembly 8310.

Cartridge liquid reservoir main body 8312 is configured to be disposed within cartridge chamber main body 8311. Likewise, atomizer housing 8340 is configured to be disposed within cartridge chamber main body 8311. Atomizer housing 8340, its contents, and cartridge liquid reservoir main body 8312 may comprise an integrated unit (a.k.a. cartomizer).

Figure 85:
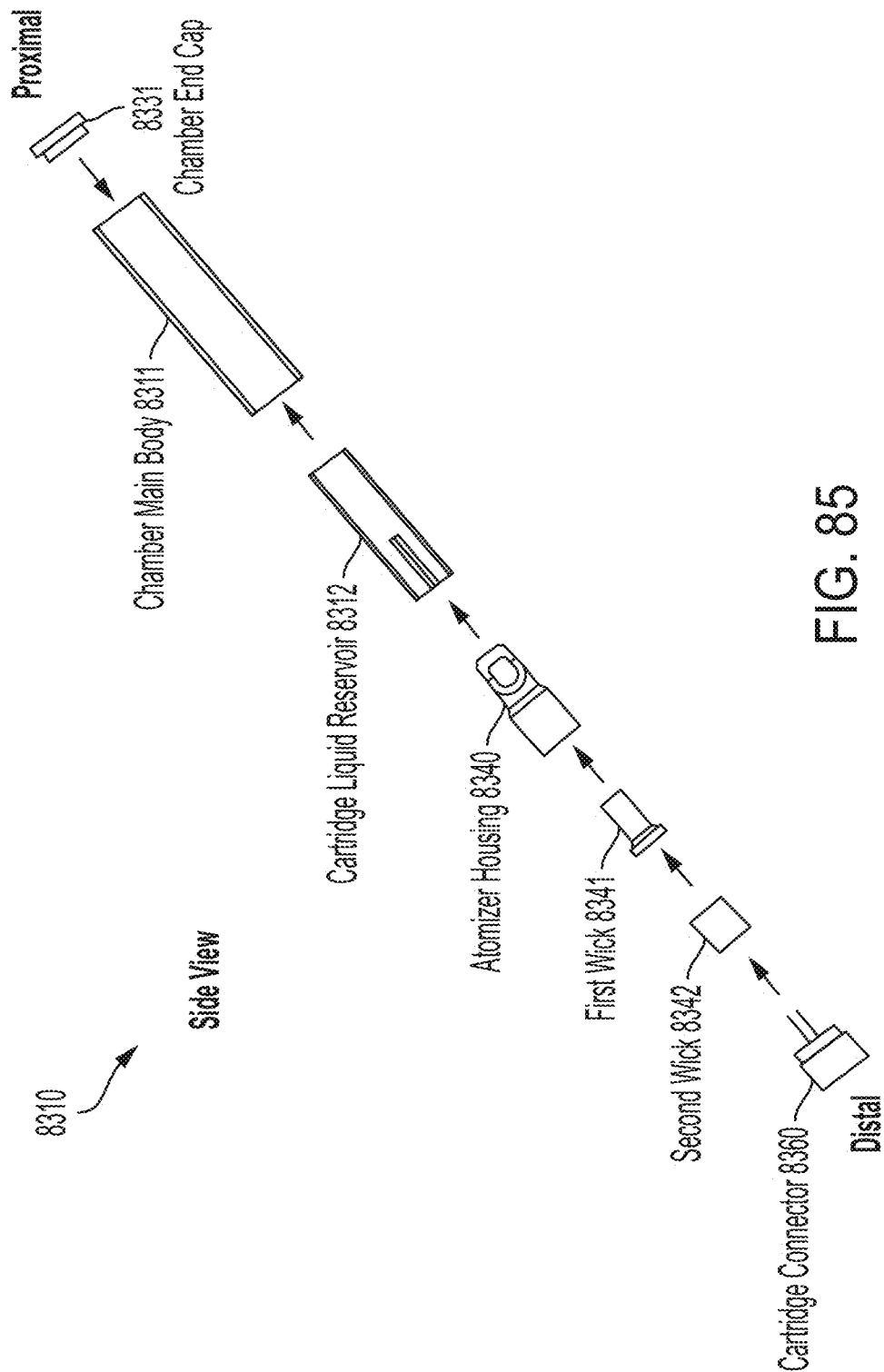
FIG. 85 is an exploded view of distal assembly.

FIG. 85 is an exploded view of the proximal assembly. As illustrated in FIG. 85, proximal assembly 8310 may be fitted with a chamber end cap 8331 on the proximal end of cartridge chamber main body 8311. Also illustrated in FIG. 85, cartridge liquid reservoir main body 8312 may be disposed within cartridge chamber main body 8311. Atomizer housing 8340 may be at least partially disposed within the distal end of cartridge liquid reservoir main body 8312. A first wick 8341 may be at least partially disposed within the distal end of atomizer housing 8340. A second wick 8342 may just be disposed in contact with the distal end of first wick 8341. As described previously herein, second wick 8342 may be disposed within cartridge chamber main body 8311, and/or atomizer housing 8340 such that an air gap exists between the distal end of first wick 8341 and the proximal end of the second wick 8342. At least a portion of cartridge connector 8360 may also be disposed within the distal end of cartridge chamber main body 8311.

Figure 86:
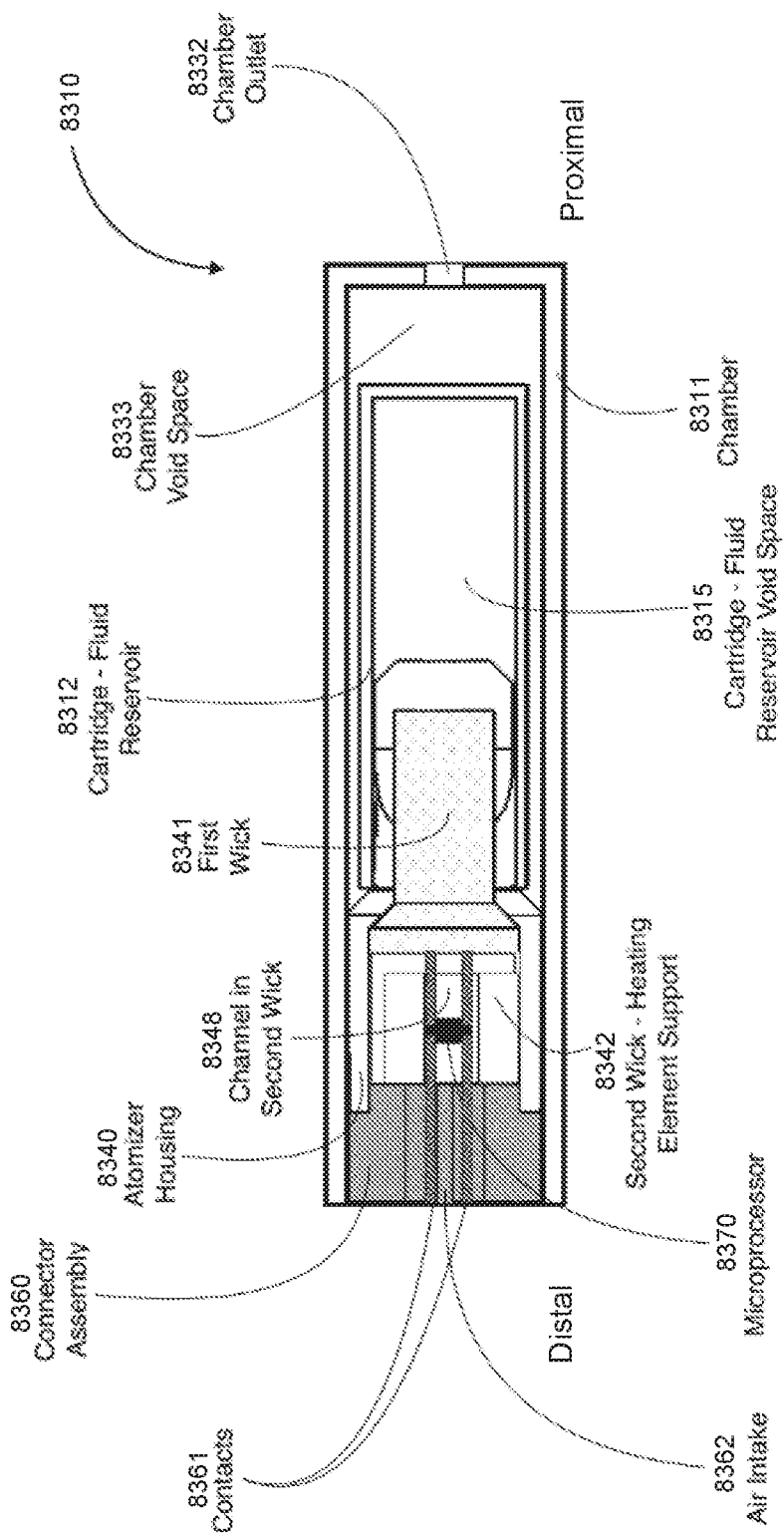
FIG. 86 is a first cross-section view of a distal assembly.

FIG. 86 is a first cross-section view of a proximal assembly. In FIG. 86, a first cross-section of proximal assembly 8310 is illustrated. Cartridge chamber main body 8311 includes a chamber outlet 8332 at the proximal end of cartridge chamber main body 8311. Also illustrated in FIG. 86 are contacts 8361, air intake 8362, microprocessor 8370, and at least one channel 8348 in second wick 8342. Second wick 8342 includes a heating element support that is also illustrated. In an embodiment (not illustrated in FIG. 86), first wick 8341 may include a heating element support.

Figure 87:
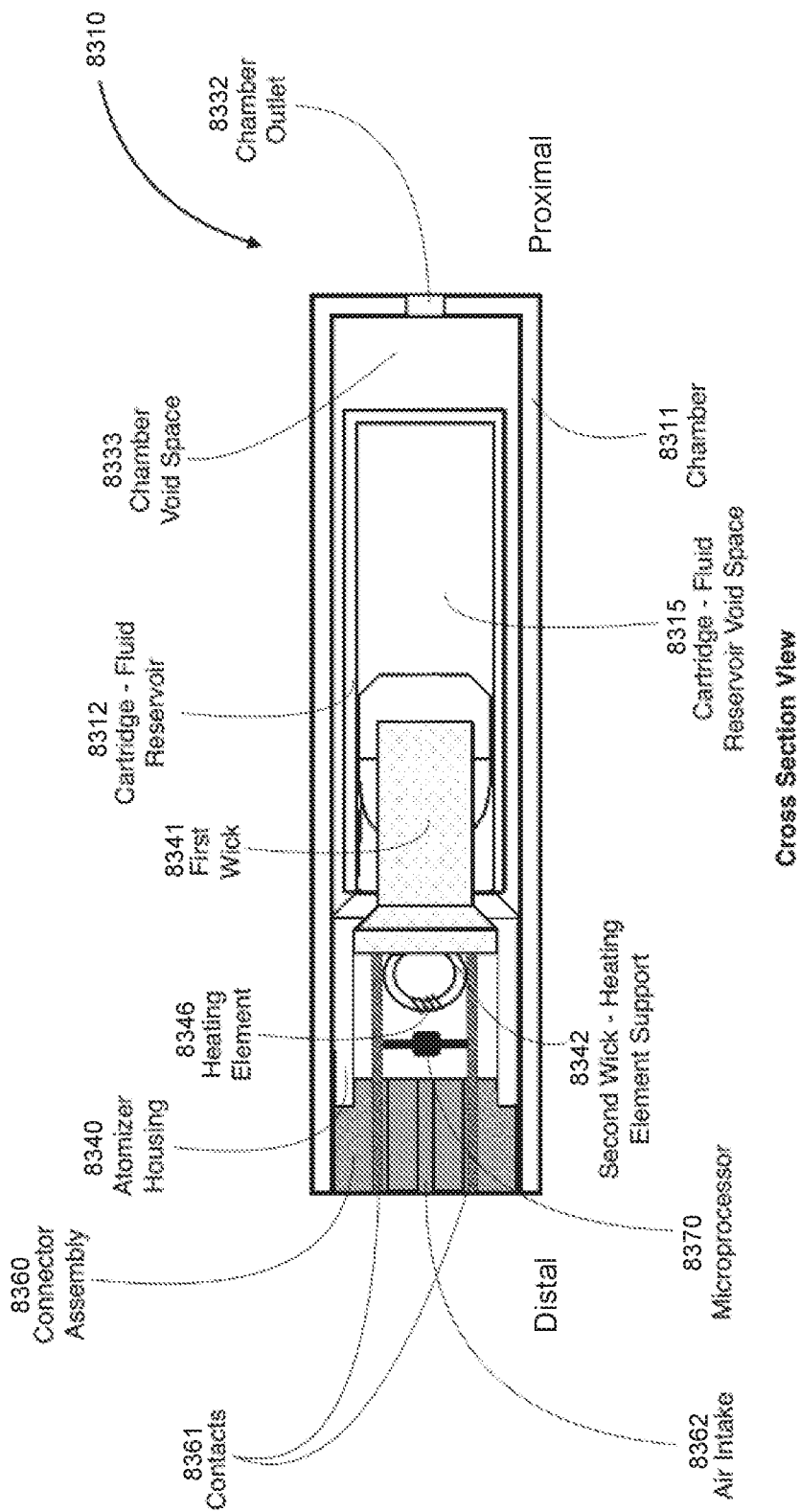
FIG. 87 is a second cross-section view of a distal assembly.

FIG. 87 is a second cross-section view of a proximal assembly. In FIG. 87, a second cross-section of proximal assembly 8310 is illustrated. The cross-section illustrated in FIG. 87 has proximal assembly 8310 rotated around its central proximal-to-distal axis by approximately 90-degrees.

Figure 88:
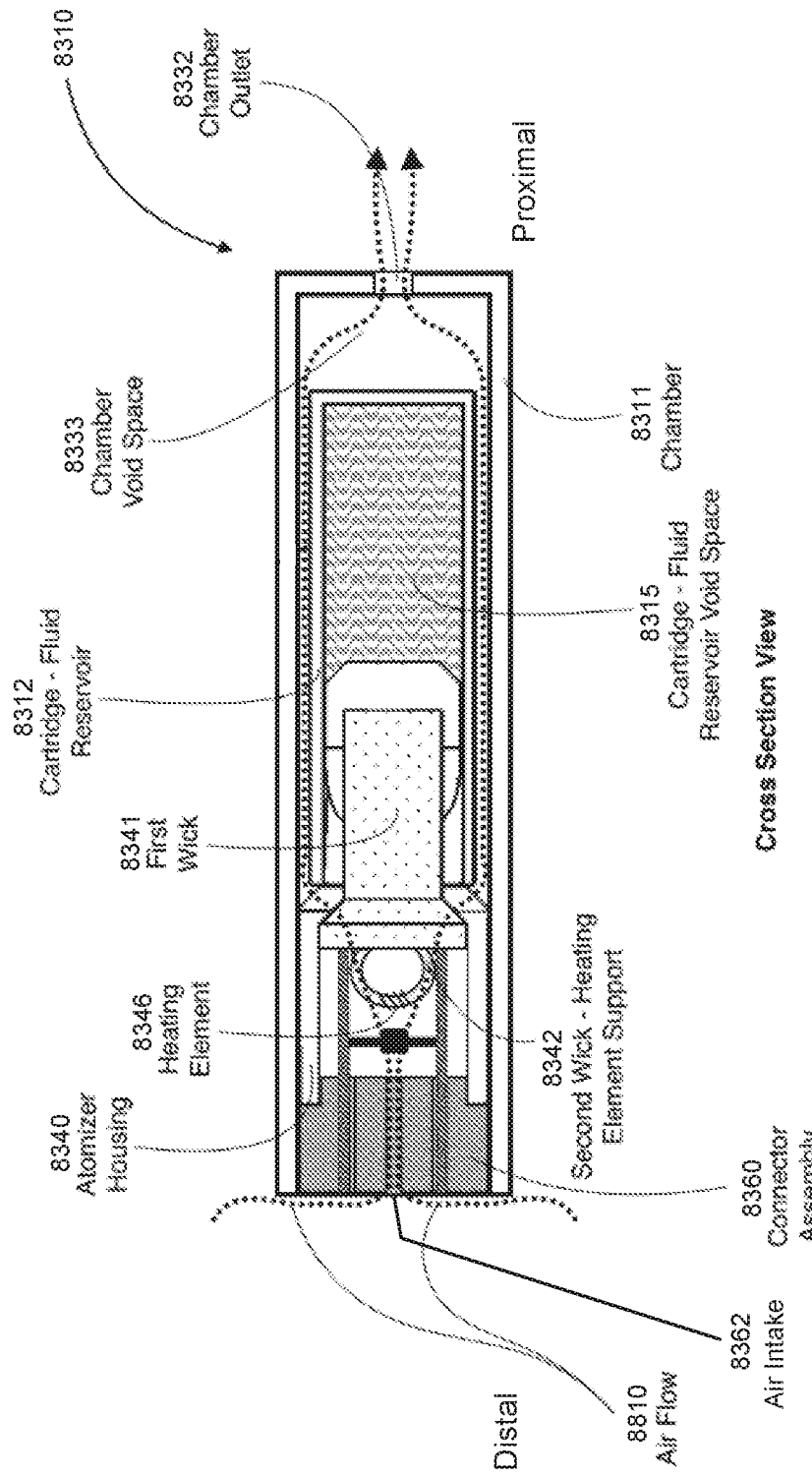
FIG. 88 is a cross-section view illustrating airflow through a distal assembly.

FIG. 88 is a cross-section view illustrating airflow through a proximal assembly. In FIG. 88 proximal assembly 8310 is illustrated using airflow arrows 8810 to show at least one path for outside air to enter proximal assembly 8310, be mixed with vaporized substances, and exit proximal assembly 8310.

In FIG. 88 airflow arrows 8810 pass from outside proximal assembly 8310 and enter proximal assembly 8310 via air intake 8362. From air intake 8362 airflow arrows 8810 pass over second wick 8342 and a heating element 8346. Airflow arrows 8810 pass through first wick 8341 entering a space between 8333 cartridge liquid reservoir main body 8312 and cartridge chamber main body 8311. After passing along cartridge liquid reservoir main body 8312 airflow arrows 8810 enter a chamber void space 8333 between cartridge liquid reservoir main body 8312 and chamber outlet 8332. After passing through chamber void space 8333, airflow arrows 8810 exit proximal assembly 8310 via chamber outlet 8332.

FIG. 89 is an illustration showing an axial cut line through a proximal assembly. FIG. 90 is a cross-section view of a proximal assembly cartridge chamber main body. In FIG. 90, a cross-section of cartridge chamber main body 8311 taken along the cut line illustrated in FIG. 89 is shown.

FIG. 91 is a cross-section view of a proximal assembly cartridge chamber main body with clean air intake. In FIG. 91, a cross-section of a cartridge chamber main body 9110 taken along the cut line illustrated in FIG. 89 is shown. In FIG. 91, cartridge chamber main body 9110 includes a chamber clean air intake 9112. Chamber clean air intake 9112 is illustrated as a perforation in a radial wall of cartridge chamber main body 9110.

FIG. 92 is a cross-section view of a proximal assembly cartridge chamber main body with clean air intake and airflow directional standoff. In FIG. 92, a cross-section of a cartridge chamber main body 9210 taken along the cut line illustrated in FIG. 89 is shown. FIG. 92 illustrates cartridge chamber main body 9210 with chamber clean air intake 9112 and airflow directional standoff 9212. Airflow directional standoff 9212 is illustrated closer to the proximal end of cartridge chamber main body 9210 than chamber clean air intake 9112. Airflow directional standoff 9212 may be configured to prevent outside air that enters chamber clean air intake 9112 from flowing directly to chamber outlet 8332.

FIG. 93 is an illustration showing a cut line through a cartridge liquid reservoir main body. FIG. 94 is a cross-section view of a cartridge liquid reservoir main body. In FIG. 94, a cross-section of a cartridge liquid reservoir main body 8312 taken along the cut line illustrated in FIG. 93 is shown.

FIG. 95 is a cross-section view of the cartridge liquid reservoir main body and cartridge liquid reservoir standoff. In FIG. 95, a cross-section of a cartridge liquid reservoir main body 9510 taken along the cut line illustrated in FIG. 93 is shown. In FIG. 95, cartridge liquid reservoir main body 9510 includes cartridge liquid reservoir standoff 9512. Cartridge liquid reservoir standoff 9512 may be configured to prevent outside air entering a proximal assembly via a clean air intake (e.g., chamber clean air intake 9112) from flowing directly to a proximal assembly chamber outlet (e.g., chamber outlet 8332).

Figure 96:
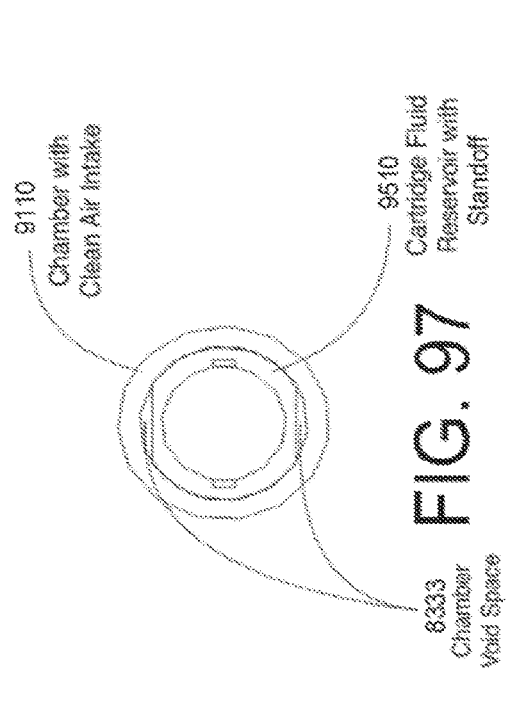
FIG. 96 is an illustration showing a cross-section cut line through a distal assembly.
Figure 97:
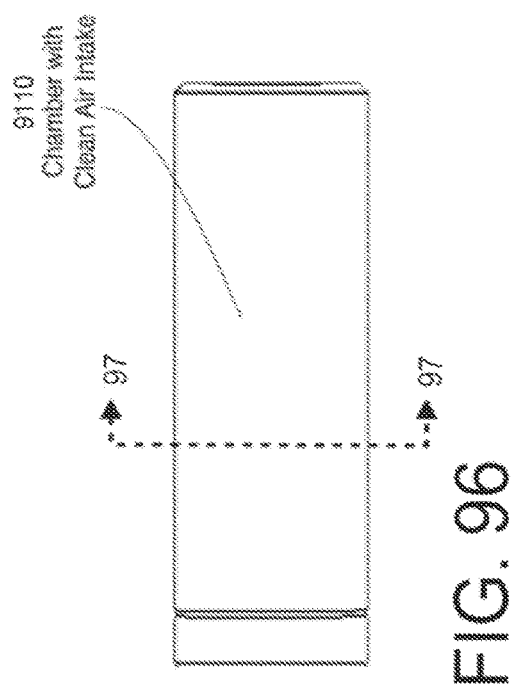
FIG. 97 is a cross-section view of the distal assembly along the cut line shown in FIG. 96.

FIG. 96 is an illustration showing a cross-section cut line through a proximal assembly. FIG. 97 is a cross-section view of a proximal assembly. In FIG. 97, a cross-section of a cartridge chamber main body 9110 taken along the cut line illustrated in FIG. 96 is shown. In FIG. 97, a cartridge liquid reservoir main body with standoff 9510 is illustrated inside a cartridge chamber main body 9110 with clean air intake. The shape of cartridge liquid reservoir main body 9510 may be such that chamber void space 8333 is formed between an outside surface of cartridge liquid reservoir main body 9510 and cartridge chamber main body 9110. In an embodiment, all or part of a chamber void space 8333 may be blocked by a cartridge liquid reservoir standoff (e.g., cartridge liquid reservoir standoff 9512) and/or a chamber airflow directional standoff (e.g., airflow directional standoff 9212). All or part of chamber void space 8333 may be blocked by a cartridge liquid reservoir standoff (e.g., cartridge liquid reservoir standoff 9512) and/or a chamber airflow directional standoff (e.g., airflow directional standoff 9212) to prevent outside air entering a proximal assembly via a clean air intake (e.g., chamber clean air intake 9112) from flowing directly to a proximal assembly chamber outlet (e.g., chamber outlet 8332).

Figure 98:
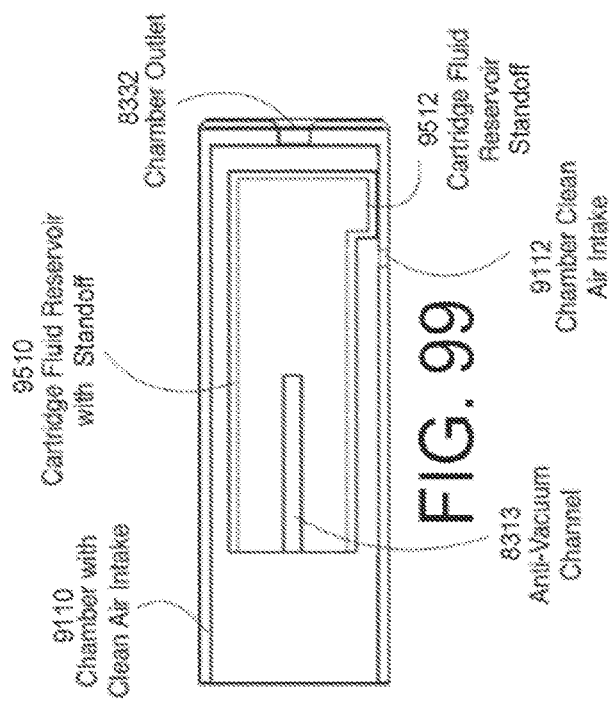
FIG. 98 is an illustration showing an axial cut line through a distal assembly.
Figure 99:
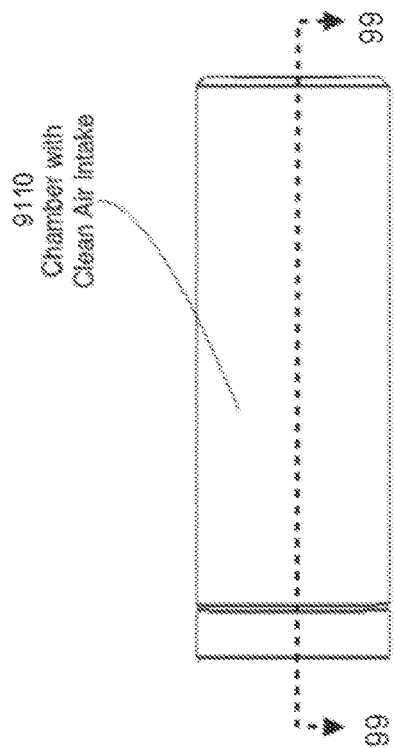
FIG. 99 is a cross-section view of a distal assembly along the cut line shown in FIG. 98.

FIG. 98 is an illustration showing an axial cut line through a proximal assembly. FIG. 99 is a cross-section view of a proximal assembly. In FIG. 99, a cross-section of a cartridge chamber main body 9110 and cartridge liquid reservoir main body 9510 taken along the cut line illustrated in FIG. 98 is shown. FIG. 99 illustrates how all or part of chamber void space 8333 may be blocked by a cartridge liquid reservoir standoff 9512 to prevent outside air entering a proximal assembly via a clean air intake (e.g., chamber clean air intake 9112) from flowing directly to a proximal assembly chamber outlet (e.g., chamber outlet 8332).

Figure 101:
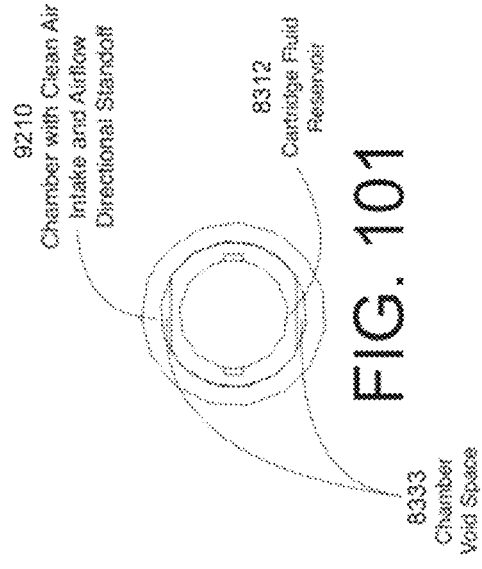
FIG. 101 is a cross-section view of a distal assembly along the cut line shown in FIG. 100.
Figure 100:
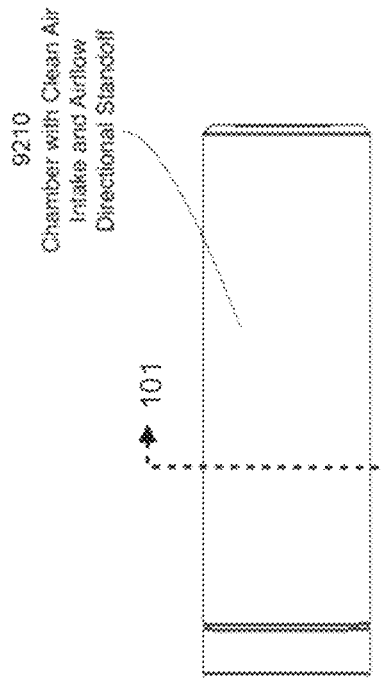
FIG. 100 is an illustration showing a cross-section cut line through a distal assembly according to another embodiment.

FIG. 100 is an illustration showing a cross-section cut line through a proximal assembly. FIG. 101 is a cross-section view of a proximal assembly. In FIG. 101, a cross-section of a cartridge chamber main body 9210 taken along the cut line illustrated in FIG. 100 is shown. In FIG. 101, a cartridge chamber main body 9210 with airflow directional standoff is illustrated holding a cartridge liquid reservoir main body 8312. The shape of cartridge chamber main body 9210 may be configured such that chamber void space 8333 is formed between an outside surface of cartridge liquid reservoir main body 8312 and cartridge chamber main body 9210. In an embodiment, all or part of chamber void space 8333 may be blocked by a cartridge liquid reservoir standoff (e.g., cartridge liquid reservoir standoff 9512) and/or a chamber airflow directional standoff (e.g., airflow directional standoff 9212). All or part of chamber void space 8333 may be blocked by a cartridge liquid reservoir standoff (e.g., cartridge liquid reservoir standoff 9512) and/or a chamber airflow directional standoff (e.g., airflow directional standoff 9212) to prevent outside air entering a proximal assembly via a clean air intake (e.g., chamber clean air intake 9112) from flowing directly to a proximal assembly chamber outlet (e.g., chamber outlet 8332).

Figure 103:
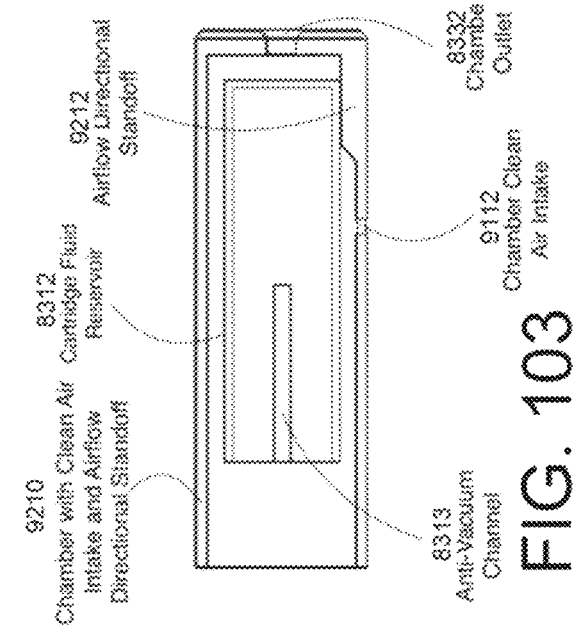
FIG. 103 is a cross-section view of a distal assembly along the cut line shown in FIG. 102.
Figure 102:
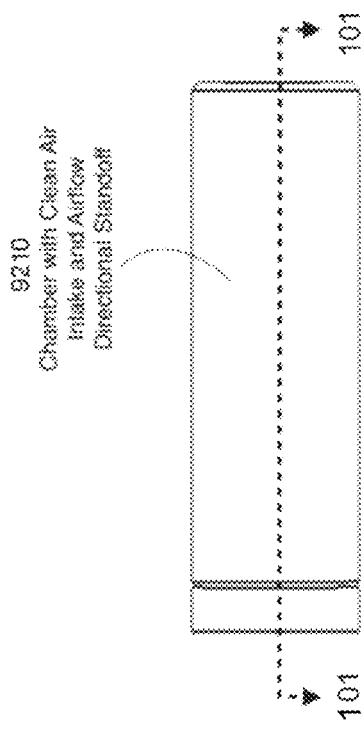
FIG. 102 is an illustration showing an axial cut line through a distal assembly.

FIG. 102 is an illustration showing a cross-section cut line through a proximal assembly. FIG. 103 is a cross-section view of a proximal assembly. In FIG. 103, a cross-section of a cartridge chamber main body 9210 and a cartridge liquid reservoir main body 8312 taken along the cut line illustrated in FIG. 102 is shown. FIG. 103 illustrates how all or part of chamber void space 8333 may be blocked by an airflow directional standoff 9212 to prevent outside air entering a proximal assembly via a clean air intake (e.g., chamber clean air intake 9112) from flowing directly to a proximal assembly chamber outlet (e.g., chamber outlet 8332).

Figure 104:
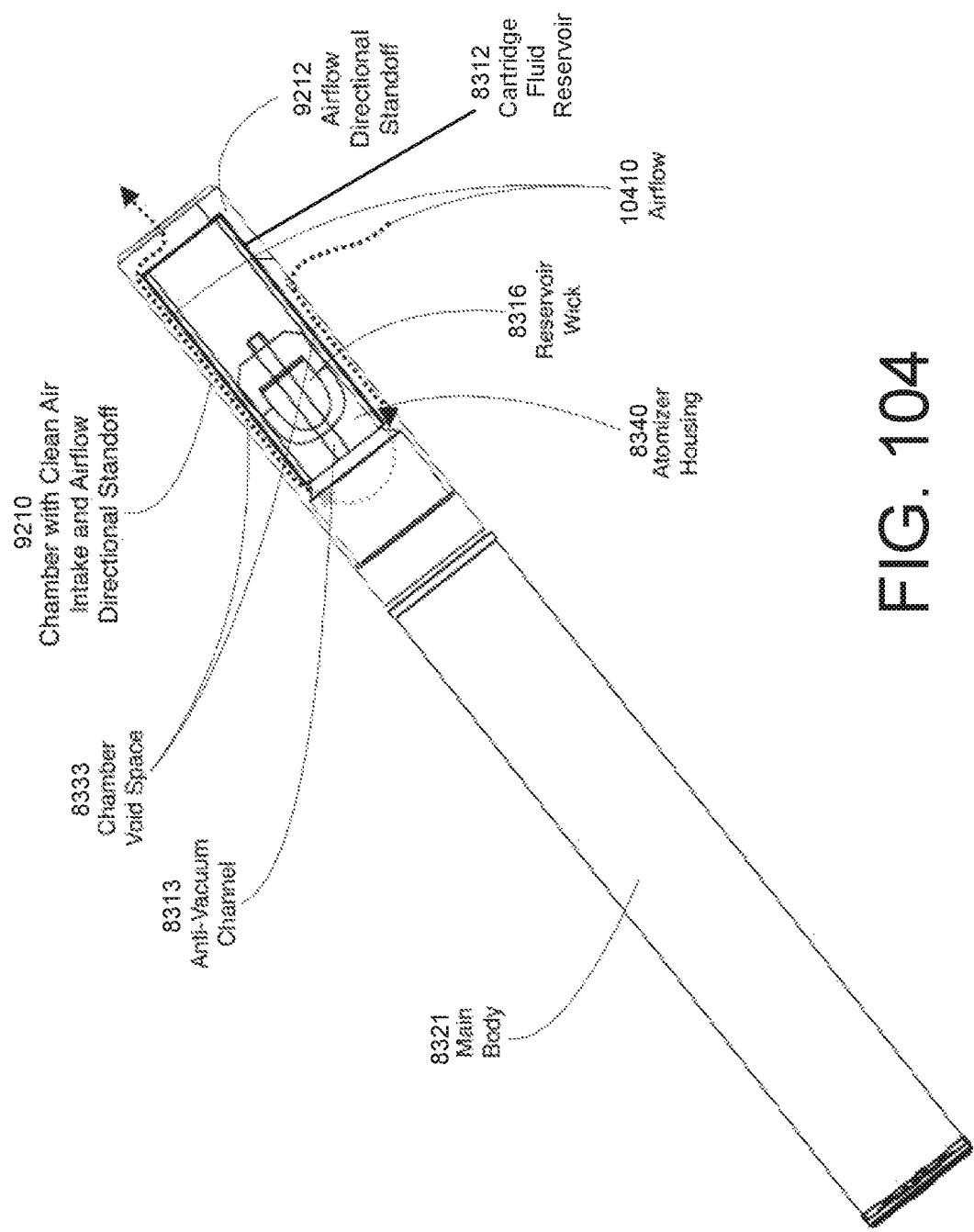
FIG. 104 is a partial cross-section view illustrating airflow through a personal vaporizer unit.

FIG. 104 is a partial cross-section view illustrating airflow through a personal vaporizer unit. In FIG. 104, airflow direction is illustrated by airflow arrow 10410. Airflow arrow 10410 originates outside of a personal vaporizer unit. Airflow arrow 10410 enters personal vaporizer unit via clean air intake (e.g., chamber clean air intake 9112). From a clean air intake airflow arrow 10410 flows along a first surface of a cartridge liquid reservoir main body (e.g., cartridge liquid reservoir main body 8312—along a first surface and in a chamber void space 8333 formed between an inside surface of cartridge chamber main body 9210 and an outside surface of cartridge liquid reservoir main body 8312). After at least some of airflow 10410 passes through an atomizer, a mixture of vaporized substance and air passes along a second surface of a cartridge liquid reservoir main body (e.g., cartridge liquid reservoir main body 8312—along a second surface and in a chamber void space 8333 formed between an inside surface of cartridge chamber main body 9210 and an outside surface of cartridge liquid reservoir main body 8312). After a mixture of vaporized substance and air passes, airflow arrow 10410 is illustrated exiting a proximal assembly to be inhaled by a user.

Figure 105:
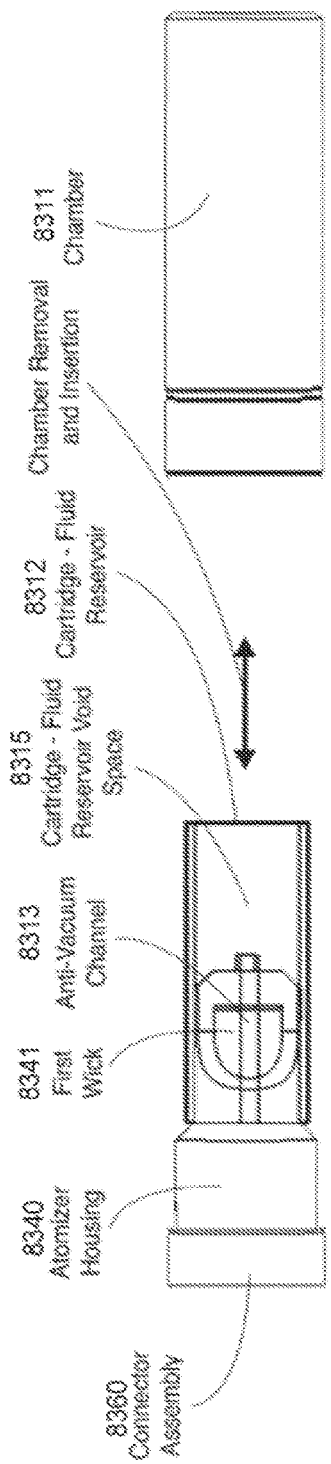
FIG. 105 is a diagram illustrating insertion and removal of a cartridge-atomizer-connector assembly from a distal assembly chamber.

FIG. 105 is a diagram illustrating insertion and removal of a cartridge-atomizer-connector assembly from a proximal assembly chamber. In FIG. 105, an assembly comprising connector assembly 8360, atomizer housing 8340, first wick 8341, anti-vacuum channel 8313, and cartridge liquid reservoir void space 8315, and cartridge liquid reservoir main body 8312 is illustrated as being removed and/or inserted into a cartridge chamber main body 8311.

Figure 106:
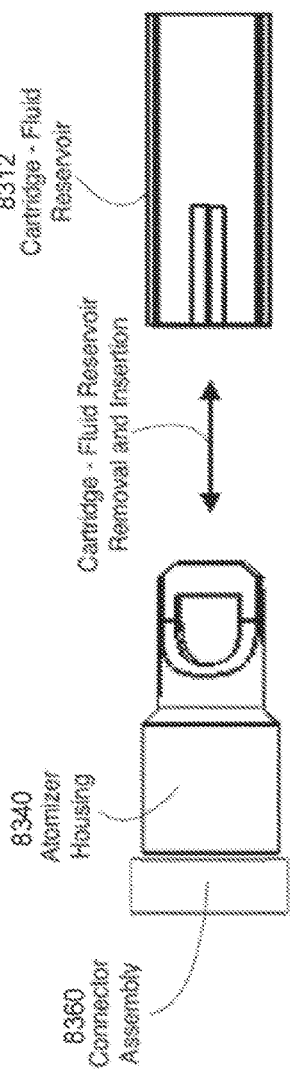
FIG. 106 is a diagram illustrating insertion and removal of a cartridge liquid reservoir from an atomizer-connector assembly.

FIG. 106 is a diagram illustrating insertion and removal of a cartridge liquid reservoir from an atomizer-connector assembly. In FIG. 106, an assembly comprising connector assembly 8360, and atomizer housing 8340 is illustrated as being removed and/or inserted into cartridge liquid reservoir main body 8312.

Figure 107:
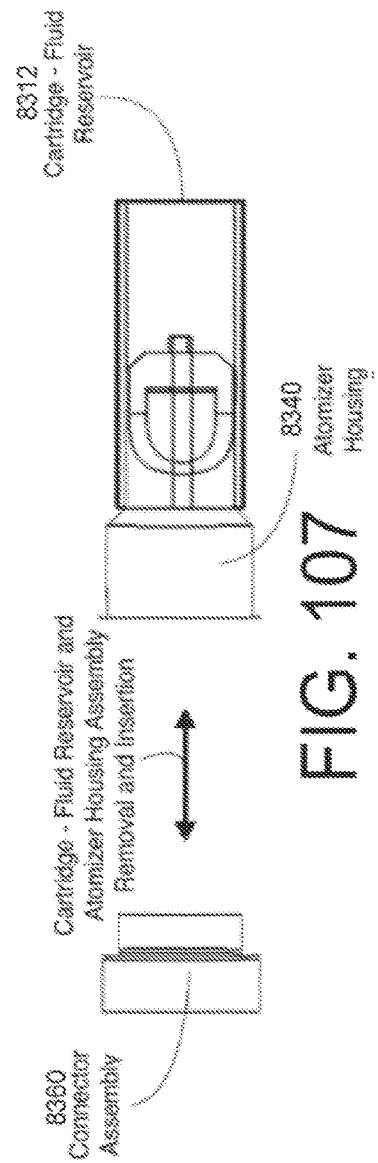
FIG. 107 is a diagram illustrating insertion and removal of a connector assembly from an atomizer-cartridge assembly.

FIG. 107 is a diagram illustrating insertion and removal of a connector assembly from an atomizer-cartridge assembly. In FIG. 107 connector assembly 8360 (which may or may not contain a microprocessor) is illustrated as being removed and/or inserted or otherwise mated with an assembly comprising an atomizer housing 8340 and optionally a cartridge liquid reservoir main body 8312.

The Use of Digital Application(s) for Device Monitoring, Device Control, Data Storage, Data Analysis, Data Transmission, User Support, Social Networking, Usage Information, and Purchasing Data/Metrics The digital applications of a vaporizer device can be used for multiple functions. Exemplary functions are described below. For example, the use of the onboard CPU/PCB and data gathering, data analysis, and data transmission methods are used to interface with digital consumer technology products such as smart phones, tablet computers, lap top/netbook/desktop computers, wearable wireless technologies such as "smart watches," and other wearable technology such as Google "Glass" or similar through the use of programming, software and GUI, general and commonly referred to as application(s) or "apps" and referred to in this section as application(s).

Wired means may be used for a connection to interface the device and device active case to digital consumer technology products for the purpose of the transmission and exchange of data from the device and device active case to the digital consumer technology products and vice-versa. Likewise, wireless means may be used for the connection to interface the device and device active case to digital consumer technology products for the purpose of the transmission and exchange of data from the device and device active case to the digital consumer technology products and vice-versa. Wireless means for connection may include Wi-Fi, Bluetooth, infrared or similar to interface the device and device active case to digital consumer technology products for the purpose of the transmission and exchange of data from the digital consumer technology products to device and device active case.

Wired or wireless means of connection may be used from the digital consumer technology products to device and device active case as a means of relaying information and data to add additional functionality to the vaporizer. Examples of the functionality are described below. Those examples may include various means for user control of the functionality, features, configurations and similar of the device and associated application through the use of various features of the application referred to as application configurations or "settings" and referred to subsequently as setting. The examples include:

1. General Usage Features and Capabilities Such As:
    a) The device and associated application having the capability for a desired number of activations cycles over a period of time.
    b) The device and associated application having the capability for setting reminders, alarms, or similar to notify the user.
    c) The device and associated application having the capability for desired dose delivery of active substance(s) per inhalation.
    d) The device and associated application having the capability for desired total delivered dose active substance(s) over a period of time such as a total daily dose.
    e) The device and associated application having the capability for power settings of the device to modulate the vapor or aerosol strength, vapor or aerosol density, vapor or aerosol volume, vapor or aerosol flavor, vapor or aerosol temperature or similar vapor or aerosol characteristics of the vapor or aerosol generated by the device. The power settings could modulate or configure the activation energy delivered to the heating element(s) as well as modulating or configuring the parameters of the heating element(s) being energized in relation to the time to peak activation or "warm up" or "ramp" and or the time of maximum or peak activation, and or the time of the heating element being deactivated or the "cool down" to effect and modulate the vapor or aerosol strength, vapor or aerosol density, vapor or aerosol volume, vapor or aerosol flavor, vapor or aerosol temperature or similar characteristics of the vapor or aerosol generated by the device.
    f) The device and associated application having the capability for power settings of the device to modulate, adjust, configure or similar the settings of the device as they relate to battery life and performance such that the user can make setting adjustment to the device to maximize battery life and the device will resultantly operate at lower energy output to preserve the maximum number of cycles that be sustained per battery charge cycle. Conversely the user could modulate, adjust, configure or similar the settings of the device to maximize performance in relation to the energy output of the device per cycle.
    g) The device and associated application having the capability related to the liquid components and formulation or similar such that the information relating to the liquid to be vaporized or aerosolized can have predetermined as well as user configurable settings to modulate, configure, adjust or similar the device activation parameters.
    h) The device and associated application having the capability related to user specific environmental configurations such as cold weather or warm weather settings such that the device optimizes heating element activation and activation parameters to optimize performance based on ambient temperature.

i) The device and associated application having the capability related to user specific environmental configurations such as high or low humidity settings such that the device optimizes heating element activation and activation parameters to optimize performance based on user locale humidity values or ranges.

j) The device and associated application having the capability related to user specific environmental configurations such as user locale altitude settings such that the device optimizes heating element activation and activation parameters to optimize performance based on end user altitude.

k) The device and associated application having the capability related to user specific temporal configurations such as the user preferring higher active component delivery per inhalation at specific times of the day. For example the device configure such that it delivers higher dosage of active component related to a time of day such that the dosage delivered to the user is highest, or at maximum value or similar in the morning and tapers down to a lower delivered dose per inhalation, or minimum value, or similar at the end of the evening. This is an example of the configurability of the device and the user could program the settings based on personal preference.

l) The device and associated application having the capability related to modulating the device performance and activation parameters to minimize or maximize the functional effects of the taste or flavor component of the vapor product such that the device can be configured to activate in such a way that the flavor delivered from the vapor or aerosol is minimized or maximized. For example components of the liquid being vaporized that may contribute to the flavor characteristics of the vapor or aerosol may be more profound, or more prevalent, or more substantial when the device is activated with higher temperature ranges being generated by the heating element then when lower temperature ranges are being generated by the heating element within the range of temperatures that the heating element may operate within in order to generate a vapor or aerosol for inhalation by the user. For example the user may set the device to perform for maximal, minimal, moderate, or another interim value of flavor for the vapor or aerosol product and the heating element activation cycle will be modulated accordingly.

m) The device and associated application having the capability related to modulating the device performance and activation parameters to minimize or maximize the functional effects related to pharmacodynamics and pharmacokinetics of the active or drug component of the vapor or aerosol product such that the device can be configured to activate in such a way that the active component or drug delivered from the vapor or aerosol is minimized or maximized in terms of target tissue or organ delivery. For example active components or drug(s) in the liquid formulation being vaporized will be absorbed into the blood stream at different rates depending on the target tissue or organ. For example active component(s) or drug(s) in the vapor having small particle size of less than 10 microns may be readily absorbed into systemic circulation through the pulmonary vasculature, as is well documented in the literature. However active component(s) or drug(s) in the vapor having small particle size of greater than 10 microns may be absorbed more preferentially through the mucosal surface of the oral and pharyngeal cavities and mucosal absorption is slower to reach the systemic circulation then is the delivery of a drug or similar to the systemic circulation through the pulmonary vasculature. To continue the example, a user may be using the device for the delivery of nicotine as the active or drug component in the vapor or aerosol and it may be desirable for the user to have the option to have more rapid delivery of the nicotine to the bloodstream, such as after a period of time of not having nicotine such that the user's urge or craving is elevated. Alternatively, at times it may be desirable for the user to have a slower absorption of nicotine into the blood stream such as at times when the users craving or urge is low, or at times when the user wants to have a more prolonged period of time before they have the urge or craving for nicotine such as prior to going to sleep, or an event where they will be unable to use the device for dosing or administration of the nicotine. The device settings relating to the activation of the device and the temperature of the heating element and heating element activation characteristics may be modulated such that for example at lower temperature activation the particle size of the drug component is larger than when at higher temperature activation of the heating element. Thus by modulating the input of thermal or heat energy inputted into the vaporization chamber by the heating element to volatize or vaporize the liquid containing the active component(s) or drug(s) the characteristics of the vapor or aerosol in relation to the particle size of the active component(s) or drug(s) can be wholly or partially modulated by the user. These settings could also be used by the end user or healthcare provider or similar to reduce dependence on the active component(s) or drug(s) such as nicotine, for example, by initially using the device configured to maximize pulmonary deliver of the nicotine and then transition to device settings that maximize mucosal delivery of the nicotine as a means to facilitate reducing nicotine dependence and could be used in conjunction with nicotine dosage reduction as a means of reducing or mitigating the users nicotine dependence or addiction.

n) The device and associated application having the capability for device alerts and notifications such as battery life status and battery condition(s) data such as number of battery cycles and battery "health" such that the user can be notified as desired to the current meaning "real time" and overall condition of the devices internal battery, and the devices charging case internal battery.

o) The device and associated application having the capability for device alerts and notifications such as the device battery requiring recharging.

p) The device and associated application having the capability for device alerts and notifications such as the device active case battery requiring recharging.

q) The device and associated application having the capability for device alerts and notifications such as the device battery being fully charged.

r) The device and associated application having the capability for device alerts and notifications such as the device active case battery being fully charged.

s) The device and associated application having the capability for device alerts and notifications such as liquid cartridge status, such as number of usages or inhalations taken.
t) The device and associated application having the capability for device alerts and notifications such as liquid cartridge status, such as number of usages or inhalations remaining.
u) The device and associated application having the capability for device alerts and notifications such as liquid cartridge status, such as number of usages or inhalations taken over a preset or predetermined period of time, for example number of usages or inhalations taken per day.
v) The device and associated application having the capability for device alerts and notifications such as liquid cartridge contents, such as active component(s) and strength or dosage or similar, and flavor profile or similar, and general formulation or similar.
w) The device and associated application having the capability for device alerts and notifications such as liquid cartridge or the liquid cartridge assembly, or similar requiring replacement.
x) The device and associated application having the capability for device alerts and notifications such as predetermined or preset times for usage of the device.
y) The device and associated application having the capability for device alerts and notifications such as device heating element status or "health" such as number of cycles performed and number of cycles remaining before suggested or required replacement of heating element or heating element assembly.
2. Device Manufacturer Data sharing capabilities such as:
a) The device and associated application having the capability for gathering, receiving, logging, storing, transmission, extrapolation or similar of anonymous or user specific usage data such as frequency of use.
b) The device and associated application having the capability for gathering, receiving, logging, storing, transmission, extrapolation or similar anonymous or user specific usage data such as activation cycle characteristics such as duration of activations and user specified activation settings if applicable.
c) The device and associated application having the capability for gathering, receiving, logging, storing, transmission, extrapolation or similar user specific data such as demographic information.
d) The device and associated application having the capability for gathering, receiving, logging, storing, transmission, extrapolation or similar user specific data such as socioeconomic information.
e) The device and associated application having the capability for gathering, receiving, logging, storing, transmission, extrapolation or similar user specific data such as user feedback through the use of surveys or similar.
f) The device and associated application having the capability for gathering, receiving, logging, storing, transmission, extrapolation or similar anonymous or user specific usage data such device errors or malfunctions.
g) The device and associated application having the capability for gathering, receiving, logging, storing, transmission, extrapolation or similar user specific data such as requests for warranty services or repairs or replacements or similar.
h) The device and associated application having the capability for gathering, receiving, logging, storing, transmission, extrapolation or similar user specific data such as requests for technical support.
i) The device and associated application having the capability for gathering, receiving, logging, storing, transmission, extrapolation or similar user specific data such as requests for product information.
j) The device and associated application having the capability for gathering, receiving, logging, storing, transmission, extrapolation or similar user specific data such as requests for usage instructions.
k) The device and associated application having the capability for gathering, receiving, logging, storing, transmission, extrapolation or similar user specific data such as requests for information on product features or functions.
l) The device and associated application having the capability for gathering, receiving, logging, storing, transmission, extrapolation or similar user specific data such as requests for information on purchasing product or acquiring the product through a prescription from a physician or healthcare provider.
m) The device and associated application having the capability for gathering, receiving, logging, storing, transmission, extrapolation or similar device data indicating misuse or abuse of the device.
n) The device and associated application having the capability for gathering, receiving, logging, storing, transmission, extrapolation or similar device data and data transmission features used to locate the device if the device is lost or stolen.
o) The device and associated application having the capability for gathering, receiving, logging, storing, transmission, extrapolation or similar notifications to the user through the device or application(s) relating to product recall(s) or similar issues.
p) The device and associated application having the capability for gathering, receiving, logging, storing, transmission, extrapolation or similar general data sharing to manufacture terms and conditions recognition and user agreement to said terms.
3. User, Usage, System, Device, and Operational Data sharing settings such as:
a) The device and associated application having the capability for relating to selecting and authorizing the sharing of all or some of the data gathering, receiving, logging, storing, transmission, extrapolation or similar by the device or gathered directly from the user through the use of an application(s) to a network(s).
b) Where network(s) may be partially or wholly social media.
c) Where network(s) may be comprised partially or wholly of the users family and or friends.
d) Where network(s) may be comprised of partially or wholly a support group or similar.
e) The device and associated application having the capability relating to the gathering, receiving, logging, storing, transmission, extrapolation of data over a network(s) that may be used to identify, contact, or connect with other users of the device.
f) Where other network(s) may be a third party service, company, organization or similar.
4. Capabilities Relating to Software configuration and firmware updating:
a) The device and associated application having the capability for relating to the sharing, transmission, gathering, receiving, logging, storing, extrapolation of data or similar required or useful to perform software configuration of the device and or the device application(s).

b) The device and associated application having the capability for relating to the sharing, transmission, gathering, receiving, logging, storing, extrapolation of data or similar of data required to perform software configuration of the device and or the device application(s) where the software is configured by the manufacturer or manufacturers subsidiary or representatives or third party or similar.

c) The device and associated application having the capability for relating to the sharing, transmission, gathering, receiving, logging, storing, extrapolation of data or similar of data required to perform software configuration of the device and or the device application(s) where the software is configured by the a third party.

d) The device and associated application having the capability for relating to the authorization for the sharing, transmission, gathering, receiving, logging, storing, extrapolation of data or similar of data required to perform firmware or similar updates to the device and or application.

e) The device and associated application having the capability for relating to the notification of the user through the device or application(s) that a firmware or similar updates to the device and or application(s) is available and or required.

f) The device and associated application having the capability for relating to the notification of the user through the device or application(s) that a firmware or similar updates to the device and or application(s) is available and or required as a means of trouble shooting the device or remediating a problem or issue with the device or application(s) preventing some aspect of intended or proper function(s).

g) The device and associated application having the capability for relating to the notification of the user through the device or application(s) that a firmware or similar updates to the device and or application(s) is available and or required as a means of providing additional functions relating to or intended to improved device performance, enhance user experiences, or similarly improve some aspect of intended or proper function(s).

5. Healthcare system data sharing such as:

a) The device and associated application having the capability for relating to the sharing, transmission, gathering, receiving, logging, storing, extrapolation of data or similar of all or some of the data gathered by the device or gathered directly from the user through the use of application(s) to the users healthcare provider.

b) The device and associated application having the capability for relating to the sharing, transmission, gathering, receiving, logging, storing, extrapolation of data or similar of all or some of the data gathered by the device or gathered directly from the user through the use of application(s) to the users healthcare network.

c) The device and associated application having the capability for relating to the sharing, transmission, gathering, receiving, logging, storing, extrapolation of data or similar of all or some of the data gathered by the device or gathered directly from the user through the use of application(s) to the users insurance provider.

d) The device and associated application having the capability for relating to the sharing, transmission, gathering, receiving, logging, storing, extrapolation of data or similar of all or some of the data gathered by the device or gathered directly from the user through the use of application(s) to the users pharmacy or prescription drug provider or similar.

e) The device and associated application having the capability for relating to the notification of the availability of a prescription issued or written for the end user being ready for pick-up, delivery, shipment to the user or similar of a prescription component intended for delivery to the patient by the device. For example, a pharmacy could send a notification to the user, through the device application, such as to notify the user that their prescription for the device or device components is available for the user to pick up from the pharmacy.

f) The device and associated application having the capability for relating to the authorization of a healthcare provider to configure, adjust, modulate, manipulate or similar the device settings.

g) The device and associated application having the capability for relating to the authorization of a healthcare provider to configure, adjust, modulate, manipulate or similar the device settings where the user is not authorized to change, alter, reconfigure or similar the settings, configurations, or similar made by the healthcare provider.

h) The device and associated application having the capability for authorizing a representative or agent or similar of the healthcare provider to configure, adjust, modulate, manipulate or similar the device settings where the user is not authorized to change, alter, reconfigure or similar the settings, configurations, or similar made by the healthcare representative or agent or similar.

i) The device and associated application having the capability for allowing for data sharing, transmission, gathering, receiving, logging, storing, extrapolation of data or similar with the healthcare provider or network to be depersonalized or otherwise made anonymous and used for other purposes such as research, analysis, publication, or similar purposes.

j) The device and associated application having the capability for allowing for healthcare providers, networks, agents, authorized third parties or similar to send alerts, messages, surveys, or similar through the device application(s).

k) The device and associated application having the capability for allowing for healthcare providers, networks, agents, authorized third parties or similar to access data that is generated as a result of surveys, or similar through the device application(s).

6. Device Capabilities Relating to Retailer, Consumer Facing Data Such as:

a) The device and associated application having the capability relating to the sharing, transmission, gathering, receiving, logging, storing, extrapolation of data or similar user specific information such as end user ownership of products relating to the device, device components, device accessories or similar.

b) The device and associated application having the capability relating to the sharing, transmission, gathering, receiving, logging, storing, extrapolation of data or similar user specific information such as end user purchasing of products relating to the device, device components, device accessories or similar.

c) The device and associated application having the capability for gathering, receiving, logging, storing, transmission, extrapolation or similar of notifications from retailer(s) or similar regarding product promotions.
d) The device and associated application having the capability for gathering, receiving, logging, storing, transmission, extrapolation or similar of notifications from retailer(s) or similar regarding product availability.
e) The device and associated application having the capability for gathering, receiving, logging, storing, transmission, extrapolation or similar of notifications from retailer(s) or similar regarding release of new product or accessories.
f) The device and associated application having the capability to use demographic or similar location services to find retail locations in geographic proximity of the user.
g) The device and associated application having the capability for the gathering, receiving, logging, storing, transmission, extrapolation or similar of data that may be used for demographic, socioeconomic, or similar marketing or promotional activities.
h) The device and associated application having the capability for the gathering, receiving, logging, storing, transmission, extrapolation or similar of data relating to device purchasing, device accessories purchasing, vaporizer liquid and associated packaging or assembly purchasing, frequency of purchasing, point of sale, discounts applied by user when purchasing, and related or similar information.
i) The device and associated application having the capability for gathering, receiving, logging, storing, transmission, extrapolation or similar of data relating to device purchasing, device accessories purchasing, vaporizer liquid and associated packaging or assembly purchasing, frequency of purchasing, point of sale, discounts applied, and related or similar information.
j) The device and associated application having the capability for the use of the application to provide incentives to the user to share information relating to device purchasing, device accessories purchasing, vaporizer liquid and associated packaging or assembly purchasing, frequency of purchasing, point of sale, discounts applied and related information such as discounts, coupons, promotional codes, free items, or similar.
k) The device and associated application having the capability for the use of the user profile to provide targeted incentives to the user to share information relating to device purchasing, device accessories purchasing, vaporizer liquid and associated packaging or assembly purchasing, frequency of purchasing, point of sale, discounts applied, promotional codes used, and related information such as discounts, coupons, free items, or similar.

7. Device Access Capabilities such as:
a) The device and associated application having the capability for rendering the device inactive and unable to be used.
b) The device and associated application having the capability for rendering the device inactive and unable to be used if a malfunction or similar has occurred.
c) The device and associated application having the capability for rendering the device inactive and unable to be used where the authorized user has a Personal Identification Number (PIN) that when entered using the application activates the device.
d) The device and associated application having the capability to rendering the device inactive and unable to be used where the authorized user has a biometric identifier that when recognized or confirmed or verified or similar using the application activates the device.
e) The device and associated application having the capability for rendering the device inactive and unable to be used where the authorized user has a biometric identifier that when recognized or confirmed or verified using the application activates the device where the biometric identifier is a fingerprint.
f) The device and associated application having the capability for rendering the device inactive and unable to be used where the authorized user has a biometric identifier that when recognized or confirmed or verified using the application activates the device where the biometric identifier is an eye or iris or similar scan.
g) The device and associated application having the capability for rendering the device inactive and unable to be used where the authorized user has a biometric identifier that when recognized or confirmed or verified using the application activates the device where the biometric identifier is facial recognition.
h) The device and associated application having the capability for where the unauthorized use of the device is prevented by using PIN or unique biometric identifier.
i) The device and associated application having the capability for the sharing of data relating to the attempted unauthorized use of the device.
j) The device and associated application having the capability for the sharing of data over a network to authorize the user and activate the device.
k) The device and associated application having the capability for sharing of data such that biometric authentication can be performed through the use of a network.
l) The device and associated application having the capability for the time or duration of time that passes after use before the device is rendered inactive and authentication is required to authorize the device.

8. Capabilities for Multiple User Settings such as:
a) The device and associated application having the capability for device data and personal settings to be saved for individual users where more than one user may use the device.
b) The device and associated application having the capability for device data and personal settings to be saved for individual users where the settings for device data and personal settings for different users can be applied to a device and the intended user through the application and the user may select their saved configurations for the device and the device will operate under that user selected configuration.
c) The device and associated application having the capability for the user or users to have one or a plurality of user setting(s) configuration(s) that is saved and can be selected by the user(s).
d) The device and associated application having the capability for allowing saved user settings such that their personal setting(s) configuration(s) may be shared by the user through the application and associated network.
e) The device and associated application having the capability for allowing other user setting(s) configuration(s) to be shared with the user through the application or associated network.
f) The device and associated application having the capability for allowing, facilitating, prompting, or similar the user to rate (such as through common methods such a 1-10 where "10" is the best, or 1-5 "stars" where "5" stars is the best) of their user configuration(s).

g) The device and associated application having the capability for allowing, facilitating, prompting, or similar the user to rate (such as through common methods such a 1-10 where "10" is the best, or 1-5 "stars" where "5" stars is the best) of other users configuration(s).

h) The device and associated application having the capability for sharing and accessing a data base of user configurations that may or may not have ratings and a being able to access the user configurations through the application and download user configurations for use in the users own device(s).

i) The device and associated application having the capability for sharing and accessing a data base of user configurations that may or may not have ratings and a being able to access the user configurations through the application and uploading their user configurations for use in other users own device(s).

9. Capabilities for Defined User Profiles such as:

a) The device and associated application having the capability for the gathering, receiving, logging, storing, transmission, extrapolation of user data to the manufacturer, manufacturers subsidiaries, manufactures agents, or a third party for the purpose of generating user profiles based on user specific usage data, demographic data, socioeconomic data or similar.

b) The device and associated application having the capability for use of user data shared with or sent to the manufacturer, manufacturers subsidiaries, manufactures agents, or a third party for the purpose of generating user profiles based on user specific usage data, demographic data, socioeconomic data or similar is utilized to determine specific user profiles.

10. Capabilities Relating to the Integration with Other Application(s):

a) The device and associated application having the capability to allow, facilitate, authorize, confirm or similar the sharing of data between the device application and other application(s) that may be installed or a component of the users personal digital device.

b) The device and associated application having the capability where other application(s) that the device application shares information with may be social media application(s).

c) The device and associated application having the capability where other application(s) that the device application shares information with may be email service, email provider, email hosting, or similar application(s).

d) The device and associated application having the capability where other application(s) that the device application shares information with may be text message, SMS, or similar application(s).

e) The device and associated application having the capability where other application(s) that the device application shares information with may be location services application(s).

f) The device and associated application having the capability where other application(s) that the device application shares information with may be map or mapping, navigation, location or similar application(s).

g) The device and associated application having the capability where other application(s) that the device application shares information with may be healthcare, healthcare provider, healthcare services, healthcare network or similar application(s).

h) The device and associated application having the capability where other application(s) that the device application shares information with may be pharmacy, or pharmacy type service provider or similar application(s).

i) The device and associated application having the capability where other application(s) that the device application shares information with may be weather, or weather forecasting, or weather reporting or similar application(s).

j) The device and associated application having the capability where other application(s) that the device application shares information with may be the device manufacturer's application(s).

k) The device and associated application having the capability where other application(s) that the device application shares information with may be research or research orientated application(s).

l) The device and associated application having the capability where other application(s) that the device application shares information with may be device retailer or similar consumer device application(s).

11. Capabilities relating to the Generation of Error Codes and Trouble Shooting:

a) The device and associated application having the capability relating to the authorization or allowance of data gathering, receiving, logging, storing, transmission, extrapolation or similar for the purpose of the device or device application sending error codes or error reports to the manufacturer, manufacturers subsidiaries, manufactures agents, or a third party for the purpose of addressing problems with device performance or function.

b) The device and associated application having the capability relating to the authorization or allowance of data gathering, receiving, logging, storing, transmission, extrapolation or similar for the purpose of the device or device application sending error codes or error reports to the manufacturer, manufacturers subsidiaries, manufactures agents, or a third party for the purpose of addressing problems with device application(s).

c) The device and associated application having the capability relating to the authorization or allowance of data gathering, receiving, logging, storing, transmission, extrapolation or similar for the purpose of the device or device application sending error codes or error reports to the manufacturer, manufacturers subsidiaries, manufactures agents, or a third party for the purpose of extrapolating data metrics that relate to device malfunctioning.

d) The device and associated application having the capability relating to the authorization or allowance of data gathering, receiving, logging, storing, transmission, extrapolation or similar for the purpose of the device or device application sending error codes or error reports to the manufacturer, manufacturers subsidiaries, manufactures agents, or a third party for the purpose of gathering, receiving, logging, storing, transmission, extrapolation or similar data that may relate to manufacturing, or quality control or similar issues or potential problems related to the device, device components, or liquid being used in the device.

e) The device and associated application having the capability relating to the gathering, receiving, logging, storing, transmission, extrapolation or similar of data for the purpose of troubleshooting device issues or problems.

f) The device and associated application having the capability relating to the gathering, receiving, logging, storing, transmission, extrapolation or similar of data for the purpose of troubleshooting device issues or problems that may relate to user error.

12. Capabilities Relating to Methods of Communication:

a) The device and associated application having the capability relating to the device or device application using methods of data transmission such as wireless and wired technologies.

b) The device and associated application having the capability relating to the device or device application using methods of data transmission such as Wi-Fi, Bluetooth, or similar for the transmission of data to the users personal digital device.

c) The device and associated application having the capability relating to the device or device application using methods of data transmission such as wired or wireless methods or similar for the transmission of data to a network.

d) The device and associated application having the capability relating to the device or device application using methods of data transmission such as text messaging or SMS.

e) The device and associated application having the capability relating to the device or device application using methods of data transmission such as electronic mail or email.

f) The device and associated application having the capability relating to the device or device application using methods of data transmission such as notifications or push notifications on the users' digital device.

The application may provide an authentication process to activate the device. The application may provide an authentication process to activate the device that verifies the users age at or prior to establishing a unique identification profile for the end user to prevent unintended use or abuse of the device by minors. User demographic, socioeconomic, and device usage data may establish a user profile. Pooled user profiles can establish a starting configuration of device settings for a new user based on pooled data on usage and settings of similar users based wholly or partially on demographic, socioeconomic, and device usage data. The application can provide information to the user on the operation of the device. The application can provide the user with information on how to configure, adjust, modulate, modify, or similar the device settings. The application can provide information on trouble shooting the device in the event of a performance issue or malfunction. The application can provide safety information relating to the device to the user. The application can provide safety information relating to the maintenance, cleaning, or similar activities for the device. The application can provide storage information for the device. The application can provide information relating to the disposal or recycling of the device. The application can provide information on the proper disassembly and assembly of the device. The application can provide information such as the manufacturers, distributors, retailers, or similar website and or contact information. The application can provide information such as a website URL or link for internet forums that may relate to the use, troubleshooting, user experience, user reviews or similar. The application can provide safety information relating to the device to the user. The application can provide information on available products, accessories, or similar that may be related to the device. The application can provide a space for advertising consumer products or services that may be related to the device. The application can provide functions relating to personal user goals for device usage and to track usage as it relates to the users defined goals and to prevent the data in the forms of charts, graphs, or similar.

Figure 108:
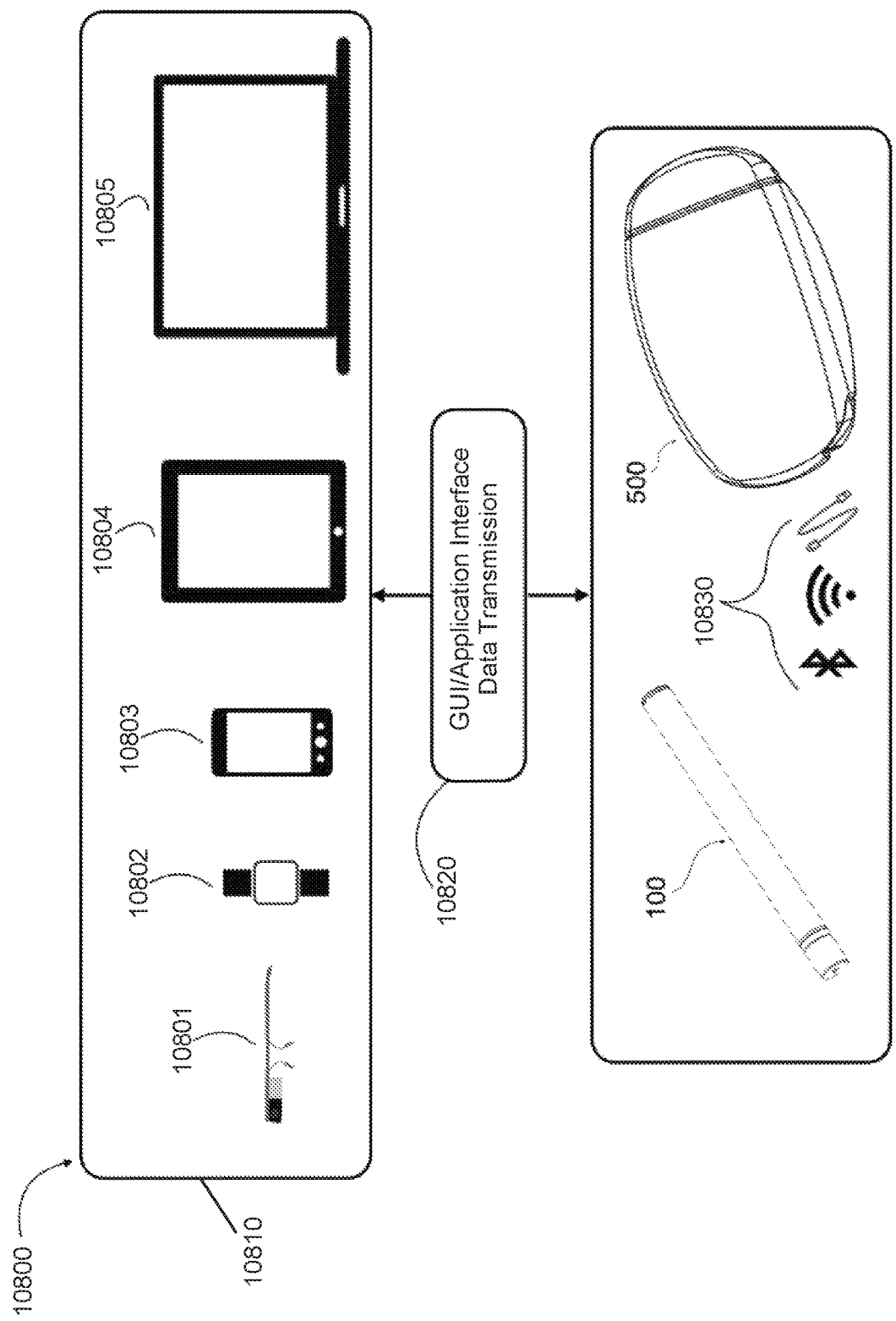
FIG. 108 illustrates a system including a personal vaporizer unit and common consumer digital products that can communicate and share data with the device.

FIG. 108 illustrates a device and common consumer digital products that can communicate and share data with the device. FIG. 108 illustrates the basic relationship between common personal digital devices such as wearable wireless devices such as smart watches, wearable digital devices or similar, smart phones, tablet computers, and laptop or desktop computers and the device and device active case. The personal digital devices are capable of sharing data with the device and device active case through both wired methods such as data cables or through wireless methods such as Wi-Fi, Bluetooth, cellular networks, IR or similar technologies. Commonly personal digital devices use software configurations collectively or commonly referred to as application(s) or "apps" that use a graphical user interface or GUI to provide a method for the user to interact with the program and software. The basic embodiment allows for the use of a software program with a GUI the "application" that facilitates the transferring of data from the device and device active case to the personal digital device and from the personal digital device to the device and device active case.

According to an embodiment, FIG. 108 illustrates a system including a personal vaporizer unit. In FIG. 108, system 10800 includes at least one personal digital device 10810, a personal vaporizer unit (PVU) 100, case 500, and an associated application 10820. Examples of personal digital devices 10810 are illustrated in FIG. 108 as wearable devices 10801, smart watch 10802, smart phone 10803, tablet computer 10804, and computer 10805. Application 10820 is operatively coupled to interface PVU 100 and/or case 500 with a personal digital device 10810. PVU 100 and/or case 500 may be operatively coupled to a personal digital device 10810 using wireless and/or wired communication 10830. PVU 100 and/or case 500 may be operatively coupled to each other using wireless and/or wired communication 10830.

A personal digital device 10810 is capable of sharing data with PVU 100 and/or case 500 through both wired methods such as data cables, and through wireless methods such as WiFi, Bluetooth, cellular networks, IR or similar technologies. Personal digital devices 10810 may use software (collectively or commonly referred to as applications or "apps") that provide a graphical user interface (GUI)—e.g., application 10820. A GUI may provide a convenient way for the user to interact with application 10820. Application 10820 may facilitate the transferring of data from PVU 100 and/or case 500 to the personal digital device 10810. Application 10820 may facilitate the transferring of data to PVU 100 and/or case 500 from the personal digital device 10810.

Figure 109:
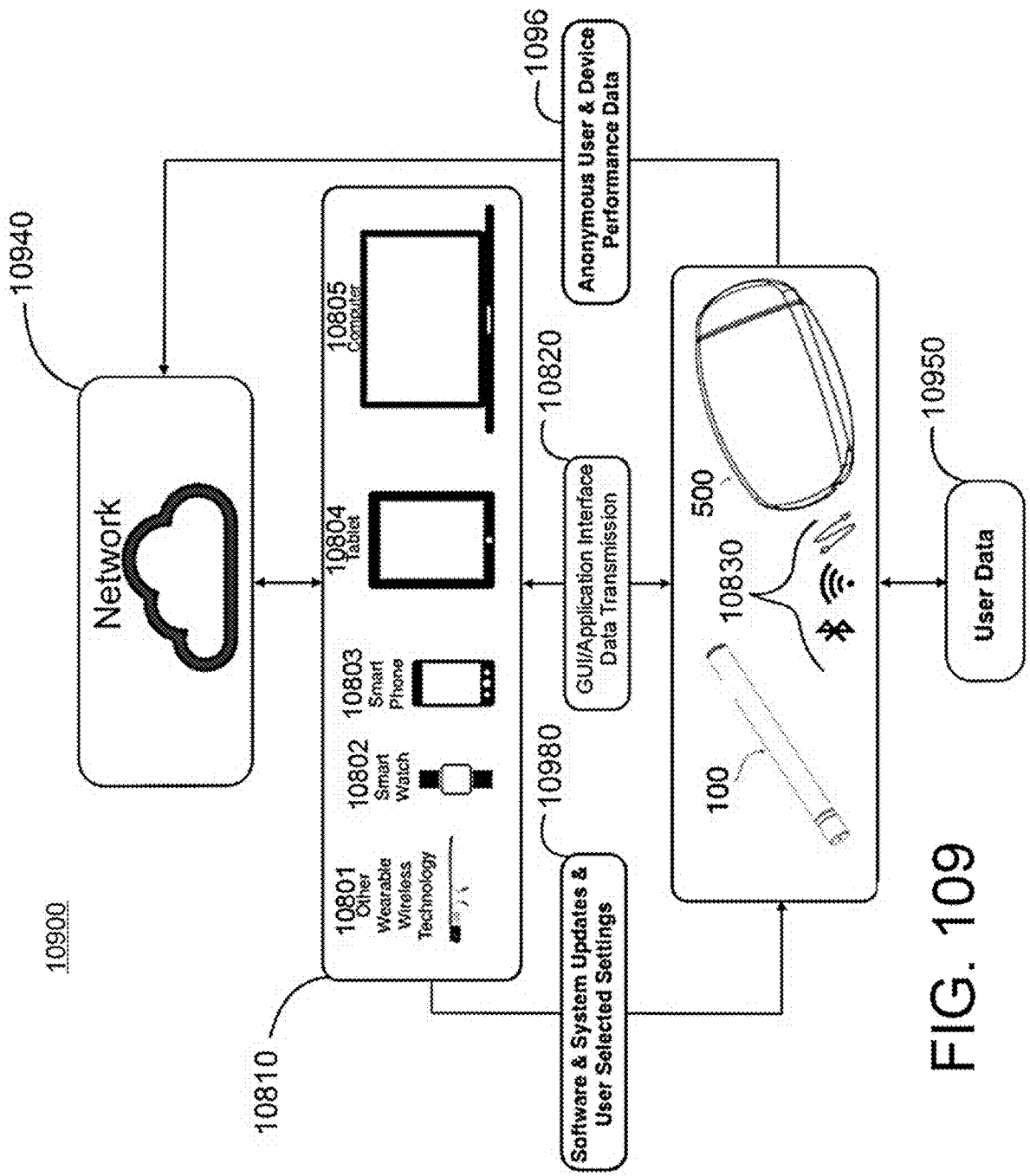
FIG. 109 is an illustration of data flows in a system including a personal vaporizer unit.

FIG. 109 illustrates the flow of data with the vaporizer and an active case connected to a network. FIG. 109 illustrates a general overview of the device and active case interacting in a network directly through the use of onboard wired and wireless data transmitting methods and indirectly through the use of wired and wireless connection methods interfacing through an application running on a personal digital device. In this embodiment some data is shared directly to the network without the use of a personal digital device and some data is shared with the network through the interface with a personal digital device. The types of data shared directly both in relation to data transmitted and data received depends on the embodiment. A personal digital device is not required for the transmission of data to the network or receipt of data from the network. A preferred embodiment uses the interface with a personal digital device as these platforms provide a desirable and common platform for interfacing with the end user.

According to an embodiment, FIG. 109 is an illustration of data flows in a system including a personal vaporizer unit. In FIG. 109, system 10900 includes at least one personal digital device 10810, a personal vaporizer unit (PVU) 100, case 500, an associated application 10820, network 10940, and user data 10950. Examples of personal digital devices 10810 are illustrated in FIG. 109 as wearable devices 10801, smart watch 10802, smart phone 10803, tablet computer 10804, and computer 10805. Application 10820 is operatively coupled to interface PVU 100 and/or case 500 with a personal digital device 10810. PVU 100 and/or case 500 may be operatively coupled to a personal digital device 10810 using wireless and/or wired communication 10830. PVU 100 and/or case 500 may be operatively coupled to a personal digital device 10810 using wireless and/or wired communication 10830 via network 10940. User data 10950 may be operatively coupled to a personal digital device 10810 using wireless and/or wired communication 10830 via PVU 100 and/or case 500 and network 10940. PVU 100 and/or case 500 may be operatively coupled to each other using wireless and/or wired communication 10830.

In an embodiment, PVU 100 and/or case 500 may interact in a network directly by using onboard wired and wireless data transmitting methods. PVU 100 and/or case 500 may interact in a network indirectly through the use of wired and wireless connection methods that interfacing via an application 10820 running on a personal digital device 10810. Some data (e.g., anonymous user and device performance data 10960) may be shared directly to network 10940 without the use of personal digital device 10810. Some data may be shared with network 10940 through application 10820 running on a personal digital device 10810. The types of data shared directly both in relation to data transmitted and data received depends on the configuration of PVU 100, case 500, and/or application 10820. Personal digital device 10810 may not be required for the transmission of data to network 10940 or receipt of data from network 10940 (e.g., software and system updates, user selected settings 10980). Personal digital device 10810 can provide a desirable and common platform (e.g., GUI) for interfacing with the end user.

Figure 110:
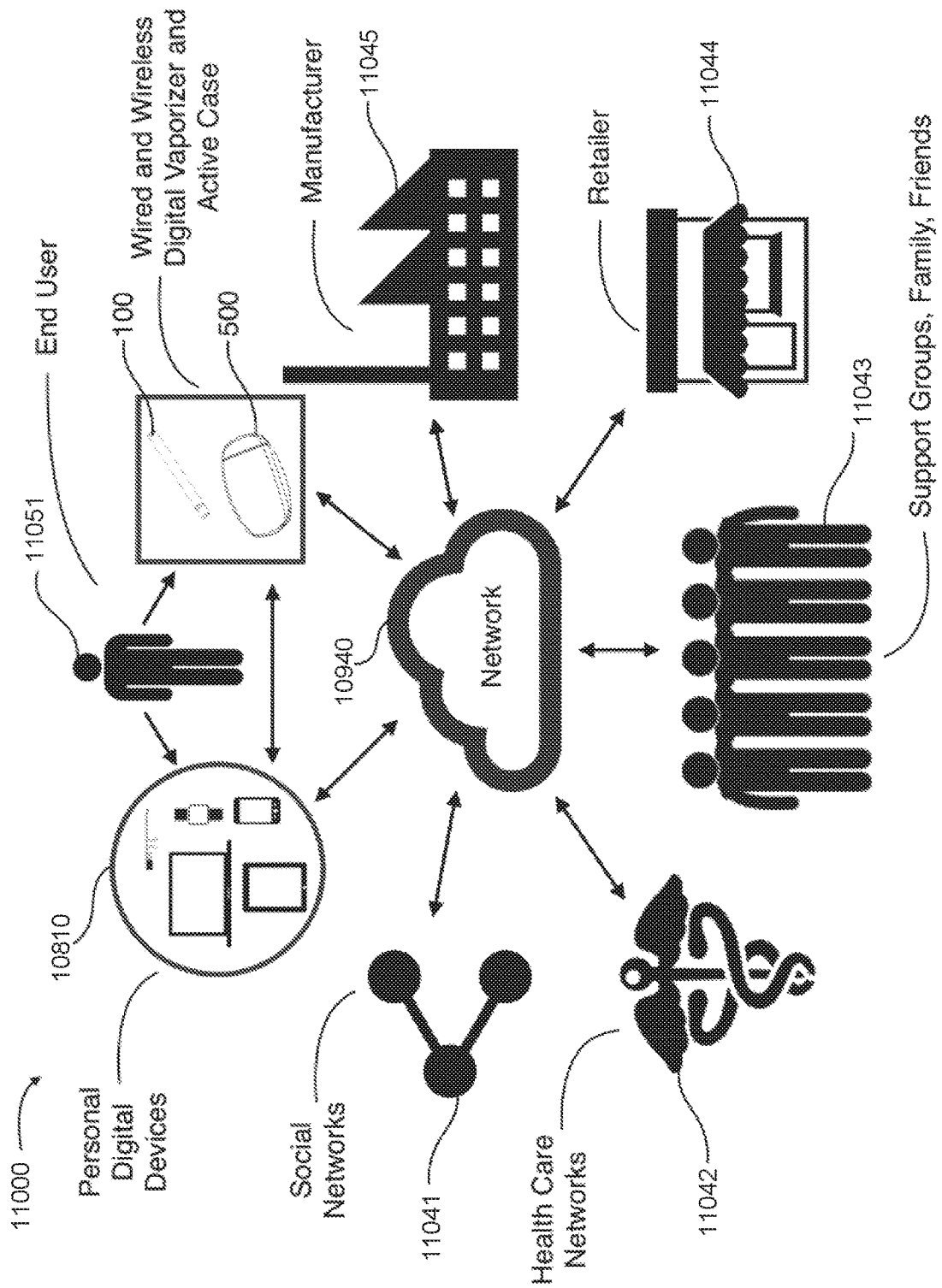
FIG. 110 is an illustration of networks interfacing with a personal vaporizer unit.

FIG. 110 illustrates an integration of the digital vaporizer into a network. FIG. 110 illustrates how the device and device active case integrate into a larger network. Some data will be shared and received directly to and from the network. Other data will be shared with the end users personal digital device(s) through the use of application(s) and then subsequently shared with the network. The end users personal digital device(s) can also be used to share data from the network to the device and device active case. Many different entities may contribute to the network data flow including the end user, the device and device active case, the end users digital devices, social media/networks, healthcare providers and networks, support groups, friends, family, device retailers, and the manufacturer and others may all contribute to the data that shared in the network.

According to an embodiment, FIG. 110 is an illustration of networks interfacing with a personal vaporizer unit. In FIG. 110, system 11000 comprises PVU 100, case 500, network 10940, end user 11051, personal digital device 10810, social network 11041, health care network 11042, social/support group 11043, retailer 11044, and manufacturer 11045. Each of social network 11041, health care network 11042, social/support group 11043, retailer 11044, and manufacturer 11045 can be operatively coupled to PVU 100 and/or case 500. Each of social network 11041, health care network 11042, social/support group 11043, retailer 11044, and manufacturer 11045 can be operatively coupled to PVU 100 and/or case 500 via network 10940. PVU 100 and/or case 500 can be operatively coupled to personal digital device 10810 (or each other) without using network 10940. PVU 100 and/or case 500 can be operatively coupled to personal digital device 10810 (or each other) via network 10940.

In an embodiment, some PVU 100 and/or case 500 data can be sent and received directly to and from network 10940. Some PVU 100 and/or case 500 data can be sent and received directly to and from network 10940 for further communication with social network 11041, health care network 11042, social/support group 11043, retailer 11044, and/or manufacturer 11045. Some data can be shared with the end user's personal digital device 10810 through the use of an application (e.g., application 10820) and then subsequently shared with via network 10940. The end users personal digital device 10810 can also be used to receive data from social network 11041, health care network 11042, social/support group 11043, retailer 11044, and/or manufacturer 11045. This data may be further shared with PVU 100 and/or case 500. Different entities may contribute to network 10940 data flow including end user 11051, PVU 100 and/or case 500, personal digital device 10810, social network 11041, health care network 11042, social/support group 11043, retailer 11044, and/or manufacturer 11045, and others, may each contribute to data that is shared in system 11000.

Figure 111:
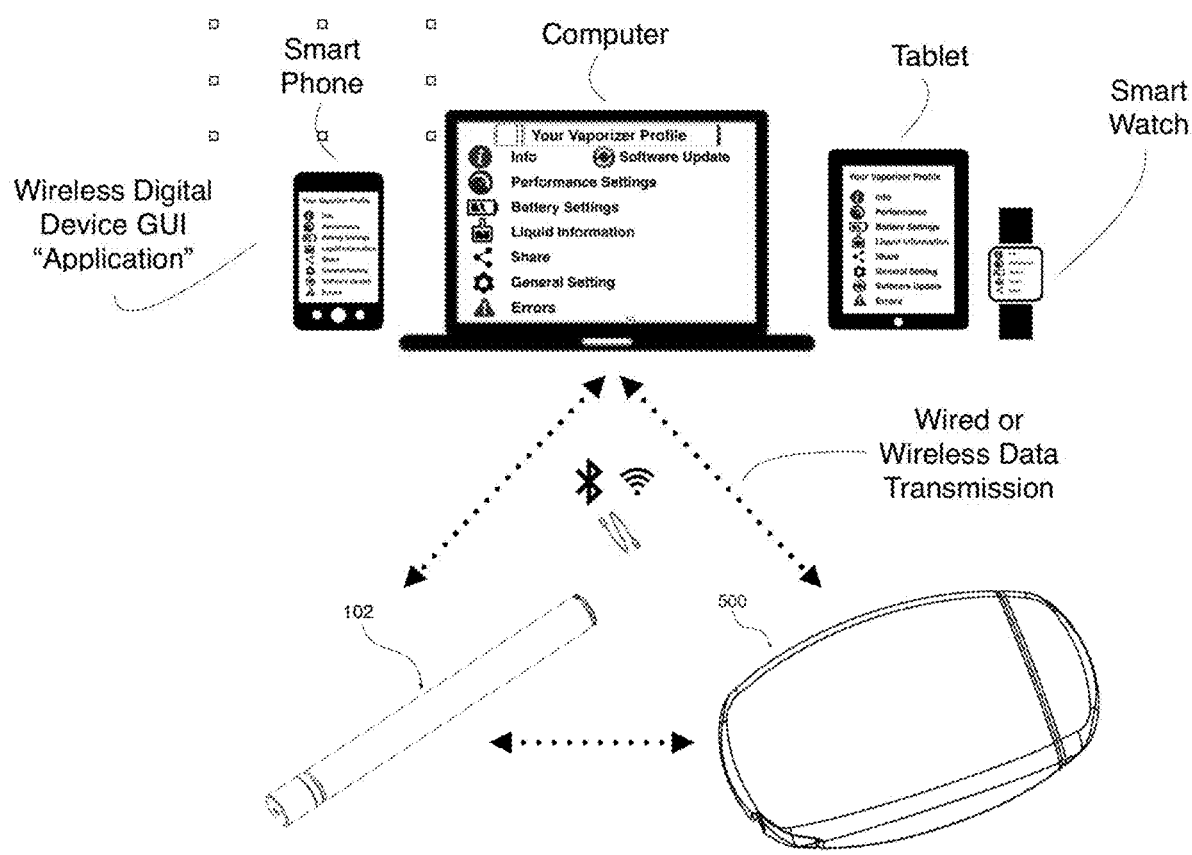
FIG. 111 is an illustration of a data communication system.

FIG. 111 illustrates a data transfer process between the device and personal digital devices interfacing with the application. FIG. 111 illustrates the interaction between the device, device active case, and the end users personal digital devices, which may be a smart phone, computer, tablet or wearable technology such as a smart watch. Other digital devices not shown in figure could also be used in this embodiment provided the device has the capability of transferring and receiving data through the use of wired or wireless methods and has an operating system capable of running application(s). The GUI provides the interface for the end user to engage and interact with the software program, collectively the "application" commonly referred to as "apps" such that the GUI provides a means of navigating the program and using the program features to perform functions related to transmitting data to and from the device. In one embodiment the user will control some aspects of the data transmission and data receiving to and from the device and some data will be transmitted and received as a background operation such that the end user does not have to initiate or authorize the data transmission or receiving process. These background processes of data transmission and receipt can occur whenever the device or device active case is connected to the end users personal digital device either through wireless or wired methods. The GUI as illustrated in the figure demonstrates an embodiment where various icons and text elements inform the user of various ways that the device settings can be adjusted or configured by the user, provides a means for the user to see information about the device such as battery information and similar device status, a means for the user to update the devices internal software sometimes referred to as firmware, allows the user to set security and authorization features of the device such as setting a PIN code to activate the device or the use of personal biometric information as a means of authentication, and a means to configure foregrounds data sharing and related settings. Further details regarding the scope of the application are described in detail in this section.

According to an embodiment, FIG. 111 is an illustration of a data communication system. In FIG. 111, communication system 11100 includes personal digital device 10810, PVU 100, and case 500. PVU 100 may be operatively coupled to personal digital device 10810 using wireless and/or wired communication 10830. Case 500 may be operatively coupled to personal digital device 10810 using wireless and/or wired communication 10830. PVU 100 may be operatively coupled to case 500 using wireless and/or wired communication 10830.

In an embodiment, an application (e.g., application 10820) running on personal digital device 10810 provides an interface for the end user to engage and interact with functions related to communication of data to and from PVU 100 and/or case 500. In an embodiment, a user can control some aspects of the data transmission and data receiving to and from PVU 100 and/or case 500. Some data can be communicated as a background operation such that the end user does not have to initiate or authorize the data communication process.

Background processes of data communication can occur whenever a respective PVU 100 and/or case 500 is operatively coupled to the end users personal digital device 10810 (either through wireless or wired methods.) Various icons and text elements may inform the user of various ways that PVU 100 and/or case 500 settings can be adjusted or configured by the user. Various icons and text elements can provide a means for the user to see information about PVU 100 and/or case 500—such as battery information and similar device status. Various icons and text elements can provide a means for the user to update PVU 100 and/or case 500 internal software (a.k.a., firmware). Various icons and text elements can provide a means for the user to set security and/or authorization features of PVU 100 and/or case 500—such as setting a PIN code to activate the device or the use of personal biometric information as a means of authentication. Various icons and text elements can provide a means to configure foreground data sharing and related settings.

Figure 112:
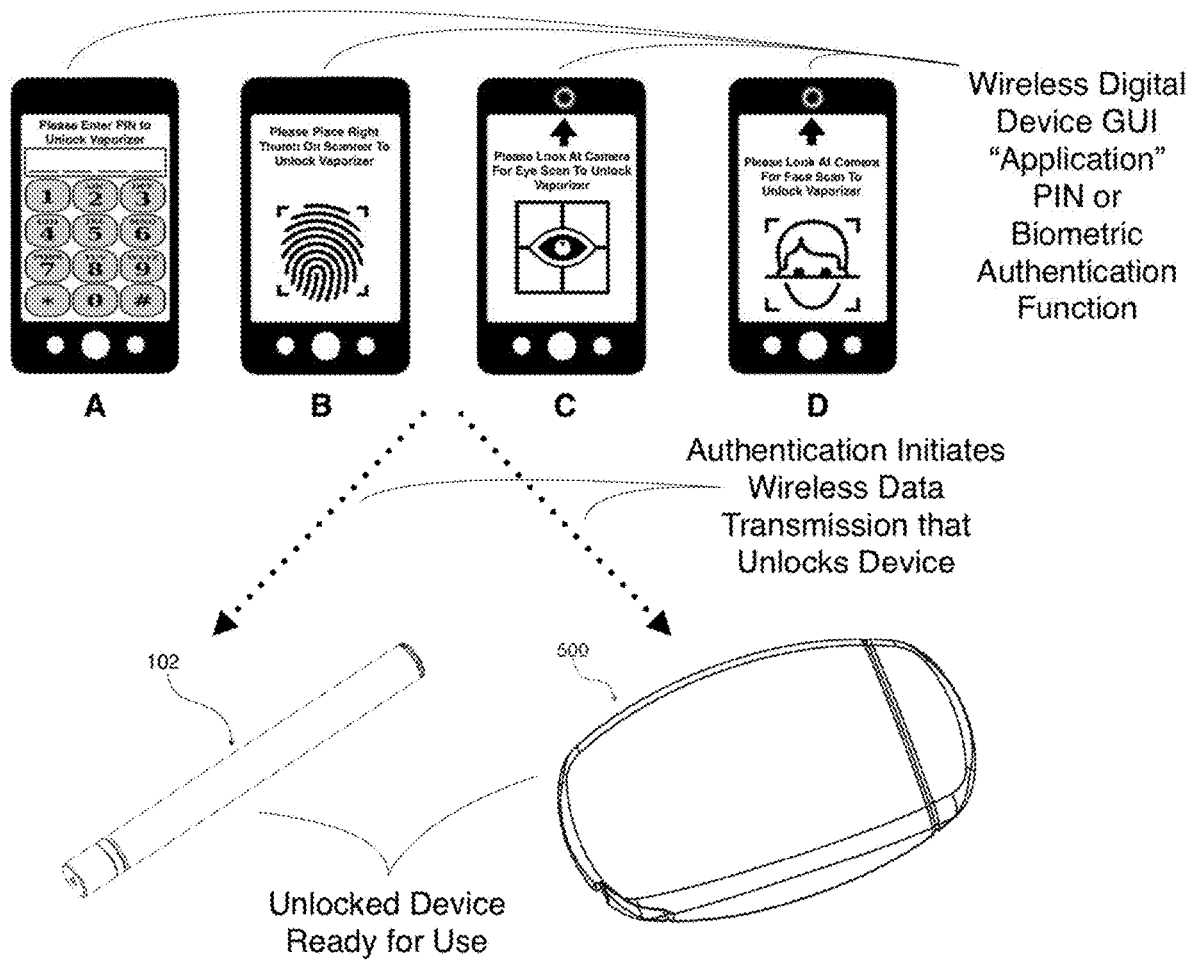
FIG. 112 illustrates a personal vaporizer authorization system.

FIG. 112 illustrates an exemplary graphical user interface for user authentication functionality. FIG. 112 illustrates several embodiments of an authentication process required for device activation. The authentication process is embodied as a feature of the application that is installed and running on the end users personal digital device. In the figure the personal digital device is illustrated as a smart phone. The end users personal digital devices may be a smart phone, computer, tablet or wearable technology such as a smart watch. Other digital devices not shown in figure could also be used in this embodiment provided the device has the capability of transferring and receiving data through the use of wired or wireless methods and has an operating system capable of running application(s). Essentially the device is rendered inactive after a period of not being used; this is similar to a computer going into "sleep mode" when there is not usage detected for a predetermined and preset period of time. In order to the device to be activated and capable of being used by the user for the purpose of generating vapor the user must be authenticated to insure that the device is being utilized by the intended end user and to prevent unauthorized use, or accidental, or unintended activation of the device, or use of the device by an individual not of legal age to ingest the active component, such as nicotine. In A) the authentication process uses a user selected PIN code to authenticate the end user; In B) the authentication process uses the user fingerprint to authenticate the end user; In C) the authentication process uses an eye or iris scan or similar to authenticate the end user; In D) the authentication process uses a face scan or image processing algorithm to authenticate the end user. In embodiments C and D the user's personal digital device would have a forward facing (on the same surface as the primary touch screen interface or similar) camera.

According to an embodiment, FIG. 112 illustrates a personal vaporizer authorization system. In FIG. 112, authorization system includes personal digital device 10810, PVU 100, and case 500. Personal digital device 10810 can be operatively coupled to PVU 100. Personal digital device 10810 can be operatively coupled to case 500. Personal digital device 10810 is illustrated running authentication software. This authentication software may include, for example, PIN based authentication 11201, fingerprint based authentication 11202, iris scan based authentication 11203, and facial recognition based authentication 11204. When authentication software 11201-11203 determines the criteria for authorization have been met (e.g., correct PIN input, matched fingerprint, etc.), the authorization software can control personal digital device 10810 to send a wireless data transmission that unlocks PVU 100 and/or case 500.

The authentication process can be embodied as a feature of an application (e.g., application 10820) that is installed and running on personal digital device 10810. In FIG. 112, personal digital device 10810 is illustrated as a smart phone. However, it should be understood that personal digital device 10810 may be digital devices not illustrated in FIG. 112. Personal digital device 10810 has the capability of communicating data through the use of wired or wireless methods and has an operating system capable of running application(s).

In an embodiment, PVU 100 and/or case 500 may be rendered inactive after a period of inactivity. This is similar to a computer going into "sleep mode" when there is no usage detected for a predetermined and preset period of time. In order for PVU 100 and/or case 500 to be activated, and thereby be capable of being used by the user for the purpose of generating vapor, the user must be authenticated to insure that the device is being utilized by the intended end user, and to prevent unauthorized use, or accidental, or unintended activation of the device, or use of the device by an individual not of legal age to ingest the active component—such as nicotine. PIN based authentication 11201 process uses a user selected PIN code to authenticate the end user. Fingerprint based authentication 11202 process uses the user fingerprint to authenticate the end user. Iris scan based authentication 11203 process uses an eye or iris scan, or the like, to authenticate the end user. Facial recognition based authentication 11204 uses a face scan or image processing algorithm to authenticate the end user. Iris scan based authentication 11203 and facial recognition based authentication 11204 are easier to use if the user's personal digital device has a forward facing (on the same surface as the primary touch screen interface or similar) camera.

Figure 113A:
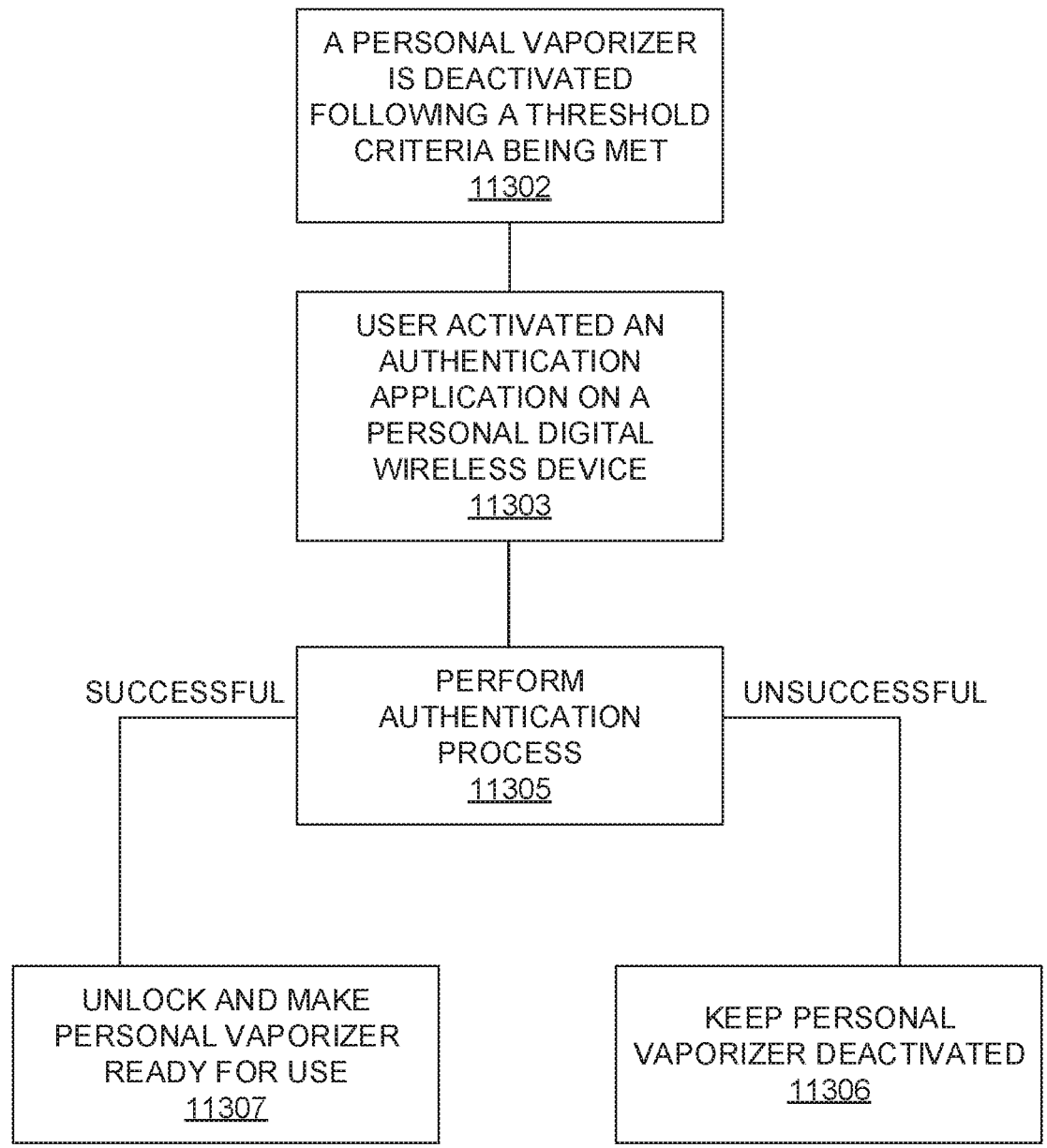
FIG. 113A is a flowchart illustrating a method of activating a personal vaporizer.

FIG. 113A is a flowchart illustrating a method of activating a personal vaporizer. The steps illustrated in FIG. 113A may be performed by one or more elements of system 10800, system 10900, system 11000, communication system 11100, and/or authorization system 11200. A personal vaporizer is deactivated following a threshold criteria being met (11302). For example, PVU 100 and/or case 500 may be rendered inactive after a period of inactivity. The period of inactivity may be preset. The period of inactivity may be a configurable parameter of PVU 100 and/or case 500. A user activated an authentication application on a personal digital wireless device (11303). For example, a user may run application 10820 on personal digital device 10810. Application 10820 may include functionality to unlock or activate PVU 100 and/or case 500. Application 10820 may include functionality to unlock or activate PVU 100 and/or case 500 using PIN based authentication 11201, fingerprint based authentication 11202, iris scan based authentication 11203, and/or facial recognition based authentication 11204. An authentication process is performed (11305). If the authentication process is unsuccessful, for example, when the authentication does not comport to the intended user, the personal vaporizer remains deactivated (11306). If the authentication process is successful, for example, when the authentication process is deemed as identifying the intended user, the personal vaporizer is unlocked and made ready for use (11307).

Figure 113B:
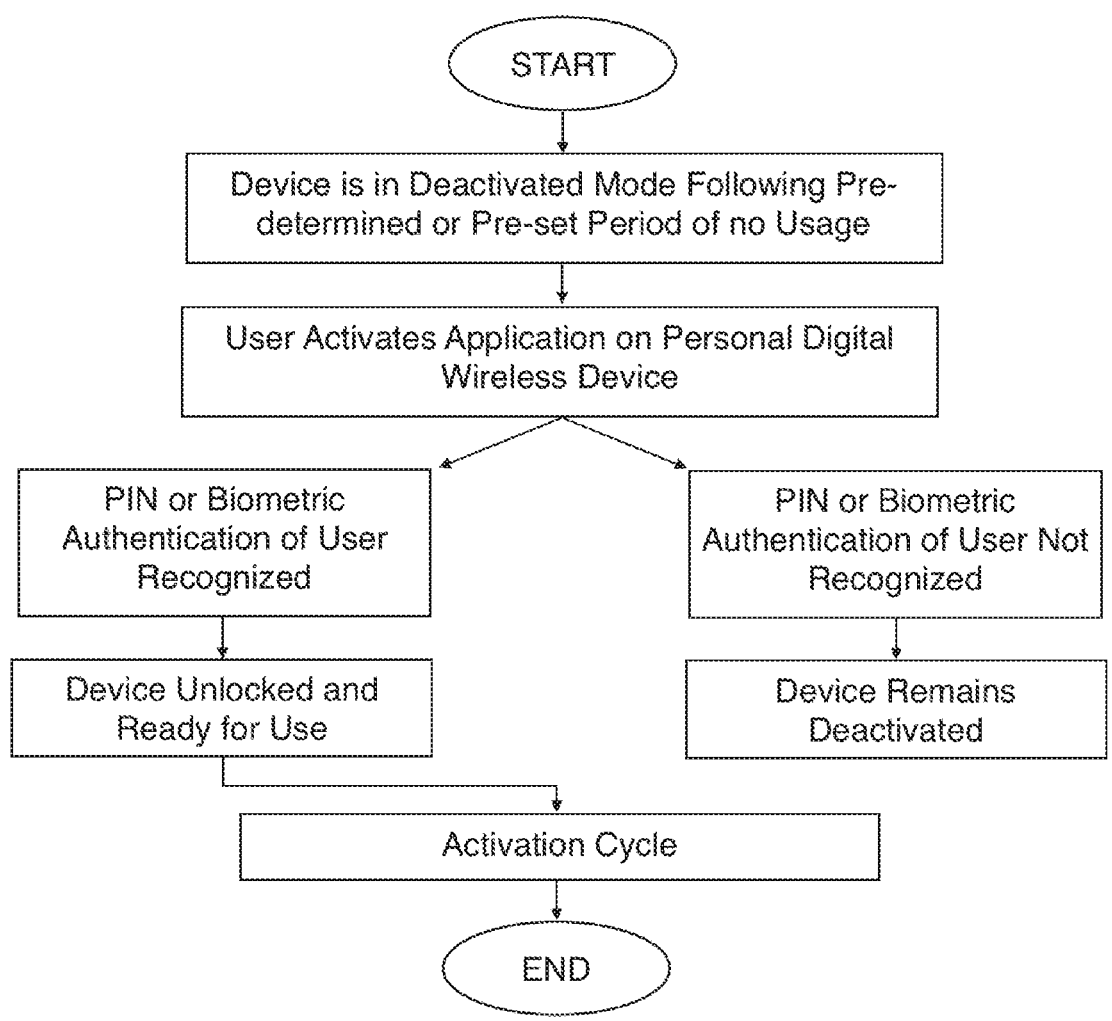
FIG. 113B illustrates a process for user authentication to activate the device.

FIG. 113B illustrates a process for user authentication to activate the device. FIG. 113B illustrates the basic process of user authentication that could be required in order to render the device active and ready to be used. This process is initiated when the device is rendered inactive after a predetermined or preset period of time. The end user then authenticates the device through the use of an application installed and running on their personal digital device, which may be a smart phone, computer, tablet or wearable technology such as a smart watch or similar. Once the authentication process has been deemed as identifying the intended end user the device is rendered active and ready for normal use. If the authentication does not comport to the intended user then the device remains deactivated and cannot be used.

In an embodiment, personal vaporizer unit 100 (and circuitry on PC-board 123, in particular) may perform onboard data gathering, data analysis, and/or the data transmission methods described herein. PVU 100 may interface with digital consumer technology products such as smart phones, tablet computers, lap top/netbook/desktop computers, wearable wireless technologies such as "smart watches," and other wearable technology such as Google "Glass," or similar through the use of programming, software, firmware, GUI, wireless communication, wired communication, and/ or software commonly referred to as application(s) or "apps." Likewise, in an embodiment, case 500 may perform data gathering, data analysis, and/or the data transmission methods described herein. Case 500 may interface with digital consumer technology products such as smart phones, tablet computers, lap top/netbook/desktop computers, wearable wireless technologies such as "smart watches," and other wearable technology such as Google "Glass," or similar through the use of programming, software, firmware, GUI, wireless communication, wired communication, and/ or software running on these devices (commonly referred to as application(s) or "apps.")

Wired means can be used to interface PVU 100 and/or case 500 to digital consumer technology products for the purpose of the transmission and exchange of data to/from PVU 100 or case 500 from/to the digital consumer technology products (and thereby also interfacing with apps running on the digital consumer technology products.) Wireless means can be used to interface PVU 100 and/or case 500 to digital consumer technology products for the purpose of the transmission and exchange of data to/from PVU 100 or case 500 from/to the digital wireless interface. PVU 100 and/or case 500 may use a wireless means/interface that includes one or more of an infrared (IR) transmitter, a Bluetooth interface, an 802.11 specified interface, and/or communications with a cellular telephone network in order to communicate with consumer technology products (and thereby also interfacing with apps running on the digital consumer technology products.).

In an embodiment, PVU 100 and/or case 500 can interface (i.e., communicate) with digital consumer technology products and with apps as a way of relaying information and data to add additional functionality to PVU 100. This additional functionality may include (but is not limited to): (a) setting and/or specifying a desired number of activation cycles over a period of time; (b) setting and/or specifying reminders, alarms, or similar to notify the user; (c) setting and/or specifying a desired dose(s) for delivery of active substance(s) per inhalation; (d) setting and/or specifying a desired total delivered dose of active substance(s) over a period of time—such as a total daily dose; (e) setting and/or specifying power settings of PVU 100 to modulate the vapor and/or aerosol strength, vapor and/or aerosol density, vapor and/or aerosol volume, vapor and/or aerosol flavor, vapor and/or aerosol temperature, and/or similar vapor and aerosol characteristics of the vapor or aerosol generated by the PVU 100; (f) setting and/or specifying power settings of PVU 100 to modulate, adjust, configure or similar the settings of the device as they relate to battery life and/or performance; (g) setting and/or specifying configurations of PVU 100 related to the liquid components and formulation; (h) setting and/or specifying ambient temperature based environmental configurations; (i) setting and/or specifying humidity based environmental configurations; (j) setting and/or specifying altitude based environmental configurations; (k) setting and/ or specifying temporal (i.e., time) based configurations; (l) setting and/or specifying parameters to minimize, maximize, and or modulate the functional effects of the taste and/or flavor component of the vapor product; (m) setting and/or specifying functional effect parameters to minimize or maximize the functional effects related to pharmacodynamics and pharmacokinetics of an active ingredient or drug component of the vapor or aerosol product; (n) receiving and/or providing to a user, PVU 100 and/or case 500 alerts and notifications; (o) receiving and/or providing to a user, PVU 100 alerts and notifications related to recharging (e.g., whether a battery 104 needs to be recharged); (p) receiving and/or providing to a user, case 500 alerts and notifications related to recharging; (q) receiving and/or providing to a user, PVU 100 alerts and notifications related to charge status (e.g., whether a battery 104 is fully or partially charged); (r) receiving and/or providing to a user, case 500 alerts and notifications related to charge status; (s) receiving and/or providing to a user, PVU 100 alerts and notifications related to liquid cartridge usage status-such as a number of usages or inhalations taken from a cartridge; (t) receiving and/or providing to a user, PVU 100 alerts and notifications related to liquid cartridge remaining status-such as a number of usages or inhalations remaining in a cartridge; (u) receiving and/or providing to a user, PVU 100 alerts and notifications related to time-based liquid cartridge usage status— such as number of usages or inhalations taken over a preset or predetermined period of time, for example number of usages or inhalations taken per day; (v) receiving and/or providing to a user, PVU 100 alerts and notifications related to liquid cartridge contents-such as active component(s), strength, dosage (or similar), flavor profile (or similar), and general formulation (or similar); (w) receiving and/or providing to a user, PVU 100 alerts and notifications related to liquid cartridge, liquid cartridge assembly, or similar, requiring replacement; (x) receiving and/or providing to a user, PVU 100 alerts and notifications related to preset times for usage of PVU 100; and, (y) receiving and/or providing to a user, PVU 100 heating element alerts and notifications status or "health"—such as number of cycles performed, and/or number of cycles remaining before suggested and/or required replacement of a heating element or heating element assembly.

In an embodiment, the power settings of PVU 100 may be set and/or specified to modulate or configure the activation energy delivered to the heating element(s) as well as modulating or configuring the parameters of the heating element(s) being energized in relation to the time to peak activation or "warm up" or "ramp" and or the time of maximum or peak activation, and or the time of the heating element being deactivated or the "cool down" to effect and modulate vapor and/or aerosol strength, vapor and/or aerosol density, vapor and/or aerosol volume, vapor and/or aerosol flavor, vapor and/or aerosol temperature, and/or similar vapor and aerosol characteristics of the vapor or aerosol generated by the PVU 100. In an embodiment, the power settings of PVU 100 may be set and/or specified such that the user can make setting adjustments to PVU 100 to maximize battery life. In this case, PVU 100 will resultantly operate at lower energy output to preserve the maximum number of cycles that be sustained per battery 104 charge cycle. Conversely the power settings of PVU 100 may be set and/or specified such that the user can maximize performance in relation to the energy output of the device per cycle.

In an embodiment, the liquid related settings of PVU 100 can be based on information about the liquid components and/or formulation, or similar such that the information relating to the liquid to be vaporized or aerosolized. The liquid related settings of PVU 100 can have predetermined as well as user configurable settings to modulate, configure, adjust or otherwise configure the device activation parameters. In an embodiment, settings related to user specific environmental configurations can be made such that PVU 100 optimizes heating element activation and activation parameters to optimize performance based on ambient temperature, humidity, and/or altitude. For example, PVU 100 may have configurations such as cold weather or warm weather settings, humidity settings, and/or altitude settings.

In an embodiment, PVU 100 can be configured (programmed) with time based settings. For example, user specific temporal configurations such as the user preferring higher active component delivery per inhalation at specific times of the day. PVU 100 can be configured such that PVU 100 delivers dosages of an active component based on the time of day. For example, PVU 100 can be configured such that such that the dosage delivered to the user is highest, or at maximum value (or similar) in the morning and tapers down to a lower delivered dose per inhalation, or minimum value (or similar) at the end of the evening. The user can program these settings (and others described herein) based on personal preference.

In an embodiment, taste and/or flavor related settings of PVU 100 can minimize, maximize, and or modulate the functional effects of the taste and/or flavor component of the vapor product. For example, PVU 100 can be configured to activate in such a way that the flavor delivered from the vapor or aerosol is minimized, maximized, or modulated over the period of an inhalation. Some components of the liquid being vaporized that may contribute to the flavor characteristics of the vapor or aerosol may be more prominent, more prevalent, or more substantial when PVU 100 is activated with higher temperature ranges being generated by the heating element than when lower temperature ranges are being generated by the heating element (within the range of temperatures that the heating element may operate in order to generate a vapor or aerosol for inhalation by the user.) For example the user may set PVU 100 to perform for maximal, minimal, moderate, or another interim value of flavor for the vapor or aerosol product. PVU 100 can modulate the heating element activation cycle accordingly.

In an embodiment, functional effect related setting of PVU 100 can minimize, maximize, or modulate the functional effects related to pharmacodynamics and pharmacokinetics of an active ingredient or drug component of the vapor or aerosol product. For example, PVU 100 can be configured to activate in such a way that the active component or drug delivered from the vapor or aerosol is minimized or maximized in terms of target tissue or organ delivery. Active components or drug(s) in a liquid formulation being vaporized can be absorbed into the blood stream at different rates depending on the target tissue or organ.

Active component(s) or drug(s) in a vapor having a small particle size of less than 10 microns may be readily absorbed into systemic circulation through the pulmonary vasculature. However active component(s) or drug(s) in a vapor having a small particle size of greater than 10 microns may be absorbed more preferentially through the mucosal surface of the oral and pharyngeal cavities. Mucosal absorption is slower to reach the systemic circulation than delivery of a drug (or similar) to the systemic circulation through the pulmonary vasculature.

A user may be using PVU 100 for the delivery of nicotine as the active or drug component in the vapor or aerosol. It may be desirable for (or by) the user to have an option for more rapid delivery of the nicotine to the bloodstream—such as after a period of time of not having nicotine (when that the user's urge or craving is likely to be elevated.) Alternatively, at times it may be desirable for (or by) the user to have a slower absorption of nicotine into the blood stream such as at times when: (i) the users craving or urge is low, (ii) when the user wants to have a more prolonged period of time before they have the urge or craving for nicotine—such as prior to going to sleep, or an event where they will be unable to use the device for dosing or administration of the nicotine. PVU settings relating to the activation of the device and the temperature of the heating element and heating element activation characteristics may be modulated such that, for example, at lower temperature activation the particle size of the drug component is larger than at times of a higher temperature activation of the heating element. Thus, by modulating the input of thermal or heat energy inputted into the vaporization chamber by the heating element to volatize or vaporize the liquid containing the active component(s) or drug(s) the characteristics of the vapor or aerosol in relation to the particle size of the active component(s) or drug(s) can be wholly or partially modulated by the user. These settings can also be used by the end user or healthcare provider (or similar) to reduce dependence on the active component(s) or drug(s)—such as nicotine. These settings can also be used, for example, by initially using the device configured to maximize pulmonary deliver of the nicotine and then transition to device settings that maximize mucosal delivery of the nicotine as a means to facilitate a reduction in nicotine dependence. This transition can also be used in conjunction with nicotine dosage reduction as a means of reducing or mitigating the users nicotine dependence or addiction.

In an embodiment, an app may receive alerts and notifications associated with PVU 100 and/or case 500. These alerts and notifications can include, for example: battery life status, battery condition data (such as number of battery cycles), battery "health" (such that the user can be notified, as desired, to the current and "real time" overall condition of the PVU 100 and/or case 500's internal battery(s).

In an embodiment, PVU 100, case 500, and/or an associated application (app) running on a digital consumer technology product may share data with a manufacturer, manufacturer affiliate, or other entity (retailer, healthcare provider, supplier, marketing entity, etc.) Case 500 may share data via an associated application. PVU 100 may share data via case 500 and/or directly to an associated application (for further sharing with another entity).

PVU 100, case 500, and/or an associated application can gather, receive, logging, store, transmit, extrapolate, and/or the like, anonymous or user specific usage data—such as frequency of use. PVU 100, case 500, and/or an associated application can gather, receive, logging, store, transmit, extrapolate, and/or the like, user specific usage data such as activation cycle characteristics such as duration of activations and user specified activation settings (if applicable.) PVU 100, case 500, and/or an associated application can gather, receive, logging, store, transmit, extrapolate, and/or the like, user specific demographic information. PVU 100, case 500, and/or an associated application can gather, receive, logging, store, transmit, extrapolate, and/or the like, user specific socioeconomic information. PVU 100, case 500, and/or an associated application can gather, receive, logging, store, transmit, extrapolate, and/or the like, user specific f information. PVU 100, case 500, and/or an associated application can gather, receive, logging, store, transmit, extrapolate, and/or the like, user specific feedback information. PVU 100, case 500, and/or an associated application can gather, receive, logging, store, transmit, extrapolate, and/or the like, user specific demographic information. PVU 100, case 500, and/or an associated application can gather, receive, logging, store, transmit, extrapolate, and/or the like, user specific feedback information through the use of surveys, polls, and the like, and/or data analytics.

PVU 100, case 500, and/or an associated application can gather, receive, logging, store, transmit, extrapolate, and/or the like, anonymous and/or user specific usage and/or reliability data such as device errors or malfunctions. PVU 100, case 500, and/or an associated application can gather, receive, logging, store, transmit, extrapolate, and/or the like, user specific usage and/or reliability data such as requests for warranty services, repairs, and or replacements, etc. PVU 100, case 500, and/or an associated application can gather, receive, logging, store, transmit, extrapolate, and/or the like, user specific customer satisfaction data such as requests for technical support. PVU 100, case 500, and/or an associated application can gather, receive, logging, store, transmit, extrapolate, and/or the like, user specific sales lead data such as requests for product information. PVU 100, case 500, and/or an associated application can gather, receive, logging, store, transmit, extrapolate, and/or the like, user specific usability data such as requests for usage instructions. PVU 100, case 500, and/or an associated application can gather, receive, logging, store, transmit, extrapolate, and/or the like, user specific information such as requests for information on product features or functions. PVU 100, case 500, and/or an associated application can gather, receive, logging, store, transmit, extrapolate, and/or the like, user specific marketing data such as requests for information on purchasing PVU 100 or case 500 and/or acquiring PVU 100 or case 500 by way of a prescription from a physician or healthcare provider.

PVU 100, case 500, and/or an associated application can gather, receive, logging, store, transmit, extrapolate, and/or the like, PVU 100 data indicating misuse or abuse of PVU 100. PVU 100, case 500, and/or an associated application can gather, receive, logging, store, transmit, extrapolate, and/or the like, PVU 100 and case 500 data and/or data transmission features that can be used to locate PVU 100 and/or case 500. PVU 100, case 500, and/or an associated application can gather, receive, logging, store, transmit, extrapolate, and/or the like, PVU 100 and case 500 data and/or data transmission features that can be used to locate PVU 100 and/or case 500 if PVU 100 or case 500 is lost or stolen. PVU 100, case 500, via an associated application, can gather, receive, logging, store, transmit, extrapolate, and/or the like, notifications regarding product recalls or similar issues and/or inform the user of such recalls or issues. PVU 100, case 500, via an associated application, can gather, receive, logging, store, transmit, extrapolate, data sharing, and/or the like, notifications manufacturer terms and conditions (e.g., cartridge manufacturer) and/or inform the user of such terms and conditions, and/or receive approval of such terms and conditions from the user.

PVU 100, case 500, via an associated application, can gather, receive, logging, store, transmit, extrapolate, data share, and/or the like, data from a network that may be used to identify, contact, or connect with other users of PVU 100. PVU 100, case 500, via an associated application, can gather, receive, logging, store, transmit, extrapolate, data share, and/or the like, data from a network that may be used to identify, contact, or connect with other users of PVU 100 wherein the network comprises a wireless communication link. PVU 100 and/or case 500 may select and/or authorize the sharing of all or some of the data gathered, received, logged, stored, transmitted, extrapolated, shared, or the like by the PVU 100 and/or case 500, or gathered directly from the user through the use of applications associated with PVU 100 and/or case 500. PVU 100 and/or case 500 may select and/or authorize the sharing, via a network, of all or some of the data gathered, received, logged, stored, transmitted, extrapolated, shared, or the like by the PVU 100 and/or case 500, or gathered directly from the user through the use of applications associated with PVU 100 and/or case 500. The network may comprise social media. The social media membership may comprise a user's family. The social media membership may comprise a user's friends. The social media membership may comprise a support group or similar (e.g., quit smoking group). The social media membership may comprise a third party service, company, organization (e.g., church), other users of PVU 100, or the like.

PVU 100, case 500, and/or an associated application can gather, receive, logging, store, transmit, extrapolate, and/or the like, data useful to perform software configuration of the device and or the device application(s). PVU 100, case 500, and/or an associated application can gather, receive, logging, store, transmit, extrapolate, and/or the like, data useful or required to perform software configuration of the PVU 100, case 500, and/or the associated application(s). PVU 100, case 500, and/or an associated application can gather, receive, logging, store, transmit, extrapolate, and/or the like, data useful or required to perform software configuration of the PVU 100, case 500, and/or the associated application(s) where the software is configured by the manufacturer or manufacturers subsidiary or representatives or third party or similar. PVU 100, case 500, and/or an associated application can gather, receive, logging, store, transmit, extrapolate, and/or the like, data useful or required to perform third party software configuration of PVU 100, case 500, and/or the associated application(s). PVU 100, case 500, and/or an associated application can gather, receive, logging, store, transmit, extrapolate, and/or the like, data useful or required to perform firmware updates of PVU 100, case 500, and/or the associated application(s). PVU 100, case 500, and/or an associated application can provide for the notification of the user via PVU 100, case 500, and/or an associated application that a firmware or similar updates to PVU 100, case 500, and/or an associated application is available and or required as a means of trouble shooting the device or remediating a problem or issue with PVU 100, case 500, and/or an associated application which is preventing some aspect of intended or proper function(s) of PVU 100, case 500, and/or an associated application. PVU 100, case 500, and/or an associated application can provide for the notification of the user via PVU 100, case 500, and/or an associated application that a firmware or similar updates to PVU 100, case 500, and/or an associated application is available and or required as a means of means of providing additional functions relating to or intended to improved PVU 100 or case 500 performance, enhance user experience, or similarly improve some aspect of intended or proper function(s) of PVU 100, case 500, and/or an associated application.

PVU 100, case 500, and/or an associated application can share data gathered by PVU 100, case 500, or gathered directly from the user through the use of the application with the user's healthcare provider. PVU 100, case 500, and/or an associated application can share data gathered by PVU 100, case 500, or gathered directly from the user through the use of the application with the user's healthcare network. PVU 100, case 500, and/or an associated application can share data gathered by PVU 100, case 500, or gathered directly from the user through the use of the application with the user's insurance provider. PVU 100, case 500, and/or an associated application can share data gathered by PVU 100, case 500, or gathered directly from the user through the use of the application with the user's pharmacy and/or prescription drug provider, or the like. PVU 100, case 500, and/or an associated application can depersonalized or otherwise made anonymous data gathered by PVU 100, case 500, or gathered directly from the user so that the depersonalized data can be shared used for purposes such as research, analysis, publication, or similar purposes.

PVU 100, case 500, and/or an associated application can provide for the notification of the user via PVU 100, case 500, and/or the associated application of the availability of a prescription issued or written for the end user being ready for pick-up, delivery, shipment to the user or similar of a prescription component intended for delivery to the patient by PVU 100. For example, a pharmacy could send a notification to the user, via PVU 100, case 500, and/or an associated application, such as to notify the user that their prescription for PVU 100 or device components (e.g., cartridges or liquids) is available for the user to pick up from the pharmacy. PVU 100, case 500, and/or an associated application can allow for healthcare providers, networks, agents, authorized third parties or similar to send alerts, messages, surveys, or similar to the user via PVU 100, case 500, and/or the associated application. PVU 100, case 500, and/or an associated application can allow for healthcare providers, networks, agents, authorized third parties or similar to access data that is generated as a result of surveys, or similar through PVU 100, case 500, and/or the associated application.

PVU 100, case 500, and/or an associated application can authorize (i.e., allow) a healthcare provider to configure, adjust, modulate, and/or manipulate PVU 100 settings. PVU 100, case 500, and/or an associated application can authorize a healthcare provider to configure, adjust, modulate, and/or manipulate PVU 100 settings which the user is not authorized to change, alter, reconfigure or change the settings, configurations, etc. made by the healthcare provider. PVU 100, case 500, and/or an associated application can authorize a representative or agent of the healthcare provider to configure, adjust, modulate, and/or manipulate PVU 100 settings which the user is not authorized to change, alter, reconfigure or change the settings, configurations, etc. made by the representative or agent of the healthcare provider.

PVU 100, case 500, and/or an associated application can share user specific information, such as end user ownership of products relating to the device, device components, device accessories or similar data, gathered by PVU 100, case 500, or gathered directly from the user through the use of the application. PVU 100, case 500, and/or an associated application can share user specific information, user specific information such as end user purchasing of products relating to the device, device components, device accessories or similar data, gathered by PVU 100, case 500, or gathered directly from the user through the use of the application. PVU 100, case 500, and/or an associated application can provide for the notification of the user via PVU 100, case 500, and/or the associated application of notifications from retailer(s) or similar regarding product promotions. PVU 100, case 500, and/or an associated application can provide for the notification of the user via PVU 100, case 500, and/or the associated application similar of notifications from retailer(s) or similar regarding product availability. PVU 100, case 500, and/or an associated application can provide for the notification of the user via PVU 100, case 500, and/or the associated application similar of notifications from retailer(s) or similar regarding release of new product or accessories.

PVU 100, case 500, and/or an associated application can use demographic or similar location services to find retail locations in geographic proximity of the user. PVU 100, case 500, and/or an associated application can gather, receive, logging, store, transmit, extrapolate, and/or the like, data relating to device purchasing, device accessories purchasing, vaporizer liquid and associated packaging or assembly purchasing, frequency of purchasing, point of sale, discounts applied by user when purchasing, and related or similar information. PVU 100, case 500, and/or an associated application can gather, receive, logging, store, transmit, extrapolate, and/or the like, data relating to device purchasing, device accessories purchasing, vaporizer liquid and associated packaging or assembly purchasing, frequency of purchasing, point of sale, discounts applied, and related or similar information.

PVU 100, case 500, and/or an associated application can provide incentives to the user to share information relating to device purchasing, device accessories purchasing, vaporizer liquid and associated packaging or assembly purchasing, frequency of purchasing, point of sale, discounts applied and related information such as discounts, coupons, promotional codes, free items, or similar. PVU 100, case 500, and/or an associated application can provide for the use of the user profile to provide targeted incentives to the user to share information relating to device purchasing, device accessories purchasing, vaporizer liquid and associated packaging or assembly purchasing, frequency of purchasing, point of sale, discounts applied, promotional codes used, and related information such as discounts, coupons, free items, or similar.

PVU 100, case 500, and/or an associated application can render PVU 100 inactive and unable to be used. PVU 100, case 500, and/or an associated application can render PVU 100 inactive and unable to be used if a malfunction or similar has occurred. PVU 100, case 500, and/or an associated application can render PVU 100 inactive and unable to be used until the authorized user enters a Personal Identification Number (PIN) using the application which then activates PVU 100. PVU 100, case 500, and/or an associated application can render PVU 100 inactive and unable to be used until the authorized user has a biometric identifier that when recognized or confirmed or verified or similar, using the application or case 500, activates PVU 100. PVU 100, case 500, and/or an associated application can render PVU 100 inactive and unable to be used until the authorized user uses a fingerprint as a biometric identifier that when recognized or confirmed or verified or similar, using the application or case 500, activates PVU 100. PVU 100, case 500, and/or an associated application can render PVU 100 inactive and unable to be used until the authorized user uses an eye, or iris, or similar scan, as a biometric identifier that when recognized or confirmed or verified or similar, using the application or case 500, activates PVU 100. PVU 100, case 500, and/or an associated application can render PVU 100 inactive and unable to be used until the authorized user is recognized or confirmed or verified or similar, using facial recognition, the application or case 500, activates PVU 100.

Unauthorized use of PVU 100, case 500, and/or an associated application can be prevented by using PIN or unique biometric identifier to enable PVU 100, case 500, and/or an associated application. PVU 100, case 500, and/or an associated application can share data relating to the attempted unauthorized use of PVU 100. PVU 100, case 500, and/or an associated application can share data over a network to authorize the user and activate PVU 100. PVU 100, case 500, and/or an associated application can share data such that biometric authentication can be performed through the use of a network. PVU 100, case 500, and/or an associated application can use time or duration of time that passes after use before PVU 100 is rendered inactive and authentication is required to authorize PVU 100.

PVU 100, case 500, and/or an associated application can save device data and personal settings for individual users so that more than one user may use PVU 100 and/or case 500. PVU 100, case 500, and/or an associated application can save device data and personal settings to be saved for individual users where the settings for device data and personal settings for different users can be applied to PVU 100 and/or case 500 and the intended user through the application and the user may select their saved configurations for PVU 100 and/or case 500 and the respective device will operate under that user selected configuration. PVU 100, case 500, and/or an associated application can have the ability for the user or users to have one or more of user settings and/or configurations that are saved and can be selected by users. PVU 100, case 500, and/or an associated application can have the ability to allow saved user settings and personal settings or configurations to be shared by the user through the application and/or an associated network. PVU 100, case 500, and/or an associated application can allow other user settings and/or configurations to be shared with the user through the application or an associated network.

PVU 100, case 500, and/or an associated application can have the ability to facilitate, prompt, or the like, a user to rate (such as through common methods such a 1-10 where "10" is the best, or 1-5 "stars" where "5" stars is the best) their user configurations. PVU 100, case 500, and/or an associated application can have the ability to facilitate, prompt, or the like, the user to rate other user configurations. PVU 100, case 500, and/or an associated application can have the ability to share and access a data base of user configurations that may or may not have ratings and be able to access the user configurations through the application and download user configurations for use in the users own device. PVU 100, case 500, and/or an associated application can have the ability to share and access a data base of user configurations that may or may not have ratings and a be able to access the user configurations through the application and upload their user configurations for use in other users devices.

PVU 100, case 500, and/or an associated application can share user data with the manufacturer, manufacturers subsidiaries, manufactures agents, or a third party for the purpose of generating user profiles based on user specific usage data, demographic data, socioeconomic data or similar. PVU 100, case 500, and/or an associated application can have the ability to utilize user data shared with the manufacturer, manufacturers subsidiaries, manufactures agents, or a third party to determine specific user profiles.

PVU 100, case 500, and/or an associated application can allow, facilitate, authorize, confirm or similar the sharing of data between the associated application and other application(s) that may be installed or a component of the user's personal digital device. PVU 100, case 500, and/or an associated application can share information and/or data with a social media application. PVU 100, case 500, and/or an associated application can share information and/or data with email service, email provider, email hosting, or similar application. PVU 100, case 500, and/or an associated application can share information and/or data with text message, SMS, or similar application. PVU 100, case 500, and/or an associated application can share information and/or data with a location based services application. PVU 100, case 500, and/or an associated application can share information and/or data with a map or mapping, navigation, location or similar application. PVU 100, case 500, and/or an associated application can share information and/or data with healthcare, healthcare provider, healthcare services, healthcare network or similar application. PVU 100, case 500, and/or an associated application can share information and/or data with pharmacy, or pharmacy type service provider or similar application. PVU 100, case 500, and/or an associated application can share information and/or data with a weather, or weather forecasting, or weather reporting, or similar application. PVU 100, case 500, and/or an associated application can share information and/or data with the device manufacturers application. PVU 100, case 500, and/or an associated application can share information and/or data with a research or research orientated application. PVU 100, case 500, and/or an associated application can share information and/or data with a PVU 100 and/or case 500 retailer or similar consumer device application.

PVU 100, case 500, and/or an associated application can have the ability to authorize or allow data gathering, receiving, logging, storing, transmission, extrapolation or similar for the purpose of the device or associated application sending error codes or error reports to the manufacturer, manufacturers subsidiaries, manufactures agents, or a third party for the purpose of addressing problems with device performance or function. PVU 100, case 500, and/or an associated application can have the ability to authorize or allow data gathering, receiving, logging, storing, transmission, extrapolation or similar for the purpose of the device or associated application sending error codes or error reports to the manufacturer, manufacturers subsidiaries, manufactures agents, or a third party for the purpose of addressing problems with device application(s). PVU 100, case 500, and/or an associated application can have the ability to authorize or allow data gathering, receiving, logging, storing, transmission, extrapolation or similar for the purpose of the device or device application sending error codes or error reports to the manufacturer, manufacturers subsidiaries, manufactures agents, or a third party for the purpose of extrapolating data metrics that relate to device malfunctioning. PVU 100, case 500, and/or an associated application can have the ability to authorize or allow data gathering, receiving, logging, storing, transmission, extrapolation or similar for the purpose of the device or associated application sending error codes or error reports to the manufacturer, manufacturers subsidiaries, manufactures agents, or a third party for the purpose of gathering, receiving, logging, storing, transmission, extrapolation or similar data that may relate to manufacturing, or quality control or similar issues or potential problems related to the device, device components, or liquid being used in the device. PVU 100, case 500, and/or an associated application can have the ability to gather, receive, log, store, transmit, extrapolate, or similar, data for the purpose of troubleshooting device issues or problems. PVU 100, case 500, and/or an associated application can have the ability to gather, receive, log, store, transmit, extrapolate, or similar, data for the purpose of troubleshooting device issues or problems that may relate to user error.

PVU 100, case 500, and/or an associated application can have the ability to use methods of data transmission such as wireless and wired technologies. PVU 100, case 500, and/or an associated application can have the ability to use methods of data transmission such as wireless and wired technologies to perform one or more of the functions, capabilities, methods, abilities, etc., described herein. PVU 100, case 500, and/or an associated application can have the ability to use methods of data transmission such as wifi, Bluetooth, cellular, 3G, 4G, near field communication (NFC), or similar for the transmission of data to the users personal digital device. PVU 100, case 500, and/or an associated application can have the ability to use methods of data transmission such as wifi, Bluetooth, cellular, 3G, 4G, near field communication (NFC), or similar for the transmission of data to a network. PVU 100, case 500, and/or an associated application can have the ability to use methods of data transmission such as text messaging or SMS. PVU 100, case 500, and/or an associated application can have the ability to use methods of data transmission such as electronic mail or email. PVU 100, case 500, and/or an associated application can have the ability to use methods of data transmission such as notifications or push notifications to the user's digital device.

PVU 100, case 500, and/or an associated application can have means for user control of the functionality, features, configurations etc. of PVU 100, case 500, and/or an associated application through the use of various features of the application referred to as configurations or settings. These settings can include, but are not limited to exemplary general usage settings listed in Table 1.

TABLE 1

| | |
|---|---|
| (a) | Desired number of activations cycles over a period of time. |
| (b) | Configuring and or setting reminders, alarms, or similar to notify the user. |
| (c) | Desired dose delivery of active substance per inhalation. |
| (d) | Desired total delivered dose over a period of time such as a total daily dose. |
| (e) | Power settings of PVU 100 to modulate the vapor or aerosol strength, vapor or aerosol density, vapor or aerosol volume, vapor or aerosol flavor, vapor or aerosol temperature or similar vapor or aerosol characteristics of the vapor or aerosol generated by the device. The power settings could modulate or configure the activation energy delivered to the heating element(s) as well as modulating or configuring the parameters of the heating element(s) being energized in relation to the time to peak activation or "warm up" or "ramp" and or the time of maximum or peak activation, and or the time of the heating element being deactivated or the "cool down" to effect and modulate the vapor or aerosol strength, vapor or aerosol density, vapor or aerosol volume, vapor or aerosol flavor, vapor or aerosol temperature or similar characteristics of the vapor or aerosol generated by the device. |
| (f) | Power settings of PVU 100 to modulate, adjust, configure or similar the settings of the device as they relate to battery life and performance such that the user can make setting adjustment to the device to maximize battery life and the device will resultantly operate at lower energy output to preserve the maximum number of cycles that be sustained per battery charge cycle. Conversely the user could modulate, adjust, configure or similar the settings of the device to maximize performance in relation to the energy output of the device per cycle. |
| (g) | Settings related to the liquid components and formulation or similar such that the information relating to the liquid to be vaporized or aerosolized can have predetermined as well as user configurable settings to modulate, configure, adjust or similar PVU 100 activation parameters. |
| (h) | Settings related to user specific environmental configurations such as cold weather or warm weather settings such that the device optimizes heating element activation and activation parameters to optimize performance based on ambient temperature. |

TABLE 1-continued

| | |
|---|---|
| (i) | Settings related to user specific environmental configurations such as high or low humidity settings such that PVU 100 optimizes heating element activation and activation parameters to optimize performance based on user locale humidity values or ranges. |
| (j) | Settings related to user specific environmental configurations such as user locale altitude settings such that PVU 100 optimizes heating element activation and activation parameters to optimize performance based on end user altitude. |
| (k) | Settings related to user specific temporal configurations such as the user preferring higher active component delivery per inhalation at specific times of the day. For example, PVU 100 can be configured such that it delivers higher dosage of active component related to a time of day such that the dosage delivered to the user is highest, or at maximum value or similar in the morning and tapers down to a lower delivered dose per inhalation, or minimum value, or similar at the end of the evening. This is an example of the configurability of PVU 100 and the user could program the settings based on personal preference. |
| (l) | Settings related to modulating PVU 100 performance and activation parameters to minimize or maximize the functional effects of the taste or flavor component of the vapor product such that PVU 100 can be configured to activate in such a way that the flavor delivered from the vapor or aerosol is minimized or maximized. For example components of the liquid being vaporized that may contribute to the flavor characteristics of the vapor or aerosol may be more profound, or more prevalent, or more substantial when PVU 100 is activated with higher temperature ranges being generated by the heating element than when lower temperature ranges are being generated by the heating element within the range of temperatures that the heating element may operate within in order to generate a vapor or aerosol for inhalation by the user. For example the user may set PVU 100 to perform for maximal, minimal, moderate, or another interim value of flavor for the vapor or aerosol product and the heating element activation cycle will be modulated accordingly. |
| (m) | Settings related to modulating PVU 100 performance and activation parameters to minimize or maximize the functional effects related to pharmacodynamics and pharmacokinetics of the active or drug component of the vapor or aerosol product such that PVU 100 can be configured to activate in such a way that the active component or drug delivered from the vapor or aerosol is minimized or maximized in terms of target tissue or organ delivery. For example active components or drug(s) in the liquid formulation being vaporized will be absorbed into the blood stream at different rates depending on the target tissue or organ. For example active component(s) or drug(s) in the vapor having small particle size of less than 10 microns may be readily absorbed into systemic circulation through the pulmonary vasculature, as is well documented in the literature. However active component(s) or drug(s) in the vapor having small particle size of greater than 10 microns may be absorbed more preferentially through the mucosal surface of the oral and pharyngeal cavities and mucosal absorption is slower to reach the systemic circulation then is the delivery of a drug or similar to the systemic circulation through the pulmonary vasculature. To continue the example, a user may be using PVU 100 for the delivery of nicotine as the active or drug component in the vapor or aerosol and it may be desirable for the user to have the option to have more rapid delivery of the nicotine to the bloodstream, such as after a period of time of not having nicotine such that the user's urge or craving is elevated. Alternatively, at times it may be desirable for the user to have a slower absorption of nicotine into the blood stream such as at times when the users craving or urge is low, or at times when the user wants to have a more prolonged period of time before they have the urge or craving for nicotine such as prior to going to sleep, or an event where they will be unable to use PVU 100 for dosing or administration of the nicotine. PVU 100 settings relating to the activation of the device and the temperature of the heating element and heating element activation characteristics may be modulated such that for example at lower temperature activation the particle size of the drug component is larger than when at higher temperature activation of the heating element. Thus by modulating the input of thermal or heat energy inputted into the vaporization chamber by the heating element to volatize or vaporize the liquid containing the active component(s) or drug(s) the characteristics of the vapor or aerosol in relation to the particle size of the active component(s) or drug(s) can be wholly or partially modulated by the user. These settings could also be used by the end user or healthcare provider or similar to reduce dependence on the active component(s) or drug(s) such as |

TABLE 1-continued

| | |
|---|---|
| | nicotine, for example, by initially using PVU 100 configured to maximize pulmonary deliver of the nicotine and then transition to device settings that maximize mucosal delivery of the nicotine as a means to facilitate reducing nicotine dependence and could be used in conjunction with nicotine dosage reduction as a means of reducing or mitigating the users nicotine dependence or addiction. |
| (n) | Device alerts and notifications such as battery life status and battery condition(s) data such as number of battery cycles and battery "health" such that the user can be notified as desired to the current meaning "real time" and overall condition of the devices internal battery, and the devices charging case internal battery. |
| (o) | Device alerts and notifications such as the PVU 100 battery requiring recharging. |
| (p) | Device alerts and notifications such as case 500 battery requiring recharging. |
| (q) | Device alerts and notifications such as PVU 100 battery being fully charged. |
| (r) | Device alerts and notifications such as case 500 battery being fully charged |
| (s) | Device alerts and notifications such as liquid cartridge status, such as number of usages or inhalations taken and number or usages remaining. |
| (t) | Device alerts and notifications such as liquid cartridge contents such as active component(s) and strength or dosage or similar, and flavor profile or similar, and general formulation. |
| (u) | Device alerts and notifications such as liquid cartridge or liquid cartridge assembly or similar requiring replacement. |
| (v) | Device alerts and notifications such as predetermined or preset times for usage of PVU 100. |
| (w) | Device alerts and notifications such as device heating element status or "health" such as number of cycles performed and number of cycles remaining before suggested or required replacement of heating element or heating element assembly. |

Settings can include, but are not limited to device manufacturer data sharing settings listed in Table 2.

TABLE 2

| | |
|---|---|
| (a) | Anonymous or user specific usage data such as frequency of use. |
| (b) | Anonymous or user specific usage data such as activation cycle characteristics such as duration of activations and user specified activation settings if applicable. |
| (c) | User specific data such as demographic information. |
| (d) | User specific data such as socioeconomic information. |
| (e) | User specific data such as user feedback through the use of surveys or similar. |
| (f) | Anonymous or user specific usage data such device errors or malfunctions. |
| (g) | User specific data such as requests for warranty services or repairs or replacements or similar. |
| (h) | User specific data such as requests for technical support. |
| (i) | User specific data such as requests for product information. |
| (j) | User specific data such as requests for usage instructions. |
| (k) | User specific data such as requests for information on product features or functions. |
| (l) | User specific data such as requests for information on purchasing product or acquiring the product through a prescription from a physician or healthcare provider. |
| (m) | Device data indicating misuse or abuse of the device. |
| (n) | Device data and data transmission features used to locate the device if the device is lost or stolen. |
| (o) | Notifications to the user through the device or application(s) relating to product recall(s) or similar issues. |
| (p) | General data sharing to manufacture terms and conditions recognition and user agreement to said terms. |

Settings can include, but are not limited to user, usage, system, device, and operational data settings listed in Table 3.

TABLE 3

| | |
|---|---|
| (a) | Settings relating to selecting and authorizing the sharing of all or some of the data gathered by the device or gathered directly from the user through the use of a application(s) to a network(s). |
| (b) | Where network(s) may be social media. |
| (c) | Where network(s) may be comprised of the users family and or friends. |
| (d) | Where network(s) may be comprised of a support group or similar. |
| (e) | Settings relating to the use of the sharing of data over a network(s) that may be used to identify, contact, or connect with other users of the device. |
| (f) | Where other network(s) may be a third party service, company, organization or similar. |

Settings can include, but are not limited to software configuration and firmware updating settings listed in Table 4.

TABLE 4

| | |
|---|---|
| (a) | Settings relating to the sharing and transmission of data required or useful to perform software configuration of the device and or the device application(s). |
| (b) | Settings relating to the sharing and transmission of data required to perform software configuration of the device and or the device application(s) where the software is configured by the manufacturer or manufacturers subsidiary or representatives or third party or similar. |
| (c) | Settings relating to the sharing and transmission of data required to perform software configuration of the device and or the device application(s) where the software is configured by the a third party. |
| (d) | Settings relating to the authorization for the sharing and transmission of data required to perform firmware or similar updates to the device and or application. |

TABLE 4-continued

| | |
|---|---|
| (e) | Settings relating to the notification of the user through the device or application(s) that a firmware or similar updates to the device and or application(s) is available and or required. |
| (f) | Settings relating to the notification of the user through the device or application(s) that a firmware or similar updates to the device and or application(s) is available and or required as a means of trouble shooting the device or remediating a problem or issue with the device or application(s) preventing some aspect of intended or proper function(s). |

Settings can include, but are not limited to healthcare system data sharing settings listed in Table 5.

TABLE 5

| | |
|---|---|
| (a) | Settings relating to the sharing of all or some of the data gathered by the device or gathered directly from the user through the use of application(s) to the users healthcare provider. |
| (b) | Settings relating to the sharing of all or some of the data gathered by the device or gathered directly from the user through the use of application(s) to the users healthcare network. |
| (c) | Settings relating to the sharing of all or some of the data gathered by the device or gathered directly from the user through the use of application(s) to the users insurance provider. |
| (d) | Settings relating to the sharing of all or some of the data gathered by the device or gathered directly from the user through the use of application(s) to the users pharmacy or prescription drug provider or similar. |
| (e) | Settings relating to the notification of the availability of a prescription issued or written for the end user being ready for pick-up, delivery, shipment to the user or similar of a prescription component intended for delivery to the patient by the device. For example, a pharmacy could send a notification to the user, through the device application, such as to notify the user that their prescription for the device or device components is available for the user to pick up from the pharmacy. |
| (f) | Settings relating to the authorization of a healthcare provider to configure, adjust, modulate, manipulate or similar the device settings. |
| (g) | Settings relating to the authorization of a healthcare provider to configure, adjust, modulate, manipulate or similar the device settings where the user is not authorized to change, alter, reconfigure or similar the settings, configurations, or similar made by the healthcare provider. |
| (h) | Settings authorizing a representative or agent or similar of the healthcare provider to configure, adjust, modulate, manipulate or similar the device settings where the user is not authorized to change, alter, reconfigure or similar the settings, configurations, or similar made by the healthcare representative or agent or similar. |
| (i) | Settings allowing for data shared with the healthcare provider or network to be depersonalized or otherwise made anonymous and used for other purposes such as research, analysis, publication, or similar purposes. |
| (j) | Settings allowing for healthcare providers, networks, agents, authorized third parties or similar to send alerts, messages, surveys, or similar through the device application(s). |
| (k) | Settings allowing for healthcare providers, networks, agents, authorized third parties or similar to access data that is generated as a result of surveys, or similar through the device application(s). |

Settings can include, but are not limited to retailer and/or consumer facing data settings listed in Table 6.

TABLE 6

| | |
|---|---|
| (a) | Settings relating to the sharing user specific information such product, device, component, accessories or similar details. |
| (b) | Settings relating to receiving notifications from retailer(s) or similar regarding product promotions. |
| (c) | Settings relating to receiving notifications from retailer(s) or similar regarding product availability. |
| (d) | Settings relating to receiving notifications from retailer(s) or similar regarding release of new product or accessories. |
| (e) | Settings relating to using demographic or similar location services to find retail locations in geographic proximity of the user. |
| (f) | Settings relating to the sharing of data that may be used for demographic, socioeconomic, or similar marketing or promotional activities. |
| (g) | Settings relating to the gathering of data relating to device purchasing, device accessories purchasing, vaporizer liquid and associated packaging or assembly purchasing, frequency of purchasing, point of sale, discounts applied by user when purchasing, and related or similar information. |
| (h) | Settings relating to the sharing of data relating to device purchasing, device accessories purchasing, vaporizer liquid and associated packaging or assembly purchasing, frequency of purchasing, point of sale, discounts applied, and related or similar information. . |
| (i) | The use of the application to provide incentives to the user to share information relating to device purchasing, device accessories purchasing, vaporizer liquid and associated packaging or assembly purchasing, frequency of purchasing, point of sale, discounts applied and related information such as discounts, coupons, promotional codes, free items, or similar. |
| (j) | Settings relating to the use of the user profile to provide targeted incentives to the user to share information relating to device purchasing, device accessories purchasing, vaporizer liquid and associated packaging or assembly purchasing, frequency of purchasing, point of sale, discounts applied, promotional codes used, and related information such as discounts, coupons, free items, or similar. |

Settings can include, but are not limited to device access settings listed in Table 7.

TABLE 7

| | |
|---|---|
| (a) | Settings relating to rendering the device inactive and unable to be used. |
| (b) | Settings relating to rendering the device inactive and unable to be used where the authorized user has a Personal Identification Number (PIN) that when entered using the application activates the device. |
| (c) | Settings relating to rendering the device inactive and unable to be used where the authorized user has a biometric identifier that when recognized or confirmed or verified or similar using the application activates the device. |
| (d) | Settings relating to rendering the device inactive and unable to be used where the authorized user has a biometric identifier that when recognized or confirmed or verified using the application activates the device where the biometric identifier is a fingerprint. |
| (e) | Settings relating to rendering the device inactive and unable to be used where the authorized user has a biometric identifier that when recognized or confirmed or verified using the application activates the device where the biometric identifier is an eye or iris or similar scan. |
| (f) | Settings relating to rendering the device inactive and unable to be used where the authorized user has a biometric identifier that when recognized or confirmed or verified using the application activates the device where the biometric identifier is facial recognition. |
| (g) | Settings where unauthorized use of the device is prevented by using PIN or unique biometric identifier. |
| (h) | Settings relating to the sharing of data relating to the attempted unauthorized use of the device. |
| (i) | Settings relating the sharing of data over a network to authorize the user and activate the device. |
| (j) | Settings relating to sharing of data such that biometric authentication can be performed through the use of a network. |

TABLE 7-continued

| | |
|---|---|
| (k) | Settings related to the time or duration of time that passes after use before the device is rendered inactive and authentication is required to authorize the device. |
| (l) | Settings related the resetting or changing of user specific authentication information such as the PIN. |

Settings can include, but are not limited multiple user settings listed in Table 8.

TABLE 8

| | |
|---|---|
| (a) | Settings relating to the sharing and transmission of data required or useful to perform software configuration of the device and or the device application(s). |
| (b) | Settings relating to the sharing and transmission of data required to perform software configuration of the device and or the device application(s) where the software is configured by the manufacturer or manufacturers subsidiary or representatives or third party or similar. |
| (c) | Settings relating to the sharing and transmission of data required to perform software configuration of the device and or the device application(s) where the software is configured by the a third party. |
| (d) | Settings relating to the authorization for the sharing and transmission of data required to perform firmware or similar updates to the device and or application. |
| (e) | Settings relating to the notification of the user through the device or application(s) that a firmware or similar updates to the device and or application(s) is available and or required. |
| (f) | Settings relating to the notification of the user through the device or application(s) that a firmware or similar updates to the device and or application(s) is available and or required as a means of trouble shooting the device or remediating a problem or issue with the device or application(s) preventing some aspect of intended or proper function(s). |

Settings can include, but are not limited to, defined usage profile settings listed in Table 9.

TABLE 9

| | |
|---|---|
| (a) | Settings related to the sharing of user data to the manufacturer, manufacturers subsidiaries, manufactures agents, or a third party for the purpose of generating user profiles based on user specific usage data, demographic data, socioeconomic data or similar. |
| (b) | Where the use of user data shared with or sent to the manufacturer, manufacturers subsidiaries, manufactures agents, or a third party for the purpose of generating user profiles based on user specific usage data, demographic data, socioeconomic data or similar is utilized to determine specific user profiles. |
| (c) | Where the user profiles are a group of setting configurations that correlate to a specific subset of users. |
| (d) | Where a subset of users may be based on demographic data, socioeconomic, personal data gathered through the use of the application, device usage data or similar. |
| (e) | Where user profiles may be specific to the subset of users and recommended device configuration base on user profile data could be available to the user of the device based on the users similarities to a subset of users. |
| (f) | Where the user experience is optimized by using cumulative data from similar users to establish a default setting configuration for the device based on the users demographic data, socioeconomic data or similar. |

Settings can include, but are not limited to setting related to integration with other applications listed in Table 10.

TABLE 10

| | |
|---|---|
| (a) | Settings to allow, facilitate, authorize, confirm or similar the sharing of data between the device application and other application(s) that may be installed or a component of the users personal digital device. |
| (b) | Where other application(s) that the device application shares information with may be social media application(s). |
| (c) | Where other application(s) that the device application shares information with may be email service, email provider, email hosting, or similar application(s). |
| (d) | Where other application(s) that the device application shares information with may be text message, SMS, or similar application(s). |
| (e) | Where other application(s) that the device application shares information with may be location services application(s). |
| (f) | Where other application(s) that the device application shares information with may be map or mapping, navigation, location or similar application(s). |
| (g) | Where other application(s) that the device application shares information with may be healthcare, healthcare provider, healthcare services, healthcare network or similar application(s). |
| (h) | Where other application(s) that the device application shares information with may be pharmacy, or pharmacy type service provider or similar application(s). |
| (i) | Where other application(s) that the device application shares information with may be weather, or weather forecasting, or weather reporting or similar application(s). |
| (j) | Where other application(s) that the device application shares information with may be the device manufacturers application(s). |
| (k) | Where other application(s) that the device application shares information with may be research or research orientated application(s). |
| (l) | Where other application(s) that the device application shares information with may be device retailer or similar consumer device application(s). |

Settings can include, but are not limited to error code an troubleshooting settings listed in Table 11.

TABLE 11

| | |
|---|---|
| (a) | Settings relating to the authorization or allowance of data sharing for the purpose of the device or device application sending error codes or error reports to the manufacturer, manufacturers subsidiaries, manufactures agents, or a third party for the purpose of addressing problems with device performance or function. |
| (b) | Settings relating to the authorization or allowance of data sharing for the purpose of the device or device application sending error codes or error reports to the manufacturer, manufacturers subsidiaries, manufactures agents, or a third party for the purpose of addressing problems with device application(s). |
| (c) | Settings relating to the authorization or allowance of data sharing for the purpose of the device or device application sending error codes or error reports to the manufacturer, manufacturers subsidiaries, manufactures agents, or a third party for the purpose of extrapolating data metrics that relate to device malfunctioning. |
| (d) | Settings relating to the authorization or allowance of data sharing for the purpose of the device or device application sending error codes or error reports to the manufacturer, manufacturers subsidiaries, manufactures agents, or a third party for the purpose of gathering data that may relate to manufacturing, or quality control or similar issues or potential problems related to the device, device components, or liquid being used in the device. |

TABLE 11-continued

| | |
|---|---|
| (e) | Settings relating to the sharing of data for the purpose of troubleshooting device issues or problems. |
| (f) | Settings relating to the sharing of data for the purpose of troubleshooting device issues or problems that may relate to user error. |

Settings can include, but are not limited to settings related to methods of communication in Table 12.

TABLE 12

| | |
|---|---|
| (a) | Settings relating to the device or device application using methods of data transmission such as wireless and wired technologies. |
| (b) | Settings relating to the device or device application using methods of data transmission such as wifi, Bluetooth, or similar for the transmission of data to the users personal digital device. |
| (c) | Settings relating to the device or device application using methods of data transmission such as wired or wireless methods or similar for the transmission of data to a network. |
| (d) | Settings relating to the device or device application using methods of data transmission such as text messaging or SMS. |
| (e) | Settings relating to the device or device application using methods of data transmission such as electronic mail or email. |
| (f) | Settings relating to the device or device application using methods of data transmission such as notifications or push notifications on the users digital device. |

Heating Element Materials and Application

The heating element may be made using direct writing (DW). The use of direct writing of a conductive metal or conductive material directly to the heating element support member or wire guide(s), or other component performs the function of the heating element(s) that is currently embodied by a metal wire or metal ribbon. This concept expands the material(s) potentially used for the heating element beyond the scope of using a metal wire or metal ribbon. The use of metal deposition methods such as plating, electroplating, or sputtering to effect the same heating element functionality as described throughout the section may be performed through the implementation of direct writing methods. The use of embedded metal into formed ceramic, or similar, components to effect the same function may be used for directly written heating element(s). Likewise, embedded metals may be used to facilitate electrical connection to directly written elements.

In an embodiment, direct writing of a conductive metal or conductive material to a heating element support member or wire guide, or other component which performs the function of a heating element can be used to construct a heating element or wire guide. Direct writing of these conductive materials or metals can be done instead of the metal wire and/or metal ribbon described previously herein. Direct writing expands the materials that can be used for the heating element beyond a metal wire or metal ribbon. In addition, metal deposition methods such as plating, electroplating, or sputtering can be used to make the same heating element and/or contact functionality as described hereinafter as performed through the implementation of direct writing methods. Likewise, the use of embedded metal into formed ceramic, or similar, components can be used to make the heating element and/or contact functionality as described hereinafter as performed through the implementation of direct writing methods. Embedded metals can be used to facilitate electrical connections to directly written elements.

Direct Writing (DW) typically refers to a printing or patterning method that employs a computerized, motion-controlled stage with a motionless pattern generating device to dispense flowable materials in a designed pattern onto a surface. Conductive flowable materials (a.k.a., "inks") that can be used in direct write applications include, but are not limited to: (i) polymeric—metallic particles in a polymeric matrix, primarily for polymeric substrates Silver, graphite, tungsten, copper; (ii) cermet—metallic particles in a glass matrix, primarily for ceramic substrates, gold, platinum, silver; (iii) nanoparticulate silver; and (iv) specialty electrode materials such as titanium, stainless steel, niobium, and/or titanium nitride.

Substrates (i.e., surfaces) that can be used in DW applications include, but are not limited to ceramics and metal. Examples of suitable ceramics include, but are not limited to: alumina, aluminum nitride, yttria-stabilized zirconia, and pyrex. Examples of suitable metals include, but are not limited to: stainless steels (e.g., 316L, 302, 304 and 430), nitinol, and titanium alloys.

In an embodiment, a heating element is comprised of a conductive (flowable) material deposited on a substrate (support member). By depositing the heating element material on a support member, the heating element is now thermally coupled to the support member through the process of direct writing the heating element directly to the support member. The heating element is created using the process of direct writing can be substantially L-shaped etc., as described herein. For example, direct writing can be used to construct heating elements in place of wires and/or metal clips illustrated in FIG. 35A, FIG. 59A, FIG. 76K, and/or FIG. 76L. Exemplary arrangements of the heating element include where the heating element comprised of a conductive (flowable) material; where the heating element is now thermally coupled to the support member through the process of direct writing the heating element directly to the support member; and/or where the heating element is created using the process of direct writing and is substantially L-shaped etc.

Figure 114:
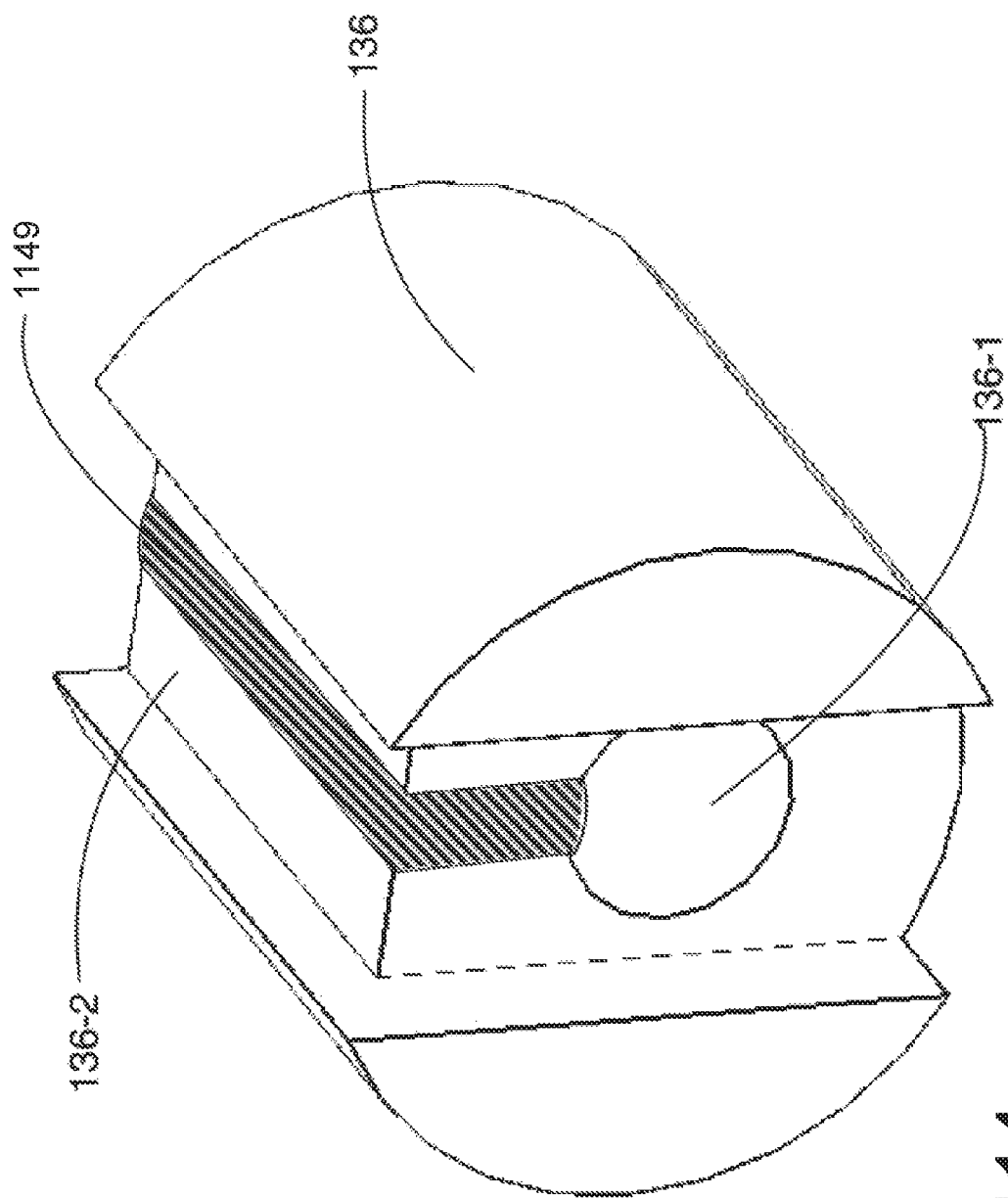

Taking FIG. 76K as an example, direct writing can be used to construct heating element 76054 on support member 76058. For another example, In FIG. 35A, a heating element is disposed through proximal wick. In this embodiment, the heating element may be directly written to the proximal wick 136 to replicate and perform the function of the heating element 139. FIG. 114 is an exemplary embodiment of FIG. 35A with a directly written heating element. FIG. 114 is a perspective view of a proximal wick element of a personal vaporizer unit that demonstrates a DW heating element from a similar perspective to FIG. 35A.

FIG. 114 illustrates a perspective view of a directly written heating element disposed through a proximal wick element of a personal vaporizer unit. As shown in FIG. 114, a directly written conductor or heating element 1149 may be wrapped around a portion of proximal wick 136 by running the conductor or heating element 1149 at least part way into internal wire passageway 136-1, around the distal end of proximal wick 136, and through external wire passageway 136-2 to return to approximately its point of origin. In another embodiment, a directly written conductor or heating element 1149 may be run primarily along external wire passageway 136-2 and not through internal wire passageway 136-1. The heating element 1149 may, when personal vaporizer unit 100 is activated, heat proximal wick 136 in order to facilitate vaporization of a substance.

Figure 114A:
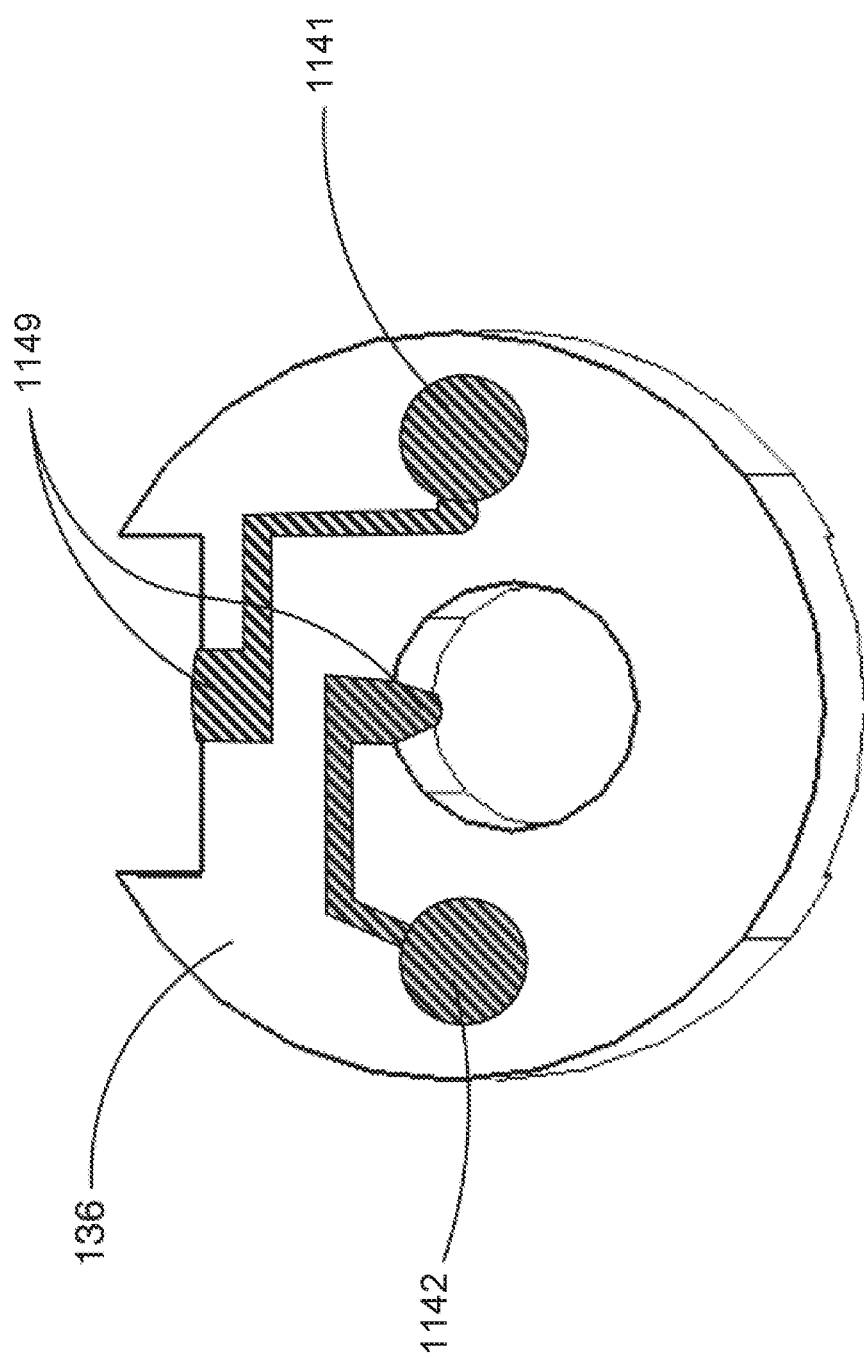

FIG. 114A is a view of the proximal end that demonstrates DW heating element contact points for energizing the heating element. FIG. 114A illustrates an end view of contact points for a directly written heating element disposed through a proximal wick element of a personal vaporizer unit. Contact pads 1141-1142 to make electrical connections with heating element 1149 may also be directly written to proximal wick 136. As shown in FIG. 114A, contact pads 1141-1142 are directly written to an end (e.g., proximal end) of proximal wick 136. These contact pads are electrically connected to heating element 1149 by directly written conductors and/or a portion of heating element 1149.

Figure 115:
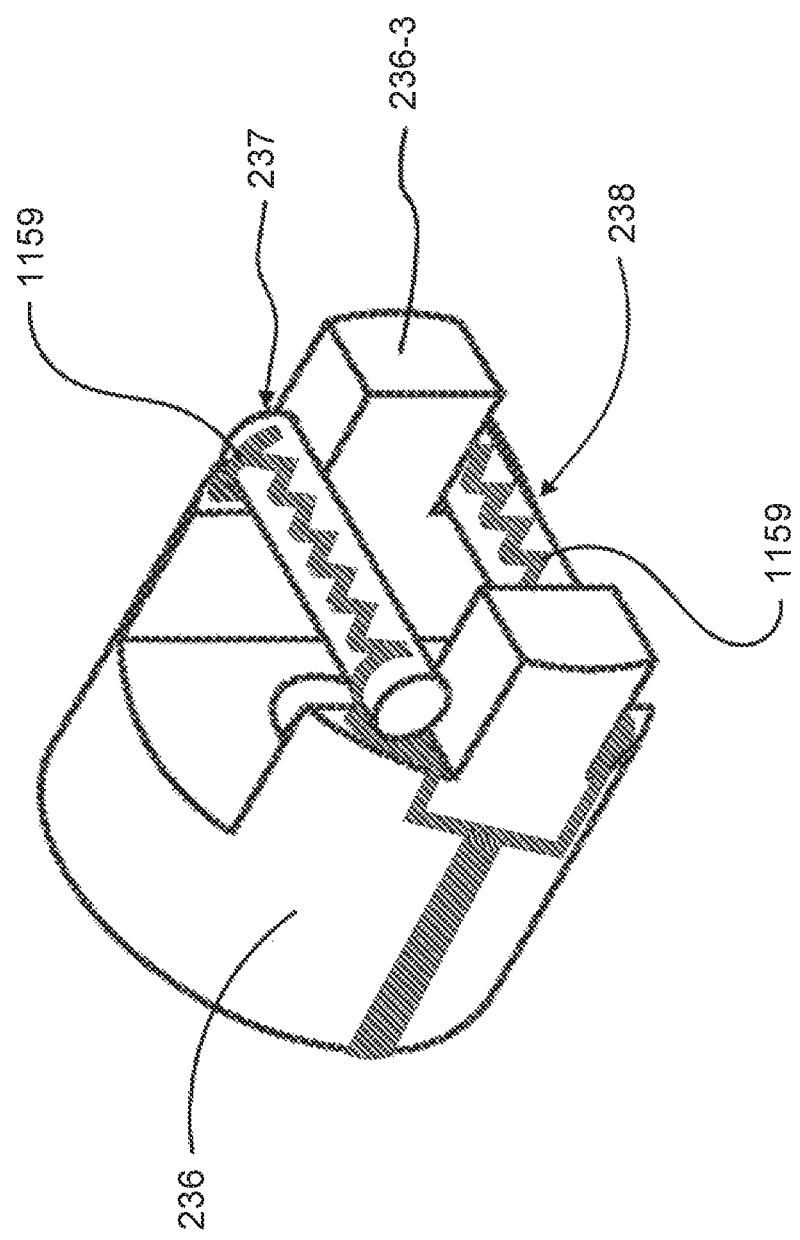

FIG. 115 is a perspective view showing directly written heating elements disposed on the wire guides of FIG. 59. FIG. 59A illustrates a heating element disposed through the proximal wick and around the wire guides. In this embodiment, the heating element may be directly written to the wire guides to replicate and perform the function of the heating element embodied in FIG. 59A. As can be seen in FIG. 115, a directly written conductor or heating element 1159 may be written on wire guide 237 and/or wire guide 238. Contact with heating element 1159 may be made by directly written conductors connected to contact pad on the proximal end of wick 236.

Figure 115A:
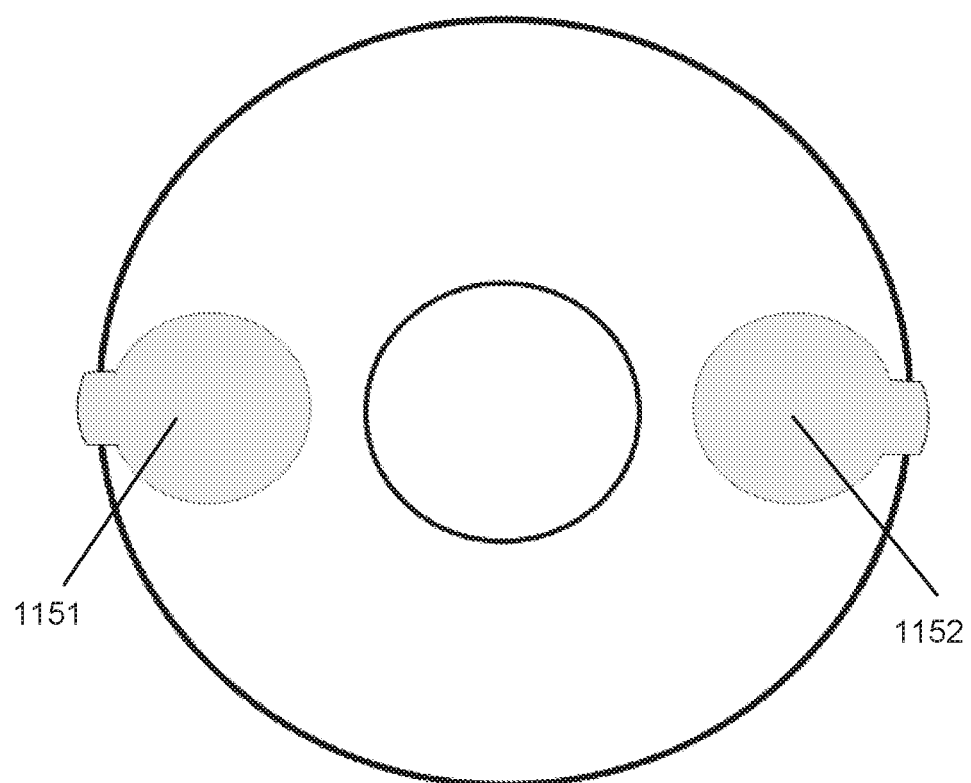

FIG. 115A illustrates an embodiment of a directly written heating element viewed at the proximal end. FIG. 115A illustrates DW heating element contact points for energizing heating element. An alternative embodiment embeds wire contacts into proximal wick to facilitate energizing the heating element. FIG. 115A illustrates an end view of contact points on a wick which supports wire guides having directly written heating elements. As shown in FIG. 115A, contact pads 1151-1152 are directly written to an end (e.g., proximal end) of proximal wick 236. These contact pads are electrically connected to heating element 1159 by directly written conductors and/or a portion of heating element 1159 interfacing with directly written conductors on proximal wick 236.

Figure 116:
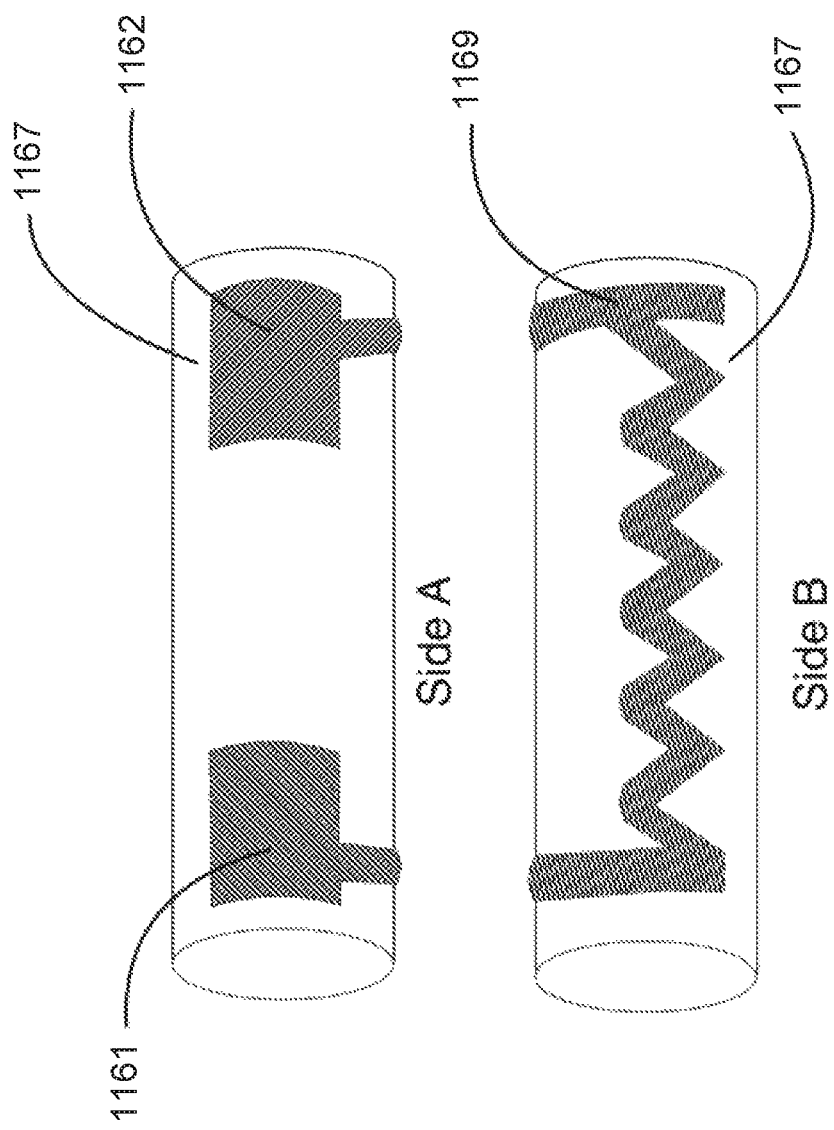

FIG. 116 is a view of wire guides shown in FIG. 59A with DW heating element. In this embodiment wire guides have a DW heating element. The top example shows the contact pads that would be in direct contact with the proximal wick. The bottom example shows the DW heating element. FIG. 116 illustrates two opposing side views of a wire guide that has a directly written heating element. As can be seen in FIG. 116, on one side of a wire guide 1167 (e.g., wire guide 237), contacts pads 1161 and 1162 are directly written. When assembled, these contact pads 1161-1162 would be in direct contact with conductors on a wick (e.g., wick 236). On the other side of wire guide 1167, an example directly written heating element 1169 is illustrated.

Figure 117:
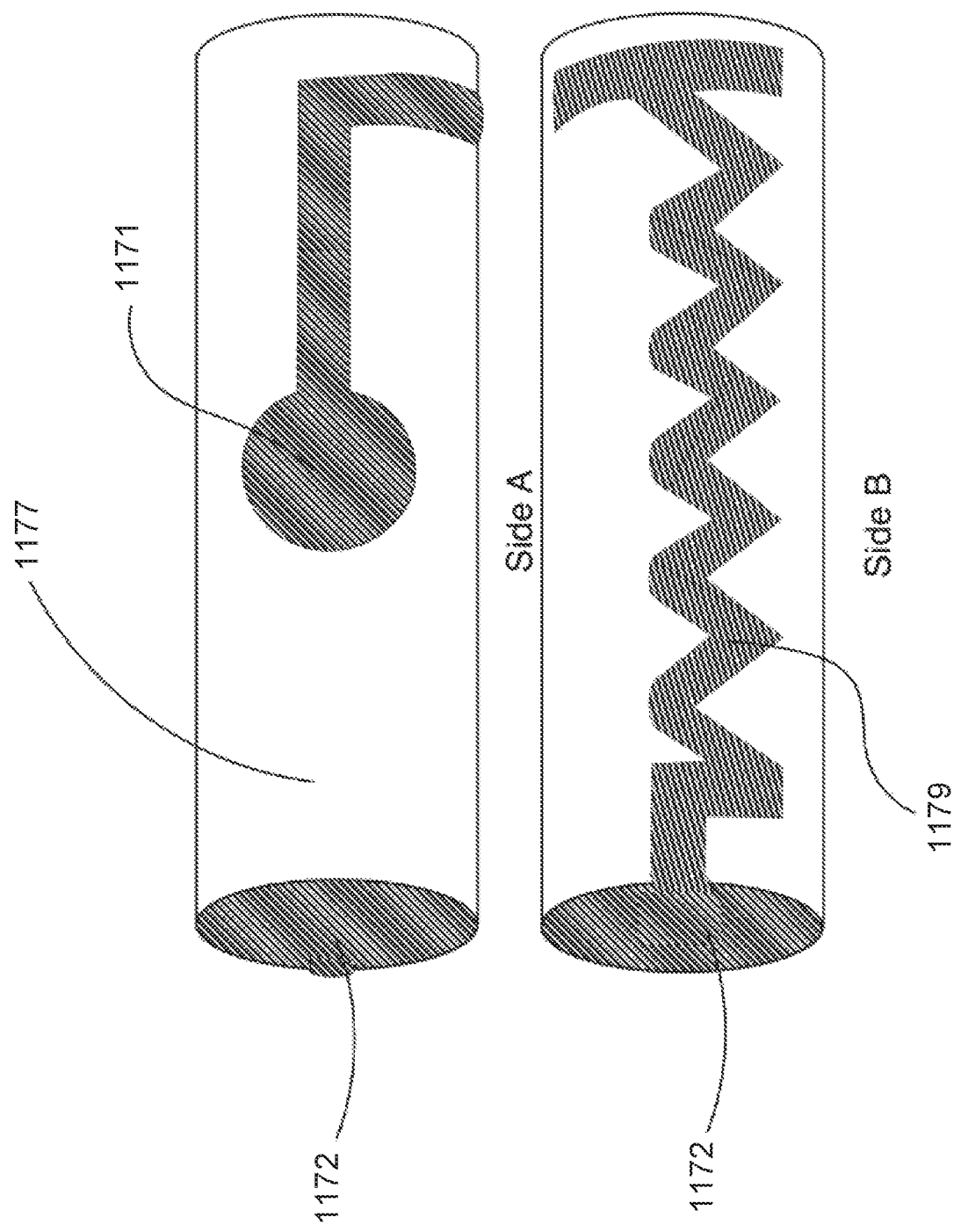

FIG. 117 illustrates two opposing side views of a support element that has a directly written heating element. FIG. 117 illustrates a cylindrical support element. As can be seen in FIG. 117, on one side of a support element 1177 (e.g., wire guide 237), a first contact pad 1171 is directly written. A second contact pad 1172 is placed on an end of the support element. On the other side of support element 1177 from the first contact pad, an example directly written heating element 1179 is illustrated.

Figure 118:
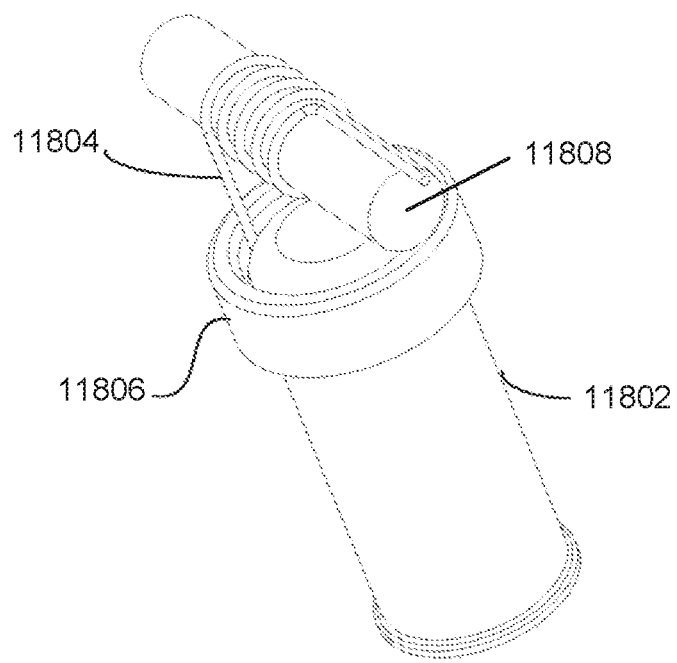

FIG. 118 illustrates a coiled wire heating element and cylindrical support member. In this embodiment the heating element would be directly written to the support member 11808 to replicate and perform the function of the heating element 11804. In the embodiment with a directly written heating element, there would be direct contact with the directly written heating element to the inner contact member 11802 and direct contact to the outer contact sleeve or pressure member 11806. FIG. 117 illustrates a support member of FIG. 118 with a directly written heating element. In this embodiment, the support member has a directly written heating element. The top example (side A) shows the contact pads that would be in direct contact to the inner contact member shown as the central contact 11802 and in contact to the outer contact sleeve shown as the end contact (not shown). The bottom example (side B) shows the directly written heating element.

FIG. 204 illustrates exemplary printed heater configurations. In particular, FIG. 204 illustrates exemplary arrangements of the DW heating element as applied to a substrate. Heater configurations 20402 and 20408 illustrate exemplary heater configurations with maximized relief for maximized air flow. Heater configuration 20406 illustrates a vertical heater with traces printed on both sides and with ink path that proceeds through the two holes. Heater configuration 20404 includes a maximized surface for the heater traces which may maximize the heat. Each embodiment illustrates contact pads on the edges for connecting with the battery for receiving current/power for heating up. The contact pads or the heater configurations may be on either side of the substrate.

The Use of Infra-Red (IR) Reflective and IR Emissive Ceramics

Materials such as certain ceramics, glasses, metals or metal coatings, and minerals such as quartz that have functional properties relating to an intrinsic ability to either be IR reflective, IR emissive, or IR absorptive may be used. These materials may be used to comprise the heating element support member, a sleeve or encasing for the heating element, adjacent wick, and the component of the vaporizer unit that embodies the inner surface of the vaporization chamber. The "vaporization chamber" and "inner surface of the vaporization chamber" are illustrated in FIG. 119 in one embodiment.

Figure 119:
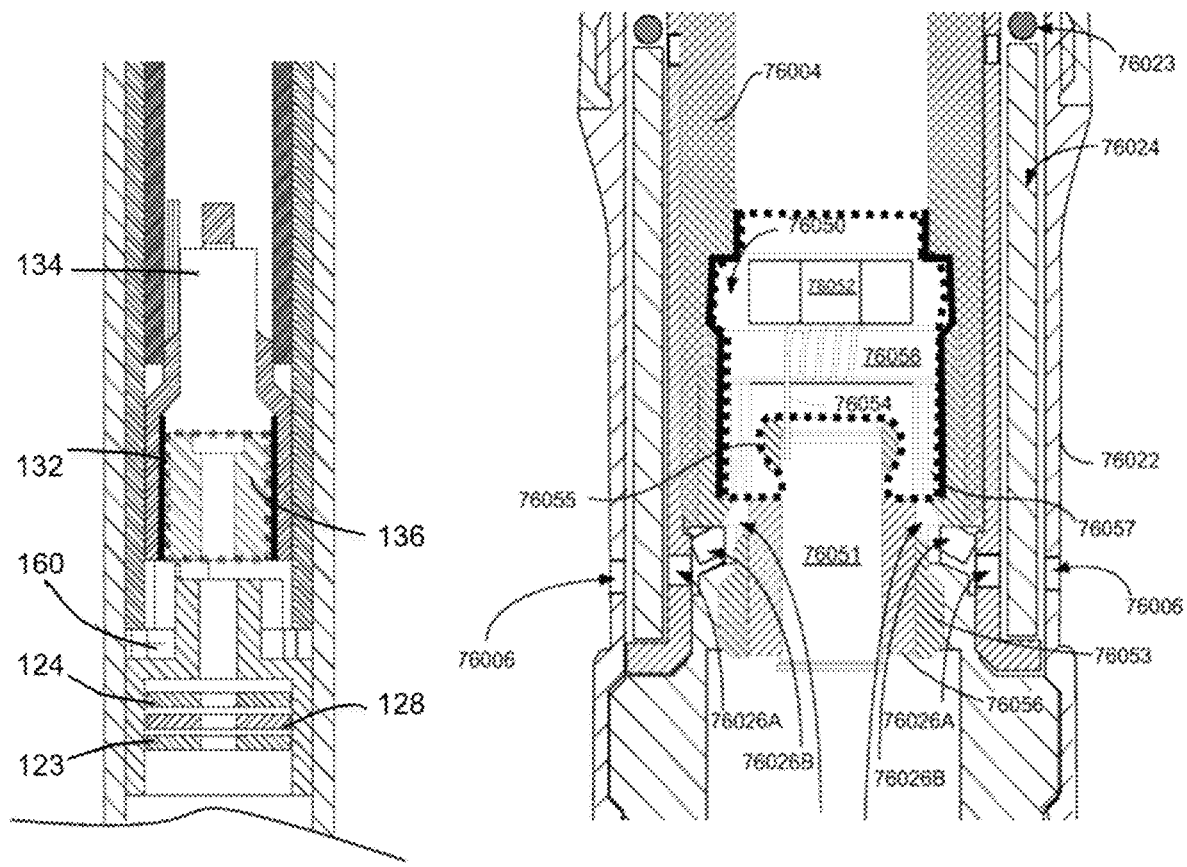
Figure 120:
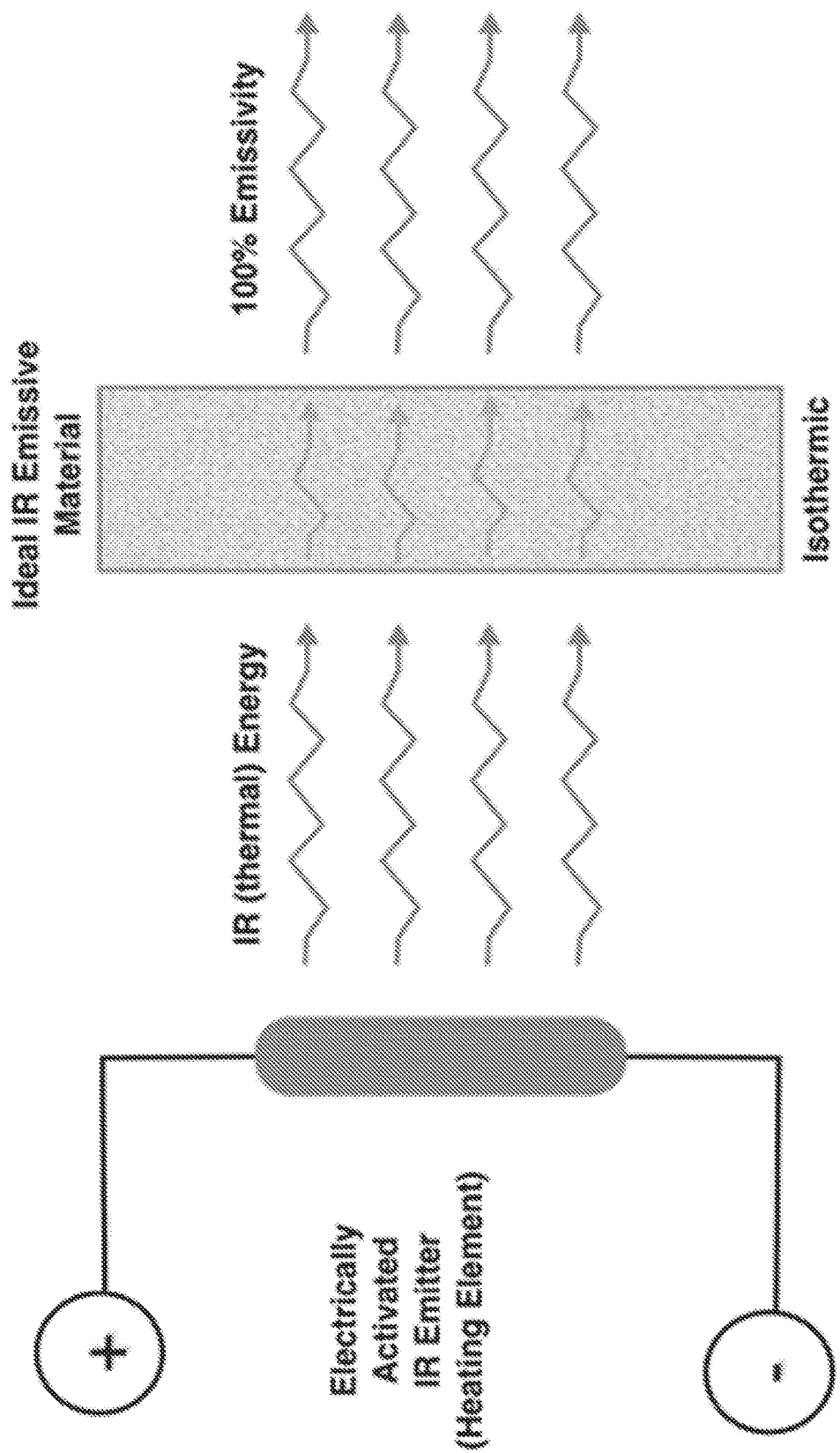
Figure 121:
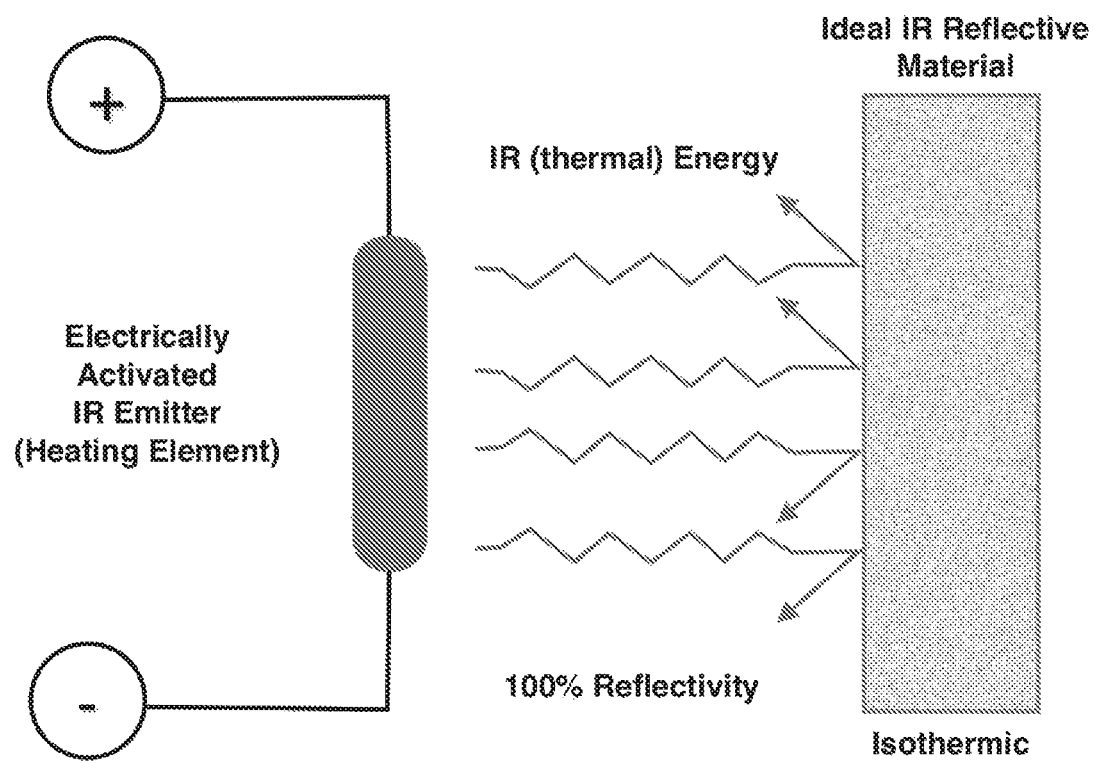
Figure 122:
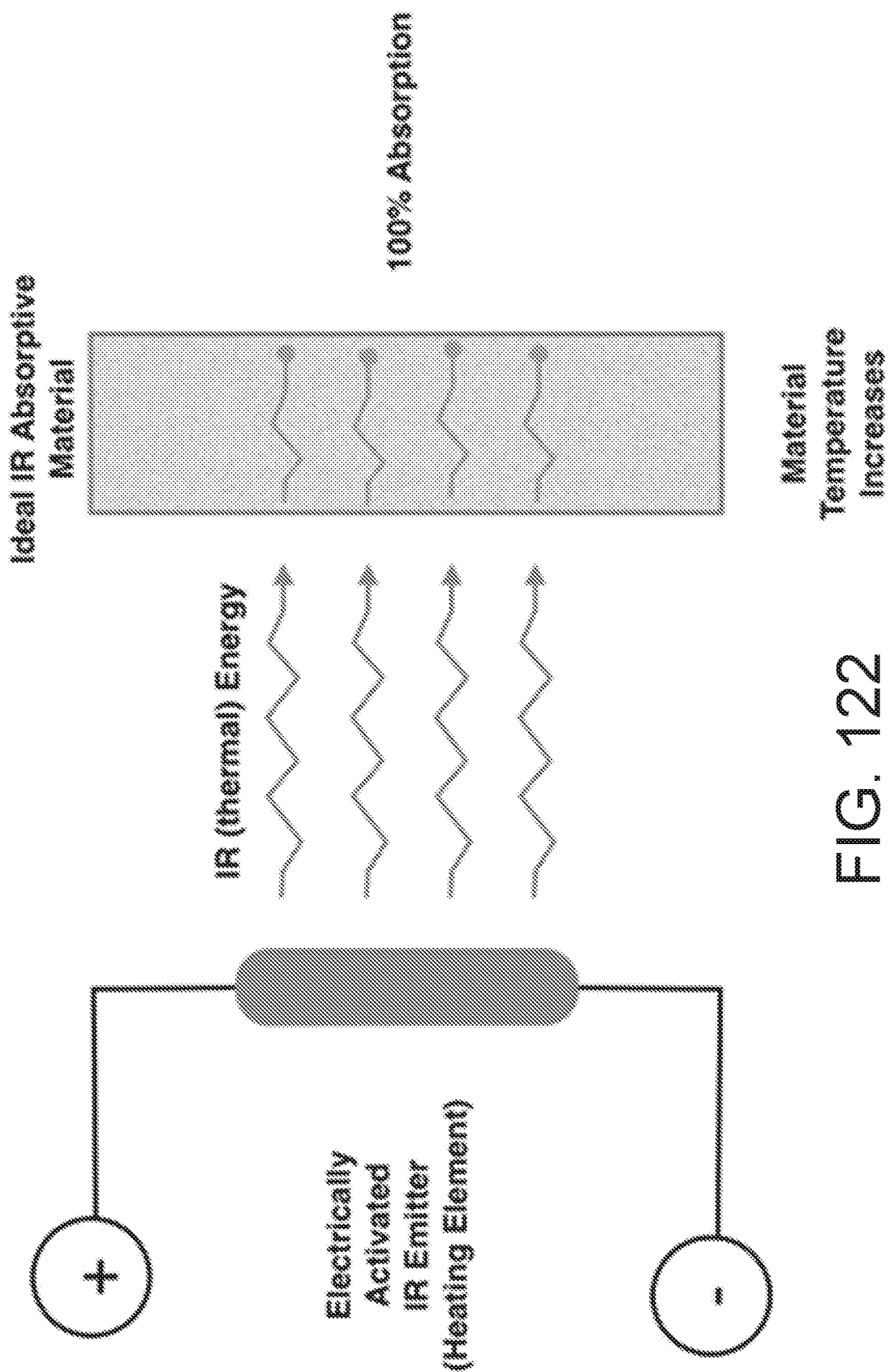
Figure 123:
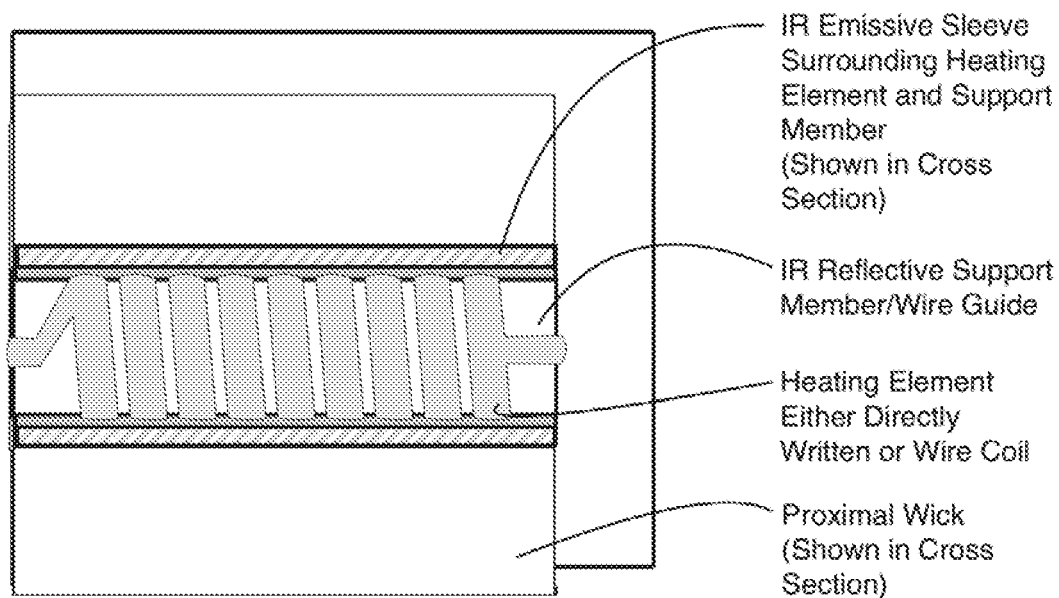

FIG. 119 illustrates a vaporization chamber cross section. In particular, the left portion of FIG. 119 is a vaporization chamber and the right portion of FIG. 119 illustrates a vaporization chamber inner surface. In the left portion of FIG. 119, the distal end portion of personal vaporizer unit comprises outer main shell 102, light pipe sleeve 140, and atomizer housing 132, distal wick 134, proximal wick 136, PC-board 123, PC-board 124, spacer 128, and main housing 160. FIG. 119 also illustrates cartridge (not labeled) inserted into the distal end of a personal vaporizer unit. The cartridge may hold a substance (e.g., a liquid or gel) in direct contact with distal wick 134. The substance may be drawn through distal wick 134 to be vaporized inside atomizer assembly. The atomizer assembly comprises atomizer housing 132, distal wick 134, proximal wick 136, and a heating element (not shown). The right portion of FIG. 119 illustrates vaporizer assembly 76020 in a cut away view to show cap 76021, outer reservoir cover 76022, a resilient O-ring 76023, absorptive ceramic reservoir 76024, a supportive inner reservoir sleeve 76025, an atomizer assembly 76050 and a supportive atomizer fluid interface 76027. As shown in FIG. 119, absorptive ceramic reservoir 76024 may be fluidly coupled with the atomizer assembly 76050 for providing the liquid to the atomizer assembly 76050, in response to aspiration by the user. As shown, air intake ports 76006 may extend through outer reservoir cover 76022, and may be fluidly coupled with the absorptive ceramic reservoir 76024 for bubbling air into the absorptive ceramic reservoir in response to aspiration by the user. The vaporizer includes an oral aspiration tube 76004 for transporting vapor to a user's mouth. A first set of liquid transport apertures 76026A may extend through supportive inner reservoir sleeve. A second set of liquid transport apertures 76026B may extend through supportive atomizer fluid interface for transporting liquid aspirated from the absorptive ceramic reservoir 76024 through the supportive atomizer fluid interface 76027. Splatter shield 76052 may be disposed within the oral aspiration tube 76004. Splatter shield 76052 may be fluidly coupled with lumen of the oral aspiration tube 76004 for substantially shielding the user's mouth from liquid splatter when the user's mouth aspirates the oral aspiration tube 76004. Wick element 76057 and heating element 76054, first pressure member 76055, inner contact member 76051, insulator 76056 and outer contact member 76053 may also be present.

The use of IR reflective material(s) for the heating element may be intended to increase the efficiency of the heating element by directing IR thermal energy away from the heating element support member or wire guide. The use of IR emissive or IR absorptive material(s) for the heating element may be intended to incorporate the heating element support member or wire guide as a part of the heating element where the heating element and heating element support member or wire guide are intended to together serve the function of the heating element. The use of the IR emissive or absorptive material(s) as the support member may allow for the functional "heating element" comprised of both the heating element and the support member to have a larger effective surface area and more uniform transmission of the IR (thermal) energy generated from the heating element. The use of IR emissive material(s) functions to encase, cover, or shield the heating element preventing direct contact of the heating element to the vaporization chamber while still allowing for the transfer of IR thermal energy into the vaporization chamber. The use of IR reflective material(s) for the construction of the component that comprises the inner surface of the vaporization chamber functions to reduce thermal loss and increase the thermal efficiency of the heating element. The inner surface of the component that comprises the inner surface of the vaporization chamber may be coated or treated with material(s) that serves to make the inner surface IR reflective.

IR reflectivity may be the intrinsic property of a material to reflect IR energy as opposed to absorbing, or transmitting the IR energy. In general, for any opaque object, emissivity is the opposite (reciprocal) of reflectivity, and Emissivity+Reflectivity=100% of IR energy. Similarly, for translucent objects, Emissivity+Reflectivity+Transmission=100% of IR energy. Exemplary IR reflective materials that can be used may include: 1) ceramic (certain formulation of macroporous, microporous, and structural Alumina based ceramics are IR reflective); 2) metals (e.g. gold, silver, and aluminum can be used as IR reflectors); 3) dielectrics such as fused silica substrate; 4) specialty layered materials such as alternating layers of polystyrene and tellurium; and 5) combination application(s) such as a gold-coated alumina based ceramic could be utilized to maximize IR reflectivity of the component.

IR emissivity may include the intrinsic property of a material to emit, or transmit IR energy as opposed to absorbing (except where indicated otherwise), or reflecting the IR energy. Examples of IR emissive materials may include ceramic (formulations of macroporous, microporous, and structural alumina based ceramics). Zirconia, Ytria Stabilized Zirconia, and most Alumina Zirconia mixed ceramics are IR emissive or absorptive. Other examples include metals (e.g. steel and titanium are IR emissive or absorptive dependent on the surface roughness and thickness of the metal), sapphire, AL203, zinc selenide, germanium, and/or silicon.

FIGS. 120-122 illustrate examples of IR emissivity, IR reflectivity, and IR absorption. FIG. 120 illustrates an idealized diagram of IR emissivity. FIG. 121 illustrates an idealized diagram of IR reflectivity. FIG. 122 illustrates a diagram of IR absorption. When the heating element is comprised of a wire or conductive (flowable) material, or when the heating element is thermally coupled to the support member (either by direct contact of a metal wire or ribbon or through the process of writing the heating element directly to the support member), then the material property of the support member in relation to IR reflectivity, IR emissivity, or IR absorption may influence the intended functionality of the heating element and subsequent vaporization. In one embodiment, the heating element may be substantially L-shaped or created using the process of direct writing and is substantially L-shaped. The heating element may comprise a directly written element and be arranged utilizing IR reflective and emissive materials to increase thermal efficiency or to functionally isolate the heating element from direct contact with the vaporization chamber or fluid to be vaporized.

FIG. 123 illustrates a cross section of a proximal wick shown in FIG. 35 with a heating element. In this embodiment, the heating element and support member/wire guide are positioned in the internal wire passageway (136-1) of the proximal wick (136). The support member/wire guide is comprised of an IR reflective material. The heating element could be comprised of a wire coil or be directly written (as pictured). The heating element is positioned inside of an IR emissive sleeve (shown in cross section) that serves to functionally isolate the heating element from the proximal wick with minimal thermal isolation of the heating element. Electrical contact (not shown) to the heating element is achieved through a contact traveling in the external wire passageway (136-2) and the other contact at the proximal aspect of the internal wire passageway (136-1).

FIG. 124 shows an embodiment of the heating element and support member/wire guide that is a tube and positioned in the internal wire passageway (136-1) of the proximal wick (136). The support member/wire guide is comprised of an IR emissive material. In A) the heating element is directly written and pictured positioned in the internal wire passageway (136-1). In B) the directly written support member/wire guide is also shown as being a directly written heating element. In C) the heating element is an embodiment comprised of a wire. In D) the support member/wire guide is shown without a directly written or wire heating element. The heating element support member is IR emissive and positioned in the internal wire passageway, the internal positioning of the heating element serves to functionally isolate the heating element from the proximal wick with minimal thermal isolation of the heating element. Electrical contact (not shown) to the heating element is achieved through a contact traveling in the external wire passageway (136-2) and the other contact at the proximal aspect of the internal wire passageway (136-1).

FIG. 125 shows a cross-section view of a proximal wick with a hollow support member positioned in the internal wire passageway. In this embodiment the heating element and support member/wire guide are positioned in the internal wire passageway (136-1) of the proximal wick (136) (shown in cross section). The proximal wick (136) is comprised of an IR emissive material. The support member/wire guide (shown in cross section) is a tube in this embodiment and comprised of an IR emissive material. The heating element could be comprised of a metal wire/ribbon or be directly written (as pictured). The Heating element when positioned inside the tubular support member which serves to functionally isolate the heating element from the proximal wick with minimal thermal isolation of the heating element. Electrical contact (not shown) to the heating element is achieved through a contact traveling in the external wire passageway (136-2) and the other contact at the proximal aspect of the internal wire passageway (136-1).

FIG. 126 is a side perspective view of the IR reflective housing for the proximal wick. FIG. 127 illustrates a distal end view and a proximal end view of the IR reflective housing and proximal wick assembly. In this embodiment, an IR reflective tube is added to the vaporizer assembly. The IR reflective tube houses the proximal wick. The wall thickness of the IR reflective tube/housing is dependent on the IR reflective properties of the material utilized in the composition of the part. Additionally, an IR reflective coating may be utilized on the interior surface of the IR reflective tube/housing in order to achieve maximum IR reflectance from the heating element.

FIG. 128 is a perspective view of an atomizer housing and wicks of a personal vaporizer unit and includes an exploded view of the atomizer housing, wire guides, and wicks. The atomizer housing and wicks shown in FIG. 128 is one embodiment for use with proximal wick 236. The embodiment uses atomizer housing 232, distal wick 234, proximal wick 236, wire guide 237, and wire guide 238. Proximal wick 236 is configured to fit within atomizer housing 232. Proximal wick 236 includes internal wire passageway 236-1. This wire passageway 236-1 allows a conductor or a heating element (not shown) to be positioned through proximal wick 236 (via internal wire passageway 236-1). The conductor or heating element may be positioned around wire guide 237 and wire guide 238. Thus, a conductor or heating element may run through wire passageway 236-1, around wire guides 237 and 238, and then back through wire passageway 236-1 to return to approximately its point of origin.

FIG. 129 is an alternative embodiment of FIG. 128. In this embodiment, the proximal wick (136, 236) has been reduced in diameter such that it can be positioned inside of the proximal wick housing, which is comprised of an IR emissive material. The proximal wick is ideally comprised of a macroporous or microporous ceramic in which the void space in the material secondary to the porosity is occupied by liquid. The proximal wick and proximal wick housing are further positioned inside of the reflective housing, which is comprised of an IR reflective material. The heating element (not shown) is positioned exterior to the proximal wick housing and interior to the reflective housing such that IR (thermal) energy emitted from the heating element should be reflected from the interior surface of the reflective housing and through the wall of the proximal wick housing to vaporize the liquid in the proximal wick. The heating element is positioned between the proximal wick housing and reflective housing, either on the inner surface of the reflective housing, or embedded in the proximal wick housing. An alternative embodiment of this configuration omits the use of the proximal wick and the space previously occupied by the proximal wick would now be defined as the vaporization chamber. Liquid is driven from the distal wick (not labeled) through the vacuum pressure generated by the user inhalation into the void space of the proximal wick housing and vaporized. This configuration in either embodiment serves to functionally isolate the vaporization chamber from the heating element while minimizing any thermal isolation.

FIG. 130 is a proximal wick housing with heating element and embedded electrical contacts. The embodiment of the proximal wick housing which is comprised of an IR emissive material such that the heating element being directly upon, or in near proximity to the exterior surface of the proximal wick housing allows for the emitted IR (thermal) energy from the heating element to pass through the wall of the proximal wick housing. This embodiment shows a heating element that is directly written onto the exterior surface of the proximal wick housing. The pictured embodiment also shows embedded wire contacts intended to facilitate the electrical connection required to activate the heating element. The heating element could also be comprised of a metal wire/ribbon positioned on the exterior surface of the proximal wick housing, in that embodiment the proximal wick housing serves the function of the heating element support member. In another embodiment the heating element comprised of a metal wire/ribbon is embedded into the proximal wick housing. In one embodiment the proximal wick housing would have the proximal wick positioned internally. In an alternative embodiment the proximal wick is omitted and the interior volume of the proximal wick housing serves as the vaporization chamber where liquid is drawn into the space from the distal wick secondary to the vacuum pressure generated by the user when inhaling and subsequently vaporized.

FIG. 131 illustrates one embodiment for the IR reflective housing and proximal wick housing. In the illustrated embodiment, the proximal wick housing has the heating element directly written onto the exterior surface of the component and embedded wire contacts to facilitate energizing the heating element. The component is comprised of an IR emissive material. The IR reflective housing is comprised of an IR reflective material and in an alternative embodiment be coated with an IR reflective material (e.g. gold) to maximize IR reflectance of the component. The proximal wick housing is comprised of an IR emissive material.

FIG. 132 illustrates an alternative embodiment where the heating element is positioned on the internal surface of the IR reflective housing. As was illustrated in FIG. 131, the embedded wire contacts are utilized to facilitate energizing the heating element. The IR reflective housing is shown with a directly written heating element and the component is comprised of an IR reflective material. The proximal wick housing is shown with a directly written heating element and the component is comprises of an IR reflective material. The embedded wire contact facilitates energizing the heating element.

FIG. 133 illustrates a proximal end view of one embodiment of a complete assembly. FIG. 134 illustrates a cross-section view of one embodiment of a complete assembly. The proximal wick housing is positioned inside a housing with an IR reflective material. Likewise, the proximal wick housing may be positioned inside a housing with an IR emissive material or a porous ceramic material.

FIG. 135 is an alternative embodiment utilizing an internal IR reflector/passive condenser. In particular, FIG. 135 shows an alternative embodiment where the proximal wick is replaced by a new component, an internal IR reflector that also serves as a passive condenser. The function of this component is to first reflect IR (thermal) energy back into the vaporization chamber which is defined as the void space between the internal surface of the proximal wick housing and the external surface of the internal IR reflector/passive condenser. The second function of the component is to prevent the escape of liquid from the vaporization chamber to the airflow channel that delivers the vapor through the aspiration tube to the user for inhalation. Holes positioned in the distal portion of the internal IR reflector/passive condenser serve to provide a means for the vapor to travel from the vaporization chamber to the flow channel. The component is to be positioned such that the outer diameter of the proximal end is of such a tolerance to match the inner diameter of the proximal wick housing in order to achieve a seal that prevents liquid from escaping through the interface of the two components. In another embodiment a seal between the internal IR reflector/passive condenser and the proximal wick housing is achieved through the use of an O-rings(s) or gasket(s), or through the use of a high temperature bonding agent or adhesive to achieve a liquid tight union between the proximal aspects of the two components. In the preferred embodiment illustrated in FIG. 135 the proximal wick housing is comprised of a porous material such as microporous ceramic such that liquid that is not vaporized and passively condensed is drawn into the void space of the proximal wick housing to facilitate subsequent vaporization of the liquid on the next activation cycle of the vaporizer and to prevent liquid from accumulating in the vaporization chamber. The internal IR reflector/passive condenser is comprised of a material that is IR reflective, and may be further coated with an IR reflective material to further increase the IR reflectance of the component, furthermore the component is composed of a functionally non-porous material. The heating element (not shown) is positioned between the proximal wick housing and reflective housing, either on the outer surface of the proximal wick housing or the inner surface of the reflective housing, or embedded in the proximal wick housing.

FIG. 136 illustrates the positioning of the components that comprise the new assembly. In this embodiment the proximal wick housing is illustrated as being comprised of a porous material and having a heating element directly written onto the external surface of the component with embedded metal contacts facilitating the electrical connection required to energize the heating element. The heating element could also be positioned on the internal surface of the IR reflective housing, or be positioned in the void space defined by the difference in the internal diameter of the IR reflective housing and the outer diameter of the proximal wick housing. The IR reflective housing component is comprised of IR reflective and non-porous material. The proximal wick housing is shown with directly written heating element on exterior surface and a component comprised of an IR emissive and porous material. The internal IR reflector/passive condenser component is comprised of IR reflective and non-porous material.

FIG. 137 shows the internal IR reflector/passive condenser from multiple perspectives. This component is positioned in the location occupied by the proximal wick in the current referenced embodiment(s) of the vaporizer. The component is comprised of a non-porous or liquid impermeable material that is IR reflective. Additionally, the component could have the external surface coated with a material to further increase IR reflectance (e.g. gold). The component is positioned such that the external surface of the proximal end is in direct contact with the internal surface of the proximal wick housing. The component serves two primary functions: 1) IR Reflector—Reflects IR (thermal) energy that impacts the component's external surface back into the vaporization chamber (which is defined as the lateral void space between the external surface of the internal IR reflector/passive condenser and the internal surface of the proximal wick housing, distally the vaporization chamber is contained by the proximal surface of the distal wick); 2) Passive Condenser—the component serves to prevent the escape or "leakage" of liquid that is not vaporized in the vaporization chamber via directing the vapor through holes or "ports" that are arranged orthogonally to the long axis of the component, and through the functional "sealing" or "plugging" of the proximal end of the vaporization chamber. Furthermore, the holes or ports may be configured to optimize or attenuate the "draw" or inhalation resistance of the vaporizer. The holes or ports are fluidly coupled to the airflow passageway that travels through the vaporizer and functions as an aspiration tube such that liquid is vaporized in the vaporization chamber and is then forced, through the vacuum pressure generated by the action of inhalation, by the user through the holes or ports and then into the proximal airflow passageway or "aspiration tube" to the user for inhalation.

FIG. 138 illustrates some relevant features of the internal IR reflector/passive condenser component. The volume of the vaporization chamber can be controlled by modifying the length of the lateral proximal surface of the internal IR reflector/passive condenser that directly contacts the proximal wick housing, allowing for optimization of the vaporization chamber volume to the preferred heating element size and energy demand. FIG. 138 also illustrates how the angled surface of the component that connects the lateral surface which engages the proximal wick housing and the distal narrow aspect that contains the "holes" or "ports" for the vapor to pass through can be geometrically optimized to better reflect IR (thermal) energy back into the vaporization chamber. FIG. 138 further demonstrates the flat aspects of the component that engage the proximal wick housing may contain one or more grooves to accommodate an O-rings(s) or similar gasket(s) in order to achieve a liquid tight seal between the internal IR reflector/passive condenser and the proximal wick housing. The grooves in the component allow for the use of o-ring(s) to achieve a seal between the component and the proximal wick housing.

FIG. 139 illustrates the nested arrangement of the components that comprise the new assembly. The proximal external surface of the internal IR reflector/passive condenser is in direct contact with the internal surface of the proximal wick housing to affect a liquid tight seal preventing escape of liquid from the vaporization chamber. There is a radial gap resulting from the difference in the outer diameter of the proximal wick housing and the inner diameter of the IR reflective housing. This radial gap facilitates the heating element which can be positioned either: 1) directly written on the external surface of the proximal wick housing; 2) directly written on the internal surface of the IR reflective housing; 3) A metal wire/ribbon occupying the radial gap between the external surface of the proximal wick housing and the internal surface of the IR reflective housing. The IR reflective housing is comprised of IR reflective non-porous material. The proximal wick housing is shown positioned inside IR reflective housing and comprised of IR emissive and porous material. The internal IR reflector/passive condenser shown positioned inside proximal wick housing is comprised of IR reflective and non-porous material.

FIG. 140 illustrates a cross-section view of the nested arrangement of the components that comprise the new assembly. The relative dimensions of the internal reflector are shown for general illustrative purposes. The ideal embodiment of the internal IR reflector/passive condenser component optimizes the following characteristics: 1) airflow from the vaporization chamber through the "holes" or "ports" in the distal narrow portion of the component in order to affect resistance similar to that created by a filtered cigarette; 2) the length as measured in the proximal to distal dimension of the flat surface of the proximal aspect of the component that serves to create a functionally liquid tight seal between the internal IR reflector/passive condenser and the proximal wick housing in order to both a) achieve a liquid tight seal that prevents liquid from escaping the vaporization chamber; b) achieve the optimal size of the vaporization chamber to allow for optimal sizing of the heating element in relation to vaporization chamber void space in order to maximize the overall efficiency of the device; 3) optimization of the geometry of the angled portion of the internal IR reflector/passive condenser that comprises the central part of the component. This is the region of the component between the flat surface that is in direct contact with the proximal wick housing and the narrow member that contains the "holes" or "ports" for the vapor to exit the vaporization chamber. The angle of the component and the concavity or parabolicity of the surface may be selected in order to maximize the IR reflectance of the component to achieve maximum reflection of IR (thermal) energy back into the vaporization chamber. The IR reflective housing is comprised of IR reflective non-porous material. The proximal wick housing is shown positioned inside IR reflective housing and comprised of IR emissive and porous material. The internal IR reflector/passive condenser shown positioned inside proximal wick housing is comprised of IR reflective and non-porous material.

FIG. 141 shows the positioning of an alternative new assembly in the distal portion of the vaporizer. Comparing with the left portion of FIG. 119, the space previously occupied by the proximal wick (136, 236), the wire guides (237, 238), and the heating element(s) (139, 239) is replaced with a new assembly.

The Use of Viscosity, Temperature, and Velocity/Flow Measurement Sensors

Sensors may be used for the measurement of the viscosity of the liquid solution contained in the cartridge. The sensor(s) may be used for the measurement of the temperature of the liquid solution contained in the cartridge. Likewise, viscosity and temperature sensors may measure the viscosity and temperature of the liquid in the cartridge for the purpose of modulating the activation of the heating element to optimize heating element performance in relation to the temperature and viscosity of the liquid. Performance characteristics of the heating element include time to maximum current input or heating element "warm up", duration of the time period between activation and maximum current, the time between maximum current and deactivation or heating element "cool down" as well peak electrical current delivered to the heating element and duration of time for peak electrical current delivered to the heating element.

The use of viscosity and temperature sensors for measuring the viscosity and temperature of the liquid in the cartridge may be for the purpose of controlling the activation of the device within an established operating range of temperature and viscosity. Preventing activation of the device under conditions that are below the cut-off range for operation and similarly preventing activation of the device at temperature above cut-off range for activation. The use of viscosity and temperature sensors measuring the viscosity and temperature of the liquid in the cartridge may be for the purpose of preventing misuse or abuse of the device by using the known temperature dependent viscosity of the proprietary liquid formulation used in the device and preventing activation of the device if a liquid used in the device does not comport with the known temperature dependent viscosity of the intended proprietary liquid formulation.

The use of a temperature sensor in the area of the vaporization chamber may be in order to monitor the temperature of the vaporization chamber and relay that temperature data to the PCB/CPU of the device that controls the heating element activation in order to modulate the current flow to the heating element to maintain optimum temperature conditions within the vaporization chamber.

The use of a temperature sensor in the area of the vaporization chamber may be in order to monitor the temperature of the vaporization chamber and relay that temperature data to the PCB/CPU of the device that controls the heating element activation in order to deactivate the device if temperatures above the desired activation range (for example <280° C. for Glycerol based solutions and (<400° C. for propylene Glycol based solutions) of the vaporization chamber are detected. Upon deactivation the device would display an error code using the LED indicator and also transmit the error to the charging case or digital interface (computer, smart phone, tablet or similar) to be relayed to the user through previously described data transferring methods. Note: The desired activation parameters of the device are dependent on the formulation of the liquid and may/should be different secondary to the addition of medications, water, alcohols, or other ingredients added to the preferred liquid formulation.

The use of a temperature sensor(s) in the area of the vaporization chamber may be in order to monitor the temperature of the vaporization chamber and relay that temperature data to the PCB/CPU of the device that controls the heating element activation in order to deactivate the device if the heating element is not capable, due to malfunction, to achieve the desired temperature range to achieve vaporization/volatilization/atomization of the liquid. Upon deactivation the device would display an error code using the LED indicator and also transmit the error to the charging case, or other digital interface (computer, smart phone, tablet or similar) to be relayed to the user through previously described data transferring methods.

A method for preventing the degradation/conversion of glycerol to acrolein (when producing a vapor from glycerol through the application of heat) may be through the use of a temperature sensor in the area of the vaporization chamber in order to monitor the temperature of the vaporization chamber and relay that temperature data to the PCB/CPU of the device that controls the heating element activation in order to deactivate the device if temperatures in the vaporization chamber are reaching temperatures required to convert glycerol to acrolein (<280° C.).

FIG. 142 is a reference formula for the chemical conversion/degradation reaction of glycerol to acrolein. The airflow through the device may be calculated by positioning a temperature or airflow velocity or combination of temperature and airflow velocity sensor(s) in the proximal portion of the device, and a senor(s) positioned at the more distal point where the vapor is exiting the vaporization chamber. Data from the sensor(s) is sent to the PCB/CPU and transferred by previously described methods to the storage case or digital interface. The data is used in conjunction with the data generated from the more distal temperature sensor in the proximity of the heating element. A method for modulating the activation of the heating element may be based on the velocity of the airflow and temperature of the vapor to optimize delivery of the vapor product to the user such that the operating temperature of the vaporization chamber is maintained at optimal temperature regardless of the velocity of the airflow generated by the user's inhalation. A method for determining the per inhalation dose delivery of desired vapor constituent may use airflow velocity measurement(s).

Exemplary temperature sensors may include resistance thermometers. Resistance thermometers may also be called resistance temperature detectors (RTDs). Examples include carbon resistor elements, strain free elements, thin film elements, wire-wound elements, and/or coiled elements. FIGS. 143-149 illustrate exemplary RTDs and configurations.

FIG. 143 is one embodiment of an RTD. The resistance thermometer is connected to leads that pass through a sheath with an insulator. FIG. 144 is one embodiment of a wire wound RTD. There may be a glass coating over the bifilar wound platinum wire, which wraps around a ceramic core. The lead wires pass into the ceramic core to the platinum wire. FIG. 145 is one embodiment of a thin film RTD. A glass coating is over an aluminum oxide ceramic substrate that includes laser etched platinum film. A protective glass coats over the welds. The lead wire is welded to platinum film. FIG. 146 is an exemplary wiring configuration for a two wire RTD. FIG. 147 is an exemplary wiring configuration for a three wire RTD. FIG. 148 is an exemplary wiring configuration for a four wire RTD. The resistance element is shown with a bridge output and three resistors. The three wire and four wire RTD include lead resistance. FIG. 149 is an alternative embodiment of a four wire RTD. FIG. 149 includes a kelvin connection RTD.

FIG. 150 is an exemplary thermocouple wiring diagram. Thermocouples may include 1) Nickel Alloy Thermocouples: Types E, J, K, M, N, T; 2) Platinum/rhodium alloy thermocouples: Types B, R, S; 3) Tungsten/rhenium alloy thermocouples: Types C, G, E; and/or 4) Pure noble metal thermocouples: Such as Au—Pt, Pt—Pd. Thermistors in some configurations may be referred to as discreet thermistors. Examples include positive temperature coefficient (PTC) thermistor and negative temperature coefficient (NTC) thermistor.

FIG. 151 is an embodiment of types of thermistor configurations. FIG. 151 illustrates several types of thermistor configurations. FIG. 152 is an embodiment of thermistor wiring configuration. An infrared temperature sensor may also be referred to as infrared thermometer. FIG. 153 is a diagram of operation and construction of an IR temperature sensor. FIG. 154 is an exemplary configuration of an IR temperature sensor. The sensor may include a fresnel lens, IR filter, amplifier and comparator for receiving thermal energy.

There may be a viscosity sensor that is also used. For example, a micro viscometers such as a process viscosity sensor can be designed or configured in conjunction with an RTD. FIG. 155 illustrates the positioning of the viscosity and temperature senor assembly in relation to an atomizer housing and the distal wick. In this embodiment the distal wick has been reduced in height to accommodate for the sensor assembly which is positioned in the atomizer housing and is occupying the distal volume of the atomizer housing and performing the function of the distal portion of the distal wick of being in direct contact with the fluid volume contained in the cartridge (not shown). Fluid should pass through the sensor assembly and liquid temperature and viscosity measurements should be made and transmitted to the device PCB/CPU. The fluid should then be in contact with the distal wick for displacement into the vaporization chamber, undergo vaporization/volatilization/aerosolization and then to the flow channel of the device for inhalation by the user. Vacuum pressure from the user when inhaling drives the fluid from the cartridge through the sensor assembly such that the only flow path for the liquid in the cartridge to travel from the cartridge to the distal wick is through the sensor assembly.

There may be a velocity or flow sensor that is also used. For example, an RTD based flow or velocity sensor may include a constant temperature anemometer or thermal anemometer. FIG. 156 illustrates a constant temperature anemometer wiring configuration. The thermal anemometer may be comprised of two sensors: an air velocity sensor and a temperature compensation sensor. The velocity sensor is heated to an elevated temperature (relative to the surrounding air) by means of control electronics. The temperature compensation sensor senses the ambient, or surrounding, air temperature and forces the velocity sensor to stay at a constant overheat above the ambient. The sensors form two opposite legs of a Wheatstone bridge (shown in FIG. 156). The circuit forces the voltage at points A and B to be equal by means of an operational amplifier. Air flowing past the velocity sensor tends to cool the sensor, thus driving down its resistance. The operational amplifier responds by immediately delivering more power to the top of the bridge to maintain voltage equilibrium at points A and B. As more air flows past the sensor, more power is required to maintain a balanced bridge. Thus, the power going into the top of the bridge is related to the velocity of the air flowing past the sensor. This is a principle of operation for constant temperature thermal anemometers. There may be an RTD based hot wire anemometer, RTD based hot film anemometer, or RTD based calorimeter flow sensors sometimes referred to as flow modules. Air velocity or flow is measured using the temperature distribution over four heating/sensor elements with serial down/up-stream arrangement. For accurate measuring a laminar flow is required to keep up the temperature distribution gradient.

FIG. 157 is a cross section showing a proximal section of a device illustrating flow channels, a path of airflow, and positioning of a calorimeter flow sensor. In particular, FIG. 157 illustrates: A) the sensor position for the measurement of temperature for the determination of velocity/air flow; and B) the flow channels in the device that comprise the functional aspiration tube that the vapor travels from the vaporization chamber to the mouthpiece. For calorimetric measurement the sensors should be placed in the region of the device with laminar flow as illustrated.

In alternative embodiments, there may be thermal mass flow sensors that are similar to RTD based sensors utilizing heat transfer principles to determine the flow velocity of a fluid. As fluid passes across the sensor, heat is carried from the sensor to the medium. This relationship is dependent upon the flow rate. As flow increases, so does the amount of heat that is transferred. By knowing the temperature of the medium, the flow rate can be determined from the amount of voltage compensation needed to maintain a constant temperature differential.

In alternative embodiments, there may be Mass airflow sensor (MAF). The MAF may include a micro-bridge mass airflow sensor, a MEMS thermal flow sensor, or a hot wire mass airflow sensor similar to a hot wire anemometer. Alternatively, a vane meter sensor also referred to as a VAF (volume air flow) sensor may be used. A membrane MAF is a technology that utilizes a very thin electronic membrane placed in the air stream. The membrane has a thin film temperature sensor printed on the upstream side, and one on the downstream side. A heater is integrated in the center of the membrane which maintains a constant temperature similar to the hot-wire approach. Without any airflow, the temperature profile across the membrane is uniform. When air flows across the membrane, the upstream side cools differently from the downstream side. The difference between the upstream and downstream temperature indicates the mass airflow.

FIG. 158 illustrates viscosities of aqueous glycerol (Glycerin) solutions in centipoises/mPa. FIG. 159 illustrates temperature viscosity of anhydrous glycols. This area for expansion is related to expanding the methods of activation and controlling the activation of the device and generally the method of operating a vaporizer and element for directly contacting the liquid to be turned into vapor and oral aspiration tube. The wick element may directly contact a liquid to be changed into a vapor and includes a viscosity sensor or viscosity and temperature sensor assembly. An oral aspiration tube that may be fluidly coupled with the heating element for transporting vapor from the heating element to the user's mouth now contains one or more sensors, and a part of the aspiration tube has features such that the flow through the aspiration tube is laminar. The heating element is electrically coupled between the inner contact member and the outer contact member for energizing the heating element when the heating element is activated, and the heating element activation is capable of being modulated secondary to temperature, viscosity, and air flow data gathered by an onboard sensor or sensors. An air gap defined between at the first portion of said wick element and second portion of the heating element support member now contains a sensor or sensor assembly. Methods of operating a vaporizer through the activation of the heating element through the flow of power or the deactivation of the heating element through the interruption of the flow of power with activation and interruption of the heating element may be entirely or partially modulated by an on board senor or sensors.

FIG. 160 illustrates exemplary locations for the sensors. The temperature and viscosity, or combined temperature and viscosity sensor is positioned at the distal end of the device in the position occupied by the distal portion of the distal wick in the referenced embodiment, such that it is in direct contact with the liquid contained inside the cartridge. The liquid passes through the sensor and then into the distal wick. The vaporization temperature sensor is positioned in the vaporization chamber (previously defined). The vaporization outlet sensor is positioned such that it is in contact with the vapor/air exiting the vaporization chamber. The proximal temperature and velocity sensor, or combined temperature and velocity sensor is positioned in the final proximal flow path of the vapor to measure the temperature and velocity of the vapor/air experienced by the user at the time of inhalation.

FIG. 161 is a diagram illustrating sensor controlled/dependent activation cycle. FIG. 161 shows an activation cycle of the device that is initially controlled by the distal viscosity and temperature sensor and further modulated by the vaporization chamber temperature sensor. The power delivered to the heating element to energize the device is determined by the viscosity and temperature data and the continued level of heating element power delivery is controlled/modulated by the vaporization chamber temperature senor.

FIG. 162 is a diagram illustrating a sensor controlled/dependent activation cycle with deactivation of device dependent on sensor readings within an acceptable range. FIG. 162 is a diagram illustrating the activation of the device where in order for the user initiated activation cycle to continue, first, the temperature dependent viscosity reading from the distal sensor assembly should fall within a predetermined acceptable range for the liquid. Then secondly the temperature of the vaporization chamber should be within the acceptable temperature range. If the sensors relay temperature dependent viscosity or vaporization chamber temperature readings that are out of range, then the device is deactivated.

The Use of Temperature, and Velocity Measurement Sensors to Perform Some Types of Lung Function or Pulmonary Function Testing and Spirometry A spirometer or similar respiratory testing device may be used in testing lung and airway capacity or function of a patient and/or for measuring the amount or volume and/or speed or flow of air that can be inhaled and/or exhaled by the patient. More particularly, the present relates to a portable, lightweight, hand-held spirometer particularly suitable for home and personal use, although equally capable of being used in hospitals, doctor's offices, and like institutions. The present is also directed to a system, software, and method for obtaining, storing, and displaying the results of spirometry tests. In general, a spirometry test measures the air entering and leaving the lungs and airways and is often used as a preliminary test for assessing the health condition of a patient's lungs and airways as well as a means for periodically tracking the progress of disease treatment and effect of medication. The spirometry test typically is performed using a device known as a spirometer, and the data provided by the test often is provided graphically in the form of a "volume-time curve" in which volume in liters is shown along the Y-axis and time in seconds is shown along the X-axis and/or in the form of a "flow-volume loop" in which the rate of airflow is shown on the Y-axis and the total volume inspired or expired is shown on the X-axis.

By way of example, a few common parameters that may be measured during respiratory testing include: Forced Vital Capacity (FVC) which is the total volume of air that can be forcibly blown out after full inspiration; Forced Expiratory Volume (FEV) at timed intervals (for instance, at 1.0 second (FEV1)); Forced Expiratory Flow (FEF) which is the average flow (speed) of air coming out of the lungs and airways during a specified period of the expiration; and Peak Expiratory Flow (PEF) which is the maximum flow (speed) of air during maximum expiration initiated after full inspiration. These parameters often are provided in raw data form (i.e., in liters, liters/second, liters/minute, etc.) and as a percentage of a predicted value (i.e., a percent of a predicted value for a patient of similar age, height, weight, gender and ethnicity).

Each test typically is repeated three times to ensure reproducibility. The obtained results of the tests are highly dependent on patient cooperation and effort. For meaningful and valid test results to be obtained, the patient should provide vigorous and maximum respiratory effort for full expiration and/or inhalation. Typically, if the test is given during an office visit or at a hospital or the like, the patient should be coached and motivated by the attending nurse, physician, or technician to keep exhaling as hard as possible for a predetermined period of time (i.e. "keep going, don't stop"). However, no such assistance is typically provided during home use of a spirometer. Hence, the obtained home test results may not necessarily be valid if maximal effort is not provided throughout the duration of full expiration or inhalation.

The tests or functions may include:
  The use of temperature and air flow/velocity sensor, sensors, or sensor assemblies in the device to perform functions analogous to a spirometer.

The use of the spirometer functionality of the device to perform spirometry for the purpose of acquiring and interpreting pulmonary or lung function testing metrics.

The vaporizer PCB/CPU collecting, storing, and transferring spirometry data.

The vaporizer having the capability of using auditory or visual cues from the on board LED light source and speaker to guide the user in performing inhalation and exhalation procedures required for the collecting of spirometric data.

The vaporizer having a user removable and replaceable assembly that is comprised of the wick elements, heating element(s), heating element support member(s) or wire guide(s), atomizer housing, proximal viscosity and sensor assembly, vaporization chamber temperature sensor(s), and associated electrical contacts and interfaces. This assembly should be referred to as the "upper removable assembly" in this section.

The vaporizer functioning with the upper removable assembly removed from the vaporizer and replaced with a cartridge designed to interface with a computer or similar digital device for the purpose of facilitating the operation of the vaporizer as a spirometer and logging real-time data from the vaporizer as the user performs inhalation and exhalation maneuvers.

Where the cartridge designed to replace the upper removable assembly, referred to in this section as the "digital interface cartridge" has a substantial air intake port such as to limit the functional restriction of airflow through the device when the user is performing inhalation and exhalation maneuvers.

Where the digital interface cartridge contains a female port on the distal aspect of the cartridge for interfacing with a USB cable such as a mini USB, or Micro USB cable or similar for the purpose of connecting the vaporizer to a computer or digital device for the purpose of data display, data storage, data transfer, and power transfer.

Where the digital interface cartridge has contacts at the proximal end on the cartridge for interfacing with the PCB/CPU in the vaporizer.

Where the airflow through the cartridge is directed such that at the proximal end of the cartridge flow passage the airflow is directed over or passed a velocity senor(s) such as the velocity sensors described in Section 3.

Where the spirometry data gathered from the device can be used for the optimization of the delivery of the desired active drug component(s) in the vapor by using the spirometry data to determine optimal vaporizer activation and heating element energizing parameters for a specific user based on their spirometry data.

Where the spirometry data such as maximum inhalation velocity can be calibrated for the user and this data can be used to energize the vaporizer heating element to correlate the generation of vapor to correspond with the user's maximum inhalation velocity to achieve maximal drug component delivery to the deep pulmonary bed.

The use of a pressure transducer in the digital interface cartridge or the vaporizer for the measurement of lung or pulmonary compliance.

The use of a digital interface such as a computer, smart phone, or tablet to provide instruction to the user for the purpose of performing inhalation and exhalation maneuvers necessary for pulmonary or lung function testing. The connection to the digital interface can be made using wireless technology or through a direct or cabled connection such a USB cable or similar technology.

The use of the spirometer functions of the device to perform incentive spirometry exercises for the purposes of improving the users lung function.

The use of spirometry data to determine a unique spirometric or lung function signature for the user.

The use of a spirometric signature to prevent unauthorized use of the vaporizer.

The transmission of data using wireless technology to perform the basic functionality, aside from power transfer, as the previously described wired connection.

As described, a spirometer is an instrument for measuring the air capacity of the lungs. Spirometry is a type of pulmonary function test that measures the amount of air taken in (volume) and exhaled as a function of time. Spirometry is generally the first and most commonly done lung function test. Pulmonary function tests are a group of tests that measure how well the lungs take in and release air and how well they move gases such as oxygen from the atmosphere into the body's circulation. The pulmonary function tests may relate how well the taking in and release of air are performed and are not related to pulmonary function tests as they relate to gas exchange, for example the movement of gases such oxygen from the atmosphere to the body's circulation.

The most common parameters measured in spirometry may include:

Vital capacity (VC): the greatest volume of air that can be expelled from the lungs after taking the deepest possible breath.

Forced vital capacity (FVC): the volume of air that can forcibly be blown out after full inspiration.

Forced expiratory volume (FEV), at timed intervals of 0.5, 1.0 (FEV1), 2.0, and 3.0 seconds: FEV1 is the volume of air that can forcibly be blown out in one second, after full inspiration. Other FEV values re correspondingly related to the time parameter.

Forced expiratory flow 25-75% (FEF 25-75): Forced expiratory flow (FEF) is the flow (or speed) of air coming out of the lung during the middle portion of a forced expiration. It can be given at discrete times, generally defined by what fraction remains of the forced vital capacity (FVC). The usual intervals are 25%, 50% and 75% (FEF25, FEF50 and FEF75), or 25% and 50% of FVC. It can also be given as a mean of the flow during an interval, also generally delimited by when specific fractions remain of FVC, usually 25-75% (FEF25-75%).

Maximal voluntary ventilation (MVV), also known as maximum breathing capacity: Maximum voluntary ventilation is a measure of the maximum amount of air that can be inhaled and exhaled within one minute. For the comfort of the patient this is done over a 15 second time period before being extrapolated to a value for one minute expressed as liters/minute.

Peak expiratory flow (PEF): PEF is the maximal flow (or speed) achieved during the maximally forced expiration initiated at full inspiration, measured in liters per minute or in liters per second.

Tidal volume (TV): Tidal volume is the amount of air inhaled and exhaled normally at rest Total lung capacity (TLC): Total lung capacity (TLC) is the maximum volume of air present in the lungs Expiratory Reserve Volume (ERV): the maximal volume of air that can be exhaled from the end-expiratory position.

Residual Volume (RV): the volume of air remaining in the lungs after a maximal exhalation.

Forced Expiratory Time (FET): measures the length of the expiration in seconds.

Slow vital capacity (SVC): is the maximum volume of air that can be exhaled slowly after slow maximum inhalation.

FIG. 163 is a spirograph showing lung capacity and pulmonary metrics relevant to function testing. Static lung compliance is not solely measured by spirometry, and may require the use of a pressure transducer. Static lung compliance ($C_{st}$) may be when estimating static lung compliance, volume measurements by the spirometer needs to be complemented by pressure transducers in order to simultaneously measure the transpulmonary pressure. When having drawn a curve with the relations between changes in volume to changes in transpulmonary pressure, $C_{st}$ is the slope of the curve during any given volume, or, mathematically, $\Delta V/\Delta P$. Static lung compliance is perhaps the most sensitive parameter for the detection of abnormal pulmonary mechanics.

There are different types of pressure transducers that can be used that include force collector types. These types of electronic pressure sensors generally use a force collector (such as a diaphragm, piston, bourdon tube, or bellows) to measure strain (or deflection) due to applied force (pressure) over an area, such as:

Piezoresistive strain gauge. Uses the piezoresistive effect of bonded or formed strain gauges to detect strain due to applied pressure. Common technology types are Silicon (Monocrystalline), Polysilicon Thin Film, Bonded Metal Foil, Thick Film, and Sputtered Thin Film. Generally, the strain gauges are connected to form a Wheatstone bridge circuit to maximize the output of the sensor and to reduce sensitivity to errors. This is the most commonly employed sensing technology for general-purpose pressure measurement. Generally, these technologies are suited to measure absolute, gauge, vacuum, and differential pressures.

Capacitive. Uses a diaphragm and pressure cavity to create a variable capacitor to detect strain due to applied pressure. Common technologies use metal, ceramic, and silicon diaphragms. Generally, these technologies are most applied to low pressures (Absolute, Differential and Gauge)

Electromagnetic. Measures the displacement of a diaphragm by means of changes in inductance (reluctance), linear variable differential transformer (LVDT), Hall Effect, or by eddy current principle.

Piezoelectric. Uses the piezoelectric effect in certain materials such as quartz to measure the strain upon the sensing mechanism due to pressure. This technology is commonly employed for the measurement of highly dynamic pressures.

Optical. Techniques include the use of the physical change of an optical fiber to detect strain due to applied pressure. A common example of this type utilizes Fiber Bragg Gratings. This technology is employed in challenging application(s) where the measurement may be highly remote, under high temperature, or may benefit from technologies inherently immune to electromagnetic interference. Another analogous technique utilizes an elastic film constructed in layers that can change reflected wavelengths according to the applied pressure (strain).

Potentiometric. Uses the motion of a wiper along a resistive mechanism to detect the strain caused by applied pressure.

Other types of electronic pressure sensors may include types of electronic pressure sensors that use other properties (such as density) to infer pressure of a gas, or liquid. For example, the types may include:

Resonant. Uses the changes in resonant frequency in a sensing mechanism to measure stress, or changes in gas density, caused by applied pressure. This technology may be used in conjunction with a force collector, such as those in the category above. Alternatively, resonant technology may be employed by exposing the resonating element itself to the media, whereby the resonant frequency is dependent upon the density of the media. Sensors have been made out of vibrating wire, vibrating cylinders, quartz, and silicon microelectromechanical systems (MEMS). Generally, this technology is considered to provide very stable readings over time.

Thermal. Uses the changes in thermal conductivity of a gas due to density changes to measure pressure. A common example of this type is the Pirani gauge.

Ionization. Measures the flow of charged gas particles (ions) that varies due to density changes to measure pressure. Common examples are the Hot and Cold Cathode gauges.

The functionality of the vaporizer may be expanded to include the functionality of a spirometer for the purpose of performing lung or pulmonary function testing and the utilization of that data to measure improvement in lung function over time and to optimize the performance of the vaporizer for the individual user based on their lung function as determined through spirometry and pulmonary compliance testing.

A digital interface cartridge may be located where a wick element for directly contacting a liquid to be changed into a vapor is replaced by the user. FIG. 164 illustrates a vaporizer with a digital interface cartridge assembly. The digital interface cartridge replaces the position of the cartridge, atomizer housing, distal wick, and proximal wick. In this embodiment, these components would be packaged/arranged in such a fashion that they were removable from the vaporizer by the user for replacement or to exchange with the digital interface cartridge. In this embodiment of the device the inlet port for airflow in the digital interface cartridge is large enough to allow for unrestricted airflow, similarly the flow channel(s) that comprise the functional element of the aspiration tube and the exit channel in the mouthpiece are also large enough to allow for unrestricted airflow. In one embodiment of the device the spirometer data is transferred to a digital interface such as a computer/smartphone/tablet via wireless methods such as RF, Bluetooth, Wi-Fi or similar methods. In another embodiment of the device the spirometry data is transmitted through means of a wired connection to the digital interface. In an embodiment of the device visual cues from the onboard LED light source and auditory signals from onboard noise generator such as a speaker provide the user with cues to perform inhalation and exhalation maneuvers in regard to both the type of maneuver and the duration of the maneuver. In another embodiment the digital interface provides the user with instructions on the inhalation and exhalation maneuvers in both regards to the type of maneuver and the duration of the maneuver. The digital interface also provides a read out of the spirometry data such as a spirogram or spirograph and metrics that are directly gathered from the spirometer and calculated metrics extrapolated from the gathered data. In one embodiment the spirometry data can be stored in the internal memory of the device. In another embodiment the data can be transferred and stored in the charging case by previously described methods. In yet another embodiment the data can be stored in the digital interface device. The data can be transferred to a network for access and review by a healthcare professional. Similarly to spirometry functions and data collection, incentive spirometer functions and maneuvers can be performed for the purpose of improving user lung function.

FIG. 165 illustrates an embodiment of a vaporizer functioning as a spirometer that is connected to a digital interface. Although illustrated as a computer in FIG. 165, it may be a smart phone, tablet or similar computing device. The digital interface in conjunction with software serves to provide the user with instructions on initiating and terminating the maneuver being performed as well as the type of inhalation or exhalation maneuver to be perfumed, and the duration of the maneuver. Additionally the digital interface displays the results of the spirometry testing and results of previous testing such that improvement or decrements in lung function can be viewed and evaluated by the user. In one embodiment the digital interface may utilize a digital representation of a "healthcare professional" to simulate the instructions and methods used by healthcare providers and technicians when performing lung or pulmonary function testing in order to achieve maximum participation and effort from the user. In another embodiment the digital interface may network in real-time with a health care provider or technician so that they may provide instructions remotely to the user as the pulmonary or lung function testing is being conducted. The wired connection also serves to provide power to the device in order to energize the onboard electronics such as the sensor assemblies, PCB/CPU, and LED(s). In one embodiment the wired connection may additionally charge the internal battery while the device is connected to a digital interface. The wired connection serves to both transfer data from the device to the digital interface for storage, analysis, extrapolation, and transmission as well as to transfer data from the digital interface to the device in order to program, calibrate, update internal software, and similar functions. Similarly the wired connection and digital interface functionality can be applied to the device when it is being utilized to perform incentive spirometry function for the purpose of improving user lung function.

FIG. 166 illustrates a general overview of the digital interface component. The component may have one or more air intake ports at the distal end of the component to facilitate unrestricted airflow and an outlet that is the open end of the primarily tube shaped main body of the component that interfaces with the device and is fluidly coupled with the flow channel(s) of the aspiration tube. The component is longer and extends further out of the distal end of the vaporizer than the cartridge to allow for the intake ports to be unobstructed and to facilitate the user plugging in the data cable. The distal surface is occupied by a port for receiving a data cable, shown in the illustration as a female port for a micro USB type B connection. The data cable connection port is electrically coupled to the PCB/CPU of the device through contacts that run from the connection port through the length of the cartridge. In the preferred embodiment the body of the new component would be comprised of a translucent or transparent plastic or similar material to allow for the transmission of light from the internal LED light source through the internal light pipe for visual recognition by the user. In the embodiment where a direct connection to the digital device is not used and wireless methods for data connection and transfer are employed the connection port pictured in FIG. 166 is omitted (not shown).

FIG. 167 illustrates the configuration of a mouthpiece intended for use with device in the spirometer application. The important feature of this modified mouthpiece from the original mouthpiece is the inclusion of a filter to prevent contamination of the aspiration tube when exhalation maneuvers are performed with device during spirometry. The filter is not restrictive and serves to prevent the deposition of saliva or other contaminants such as bacteria or microbes from the user oral cavity into the aspiration tube. The mouthpiece in one embodiment could be disposable or in another embodiment could be cleaned and reused. The basic operation of the device as a vaporizer would be converted for use as a spirometer by removing the mouthpiece and replacing with the filtered mouthpiece component and the removal of the upper removable assembly for replacement with the digital interface cartridge.

FIG. 168 is a diagram illustrating sensor controlled/dependent activation cycle with deactivation of device dependent on sensor readings for a user specific spirometric profile within an acceptable range. FIG. 168 shows a simple flow diagram illustrating how activation of the device and deactivation of the device are dependent on the recognition of a spirometric profile for the specific user. As the vaporizer undergoes routine use a spirometric profile is built for the user using the data gathered from on board temperature, airflow velocity, and pressures sensors, or a combination of sensor assemblies. As oral cavity volume and mouth maneuvers that generate the vacuum pressure to draw air through the device are unique to the individual user operating the device, a unique "signature" for the user may be determined based on these unique characteristics. After a minimum number of inhalations to achieve repeatability in the inhalation profile to determine the unique signature, the activation of the device is dependent on the unique signature being recognized by the device in order for the device to be activated and the heating element energized. If the inhalation performed by the user does not fall within the "profile" then the device is deactivated, and a "user not recognized" error code is generated.

New or Spent Cartridge Recognition and Vaporizer Activation, Cartridge Content Recognition and Vaporizer Activation, Cartridge Content and Usage Data Gathering An electromechanical interface connections may be used between the cartridge and the atomizer. The electromechanical interface connection may convey a resistance measurement from the cartridge to the device. The resistance measurement conveyed from the cartridge to the device may serve as a requirement for the device to be activated. The resistance measurement conveyed from the cartridge to the device may serve to modulate the activation parameters of device, such as peak activation temperature, to optimize the vaporization of the fluid contained in the cartridge. The use of a seal on the cartridge that has a contact surface may be used for interfacing with the atomizer housing and convey that the cartridge seal is intact. Likewise, a seal on the cartridge that is conductive may be used such that when intact it completes a circuit by bridging two contact points in the puncturing element of the atomizer housing. The use of a seal on the cartridge that is conductive and when intact completes a circuit by bridging two contact points in the puncturing element of the atomizer housing may be used such that the completed circuit constitutes a signal to the device that the cartridge is new and unused. The device being rendered inactive if contact surface on the cartridge is not recognized by the interface with the atomizer as being intact.

The use of an electromechanical interface connections and resistance measurements may effect a one-time-use configuration such that once a cartridge is inserted into the device and used it cannot be refilled and reused by the user for subsequent use in the vaporizer. The use of a fuse wire or "fused element" in the cartridge may prevent reuse of the cartridge by the user. A fused element may be used in the cartridge such that when a "dry wick" is detected which corresponds the content of the cartridge being entirely consumed the fuse is energized in such a way to melt the fuse wire and render the cartridge inactive. The device may be rendered inactive when an inactive cartridge is present in the device.

The cartridge may have an internal contact positioned such that it is in contact with the outer lateral surface of the atomizer when the cartridge is fully inserted into the device. The cartridge may have an internal contact positioned such that it is in contact with the outer lateral surface of the atomizer when the cartridge is fully inserted into the device that serves to complete a circuit by bridging two contact points on the opposing lateral surface of the atomizer housing. The cartridge may have an internal contact positioned such that it is in contact with the outer lateral surface of the atomizer when the cartridge is fully inserted into the device that serves to complete a circuit by bridging two contact points on the opposing lateral surface of the atomizer housing. The completion of the circuit serves as a signal that the cartridge is fully inserted. The internal contact may be a fuse element or wire. The cartridge may have an internal contact positioned such that it is in contact with the outer lateral surface of the atomizer when the cartridge is fully inserted into the device that serves to complete a circuit by bridging two contact points on the opposing lateral surface of the atomizer housing. The internal contact may be a fuse element or wire and if the element or wire is melted then the cartridge is inactive or used and should not be able to be used again if refilled or reinserted into the device.

The cartridge may have an internal contact positioned such that it is in contact with the outer lateral surface of the atomizer when the cartridge is fully inserted into the device that serves to complete a circuit by bridging two contact points on the opposing lateral surface of the atomizer housing. Where the internal contact is a fuse element or wire. Where the atomizer housing that is in contact with internal contact has at least two different circuits that are arranged proximal to distal such that as the cartridge is inserted it activates the distal circuit first and the proximal circuit when fully inserted. Similarly when the cartridge is removed the proximal circuit is broken (no longer electrical coupled) and the distal circuit is activated as the cartridge is removed.

The cartridge may have an internal contact positioned such that it is in contact with the outer lateral surface of the atomizer when the cartridge is fully inserted into the device that serves to complete a circuit by bridging two contact points on the opposing lateral surface of the atomizer housing. Where the internal contact is a fuse element or wire. Where the atomizer housing that is in contact with internal contact has at least two different circuits that are arranged proximal to distal such that as the cartridge is inserted it activates the distal circuit first and the proximal circuit when fully inserted. Similarly when the cartridge is removed the proximal circuit is broken (no longer electrical coupled) and the distal circuit is activated as the cartridge is removed. Where the activation of the distal circuit on removal of the cartridge energized the fuse element or wire in order to melt the element or wire. Exemplary types of fuse elements or fuse wire may include Zinc, Copper, Silver, Aluminum, or Alloys.

The device may have a two stage process to recognize that a cartridge is new and sealed when inserted into the device, with the first stage being the contact surface on the seal of the cartridge, and the second stage being the internal contact such that each contact should be made sequentially e.g. the cartridge seal contact should be followed by the internal cartridge contact in order for the device to be rendered active and ready for use, if the two stage contact is not made e.g. only the internal contact is made (as would be the case in an already used cartridge being reinserted) then the device is rendered inactive.

The device may register a process where the cartridge is inserted to the point of contact of the seal with the puncturing element of the atomizer housing, then the cartridge makes contact with the internal contact and atomizer in the fully inserted or seated portion, and finally the third step of the process where the internal contact is "broken" i.e. no longer in direct physical contact with the distal lateral surface of the atomizer upon removal of the cartridge. This process at completion renders the device inactive until steps one and two are repeated with a new cartridge. The device may recognize the cartridge cycles such that activation cycle data in terms of number and duration of activations per cartridge can be gathered. The use of a resistance value from the cartridge to atomizer housing contacts to relate "cartridge type" or "cartridge content(s)" date to the vaporizer.

The utilizing of cartridge use cycles and the cartridge content may be used to calculate per inhalation and per cartridge dose delivery of active component to the user. The storage, extrapolation, transfer or transmission of the data gathered by the cartridge device interface may be used. The contacts on the external surface of the vaporizer may be used to interface with contacts on the internal surface of the light pipe sleeve. The use of contacts on the external surface of the vaporizer may interface with contacts on the internal surface of the light pipe sleeve. The most distal external contact is coupled to the cartridge seal and when the seal is broken the contact is no longer electrically coupled.

The use of contacts on the external surface of the vaporizer may interface with contacts on the internal surface of the light pipe sleeve. The most distal external contact is coupled to the cartridge seal and when the seal is broken the contact is no longer coupled. A cartridge that has a punctured seal and the proximal contact is no longer coupled to the seal the cartridge is determined to have been used. The use of the external contacts described above may be used to perform a process of cartridge recognition such that a stepwise process activates a series of circuits as the cartridge is inserted or removed.

The use of the external contacts may perform a process of cartridge recognition such that a stepwise process activates a series of circuits as the cartridge is inserted or removed such that if the cartridge is removed, activated the described series of circuits prior to a certain number of activations, or prior to a "dry wick" indication signaling the cartridge contents have been consumed the device is rendered inactive until another cartridge completes the insertion process with an intact proximal contact. A set of features on the cartridge may correspond to features on the light pipe sleeve that serve to align the cartridge for insertion into the device such that the cartridge should be "clocked" with the light pipe sleeve so that it can be inserted into the device and if the cartridge is not clocked or aligned with the light pipe sleeve the cartridge cannot be inserted. Cartridge recognition may prevent insertion and use of the "wrong" cartridge not containing the intended active component or component dosage.

The functionality of the vaporizer may include functions to prevent misuse or abuse of the vaporizer by preventing the reuse of spent cartridges, prevent the refilling of cartridges with different fluids not intended by the manufacturer, or adding ingredients to a sealed cartridge. This may apply to the ability of the device to recognize the contents of the cartridge and the storage of that data to be used in extrapolating per inhalation and per cartridge dosing information, furthermore the cartridge content/formulation data can be used to optimize the activation of the device in terms of peak operating temperature, and time to peak operating temperature. A wick element for directly contacting a liquid to be changed into a vapor now contains contact element to interface with contact element on the liquid cartridge.

FIG. 169 illustrates a cartridge with seal and resistive section for interfacing with contacts on the atomizer housing. FIG. 169 illustrates the interaction between the cartridge seal with a resistive center element and the atomizer hosing with contacts for interfacing with the cartridge. In this embodiment the "signal" is a resistance value transmitted to the device PCB/CPU that correlates to the formulation of the liquid in the cartridge and as such allows for the device to "recognize" the cartridge. Cartridge recognition allows for modulation of activation parameters to optimize device performance for a particular formulation and to allow for the formulation information to be used in conjunction with activation cycle data to extrapolate per activation dose delivery, and number of doses delivered for the cartridge, and similar usage data.

FIG. 170 illustrates an atomizer housing contacts and cartridge weal and internal cartridge contact arrangement. FIG. 170 shows an embodiment of the atomizer housing (132) and liquid cartridge (150) arranged with coordinating contacts. Illustrated is the stepwise process of cartridge insertion and corresponding cartridge contact interfaces. Interface #1 represents the initial engagement of the atomizer housing and the cartridge where the contacts on the most distal aspect of the atomizer housing come into contact with the seal on the liquid cartridge. The contact area on the cartridge seal has a specific resistance value that corresponds to the contents of that cartridge such that several points of data are conveyed through this initial interface: a) that the cartridge seal is intact; b) and that an intact cartridge seal conveys that the cartridge has not been tampered with; c) the cartridge contents in terms of formulation and active component such that the activation characteristic of the device can be appropriately modulated to optimize the vaporization process; d) active component/formulation data can be used to extrapolate dose delivery; e) that the active component/formulation is the correct active component/dosage for the user. Interface #1 is transient and is terminated with the cartridge is further inserted and the puncturing element of the atomizer housing breaks the cartridge seal. Interface #2 is also transient and occurs when the proximal internal cartridge contact passes the distal lateral atomizer housing contact. The lateral contact of the atomizer represents an open circuit and the internal cartridge closes that circuit, the closing of the circuit represents the signal from the interface. In the illustrated embodiment the proximal internal cartridge contact is shown as being fused, or comprised or partially comprised of a fuse wire or element. Upon removal of the cartridge the circuit is energized and the fused proximal internal contact is melted such that it can no longer serve to complete the circuit. Completion of the circuit on insertion conveys to the device that the cartridge is new and has not been previously used. By melting the fused contact upon removal of the cartridge it prevents reuse or tampering with the cartridge or cartridge contents. Interface #3 occurs when the cartridge is in the fully seated or inserted position. This contact is maintained for the "life span" of the cartridge, that is, until all liquid has been delivered to the wick element of the device and a "dry wick" signal is received from the device when all the liquid from the cartridge has been delivered to the wick elements. Interface #3, similar to interface #2, is the simple completion of an open circuit and the circuit being complete conveys a signal to the device that the cartridge is fully inserted and the device is ready to be activated by the user. Removal of the cartridge initiates a process in the device where the first signal is the breaking of the circuit made by the #3 interface. This signal energizes the distal lateral atomizer contacts such that when the proximal internal cartridge contact comes into contact the fused contact is melted and the cartridge is rendered inactive and cannot be reused.

FIG. 171 illustrates an atomizer housing contacts, light pipe sleeve contacts, cartridge seal and external cartridge contact arrangement. FIG. 171 illustrates an embodiment of the cartridge/device sensor assembly where the cartridge contacts are on the external aspect of the cartridge (150). The cartridge seal contact and resistive aspects of the seal interface with distal contacts on the puncturing element of the atomizer housing (132) in the same manner as illustrated in FIG. 170. The external cartridge contacts engage with contacts on the internal surface of the light pipe sleeve (140). Collectively the cartridge (150), atomizer housing (132), and light pipe sleeve (140) are referred to in the figure as the "Complete Assembly." The proximal external cartridge contact is a fused wire or element similar to the internal cartridge contact illustrated and described in FIG. 170. The functionality of the assembly for the cartridge insertion process begins with the initial contact made between the resistive surface of the cartridge seal coming into contact with the distal contacts on the puncturing element of the atomizer housing. This contact occurs during the insertion and ends when the cartridge seal is punctured. The "signal" from this contact interface is a resistance value interpreted by the PCB/CPU and conveys at a minimum two pieces of data: 1) the cartridge has an intact seal and is new and unused; 2) the resistance value corresponds to the cartridge formulation and active component (drug compound) such that the dosage delivery per inhalation, and per cartridge can be extrapolated. The second contact interface can occur in conjunction with the initial contact to effect a sequential control process such that if the second contact made by the proximal external cartridge contact and the distal internal light pipe sleeve contact completes a circuit that is the "signal" and if that signal is not followed by the third and final contact interface signal the device is rendered inactive. This prevents the initial contact being completed and a different cartridge being subsequently inserted, as this would activate the second interface twice which would result in device deactivation secondary to the improper cartridge insertion sequence. Both the first and second interfaces are transient as they are occurring during the process of active cartridge insertion. The third and final contact interface is a stable interface and the cartridge is in the fully inserted position where the proximal external cartridge contact comes into direct contact with the proximal internal light pipe sleeve contact and the distal external cartridge contact is in direct contact with the distal internal light pipe sleeve contact. The contact engagement completes a circuit, which is the "signal" sent to the PCB/CPU to convey the completed cartridge insertion process. The process is such that once the cartridge insertion process is initiated it should be completed with that specific cartridge or the failure of the sequential contact interface engagement registers an error code and the device is deactivated until a full and correct cartridge insertion process is completed. The external cartridge contacts are fully circumferential around the external surface of the cartridge. The internal light pipe sleeve contacts are not fully circumferential around the internal surface of the light pipe sleeve such that when the external cartridge contact interfaces with the corresponding light pipe sleeve contact the electrical coupling completes a circuit. The removal process is also sequential, when the cartridge is removed the stable/static interface is disrupted and the distal internal light pipe sleeve is energized such that when the proximal external cartridge contact (the fuse contact) passes the energized light pipe sleeve contact and the circuit is completed the fused cartridge contact is energized sufficiently to melt the contact. This process renders the cartridge "inactive" and prevents further use of the cartridge as the melted fused contact is no longer able to properly interface with the light pipe sleeve contact and effect the completion of the circuit required to signal the PCB/CPU. The used cartridge in effect has two intrinsic elements that prevent reuse, misuse, or abuse; 1) the broken seal which cannot effectively interface with the distal atomizer housing contact and 2) the melted fuse contact that cannot effect the completion of the circuit when engaging with the light pipe sleeve contact.

FIG. 172 illustrates a contact mediated sequential cartridge insertion process. FIG. 172 provides a detailed overview of the cartridge insertion process. The process is initiated by the user when the device does not have a cartridge inserted. A new, unused cartridge (150) is inserted into the device and slides freely through the light pipe sleeve (140) until the cartridge seal comes into contact with the distal aspect of the atomizer housing (132). Pressure should be applied to rupture the seal and this also represents Interface #1 where the distal atomizer housing contacts engage the resistive section of the atomizer seal to effect a "signal" to the PCB/CPU as previously described. Additionally, as this resistive value correlates to a cartridge contents value by the onboard PCB/CPU and software this represents a safety feature the "cartridge validation" in that if the device does not recognize the cartridge having the proper contents (wrong dose, wrong formulation, wrong active component/drug) the device can send a visual and/or auditory signal to the user indicating that cartridge is or is not the correct cartridge (e.g. green light from LED and pleasant auditory cue for "correct cartridge" red light from LED and unpleasant beep or buzz cue for "incorrect cartridge." This serves to prevent usage and dosage errors and can be achieved prior to cartridge rupture such that an incorrect cartridge could be removed and replaced with the correct cartridge. Once the initial interface is completed, including the described cartridge validation step and the seal is punctured Interface #2 occurs. Interface #1 and #2 can be set to occur in a time dependent manner such that only a predetermined period of time may laps once a "correct cartridge" cue is sent from the user. This time period would be brief to insure that the same cartridge is being utilized to complete the insertion cycle. This is relevant in the embodiment where the cartridge contacts are internal as Interface #1 and #2 occur sequentially and not concomitantly as occurs in the embodiment where the cartridge contacts are external. Interface #2 is transient as described previously and occurs when the cartridge contacts serve to close the open circuit of either the distal lateral atomizer housing contacts or the distal internal light pipe sleeve contacts depending on the embodiment. As described previously Interface #3 should occur sequential to Interface #2. The stable or static Interface #3 activates the device so the user can activate it as needed throughout the cartridge life span.

FIG. 173 illustrates contact mediated sequential cartridge removal process. FIG. 173 provides a detailed overview of the cartridge removal process. The process begins when the user initiates the removal of the cartridge and the stable/static Interface #3 is disrupted. The Interface #3 circuit transitioning from closed to open signals the PCB/CPU to energize the interface #2 device contact such that when the fused contact on the cartridge transiently passes the contact the fuse is melted rendering the cartridge inactive and incapable of being reused. The device is in a state of deactivation and cannot be reactivated until the cartridge insertion process is completed.

FIG. 174 illustrates a liquid cartridge and light pipe sleeve features. FIG. 174 illustrates additional features on the cartridge (150) and the light pipe sleeve to serve two primary functions: 1) to insure proper alignment or "clocking" of the cartridge and the light pipe sleeve to achieve proper contact engagement; and 2) to provide surfaces for linear contacts which represent an alternative embodiment for the contacts previously illustrated in this section. As illustrated the features comprise a groove and corresponding rib present on the components with each component having the complementary feature to the other.

Liquid pH Measurement and Vaporizer Activation and Control

A pH measurement sensor may be used to sample the cartridge fluid and convey pH of measured fluid to onboard PCB/CPU and software interface. The device may be deactivated if the pH of the sampled fluid does not fall within the specified range of pH for the intended fluid. The pH values of the liquid may be used to convey formulation and active component/drug data to the onboard PCB/CPU and software interface. The pH values of the liquid may be used to convey formulation and active component/drug data to the onboard PCB/CPU and software interface to optimize the heating element activation to optimize device performance for the formulation.

There are several types of pH sensors that may be used. Several different modalities of small form or "micro" or "mini" pH sensors/probes may be used. For example, the sensors may include: 1) non-invasive pH sensors, sometimes referred to a "sensor" spots transmits data to a fiber optic receiver; 2) flow through cell (FTC) also called flow through pH minsensors; or pH Microsensors which are miniaturized pH sensors designed for measuring in small volumes and high spatial resolution. The sensor tip is typically below 150 µm. The sensors are normally based on a 140 µm silica fiber which enables integration into a manifold of small scale environments. These sensors do not require reference electrodes and there is no leakage of electrolytes, a clear advantage over common electrodes. Alternatively, there may be various electrochemical methods or non-electrochemical methods such as catalytic, calorimetric, and optodes for sensing pH.

FIG. 175 illustrates a configuration of a microelectrode for the purpose of measuring pH in a liquid medium. Microelectrodes can be configured with tip diameters and sensitive tip lengths in the millimeter to micrometer range.

FIG. 176 illustrates a pH sensor assembly where the sensor is effectively impermeable except for Hydrogen ions that allow for pH measurement of the sample fluid. This sensor type may be used in subsequent FIGS. below to illustrate the sensor assembly positioning and configuration.

FIG. 177 illustrates various methods and technologies for measuring pH in liquid samples. These methods could be deployed in various embodiments of the device in order to measure the pH of the liquid exiting the cartridge. Methods of pH measurement that do not require the use of a reference electrode are more suitable for this intended application. Methods of pH measurement that allow for small scale form factor are also preferred due to the size constraints imposed by the form factor of the preferred embodiment of the device, which is embodied as being closely equivalent in size to a cigarette.

The methods of activation and controlling the activation of the device may include expanding the mechanisms for controlling the activation of the device through the measurement of the pH of the liquid and methods for preventing the misuse or abuse of the device by preventing the use of nonproprietary liquids. Additionally this may be used for the identification of the liquid in relation to formulation. A wick element that is used for directly contacting a liquid to be changed into a vapor may include a pH sensor assembly.

FIG. 178 illustrates a pH sensor assembly and housing in relation to the atomizer housing and distal wick. FIG. 178 illustrates the new component that is comprised of a pH sensor and sensor housing. The new component is positioned such that the outer diameter of the housing has tight fitment to the inner diameter of the atomizer housing (132). The new component is positioned in the internal space of the atomizer housing and lateral fitment is such that the passage of fluid between the outer lateral surface of the new component and the inner lateral surface of the atomizer housing is mitigated. The distal portion of the new component extends beyond the distal portion of the atomizer housing such that the new component distal element functions as a puncturing element to pierce/puncture the seal on the liquid cartridge. The distal end of the component is in direct contact with the liquid contained in the cartridge, replacing the position previously occupied by the distal wick. Liquid flow from the cartridge (not shown) passes through the flow channel over the pH sensor assembly which is shown positioned in the flow channel. Flow port(s) on the distal aspect of the pH sensor housing serve as the liquid intake for liquid to exit the cartridge. The liquid flows through a center channel in the pH sensor housing that contains the pH sensor such that the pH of the liquid can be measured immediately upon exiting the cartridge. The liquid exits the center channel of the pH sensor housing and flows to the distal surface of the distal wick (134). In this embodiment the distal wick has been reduced in overall length to allow for space to position the new component. However the function of the distal wick is the same as in prior embodiments with exception of the embodiment where the distal wick also serves as a puncturing element for the cartridge as this function is now performed by the pH sensor housing.

FIG. 179 illustrates a pH sensor housing. FIG. 179 provides an overview of the pH sensor housing. The cross sectional side view of the component illustrates the cavity where the pH sensor/probe is positioned and also represents the fluid flow path for the liquid traveling from the liquid cartridge (150) to the distal wick (134). The distal aspect of the pH sensor housing functions as a puncturing element to pierce the seal on the proximal end of the cartridge allowing for the fluid to exit the cartridge and enter the device. Flow ports direct the fluid into the center of the cavity to insure the pH sensor/probe comes into immediate contact with the liquid as it exits the cartridge. The ports are shown in this embodiment as being angled inward to reduce the possibility of becoming clogged during the process of rupturing the cartridge seal. Suction from the user during inhalation drives the fluid from the cartridge through the central channel in the pH sensor housing and subsequently to the distal wick. The exit port for the pH sensor lead is shown in this embodiment as being positioned on the lateral proximal aspect of the pH sensor housing. The pH sensor housing could be comprised of a metal or alloy, ceramic, plastic, composite or similar. In one embodiment the component would be comprised of glass, sapphire, or optically clear plastic such as acrylic or polycarbonate in order to facilitate the use of a pH sensor positioned in the internal cavity and a wireless sensor receiver positioned adjacently on the external surface of the component. These sensor types (Non-invasive pH sensors, sometimes referred to as a "sensor" spots) require the use of a transparent material and obviate the need for the pH sensor lead port.

FIG. 180 illustrates a pH sensor housing and pH sensor assembly. FIG. 180 illustrates the pH Sensor housing (shown in cross section) and pH sensor assembly general arrangement. Fluid flows through the housing and passes the sensor, the liquid flow path is illustrated in the figure by light grey dotted lines.

FIG. 181 illustrates a cross-section view of a pH sensor assembly and housing. FIG. 181 illustrates the pH sensor and sensor housing positioned in the fully assembled device.

FIG. 182 illustrates a pH sensor controlled/dependent activation cycle. FIG. 182 illustrates pH dependent or mediated activation of the device. In this embodiment of the device control the formulation of the liquid is designed to have a pH within a specific range that corresponds to several pieces of data conveyed to the device: 1) proprietary cartridge contents intended for use in the device, 2) the formulation of the liquid and active component. This information is used for two primary purposes: 1) to prevent misuse or abuse of the device by preventing the activation of the device for use with liquids not provided by the manufacturer and liquids from the manufacturer that may have been altered, and to prevent the use of liquid from the manufacturer that has expired or degraded secondary to improper storage, premature rupture of the seal, or passing the intended usage date, 2) conveying the cartridge formulation information to optimize the device activation cycle, explained in further detail in FIG. 183.

FIG. 183 illustrates a pH sensor controlled/dependent device modulation. FIG. 183 outlines the modulation of the device activation cycle in relation to the timing and peak activation of the heating element to optimize the performance of the vaporizer for specific formulations. The specific formulation of the liquid is conveyed to the device as a pH value of the cartridge contents as measured by the onboard pH sensor. The user activates the device and the pH sensor is activated and data is transmitted. The pH value is determined and corresponds to specific liquid formulation and contents. The heating element power flow is modulated to maintain a temperature through the activation cycle. The device can then be deactivated.

The Use of Light Emitter and Light Sensor in Conjunction with a Turbine for Determining Flow Velocity and Volume, Unique User Inhalation Signature, and Device Control The assembly may include an emitter and sensor with a turbine positioned in between such that the beam is temporarily interrupted by the turbine vane(s) when rotating. The positioning of the assembly in the flow path of the device may be such that airflow through the device passes through the turbine impacting the vanes and causing the turbine to rotate. The interruption of the beam by the turbine vane may be a static signal when the turbine is not rotating, or pulse signal when the turbine is rotating. The pulse signal may be used to activate the device. The beam interruption frequency may correlate with the airflow velocity through the turbine. The turbine vane(s) may have a leading edge that initiates the interruption of the beam and a trailing edge that once passed the path of the beam the interruption of the beam ends. The device when under operation may have a pulse signal from the turbine vane interruption of the beam being recognized as a "normal operation" signal. The device is deactivated when activated through existing conductive methods (described in existing filings) and the pulse signal in not present. The flow velocity determines flow volume and subsequently determine per inhalation dose delivery of active compound.

This may be used to prevent overuse or abuse of the active compound being delivered by the device through the deactivation of the device if the maximum intended dose over time has been delivered to the user by the device. The flow velocity is used to modulate the activation parameters of the heating element such that heating element energizing is correlated to flow velocity. A pulse signal may determine time or duration of inhalation and pulse signal frequency and duration determines the inhalation signature of the specific user. The use of the inhalation signature of the user can prevent unauthorized use of the device by an unintended user by deactivating the device if the unique inhalation signature does not match the unique inhalation signature of the intended user.

FIG. 184 illustrates a modified embodiment of the vaporizer mouthpiece that has a larger internal diameter to allow for space to position the turbine assembly. FIG. 185 illustrates a cross-section view of a mouthpiece with a turbine assembly. FIG. 185 illustrates the mouthpiece with larger internal diameter and the turbine positioned such that airflow through the mouthpiece is directed through the turbine. Airflow through the mouthpiece is generated by the user while inhaling and when the airflow through the mouthpiece impacts the vanes of the turbine the result is rotation. The airflow through the devices is from distal to proximal and this is shown in the figure by grey broken lines with arrowheads indicating directionality of the flow through the mouthpiece. The turbine in this embodiment is illustrated as having two vanes and could be comprised of more than two vanes in alternative embodiments. The vanes are positioned such that there is a gap or space between adjacent vanes such that the beam from the emitter can pass through the turbine assembly uninterrupted and only be interrupted at certain positions of the vanes when the turbine is undergoing rotation.

FIG. 186 illustrates a cross section of a mouthpiece with a turbine assembly, emitter, and sensor. FIG. 186 illustrates the mouthpiece with the turbine assembly and the emitter and sensor assembly. In this embodiment the emitter emits a beam of electromagnetic radiation labeled as "light beam" in the illustration to a sensor arranged such that between the emitter and the sensor is the turbine assembly. The configuration of the components is such that when airflow through the mouthpiece results in rotation of the turbine the beam from the emitter is disrupted first by the leading edge of a vane and then by the face of the vane and finally by the trailing edge of the vane. Once the trailing edge of the vane rotates out of the path of the beam the beam impacts the sensor until the leading edge of the next vane disrupts the beam. This sequential interruption of the beam by the rotating turbine results in an intermittent signal to the sensor or "pulse signal." The pulse signal corresponds to the rotation speed of the turbine, and the rotational speed of the turbine is dependent on the airflow velocity through the mouthpiece. The pulse signal can be processed by the onboard PCB/CPU to extrapolate the airflow volume through the device. Additionally, the pulse signal can be used to indicate activation of device such that when the signal is static the PCB/CPU interprets the static signal as indication of an "inactive" status and the pulse signal as an "activation" signal for the purpose of energizing the heating element. Under normal conductive activation (described in detail in previous patent filings) the pulse signal can serve as a secondary activation signal to prevent unintended activation of the vaporizer.

FIG. 187 illustrates a mouthpiece cover with turbine and sensor assembly. FIG. 187 illustrates an alternative embodiment of the turbine, emitter, and sensor assembly that is functionally equivalent but alternatively positioned in the mouthpiece cover. In this embodiment the mouthpiece cover has a longer overall length than as shown in prior illustrations/embodiments of the component. This embodiment allows for potential user replacement of the sensor assembly if needed. This illustration also shows the addition of a screen or similarly air permeable barrier at the proximal mouthpiece cover orifice to prevent intentional or unintentional damage, or tampering with the turbine and sensor assembly. As the turbine, emitter, and sensor assembly is in the vapor path it may be preferred to have the assembly user replaceable as the vapor may deposit onto the components and impede functionality of the components after a certain number of activation cycles, if the number of activation cycles required to impede the function of the component is less than the number of activation cycles the device is capable of performing before the battery or heating element has reached the end of their respective service lives then occasional replacement of the assembly may be preferred. If the functional service life of the turbine, emitter, and sensor assembly is equal to or greater than the battery and/or heating element service life then it would be preferable to have the mouthpiece cover be non-removable to prevent damage or tampering with the components. The other benefit of positioning the assembly in the mouthpiece cover is the larger internal diameter of the component, which allows for a larger turbine assembly, which could be of practical importance when manufacturing and/or assembling the components.

FIG. 188 illustrates a pulse signal mediated activation of the vaporizer. FIG. 188 outlines the use of the pulse signal as a secondary control measure to prevent accidental or unintentional activation of the device. When the device is activated, by the previously described and filed conductive contact methods, the emitter and sensor are activated. If the signal from the emitter and sensor is static for a period of time immediately following conductive activation of the device, the activation is determined to be "unintentional" and the heating element is not energized. If the emitter and sensor relay a pulse signal following conductive activation, this is interpreted by the PCB/CPU as the corresponding user inhalation, and an "intentional", and the heating element is energized.

FIG. 189 illustrates a pulse signal mediated deactivation of the vaporizer. FIG. 189 outlines the use of the pulse sensor to provide a secondary method of deactivating the vaporizer following intentional activation of the vaporizer by the user. In this device control embodiment the device can be deactivated by either the termination of the conductive contact or if the pulse signal terminates. This additional deactivation measure provides an additional safety feature that prevents prolonged unintentional activation of the device when the conductive contact remains active after the user intended activation cycle. Unintentional conductive contact activation after intended activation could occur as a result of the device remaining in the conductive contact position after the inhalation and activation cycle. This could result from user specific engagement with the conductive contacts, which are intended to be separately engaged by the user's finger(s) and lips, however, lip and/or finger positioning could result in continued unintentional conductive contact activation occurring after an intentional activation cycle.

FIG. 190 is a process for turbine and sensor assembly device activation. The user removes the device from a case and the device emitter and sensor assembly are activated. The signal is static until user inhalation rotates the turbine and the pulse signal is generated. The pulse signal is sent and the heating element is energized until a pulse signal is static. The user places the device in a case and the device emitter and sensor assembly are deactivated.

Preventing the Reuse of the Liquid Cartridge in the Vaporizer.

In one embodiment, there may be a "one time use" liquid cartridge. The use of one, two, or a plurality of directional blades may slice, cut, or transect the liquid cartridge upon removal of the cartridge by the user. The directional blade(s) may be positioned in the light pipe of the device, which serves as the receiving component for the liquid cartridge. The use of a rod, pin, or similar may serve as the axis of the blade allowing for the blade to rotate about the axis. The rotation blade(s) may be shaped such that there is a limit to the rotation in the fully extended position such that the blade(s) should not be able to rotate further than the fully extended position. A spring may be positioned about the blade axis to assist the positional rotation of the blade. The blade may be designed such that there are ridges, teeth, grooves, or similar designed to facilitate the rotation of the blade into the cutting position when the cartridge is being removed from the device.

The rotation blade may have multiple positions: a) fully depressed during the cartridge insertion and while the cartridge remains fully inserted; b) the fully extended cutting position where the blade is substantially orthogonal to the long axis of the cartridge such that the blade is extended and able to transect, cut, slice or similar the wall(s) of the cartridge; c) a transient position which is the range of rotation about the axis between the fully depressed and the fully extended position. The cartridge may be sliced, or cut, in such a fashion that there is a cut or cuts that fully divide the wall(s) of the cartridge for the majority of the length of the cartridge (distal to proximal) preventing the cartridge from serving as a reservoir or container for liquid.

Directional blade(s) may be used such that the distal aspect of the blade is non-cutting such that the cartridge can be inserted into the device without being cut. The cartridge may be wholly or partially comprised of a plastic, polymer, or similar that is readily dividable, or easily cut or sliced, or similar to facilitate the use of the cutting blades. The cartridge may be wholly or partially comprised of a plastic, polymer, or similar that is readily able to be punctured, pierced or similar by a sharp object such as a sharp point, blade edge or similar. The cartridge may be wholly or partially comprised of a plastic, polymer, or similar that when cut, sliced, or similar does not maintain the shape or geometry of the cartridge prior to being cut. For example the proximal aspect of the cartridge would flare outward thus increasing the outer diameter of the cartridge such to prevent reinsertion of the cartridge into the light pipe sleeve.

The cartridge once removed may be rendered unusable, as the cartridge should no longer be capable of containing fluid such that the cut(s) or slice(s) provide a means for fluid to escape the cartridge if the cartridge was refilled. The rotational blade(s) and cartridge may be used to effect a "one time use" cartridge configuration. The prevention of reuse, misuse, or abuse of the device where the one time use cartridge should not be able to be refilled or reinserted into the device. Rotational blades may be used in conjunction with cartridge recognition methods described above. The rotation blades may serve as a means to prevent cartridge reuse, misuse, or abuse by rendering cartridge recognition methods, described in detail above, unusable upon removal of the cartridge.

The use of the described directional features on the distal aspect of the rotational blades may prevent unwanted, unintended, or accidental displacement or removal of the cartridge from the device once inserted. The cartridge in the device may be engaged securely through the use of directional features on the rotational blade(s) or similar component that allow for the cartridge to be inserted into the device using less force than required to remove the cartridge as the removal of the cartridge involves the interfacing of the outer wall of the cartridge lateral surface being in contact with the directional features of the rotation blade(s) or similar component.

FIG. 191 illustrates the positioning and rotational dynamics of the rotating blade(s). The blade(s) are positioned in this embodiment at the distal aspect of the light pipe sleeve such that when the cartridge is removed the blade(s) should engage the cartridge at the distal portion of the cartridge to effect a transection, cut, slice or similar down the majority of the length of the cartridge. The blade(s) rotation is shown such that three positions of rotation about the axis are seen; 1) the fully depressed position where the non-cutting distal aspect of the blade(s) is in contact with the cartridge during insertion and use; 2) the transient range of rotation that represents the entire range of rotation between the fully depressed and fully extended positions; 3) the fully extended position. The blade in this embodiment is illustrated as being held in position through the use of a rod, pin, or similar serving to both position the blade(s) in the light pipe sleeve and to serve as the axis of rotation for the blade(s). The distal aspect of the blade is non-cutting and is designed such that the cartridge can be inserted in the light pipe sleeve and not be damaged, sliced, or cut. The distal aspect of the blade(s) has grooves, ridges, teeth, or similar designed such that they do not grab, engage, or substantially engage with the cartridge outer surface through friction or other mechanical means when the cartridge is inserted. When the cartridge is removed the grooves, ridges, teeth, or similar are deigned to grab, engage, interface or similar with the outer surface of the cartridge such that the removal of the cartridge rotates the blade(s) into the cutting position through the interface with these features on the distal aspect of the blade(s). The rotation of the blade(s) results in the blade(s) puncturing, piercing, cutting into, or similar the cartridge wall(s). The proximal aspect of the blade is sharpened and engages with the entirety of the wall thickness of the cartridge such that the cartridge is cut, sliced, transected or similar down the length of the cartridge from the point of the blade(s) initial engagement through the most proximal aspect of the cartridge. The user supplies the force required to effect the cutting of the cartridge by the blade(s) during the cartridge removal process.

FIG. 192 illustrates the positioning of the liquid cartridge (150) in the light pipe sleeve (140) and the corresponding positioning of the rotational blade(s). During cartridge insertion the blade(s) are positioned by the interface with the outer surface of the lateral aspect of the cartridge to the or their fully depressed position. The blade(s) are designed such that they do not provide substantial resistance or friction when the user is inserting the cartridge into the light pipe sleeve. The geometry of the light pipe sleeve may be modified from a cylinder to a modified cylinder or similar to provide a more robust support for the positioning of the blades and rod, pin, or similar used as the axis of rotation for the blade(s). In such an embodiment the geometry of the cartridge would be also modified as to be shaped such that it is readily inserted into the light pipe sleeve such that the outer diameter and geometry of the cartridge is shaped and sized as to match for fitment the internal diameter and geometry of the light pipe sleeve. The cartridge insertion process requires less applied force from the user than the cartridge removal process as the distal features of the rotational blade(s) are designed such that frictional resistance is minimal during the insertion of the cartridge by the user and that frictional resistance is substantial enough to effect the rotation of the blade(s) into the extended position during removal by the user. The increased resistance required to remove the cartridge from the device also serves to prevent the cartridge of unwanted, unintentional, or accidental removal during normal use.

FIG. 193 illustrates the cartridge removal process from the light pipe sleeve and the interfacing of the rotational blade(s) during the cartridge removal process. In A) the cartridge is fully inserted into the light pipe sleeve and the rotational blade(s) are fully depressed. In B) the cartridge removal process has been initiated and the directional features on the distal aspect of the rotational blades interface with the outer surface of the cartridge. The force applied by the user in removing the cartridge serves to rotate the blade(s) through the frictional engagement of the blade(s) directional features on the distal aspect. In C) the blade(s) are in the fully extended and cutting position. In D) the cartridge has been removed and the blades will again be in the fully depressed position upon insertion of a new cartridge.

FIG. 194 illustrates the cartridge after removal. In this embodiment two rotational blades positioned 180 degrees apart in the light pipe sleeve effected two corresponding cuts, or slices through the wall of the cartridge down the majority of the length of the cartridge. The cartridge is now "used" or "spent" and is no longer capable for functioning as a liquid reservoir. In another embodiment the cuts would also serve to alter the geometry of the cartridge such that the proximal aspect of the cartridge was no longer capable of achieving insertion into the light pipe sleeve as the cut(s) serve to cause the proximal aspect of the cartridge to flare outwards altering the effective outer diameter of the proximal aspect of the cartridge.

Methods for Reducing or Mitigating the Risk of Choking on Vaporizer Components, Choking Risk Reduction Packaging of Vaporizer Cartridge and Vaporizer Cartridge Assemblies The Consumer Product Safety Commission states any toy that is small enough to fit through a circle an inch and a half in diameter (the size of a toilet paper tube) or is less than two and a quarter inches long is unsafe for small children. Packaging for the user removable and user replaceable cartridge may be designed to reduce the risk of choking by providing a packaging such that at least one dimension is greater in length of 2.25 inches. The use of packaging for the user removable and user replaceable cartridge or cartridge assembly ("upper removable assembly") may be designed to reduce the risk of choking by providing a packaging such that at least one dimension is greater in length of 2.25 inches.

The use or application of packaging for the liquid cartridge, liquid cartridge assembly, or upper removable assembly may be designed and intended to be sized and shaped in such a manner that the risk of the liquid cartridge, liquid cartridge assembly, or upper removable assembly (when combined with the packaging wholly, substantially, or similarly) reduces the risk of being a choking hazard. Additionally the force applied by the user to remove the liquid cartridge, liquid cartridge assembly, or upper removable assembly from the packaging and or the dexterity needed for removing the liquid cartridge, liquid cartridge assembly, or upper removable assembly from the packaging may be intended to be such that these maneuvers would be difficult for a young child to perform as a means to further reduce the risk or potential hazard or similar of the liquid cartridge, liquid cartridge assembly, or upper removable assembly being a choking hazard.

When the packaging for the cartridge or cartridge assembly or upper removable assembly is a strip or substantially flat member or similar of paper, plastic, cardboard, or similar with one or more surface(s) having an adhesive component, then the strip or substantially flat member or similar such that the overall length greater than 5.5 inches which is folded along the midline of the length such that the length of the strip or substantially flat member or similar is greater than 2.25 inches when folded with the cartridge or cartridge assembly or upper removable assembly or upper removable assembly is positioned in the center of the folded strip or substantially flat member or similar such that it is in between the folded strip or substantially flat member or similar elements or similar. When the packaging for the cartridge or cartridge assembly or upper removable assembly is a strip or substantially flat member or similar of paper, plastic, cardboard, or similar with one or more surface(s) having an adhesive component, then the strip or substantially flat member or similar such that the overall length greater than 5.5 inches which is folded along the midline of the length such that the length of the strip or substantially flat member or similar is greater than 2.25 inches when folded with the cartridge or cartridge assembly or upper removable assembly is positioned in the center of the folded strip or substantially flat member or similar such that it is in between the folded strip or substantially flat member or similar and the user would peel the ends of the strip or substantially flat member or similar to overcome the adhesive bond between the folded surface to free the cartridge or cartridge assembly or upper removable assembly from the strip or substantially flat member or similar packaging for use in the device.

When the packaging for the cartridge or cartridge assembly or upper removable assembly is a strip or substantially flat member or similar of paper, plastic, cardboard, or similar with one or more surface(s) having an adhesive component, then the strip or substantially flat member or similar such that the overall length greater than 2.25 inches and cartridge or cartridge assembly or upper removable assembly is positioned and held in place the center of the strip or substantially flat member or similar. When the packaging for the cartridge or cartridge assembly or upper removable assembly is a strip or substantially flat member or similar of paper, plastic, cardboard, or similar with one or more surface(s) having an adhesive component, then the strip or substantially flat member or similar such that the overall length greater than 2.25 inches and cartridge or cartridge assembly or upper removable assembly is positioned and held in place the center of the strip or substantially flat member or similar where the user must remove the cartridge or cartridge assembly or upper removable assembly from the strip or substantially flat member or similar packaging for use in the device. When the packaging for the cartridge or cartridge assembly or upper removable assembly is a molded or similarly formed plastic strip or substantially flat member or similar with an overall length greater than 2.25 inches, then the plastic strip or substantially flat member or similar having a feature, element, or similar that is substantially circular or "C" shaped in such a manner to trap, position, or otherwise hold the cartridge or cartridge assembly or upper removable assembly in place at a point along the length of the stip.

When the packaging for the cartridge or cartridge assembly or upper removable assembly is a molded or similarly formed plastic strip or substantially flat member or similar with an overall length greater than 2.25 inches, then the plastic strip or substantially flat member or similar having a feature, element, or similar that is substantially circular shape in such a manner to trap, position, or otherwise hold the cartridge or cartridge assembly or upper removable assembly in place at a point along the length of the strip or substantially flat member or similar where the feature being substantially circular the user would pull the cartridge or cartridge assembly or upper removable assembly to remove the cartridge or cartridge assembly or upper removable assembly from the circular portion of the packaging for use in the device. When the packaging for the cartridge or cartridge assembly or upper removable assembly is a molded or similarly formed plastic strip or substantially flat member or similar with an overall length greater than 2.25 inches and the plastic strip or substantially flat member or similar having a feature, element, or similar that is substantially "C" shaped in such a manner to trap, position, or otherwise hold the cartridge or cartridge assembly or upper removable assembly in place at a point along the length of the strip or substantially flat member or similar where the feature being substantially C shaped the user would pull or pry or similar the cartridge or cartridge assembly or upper removable assembly to remove the cartridge or cartridge assembly or upper removable assembly from the packaging.

The packaging may have one or a plurality of surfaces where instructions for the user relating to how to remove the packaging from the cartridge or cartridge assembly or upper removable assembly from the packaging may be printed, imbedded, etched or similar. The packaging may have one or a plurality of surfaces where information relating to the cartridge contents, expiration or "best if used by" date, warnings, ingredient information or similar may be printed, imbedded, etched or similar. The packaging may have one or a plurality of surfaces where information relating to reducing the risk of choking by leaving the cartridge or cartridge assembly or upper removable assembly in the packaging until the user is ready to place the cartridge in the vaporizer, or similar, may be printed, imbedded, etched or similar.

The packaging for a new unused cartridge or cartridge assembly or upper removable assembly is reusable such that a spent or used cartridge may be placed in the packaging such that a used or spent cartridge or cartridge assembly or upper removable assembly would be held in the packaging in the same fashion or manner or similar as an unused cartridge or cartridge assembly or upper removable assembly to reduce the risk of choking on a spent or used cartridge or cartridge assembly or upper removable assembly. The packaging may have one or a plurality of surfaces where information relating to reducing the risk of choking by placing the used or spent cartridge or cartridge assembly or upper removable assembly into the packaging prior to disposal, recycling or similar, may be printed, imbedded, etched or similar. The packaging containing the cartridge or cartridge assembly or upper removable assembly may require a degree of dexterity to remove the cartridge or cartridge assembly or upper removable assembly from the packaging such as to make the removal of the cartridge or cartridge assembly or upper removable assembly difficult for a child to perform. The packaging containing the cartridge or cartridge assembly or upper removable assembly may require a degree of force to remove the cartridge or cartridge assembly or upper removable assembly from the packaging such as to make the removal of the cartridge or cartridge assembly or upper removable assembly difficult for a child to perform. The packaging material may be resistant to moisture such that the packaging will not degrade, or lose shape, form, structure, or similar if exposed to a moist or wet environment. The packaging material may be resistant to moisture such that the packaging will not degrade, or lose shape, form, structure, or similar if exposed to a moist or wet environment such as the oral cavity of a child.

FIG. 195 illustrates an adhesive strip type of packaging embodiment. FIG. 195 illustrates the general configuration of an adhesive strip or substantially flat member or similar type of packaging. The adhesive strip or substantially flat member or similar could be comprised of various materials such as plastic, heavy paper stock, cardboard, or similar. The material should be of sufficient rigidity to prevent the packaging from readily folding, crumpling, collapsing, or similar. The material should be of sufficient strength to prevent being easily, or readily torn, ripped, or similar. The material should also be wholly or partially resistant to moisture such that that packaging does not lose shape, structure, form or similar when exposed to moisture such as to prevent the packaging material from being degraded if exposed to environmental moisture or placed in the mouth of a child or similar to a degree to which the packaging would present a choking hazard. In this embodiment the packaging would be folded along the midline such as to contain the cartridge in which the packaging has one of the major surfaces being covered with an adhesive. The adhesive should be of sufficient strength as to require some degree of force readily applied by an adult but more difficult to be applied by a child to separate the adhered surfaces to facilitate the removal of the cartridge or cartridge assembly or upper removable assembly for use in the vaporizer. The major surface of the packaging having an adhesive surface is embodied as having the end portions along the length as not having an adhesive surface such to provide an area of purchase for the user to engage the packaging component to separate the adhered surfaces to remove the cartridge or cartridge assembly or upper removable assembly for use in the device. The engagement of the end portions to pull apart or otherwise separate the adhered surfaces should require some degree of dexterity readily performed by an adult and more difficult to perform for a small child. The major surface of the packaging that is not wholly, partially, substantially, or similarly covered with an adhesive may provide a surface where instruction, warnings, information, logo, or similar may be printed, embossed, molded, etched, or similar as a means of conveying the information to the user. Such information may include a warning relating to how the cartridge or cartridge assembly or upper removable assembly should be kept in the packaging until used as a means to reduce the risk of the cartridge or cartridge assembly or upper removable assembly being a potential choking hazard. The over length of the packaging is such that when the cartridge or cartridge assembly or upper removable assembly is held, positioned, made captive, contained or similar the length in one or more dimensions of the packaged product is greater than 2.25 inches as to reduce the hazard of choking on the package product.

FIG. 196 illustrates the adhesive strip packaging embodiment with a liquid cartridge. FIG. 196 illustrates the use of an adhesive strip or substantially flat member or similar packaging embodiment with a cartridge. The adhesive strip or substantially flat member or similar packaging material having an adhesive surface as previously described contains, traps, affixes, positions or similar the cartridge or cartridge assembly or upper removable assembly in the middle portion of the adhesive strip or substantially flat member or similar and then wholly or partially wraps around the circumference of the cartridge or cartridge assembly or upper removable assembly and then adheres to itself for the majority of the length of the strip or substantially flat member or similar. The end elements, as illustrated, are non-adhesive in this embodiment in order to provide a point of engagement for the user to separate the adhered surfaces. Note the packaging is of such a length in at least one dimension to reduce the risk or likelihood of the packaged cartridge or cartridge assembly or upper removable assembly being a choking hazard.

FIG. 197 illustrates cartridge packaging having a C-shaped cartridge capturing element. FIG. 197 illustrates an embodiment of packaging for the cartridge or cartridge assembly or upper removable assembly comprised of a rigid or semi rigid plastic or similar molded or formed or shaped in such a fashion as to have an element that is substantially "C" shaped for the purpose of engaging, positioning, holding, securing, affixing, or similar the cartridge or cartridge assembly or upper removable assembly. Two embodiments are illustrated in FIG. 197 that differ in location of the C shaped element. In either embodiment the material comprising the component is flexible such that the user may apply pressure or force to the packaging that results in the packaging flexing, bending, or similar in such a fashion as the functional diameter of the C-shaped element increases as does the open section of the element in such a fashion as to allow for the removal or insertion of a cartridge or cartridge assembly or upper removable assembly, this is illustrated in further detail in FIG. 201. Note that the packaging is of a dimension in length such that with or without the cartridge or cartridge assembly or upper removable assembly the packaging is of sufficient size not to pose a substantial choking hazard. Additionally, the packaging is designed to be reusable such that spent or used cartridge or cartridge assembly or upper removable assembly may be stored for disposal or recycling in the packaging by reversing the method for cartridge or cartridge assembly or upper removable assembly removal from the packaging such that spent or used cartridge or cartridge assembly or upper removable assembly does not pose a choking hazard.

FIG. 198 illustrates cartridge packaging having a C-shaped cartridge capturing element with the cartridge. FIG. 198 illustrates the packaging having a substantially C shaped element, member or similar to capture, position, retain, hold, affix, place, or similar the cartridge or cartridge assembly or upper removable assembly. The embodiment illustrated has the substantially C-shaped element or member or similar positioned in the central portion of the packaging component. In other embodiments the C-shaped element or member or similar could be positioned in another portion of the packaging component as has been shown in prior illustrations. A cartridge is illustrated in the embodiment and the component can be used as packaging for a cartridge, as shown, or cartridge assembly or upper removable assembly. Note the dimensions of the packaging are such as they should not pose a significant or substantial risk as a choking hazard.

FIG. 199 illustrates a cartridge packaging embodiment having a substantially circular shaped cartridge capturing element. FIG. 199 illustrates an embodiment of packaging for the cartridge or cartridge assembly or upper removable assembly comprised of a rigid or semi rigid plastic or similar molded or formed or shaped in such a fashion as to have an element that is substantially circular shaped for the purpose of engaging, positioning, holding, securing, affixing, or similar the cartridge or cartridge assembly or upper removable assembly. Two embodiments are illustrated in FIG. 199 that differ in location of the circular shaped element. In either embodiment the fitment of cartridge or cartridge assembly or upper removable assembly is such that the user must grasp the packaging and the cartridge or cartridge assembly or upper removable assembly and apply force or resistance or similar in opposing directions in order to remove the cartridge or cartridge assembly or upper removable assembly, this is illustrated in further detail in FIG. 201. Note that the packaging is of a dimension in length such that with or without the cartridge or cartridge assembly or upper removable assembly the packaging is of sufficient size not to pose a substantial choking hazard. Additionally, the packaging is designed to be reusable such that spent or used cartridge or cartridge assembly or upper removable assembly may be stored for disposal or recycling in the packaging by reversing the method for cartridge or cartridge assembly or upper removable assembly removal from the packaging such that spent or used cartridge or cartridge assembly or upper removable assembly does not pose a choking hazard.

FIG. 200 illustrates a cartridge packaging embodiment having a substantially circular shaped cartridge capturing element with the cartridge. FIG. 200 illustrates the packaging having a substantially circular shaped element, member or similar to capture, position, retain, hold, affix, place, or similar the cartridge or cartridge assembly or upper removable assembly. The embodiment illustrated has the substantially circular shaped element or member or similar positioned in the central portion of the packaging component. In other embodiments the circular shaped element or member or similar could be positioned in another portion of the packaging component as has been shown in prior illustrations. A cartridge is illustrated in the embodiment and the component can be used as packaging for a cartridge, as shown, or cartridge assembly or upper removable assembly. Note the dimensions of the packaging are such as they should not pose a significant or substantial risk as a choking hazard.

FIG. 201 illustrates removal of the cartridge or cartridge assembly from the packaging. FIG. 201 illustrates a means or method or procedure or similar for the removal of the cartridge, as shown, or cartridge assembly or upper removable assembly from A) the packaging having a substantial circular shaped member or element and; B) the packaging having a substantial C-shaped member or element.

FIG. 202 illustrates a process of removing a cartridge or cartridge assembly from the packaging and inserting into the device for usage. FIG. 202 illustrates the basic application of the packaging for storing, holding, containing, positioning, affixing, capturing or similar the cartridge, as shown, or cartridge assembly or upper removable assembly in such a manner to prevent the risk of the cartridge, as shown, or cartridge assembly or upper removable assembly being a choking hazard and the basic process of the user removing the cartridge, as shown, or cartridge assembly or upper removable assembly from the packaging and inserting the cartridge, as shown, or cartridge assembly or upper removable assembly into the vaporizer for use.

FIG. 203 illustrates a process of removing a cartridge or cartridge assembly from the device and inserting into the packaging for disposal. FIG. 203 illustrates the basic application of the packaging for storing, holding, containing, positioning, affixing, capturing or similar the cartridge, as shown, or cartridge assembly or upper removable assembly in such a manner to prevent the risk of the cartridge, as shown, or cartridge assembly or upper removable assembly being a choking hazard and the basic process of the user removing the spent, used, empty, or similar cartridge, as shown, or cartridge assembly or upper removable assembly from the device and inserting the cartridge, as shown, or cartridge assembly or upper removable assembly into the packaging for disposal or recycling or similar such that a spent or sued or empty or similar cartridge, as shown, or cartridge assembly or upper removable assembly does not pose a substantial choking hazard.

FIG. 205 illustrates the personal vaporizer unit (PVU) showing the proximal end of the device at the mouthpiece where it interfaces with the users mouth and the distal end being a user replaceable cartridge or cartridge assembly. A main body of the PVU connects these components. The user replaceable cartridge may be liquid filled or filled with a gel consistency material or similar. The liquid or gel may contain a medicament such as nicotine or tobacco derived material or another medicament or plurality of medicaments or similar. The liquid or gel material may be primarily composed of a material, compound, or substance that is capable of being vaporized, aerosolized, or volatized with the application of heat.

The cartridge in a cartridge assembly embodiment may include at least the cartridge and a proximal wick that serves to transfer, transport, or similarly deliver the liquid or gel material from the cartridge to the heating element or elements. The proximal wick may serve to transfer, transport, or similarly deliver the liquid or gel material to a distal wick that may be fluidly coupled to the heating element(s) or be in close proximity to the heating element. The proximal wick may use passive diffusion, active diffusion, capillary action, or similar to deliver the liquid or gel material to the heating element(s). The distal wick or the proximal wick, or the distal wick and proximal wick may together in sequence or simultaneously or independently serve to deliver aerosolized droplets from the wick element to the heating elements, or to within close proximity of the heating element(s) such that the heating element may vaporize, volatize, or further aerosolize the liquid or gel material for the purpose of generating an inhalable vapor or aerosol. The proximal wick may also function as support structure, lattice, substrate, stabilization member, positioning element, scaffold or similar for the heating element(s). The heating element(s) may be etched, plated, deposited, sputtered, directly written, or otherwise deposited, or applied on the proximal wick. The proximal wick may be a functional part of the heating element(s) such that thermal energy from the heating element is absorbed, emitted, reflected, or transferred to the proximal wick from the heating element(s). The heating element(s) may be connected to a microprocessor that serves to control, manage, modulate, regulate, monitor, cycle, or otherwise mediate, control or similar the activation of the heating element(s). In some embodiments, the heating element may be comprised a metal wire or coil, metal ribbon, a resistive element(s), a Microheater(s), a MEMS style Microheater(s), infrared (IR) emitter(s), grey body emitter(s), or similar.

The cartridge assembly thus may include the cartridge, liquid or gel material and medicament, distal wick, proximal wick, heating element(s), microprocessor(s), PCB(s), and an interface or similar type connector(s) to link the cartridge assembly to the main PVU component(s) which consist primarily of the remaining elements and components, such as those not described previously as being a part of the cartridge assembly as illustrated in FIG. 205, and henceforth described in this document as the "main PVU." Where in an embodiment the main PVU is intended to be reusable such that the battery component or a capacitor component (not shown) may be charged or similarly replenished such that the main PVU can be used multiple times by the user to vaporize, volatile, aerosolize or similar more then one cartridge or cartridge assembly before requiring replacement. In such an embodiment the PVU is broadly composed of two primary components, a consumable component that is the cartridge or cartridge assembly, which is consumable or otherwise disposable and intended for a one-time use configuration, and the second component that is the reusable component that is comprised of the main PVU. The term "one-time use" may refer to the consumption of the contents of the cartridge which is intended to deliver a finite number of inhalations (e.g. 300-500 inhalation or 500-1000 inhalation or similar). The plurality of inhalations required to substantially consume the contents of the cartridge or cartridge assembly before the cartridge needs to be replaced is the one-time use embodiment. In yet another embodiment the user may be able to refill the cartridge or cartridge assembly such that the PVU is reusable and capable of delivering numerous operations such that the PVU would not need to be replaced until the heating element, battery, or capacitor, or combination of element, battery, and or capacitor, had reached their functional life in terms of total activation cycles.

The connector may be a threaded type connection, a latching type interface, a magnetic or electromagnetic connection such that the cartridge assembly has a magnetic or electromagnetic that is of opposite polarity as the magnet or electromagnet connector on the main PVU and the magnetic attraction serves to engage and establish the interface, the connector may be a male female type data connection such as USB or similar. The connector may comprise components for delivering electrical energy from the battery. The connector may include a connection or interface that serve to transfer, gather, or transmit data between the cartridge assembly and the PVU.

The cartridge assembly may be a consumable, or disposable assembly that once the liquid or gel material is consumed the assembly is removed and replaced by the user. The cartridge or cartridge assembly in a generally cylindrical embodiment (shown) is inserted into the distal end of the main PVU where the light transmitting sleeve is comprised such that the inner diameter of the light transmitting sleeve is in close tolerance to the outer diameter of the cartridge such as to effect a wholly, or partially airtight interface.

The cartridge may have one or a plurality of geometric features to allow for one or a plurality of void(s), galley(s), channel(s), or similar to allow for airflow to enter and travel down the feature(s) in between the outer surface of the cartridge and the inner surface of the light transmitting sleeve. In the cylindrical embodiment this may be as the circular diameter of the cartridge having one or a plurality of geometries such that part of the circular shape is removed and replace by a linear line where the removal of the portion of the circular shape results in a void space when the cylindrical element of the cartridge is inserted in to the tubular light transmitting sleeve (e.g. FIG. 209). Other embodiments are also possible and envisioned using compatible geometries such as an ovoid cartridge or cartridge assembly and light transmitting sleeve or pipe or similar, triangle shaped cartridge or cartridge assembly and light transmitting sleeve or pipe or similar, square or rectangular cartridge or cartridge assembly and light transmitting sleeve or pipe or similar, trapezoidal cartridge or cartridge assembly and light transmitting sleeve or pipe or similar, or multisided geometries such as pentagonal, hexagonal, heptagonal, octagonal, or and n-gonal (where "n" is the number of sides of the multisided shape) cartridge or cartridge assembly and light transmitting sleeve or pipe or similar.

The alteration of a geometric feature or features of the cartridge outer diameter or dimension allows for control of the amount of airflow that may be drawn into the PVU by the user through the suction, or vacuum pressure, generated during inhalation. The airflow may be limited, restricted, of otherwise mediated through the modification of the geometries of the outer surface of the cartridge and inner surface of the light transmitting sleeve. It may be desirable to modify, mediate, or set the resistance of the device during inhalation, in one embodiment the draw resistance of the PVU would match the draw resistance of a typical smoking article such as a cigarette. In one embodiment, the airflow that flows into the device may be controlled such that it displaces the fluid from the distal wick, or the distal wick and proximal wick such that the air flow travels down the space between the outer surface of the cartridge and inner surface of the light transmitting sleeve and then is forced into the air intake port of the atomizer housing, once the airflow enters the atomizer housing it must passed through liquid or gel saturated wick material, such as a porous ceramic where the liquid or gel in the porous ceramic is forced as droplets or micro-droplets or as an aerosol of droplets or micro-droplets of the approximate size of the pores of the ceramic onto or in close proximity of the heating element to be vaporized.

In some embodiments, for optimal PVU operation there may be an adjustment of the amount of allowable airflow to be correlated to the type of liquid or gel material being used in the vaporizer. Less airflow may be desirable for highly viscous or gel type materials and greater airflow may be desirable for less viscous and more liquid type material. As more liquid materials will diffuse more rapidly, or be more actively transported though capillary action by and through the wick material such that having a greater allowable airflow results in greater delivery of liquid material to the heating element or heating element proximity. Conversely, as more viscous or gel type material does not diffuse as rapidly as less viscous material and does not transfer by capillary action as quickly as less viscous material resultantly it would be desirable in order to effect optimal activation of the PVU to reduce the airflow such that the airflow is metered to account for the slower rate of transport of the more viscous or gel type material by diffusion or capillary action. This may allow for the metering of the airflow to corresponded the amount of fluid displaced from the wick or wicks such that am optimal fluid to air ratio is achieved to allow for optimal vaporization, volatilization, or aerosolization of the material for inhalation by the user. In another embodiment, the air intake fluid displacement ratio may be modulated, adjusted, configured such as to achieve a desirable particle size for the inhalation product (e.g. 1-3 micron, 3-5, micron, 3-10 micron, 5-10 micron, 5-15 micron, 10-20 micron, or greater then 15 micron, or greater then 20 micron particle size, or range of particle sizes, or similar) to achieve pulmonary delivery of the active compound or medicament(s), to the pulmonary vasculature, or to the oral pharyngeal mucosa, or to selectively the pulmonary vasculature and the oral pharyngeal mucosa or to both the pulmonary vasculature and the oral pharyngeal mucosa. In such an embodiment it may be desirable to deliver liquid components that have a flavor component to the oral mucosa such that the particles interact with the taste receptors on the user's tongue. In another embodiment, it may be desirable to deliver the medicament or active component to the oral mucosa or oral pharyngeal mucosa for slower systemic absorption or absorption than absorption or absorption achieved through the more rapid systemic absorption or absorption achieved by pulmonary deliver of the medicament(s). In another embodiment, it may be desirable to deliver the medicament to the pulmonary vasculature (e.g. nicotine to replicate the pharmacodynamics of nicotine delivered by smoking tobacco).

Additionally, the light transmitting sleeve is positioned such that the proximal aspect of the light transmitting component is in contact or close proximity with a light emitting diode (LED) or LED array such that light from the LED is transferred, transmitted, or conveyed from the LED to the light transmitting sleeve. The light transmitting sleeve may be configured to be in proximity to the cartridge, or cartridge element of the cartridge assembly such that light is transferred, transmitted, or conveyed to the cartridge. This allows for the light transmitting sleeve and cartridge to send visual indicators to the user. Visual indicators may include indicators of device activation, cartridge status such as an empty cartridge or new cartridge or cartridge status in the range of either being new and fully or partially consumed, cartridge or cartridge assembly recognition such that the cartridge or cartridge assembly is recognized as being the correct cartridge, battery or capacitor or battery and capacitor status, charging status, remaining activation cycles, reminder notifications, device error(s), and similar.

Following vaporization, volatilization, or aerosolization, collectively referred to in this paragraph as the "vapor" of the liquid or gel type material by the heating element airflow generated by the user forces the vapor out of the atomizer housing and related area of the heating element and proximal wick through a flow galley, or galleys, that serve as the aspiration tube. This area of the device may be the space between the outer diameter or the surface of the battery and the inner surface or diameter of the main body of the PVU. In one embodiment, the battery is encapsulated, shielded, encased, or otherwise isolated from the aspiration tube such that the vapor and airflow though the device does not come into contact with the battery or capacitor directly. The vapor and airflow then passes through the mouthpiece to the user for inhalation.

FIG. 206 illustrates the cartridge assembly. The cartridge assembly may include the cartridge, the element that serves as a liquid storage tank component of the cartridge that contains the liquid or gel material and medicament(s) if desired, distal wick, proximal wick (not shown), heating element(s) (not shown), microprocessor(s) (not shown), PCB(s) (not shown), and an interface or similar type connector to link, connect, interface or similar the cartridge assembly to the main PVU component (not shown), the atomizer housing which has an air intake or plurality of air intake ports. In one embodiment, the cartridge assembly may have a seal, plug, or similar to prevent liquid from leaking out of the cartridge or from becoming contaminated by exposure to the outside environment. In one embodiment, the seal is a tear away, or peel away seal to be removed by the user prior to insertion into the main PVU. In another embodiment the seal is a puncture type seal such as a foil seal or similar. In another embodiment, there may be a seal or plug that prevents fluid leaking or contamination. The cartridge may be clear or translucent such that the liquid or fluid is visible in the cartridge and that light from the LED or similar internal light source may serve to illuminate the cartridge. The cartridge material may be an ultra violet (UV) resistant material to prevent oxidative degradation or oxidization or similar degradation or decomposing of the liquid or gel type material. The cartridge material may be an ultra violet (UV) permeable material such that the cartridge may be UV sterilized.

FIG. 207 illustrates an exploded view of the main cartridge assembly. The main cartridge assembly may comprise the cartridge, the element of the liquid storage tank component of the cartridge that contains the liquid or gel material and medicament(s) if desired, distal wick, proximal wick, heating element(s) (not shown), microprocessor(s) (not shown), PCB(s) (not shown), circuitry (not shown), and an interface or similar type connector to link, connect, interface or similar the cartridge assembly to the main PVU component (not shown), the atomizer housing which has an air intake or plurality of air intake ports. Other features of the cartridge are also illustrated such as the surface geometry of the cartridge that serves to make the cartridge only a partial cylinder such that the non-cylindrical surface feature(s) of the cartridge provide for an air intake channel(s) by providing a space(s), galley or galleys for outside "clean air" (atmospheric) to enter the PVU and travel to the atomizer housing. FIG. 207 illustrates anti-vacuum feature(s) such that air can flow into the cartridge to allow air to enter the cartridge to replace the volume of liquid displaced from the cartridge into the wick elements and also the liquid or gel material that has undergone vaporization, volatilization, or aerosolization. The channel(s) are designed to allow for small volume of airflow into the cartridge while being of a small enough surface area to prevent, deter, or diminish, the leaking of fluid from the anti-vacuum channel secondary to the surface tension of the liquid or gel material.

FIG. 208 is an alternative view of the cartridge assembly positioned with a light transmitting sleeve. The cartridge assembly may include a cartridge, the element that serves as a liquid storage tank component of the cartridge that contains the liquid or gel material and medicament(s) if desired, distal wick, proximal wick (not shown), heating element(s) (not shown), microprocessor(s) (not shown), PCB(s) (not shown), and an interface or similar type connector to link the cartridge assembly to the main PVU component (not shown), the atomizer housing which has air intake or plurality of air intake ports. The outer surface, or outer diameter surface geometry of the cartridge may be in relationship and positioning with the light transmitting sleeve. Airflow from the distal air intake between the stand-off features on the proximal aspect of the cartridge distal element and the most distal aspect of the light pipe sleeve and main body (not shown) direct airflow into a channel created by the surface feature(s), geometry, arrangement of the cartridge outer surface and the light transmitting sleeve. This creates a space(s), channel(s), galley or galleys for outside "clean air" (atmospheric) to enter the PVU and travel to the atomizer housing. This airflow is illustrated distal to proximal by a black dotted line with arrowhead indication the path of the airflow through the assembly. When the airflow enters the atomizer housing, the flow is illustrated by the dotted line, as the airflow is internal to the atomizer housing.

FIG. 209 is a proximal view of the cartridge and light transmitting sleeve. The cartridge inserted into the light transmitting sleeve in FIG. 209 illustrates the previously described features of the light transmitting sleeve and the cartridge. This illustrates the void(s), channel(s), gap(s), galley or galleys, created by the difference in the outer surface geometry of the cartridge and the inner surface of the light transmitting sleeve. The liquid reservoir has an inner diameter and outer diameter. Between the inner and outer diameters are gaps for air flow from outside air to the device. This feature geometry may be used to regulate air intake volume. The outer diameter of the liquid reservoir is surrounded by a light transmitting sleeve.

FIG. 210 is another embodiment of the cartridge and cartridge assembly. The top embodiment illustrates a cartridge with a foil type seal and an internal gasket, diaphragm, or similar. This embodiment may prevent leakage of the contained liquid or gel and also serves to prevent refilling of the cartridge. This diaphragm or plug may be comprised of a silicon or similar type material, such materials may be "self-healing" such that once punctured they may be removed and the diaphragm or plug still prevents the leakage or contamination of the contained liquid or gel. This provides an embodiment where the cartridge may be partially used and then removed by the user for subsequent use. The user may want to use a different cartridge that contains a liquid or gel that contains a different medicament(s), dosage of medicament(s), or other variation of flavor or similar traits of the liquid or gel components. A puncturing element (not shown) is utilized to access the cartridge and transfer, transport, convey or similar the liquid to the wick or wick element(s).

The middle embodiment of FIG. 210 illustrates the cartridge where a puncture type seal contains the fluid in the cartridge and prevents contamination, additionally the cartridges once filled may be purged with nitrogen gas or similar such as to prevent degradation from atmospheric air being contained within the cartridge during filling, the purging of the cartridge or similar extends the storage life and freshness of the contained liquid or gel material. The cartridge when inserted into the PVU is accessed by a puncturing element composed of the distal element of the atomizer housing or in an alternative embodiment the distal wick directly. The cartridge may have a unique serial or identification number. This serial or identification number may be used to convey information about the cartridge and cartridge contents to the user, health care provider, pharmacist or another third party, such information may include but is not limited to the cartridge manufacturer, date of manufacturer, contents, dose of medicament(s), other contents, "use by" date and similar.

The bottom embodiment in FIG. 210 illustrates the cartridge assembly described herein. In this embodiment, a foil type seal is used to prevent contamination or leakage of the cartridge contents. This embodiment illustrates the heating element assembly and/or the wick/atomizer are engaged at the proximal end of the PVU. In particular, the proximal/puncture end (e.g. shown in the top and middle embodiments) is where the wick or atomizer or heating element assembly is located. That assembly may puncture the liquid reservoir so that the atomizer can create a vapor from the stored liquid or material in the cartridge.

FIG. 211 is side view of the PVU without the cartridge or cartridge assembly. There may be a window or a cut out in the main body with a clear or translucent light transmitting sleeve to view into the cartridge. The window in the main body of the device may be located such that through the window and transparent light transmitting sleeve the cartridge is visible and the contents and amount of contents can be directly visualized by the user. In particular, the cut out in the main body may be used to check a fill level of a liquid reservoir in the cartridge. Additionally, the contents may be illuminated by the use of the previously described LED(s) or light(s) that transmit, convey, transfer visible light through the light transmitting sleeve and then to the cartridge.

FIG. 211 also demonstrates areas for labeling or placing a logo on the device. The main body as may be comprised of a metal, and in other embodiments, the main body may be comprised of other materials such as composites, carbon fiber, ceramic, plastics, polymers, glasses, ceramics, papers, paper composites, natural fiber materials, or similar. In one embodiment, the opening in the main body may be a logo, or text that is cut out or otherwise removed from the main body such that it serves the same functional purpose of the window for the visualization of the cartridge contents by the user.

FIG. 212 is a side view of the PVU without the cartridge or cartridge assembly installed and mouthpiece/proximal connector cover removed. FIG. 212 is similar to FIG. 211 in showing the window or cut out in the main body described above. FIG. 212 also illustrates the mouthpiece or proximal connector cover removed. In particular, the proximal end may include a cover or connector that attaches to the main body. The connection may be through a screw mechanism, a snapping mechanism, or other attachment mechanisms. The proximal connector may interface for charging. The proximal connector may also interface for data transfer.

FIG. 213 illustrates the process of cartridge insertion. Cartridge removal is performed by reversing the illustrated sequence. In particular, the cartridge insertion is shown in FIG. 213 such that each diagram (top down) shows how the cartridge is inserted into the distal end of the PVU. The top diagram illustrates the cartridge completely removed from the PVU, while the bottom diagram illustrates the cartridge fully inserted into the PVU. There may be a connector with the cartridge to establish the cartridge assembly. The connector may function to attach the cartridge to the main body of the PVU. The main body may include a corresponding internal connector (not shown) for receiving the connector from the cartridge.

FIG. 214 is an embodiment of a case with closed PVU storage that includes PVU charging and PVU data logging. The case may be a carrying case for transporting the one or more PVUs. The multi-functional case for the PVU may interface with the PVU proximal connection to charge the PVU internal battery or capacitor. In some embodiments, the case may interface/connect/link with the PVU using one or more connectors. The case may include one or more PVUs. The opened case shown in FIG. 215 includes two PVUs, but that is merely exemplary. The case has an internal power source such as a battery and/or capacitor that is capable of recharging the PVU multiple times before the case itself requires recharging such that the case internal battery has a capacity that is several times the capacity of the PVU. The case is capable of being connected to a digital device such as a computer (partially shown) by wired means such as USB data cable or similar (shown). The case may also transfer data from the PVU to a digital device by the same wired means. In another embodiment, the case may be charged by AC or DC methods using a power cable. The case may also transfer, transmit, receive, gather, assimilate, extrapolate, analyze, input, output, or similar data from the PVU or digital device through wireless methods such as Bluetooth, Wi-Fi, IR, or cellular methods. The case may have a microprocessor(s), CPU(s), circuitry, software, application(s), or similar computer systems.

The case in one embodiment has an external LED or similar light source for indication case status such as charging, discharging, data transfer, or similar (shown). The case may have an interior storage for PVU accessories such as mouthpieces and spare cartridges or cartridge assemblies. The case may be designed such that a part or the whole of the distal aspect of the contained PVU(s) are visible such that the charging status, or other device status, of the PVU(s) as indicated by the distal LED in the case can be visualized by the user without having to open the case. The case may be designed to be pocket friendly with a convex top surface containing the LED indicator and a partially concave bottom surface (not shown) to optimize the case for being pocket friendly. In another embodiment the case may approximate dimensions to a pack of 20 "100" length cigarettes.

FIG. 215 is an embodiment of an open case. In particular, the case in FIG. 214 is shown in an open state in FIG. 215. The case may include two PVUs in one embodiment. The case also includes storage for spare mouthpiece/connector covers, and spare cartridges or cartridge assemblies. The LED from the PVUs may be displayed near an edge of the case to indicate charging status or other data.

The above description and associated figures teach the best mode of the invention. The following claims specify the scope of the invention. Note that some aspects of the best mode may not fall within the scope of the invention as specified by the claims. Those skilled in the art will appreciate that the features described above can be combined in various ways to form multiple variations of the invention. As a result, the invention is not limited to the specific embodiments described above, but only by the following claims and their equivalents.

We claim:

1. A personal vaporizer unit comprising:
 a cartridge storing a substance to be vaporized;
 an atomizer configured to vaporize the substance;
 a microprocessor; and
 a communication module disposed within the vaporizer unit and configured to affect a communication link with a computing device, wherein the communication module is also configured to exchange data with an application program associated with the computing device, wherein the application program comprises authentication capabilities configured to verify a user's age prior to activation of the device.

2. The personal vaporizer unit of claim 1, wherein the data comprises a unique identifier for securing the personal vaporizer unit.

3. The personal vaporizer unit of claim 2, wherein the vaporizer unit remains inactive until a correct unique identifier is exchanged.

4. The personal vaporizer unit of claim 3, wherein the vaporizer unit deactivates after a threshold criteria is met.

5. The personal vaporizer unit of claim 4, wherein the threshold criteria comprises at least one of a period of non-use, a vaporizer unit malfunction, an incorrect inhalation signature, a number of use cycles, a delivered dosage, the vaporizer unit is put into storage, or a manual input.

6. The personal vaporizer unit of claim 2, wherein the unique identifier comprises at least one of a personal identification number or a biometric identifier.

7. The personal vaporizer unit of claim 6, wherein the biometric identifier comprises at least one of a fingerprint, an iris scan, facial recognition, or an inhalation signature.

8. The personal vaporizer unit of claim 2, wherein the microprocessor comprises a data storage module configured to store at least one of a user profile or usage data.

9. The personal vaporizer unit of claim 8, wherein the authentication capabilities include associating the unique identifier with a specific user profile or usage data.

10. The personal vaporizer unit of claim 9, wherein the specific user profile or usage data include at least one of a desired number of activations cycles over a period of time, user notifications, a desired dose delivery of an active substance per inhalation, a desired total delivered dose over a period of time, specific temporal configurations, demographic data, environmental conditions, data sharing permissions, or an inhalation signature.

11. The personal vaporizer unit of claim 2, wherein at least one of the vaporizer unit or the computing device comprises a graphical user interface.

12. The personal vaporizer unit of claim 11, wherein the graphical user interface is configured to allow a user to at least one of input the unique identifier, change the unique identifier, add a second unique identifier, transfer data, or configure settings.

13. The personal vaporizer unit of claim 1, wherein the communication module comprises a wireless interface.

14. The personal vaporizer unit of claim 13, wherein the wireless interface communicates via one or more of Wi-Fi, Bluetooth®, cellular, 3G, 4G, near field communication (NFC), an infrared (IR) transmitter, or an 802.11 specified interface.

15. The personal vaporizer unit of claim 1, wherein the computing device comprises one or more of a personal digital device, a network, a smart watch, a wearable digital device, a smart phone, a tablet computer, a laptop computer, or a desktop computer.

16. The personal vaporizer unit of claim 1, wherein at least one functional element of the personal vaporizer unit is controllable from the computing device.

17. The personal vaporizer unit of claim 1, wherein the application program comprises messaging capabilities and the data comprises one or more of a text message, an email, or an alert.

18. The personal vaporizer unit of claim 1 further comprising a case configured to hold the personal vaporizer unit, wherein the case comprises a power source for recharging the personal vaporizer unit.

19. The personal vaporizer unit of claim 18, wherein the case comprises a second communication interface configured to exchange data with one or more of the personal vaporizer unit, the computing device, or a second computing device.

* * * * *